(12) United States Patent
Fang et al.

(10) Patent No.: US 10,155,035 B2
(45) Date of Patent: Dec. 18, 2018

(54) PORCINE REPRODUCTIVE AND RESPIRATORY SYNDROME VACCINE VIRUS

(71) Applicant: Elanco US Inc., Indianapolis, IN (US)

(72) Inventors: Ying Fang, Manhattan, KS (US); Stephen Qitu Wu, Fishers, IN (US)

(73) Assignee: Elanco US Inc., Greenfield, IN (US)

( * ) Notice: Subject to any disclaimer, the term of this patent is extended or adjusted under 35 U.S.C. 154(b) by 0 days.

(21) Appl. No.: 15/429,206

(22) Filed: Feb. 10, 2017

(65) Prior Publication Data

US 2017/0239343 A1     Aug. 24, 2017

Related U.S. Application Data

(60) Provisional application No. 62/296,658, filed on Feb. 18, 2016.

(51) Int. Cl.
*A61K 39/12* (2006.01)
*C12N 7/00* (2006.01)
*A61K 39/00* (2006.01)

(52) U.S. Cl.
CPC ............... *A61K 39/12* (2013.01); *C12N 7/00* (2013.01); *A61K 2039/5254* (2013.01); *A61K 2039/552* (2013.01); *C12N 2770/10021* (2013.01); *C12N 2770/10034* (2013.01); *C12N 2770/10064* (2013.01)

(58) Field of Classification Search
None
See application file for complete search history.

(56) References Cited

U.S. PATENT DOCUMENTS

2017/0239343 A1* 8/2017 Fang ..................... A61K 39/12

OTHER PUBLICATIONS

An et al. (Veterinary Microbiology. 2011; 149: 104-12).*
Vu et al. (Veterinary Microbiology. 2017; 206: 29-34).*
Lawson, Steven, Joan Lunney, Federico Zuckermann, Fernando Osorio, Eric Nelson, Craig Welbon, Travis Clement et al. "Development of an 8-plex Luminex assay to detect swine cytokines for vaccine development: assessment of immunity after porcine reproductive and respiratory syndrome virus (PRRSV) vaccination." *Vaccine* 28, No. 32 (2010): 5356-5364.
Park, Changhoon, Hwi Won Seo, Kiwon Han, Ikjae Kang, and Chanhee Chae. "Evaivation of the efficacy of a new modified live porcine reproductive and respiratory syndrome virus (PRRSV) vaccine (Fostera PRRS) against heterologous PRRSV challenge." *Veterinary microbiology* 172, No. 3 (2014): 432-442.
Geldhof, Marc F., Merijn Vanhee, Wander Van Breedam, Jan Van Doorsselaere, Uladzimir U. Karniychuk, and Hans J. Nauwynck. "Comparison of the efficacy of autogenous inactivated Porcine Reproductive and Respiratory Syndrome Virus (PRRSV) vaccines with that of commercial vaccines against homologous and heterologous challenges," *BMC veterinary research* 8, No. 1 (2012): 182.
Kim, Hyunil, Hye Kwon Kim, Jung Ho Jung, Yoo Jung Choi, Jiho Kim, Chang Gyu Urn, Su Bin Hyun et al. "The assessment of efficacy of porcine reproductive respiratory syndrome virus inactivated vaccine based on the viral quantity and inactivation methods." *Virology journal* 8, No. 1 (2011): 323.
Leng, Xue, Zhenguang L, Mingdi Xia, Yanliang He, and Hua Wu. "Evaluation of the efficacy of an attenuated live vaccine against highly pathogenic porcine reproductive and respiratory syndrome virus in young pigs," *Clinical and Vaccine Immunology* 19, No. 8 (2012): 1199-1206.
Graham, Patrick L., and Peggy Anne Hawkins. "MJ PRRS vaccine: Field efficacy."
Li, Xiangdong, Amy Galliher-Beckley, Jerome C. Nietfeld, Kay S. Faaberg, and Jishu Shi. "Montanide TM Gel01 ST adjuvant enhances PRRS modified live vaccine efficacy by regulating porcine humoral and cellular immune responses." World Journal of Vaccines, No. 3 (2013): 1-9.
Sun, Zhi, Yanhua Li, Russell Ransburgh, Eric J. Snijder, and Ying Fang. "Nonstructural protein 2 of porcine reproductive and respiratory syndrome virus inhibits the antiviral function of interferon-stimulated gene 15." *Journal of virology* 86, No. 7 (2012): 3839-3850.

* cited by examiner

*Primary Examiner* — Shanon A. Foley
(74) *Attorney, Agent, or Firm* — David L Pflugh

(57) ABSTRACT

The present invention relates to modified, live Porcine Reproductive and Respiratory Syndrome viruses. Viruses were genetically analyzed and selected based on phylogenetic grouping for modification by repeated passage in tissue culture. The modified, live viruses were assessed for the ability to provide protective immunity to heterologous viruses. The modified, live viruses are useful in vaccines, particularly in vaccines which can treat infection of swine by multiple heterologous viruses.

13 Claims, 5 Drawing Sheets

Figure 1:
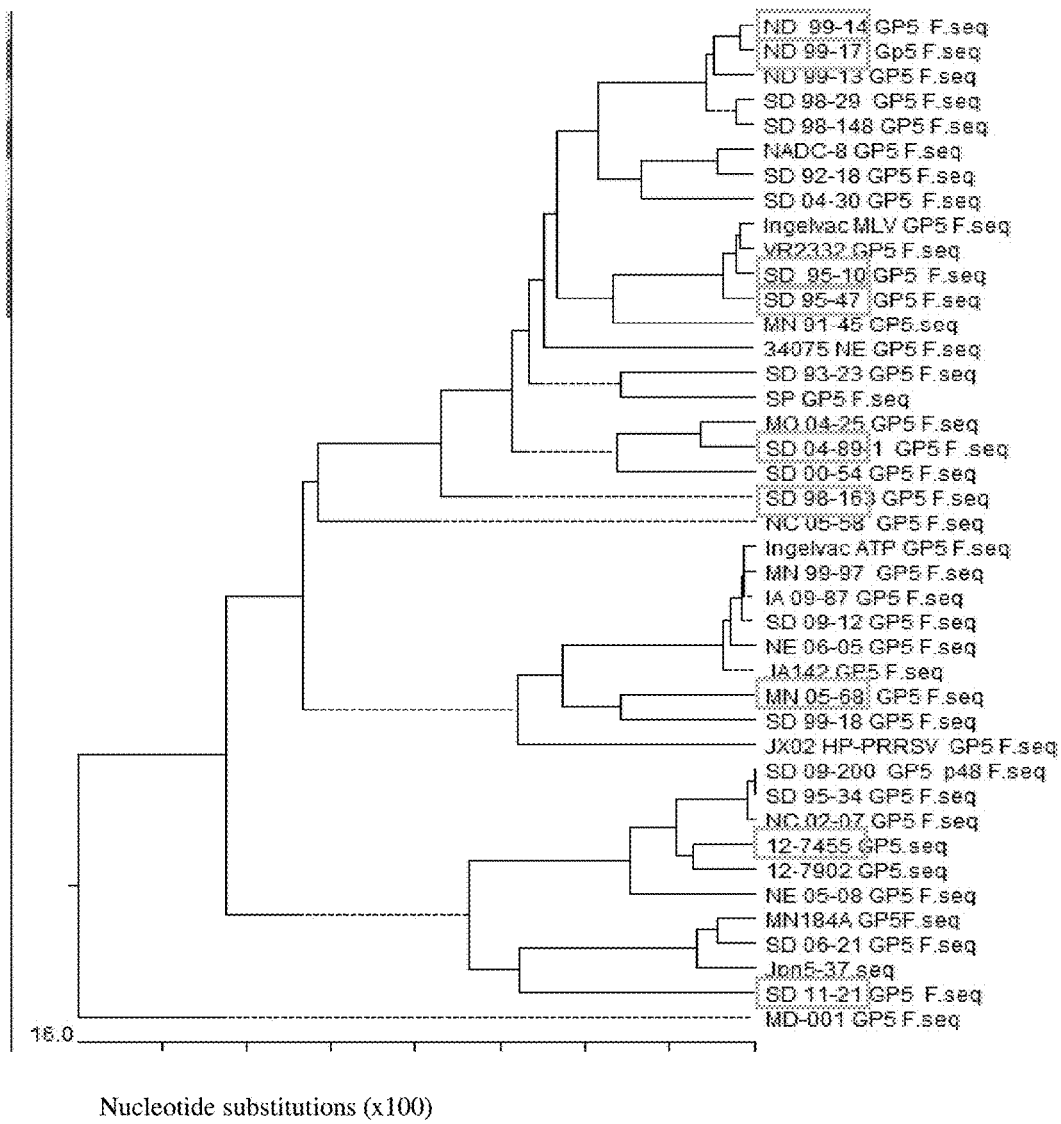

Specification includes a Sequence Listing.

Figure 2.

PORCINE REPRODUCTIVE AND RESPIRATORY SYNDROME VACCINE VIRUS

The present application claims benefit of priority to U.S. Patent Application Ser. No. 62/296,658, filed Feb. 18, 2016, which is hereby incorporated by reference in its entirety.

The present invention relates to modified, live Porcine Reproductive and Respiratory Syndrome viruses. The modified, live viruses are useful in vaccines, particularly in vaccines which provide protection against heterologous viruses.

Porcine Reproductive and Respiratory Syndrome (PRRS), originally called Mystery Swine Disease, was first described in Europe but has now spread worldwide. PRRS causes late-stage abortions, stillbirths, and infertility in breeding age sows, and respiratory disease, decreased growth performance, and even death in nursery and growing/finishing pigs. PRRS causes economic losses of over $600 million each year in the US alone.

Symptoms of PRRS virus infection in adult porcine animals include, without limitation, reduced appetite, lethargy, fever, and behavioral changes such as loss of balance, circling, and falling to one side. Pregnant sows may prematurely farrow, abort fetuses, or deliver mummified or stillborn piglets, and up to 10% of pregnant sows may die from PRRS virus infection. Infected piglets have a high pre-weaning mortality rate, are often weak, and can have edema around the eyes. PRRS virus infection in weaned nursery or grow/finish pigs can cause, without limitation, a failure to thrive, respiratory distress, labored or rapid breathing, blotchy reddening of the skin, and rough hair coats.

The PRRS virus is an enveloped virus with an approximately 15 kb, linear, positive-stranded, single-stranded RNA genome, and the virus has been classified to the family Arteriviridae. To date at least nine open reading frames have been identified in the genome. PRRS viruses are divided into two general subtypes. The European subtype, Type 1 PRRS viruses, is exemplified by the Lelystad strain, while the Type 2 North American PRRS viruses are exemplified by the strain VR-2332.

The two subtypes can have as little as about 60% sequence identity in their genomes, and even within subtypes individual strains can vary up to about 20% in the identity of their genomes. This variability has complicated the development of vaccines to effectively treat and/or prevent PRRS. Modified, live virus (MLV) variants of the PRRS virus can generate immunity against challenge with PRRS viruses, but the vaccine is most effective when the challenge is with a PRRS virus genetically homologous to the MLV. The MLV vaccines have been less effective against challenge with heterologous viruses. Further, MLV have shown some reversion to virulence, such that the vaccine virus causes disease in vaccinated animals. Vaccines containing inactivated (i.e. killed) PRRS viruses have better safety profiles, but efficacy against heterologous challenge has been limited.

Because current PRRS vaccines do not show sufficient safety and efficacy to reduce the economic impact of PRRS virus infection, new and improved vaccines are needed. Preferably, those vaccines would be both safe and efficacious. If the vaccines comprise attenuated MLV, those attenuated MLV should not demonstrate reversion to virulence in order to be considered safe to use in the field. For example, by adapting a PRRS strain to growth in tissue culture cells for at least 80 passages, or preferably at least 100 passages, the MLV should not demonstrate reversion to virulence. To be efficacious, a vaccine virus strain should be able to elicit protective immunity in a porcine animal against a range of phylogenetically diverse wild type PRRS strains. Preferably, a new PRRS vaccine virus strain would be able to elicit protective immunity in a porcine animal against at least three phylogenetically diverse wild type PRRS strains.

The present invention provides for a modified, live Porcine Reproductive and Respiratory Syndrome (PRRS) vaccine virus strain, wherein the consensus complementary DNA sequence of said PRRS strain is at least 90% identical to a sequence selected from the group of SEQ ID NO: 4, SEQ ID NO: 9, SEQ ID NO: 10, SEQ ID NO: 11, SEQ ID NO: 12, and SEQ ID NO: 13. Preferably, the modified, live strain could have a consensus complementary DNA sequence that is at least 95% identical to a sequence selected from the group of SEQ ID NO: 4, SEQ ID NO: 9, SEQ ID NO: 10, SEQ ID NO: 11, SEQ ID NO: 12, and SEQ ID NO: 13. More preferably, the modified, live strain could also have a consensus complementary DNA sequence that is at least 98% identical to a sequence selected from the group of SEQ ID NO: 4, SEQ ID NO: 9, SEQ ID NO: 10, SEQ ID NO: 11, SEQ ID NO: 12, and SEQ ID NO: 13. As a person of ordinary skill will appreciate, due to the high mutation rate of the PRRS virus, a modified, live PRRS strain might comprise a multiplicity of subpopulations, each having a homologous but not identical genome.

The present invention provides for a modified, live Porcine Reproductive and Respiratory Syndrome (PRRS) virus strain, wherein the PRRS virus strain is a ND 99-14 strain or a SD 11-21 strain. The PRRS virus strain should be passaged preferably at least 80 times, or more preferably 84 times, in tissue culture cells. Most preferably, the PRRS virus strain should be passaged 100 times in tissue culture cells. Such passaging in tissue culture cells is useful in properly attenuating the modified, live PRRS virus strain. Attenuated PRRS virus strains may cause subclinical but not clinical disease when those strains are administered to porcine animals. Modified, live PRRS virus strains passaged at least 80 times have a low probability of reverting to wild-type virulence. Most preferably, modified, live PRRS virus strains passaged 100 times have a low probability of reverting to wild-type virulence.

The present invention provides for an immunogenic composition comprising a modified, live PRRS virus strain having a consensus complementary DNA sequence at least 90% identical to a sequence selected from the group of SEQ ID NO: 4, SEQ ID NO: 9, SEQ ID NO: 10, SEQ ID NO: 11, SEQ ID NO: 12, and SEQ ID NO: 13. Preferably, the modified, live strain could have a consensus complementary DNA sequence that is at least 95% identical to a sequence selected from the group of SEQ ID NO: 4, SEQ ID NO: 9, SEQ ID NO: 10, SEQ ID NO: 11, SEQ ID NO: 12, and SEQ ID NO: 13. More preferably, the modified, live strain could also have a consensus complementary DNA sequence that is at least 98% identical to a sequence selected from the group of SEQ ID NO: 4, SEQ ID NO: 9, SEQ ID NO: 10, SEQ ID NO: 11, SEQ ID NO: 12, and SEQ ID NO: 13. As a person of ordinary skill will appreciate, due to the high mutation rate of the PRRS virus, a modified, live PRRS strain might comprise a multiplicity of subpopulations, each having a homologous but not identical genome.

The present invention provides for an immunogenic composition comprising a modified, live PRRS virus strain, wherein said PRRS virus strain is ND 99-14 or SD 11-21. The ND 99-14 strain or the SD 11-21 strain may be passaged at least 80 times, or preferably even 84 times, in tissue culture cells. Most preferably, the ND 99-14 strain or the SD 11-21 strain may be passaged 100 times in tissue culture cells. The immunogenic composition may further comprise a pharmaceutically-acceptable excipient, stabilizer, solubilizer, or diluent. The immunogenic composition may also comprise a further antigen from a different virus or from a bacterial strain or from a parasite.

The present invention provides for a vaccine comprising a modified, live PRRS virus strain, wherein the consensus complementary DNA sequence of said PRRS strain is at least 90% identical to a sequence selected from the group of SEQ ID NO: 4, SEQ ID NO: 9, SEQ ID NO: 10, SEQ ID NO: 11, SEQ ID NO: 12, and SEQ ID NO: 13. Preferably, the modified, live strain could have a consensus complementary DNA sequence that is at least 95% identical to a sequence selected from the group of SEQ ID NO: 4, SEQ ID NO: 9, SEQ ID NO: 10, SEQ ID NO: 11, SEQ ID NO: 12, and SEQ ID NO: 13. Most preferably, the modified, live strain could also have a consensus complementary DNA sequence that is at least 98% identical to a sequence selected from the group of SEQ ID NO: 4, SEQ ID NO: 9, SEQ ID NO: 10, SEQ ID NO: 11, SEQ ID NO: 12, and SEQ ID NO: 13. The vaccine may further comprise an adjuvant. The vaccine may further comprise a pharmaceutically-acceptable excipient, stabilizer, solubilizer, or diluent. The vaccine may comprise a further antigen from a different virus or from a bacterial strain or from a parasite.

The present invention provides for a vaccine for use in treating or preventing Porcine Reproductive and Respiratory Syndrome in a porcine animal. As PRRS is caused by a PRRS virus, the present invention provides a vaccine for use in treating a PRRS virus infection. The present invention also provides for a vaccine for use in treating a porcine animal for a symptom caused by a PRRS virus infection. The infection may be from a wild-type virulent strain of a PRRS virus. A symptom may be, without limitation, reduced appetite, lethargy, fever, behavioral changes such as loss of balance, circling, and falling to one side, premature farrowing, abortion, stillbirths, edema, a failure to thrive, cough, respiratory distress, labored or rapid breathing, blotchy reddening of the skin, rough hair coats, lung lesions, viral shedding, and mortality. The present invention provides for a vaccine for use in therapy of a porcine animal. The present invention also provides for a vaccine for use in therapy of PRRS in a porcine animal. Preferably, the vaccine comprises a modified, live PRRS strain having a consensus complementary DNA sequence that is at least 90%, at least 95%, or at least 98% identical to a sequence selected from the group of SEQ ID NO: 4, SEQ ID NO: 9, SEQ ID NO: 10, SEQ ID NO: 11, SEQ ID NO: 12, and SEQ ID NO: 13. Most preferably, the vaccine comprises a modified, live PRRS strain which is ND 99-14 or SD 11-21. The vaccine may further comprise an adjuvant. The vaccine may further comprise a pharmaceutically-acceptable excipient, stabilizer, solubilizer, or diluent. The vaccine may comprise a further antigen from a different virus or from a bacterial strain or from a parasite.

The present invention provides for a vaccine comprising a modified, live PRRS virus strain for use in the treatment or prevention of Porcine Reproductive and Respiratory Syndrome in a porcine animal. The present invention also provides for a vaccine comprising a modified, live PRRS virus strain for use in the treatment or prevention of a symptom caused by a PRRS virus infection in a porcine animal. A symptom may be, without limitation, reduced appetite, lethargy, fever, behavioral changes such as loss of balance, circling, and falling to one side, premature farrowing, abortion, stillbirths, edema, a failure to thrive, cough, respiratory distress, labored or rapid breathing, blotchy reddening of the skin, rough hair coats, lung lesions, viral shedding, and mortality. The present invention provides for a vaccine comprising a modified, live PRRS virus strain for use in therapy of a porcine animal. The present invention also provides for a vaccine comprising a modified, live PRRS virus strain for use in therapy of PRRS in a porcine animal. The infection may be from a wild-type virulent strain of a PRRS virus heterologous to the modified, live PRRS virus in the vaccine. Preferably, the vaccine comprises a modified, live PRRS strain having a consensus complementary DNA sequence that is at least 90%, at least 95%, or at least 98% identical to a sequence selected from the group of SEQ ID NO: 4, SEQ ID NO: 9, SEQ ID NO: 10, SEQ ID NO: 11, SEQ ID NO: 12, and SEQ ID NO: 13. Most preferably, the vaccine comprises a modified, live PRRS strain which is ND 99-14 or SD 11-21. The vaccine may further comprise an adjuvant. The vaccine may further comprise a pharmaceutically-acceptable excipient, stabilizer, solubilizer, or diluent. The vaccine may comprise a further antigen from a different virus or from a bacterial strain or from a parasite.

The present invention provides for a method of treating or preventing a symptom of Porcine Reproductive and Respiratory Syndrome in a porcine animal, comprising administering to said porcine animal an immunogenic composition comprising a modified, live PRRS virus strain. The present invention also provides for a method of treating or preventing Porcine Reproductive and Respiratory Syndrome in a porcine animal, comprising administering to said porcine animal an immunogenic composition comprising a modified, live PRRS virus strain. Preferably, the modified, live PRRS virus strain for use in the method would have a consensus complementary DNA sequence at least 90% identical to a sequence selected from the group of SEQ ID NO: 4, SEQ ID NO: 9, SEQ ID NO: 10, SEQ ID NO: 11, SEQ ID NO: 12, and SEQ ID NO: 13. More preferably, the modified, live PRRS virus strain for use in the method would have a consensus complementary DNA sequence that is at least 95% identical to a sequence selected from the group of SEQ ID NO: 4, SEQ ID NO: 9, SEQ ID NO: 10, SEQ ID NO: 11, SEQ ID NO: 12, and SEQ ID NO: 13. Most preferably, the modified, live PRRS virus strain for use in the method would have a consensus complementary DNA sequence that is at least 98% identical to a sequence selected from the group of SEQ ID NO: 4, SEQ ID NO: 9, SEQ ID NO: 10, SEQ ID NO: 11, SEQ ID NO: 12, and SEQ ID NO: 13. The immunogenic composition may further comprise a pharmaceutically-acceptable excipient, stabilizer, solubilizer, or diluent. The immunogenic composition may comprise a further antigen from a different virus or from a bacterium or from a parasite.

The present invention provides for a method of treating or preventing Porcine Reproductive and Respiratory Syndrome in a porcine animal, comprising administering to said porcine animal an immunogenic composition comprising a modified, live Porcine Reproductive and Respiratory Syndrome (PRRS) virus strain, wherein the said PRRS virus strain is ND 99-14 or SD 11-21. The ND 99-14 strain or the SD 11-21 strain for use in the method may be passaged at least 80 times, or preferably even 84 times, in tissue culture cells. Most preferably, the ND 99-14 strain or the SD 11-21 strain for use in the method is passaged 100 times in tissue culture cells. The immunogenic composition may further comprise a pharmaceutically-acceptable excipient, stabilizer, solubilizer, or diluent. The immunogenic composition may comprise a further antigen from a different virus or from a bacterial strain or from a parasite.

The present invention provides for a method of treating or preventing a symptom caused by a PRRS virus infection in a porcine animal, comprising administering to said porcine animal an immunogenic composition comprising a modified, live Porcine Reproductive and Respiratory Syndrome (PRRS) virus strain, wherein the consensus complementary DNA sequence of said PRRS strain is preferably at least 90% identical to a sequence selected from the group of SEQ ID NO: 4, SEQ ID NO: 9, SEQ ID NO: 10, SEQ ID NO: 11, SEQ ID NO: 12, and SEQ ID NO: 13. More preferably, the modified, live strain for use in the method could also have a consensus complementary DNA sequence that is at least 95% identical to a sequence selected from the group of SEQ ID NO: 4, SEQ ID NO: 9, SEQ ID NO: 10, SEQ ID NO: 11, SEQ ID NO: 12, and SEQ ID NO: 13. Most preferably, the modified, live strain for use in the method could also have a consensus complementary DNA sequence that is at least 98% identical to a sequence selected from the group of SEQ ID NO: 4, SEQ ID NO: 9, SEQ ID NO: 10, SEQ ID NO: 11, SEQ ID NO: 12, and SEQ ID NO: 13. The immunogenic composition may further comprise a pharmaceutically-acceptable excipient, stabilizer, solubilizer, or diluent. The immunogenic composition may also comprise a further antigen from a different virus or from a bacteria strain or from a parasite.

The present invention provides for a method of treating or treating a symptom caused by a PRRS virus infection in a porcine animal, comprising administering to said porcine animal an immunogenic composition comprising a modified, live Porcine Reproductive and Respiratory Syndrome (PRRS) virus strain, wherein the said PRRS virus strain is ND 99-14 or SD 11-21. The ND 99-14 strain or the SD 11-21 strain for use in the method may be passaged at least 80 times, or preferably even 84 times, in tissue culture cells. Most preferably, the ND 99-14 strain or the SD 11-21 strain for use in the method may be passaged 100 times in tissue culture cells. The immunogenic composition may further comprise a pharmaceutically-acceptable excipient, stabilizer, solubilizer, or diluent. The immunogenic composition may also comprise a further antigen from a different virus or from a bacteria strain or from a parasite. The PRRS virus infection may be an infection by a virulent PRRS virus heterologous to the modified, live PRRS virus strain in the immunogenic composition. Two PRRS virus strains are considered to be heterologous if a genomic consensus sequence of each virus strain maps to a different phylogenetic group. Two PRRS virus strains are considered to be heterologous if a complementary DNA consensus sequence of each virus strain maps to a different phylogenetic group.

The present invention provides for the use of a modified, live PRRS virus strain in the manufacture of a medicament for treating or preventing a symptom of PRRS, wherein the modified, live PRRS virus comprises a consensus complementary DNA sequence at least 90% identical to a sequence selected from the group of SEQ ID NO: 4, SEQ ID NO: 9, SEQ ID NO: 10, SEQ ID NO: 11, SEQ ID NO: 12, and SEQ ID NO: 13. Preferably, the modified, live strain could also have a consensus complementary DNA sequence that is at least 95% identical to a sequence selected from the group of SEQ ID NO: 4, SEQ ID NO: 9, SEQ ID NO: 10, SEQ ID NO: 11, SEQ ID NO: 12, and SEQ ID NO: 13. More preferably, the modified, live strain could also have a consensus complementary DNA sequence that is at least 98% identical to a sequence selected from the group of SEQ ID NO: 4, SEQ ID NO: 9, SEQ ID NO: 10, SEQ ID NO: 11, SEQ ID NO: 12, and SEQ ID NO: 13.

The present invention provides for the use of a modified, live PRRS virus strain comprising a ND 99-14 strain or a SD 11-21 strain in the manufacture of a medicament for treating or preventing a symptom of PRRS. The modified, live PRRS virus strain should be passaged at least 80 times, or preferably even 84 times, in tissue culture cells. Further, the PRRS virus strain should be passaged 100 times in tissue culture cells. Such passaging in tissue culture cells is useful in properly attenuating the modified, live PRRS virus strain. Attenuated PRRS virus strains may cause subclinical but not clinical disease when those strains are administered to porcine animals. Modified, live PRRS virus strains passaged at least 80 times have a low probability of reverting to wild-type virulence. Modified, live PRRS virus strains passaged 100 times have a low probability of reverting to wild-type virulence.

The present invention provides for the use of an immunogenic composition comprising a modified, live PRRS virus strain in the manufacture of a medicament for treating a PRRS virus infection, wherein the modified, live PRRS virus strain comprises a consensus complementary DNA sequence at least 90% identical to a sequence selected from the group of SEQ ID NO: 4, SEQ ID NO: 9, SEQ ID NO: 10, SEQ ID NO: 11, SEQ ID NO: 12, and SEQ ID NO: 13. The modified, live strain for such use could also have a consensus complementary DNA sequence that is at least 95% identical to a sequence selected from the group of SEQ ID NO: 4, SEQ ID NO: 9, SEQ ID NO: 10, SEQ ID NO: 11, SEQ ID NO: 12, and SEQ ID NO: 13. The modified, live strain for such use could also have a consensus complementary DNA sequence that is at least 98% identical to a sequence selected from the group of SEQ ID NO: 4, SEQ ID NO: 9, SEQ ID NO: 10, SEQ ID NO: 11, SEQ ID NO: 12, and SEQ ID NO: 13.

The present invention provides for the use of an immunogenic composition comprising a modified, live PRRS virus strain comprising a ND 99-14 strain or a SD 11-21 strain in the manufacture of a medicament for treating a PRRS virus infection. The PRRS virus strain should be passaged at least 80 times, or preferably even 84 times, in tissue culture cells. Further, the PRRS virus strain should be passaged 100 times in tissue culture cells. Such passaging in tissue culture cells is useful in properly attenuating the modified, live PRRS virus strain. Attenuated PRRS virus strains may cause subclinical but not clinical disease when those strains are administered to porcine animals. Modified, live PRRS virus strains passaged at least 80 times have a low probability of reverting to wild-type virulence. Modified, live PRRS virus strains passaged 100 times have a low probability of reverting to wild-type virulence.

The present invention provides for the use of an immunogenic composition comprising a modified, live PRRS virus strain in the manufacture of a medicament for protecting a porcine animal from a PRRS virus infection, wherein the modified, live PRRS virus strain comprises a consensus complementary DNA sequence at least 90% identical to a sequence selected from the group of SEQ ID NO: 4, SEQ ID NO: 9, SEQ ID NO: 10, SEQ ID NO: 11, SEQ ID NO: 12, and SEQ ID NO: 13. The modified, live strain for such use could also have a consensus complementary DNA sequence that is at least 95% identical to a sequence selected from the group of SEQ ID NO: 4, SEQ ID NO: 9, SEQ ID NO: 10, SEQ ID NO: 11, SEQ ID NO: 12, and SEQ ID NO: 13. The modified, live strain for such use could also have a consensus complementary DNA sequence that is at least 98% identical to a sequence selected from the group of SEQ ID NO: 4, SEQ ID NO: 9, SEQ ID NO: 10, SEQ ID NO: 11, SEQ ID NO: 12, and SEQ ID NO: 13.

The present invention provides for the use of an immunogenic composition comprising a modified, live PRRS virus strain comprising a ND 99-14 strain or a SD 11-21 strain in the manufacture of a medicament for protecting a porcine animal from a PRRS virus infection. The PRRS virus strain should be passaged at least 80 times, or preferably even 84 times, in tissue culture cells. Further, the PRRS virus strain should be passaged 100 times in tissue culture cells. Such passaging in tissue culture cells is useful in properly attenuating the modified, live PRRS virus strain. Attenuated PRRS virus strains may cause subclinical but not clinical disease when those strains are administered to porcine animals. Modified, live PRRS virus strains passaged at least 80 times have a low probability of reverting to wild-type virulence. Modified, live PRRS virus strains passaged 100 times have a low probability of reverting to wild-type virulence.

FIG. 1. Phylogenetic analysis of type 2 PRRSV ORF5 nucleotide sequences.

Figure 2:
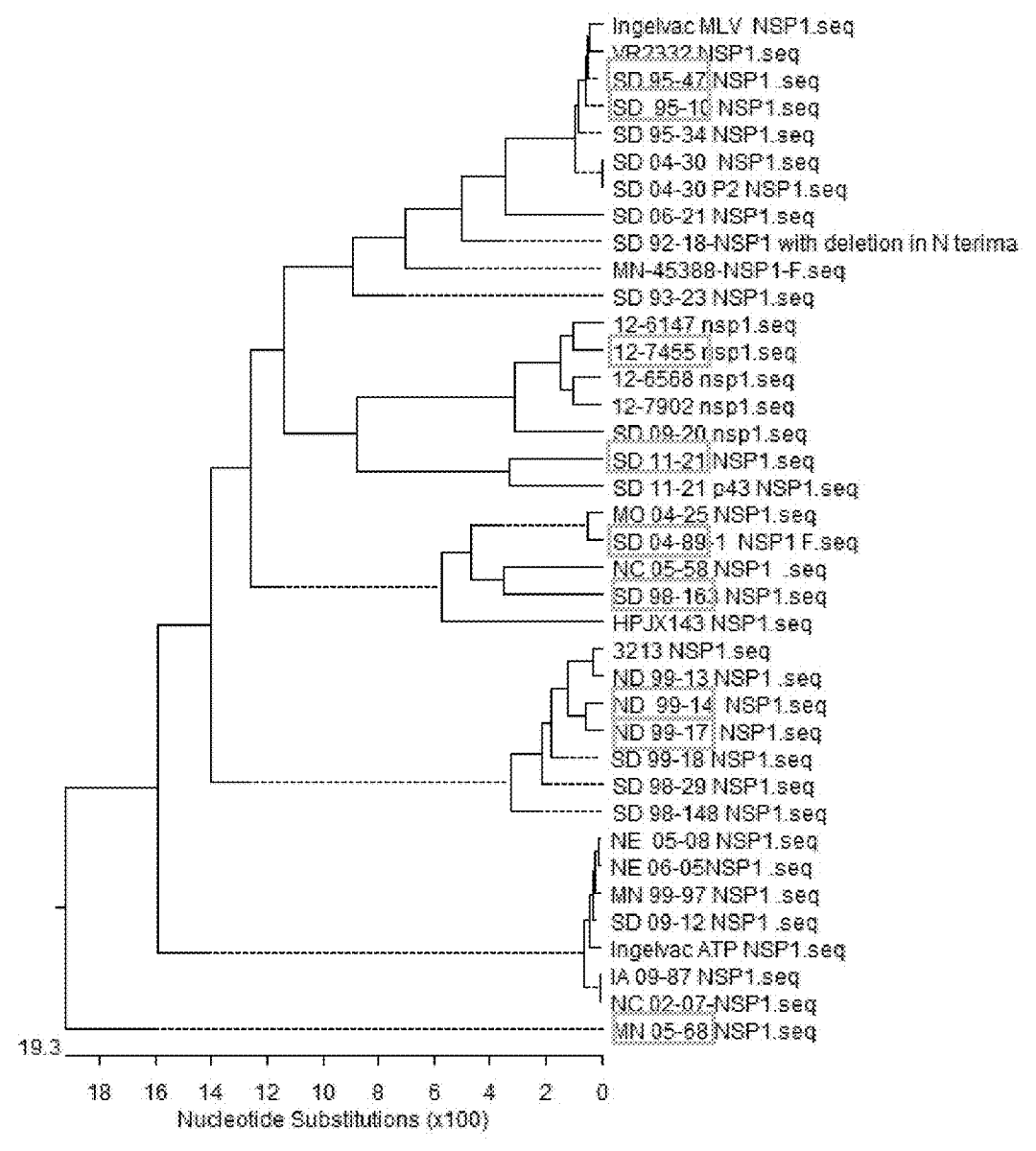

FIG. 2. Phylogenetic analysis of type 2 PRRSV nsp1 nucleotide sequences.

Figure 3:
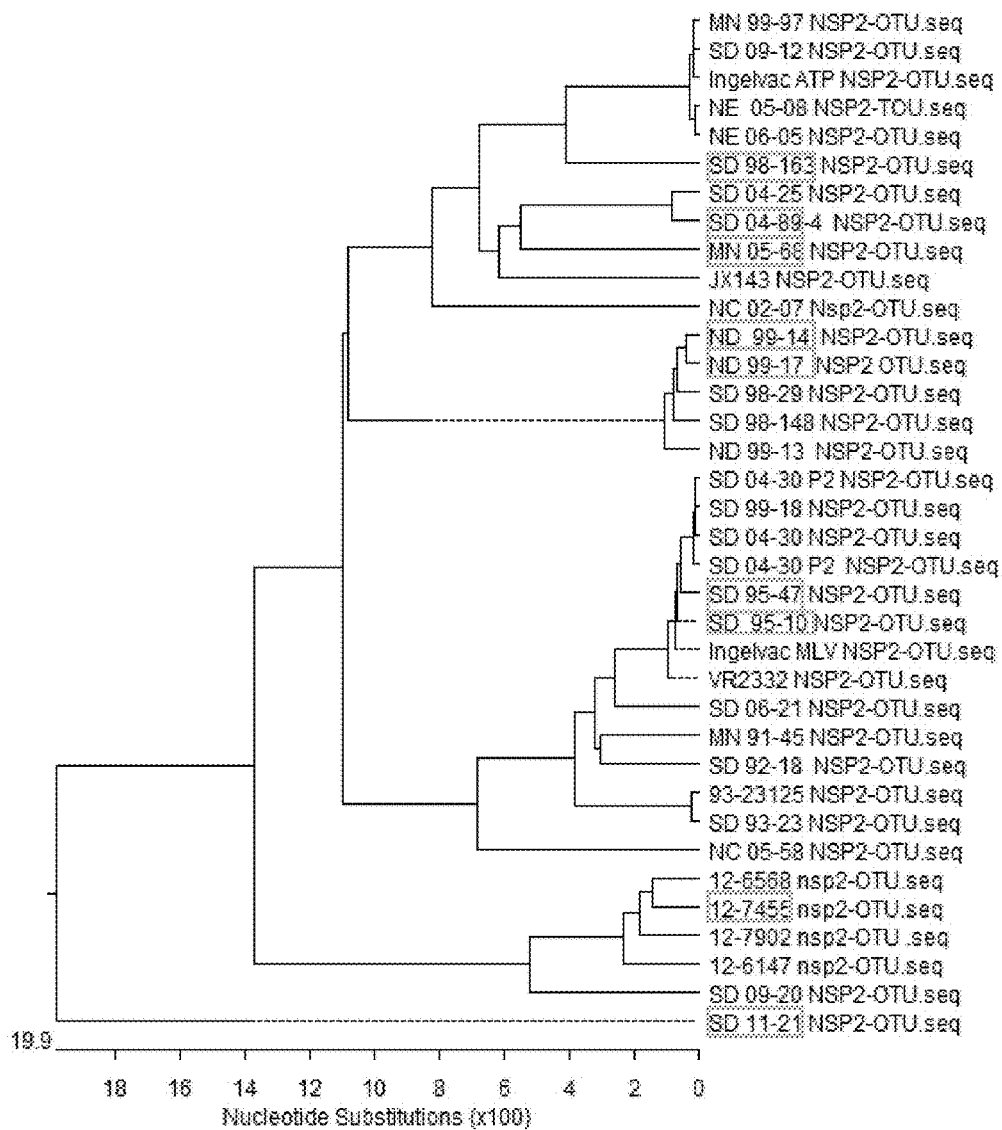

FIG. 3. Phylogenetic analysis of type 2 PRRSV nsp2 OTU domain nucleotide sequences.

Figure 4:
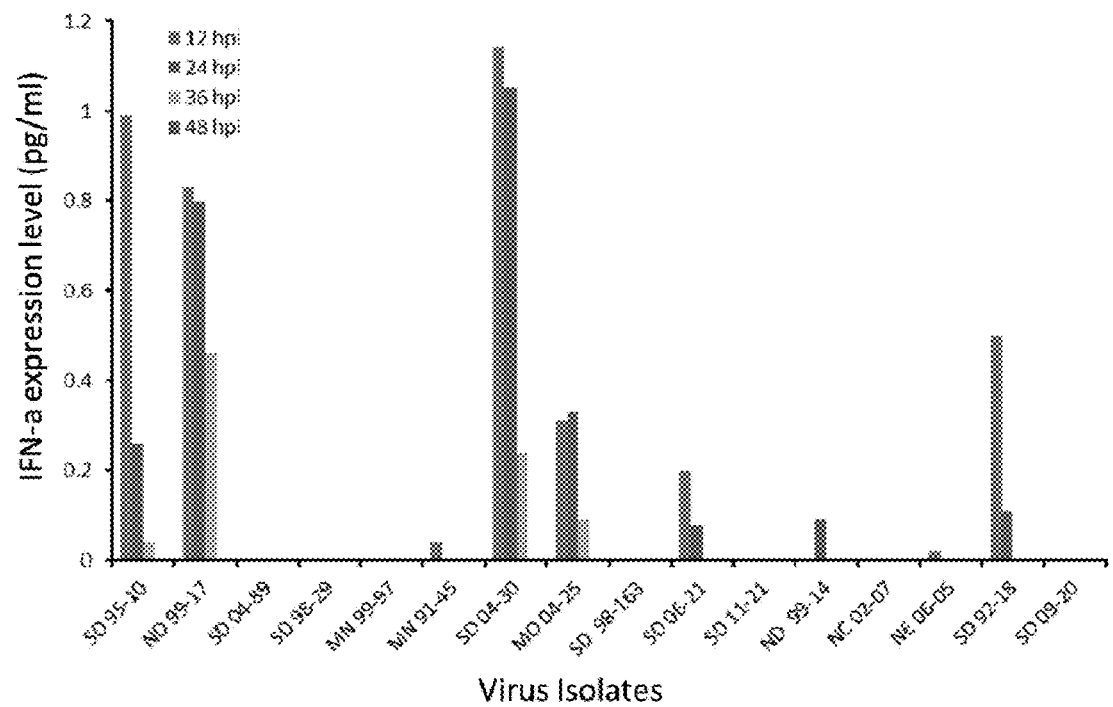

FIG. 4. Variation of different PRRSV field isolates on the stimulation of IFN-alpha (IFN-α) expression.

Figure 5:
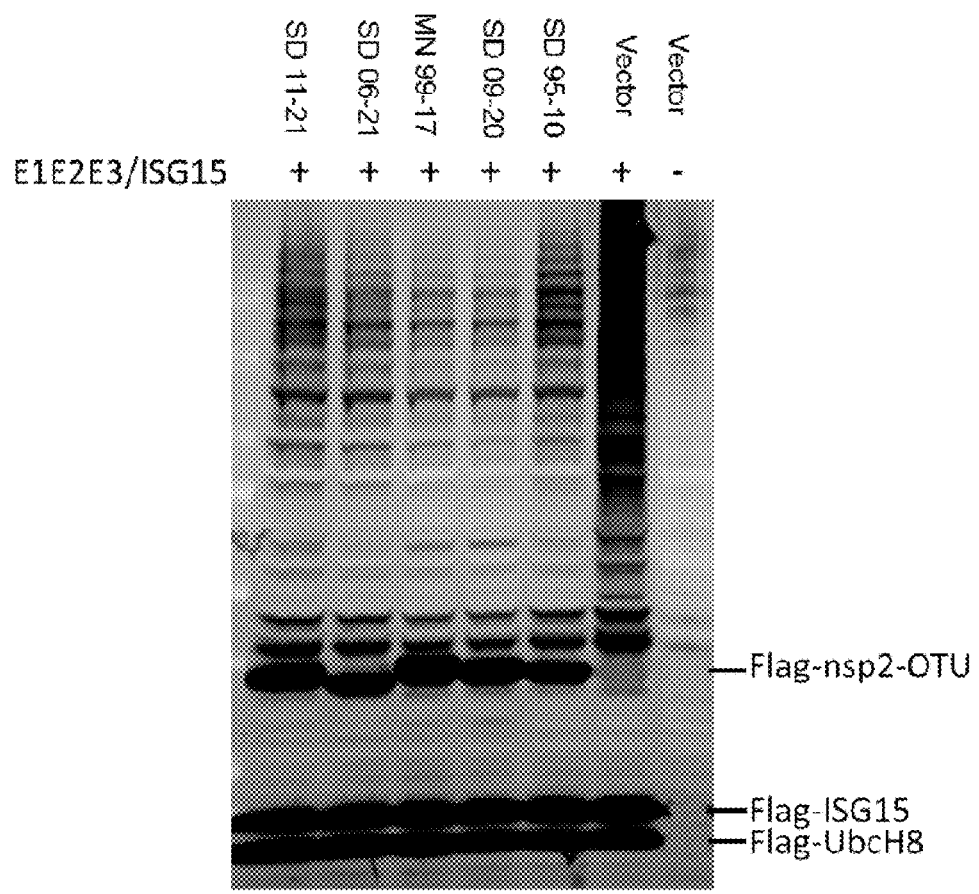

FIG. 5. DeISGylation assay with different field PRRSV isolates.

As used in the following discussion, the terms "a" or "an" should be understood to encompass one or more, unless otherwise specified.

As used herein, the term "virus" could mean either the species of virus, or, interchangeably, an individual infectious unit which may contain nucleic acids, proteins, and a lipid membrane. An individual infectious unit is also called a "viral particle" or a "virion", the latter terms being synonymous.

As used herein, a "strain" or "isolate" a virus means a collection of genetically homologous virions. Two viruses would be considered "homologous" if those viruses map to the same phylogenetic clade. Two viruses would be considered "heterologous" if those viruses map to different phylogenetic clades. As the PRRS virus has a high mutation rate, it will be appreciated that a single PRRS strain comprises individual virions with related but variable genetic sequences. Thus, subpopulations of strains exist within each PRRS strain, and the genetic sequence of a PRRS strain is a consensus sequence such that the genetic sequence of an individual member of the PRRS strain may not be identical to the consensus sequence for that strain. A "consensus" sequence is a nucleic acid sequence in which each nucleic acid residue at a given position is present in >50% of the polynucleotides in a PRRS virus strain or isolate.

"Percent identity" can be determined by calculating the number of identical nucleotides or amino acids at the same positions in a nucleic acid or protein. Calculation of percent identity includes determination of the optimal alignment between two or more sequences. Alignment can take into account insertions and deletions (i.e. "gaps") in each of the sequences to be tested, such as, without limitation, in the non-coding regions of nucleic acids and truncations or extensions of polypeptide sequences. Computer programs and algorithms such as the Basic Local Alignment Search Tool (BLAST) may be used to determine the percent identity. BLAST one of the many resources provided by the U.S. National Center for Biotechnology Information. Because the genetic code is degenerate, and more than one codon can encode a given amino acid, coding regions of nucleic acids are considered identical if the nucleic acids encode identical polypeptides. Thus, percent identity could also be calculated based on the polypeptide encoded by the nucleic acid. Percent identity could be calculated based on full length consensus genomic sequences or on a fraction of the genomic sequence, such as for example without limitation on individual open reading frames (ORFs).

As used herein, the term "modified, live virus" applies to any individual viral particle (i.e. a "virion") or to a multiplicity of viral particles whose genetic sequence has been altered from the genetic sequence of a naturally-occurring wild type virus. Alterations include, without limitation, genetic mutations such as insertions and deletions of nucleotides and transitions and transversions which change one nucleotide for another nucleotide. Alterations can be accomplished by adapting a wild-type virus to replication in a tissue culture system, and continuing to passage a virus in a tissue culture system, whereby the virus accumulates genetic mutations. Alterations can also be accomplished using molecular techniques. Attenuated viruses form a subset of modified, live viruses.

As used herein, the term "attenuated" or "attenuation" means the ability of virus to cause or exacerbate clinical disease has been reduced or eliminated. An attenuated virus can still infect a host cell, either in vitro or in vivo, and that infection may result in subclinical effects in the host organism, but that infection does not result in one or more clinical disease symptoms.

In contrast, as used herein, "inactivated" viruses mean viruses which can no longer replicate in a host cell. Inactivated viruses are considered to be killed or dead viruses. Inactivation can be accomplished by a variety of methods, including but not limited to chemical alteration of viral proteins, to chemical or physical alterations in the structure of a virion, or to chemical or physical alterations in viral nucleic acids.

An "antigen" is any molecule capable of being specifically detected by the immune system of an organism. Typically a viral antigen is a viral protein encoded by the viral genome or derived from products of the viral genome. The presence of viral antigens can be specifically detected by the surface antigen receptors of both host T lymphocytes and host B lymphocytes and by antibody molecules synthesized by host cells.

"Immunogenicity" refers to the ability of an antigen to elicit an immune response, said immune response comprising both antigen-specific responses and non-antigen-specific responses or innate immune responses. "Protective immunity" is an immune response which can reduce or prevent clinical symptoms when an immunized animal is challenged or exposed to a pathogenic virus strain. As one skilled in the art would appreciate, protective immunity may decline with time or increased age of the immunized animal. Protective immunity as used herein should be effective for at least four months, but preferably at least six months, from the latest date of immunization. Protective immunity may be elicited with a single dose of a vaccine. A second or further dose may be used to increase or prolong the protective immune response. For example, increasing the protective immune response in a breeding sow may result in an increased level of maternally derived antibody in piglets.

In contrast to an antigen, an "adjuvant" is a non-specific stimulator of an immune response. An adjuvant could stimulate the innate immune response by binding and activating a pattern recognition receptor (PRR). Such stimulators of PRRs could be, for example, viral or bacterial nucleic acids, lipids from bacteria or parasites, or bacterial proteins or toxins, or any artificially-constructed mimic of such molecules. Adjuvants also include, without limitation: inorganic compounds that aggregate antigens to facilitate recognition by B lymphocytes or uptake by phagocytes, such as alum, aluminum hydroxide, aluminum phosphate, calcium phosphate hydroxide or ammonium sulfate; oils; and detergents. Adjuvants could also be host mediators of immune signaling, such as, without limitation, cytokines, lymphokines, chemokines, interferons, anaphylatoxins, growth factors, differentiation factors, and adhesion molecules.

As used herein, an "immunogenic composition" is a composition that elicits an immune response when administered to an animal. An immunogenic composition comprises at least one antigen and at least one pharmaceutically-acceptable excipient, stabilizer, solubilizer, or diluent. A description of pharmaceutically-acceptable excipients, stabilizers, solubilizers, or diluents can be found, for example, in "Remington: The Science and Practice of Pharmacy," Lloyd V. Allen, ed., Pharmaceutical Press, London, UK, $22^{nd}$ edition, 2012. The antigen can be a whole virus, bacterium, or other pathogen, either live or inactivated. The antigen can also be isolated, purified, or partially purified antigenic molecule from a virus, bacterium, or other pathogen. The antigen can be a polypeptide, a polysaccharide, a nucleic acid, or a lipid.

As used herein, a "vaccine" is an immunogenic composition which confers protection from, resistance to, prevention of, or treatment for a disease symptom when administered to an animal, wherein said symptom is caused by a pathogenic organism, for example a virus. A PRRS vaccine may include, without limitation, viral antigens or intact virions, either live or inactivated, in composition with pharmaceutically-acceptable adjuvants, excipients, stabilizers, solubilizers, or diluents.

As used herein, the terms "treating", "to treat", or "treatment", include without limitation restraining, slowing, stopping, reducing, ameliorating, or reversing the progression or severity of an existing symptom, disorder, condition, or disease. A treatment may be applied or administered therapeutically.

As used herein, the terms "preventing", "to prevent", or "prevention", include without limitation decreasing, reducing, or ameliorating the risk of a symptom, disorder, condition, or disease, and protecting an animal from a symptom, disorder, condition, or disease. A prevention may be applied or administered prophylactically.

As used herein, "administering to an animal" includes but is not limited to cutaneous, subcutaneous, intramuscular, mucosal, submucosal, transdermal, oral or intranasal administration. Administration could include injection or topical administration.

The following experimental examples are illustrative of modified, live PRRS viruses. The following experimental examples are also illustrative of immunogenic compositions comprising modified, live PRRS viruses. The following experimental examples are also illustrative of using modified, live PRRS viruses to treat porcine animals for symptoms of PRRS. It will be appreciated that other embodiments and uses will be apparent to those skilled in the art and that the invention is not limited to these specific illustrative examples or preferred embodiments.

EXAMPLE 1

We intend to develop a broadly protective MLV vaccine for PRRS. Unique regions in vaccine viruses are identified for genetic marker and differential diagnostic test development. Specific objectives are: 1) to establish the candidate PRRS vaccine strains; 2) to identify the unique marker region in candidate vaccine virus and develop differential diagnostic reagents and tests for differentiation of the vaccinated animals from wild-type virus infected animals; and 3) to perform in vivo evaluation of the safety and efficacy of candidate vaccines and assess the differential ability of companion diagnostic assays.

We have generated nine candidate vaccine viruses. Detailed characterization of these candidate viruses is presented below.

Virus is initially isolated by growth in porcine alveolar macrophages, obtained from the lungs of conventionally raised 3- to 9-week-old pigs. The lungs are excised and washed three or four times with phosphate-buffered saline, pH 7.2. Cells are centrifuged for 10 min at 800×g at 4° C. Supernatant fluid is decanted, and cells are washed in phosphate-buffered saline and re-pelleted two times. Cells are resuspended in RPMI 1640 medium supplemented with 10% irradiated fetal bovine serum and appropriate levels of antibiotics. Macrophages are seeded at $10^6$ cells/ml to 24-well plates and allowed to adhere for 7 h. Non-adherent cells are decanted, and wells are refilled with 10% fetal bovine serum and RPMI medium. Field swine serum samples confirmed to be PRRSV positive by RT-PCR are used to inoculate the macrophages at 72 h post culture of the macrophages. At 48 h post inoculation, infection is confirmed by a direct fluorescent antibody test using monoclonal antibody (mAb) against the PRRSV nucleocapsid protein.

Each virus isolate is then plaque-purified. Confluent cell monolayers are infected with viruses at a multiplicity of infection (MOI) of 0.1. After 2 h, cell culture supernatant is removed and an agar overlay is applied. Plaques are detected after 5 days at 37° C. At least 10 single plagues from each virus isolate are picked and expanded in cultured cells.

Subsequent passage of the virus is performed by infecting cells with plaque-purified viruses at an MOI of 0.1. After 3 days, the culture supernatant is layered onto a 0.5 M sucrose cushion and centrifuged at 100,000×g for 14 h. Virus pellets are washed with PBS and could be stored at −80° C.

To determine the genomic sequence of each virus isolate, RNA is extracted from the sucrose cushion purified viruses using a QiaAmp viral RNA kit (Qiagen). The full-length genome sequences are determined using next generation sequencing at the Purdue University Genomic Core Facility.

The nucleotide sequences are aligned using the CLUSTAL W multiple sequence alignment program. The neighbor-joining distance analysis is performed on the resulting distance matrix using the Molecular Evolutionary Genetics Analysis (MEGA4) software available from the Center for Evolutionary Medicine and Informatics (Tempe, Ariz., USA). The bootstrap option is carried out with NJBOOT from 5000 replicates to assess the robustness of interior branches of the phylogenetic tree.

A total of 32 PRRSV field isolates have been evaluated for their potential as vaccine candidates. Initially, three of the most hyper-variable regions of the virus (nsp1, nsp2 and ORF5) have been sequenced for phylogenetic analysis. FIGS. 1-3 show the result of phylogeny trees constructed by neighbor-joint method based on the sequences of nsp1, nsp2 ovarian tumor (OTU) domain, or ORF5. Nine isolates (highlighted in boxes) representing each major cluster in the phylogenetic tree have been selected for further characterization. In all three phylogeny trees, isolates ND99-14 and ND99-17 locate in a separate clade from clades containing current commercial PRRSV vaccine strains. These two viruses also have ability to stimulate interferon (IFN)-α production (see FIG. 4). Isolates SD95-10 and SD95-47 are grouped in a same clade as the VR2332 and INGELVAC® PRRS MLV strains which was derived from VR2332. Isolates 12-7455 and SD11-21 represent a clade of more recent field stains. In nsp1 and nsp2 OTU domain phylogeny trees, SD04-89 and SD98-163 are grouped in a clade with the Chinese highly pathogenic stain JX143 and INGELVAC® PRRS ATP strain, which was derived from the JA142 strain. In ORF5 and nsp2 OTU domain phylogeny trees, MN05-68 is grouped in a clade with the JX143 and INGELVAC® PRRS ATP strains.

One of the criteria for vaccine development is that the candidate virus should have the ability to stimulate the host immune responses. Previous studies have shown that PRRSV suppresses the host cellular innate immune response and nsp2 is one of the innate antagonists to suppress the expression of interferon (IFN) and interferon stimulated genes (ISGs). To assess whether virus strains can induce interferon alpha (IFN-α), swine macrophages are either infected with different field isolates at an MOI of 1, or were mock infected. At 24 hour post infection, cell-culture supernatant was harvested for the quantification of IFN-α expression using fluorescent microsphere immunoassay as described previously (Lawson et al., *Vaccine* 28: 5356-64 (2010)). The quantity of IFN-α was determined using mean fluorescent intensity values, and the result was compared with the mean values from mock-infected control cells.

The in vitro delSGylation assay has been performed to select viruses that have weak ability to suppress the ISG expression. The delSGylation assay is conducted as described previously (Sun et al., *J. Virology* 86(7): 3839-50 (2012)). Briefly, HeLa cells are co-transfected with plasmid DNA expressing conjugation enzymes E1/E2/E3, FLAG-tagged ISG15 and PRRSV PLP2 (aa386-578). The empty vector plasmid is included as a control. At 6 h post-transfection, cells are stimulated with 1,000 U/ml of IFN-α. Cells are harvested at 24 h post-stimulation and analyzed by immunoblotting. The membrane is probed with anti-FLAG antibody to detect the expression of free and conjugated forms of ISG15. The expression of PRRSV PLP2 is detected using an nsp2-specific monoclonal antibody. As shown in FIG. 5, isolates SD95-10 and SD11-21 have less effect on the ISGylation of cellular proteins, suggesting these two isolates would have potential being used for future vaccine development. We further tested the ability of viruses to stimulate IFN-α expression. The SD04-30 and M004-25 were documented previously to be able to enhance IFN-α production. Using these two isolates as controls, IFN-α expression levels are measured in PRRSV-infected swine alveolar macrophages. As we expected, the SD04-30 and M004-25 stimulate significant amount of IFN-α expression (FIG. 4). In contrast, isolates SD95-21, ND99-17, SD06-21 and SD92-18 stimulate a level of IFN-α compatible to that of SD04-30 and M004-25. The isolates MN91-45, ND99-14 and NE06-05 show weak stimulation of IFN-α expression.

Based on the immune assay result and phylogeny analysis, nine Type 2 isolates are initially selected for continued passage in cultured non-swine cells for 80 passages. In addition to these nine type 2 viruses, SD03-15 (type 1 strain), SD02-11 (type 1 strain) and SD02-10 (mix of type 1 and type 2 viruses) are also included in further analysis. A total of nine passage-80 (P80) viruses are selected for plaque purification two times in cell culture, and passage-82 (P82) viruses are further purified through sucrose cushion and stored as virus stock. The virus titers are determined during the passage of each candidate vaccine virus, which were ranged between 4.5-7 logs of fluorescent focus unit (FFU)/ml. Virus isolates with titer lower than 5 logs of FFU/ml are excluded from further study. Full-length genome sequences for eleven candidate virus isolates were initially determined on Feb. 11, 2013, and the final products of nine candidate vaccine viruses (P83) purified by plaque purification and sucrose cushion were sequenced again and documented on Dec. 22, 2013.

The cDNA consensus sequences for nine PRRS virus isolates at passage 83 (P83) were deposited in GenBank genetic sequence database, an annotated collection of all publicly available nucleic acid sequences. The GenBank database is maintained by the National Center for Biotechnology Information (NCBI), part of the United States National Institutes of Health (NIH). GenBank is part of the International Nucleotide Sequence Database Collaboration.

The cDNA consensus sequence of PRRS strain SD 95-10 at P83 has been assigned GenBank Accession number KU131565 (SEQ. ID. NO:1). The cDNA consensus sequence designated SEQ. ID. NO:1 is:

```
  1  ATGACGTATA GGTGTTGGCT CTATGCCATG ACATTTGTAT AGTCAGGAGC TGCGACCATT
 61  GGTACAGCCC AAAACTTGCT GCACGGAAAC GCCCTTCCGT GACAGCCCTC TTCAGGGGAG
121  TTTAGGGGTC TATCCCTAGC ACCTTGCTTC CGGAGTTGCA CTGCTTTACG GTCTCTCCAA
181  CCCTTTAACC ATGTCTGGGA TACTTGATCG GTGCACGTGT ACCCCCAATG CCAGGGTGTT
241  CATGGCGGAG GGCCAAGTCT ACTGCACACG ATGTCTCAGT GCACGGTCTC TCCTTCCTCT
301  GAATCTCCAA GTTCCCGAGC TTGGAGTGCT GGGCCTATTT TACAGGCCCG AAGAGCCGCT
361  CCGGTGGACG TTGCCACGTG CATTCCCCAC TGTCGAGTGC TCCCCCGCCG GGGCTTGCTG
421  GCTTTCTGCG ATCTTCCCAA TTGCACGAAT GACCAGTGGA AACCTGAACT TCAACAAAG
481  AATGGTGCGG GTCGCTGCCG AGATTTACAG AGCCGGCCAG CTCACCCCTG CAGTCTTGAA
541  GGCTCTACAA GTTTATGAAC GGGGTTGCCG CTGGTACCCC ATTGTCGGAC CTGTCCCTGG
601  AGTGGCCGTT TTCGCCAACT CCCTACATGT GAGTGACAAA CCTTTTCCGG GAGCAACTCA
661  TGTGTTAACC AATCTACCGC TCCCGCAGAG GCCCAAGCCT GAAGACTTTT GCCCTTTTGA
721  GTGTGCTATG GCTGACATCT ATGACATCGG TCATGACGCC GTCATGTATG TGGCCGGAGA
```

-continued

```
 781 GAAAGTCTCC TGGGCCCCTC GTGGCGGGGA TGAAGTGAAA TTTGAAAATG TTCCCAAGGA
 841 GTTGAAGTTG ATTGCGAACC GACTCCACAT CTCCTTCCCG CCCCACCACG TAGTGGACAT
 901 GTCCAAGTTT ACCTTCATAG CCCCCGGGAG TGGTGTCTCC ATGCGGGTTG AGTGCCAACA
 961 CGGCTGCCTC CCCGCTGATA CTGTTCCTGA AGGAAACTGC TGGTGGCGCT TGTTCGACTC
1021 GCTCCCGCCG GAAGTCCAGC ACAAAGAAAT TCGCTATGCT AACCAATTTG GTTATCAAAC
1081 CAAGCATGGT GTCTCTGGCA AGTACCTACA GCGGAGGCTG CAAGTTAACG GTCTCCGAGC
1141 AGTGACCGAC GTACATGGAC CTATCGTCAT ACAGTACTTC TCTGTTAAGG AGAGTTGGAT
1201 CCGCCACTTC AGGCTGGCGG AAGAACCTAG CCTCCCTGGG TTCGAAGACC TCCTCAGAAT
1261 TAGGGTTGAG CCCAATACAT CACCACTGGC TGGCGAGGAT GGGAAGATCT TCCGGTTTGG
1321 CAGTCACAAG TGGTACGGTG CTGGAAGGAG AGCAAGGAAA GCACGTTCTG GTGCGACCAC
1381 CATGGTCGCT CATCGCGCTT TGTCCGCTCG TGAAACCCAG CAGGCAAAGA AGGACGAGGG
1441 TGCCGACGCT AACAAGGCTG AGCATCTCAA GCACTACTCT CCGCCCGCCG AAGGGAACTG
1501 TGGTTGGCAC TGTATTTCCG CCATCGCCAA CCGGATGATA AATTCCAAAT TTGAAACTAC
1561 CCTTCCCGAA AGAGTAAGGC CTCTGGATGA CTGGGCTACT GACGAGGATC TTGTGAATAC
1621 CATCCAAATC CTCAGGCTCC CCGCGGCCTT GGATAGGAAC GGTGCTTGTA GTAGCGCCAA
1681 GTACGTGCTT AAGCTGGAAG GTGTGCATTG GACTGTCTCT GTGACCCCTG GATGTCCCC
1741 TTCCTTGCTC CCCCTTGAAT GTGTTCAGGG CTGTTGCGAG CATAAGGGCG GTTTTGGCTC
1801 CCCAGATGCG GTCGAAGTTT CCGGATTTGA CCCTGCCTGC CTTGACCGAC TGGCTGAGGT
1861 AATGCACTTG CCTAGCAGTG CCATCCCAGC CGCTCTGGCC GAAATGTCCG GCGACTCCAA
1921 TCGTCCGGCT TCCCCGGTCA ACACTGTGTG GACTGTTTCG CAATTCTATG CCCGTCATAC
1981 AGGAGGAAAT CATCCTGACC AGGTGTGCTT AGAGCAGATC ATTAATCTCT GTCAGGTTAT
2041 TGAGGTTTGT TGCTGCCATC AAAACAAAAC CAACCGGGCC ACCCCGGAAG AGGTCGCGGC
2101 AAAGATTGAT CAGTACCTCC GTGGTGCAAC AAATCTTGAA GAATGCTTGA CCAGGCTTGA
2161 GAGGGTTTGC CCGCCGAGCG CTGCGGACAC CTCCTTTGAT TGGAATGTTG TGCTCCCTGG
2221 GGTTGAGGCT GCAACTCAGA CAACCAAACA GCCCCACGTC AACCAGTGCT GCGCTCTGGT
2281 TCCTGTCGTG ACTCAAGAGC CTTTGGACAA AGACTCGGTC CCTCTGACCG CCTTCTCGCT
2341 GTCCAATTGC TACTACCCTG CACAAGGTGA AGAGGTTCGT CACCGTGAGA GACTAAACTC
2401 CGTACTCTCG AAGTTGGAGG GGGCTGTTCG TGAGGAATAT GGGCTCACGC CAACTGAACC
2461 TGGCCTGCAA CCCGCACTAC CGAACGGGCT CGACGAACTT AAAGACCGGA TGGAGGAGGA
2521 TCTGCTGAAA CTAGTCAACG CTCAGGCAAC TTCAGAAATG ATGGCCTGGG CAGCCGAGCA
2581 GATTGATTTA AAAGCTTGGG TCAAAAACTA CCCACGGTGG ACACCGCCAC CCCCTCCACC
2641 AAGAGCTCAG CCTCGGAAAA CGAAGTCTGT TAAGAGCTTG CCAGGGAACA AGCCTATCCC
2701 TGCTCCACGC AGGAAGGTCA GATCTGATTT GACTGTTAAT GGCCCCCTTG ATCTTTCGAC
2761 ACCATCCGAG CCGATGACAC CCCTGAGTGA GCCTGCACTT ATGCCCGCGT TGCAACATAT
2821 TTCTAGGCCA GTGACATCTT TGAGTGAGCC GGTCCCAGTT CCTGCACCGC GTAGAGCTGT
2881 GTCCCGACCG GTGACGCCCT TGAGTGGGCC AACTTTTGAG TTTGCGCCGC GACACAAATT
2941 TCAGCAGGTG GGAGAAGTGA ATCGGCGGC AACAACGCTG ACGCACCAGG ACGAACCTCT
3001 AGATTTGTCT GCATCCTCAC AGACTGAATA TGAGGCTTCT CCCCTAGTAC CACCGCAGAA
3061 CATGGGTATC CTGGGGGTGG GGGGGCAAGA GGCTGAAGAA GTTCTGAGTG AAATCTCGGA
3121 TATACTGAGT GACATTAACC CTGCACCTGT GTCATTAAGC AGCTCCCTGT CAAGTGTTAA
```

-continued

```
3181 GATCACACGC CCAAAATACT CAGCTCAAGC CATCATTGAC TCGGGCGGGC CCTGCAGTGG

3241 GCATCTCCGA AGGGAAAAAG AAGCATGCCT CAGCGTCATG CGTGAGGCTT GTGATGCGGC

3301 TAAACTTAGC GACCCTGCCA CGCAGGAATG CTTTCTCGC ATGTGGGATA GGGTTGACAT

3361 GCTGACCTGG CGCAATAAGT CTGCTTACCA GGCGTTTCGC ATCTTGGATG CAGGTTTGA

3421 GTTTCTCCCA AAGATGATAC TCGAGACACC GCCGCCCTAT CCGTGTGGGT TTGTGATGCT

3481 GCCTCACACG CCTGCACCTT CCGTGAGTGC AGAGAGTGAC CTTACCATTG GTTCAGTCGC

3541 CACTGAAGAT GTTCCACGCA TCCTCGGGAA AATAGAAAAC GCCGGCGAGG TGCCCAACCA

3601 GGGGCTCTCG GCATCCTCCG GGGAAGAACC GATGTATGAC CAACCTGCCA AAGACTCCCG

3661 GATGTCGTCG CGGGGGTTTG ACGAGAGCAT AACGGCTCCG TCCGTAGGTA CAGGTGGCGC

3721 TGACTTACTC ACTGATTTGC CACCTTCAGG TGGTGTGGAT GTGGACGGGG GGGGGCCGTT

3781 ACGGACGGTA AGAAAGAAAA TTGAAAGGCT CTTCGACCAA TTTAGCCGTC AGGTTTTTAA

3841 CCTCGTCTCC CATCTCCCTG TTTTCTTCTC ACACCTCTTC AAACCTGACA GTGGTTATTC

3901 TCCGGGTGAT TGGGGTTTTG CAGCTTCAC TCTACTTTGC CTCTTTTTGT GTTATAGCTA

3961 CCCATTCTTT GGCTTCGCTC CCCTCTTGGG TGTATTTTCT GGGTCTTCTC GGAGGGTGCG

4021 CATGGGGGTT TTTGGCTGCT GGTTGGCTTT TGCTGTTGGC CTGTTCAAGC CTGTGTCCGA

4081 CCCAGTCGGC ACTGCTTGTG AATTTGACTC GCCAGAGTGT AGGAACGTCC TTCATTCTTT

4141 TGAGCTTCTC AAACCTTGGG ACCCTGTTCG CAGCCTTGTT GTGGGCCCCG CAGGTCTCGG

4201 TCTTGCCATT CTTGGCAGGT TACTGGGCGG GGCACGCTAC ATCTGGCATT TTTTGCTTAG

4261 GCTTGGCATT GTTGCAGATT GTGTCTTGGC TGGAGCTTAT GTGCTTTCTC AAGGTAGGTG

4321 TAAAAAGTGC TGGGGATCTT GTATAAGAAC TGCTCCTAAT GAAATCGCCT TCAACGTGTT

4381 CCCTTTCACG CGTGCGACCA GGTCGTCACT CATCGACCTG TGCGACCGGT TTCGTGCGCC

4441 AAAAGGCATG GACCCTGTTT TCCTCGCTAC TGGGTGGCGC GGGTGCTGGA CCGGTCAAAG

4501 TCCCATTGAG CAACCCTCTG AAAAACCCAT CGCGTTCGCC CAGTTGGATG AAAAGAGGAT

4561 CACGGCTAGA ACTGTGGTCG CTCAGCCTTA TGATCCTAAC CAAGCCGTAA AGTGCTTGCG

4621 GGTGCTACAG GCGGGTGGGG CGATGGTGGC CGAGGCAGTC CCAAAAGTGG TCAAGGTTTC

4681 CGCTATTCCA TTCCGAGCCC CCTTTTTTCC CACCGGAGTG AAGGTTGATC CTGAGTGCAG

4741 GATCGTGGTC GACCCCGACA CTTTTACTAC AGCTCTCCGG TCTGGTTACT CCACCACAAA

4801 CCTCGTCCTT GGTGTGGGGG ACTTTGCCCA ATTGAATGGA TTGAAAATCA GGCAAATTTC

4861 CAAGCCTTCG GGAGGAGGCC CACACCTCAT TGCTGCCCTG CATGTTGCGT GCTCTATGGC

4921 GTTGCACATG CTTGCTGGGG TTTATGTAAC TGCAGTGGGG TCTTGCGGTA CCGGCACCAA

4981 CGATCCGTGG TGCACTAACC CATTCGCCGT CCCTGGCTAC GGACCTGGCT CTCTCTGCAC

5041 GTCCAGATTG TGCATCTCCC AACATGGCCT CACCCTGCCC TTGACAGCAC TTGTGGCAGG

5101 ATTCGGTCTT CAGGAAATTG CCTTAGTCGT TTTGATTTTC GTTTCCATCG GAGGCATGGC

5161 TCATAGGTTG AGTTGTAAGG CTGACATGCT GTGCATCTTA CTTGCAATCG CCAGCTATGT

5221 TTGGGTACCC CTTACCTGGT TGCTCTGTGT GTTTCCTTGC TGGTTGCGCT GGTTCACTTT

5281 GCACCCTCTC ACCATCCTAT GGTTGGTGTT TTTCCTGATT TCTGTAAATA TGCCTTCGGG

5341 AATCTTGGCC ATGGTGTTAT TGGTTGCTCT TTGGCTTTTA GGCCGTTATA CTAATGTTGT

5401 TGGTCTTGTT ACCCCCTATG ATATTCACCA TTACACCAGT GGCCCCCGCG TGTAGCCGC

5461 CTTGGCCACC GCACCAGATG GGACTTACTT GGCCGCTGTC CGCCGCGCTG CGTTGACTGG

5521 CCGCACCGTG CTGTTTACCC CGTCTCAGCT TGGGTCCCTT CTTGAGGGCG CTTTCAGGAC

5581 TCGAAAGCCC TCATTGAACA CCGTCAATGT GGTCGGGTCC TCCATGGGCT CTGGCGGAGT
```

```
5641  GTTCACTATC GACGGGAAAA TCAAGTGCGT GACTGCCGCA CATGTCCTTA CGGGTAATTC

5701  AGCCAGGGTT TCCGGGGTCG GCTTCAATCA AATGCTTGAC TTTAATGTAA AGGGGGACTT

5761  CGCCATAGCT GATTGCCCGA ATTGGCAAGG GGCTGCTCCC AAGACCCAAT TCTGCGAGGA

5821  TGGATGGACT GGTCGTGCCT ATTGGCTGAC ATCCTCTGGT GTCGAACCCG GTATCATTGG

5881  GAATGGATTT GCCTTCTGCT TCACCGCGTG CGGCGATTCT GGATCCCCAG TGATTACCGA

5941  AGCCGGTGAG CTTGTCGGCG TTCACACAGG ATCGAACAAA CAAGGAGGAG GCATTGTCAC

6001  GCGCCCCTCG GGCCAGTTTT GTAATGTGGC GCCCATCAAG CTGAGCGAAT TGAGTGAATT

6061  CTTCGCTGGA CCTAAGGTCC CGCTCGGTGA TGTGAAGGTT GGCAGCCACA TAATTAAAGA

6121  CATATGCGAG GTACCTTCAG ACCTTTGCGC CTTGCTTGCT GCCAAACCCG AACTGGAAGG

6181  AGGCCTCTCT ACCGTCCAAC TTCTGTGTGT GTTTTTCCTC CTGTGGAGAA TGATGGGCA

6241  TGCCTGGACG CCCTTGGTTG CTGTGGGGTT TTTTATCTTG AATGAGGTCC TCCCAGCTGT

6301  CCTGGTCCGG AGTGTTTTCT CCTTTGGAAT GTTTGTGCTA TCTTGGCTCA CGCCATGGTC

6361  TGCGCAAGTT CTGATGATCA GGCTTCTAAC AGCAGCTCTT AACAGGAACA GATTTTCACT

6421  CGCCTTTTAC AGCCTTGGTG CAGCGACCGG TTTTGTCGCA GATCTGGCGA CAACTCAAGG

6481  GCATCCGTTG CAGGCAGTAA TGAATTTAAG TACCTATGCC TTCCTGCCTC GGATGATGGT

6541  TGTGACATCA CCAGTCCCAG TGATTGCGTG TGGTGTTGTG CACCTCCTTG CCATAATTTT

6601  GTACTTGTTC AAGTACCGTT GCCTGCACAA TGTCCTTGTT GGCGACGGAG CGTTCTCTGC

6661  GGCTTTTTTC TTGCGATACT TTGCCGAGGG AAAGTTGAGA GAAGGGGTGT CGCAGTCCTG

6721  CGGGATGAAT CACGAGTCAC TGACTGGAGC CCTCGCTATG AGACTCAATG ACGAGGACTT

6781  GGACTTCCTT ACGAAATGGA CTGATTTTAA GTGCTTTGTT TCTGCTTCCA ATATGAGGAA

6841  TGCAGCGGGC CAATTCATCG AGGCAGCCTA TGCTAAAGCA CTTAGAATAG AACTTGCCCA

6901  GTTGGTGCAG GTCGACAAGG TTCGAGGTGT TTTGGCCAAA CTTGAAGCTT TTGCTGATAC

6961  TGTGGCACCC CAACTCTCGC CCGGTGACAT TGTCGTTGCT CTTGGCCATA CGCCTGTTGG

7021  TAGTATCTTC GACCTAAAGG TTGGTAGCAC CAAGCATACT CTCCAAGCCA TTGAGACCAG

7081  AGTCCTTGCC GGGTCCAAGA TGACCGTGGC GCGCGTCGTT GACCCAACCC CCACGCCCCC

7141  ACCCGCACCC GTGCCTATCC CCCTCCCGCC AAAAATTCTG GAGAATGGTC CCAACGCCTG

7201  GGGGGATGAG GACCGTTTGA ATAAGAAGAA GAGGCGCAGG ATGGAAGCCG TTGGCATCTT

7261  TGTTATGGGC GGGAAGAAGT ACCAGAAATT TTGGGACAAG AGCTCCGGTG ATGTGTTTTA

7321  CGAGGAAGTC CATGATAACA CAGATGCATG GGAGTGCTTC AGAGTTGACA ACCCTGCCGA

7381  CTTTGACCCT GAGAAGGGAA CTCTGTGTGG GCATACCACC ATTGAAAATA AGGCTTACAA

7441  TGTCTACGTC TCCCCATCTG GCAGGAAGTT CTAGTCCCT GTCAACCCAG AGAGTGGAAA

7501  AGCCCAATGG GAAGCTGCAA GGCTTTCCGT GGAGCAGGCC CTTGGCATGA TGAATGTCAA

7561  CGGTGAACTG ACAGCCAAAG AACTGGAGAA ACTGAAAAGA ATAATTGACA AACTCCAGGA

7621  CCTGACTAAG GAGCAGTGTT TAAACTGCTA GCCGCCAGCG GCTTGACCCG CTGTGGTCGC

7681  GGCGGCTTAG TTGTTACTGA GACAGCGGTA AAAATAGTCA AATTTCACAA CCGGACCTTC

7741  ACCCTAGGAC CCGTAAACTT AAAAGTGGCC AGTGAGGTTG AGCTAAAAGA CGCGGTCGAG

7801  CATAACCAAC ACCCGGTTGC AAGACCGGTT GATGGCGTG TTGTGCTCCT GCGCTCCGCA

7861  GTTCCTTCGC TTATAGACGT CTTGATCTCC GGCGCTGATG CATCTCCTAA GTTACTCGCC

7921  CGCCACGGGC CGGGAAACAC TGGGATCGAT GGCACGCTTT GGGACTTTGA GGCCGAGGCC

7981  ACTAGAGAGG AAATTGCACT CAGTGCGCAA ATAATACAGG CTTGTGACAT TAGGCGCGGC
```

-continued

```
 8041 GACGCGCCCG AAATTGGTCT TCCTTATAAG CTGTACCCTG TTAGGGGCAA CCCTGAGCGG

8101 GTAAAAGGAG TTTTACAGAA CACAAGGTTT GGAGACATAC CTTACAAAAC CCCCAGTGAC

8161 ACTGGAAGCC CAGTACACGC GGCTGCCTGC CTCACGCCCA ATGCCACTCC GGTGACTGAT

8221 GGGCGCTCCG TCTTGGCTAC GACTATGCCC TCCGGTTTTG AGTTGTATGT ACCGACCATT

8281 CCAGCGTCTG TCCTTGATTA TCTTGATTCT AGGCCTGACT GCCCTAAACA GTTGACAGAG

8341 CACGGTTGTG AGGATGCCGC ATTGAGAGAC CTCTCCAAGT ATGACTTGTC CACCCAAGGT

8401 TTTGTTTTGC CTGGAGTTCT TCGCCTTGTG CGGAAGTACC TGTTTGCCCA TGTGGGTAAG

8461 TGCCCGTCCG TTCATCGGCC TTCCACTTAC CCTGCCAAGA ATTCTATGGC TGGAATAAAT

8521 GGGAACAGGT TTCCAACCAA GGACATTCAG AGCGTCCCTG AAATCGACGT TCTGTGCGCA

8581 CAGGCCGTGC GAGAGAACTG GCAAACTGTC ACCCCTTGTA CCCTCAAGAA ACAGTATTGT

8641 GGGAAGAAGA AGACTAGGAC AATACTCGGC ACCAATAACT TCATTGCGTT GGCCCACCGA

8701 GCAGCGTTGA GTGGTGTCAC CCAGGGCTTC ATGAAAAAGG CGTTTAACTC GCCCATCGCC

8761 CTCGGGAAAA ACAAATTTAA GGAGCTGCAG ACTCCGGTCT TAGGCAGGTG CCTTGAAGCT

8821 GATCTTGCAT CCTGCGATCG ATCCACACCA GCAATTGTTC GCTGGTTTGC CGCCAATCTT

8881 CTTTATGAAC TTGCCTGTGC TGAGGAGCAT CTGCCATCGT ACGTGCTGAA CTGCTGCCAC

8941 GACTTACTGG TCACGCAGTC CGGCGCGGTG ACTAAGAGAG GTGGCCTGTC GTCTGGCGAC

9001 CCGATTACTT CTGTGTCAAA CACCATTTAC AGCTTGGTGA TATATGCACA GCACATGGTG

9061 CTCAGTTACT TTAAAAGTGG TCACCCTCAT GGCCTTCTGT TTCTGCAAGA CCAGCTGAAG

9121 TTTGAGGACA TGCTCAAGGT TCAACCCCTG ATCGTCTATT CGGACGACCT CGTGCTGTAT

9181 GCCGAGTCTC CCACCATGCC AAACTACCAC TGGTGGGTGG AACATCTGAA TCTTATGCTG

9241 GGTTTTCAGA CGGACCCAAG GAAGACAGCC ATAACAGATT CGCCATCATT TCTAGGCTGT

9301 AGGATAATAA ATGGACGCCA ACTAGTCCCC AACCGTGACA GGATCCTCGC GGCCCTCGCT

9361 TACCATATGA AGGCAAGCAA TGTTTCTGAA TACTACGCCT CGGCGGCTGC AATACTCATG

9421 GACAGCTGTG CTTGTTTAGA GTATGATCCT GAATGGTTTG AAGAGCTCGT GGTTGGGATG

9481 GCGCAGTGCG CCCGCAAGGA CGGCTATAGT TTCCCTGGCC CGCCGTTCTT CTTGTCCATG

9541 TGGGAAAAAC TCAGGTCCAA TCATGAAGGG AAGAAGTCCA GAATGTGCGG GTACTGCGGG

9601 GCCCCGGCTC CGTACGCCAC TGCCTGTGGC CTCGACGTCT GTGTTTATCA CACCCACTTT

9661 CACCAGCATT GTCCAGTCAT AATCTGGTGT GGCCATCCGG CTGGTTCTGG TTCTTGCAGT

9721 GAGTGCAAAC CCCCCTTAGG GAAAGGCACA AGCCCTCTAG ATGAGGTGTT AGAACAAGTC

9781 CCGTACAAGC CTCCACGGAC TGTAATCATG CATGTGGAGC AGGGTCTCAC CCCTCTTGAC

9841 CCAGGTAGAT ACCAGACTCG CCGCGGATTA GTCTCCGTTA GGCGTGGCAT CAGGGGAAAT

9901 GAAGTTGACC TACCAGACGG TGATTATGCT AGTACCGCCC TGCTCCCCAC TTGTAAAGAG

9961 ATCAACATGG TCGCTGTCGC CTCTAACGTG TTGCGCAGCA GGTTCATCAT CGGTCCGCCT

10021 GGTGCTGGGA AAACATACTG GCTCCTTCAA CAGGTCCAAG ATGGTGATGT CATTTACACG

10081 CCGACTCACC AGACCATGCT CGACATGATT AGGGCTTTGG GACGTGCCG GTTCAACGTC

10141 CCGGCAGGTA CAACGCTGCA ATTCCCCGCC CCCTCCCGTA CCGGCCCGTG GGTTCGCATC

10201 CTAGCCGGCG GTTGGTGTCC TGGTAAGAAT TCCTTCCTGG ATGAAGCAGC GTATTGCAAT

10261 CACCTTGATG TCTTGAGGCT TCTTAGCAAA ACTACCCTTA CCTGCCTAGG AGACTTCAAA

10321 CAACTCCACC CGGTGGGTTT TGACTCTCAT TGCTATGTTT TTGACATCAT GCCTCAGACC

10381 CAACTGAAGA CCATCTGGAG GTTTGGACAG AACATCTGTG ATGCCATCCA ACCAGATTAC

10441 AGGGACAAAC TTGTATCCAT GGTCAACACA ACCCGTGTAA CCTACGTGGA AAGACCTGTC
```

```
10501 AATTATGGGC AAGTCCTCAC CCCTTACCAC AGGGACCGAG AGGACGGCGC CATCACAATT
10561 GACTCCAGTC AAGGCGCCAC ATTTGATGTG GTTACACTGC ATCTGCCCAC TAAAGACTCA
10621 CTCAACAGGC AAAGAGCCCT TGTTGCTATC ACCAGGGCAA GACATGCTAT CTTTGTGTAT
10681 GACCCACACA GGCAACTGCA GAGCATGTTT GATCTTCCTG CGAAAGGCAC ACCCGTCAAC
10741 CTCGCTGTGC ACCGTGACGA GCAGCTGATC GTACTAGATA GAAATAACAA GAATGCACG
10801 GTTGCTCAGG CTCTAGGCAA TGGGGATAAA TTCAGGGCCA CAGACAAGCG CGTTGTAGAT
10861 TCTCTCTGCG CCATTTGTGC AGATCTGGAA GGGTCGAGCT CTCCGCTCCC CAAGGTCGCA
10921 CACAACTTGG GGTTTTATTT CTCACCTGAT TTGACACAGT TTGCTAAACT CCCGGTAGAA
10981 CTTGCACCCC ACTGGCCCGT GGTGACAACC CAGAACAATG AAAAGTGGCC AGACCGGCTG
11041 GTTGCCAGTC TTCGCCCTGT CCATAAGTAT AGCCGTGCGT GCATCGGTGC CGGCTACATG
11101 GTGGGCCCCT CAGTGTTTCT AGGCACCCCT GGGGTTGTGT CATACTATCT CACAAAATTT
11161 GTCAAGGGCG AGGCTCAAAT GCTTCCGGAG ACAGTTTTCA GCACCGGCCG AATTGAGGTA
11221 GATTGCCGGG AGTATCTTGA TGACCGGGAA CGAGAAATTG CTGAGTCCCT CCCCCATGCC
11281 TTCATTGGCG ACGTCAAAGG CACTACCGTT GGAGGATGTC ACCATGTCAC CTCCAAATAC
11341 CTTCCGCGCT TCCTTCCCAA GGAATCAGTC GCGGTAGTCG GGGTTTCAAG CCCCGGGAAA
11401 GCCGCAAAAG CAGTTTGCAC ATTAACAGAT GTGTACCTCC CAGACCTTGA GGCTTACCTC
11461 CACCCAGAGA CCCAGTCCAG GTGCTGGAAA ATGATGTTGG ACTTCAAGGA AGTTCGACTG
11521 ATGGTCTGGA AAGACAAGAC GGCCTATTTT CAACTTGAAG GCCGCCATTT CACCTGGTAT
11581 CAGCTTGCGA GCTATGCCTC GTACATCCGA GTTCCTGTTA ACTCTACGGT GTATTTGGAC
11641 CCATGCATGG GCCCTGCCCT TTGCAATAGA AGGGTTGTCG GGTCCACCCA TTGGGGAGCT
11701 GACCTCGCAG TCACTCCTTA TGATTATGGT GCCAAGATCA TTTTGTCTAG TGCATACCAT
11761 GGTGAAATGC CTCCTGGGTA CAAAATCCTA GCGTGTGCGG AGTTCTCGCT TGATGATCCA
11821 GTGAGGTACA AGCACACCTG GGGATTTGAA TCGGATACAG CGTATCTGTA CGAGTTCACC
11881 GGAAACGGTG AGGACTGGGA GGATTACAAT GATGCGTTTC GTGCGCGCCA GAAAGGGAAA
11941 ATTTATAAGG CCACTGCCAC CAGCATGAGG TTTCATTTTC CCCCGGGCCC TGTCATTGAA
12001 CCAACTTTGG GCCTGAACTG AAATGAAATG GGGGCTATGC AAAGCCTTTT CTACAAAATT
12061 GGCCAACTTT TTGTGGATGC TTTCACGGAG TTTTTGGTGT CCATTGTTGA TATCATCATA
12121 TTTCTGGCCA TTTTGTTTGG CTTCACCATC GCCGGCTGGC TGGTGGTCTT CTGCATCCGA
12181 TTGGTTTGCT CCGCGGTACT CCGTGCGCGC CCTACCGTTC ACCCTGAGCA ATTACAGAAG
12241 ATCTTATGAG GCCTTTCTTT CTCAGTGCCA GGTGGACATT CCCACCTGGG GAACCAAACA
12301 TCCCTTGGGG ATGCTTTGGC ACCATAAGGT GTCAACCCTG ATTGATGAAA TGGTGTCGCG
12361 TCGAATGTAC CGCATCATGG AAAAAGCAGG ACAGGCTGCC TGGAAACAGG TGGTGAGCGA
12421 GGCCACGCTG TCTCGTATTA GTGGTTTGGA TGTGGTGGCT CATTTTCAGC ATCTTGCTGC
12481 CATTGAAGCC GAGAACTGTA AATATTTGGC CTCTCGGCTG CCCATGCTAC ACAACCTGCG
12541 CATGACAGGG TCAAATGTAA CCTTAGTGTA TAATAGCACT TTGAATCAGG TGTTCGCTAT
12601 CTTTCCAACC CCTGGTTCCC GGCCAAAGCT TCATGATTTT CAGCAATGGC TAATAGCTGT
12661 ACATTCCTCT ATATTTCCT CCGTTGCGGC TTCTTGTACT CTTTTTGTTG TGCTGTGGTT
12721 GCGAATCCCA ATTCTACGTA CTGTTTTTGG TTTCCACTGG TTAGGGCAA TTTCTCTTTC
12781 GAACTCACAG TGAATTACAC GGTGTGCCCA CCTTGCCTCA CCCGACAAGC AGCCGCTGAG
12841 ATCTATGAAC CCGGCAGGTC TCTTTGGTGC AGGATAGGGA ATGACCGATG TAGTGAGAGC
```

```
12901 GATCATGACG AACTAGGGTT CATGGTTCCG TCTGGCCTCT CCAGCGAAGG CCACTTGACC

12961 AGTGTTTACG CTTGGTTGGC GTTTCTGTCC TTCAGCTACA CGGCCCAGTT CCATCCCGAG

13021 ATATTTGGGA TAGGGAATGT GAGTAAAGTT TATGTTGACA TCAAGCACCA ATTAATCTGC

13081 GCCGTTCATG ACGGGCAGAA CACCACCTTG CCTCGCCATG ACAATATTTC AGCCGTATTT

13141 CAGACCTATT ATCAACATCA GGTCGACGGC GGCAACTGGT TTCACCTAGA ATGGCTGCGT

13201 CCCTTCTTTT CCTCTTGGTT GGTTTTAAAT GTTTCGTGGT TTCTCAGGCG TTCGCCTGCA

13261 AGCCATGTTT CAGTTCGAGT CTTTCGGACA TCAAGACCAA CACTACCGCA GCATCAGGCT

13321 TTGTCGTCCT CCAGGACATC AGCTGCCTTA GGCATGGCGA CTCGTCCTCT CAGACGATTC

13381 GCAAAAGCTC TCAGTGCCGC ACGGCGATAG GGACGCCCGT GTACATCACC ATGACAGCCA

13441 ATGTCACAGA TGAGAATTAT TTGCATTCTT CTGATCTCCT CATGCTTTCT TCTTGCCTTT

13501 TCTATGCTTC TGAGATGAGT GAAAAGGGAT TCAAGGTGGT GTTTGGCAAT GTGTCAGGCA

13561 TCGTGGCTGT GTGTGTCAAC TTTACCAGCT ACGTCCAACA CGTCAAGGAG TTCACCCAAC

13621 GCTCCTTGGT AGTCGATCAT GTGCGGCTGC TTCACTTCAT GACACCTGAG ACCATGAGGT

13681 GGGCAACCGT TTTAGCCTGT CTTTTTGCCA TCTTGCTGGC AATTTGAATG TTCAAGTATG

13741 TTGGGGAAAT GCTTGACCGC GGGCTGTTGC TCGCGATTGC CTTTTTTGTG GTGTATCGTG

13801 CCGTTCTGTT TTGCTGTGAT CGTCGACGCC AACAGCAACA GCAGCTCTCA TTTCCAGTTG

13861 ATTTATAACT TGACGTTATG CGAGCTGAAT GGCACAGATT GGCTGGTTGA TAAATTTGAT

13921 TGGGCAGTGG AGACTTTTGT CATTTTTCCC GTGTTGACTC ACATTGTTTC TTATGGTGCA

13981 CTCACCACCA GCCATTTCCT TGACACAGTT GGTCTGGTTA CTGTATCCGC CGCCGGGTTT

14041 TGTCACGGGC GGTATGTCTT GAGTAGCATC TACGCGGTCT GTGCCCTGGC TGCGTTGGTT

14101 TGCTTTGTCA TCAGATTTGC GAAGAACTGC ATGTCCTGGC GCTACTCATG TACTAGATAC

14161 ACCAACTTCC TTCTAGACAC TAAGGGCAGA CTCTATCGTT GGCGGTCGCC TGTCATCATA

14221 GAGAAAAGGG GCAAGGTTGA GGTCGAAGGC CATCTGATCG ACCTCAAAAA AGTTGTGCTT

14281 GATGGTTCCG CGGCAACCCC TTTAACCAGA ATTTCAGCGG AACAATGGTG TCGTCCCTAG

14341 ACGACTTTTG CAATGATAGC ACAGCTCCAC GGAAGGTGCT CTTGGCGTTT TCTATCACCT

14401 ACACGCCAGT GATGATATAT GCTCTAAAGG TAAGTCGCGG CCGACTGTTG GGGCTTCTGC

14461 ACCTTTTGAT TTTTCTGAAC TGTGCCTTTA CCTTCGGGTA CATGACATTC ACGCACTTTC

14521 AGAGCACAAA TAGGGTCGCG CTCACTATGG GAGCAGTAGT CGCACTCCTT TGGGGGGTGT

14581 ACTCAGCCAT AGAAACCTGG AAATTCATCA CCTCCAGATG CCGTTTGTGC TTGCTAGGCC

14641 GCAAGTACAT TTTGGCCCCT GCCCACCACG TCGAAAGTGC CGCGGGCTTT CATCCGATTG

14701 CGGCAAATGA TAACCACGCA TTTGTCGTCC GGCGTCCCGG CTCCACTACG GTCAACGGCA

14761 CATTGGTGCC CGGGTTGAAA AGCCTCGTGT TGGGTGGCAG AAAAGCTGTT AAACAGGGAG

14821 TGGTAAACCT TGTCAAATAT GCCAAATAAC AACGGCAAGC AGCAAAAGAA AAAGAAGGGG

14881 AATGGCCAGC CAGTCAATCA GCTGTGCCAG ATGCTGGGTA AGATCATCGC CCAGCAAAAC

14941 CAGTCCAGAG GTAAGGGACC GGGGAAGAAA ATAAGAAGA AAAACCCGGA GAAGCCCCAT

15001 TTTCCTCTAG CGACCGAAGA TGACGTCAGG CATCACTTTA CCCCTAGTGA GCGGCAATTG

15061 TGTCTGTCGT CGATCCAGAC TGCCTTTAAC CAGGGCGCTG GAACTTGCAC CCTGTCAGAC

15121 TCAGGGAGGA TAAGTTACAC TGTGGAGTTT AGTTTGCCGA CGCATCATAC TGTGCGCCTG

15181 ATTCGCGCCA CAGCATCAAC CTCAGCATGA TGGGCTGGCA TTCTTGAAGC ACCACAGTGT

15241 TAGGATTGGA AGAATGTGTG GTGAATGGCA CTGATTGACA CTGTGCCTCT AAGTCACCTA
```

```
15301 TTCAATTAGG GCGACCGTGT GGGGGTAAAG TTTAATTGGC GAGAACCATG CGGCCGCAAT

15361 TAAAAAAAAA AAAAAAAAAA AAAAAA
```

The cDNA consensus sequence of PRRS strain SD 95-47 at P83 has been assigned GenBank Accession number KU131564 (SEQ. ID. NO:2). The cDNA consensus sequence designated SEQ. ID. NO:2 is:

```
   1 TATGTACGTA TAGGTGTTGG CTCTATGCCT TTGGCATTTG TATTGTCAGG AGCTGTGACC

61 ATTGGCACAG CCCAAAACTT GCTACACAGA AACACCCTTC TGTGATAGCC TCCTTCAGGG

121 GAGCTTAGGG TTTGTCCCTA GCACCTTGCT TCCGGAGTTG CACTGCTTTA CGGTCTCTCC

181 ACCCCTTTAA CCATGTCTGG GATACTTGAT CGGTGCACGT GTACCCCCAA TGCCAGGGTG

241 TTTATGGCGG AGGGCCAAGT CTACTGCACA CGATGCCTCA GTGCACGGTC TCTCCTTCCC

301 CTGAACCTCC AAGTTTCTGA GCTCGGGGTG CTAGGCCTAT TCTACAGGCC CGAAGAGCCA

361 CTCCGGTGGA CGTTGCCACG TGCATTCCCC ACTGTTGAGT GCTCCCCGC CGGGGCCTGC

421 TGGCTTTCTG CAATCTTTCC AATCGCACGA ATGACCAGTG GAAACCTGAA CTTCCAACAA

481 AGAATGGTAC GGGTCGCAGC TGAGCTTTAC AGAGCCGGCC AGCTCACCCC TGCAGTCTTG

541 AAGGCTCTAC AAGTTTATGA ACGGGGTTGC CGCTGGTACC CCATTGTTGG ACCTGTCCCT

601 GGAGTGGCCG TTTTCGCCAA TTCCCTACAT GTGAGTGATA AACCTTTCCC GGGAGCAACT

661 CACGTGTTGA CCAACCTGCC GCTCCCGCAG AGACCCAAGC TGAAGACTT TTGCCCCTTT

721 GAGTGTGCTA TGGCTACTGT CTATGACATT GGTCATGACG CCGTCATGTA TGTGGCCGAA

781 AGGAAAATCT CCTGGGCCCC TCGTGGCGAG GATGAAGTGA AATTTGAAGC TGTCCCCGGG

841 GAGTTGAAGT TGATTGCGAA CCGGCTCCGC ACCTCCTTCC CGCCCCACCA CACAGTGGAC

901 ATGTCTAAGT TCGCCTTCAC AGCCCCTGGG TGTGGTGTTT CTATGCGGGT CGAATGCCAA

961 CACGGCTGCC TTCCCGCTGA CACTGTCCCT GAAGGCAACT GCTGGTGGAG CTTGTTTGAC

1021 TTGCTTCCAC TGGAAGTTCA GAACAAAGAA ATTCGCCATG CTAACCAATT TGGCTACCAG

1081 ACCAAGCATG GTGTCTCTGG CAAATACCTA CAGCGTAGGC TGCAAGTTAA TGGTCTCCGA

1141 GCAGTAACTG ACCTAAACGG ACCTATCGTC GTACAGTACT TCTCCGTTAA GGAGAGTTGG

1201 ATCCGCCATT TGAAACTGGC GGGAGAACCC AGCTACTCTG GGTTTGAGGA CCTCCTCAGA

1261 ATAAGGGTTG AGCCTAACAC GTCGCCATTG GCTGACAAGG AAGAAAAAAT TTTCCGGTTT

1321 GGCAGTCACA AGTGGTACGG CGCTGGAAAG AGAGCAAGAA AAGCGCGCTC TTGTGCGACT

1381 GCTACAGTCG CTGGCCGCGC TTTGTCCGTT TGTGAAACCC GGCAGGCCAA GGAGCACGAG

1441 GTTGCCGGCG CCAACAAGGC TGAGCACCTC AAACACTACT CCCCGCCTGC CGAAGGGAAT

1501 TGTGGTTGGC ACTGCATTTC CGCCATCGCC AACCGGATGG TGAATTCCAA ATTTGAAACC

1561 ACCCTTCCCG AAAGAGTGAG ACCTTCAGAT GACTGGGCTA CTGACGAGGA TCTTGTGAAT

1621 GCCATCCAAA TCCTCAGACT CCCTGCGGCC TTAGACAGGA ACGGTGCTTG TACTAGCGCC

1681 AAGTACGTAC TTAAGCTGGA AGGTGAGCAT TGGACTGTCA CTGTGACCCC TGGGATGTCC

1741 CCTTCTTTGC TCCCTCTTGA ATGTGTTCAG GGCTGTTGTG GCACAAGGG CGGTCTTGGT

1801 ACCCCAGATG CAGTCGAGGT CTCCGGATTT GACCCTGCCT GCCTTGACCG GCTGGCTGAG

1861 GTGATGCACC TGCCTAGCAG TGCTATCCCA GCCGCTCTGG CCGAAATGTC TGGCGATTCC

1921 GATCGTTCGG CTTCTCCGGT CACCACCGTG TGGACTGTTT CGCAGTTCTT TGCCCGTCAC

1981 AGCGGAGGGA ATCACCCTGA CCAAGTGCGC TTAGGGAAAA TTATCAGTCT TTGTCAGGTG

2041 ATTGAGGACT GCTGCTGTTC CCAGAACAAA ACCAACCGGG TCACCCCGGA GGAGGTCGCA
```

```
2101  GCAAAGATTG ACCTGTACCT CCGTGGTGCA ACAAATCTTG AAGAATGCTT GGCCAGGCTT

2161  GAGAAAGCGC GCCCGCCGCG CGTAATCGAC ACCTTCTTTG ATTGGGATGT TGTGCTCCCT

2221  GGGGTTGAGG CGGCAACCCA GACGATCAAG CTGCCCCAGG TCAACCAGTG TCGTGCTCTG

2281  GTCCCTGTTG TGACTCAAAA GTCCTTGGAC AACAACTCGG TCCCCCTGAC CGCCTTTTCA

2341  CTGGCTAACT ACTACTACCG TGCGCAAGGT GACGAAGTTC GTCACCGTGA AAGACTAACC

2401  GCCGTGCTCT CCAAGTTGGA AAAGGTTGTT CGAGAAGAAT ATGGGCTCAT GCCAACCGAG

2461  CCTGGTCCAC GGCCCACACT GCCACGCGGG CTCGACGAAC TCAAAGACCA GATGGAGGAG

2521  GACTTGCTGA AACTGGCTAA CGCCCAGACG ACTTCGGACA TGATGGCCTG GGCAGTCGAG

2581  CAGGTTGACT TAAAAACTTG GGTCAAGAAC TACCCGCGGT GGACACCACC ACCCCCTCCG

2641  CCAAAAGTTC AGCCTCGAAA AACGAAGCCT GTCAAGAGCT TGCCGGAGAG AAAGCCTGTC

2701  CCCGCCCCGC GCAGGAAGGT TGGGTCCGAT TGTGGCAGCC CGGTTTCATT AGGCGGCGAT

2761  GTCCCTAACA GTTGGGAAGA TTTGGCTGTT AGTAGCCCCT TTGATCTCCC GACCTCACCT

2821  GAGCCGGCAA CACCTTCAAG TGAGCTGGTG ATTGTGTCCT CACCGCAATG CATCTTCAGG

2881  CCGGCGACAC CCTTGAGTGA GCCGGCTCCA ATTCCCGCAC CTCGCGGAAC TGTGTCTCGA

2941  CCGGTGACAC CCTTGAGTGA GCCGATCCCT GTGCCCGCAC CGCGGCGTAA GTTTCAGCAG

3001  GTGAAAAGAT TGAGTTCGGC GGCGGCAATC CCACCGTACC AGAACGAGCC CCTGGATTTG

3061  TCTGCTTCCT CACAGACTGA ATATGAGGCC TCTCCCCAG CACCGCCGCA GAGCGGGGGC

3121  GTTCTGGGAG TAGAGGGGCA TGAAGCTGAG GAAACCCCGA GTGAAATCTC GGACATGTCG

3181  GGTAACATTA AACCTGCGTC CGTGTCATCA AGCAGCTCCT TGTCCAGCGT GAGAATCACA

3241  CGCCCAAAAT ACTCAGCTCA AGCCATCATC GACTCGGGCG GGCCCTGCAG TGGGCATCTC

3301  CAAGAGGTAA AGGAAACATG CCTTAGTGTC ATGCGCGAGG CATGTGATGC GACTAAGCTT

3361  GATGACCCTG CTACGCAGGA ATGGCTTTCT CGCATGTGGG ATCGGGTGGA CATGCTGACT

3421  TGGCGCAATA CGTCTGCTTA CCAGGCGATT TGCACCTTAG ATGGCAGGTT AAAGTTCCTC

3481  CCAAAAATGA TACTCGAGAC ACCGCCGCCC TATCCGTGTG AGTTTGTGAT GATGCCTCAC

3541  ACGCCTGCAC CTTCCGTAGG TGCGGAGAGC GACCTTACCA TTGGCTCAGT TGCTACTGAA

3601  GATGTTCCAC GCATCCTCGA GAAAATAGAA AATGTCGGCG AGATGGCCAA CCAGGGACCC

3661  TTGGCCTTCT CCGAGGATAA ACCGGTAGAT GACCAACTTG TCAACGACCC CCGGATACCG

3721  TCGCGGAGGC CTGACGAGAG CACATCAGCT CCGTCCGCAG GCACAGGTGG CGCCGGCTCT

3781  TTTACCGATT TGCCGCCTTC AGATGGCGCG GATGCGGACG GGGGGGGGCC GTTTCGGACG

3841  GTAAAAGAA AAGCTGAAAG GCTCTTTGAC CAACTGAGCC GTCAGGTTTT TGACCTCGTC

3901  TCCCATCTCC CTGTTTTCTT CTCACGCCTT TTCTACCCTG GCGGTGGTTA TTCTCCGGGT

3961  GATTGGGGTT TTGCAGCTTT TACTCTATTG TGCCTCTTTT TATGTTACAG TTACCCAGCC

4021  TTTGGTATTG CTCCCCTCTT GGGTGTGTTT TCTGGGTCTT CTCGGCGCGT TCGAATGGGG

4081  GTTTTTGGCT GCTGGTTGGC TTTTGCTGTT GGTCTGTTCA AGCCTGTGTC CGACCCAGTC

4141  GGCGCTGCTT GTGAGTTTGA CTCGCCAGAG TGTAGAAACA TCCTTCATTC TTTTGAGCTT

4201  CTCAAACCTT GGGACCCTGT TCGCAGCCTT GTTGTGGGCC CCGTCGGTCT CGGTCTTGCC

4261  ATTCTTGGCA GGCTACTGGG CGGGGCACGC TGTATCTGGC ACTTTTTGCT TAGGCTTGGC

4321  ATTGTTGCAG ACTGTATCTT GGCTGGAGCT TACGTGCTTT CTCAAGGTAG GTGTAAAAAG

4381  TGCTGGGGAT CTTGTATAAG AACTGCTCCT AATGAGGTCG CTTTTAACGT GTTTCCTTTC

4441  ACACGTGCGA CCAGGTCGTC ACTTATCGAC CTGTGCGATC GGTTTTGTGC ACCAAAAGGA

4501  ATGGACCCCA TTTTTCTCGC CACTGGGTGG CGCGGGTGCT GGGCCGGCCG AAGCCCCATT
```

-continued

```
4561 GAGCAACCCT CTGAAAAACC CATCGCGTTT GCCCAATTGG ATGAAAAGAA GATTACGGCT
4621 AGGACTGTGG TCGCCCAGCC TTATGACCCC AACCAAGCCG TAAAGTGCTT GCGGGTGTTG
4681 CAGGCGGGTG GGGCGATGGT GGCTGAGGCG GTCCCAAAAG TGGTCAAGGT TTCCGCTGTT
4741 CCATTCCGAG CCCCCTTCTT TCCCACTGGA GTGAAAGTTG ATCCTGATTG CAGGGTCGTG
4801 GTTGACCCTG ATACTTTCAC TGCAGCTCTC CGGTCTGGCT ACTCCACCAC AAACCTCGTC
4861 CTTGGTGTAG GGGACTTTGC CCAGCTGAAT GGATTAAAAA TCAGGCAAAT TTCCAAGCCT
4921 TCAGGGGGAG GCCCACATCT CATGGCTGCC CTGCATGTTG CCTGCTCGAT GGCTCTGCAC
4981 ATGCTTGCTG GGATCTATGT GACTGCGGTG GGTTCTTGCG CACCGGCAC CAACGACCCG
5041 TGGTGCGCTA ACCCGTTTGC CGTCCCTGGC TACGGACCTG GCTCTCTCTG CACGTCCAGA
5101 TTGTGCATTT CCCAACACGG CCTTACCCTG CCCTTGACAG CACTTGTGGC GGGATTCGGT
5161 ATTCAAGAAA TTGCCTTAGT CGTTTTGATT TTTGTTTCCA TCGGAGGCAT GGCTCATAGG
5221 TTGAGCTGTA AGGCTGACAT GCTGTTTGTT TTGCTTGCAA TCGCCAGCTA TGTTTGGGTA
5281 CCTCTTACCT GGTTGCTTTG TGTGTTTCCT TGCTGGTTGC GCTGTTTTTC TTTGCACCCC
5341 CTCACCGTCC TATGGTTGGT GTTTTTCTTG ATTTCTGTGA ATATGCCTTC AGGAATCTTG
5401 GCCATGGTGT TGTTGGTTTC TCTTTGGCTT CTTGGTCGTT ATACTAATGT TGCTGGCCTT
5461 GTCACCCCCT ACGACATTCA CCATTACACC AGCGGCCCCC GCGGTGTTGC CGCCTTGGCT
5521 ACCGCTCCAG ATGGGACCTA CTTGGCCGCT GTCCGCCGCG CTGCGTTGAC TGGCCGCACC
5581 ATGCTGTTTA CCCCGTCCCA GCTGGGTCT CTTCTTGAGG GTGCTTTCAG AACTCGAAAG
5641 CCCTCACTGA ACACCGTCAA TGTGATCGGG TCCTCCATGG GCTCTGGCGG GGTGTTTACC
5701 ATCGACGGGA AAGTCAAGTG CGTAACTGCC GCACATGTCC TTACGGGCAA TTCAGCTCGG
5761 GTTTCCGGGG TCGGCTTCAA TCAAATGCTT GACTTTGACG TAAAGGGAGA TTTTGCTATA
5821 GCTGATTGCC CGAATTGGCA AGGGGCTGCC CCCAAGACCC AATTCTGCAC GGATGGATGG
5881 ACTGGCCGTG CCTATTGGCT AACATCCTCT GGCGTCGAAC CCGGCGTCAT GGAAAAGGA
5941 TTCGCCTTCT GCTTCACCGC ATGTGGCGAT TCCGGGTCCC CAGTGATCAC CGAGGCCGGT
6001 GAGCTTGTCG GCGTTCACAC GGGATCGAAT AAACAAGGGG GGGCATTGT TACGCGCCCC
6061 TCAGGCCAGT TTTGTAATGT GGCACCCATC AAGCTAAGCG AATTAAGTGA ATTCTTTGCT
6121 GGGCCTAAGG TCCCGCTCGG TGATGTGAAG GTCGGCAGCC ACATAATTAT AGACATAAGC
6181 GAGGTGCCTT CAGATCTTTG TGCCTTGCTT GCTGCCAAAC CTGAACTGGA AGGAGGCCTC
6241 TCCACCGTCC AACTTCTTTG TGTGTTTTTT CTCCTGTGGA GAATGATGGG ACATGCCTGG
6301 ACGCCCTTGG TTGCTGTGAG TTTCTTTATT CTGAATGAGG TTCTCCCTGC CGTCCTGGTC
6361 CGGAGTGTTT TCTCCTTTGG AATGTTTGTG CTATCCTGGC TCACGCCATG GTCTGCGCAA
6421 GTTCTGATGA TCAGGCTTCT GACAGCAGCT CTTAACAGGA ACAGATGGTC ACTTGCCTTT
6481 TTCAGCCTCG GTGCAGTGAC CGGTTTTGTC GCAGATCTTG CGGCCACTCA GGGCATCCG
6541 TTGCAGGCAG TGATGAATTT GAGCACCTAT GCATTCCTGC CTCGGATGAT GGTTGTGACC
6601 TCACCAGTCC CAGTGATCAC GTGTGGTGTC GTGCACCTAC TTGCCATCAT TTTGTACTTG
6661 TTTAAGTACC GTGGCCTGCA CCATATCCTT GTTGGCGATG GAGTGTTCTC TGCGGCTTTC
6721 TTCTTGAGAT ACTTTGCCGA GGGAAAGTTG AGGGAAGGGG TGTCGCAATC CTGCGGAATG
6781 AATCATGAGT CTCTGACTGG TGCCCTCGCT ATGAGACTCA ATGACGAGGA CTTGGATTTC
6841 CTTATGAAAT GGACTGATTT TAAGTGCTTT GTTTCTGCGT CCAACATGAG GAATGCAGCG
6901 GGTCAATTTA TCGAGGCTGC CTATGCTAAA GCACTTAGAG TAGAACTGGC CCAGTTGGTG
```

-continued

```
6961 CAGGTTGATA AAGTTCGAGG TACTTTGGCC AAACTTGAAG CTTTTGCTGA TACCGTGGCA
7021 CCTCAACTCT CGCCCGGTGA CATTGTTGTC GCTCTCGGCC ACACGCCTGT TGGCAGTATC
7081 TTCGACCTAA AGGTTGGTAG CACCAAGCAT ACCCTCCAAG CCATTGAGAC CAGAGTCCTT
7141 GCTGGGTCCA AAATGACCGT GGCGCGCGTC GTCGACCCGA CCCCCACGCC CCCGCCCGCA
7201 CCCGTGCCCA TCCCCCTCCC ACCGAAAGTT CTGGAGAATG GCCCAACGC TTGGGGGGAT
7261 GAGGACCGTT TGAATAAGAA GAAGAGGCGC AGGATGGAAG CCCTCGGCAT CTATGTTATG
7321 GGCGGGAAAA AGTACCAGAA ATTTTGGGAC AAGAATTCCG GTGATGTGTT TTATGAGGAG
7381 GTCCATAATA ACACAGATGA TTGGGAGTGT CTCAGAGTTG GCGACCCTGC CGACTTTGAC
7441 CCTGAGAAGG GAACTCTGTG TGGACATGTC ACCATTGAAA ACAAGGCTTA CCATGTTTAC
7501 ACCTCCCCAT CTGGTAAGAA GTTCTTGGTC CCCGTCAACC CAGAGAATGG AAGAGTTCAA
7561 TGGGAAGCTG CAAAGCTTTC CGTGGAGCAG GCCCTAGGTA TGATGAATGT CGACGGCGAA
7621 CTGACTGCCA AGAACTGGA GAAACTGAAA AGAATAATTG ACAAACTCCA GGGCCTGACT
7681 AAGGAGCAGT GTTTAAACTG CTAGCCGCTA GCGACTTGAC CCGCTGTGGT CGCGGCGGCT
7741 TGGTTGTTAC TGAAACAGCG GTAAAAATAG TCAAATTTCA CAACCGGACC TTCACCCTGG
7801 GACCTGTGAA TTTAAAAGTG GCCAGTGAGG TTGAGCTAAA AGACGCGGTT GAGCACAACC
7861 AACACCCGGT TGCGAGACCG ATCGATGGTG GAGTTGTGCT CCTGCGTTCC GCGGTTCCTT
7921 CGCTTATAGA CGTCTTGATC TCCGGTGCTG ATGCATCTCC CAAGTTACTT GCCCATCACG
7981 GGCCGGGAAA CACTGGGATC GATGGCACGC TCTGGGATTT TGAGTCCGAA GCCACTAAAG
8041 AGGAAGTCGC ACTCAGTGCG CAAATAATAC AGGCTTGTGA CATTAGGCGC GGCGACGCTC
8101 CTGAAATTGG TCTCCCTTAC AAGCTGTACC CTGTTAGGGG TAACCCTGAG CGGGTGAAAG
8161 GAGTTCTGCA GAATACAAGG TTTGGAGACA TACCTTACAA ACCCCCAGT GACACTGGAA
8221 GCCCAGTGCA CGCGGCTGCC TGCCTTACGC CCAACGCCAC TCCGGTGACT GATGGGCGCT
8281 CCGTCTTGGC CACGACCATG CCCCCCGGGT TTGAGTTATA TGTACCGACC ATACCTGCGT
8341 CTGTCCTTGA TTACCTTGAC TCTAGGCCTG ACTGCCCTAA ACAGCTGACA GAGCACGGCT
8401 GCGAAGATGC CGCACTGAAA GACCTCTCCA AATATGACTT GTCCACCCAA GGCTTTGTTT
8461 TACCTGGAGT TCTTCGCCTT GTGCGGAAAT ACCTGTTTGC CCATGTAGGT AAGTGCCCAC
8521 CCGTTCATCG GCCTTCTACT TACCCTGCTA AGAATTCTAT GGCTGGAATA AATGGGAATA
8581 GGTTCCCAAC CAAGGACATT CAGAGCGTCC CTGAAATCGA CGTTCTGTGC GCACAGGCTG
8641 TGCGAGAAAA CTGGCAAACT GTCACCCCTT GCACTCTTAA GAAACAGTAT TGCGGAAGA
8701 AGAAGACTAG GACCATACTC GGCACCAATA ACTTCATCGC ACTAGCCCAC CGAGCAGTGT
8761 TGAGTGGTGT TACCCAGGGC TTCATGAAAA AGGCGTTTAA CTCGCCCATC GCCCTCGGAA
8821 AGAACAAGTT TAAGGAGCTA CAGACTCCGG TCCTGGGCAG GTGCCTTGAA GCTGATCTCG
8881 CATCCTGCGA TCGATCCACG CCTGCAATTG TCCGCTGGTT TGCCGCCAAC CTTCTTTATG
8941 AACTTGCCTG TGCTGAAGAG CATCTACCGT CGTACGTGCT GAACTGCTGC CACGACTTAC
9001 TGGTCACGCA GTCCGGCGCA GTGACTAAGA GAGGTGGCCT GTCGTCTGGC GACCCGATCA
9061 CCTCTGTGTC TAACACCATT TATAGTTTGG TGATCTATGC ACAGCATATG GTGCTTAGTT
9121 ACTTCAAAAG TGGTCACCCC CATGGCCTTC TGTTCTTACA AGACCAGCTA AAGTTTGAGG
9181 ACATGCTCAA GGTTCAACCC CTGATCGTCT ATTCGGACGA CCTCGTGCTG TATGCCGAGT
9241 CTCCCACCAT GCCAAACTAT CACTGGTGGG TTGAACATCT GAATTTGATG CTGGGGTTTC
9301 AGACGGACCC AAAGAAGACA GCAATAACAG ACTCGCCATC ATTTCTAGGC TGTAGAATAA
9361 TAAATGGGCG CCAGCTAGTC CCCAACCGTG ACAGGATCCT CGCGGCCCTC GCCTATCACA
```

-continued

```
 9421 TGAAGGCGAG TAATGTTTCT GAATACTATG CCTCAGCGGC TGCAATACTC ATGGACAGCT
 9481 GTGCTTGTTT GGAGTATGAT CCTGAATGGT TTGAAGAACT TGTAGTTGGA ATAGCGCAGT
 9541 GCGCCCGCAA GGACGGCTAC AGCTTTCCCG GCACGCCGTT CTTCATGTCC ATGTGGGAAA
 9601 AACTCAGGTC CAATTATGAG GGGAAGAAGT CGAGAGTGTG CGGGTACTGC GGGGCCCCGG
 9661 CCCCGTACGC TACTGCCTGT GGCCTCGACG TCTGCATTTA CCACACCCAC TTCCACCAGC
 9721 ATTGTCCAGT CACAATCTGG TGTGGCCATC CAGCGGGTTC TGGTTCTTGT AGTGAGTGCA
 9781 AATCCCCTGT AGGGAAAGGC ACAAGCCCTT TAGACGAGGT GCTGGAACAA GTCCCGTATA
 9841 AGCCCCCACG GACCGTTATC ATGCATGTGG AGCAGGGTCT CACCCCCCTT GATCCAGGTA
 9901 GATACCAAAC TCGCCGCGGA CTGGTCTCTG TCAGGCGTGG AATTAGGGGA AATGAAGTTG
 9961 AACTACCAGA CGGTGATTAT GCTAGCACCG CCTTGCTCCC TACCTGCAAA GAGATCAACA
10021 TGGTCGCTGT CGCTTCCAAT GTATTGCGCA GCAGGTTCAT CATCGGCCCA CCCGGTGCTG
10081 GGAAAACATA CTGGCTCCTT CAACAGGTCC AGGATGGTGA TGTTATTTAC ACACCAACTC
10141 ACCAGACCAT GCTTGACATG ATTAGGGCTT TGGGGACGTG CCGGTTCAAC GTCCCGGCAG
10201 GCACAACGCT GCAATTCCCC GTCCCTCCC GCACCGGTCC GTGGGTTCGC ATCCTAGCCG
10261 GCGGTTGGTG TCCTGGCAAG AATTCCTTCC TAGATGAAGC AGCGTATTGC AACCACCTTG
10321 ATGTTTTGAG GCTTCTCAGT AAAACTACCC TCACCTGTCT AGGAGACTTC AAGCAACTCC
10381 ACCCAGTGGG TTTTGATTCT CATTGCTATG TTTTTGACAT CATGCCTCAA ACTCAACTGA
10441 AGACCATCTG GAGGTTTGGA CAGAATATCT GTGATGCCAT TCAGCCAGAT TACAGGGACA
10501 AACTCATGTC CATGGTCAAC ACAACCCGTG TGACCTACGT GGAAAAACCT GTCAGGTATG
10561 GGCAGGTCCT CACCCCCTAC CACAGGGACC GAGAGGACGA CGCCATCACT ATTGACTCCA
10621 GTCAAGGCGC CACATTCGAT GTGGTTACGT TGCATTTGCC CACTAAAGAT TCACTCAACA
10681 GGCAAAGAGC CCTTGTTGCC ATCACCAGGG CAAGACACGC TATCTTTGCG TATGACCCAC
10741 ACAGGCAGCT GCAGGGCTTA TTTGATCTTC CTGCAAAAGG CACACCCGTC AACCTCGCAG
10801 TGCACCGCGA CGGGCAGCTG ATCGTGCTGG ATAGAAATAA CAAAGAATGC ACGGTTGCTC
10861 AGGCTCTAGG CAACGGGGAT AAATTTAGGG CCACAGATAA GCGTGTTGTA GATTCTCTCC
10921 GCGCCATTTG TGCTGATCTA GAAGGGTCGA GCTCTCCGCT CCCCAAGGTC GCACACAACT
10981 TGGGATTTTA TTTCTCACCT GATTTAACAC AGTTTGCTAA ACTCCCAGTA GAACTTGCAC
11041 CTCACTGGCC CGTGGTGACA ACCCAGAACA ATGAAAAGTG GCCAGATCGG CTGGTTGCCA
11101 GCCTTCGCCC TATCCATAAA TACAGCCGCG CGTGCATCGG TGCCGGCTAT ATGGTGGGCC
11161 CTTCGGTGTT TCTAGGCACT CCTGGGGTCG TGTCATACTA TCTCACAAAA TTTGTTAAGG
11221 GCGAGGCTCA ATTGCTTCCA GAGACGGTTT TCAGCACCGG CCGAATTGAG GTAGACTGCC
11281 GGGAATATCT TGATGATCGG GAGCGAGAAG TTGCTGCGTC CCTCCCACAC GCTTTCATTG
11341 GCGACGTCAA AGGCACTACC GTTGGAGGAT GTCATCATGT CACCTCCAGA TACCTCCCGC
11401 GCGTCCTTCC CAAGGAATCA GTTGCGGTAG TCGGGGTTTC AAGCCCCGGA AAAGCCGCGA
11461 AAGCATTGTG CACACTGACA GATGTGTACC TCCCAGATCT TGAAGCCTAT CTCCACCCGG
11521 AGACCCAGTC CAAGTGCTGG AAAATGATGT TGGACTTCAA AGAAGTTCGA CTAATGGTCT
11581 GGAAAGACAA AACAGCCTAT TTCCAACTTG AAGGTCGCTA TTTCACCTGG TATCAGCTTG
11641 CCAGCTATGC CTCGTACATC CGTGTTCCTG TCAACTCTAC GGTGTACTTG GACCCCTGCA
11701 TGGGCCCCGC CCTTTGCAAC AGGAGAGTCG TCGGGTCCAC CCATTGGGGG GCTGACCTCG
11761 CGGTCACCCC TTATGATTAC GGCGCTAAAA TTATCCTGTC TAGCGCGTAC CATGGTGAAA
```

-continued

```
11821 TGCCCCCCGG ATACAAAATT CTGGCGTGCG CGGAGTTCTC GTTGGATGAC CCAGTTAAGT

11881 ACAAACATAC CTGGGGGTTT GAATCGGATA CAGCGTATCT GTATGAGTTC ACCGGAAACG

11941 GTGAGGACTG GGAGGATTAC AATGATGCGT TTCGTGCGCG CCAGGAAGGG AAAATTTACA

12001 AGGCCACTGC CACCAGCTTG AAGTTTCATT TTCCCCCGGG CCCTGTCATT GAACCAACTT

12061 TAGGCCTGAA TTGAAATGAA ATGGGGTCCA TGCAAAGCCT TTTTCACAAA ATTGGCCAAC

12121 TTTTTGTGGA TGCTTTCACG GAGTTCTTGG TGTCCATTGT TGATATCATC ATATTTTTGG

12181 CCATTTTGTT TGGCTTCACC ATCGCCGGTT GGCTGGTGGT CTTTTGCATC AGATTGGTTT

12241 GCTCCGCGAT ACTCCGTACG CGCTCTGCCA TTCACTCTGA GCAATTACAG AAGATCTTAT

12301 GAGGCCTTTC TTTCCCAGTG CCAAGTGGAC ATTCCCACCT GGGGAACTAA ACATCCTTTG

12361 GGGATTCTCT GGCACCATAA GGTGTCAACC CTGATTGATG AAATGGTGTC GCGTCGAATG

12421 TACCGCATCA TGGAAAAATC AGGGCAGGCT GCCTGGAAAC AGGTGGTGAG CGAGGCTACG

12481 CTGTCTCGCA TTAGTAGTTT GGATGTGGTG GCTCATTTTC AGCATCTAGC CGCCATTGAA

12541 GCCGAGACCT GTAAATATTT GGCCTCCCGG CTGCCCATGC TACACAACCT GCGCATGACA

12601 GGTTCAAATG TAACCATAGT GTATAATAGC ACTTTGAATC AGGTGTTTGC TATTTTTCCA

12661 ACCTCTGGTT CCCGGCCAAA GCTTCATGAT TTTCAGCAAT GGTTAATAGC TGTACATTCC

12721 TCCATATTTT CCTCTGTTGC AGCTTCTTGT ACTCTTTTTG TTGTGCTGTG GTTGCGTGTT

12781 CCAATACTAC GTACTGTTTT TGGTTTCCGC TGGTTAGGGG CAATTTTTCT TTCGAACTCA

12841 CAGTGAATTA CACGGTGTGT CCACCTTGCC TCACCCGGCA AGCAGCCGCA GAGATCTACG

12901 AACCCGGTAG GTCTCTTTGG TGCAGGATAG GGTATGACCG ATGTGAGGAG GATGATCATG

12961 ACGAGCTAGG GTTTATGGTA CCGCCTGGCC TCTCCAGCGA AGGCCACTTG ACTAGTGTTT

13021 ACGCCTGGTT GGCGTTCTTG TCCTTCAGCT ACACGGCCCA GTTCCATCCC GAGATATTCG

13081 GGATAGGGAA TGTGAGTCGA GTTTATGTTG ACATCAAACA TCAACTCATC TGCGCCGAAC

13141 ATGACGGGCA GAACACCACC TTGCCTCGTC ATGACAACAT TTCAGCCGTG TTTCAGACCT

13201 ATTACCAACA TCAAGTCGAT GGCGGCAATT GGTTTCACCT AGAATGGCTT CGTCCCTTCT

13261 TTTCCTCGTG GCTGGTTTTA AATGTCTCTT GGTTTCTCAG GCGTTCGCCT GCAAACCATG

13321 TTTCAGTTCG AGTCTCGCAG ATATTGAGAC CAACACCACC GCAGCGGCAA GCTTTGCTGT

13381 CCTCCAAGAC ATCAGTTGCC TTAGGCATCG CGACTCGGCC TCTGAGGCGA TTCGCAAAAT

13441 CCCTCAGTGC CGTACGGCGA TAGGGACACC CGTGTATATT ACTATCACAG CCAATGTGAC

13501 AGATGAGAAT TATTTACATT CTTCTGATCT CCTCATGCTT TCTTCTTGCC TTTTCTATGC

13561 TTCTGAGATG AGTGAAAAGG GATTTAAGGT GGTATTTGGC AATGTGTCAG GCATCGTGGC

13621 TGTGTGTGTC AATTTTACCA GCTACGTCCA ACATGTCAAG GAGTTCACCC AACGCTCCCT

13681 GGTGGTCGAC CATGTGCGGT TGCTCCATTT CATGACACCT GAGACCATGA GGTGGGCAAC

13741 TGTTTTAGCC TGTCTTGTTG CCATTCTGTT GGCAATTTGA ATGTTTAAGT ATGTTGGAGA

13801 AATGCTTGAC CGCGGGCTGT TGCTCGCAAT TGCTTTCTTT GTGGTGTATC GTGCCGTTCT

13861 GTTTTGCTGT GCTCGCCAAC GCCAGCAGCG ACAGCAGCTC CCATCTACAG CTGATTTACA

13921 ACTTGACGCT ATGTGAGCTG AATGGCACAG ATTGGCTAGC TGACAAATTT GATTGGGCAG

13981 CGGAGAGTTT TGTCATCTTT CCCGTTTTGA CTCACATTGT CTCCTATGGT GCCCTCACTA

14041 CTAGCCATTT CCTTGACACG GTCGCTTTAG CCACTGTGTC TACCGCCGGG TTTGTTCACG

14101 GCGGGTATGT CCTAAGTAGC ATCTACGCGG TCTGTGCCCT GGCTGCGTTG ACTTGCTTCG

14161 TCATTAGGTT TGCAAAGAAT TGCATGTCCT GGCGCTACGC GTGTACCAGA TATACCAACT

14221 TTCTTCTGGA CACTAAGGGC AGACTCTATC GTTGGCGGTC GCCTGTCATC ATAGAGAAAA
```

-continued

```
14281 GGGGCAAAGT TGAGGTCGAA GGTCATCTGA TCGACCTCAA AAGAGTTGTG CTTGATGGTT
14341 CCGTGGCAAC CCCTATAACC AGAGTTTCAG CGGAACAATG GGGTCGTCCT TAGATGACTT
14401 CTGTCATGAT AGCACGGCTC CAGAAAAGGT GCTTTTGGCG TTTTCTATTA CCTACACGCC
14461 AGTGATGATA TATGCCCTAA AGGTGAGTCG CGGCCGACTG CTAGGGCTTC TGCACCTTTT
14521 GATCTTCCTG AATTGTGCTT TCACCTTCGG GTACATGACT TTCGCGCACT TTCAGAGTAC
14581 AAATAAGGTC GCGCTCACTA TGGGAGCAGT AGTTGCACTC CTTTGGGGGG TGTACTCAGC
14641 CATAGAAACC TGGAAATTCA TCACCTCCAG ATGCCGTTTG TGCTTGCTAG GCCGCAAGTA
14701 CATTCTGGCC CCTGCCCACC ACGTTGAAAG TGCCGCAGGC TTTCATCCGA TTGCGGCAAA
14761 TGATAACCAC GCATTTGTCG TCCGGCGTCC CGGCTCCACT ACGGTCAACG GCACATTGGT
14821 GCCCGGGTTA AAAAGCCTCG TGTTGGGTGG CAGAAAAGCT GTTAAACAGG GAGTGGTAAA
14881 CCTTGTCAAA TATGCCAAAT AACAACGGCA AGCAGCAGAA GAGAAAGAAG GGGGATGGCC
14941 AGCCAGTCAA TCAGCTGTGC CAGATGCTGG GTAAGATCAT CGCTCAGCAA AACCAGTCCA
15001 GAGGCAAGGG ACCGGGAAAG AAAAATAAGA AGAAAAACCC GGAGAAGCCC CATTTTCCTC
15061 TAGCGACTGA AGATGATGTC AGACATCACT TTACCCCTAG TGAGCGGCAA TTGTGTCTGT
15121 CGTCAATCCA GACCGCCTTT AATCAAGGCG CTGGGACTTG CACCCTGTCA GATTCAGGGA
15181 GGATAAGTTA CACTGTGGAG TTTAGTTTGC CTACGCATCA TACTGTGCGC CTGATCCGCG
15241 TCACAGCATC ACCCTCAGCA TGATGGGCTG GCATTCTTGA GACATCTCAG TGTTTGAATT
15301 GGAAGAATGT GTGGTAATG GCACTGATTG ACATTGTGCC TCTAAGTCAC CTATTCAATT
15361 AGGGCGACCG TGTGGGGGTG AGATTTAATT GGCGAGAACC ATGCGGCCGA AATTAAAAAA
15421 AAAAAAAAAA AAAAAAAAAA AAAA
```

The cDNA consensus sequence of PRRS strain SD 98-163 at P83 has been assigned GenBank Accession number KU131563 (SEQ. ID. NO:3). The cDNA consensus sequence designated SEQ. ID. NO: 3 is:

```
1 ATGACGTATA GGTGTTGGCT CTATGCCACG GCATTTGTAT TGTCAGGAGC TGTGACCATT
61 GGCACAGCCC AAAACTTGCT GCACGGAAAA CGCCCTTCCG TGACAGCCTT CTTCAGGGGA
121 GCTTAGGGGT CTGTCCCTAA CACCTTGCTT CTGGAGTTGC ACTGCTTTAC GGTCTCTCCA
181 ACCCTTTAAC CATGTCTGGG ATACTTGATC GGTGCACGTG CACCCCCAAT GCCAGGGTGT
241 TTATGGCGGA GGGCCAAGTC TACTGCACAC GATGTCTCAG TGCACGGTCT CTCCTTCCTC
301 TGAATCTCCA AGTTTCTGAG CTTGGAGTGC TGGGCCTATT TTATAGGCCC GAAGAGCCAC
361 TCCGGTGGAC GTTGCCACGT GCATACCCCA CTGTCGAGTG CTCCCCCGCC GGGGCCTGCT
421 GGCTTTCTGC GATCTTTCCA ATTGCACGAA TGACCAGTGG GAACCTGAAC TTTCAACAAA
481 GAATGGTGCG GGTCGCAGCT GAGATTTACA GAGTCGGTCA GCTCACCCCC ACAGTCTTGA
541 AGAATCTACA AGTTTATGAA CGGGGTTGCC GCTGGTACCC CATTGTCGGA CCTGTCCCTG
601 GAGTGGCCGT TTTCGCCAAT TCCCTACATG TGAGTGACAA ACCTTTTCCG GGAGCAACTC
661 ATGTGTTAAC TAATCTACCG CTCCCGCAGA GGCCCAAGCC TGAAGACTTT TGTCCTTTTG
721 AGTGTGCTAT GGCTGACATC TATGACATTG GTCATGACGC CGTCATGTAT GTGGCCGGAG
781 GGAAAGTCTC CTGGGCCCCT CGTGGCGGGG ATGAAGGGAA ATTTGAAACT GTCCCCGAGG
841 AGTTGAAGTT AATTGCGAAC CGACTTCACA TCTCCTTCCC GCCCCACCAC GTAGTGGACA
901 TATCTAAGTT TGCCTTTATA GCCCCCGGGA GTGGTGTCTC CATGCGGGTT GAGTGCCAAC
961 ATGGCTGCCT CCCCGCTGAT ACTGTTCCTG GAGGGAACTG CTGGTGGCGC TTGTTCGACT
```

-continued

```
1021 CGCTCCCACC GGAAGTTCAG AATAAAGAAA TTCGCTATGC TAACCAATTT GGTTATCAAA

1081 CCAAGCATGG TGTCTCTGGC AAGTACCTAC AGCGGAGGCT GCAAGTTAAT GGTCTCCGAG

1141 CAGTGACTGA TACAAGTGGG CCTATCGTCG TACAGTATTT CTCTGTTAAG GAGAGTTGGA

1201 TCCGCCACTT AAGGCTGGCG GAAGAACCTA GCCTCCCTGG GTTTGAGGAC CTCCTCAGAA

1261 TAAGGGTTGA GCCCAATACG TCACCATTGG TTGGCAAGGA TGTGAAAATC TTCCGGTTTG

1321 GCAATCACAA ATGGTACGGC GCTGGAAAGA GAGCAAGGAA ATCACGCTCT GGTGCGACTG

1381 CCACGGTCGC TCACCGCGCT TTACCCGTTC GTGAAACCCT GCAGGCTAAG AGGCGCGAGG

1441 TTGCCAGCGC CAACAGGGCT GAGCATATCA AGCACTATTA TCCGCCAGCC GACGGAAACT

1501 GTGGTTGGCA CTGCATTTCC GCTATTGTCA ACCGGATGGT GAATTCTAAA TTTGAAACTG

1561 CTCTTCCCGA GAGAGCGAGA CCTTCTGATG ACTGGGCTAC TGACGAGGAC CTTGTGAATA

1621 CCATCCAAAT CCTCAGACTC CCTGCGGCCT TGGACAGGGA CGGTGCTTGT GTTAGCGCCA

1681 AGTACGTGCT TAAACTAGAA GGCGAGCATT GGACTGTCTC TGTGACCCCT GGGATGTCCC

1741 CTTCTTTGCT CCCCCTTGAA TGTGTTCAGG GCTGTTGTGA ACATAAGAAC GGCCTTGGTC

1801 CCCCAGATGC GGTCGAAAGT TTTGGATTTG ACCCTGCCTG CCTTGACCGA CTGGCTGAGG

1861 TAATGCACTT GCCTAGTAGT GTCATCCCAG CTGCTCTGGC CGAAATGTCC GGTGACCCCA

1921 ATTGTCCGGC ATCCCCGGTC ACCACTGTGT GGACTGTTTC ACAATTCTTT GCCCGCCACA

1981 GAGGAGGAGA GCACCCTGAT CAGGTGCGCT TAGGAAAGAT CATCAGCCTT TGTCAAGTTG

2041 TTGAGGAATG CTGTTGCCAT CAGAATAAAA CCAACCGGGC CACCCCGGAA GAGGTCGCGG

2101 CAAAGATTAA TCAGTACCTC CATGGTGCAA CAAGTCTTGA AGACTGCTTG ACTAGGCTTG

2161 AGAGGGCTTG CCCGCCGAGT GCTGCGGACA CCTTCTTTGA TTGGAACGTT GTGCTCCCTG

2221 GGGTTGAGGC TGCAACTCCG CCACCCCCTC CACCAAGAGT TCAGCCTCGA AAAACAAAGT

2281 CTGTCAAGAG CTTGCCGGGA ACAATCCTG TCCCCGCTCC ACGCAGGAAG GTTAGATCTG

2341 ACTGTGGCAG CCCGATTTTG ACGGGCGACA ATGATCTTTC GACGCCATCC GAGCCGATGA

2401 CATCTCTGAA TGAGCCTGCG CTTATGCCTG CGTTGCAATG TATCTCTAGG CCAGTGACAT

2461 CTTTGAGTGT GCCGGCCCCA GTTCCTGCAC CGCGTAGAGC TGTGTCCCGA CCGGTGACGC

2521 CCTTGAGTGA GCCAGTTTTT TTGTCTGCAC CGCGACACAA ATTTCAGCAG GTGAAAGAAG

2581 CGAATCTGGT GGCAACAACG CTGATGTGCC AGGACGAACC TCTAGATTTG TCTGCATCCT

2641 CACAGACTGA ATATGAAGCT TCCCCCCCAG CACCACTGCA GAACATGGGT ATTCTGGAGG

2701 TGGGGGGACA AGAAGCTGTG GAAGTTCTGA GTGAAATCTC GGATACACTG AATGACACCA

2761 ACCCTGCACC TGTGTCATCA AGCAGCTCCC TGTCAAGTGT TAAGATCACA CGCCCAAAAT

2821 ACTCAGCTCA AGCCATCATT GATTCGGGCG GGCCCTGCAG TGGGCACCTC CGAAGGGGAA

2881 AAGAAGCATG CCTCAGCCTC ATGCGTGAGG CTTGTGATGC GGCTAAGCTT AGTGACCCTG

2941 CCACGCAAGA ATGGCTTTCT CGCATGTGGG ATAGGGTTGA CATGCTGACC TGGCGCAACA

3001 CGTCTGCCTA CCAGGCGTTT CGCATCTTAG ATGGTAGGTT TGAGTTTCTC CCAAAGATGA

3061 TACTCGAGAC ACCGCCGCCC TACCCGTGTG GGTTTGTGAT GCTGCCTCAC ACGCCTGCAC

3121 CTTCCGTGAG TGCAGAGAGC GACCTTACCA TTGGTTCAGT CGCCACTGAA GATGTTCCAC

3181 GCATTCTCGG GAAAATAGAA AACGCCGGCG AGACGCCCAA CCAGGGGCTC TTGGCACCCT

3241 TCGGGGAAGA ACCGGTGTGC GACCAACCTG TCAAAGACTC CCGGATGTTG TCGCGGGGGT

3301 TTGACGAGAG CACGACGGCT CCGTCCGCAG GTACAGGTGG CGCTGACTTA CCCACTGATT

3361 TGCCACCTTC AGATGGTGTG GATGCGGACG GGGTGGGGCT GTTACGGACG GTAAGAAAGA

3421 AAGCTGAAAG GCTCTTCGAC CAATTGAGCC GTCAGGTTTT TAACCTCGTC TCCCATCTCC
```

-continued

```
3481 CTGTTTTCTT CTCACACCTC TTCAAATCTG ACAGTGGTTA TTCTCCGGGT GATTGGGGTT
3541 TTGCAGCTTT TACTTTATTT TGCCTCTTTT TATGTTACAG CTACCCATTC TTCGGTTTCG
3601 CTCCCCTCTT GGGTGTGTTT TCTGGGTCTT CTCGGCGCGT GCGCATGGGG GTTTTTGGCT
3661 GCTGGTTGGC TTTTGCTGTT GGCCTGTTCA AGCCTGTGTC CGACCCAGTC GGCACTGCTT
3721 GTGAGTTTGA CTCGCCAGAG TGTAGGAACG TCCTTCATTC TTTTGAGCTT CTCAAACCTT
3781 GGGACCCTGT CCGCAGCCTT GTTGTGGGCC CCGTCGGTCT CGGTCTTGCC ATTCTTGGCA
3841 GGTTACTGGG CGGGGCACGC TACATCTGGC ATTTTTTCCT TAGGCTTGGC ATTGTTGCAG
3901 ATTGCTTCTT GGCTGGAGCT TATGTGCTTT CTCAAGGTAG GTGTAAAAAA TGCTGGGGAT
3961 CTTGTGTAAG AACTGCTCCT AATGAAATCG CCTTCAACGT GTTCCCTTTT ACGCGTGCGA
4021 CCAGGTCGTC ACTCATCGAC CTGTGCGATC GGTTTTGTGC GCCAAAAGGC ATGGACCCCA
4081 TTTTCCTCGC TACTGGGTGG CGTGGGTGCT GGACCGGCCG GAGTCCCATT GAGCAACCCT
4141 CTGAAAAACC TATCGCGTTC GCCCAGTTGG ATGAGAAGAG GATTACGGCT AGAACTGTGG
4201 TCGTTCAGCC TTATGATCCT AACCAAGCCG TAAAGTGCTT GCGGGTGTTA CAGGCGGGTG
4261 GGGCGATGGT GGCCGAGGCA GTCCCAAAAG TGGTCAAGGT TTCCGCCATT CCATTCCGAG
4321 CTCCCTTTTT TCCCACCGGA GTGAAGGTTG ATCCTGAGTG CAGGATCGTG GTCGACCCCG
4381 ACACTTTTAC TACAGCTCTC CGGTCTGGTT ACTCCACCAC AAACCTCGTC CTTGGTGTGG
4441 GGGACTTTGC CCAACTGAAT GGATTAAAAA TCAGGCAAAT TTCCAAGTCT TCGGGGGGAG
4501 GCCCACACCT CATTGCTGCC CTGCATGTTG CTTGCTCGAT GGCGTTGCAC ATGCTTGCTG
4561 GGGTTTATGT AACTGCAGTG GGGTCTTGCG GTACCGGCAC CAATGATCCG TGGTGCACTA
4621 ACCCATTCGC CGTCCCTGGC TACGGACCTG GCTCTCTCTG CACGTCCAGA TTGTGCATCT
4681 CCCAACATGG CCTTACCCTG CCCTTGACAG CACTTGTGGC AGGATTCGGT CTTCAGGAAA
4741 TTGCCTTAGT CGTTTTGATT TTTGTTTCCA TCGGAGGCAT GGCTCATAGG TTGAGTTGCA
4801 AGGCTGATAT GCTGTGCGTC TTACTTGCAA TCGCAAGCTA TGTTTGGGTA CCCCTTACCT
4861 GGTTGCTCTG TGTGTTTCCT TGCTGGTTGC GCTGGTTCTC TTTGCACCCT CTCACCATCC
4921 TATGGTTGGT GTTTTTCTTA ATTTCCGTAA ATATGCCTTC GGGAATCTTG GCCGTGGTGT
4981 TATTGGTTGC TCTTTGGCTT CTAGGCCGTT ATACTAATGT TGTTGGTCTT GTTACCCCCT
5041 ATGATATTCA TCATCACACC AGTGGCCCCC GCGGTGTTGC CGCCTTGGCT ACCGCACCGG
5101 ATGGGACTTA TTTGGCCGCT GTCCGCCGCG CTGCGTTGAC TGGCCGCACC GTGTTGTTTA
5161 CCCCGTCCCA GCTTGGGTCC CTCCTTGAGG GCGCTTTCAG AACTCGAAAG CCCTCACTGA
5221 ACACCGTCAA TGTGGTCGGG TCCTCTATGG GCTCTGGCGG AGTGTTCACT ATCGATGGGA
5281 AAATTAAGTG CGTGACTGCC GCACATGTCC TTACGGGTAA TTCAGCTAGG GTTTCCGGGG
5341 TTGGCTTCAA TCAAATGCTT GACTTTGATG TAAAAGGGGA CTTCGCCATA GCTGATTGCC
5401 CGAATTGGCA AGGGGCTGCT CCTAAGACCC AATTCTGCGA GGATGGGTGG ACTGGCCGTG
5461 CCTATTGGCT GACATCCTCT GGTGTCGAAC CCGGCGTCAT TGGGAATGGA TTCGCCTTCT
5521 GCTTCACCGC GTGCGGCGAT TCTGGGTCCC CAGTGATCAC CGAAGCCGGT GAGCTTGTCG
5581 GCGTTCACAC AGGATCAAAT AAACAAGGAG GAGGCATTGT TACGCGCCCC TCAGGCCAGT
5641 TTTGTAATGT GGCACCCATC AAGCTGAGCG AATTAAGTGA GTTCTTTGCT GGACCTAAGG
5701 TCCCGCTCGG TGATGTGAAG GTTGGCAGCC ACATAATTAA AGATATATGC GAGGTACCTT
5761 CAGACCTTTG CGCCTTGCTT GCCGCCAAAC CCGAATTGGA AGGAGGCCTC TCCACCGTCC
5821 AACTTTTATG TGTGTTTTTC CTCCTGTGGA GAATGATGGG ACATGCCTGG ACACCCTTGG
```

-continued

```
5881 TTGCTGTGGG TTTTTTTATC TTGAATGAAG TCCTCCCAGC TGTCCTGGTC CGGAGTGTTT

5941 TCTCCTTTGG AATGTTTGTG CTATCTTGGC TCACACCATG GTCTGCGCAA GTTCTGATGA

6001 TCAGGCTTCT AACAGCAGCT CTCAACAGGA ACAGATTGTC ACTCGCCTTT TACAGCCTTG

6061 GTGCGGCGAC CGGCTTTGTC GCAGATCTGG CGGCAACTCA AGGGCATCCG TTGCAAGCAG

6121 TAATGAATTT AAGTACCTAT GCCTTCCTGC CTCGGATGAT GGTTGTGACC TCACCAGTCC

6181 CAGTTATTGC GTGTGGTGTC GTGCACCTCC TTGCCATAAT TTTGTACTTG TTTAAGTACC

6241 GCTGCCTGCA CAATGTTCTT GTTGGCGATG GAGCGTTCTC TGCGGCTTTC TTTTTGCGAT

6301 ACTTTGCCGA GGGGAAATTG AGGGAAGGGG TGTCGCAATC CTGCGGGATG AATCATGAGT

6361 CGCTGACTGG TGCCCTCGCT ATGAGACTCA ATGACGAGGA CTTGGATTTC CTTACGAAAT

6421 GGACTGATTT TAAGTGCTTT GTTTCTGCGT CCAACATGAG GAATGCGGCG GGCCAGTTCA

6481 TCGAGGCTGC CTATGCAAAA GCACTTAGAA TTGAACTTGC CCAGTTGGTG CAGGTTGATA

6541 AGGTTCGAGG TACTATGGCC AAACTTGAAG CTTTTGCTGA TACCGTGGCA CCCCAACTCT

6601 CGCCCGGTGA CATTGTTGTT GCTCTTGGCC ATACACCTGT TGGCGGTATC TTCGACCTAA

6661 AGGTTGGTAG CACCAAGCAC ACCCTCCAAT CCATTGAGAC CAGAGTCCTT GCCGGGTCCA

6721 AAATGACCGT GGCGCGTGTC GTTGACCCAA CCCCCACACC CCCACCCGCA CCCGTGCCCA

6781 TCCCCCTCCC ACCGAAAGTT CTGGAGAATG GTCCTAACGC CTGGGGGGAT GAGGATCGTT

6841 TGAACAAGAA GAAGAGGCGC AGGATGGAAG CCGTCGGCAT CTTTGTTATG GGTGGAAAGA

6901 AATACCAGAA ATTTTGGGAC AAGAATTCCG GTGATGTGTT TTATGAGGAG GTCCATGATA

6961 ACACAGACGC GTGGGAGTGC CTCAGAGTTG ACAACCCTGC CGACTTTGAC CCTGAGAAGG

7021 GAACTCTGTG TGGGCATACT ACCATTGAAG GTAAGGCTTA CAATGTCTAC GCCTCCCCAT

7081 CTGGCAAGAA GTTTCTGGTC CCCGTCAACC CAGAGAGTGG AAGAGCCCAA TGGGAAGCTG

7141 CAAAGCTTTC CGTGGAGCAG GCCCTTGGCA TGATGAATGT CGACGGTGAG CTGACAGCCA

7201 AAGAACTGGA GAAACTGAAA AGAATAATTG ACAAACTCCA GGGTCTGACT AAGGAGCAGT

7261 GTTTAAACTG TTAGCCGCCA GCGGCTTGAC CCGCTGTGGT CGCGGCGGCT TGGTTGTTAC

7321 TGAGACAGCG GTAAAAATAG TCAAATTTCA CAACCGGACC TTCACCCTAG GACCTGTGAA

7381 CTTAAAAGTG GCCAGTGAGG TTGAGCTAAA AGACGCGGTC GAGCACAACC AACACCCGGT

7441 TGCAAGACCG GTTGATGGTG GCGTTGTACT CCTGCGCCCC GCAGTTCCTT CGCTTGTAGA

7501 TGTCTTGATC TCTGGCGCTG ATGCATCCCC TAAGTTACTC GCCCGCCATG GGCCGGGAAA

7561 CACTGGGATC GATGGCACGC TTTGGGATTT TGAGACCGAA GCCACCAAAG AGGAAATTAC

7621 ACTTAGTGCG CAAATAATAC AGGCTTGTGA CATTAGGCGC GGCGACGCAC CTGAAATTGG

7681 TCTCCCTTAT AAGCTGCACC CTGTTAGGGG CAACCCTGAG CGGATAAAAG GAGTTTTACA

7741 GAATACAAGG TTTGGGGACA TACCTTACAA AACCCCCAGT GACACTGGCA GCCCAGTGCA

7801 TGCGGCTGCC TGCCTCACGC CCAATGCCAC TCCGGTGACC GATGGGCGCT CCGTCTTGGC

7861 TACGACTATG CCCTCCGGTT TTGAGTTGTA TATACCGACC ATTCCATCGT CTGTCCTTGA

7921 TTATCTTGAT TCTAGGCCTG ACTGCCCCAA ACAGTTAACA GAGCACGGCT GTGAGGATGC

7981 CGCATTGAGA GACCTCTCCA AGTATGACTT GTCCACCCAA GGCTTTGTTT TGCCTGGAGT

8041 TCTTCGCCTA GTGCGTAAGT ACCTGTTTGC TCATGTGGGT AAGTGCCCGC CGTTCATCG

8101 GCCTTCCACT TATCCTGCCA AGAACTCTAT GGCTGGAATA AATGGGAACA GGTTTCCAAC

8161 CAAGGACATT CAGAGCATCC CTGAAATCGA CGTTCTGTGC GCACAGGCTG TGCGAGAAAA

8221 CTGGCAAACT GTTACCCCTT GCACCCTCAA GAAACAATAT TGTGGGAAGA AGAAGACTAG

8281 GACAATACTC GGCACCAATA ACTTCGTTGC GTTGGCCCAC CGGGCAGCGT TGAGTGGTGT
```

-continued

```
 8341 CACCCAGGGC TTTATGAAAA AGGCGTTTAA CTCGCCCATT GCCCTCGGGA AAAACAAATT
 8401 TAAAGAGCTA CAGACTCCGG TCTTAGGCAG GTGCCTTGAA GCTGATCTTG CATCCTGCGA
 8461 TCGGTCCACA CCTGCAATTG TCCGCTGGTT TGCCGCCAAT CTTCTTTATG AACTTGCCTG
 8521 TACTGAAGAA CATCTACCGT CGTACGTGCT GAACTGCTGC CACGACCTAC TGGTCACGCA
 8581 GTCCGGCGCG GTGACTAAGA GAGGTGGCCT GTCGTCTGGC GACCCGATTA CCTCTGTGTC
 8641 AAACACCATT TACAGCTTAG TGATATATGC ACAGCACATG GTGCTCAGTT ACTTTAAAAG
 8701 TGGTCACCCT CACGGCCTTC TGTTTCTGCA AGACCAGCTA AAGTTTGAGG ACATGCTCAA
 8761 GGTTCAACCC CTGATCGTCT ATTCGGACGA CCTCGTGCTG TATGCCGAGT CTCCCACCAT
 8821 GCCAAACTAC CACTGGTGGG TTGAACATCT GAATCTTATG TTGGGTTTTC AAACGGACCC
 8881 AAGGAAGACA GCCATAACAG ACTCACCATC TTTTCTAGGC TGTAGAATAA TAAATGGGCG
 8941 CCAGCTAGTC CCCCACCGTG ACAGGATTCT CGCGGCCCTT GCCTACCATA TGAAAGCAAG
 9001 CAATGTTTCT GAATATTACG CCTCGGCGGC TGCAATACTC ATGGACAGCT GTGCTTGTTT
 9061 AGAGTATGAT CCTGAATGGT TTGAAGAGCT CGTGGTTGGG ATGGCGCAGT GCGCCCGCAA
 9121 GGACGGCTAC AGTTTTCCTG GCCCGCCGTT CTTCTTGTCC ATGTGGGAAA AACTCAGGTC
 9181 CAACCACGAG GGAAAGAAGT CCAGAATGTG CGGGTACTGC GGGGCCCCGG CTCCGTACGC
 9241 CACTGCCTGT GGCCTCGATG TCTGTGTTTA CCACACCCAC TTCCACCAGC ATTGTCCAGT
 9301 CATAATCTGG TGTGGCCATC CGGCGGGTTC TGGTTCTTGT AGTGAGTGCA AACCCCCCCT
 9361 AGGGAAAGGC ACAAGCCCTC TGGATGAGGT GTTGAACAA GTCCCGTACA AGCCTCCGCG
 9421 GACTGTAATC ATGCATGTGG AGCAGGGTCT CACCCCTCTT GACCCAGGTA GATACCAAAC
 9481 TCGCCGCGGA TTAGTCTCCG TTAGGCGTGG CATCAGGGGA AATGAAGTTG ACCTACCAGA
 9541 CGGTGATTAT GCCAGTACCG CCCTGCTCCC TACTTGTAAA GAGATCAACA TGGTCGCTGT
 9601 CGCCTCTAAT GTGTTGCGCA GCAGGTTCAT CATCGGTCCG CCCGGTGCTG GGAAAACATA
 9661 CTGGCTCCTT CAACAGGTCC AGGATGGTGA TGTCATTTAC ACACCAACTC ACCAGACCAT
 9721 GCTTGACATG ATTAGGGCTT TGGGGGCGTG CCGGTTCAAC GTCCCAGCAG GCACAACGCT
 9781 GCAATTCCCT GCCCCCTCCC ATACCGGCCC GTGGGTTCGC ATCCTAGCCG GCGGTTGGTG
 9841 TCCTGGTAAG AATTCCTTCC TGGATGAAGC AGCGTATTGT AATCACCTTG ATGTCTTGAG
 9901 GCTCCTTAGC AAAACTACCC TCACCTGTCT AGGAGATTTC AAACAACTCC ACCCAGTGGG
 9961 TTTTGATTCT CATTGCTATG TTTTTGACAT TATGCCTCAG ACTCAACTGA AGACCATCTG
10021 GAGATTTGGA CAGAATATCT GCGATGCCAT TCAGCCAGAT TACAGGGACA AACTTGTATC
10081 CATGGTCAAC ACAACCCGTG TAACCTACTT GGAAAAACCT GTCAAGTATG GGCAAGTCCT
10141 CACCCCTTAC CACAGGGACC GAGAGGACGG CGCCATCACA ATTGACTCTA GTCAAGGCGC
10201 CACATTTGAT GTGGTTACAC TGTATTTGCC CACTAAAGAT TCACTCAACA GGCAAAGAGC
10261 CCTTGTTGCT ATCACCAGGG CAAGACATGC TATCTTTGTG TATGACCCAC ACAGGCAACT
10321 GCAGAGCATG TTTGATCTTC CCGCGAAAGG CACACCCGTC AACCTCGCTG TGCACCGTGA
10381 CGAGCAGCTG ATCGTACTAG ATAGAAACAA CAAAGAATGC TCGGTTGCTC AGGCTCTAGG
10441 CAATGGGGAT AAATTCAGGG CCACAGACAA GCGCGTTGTA GATTCTCTCC GCGCCATTTG
10501 TGCAGATCTT GAAGGGTCGA GCTCCCCGCT TCCCAAGGTC GCACACAACT TGGGATTTTA
10561 TTTCTCGCCT GATTTGACAC AGTTTGCCAA ACTCCCGGTA GAACTTGCAC CCCACTGGCC
10621 CGTGGTGACA ACACAGAACA ATGAAAAGTG GCCAGACCGG TTGGTTGCTA GCCTTCGCCC
10681 TGTCCATAAG TATAGCCGCG CGTGCATCGG TGCCGGCTAC ATGGTGGGCC CCTCAGTGTT
```

-continued

```
10741 TCTAGGCACC CCTGGGGTTG TGTCATACTA TCTCACAAAA TTTGTCAGGG GCGAGGCTCA

10801 AATGCTTCCG GAGACAGTCT TCAGCACCGG CCGAATTGAG GTAGATTGCC GGGAGTACCT

10861 TGATGACCGG GAGCGAGAAA TTGCTGAGTC CCTCCCCCAT GCTTTCATTG GTGACGTCAA

10921 AGGTACTACC GTTGGAGGAT GTCACCATGT CACCTCCAAA TACCTTCCGC GCTTCCTTCC

10981 CAAGGAATCA GTCGCGGTAG TCGGGGTTTC AAGCCCCGGG AAAGCCGCAA AGCAGTTTG

11041 CACATTAACA GATGTGTATC TCCCAGACCT TGAAGCTTAC CTCCACCCAG AGACCCAGTC

11101 CAAGTGCTGG AAAATGATGT TGGACTTCAA GGAAGTTCGA CTGATGGTCT GGAAAGGCAA

11161 GACGGCCTAT TTTCAACTTG AAGGCCGCCA TTTCACCTGG TATCAGCTTG CAAGCTACGC

11221 CTCGTACATC CGAGTACCTG TTAATTCTAC GGTGTATTTG GACCCCTGCA TGGGCCCTGC

11281 CCTTTGCAAC AGAAGAGTTG TCGGGTCCAC CCATTGGGGA GCCGACCTCG CAGTCACCCC

11341 TTATGATTAC GGTGCCAAAG TCATTCTGTC TAGTGCATAC CATGGTGAAA TGCCTCCTGG

11401 GTACAAAATC CTGGCGTGCG CGGAGTTCTC GCTTGACGAT CCAGTTAGGT ACAAACGCAC

11461 CTGGGGGTTT GAATCGGATA CAGCGTATCT GTATGAGTTC ACCGGAAACG GTGAGGACTG

11521 GGAAGACTAC AATGATGCGT TTCGTGCGCG CCAGAAAGGG AAAATTTATA AGGCCACTGC

11581 CACCAGCATG AGGTTTCATT TTCCCCCGGG CCCTGTTATT GAACCAACTT TAGGCCTGAA

11641 TTGAGATGAA ATGGGGTCTA TGCAAAGCCT CTTTAACAAA ATTGGCCAAC TTTTTGTGGA

11701 TGCTTTCACG GAATTTTTGG TGTCCATTGT TGATATCATC ATATTTTTGG CCATTTTGTT

11761 TGGCTTCACC ATCGCAGGTT GGCTGGTGGT CTTCTGCATC AGATTGGTTT GCTCCGCGGT

11821 ACTCCGTGCG CGCCCTGCCA TTCACCCTGA GCAATTACAG AAGATCCTAT GAGGCCTTTC

11881 TTTCTCAGTG CCGGGTGGAC ATTCCCACCT GGGGAACTAA ACATCCTTTG GGGATATTGT

11941 GGCACCATAA GGTGTCAACC CTGATTGATG AAATGGTGTC GCGTCGAATG TACCGCACCA

12001 TGGAAAAAGC AGGACAGGCT GCCTGGAAAC AGGTGGTGAG CGAGGCCACG TTGTCTCGC

12061 TTAGTGGTTT GGATGTGGTG GCTCATTTTC AGCATCTTGC CGCCATTGAA GCCGAGACCT

12121 GTAAATATTT GGTTTCTCGG CTGCCCATGC TACACAACCT GCGCATGACA GGGTCAAATG

12181 TAACCATAGT GTATAATAGC ACTTTAAATC AGGTGTTTGC CATTTTTCCA ACCCCTGGTT

12241 CCCGGCCAAG GCCTCATGAT TTTCAGCAAT GGCTAATAGC TGTGCATTCC TCCATATTTT

12301 CCTCTGTTGC GGCTTCTTGT ACTCTTTTTG TTGTGCTGTG GTTGCGGATC CCAATGCTAC

12361 GTACTGTTTT TGGTTTCCAC TGGTCAGGGG CAATTTTTCT TTCGAACTCA CGGTGAATTA

12421 CACGGTGTGC CCACCTTGCC TCACCCGGCA AGCAGCCGCT GAGATCTACG AATCCGGCAG

12481 GTCTCTTTGG TGCAGGATAG GGCATGACCG ATGTAGTGAG GACGATCACG ACGAACTAGG

12541 GTTCATGGTT CCGCCTGGCC TCTCCAGCGA AGGCCACTTA ACCAGTGTTT ATGCCTGGTT

12601 GGCGTTCCTG TCTTTCAGCT ACACGGCCCA ATTCCATCCC GAGATATTTG GGATAGGGAA

12661 TGTGAGTAAA GTTTATGTTG ACGTCAAGCA CCAATTCATC TGCGCCGTTC ATGACGGACA

12721 AAACACCACC TTGCCCCGCC ATGACAACAT TCAGCCGTA TTTCAGACCT ACTATCAACA

12781 TCAGGTCGAC GGCGGCAATT GGTTCCACCT AGAATGGCTG CGTCCCTTCT TTTCCTCTTG

12841 GTTAGTTTTA AATGTTTCGT GGTTTCTCAG GCGTTCGCCT GCAAGCCATG TTTCAGTTCA

12901 AGTCTTTCAG ACATCAAAAC CAACACCACT GCAGCATCAG GCTTCGTTGT CCTCCAGGAC

12961 ATCAGCTGCC TTAGGTATGG CGACTCGTCC TCTCCGACGA TTCGCAAAAG CTCTCAATGC

13021 CGCACGGCGA TAGGGACACC CGTGTATATT ACCATCACAG CCAATGTGTC AGACGAGAAT

13081 TACTTACATT CTTCAGATCT CCTCATGCTT TCTTCTTGCC TTTTCTATGC CTCTGAGATG

13141 AGTGAAAAGG GGTTCAAGGT GATATTTGGC AATGTTTCAG GCATTGTGGC TGTGTGTGTC
```

```
13201 AACTTTACCA GCTACGTCCA ACATGTTAGG GAGTTCACCC AACGCTCTCT GGCGGTCGAT

13261 CATGTGCGGC TGCTTCATTT CATGACACCT GAGACCATGA GGTGGGCAAC CGTTTTAGCC

13321 TGTCTTGTTG CCATCCTTTT GGCAATTTGA ATGTTTAAGT ATGTTGGGGA AATGCTTGAC

13381 CGCGGGCTAT TGCTCGCGAT TGCCTTTTTT GTGGTGTATC GTGCCGTTCT GTTTTGCTGT

13441 GATCGTCAAC GCCAGCAGCA ACAGCAGCTC TCATTTTCAG TCGATTTATA ACTTGACGCT

13501 ATGTGAGCTG AATGGCACAG ATTGGCTGGC TGGTAAATTT GATTGGGCAG TGGAGACTTT

13561 TGTTATCTTT CCCGTGTTGA CTCACATTGT TTCCTATGGT GCACTTACCA CCAGCCATTT

13621 CCTTGACACA GTTGGTCTGG TTATTGTGTC CACCGCCGGG TTTTATCATG GGCGGTATGT

13681 CTTGAGTAGC GTCTACGCAG TCTGTGCCCT GGCTGCGTTG ATTCGCTTTG TCATTAGATT

13741 TGCGAAGAAC TGCATGTCCT GGCGCTACTC ATGTACCAGA TATACCAACT TCCTTCTAGA

13801 TACCAAGGGC AAACTCTATC GTTGGCGGTC GCCTGTTATC ATAGAGAAAG GGGGTAAGGT

13861 TGAGGTCGAA GGTCACCTGA TCGACCTCAA AAGAGTTGTG CTTGATGGTT CCGTGGCAAC

13921 TCCTTTAACC AGAGTTTCAG CTGAACAATG GGGTCGTCCC TAGACGACTT TTGCAATGAT

13981 AGCACGGCTC CGCAAAAGGT GCTTCTGGCG TTTTCCATTA CCTACACGCC AGTGATGATA

14041 TATGCTCTGA AGGTAAGTCG CGGCCGCCTG CTAGGGCTTC TGCACCTTTT AATCTTTCTG

14101 AATTGTGCTT TCACCTTCGG GTACATGACA TTCGCGAACT TTCAGAGCAC AAACAGGGTT

14161 GCGCTCACTA TGGGAGCAGT AGTTGCACTT CTTTGGGGGG TGTACTCAGC CATAGAAACC

14221 TGGAAATTCA TCACCTCCAG ATGCCGTTTG TGCTTGCTAG GCCGCAGGTA CATTCTGGCC

14281 CCTGCCCACC ACGTCGAAAG TGTCGCAGGC TTTCATCCGA TTGCGGCAAG TGATAACCAC

14341 GCATTTGTCG TCCGGCGTCC CGGCTCCACT ACGGTTAACG GCACATTGGT GCCCGGGTTG

14401 AAAAGCCTCG TGTTGGGTGG CAGAAAAGCT GTTAAACAGG GAGTGGTAAA CCTTGTCAAA

14461 TATGCCAAAT AACAATGGCA GGCAGCAAAA AAGAAATAAG GGGACGGCC AGCCAGTCAA

14521 TCAGCTGTGT CAGATGCTGG GTAAGATCAT CGCCCAGCAA AATCAGTCCA GAGGCAGGGG

14581 ACCGGGGAAG AAAAATAAAA AGAAAACCC GGAGAAGCCC CATTTTCCTC TAGCGACCGA

14641 AGATGACGTC AGGCATCACT TCACCCCTAG TGAGCGGCAA TTGTGTCTGT CGTCGATCCA

14701 GACTGCCTTT AACCAGGGCG CTGGAACTTG TACCCTGTCA GATTCAGGGA GGATAAGTTA

14761 CACTGTGGAG TTTAGTTTGC CGACGCATCA CACTGTGCGC CTGATTCGCG CCACAGCATC

14821 ACCCTCAGCG TGATGGGCTG GCATTCTTGA AGCACCTCAG TGTTAGAATT GGAAGAATGT

14881 GTGGTGGATG GCACTGATTG ACACTGTGCC TCTAAGTCAC CTATTCAATT AGGGCGACCG

14941 TGTGGGGGTA AGTTTAATT GGCGAGAACC ATGCGGCCGA AATTAAAAAA AAAAAAAAA

15001 AAAAAAAAAA AAA
```

The cDNA consensus sequence of PRRS strain ND 99-14 at P83 has been assigned GenBank Accession number KU131562 (SEQ. ID. NO:4). The cDNA consensus sequence designated SEQ. ID. NO:4 is:

```
  1 ATGACGTATA GTTGTTGGCT CTATGTCGTG ACATTTGTAT AGTCAGGAGC TGCGACCATT

61 GGTACAGCCC AAAACTTGCT GCGCGGGAAC GCCCTTCCGT GACAGCCTTC TTCAGGGGAG

121 TTTAGGGGTC TATCCCTAGC ACCTTGCTTC CGGAGTTGCA CTGCTTTACG GTCTCTCCAC

181 CCCTTTAACC ATGTCTGGGA TACTTGATCG GTGCACGTGT ACCCCCAATG CCAGGGTGTT

241 TGTGGCGGAG GGCCAAGTCT ACTGCACACG ATGTCTCAGT GCACGGTCTC TCCTTCCTTT

301 GAATCTCCAA GTTTCTGAGC TTGGGGTGCT GGGCTTATTT TATAGGCCCG AAGAGCCGCT
```

-continued

```
 361 CCGGTGGACG TTGCCACGTG CATTCCCCAC TGTCGAGTGC TCCCCCGCCG GGGCCTGCTG

421 GCTTTCTGCG ATTTTTCCAA TTGCACGAAT GACCAGTGGA AACCTGAACT TTCAACAAAG

481 AATAGTGCGG GTCGCAGCTG AGCTCTACAG AGCCGGTCAG CTCACCCCCG TAGTCTTGAA

541 GAATCTACAG GTTTATGAAC GGGGTTGCCG TTGGTACCCC ATCGTTGGAC CTGTTCCTGG

601 AGTGGCTGTT TATGCCAATT CCTTACACGT GAGTGACAAA CCTTTCCCGG GAGCAACTCA

661 TGTGTTAACC AACCTACCGC TCCCGCAGAG GCCCAAGCCT GAAGACTTTT GCCCCTTTGA

721 GTGTGCTATG GCTGACGTCT ATGACATTGG TCATGACGCT GTCATGTATG TGGCCGGAGG

781 GAGAGTCTCC TGGGCCCCTC GTGGCGGGGA CAAAGGAAAA TTTGAAATAG TTCCCAAGGA

841 GTTGAAGTTG ATTGCGAATC GACTCCACAT TTCCTTCCCG CCCCACCACG CAGTGGACAT

901 GTCCAAGTTT GCCTTTATAA GCCCTGGGAG TGGTGTTTCC ATGCGGGTCG AGTACCAACA

961 TGGCTGTCTC CCCGCTGATA CTGTCCCTGA AGGAAACTGT TGGTGGCGCT TGTTTGACTT

1021 GCTTCCACCG GAAGTTCAGA ACAAAGAGAT TCGCCATGCT AACCAACTCG GCTATCAGAC

1081 CAAGCATGGT GTCGCTGGCA AGTACCTACA GCGGAGGCTG CAAGTTAATG GACTCCGAGC

1141 AGTAACTGAC GCGAATGGAC CTATCGTCAT ACAGTATTTT TGTGATAGGG AAAGCTGGAT

1201 CCGCCACTTA AGACTGGTAG AAGAACCTAG CCTCCCTGGG TTTGAGGACC TCCTCAGAAT

1261 AAGAGTTGAG CCCAATACGT TGCCATTGGT TGGCGAGGAT GAGAAAATCT TCCGATTTGG

1321 CAATCACAAA TGGTACGGTG CTGGAAAGAG GGCAAGGAAA GCACGCTTTG GTGCGGCTGC

1381 CACGGTCGCT CACCGCGCTT TGCCCGCTCA CGAAACCCAG CAGGCCAAGA AGCACGAAGT

1441 TACCAGCGCC AACAGGGCTG AGCATCTCGA GCACTATTCC CCGCCTACCG ACGGGAACTG

1501 TGGTTGGCAC TGCGTTTCCG CCATTGTCAA CCGGATTGTG AATTCCAAAT TTGAAACCAC

1561 CCTTCCCGAG AGAGTGAGAC CTTTAGATGA CTGGGCTACT GACGAGGATC TTGTGAATAC

1621 TATCCAAATC CTCAGGCTCC CTGCGGCCTT GGACAGGAAC GGTGCTTGTG TCGGCGCCAA

1681 GTACGTGCTC AAGCTGGAAG GTGTGCACTG GACAGTCTCT GTGGCCCCTG GGATGACCCC

1741 TTCTCTGCTC CCCCTTGAAT GTGTTCAGGG CTGTTGTGAG CATAAGAGCG GTCTTGGTCC

1801 CCCAGATGTG GCTGAAGTTT CCGGATTTGA CCCTGCCTGC CTTAACCGAC TGGCTGAGGT

1861 AATGCACTTG CCTAGTTGTG TCATCCCAGC TGCTCTGGCT GAAATGTCCG ACGACCCCAA

1921 TCGCCCGGCT TCCCCAGTCA CCACTGTGTG GACTATTTCG CAATTCTTTG CCCATTATAG

1981 AGGAGGAGAG CACCCTGATC AGGTGTGCTT AGGGAAAATC ATCAGCCTTT GTCAGGTGAT

2041 TGAGGAATGC TGTTGTTCCC AGAACAAAAC CAACCGGGCC ACCCCGGAAG AGGTCGCGGC

2101 AAAAATTGAC CAGTACCTCC GTGATGCAGC AAGCCTTGGA GAATGCTTAG CCAAGCTTGA

2161 GAGGGCTCGC CCGCCGAGCG CGATGGACAC CTCCTTTGAT TGGAATGTTG TGCTTCCTGG

2221 GGTTGAGGCG GCGAACCAGA CGACCAAACA GCTCCATGTC AACCAGCACC GTGCTCCGGT

2281 TCCTGCCATG ACTCAGGAGC CTTTGGACAA AGACTCGGTC CCTTTGACCG CCTTCTCGCT

2341 GTCTAATTGC TACTACCCTG CACAAGGTGA CGAGGTTCGT CACCGTGAGA GGCTGATCTC

2401 CGTGCTCTCT AAGTTGGAGG AGGTTGTTCG TGAGGAATAT GGGCTCACGC AACTGGATC

2461 TGGCCCGCGA CCCGCACTGC CGAACGGGCT CGACGAGCTC AAAGACCAGA TGGAAGAGGA

2521 TCTGTTGAAA CTGGTCAACG CCCAGGCAAC TTCAGAAATG ATGGCCCGGG CAGCTGAGCA

2581 GGTTGATCTA AAAGTTTGGG TCAAAAATTA CCCACGGTGG ACACCGCCAC CCCCTCCACC

2641 AAGAGTTCAG CCTCGAAAAA CAAAGTCTGC TAAGAGCCTG CCAGAGAACA AGCCTGTCCC

2701 TGCTCCGCGC AGGAAAGTCA GATCTGATTG TGGCAGCCCG ACTTTGAGGG GCAACAATGT

2761 TCCTAACGGT TGGGAAGACT TGGCCGTTGG TGGTCCTCTT GATCTTTCGA CACCATCCGA
```

-continued

```
2821 GCCGATGACA CCTCTGAGTG AGCCTGCACT TATGCCCGTG TTGCAACATA TTTCTGGACC
2881 AGTGACGCCT TTGAGCGTGC CGGCCCCTAT TCCTGCACCG CGTAAAGCTG TGTCCCGACC
2941 GATGGCGCCC TCGAGTGAGC CAATTTTTGT GTCTGCACCG CGGCAAAAAT TTCAGCAGGT
3001 GGAAGAAGCA AATCTGGCGG CAACAACGCT GACATACCAG GACGAACCTA TAGATCTGTC
3061 AGCATCCTCA CAGACTGAAT ATGAGGCTCC TTCCCTAGCA CCACTGCAGA ACATAGGTAC
3121 TCTGGAGGTG GGGGGGCAAG AAGCTGAGGA AATTCTGAGT GAAACCTCGG ATATACCGAA
3181 TGACATCAAC CCTGTGCCTG TATCATCAAG CAGCTCCTTG TCAAGCGTTA AGATCACACG
3241 CCCAAGACAC TCAGCTCAAG CCATCATCGA CTCGGGCGGG CCCTGCAGTG GGCATCTCCA
3301 AAGGGAGAAA GAAGCGTGCC TCCGCATCAT GCGTGAGGCT TGTGATGCGA CTAAGCTTAG
3361 TGACCCTGCC ACGCAGGAAT GGCTTTCTCG CATGTGGGAT AGGGTGGACA TGCTGACTTG
3421 GCGCAACACG TCTGCTTTCC AGGCGTTTCG CATCTTAGAC GGCAGGCTTG AGTTTCTTCC
3481 AAAGATGATA CTCGAGACGC CGCCGCCCTA CCCGTGTGGG TTTGTGATGC TGCCTCACAC
3541 CCCTGCACCT TCCGTGAGTG CAGAGAGCGA CCTTACCATC GGTTCAGTCG CCACTGAAGA
3601 TATTCCACGC ATCCTCGGGA AAATAGAAAA CACCAGTGAG ATGATCAACC AGGGACCCTT
3661 GGCATCCTCT GAGGAAAAAC CGGCATACAA CCAACCCGCT AAGGACTCCC TGATATCGTC
3721 GCGGGGGTTT GACGAGAGCA CAGCAGCTCC GTCCGCAGGT ACGGGTGGCG CCGGCTTGTT
3781 TACTGATTTG CCACCTTCAG ACGGTGTAGA TGCGGACGGG GGGGGCCGC TGCAGACGGT
3841 GAAAAGAAC GCTGAAAGGC TCCTCGACCG ATTGAGCCGT CAGGTTTTTA ACCTCGTCTC
3901 CCATCTCCCT GTTTTCCTCT CACACCTCTT CAAATCTGAC AGTGGTTATT CTCCGGGTGA
3961 TTGGGGTTTT GCAGCTTTTA CTCTATTTTG CCTCTTTTTA TGTTACAGCT ACCCATTCTT
4021 TGGTTTCGCT CCCCTTTTGG GTGTGTTTTC TGGGTCTTCT CGGCGCGTGC GCATGGGGGT
4081 TTTTGGCTGC TGGTTGGCTT TTGCTGTTGG TTTGTTCAAG CCTGTGTCCG ACCCAGTCGG
4141 CACTGCTTGT GAGTTTGATT CGCCAGAGTG TAGGAATGTC CTTCATTCTT TTGAGCTTCT
4201 CAAACCTTGG GACCCTGTTC GCAGCCTTGT TGTGGGCCCC GTCGGTCTCG GTCTTGCCAT
4261 TCTTGGCAGG TTACTGGGCG GGGCACGCTA CATCTGGCAT TTTCTGCTTA GGCTTGGCAT
4321 TGTTACAGAC TGTATCCTGG CTGGAGCTTA TGTGCTTTCT CAAGGTAGGT GTAAAAAGTG
4381 CTGGGGATCT TGCATAAGAA CAGCTCCTAA TGAGATTGCC TTTAACGTGT TCCCTTTTAC
4441 ACGTGCGACT AGGTCGTCAC TCATCGACCT GTGCAATCGG TTTTGTGCGC CAAAGGGCAT
4501 GGACCCTATT CTCCTCGCCA CTGGGTGGCG TGGGTGCTGG ACCGGCCGAA GCCCCATTGA
4561 ACAACCCTCT GAAAACCCA TCGCGTTTGC CCAGTTGGAC GAAAAGAGGA TTACGGCCAG
4621 GACCGTGGTC GCCCAGCCTT ATGACCCCAA CCAAGCCGTA AAGTGCTTGC GGGTGTTACA
4681 GGCGGGCGGG GCGATGGTGG CTGAGGCAGT CCCAAAAGTG GTCAAAGTTT CCGCTATTCC
4741 ATTCCGAGCC CCCTTTTTTC CCACCGGAGT GAAAGTTGAC CCTGAGTGTA GGATCGTGGT
4801 TGACCCCGAC ACTTTTACTA CAGCCCTCCG GTCCGGCTAT TCCACCACAA ACCTCGTTCT
4861 TGGTGTGGGG GACTTTGCCC AGCTGAATGG ATTAAAAATC AGGCAAATTT CCAAGCCTTC
4921 GGGAGGAGGC CCGCACCTCA TTGCTGCCCT ACATGTTGCC TGCTCGATGG CGTTGCACAT
4981 GCTTGCTGGG GTTTATGTAA CTGCAGTGGG GTCTTGCGGT ACCGGCACCA ACGATCCGTG
5041 GTGCACCAAC CCGTTTGCCG TCCCTGGCTA CGGGCCTGGT ACTCTTTGCA CGTCCAGATT
5101 GTGCATCTCC CAACATGGCC TTACCCTGCC CTTGACAGCA CTTGTGGCAG GATTCGGTCT
5161 TCAGGAAATT GCCTTGGTTG TTTTGATTTT CGTTTCCATC GGAGGCATGG CTCACAGGTT
```

```
5221 GAGTTGCAAG GCTGACATGC TGTGCGTTTT ACTTGCAATC GCCAGCTATG TTTGGGTGCC

5281 CCTTACCTGG TTTCTTTGTG TGTTTCCTTG CTGGTTGCGC TGGTTCTCTT TGCATCCCCT

5341 CACCATCCTA TGGTTGGTGT TTTTCTTGAT TTCTGTAAAT GTGCCTTCGG GAATCTTGGC

5401 TGTGGTGTTG TTAGTTTCTC TTTGGCTCTT AGGTCGTTAC ACTAATGTTG CTGGTCTTGT

5461 CACCCCATAT GACATTCATC ATCACACCAG TGGCCCCCGA GGTGTTGCCG CCTTGGCTAC

5521 TGCACCGGAT GGGACCTACT TGGCCGCCGT TCGCCGTGCT GCGTTGACCG TCGTACCAT

5581 GCTGTTTACC CCGTCTCAGC TTGGGTCCCT TCTTGAGGGT GCTTTCAGAA CTCAAAAGCC

5641 CTCACTGAAC ACCGTCAATG TGGTCGGATC CTCTATGGGC TCCGGCGGGG TGTTCACCAT

5701 CGACGGGAAA ATTAAGTGCG TAACAGCCGC ACATGTCCTT ACGGGTAATT CAGCTAGGGT

5761 TTCCGGGGTC GGCTTCAACC AAATGCTTGA TTTTGATGTG AAAGGGGACT CGCCATAGC

5821 TGATTGCCCG AATTGGCAAG GAGCTGCCCC CAAGACCCAA TTCTGCGAGG ATGGATGGAC

5881 TGGCCGTGCC TATTGGCTGA CATCCTCTGG AGTCGAACCC GGTGTCATTG GAATGGATT

5941 CGCCTTCTGC TTCACCGCGT GCGGCGATTC TGGATCCCCG GTGATTACCG AAGCCGGTGA

6001 GCTTGTCGGC GTTCACACAG GATCAAACAA ACAAGGAGGA GGCATAGTCA CACGCCCCTC

6061 AGGCCAGTTT TGTAATGTGG CGCCCATCAA GCTGAGCGAA TTGAGTGAAT TCTTCGCTGG

6121 ACCTAAGGTC CCGCTCGGTG ATGTGAAGAT TGGCAGCCAC ATAATTAAAG ACGTATGCGA

6181 GGTACCTTCA GATCTTTGCG CCTTGCTCGC TGCCAAACCC GAACTGGAAG GAGGCCTCTC

6241 CACCGTCCAA CTTCTGTGTG TGTTTTTCCT CCTGTGGAGA ATGATGGGAC ATGCCTGGAC

6301 GCCCTTGGTT GCTGTGGGGT TTTTTATCTT GAATGAGGTT CTCCCAGCTG TCCTGGTCCG

6361 GAGTGTCTTC TCCTTTGGTA TGTTTGTGCT ATCTTGGCTT ACACCATGGT CTGCGCAAGT

6421 CCTGATGATC AGGCTTCTAA CAGCAGCTCT TAACAGGAAC AGGGGGTCAC TCGCCTTCTA

6481 CAGCCTCGGT GCAGTGACCG GATTTATCGC AGATCTTGCA GCAACTCAGG GGCATCCGCT

6541 GCAGGCAGTG ATGAACTTAA GCACCTATGC CTTCCTGCCT CGGATGATGG TTGTGACCTC

6601 ACCAGTCCCA GTGCTTGCTT GTGGTGTTGT GCACCTCCTT GCCATAATTT TGTACCTGTT

6661 TAAGCACCGT TGCCTGCATT ATGTCCTTGT TGGCGATGGA GTGTTCTCTA AAGCCTTCTT

6721 CTTGCGATAC TTTGCCGAAG GGAAGTTGAG GGAAGGGGTG TCGCAGTCCT GCGGGATGAA

6781 TCACGAGTCA CTGACTGGTG CCCTCGCTAT GAGACTCAAT GACGAAGACT GGACTTCCT

6841 TACGAAATGG ACTGATTTTA AGTGCTTTGT TTCTGCGTCC AACATGAGGA ATGCAGCGGG

6901 CCAATTCATC GAGGCTGCCT ATGCAAAAGC ACTTAGAATT GAGCTTGCCC AGTTAGTACA

6961 GGTTGATAAG GTTCGAGGTA CTTTGGCCAA ACTTGAAGCC TTTGCTGATA CCGTGGCACC

7021 CCAGCTCTCG CCCGGTGACA TTGTTGTTGC TCTTGGCCAC ACGCCTGTTG GCAGTATCTT

7081 CGACCTAAAG GTTGGCAGTA CCAAGCATAC CCTCCAGGCC ATTGAGACCA GAGTCCTTGC

7141 CGGGTCCAAA ATGACCGTGG CGCGTGTCGT TGATCCAACC CCCACGCCCC CACCCGCACC

7201 CGTGCCCATC CCCTCCCAC CGAAAGTCCT GGAGAACGGC CCCAACGCCT GGGGGGATGA

7261 GGACCGGTTG AATAAGAGGA AGAGACGCAG GATGGAAGCC GTCGGCATCT TTGTTATGGG

7321 TGGGAAGAAG TACCAAAAAT TTGGGACAA GAATTCCGGT GATGTGTTTT ACGAGGAGGT

7381 CCATGATAAC ACAGATGCGT GGGAGTGCCT CAGAGTTGGT GACCCTGCCG ACTTTGACCC

7441 TGAGAAGGGA ACTCTGTGTG GCATACTAC CATTGAAGAC AAGGCTTATA ATGTCTACAC

7501 CTCCCCATCT GGCAGGAAGT TCCTGGTCCC CGTCAACCCA GAGAGCGGAA GAGCCCAATG

7561 GGAAGCTGCA AAGCTTTCCG TAGAGCAGGC CCTTAGCATG ATGAATGTCG ACGGTGAGCT

7621 GACAGCCAAA GAACTGGAGA AACTGAAAAG AATAATTGAC AAACTCCAGG GCCTAACTAA
```

-continued

```
 7681 GGAGCAGTGT TTAAACTGCT AGCCGCCAGC GGCTTGACCC GCTGTGGTCG CGGCGGCTTG

7741 GTTGTTACTG AGACAGCGGT GAAAATAGTT AAATTTCACA ACCGGACCTT CACCCTAGGA

7801 CCTGTGAATT TAAAAGTGGC CAGTGAGGTT GAGCTAAAAG ACGCAGTCGA GCATAACCAA

7861 CACCCGGTTG CAAGACCGGT TGATGGTGGT GTTGTGCTCC TGCGCTCCGC AGTTCCTTCG

7921 CTTATAGACG TCTTGATCTC TGGCGCTGAT GCATCTCCTA AGTTACTCGC CCACCACGGG

7981 CCGGGAAACA CTGGGATCGA TGGTTCGCTT TGGGATTTTG AGGCCGAGGC CACCAAAGAG

8041 GAAATTGCAC TCAGTGCGCA AATAATACAG GCTTGTGACA TTAGGCGCGG CGACGCACCC

8101 GAAATTGGTC TTCCTTATAA GCTGCACCCT GTTAGGGGCA ACCCTGAGCG GGTAAAAGGG

8161 GTTTTACAGA ATACAAGGTT TGGAGACATA CCTTATAAAA CCCCCAGTGA CACTGGGAGC

8221 CCAGTGCACG CGGCTGCCTG CCTCACGCCC AATGCCACTC CGGTGACTGA CGGTCGTTCC

8281 GTCTTGGCTA CGACCATGCC CTCCGGTTTT GAGTTGTATG TACCGACCAT TCCAGCGTCT

8341 GTCCTTGATT ATCTTGATTC CAGGCCTGAT TGCCCCAAAC AGTTGACAGA GCACGGCTGT

8401 GAGGATGCCG CATTAAGAGA CCTCTCCAAG TATGACTTGT CCACCCAAGG CTTTGTCTTG

8461 CCTGGAGTTC TTCGCCTTGT GCGTAAGTAC CTGTTTGCTC ATGTGGGTAA GTGCCCGCCT

8521 ATTCATCGGC CTTCCACTTA CCCTGCCAAG AATTCCATGG CTGGAATAAA TGGGAACAGG

8581 TTTCCAACCA AGGACATTCA GAGCGTCCCT GAAATCGACG TTTTGTGCGC ACAGGCCGTG

8641 CGAGAAAACT GGCAAACTGT TACTCCTTGT ACCCTCAAGA AGCAGTATTG CGGGAAGAAG

8701 AAGACTAGGA CAATACTCGG CACTAATAAC TTCATTGCGC TGGCCCACCG GGCAGCATTG

8761 AGTGGTGTCA CCCAGGGCTT CATGAAAAAA GCGTTTAACT CGCCCATCGC ACTCGGGAAA

8821 AACAAATTCA AGGAGCTGCA GACTCCGGTC TTGGGCAGAT GTCTTGAAGC TGACCTTGCA

8881 TCCTGTGACC GATCCACACC CGCAATTGTC CGCTGGTTTG CCGCCAATCT TCTTTATGAA

8941 CTTGCCTGTG CTGAGGAGCA TATACCATCG TACGTGTTGA ACTGCTGCCA CGACTTACTG

9001 GTCACGCAGT CCGGCGCGGT GACTAAGAGA GGTGGCCTAT CGTCTGGCGA CCCGATTACT

9061 TCTGTATCAA ACACCATTTA CAGCTTGGTG ATATATGCAC AGCACATGGT ACTCAGTTAT

9121 TTTAAAGTG GTCACCCCCA TGGCCTTCTG TTTCTACAAG ACCAGCTAAA GTTGAGGAC

9181 ATGCTCAAGG TTCAGCCCCT GATCGTCTAT TCGGACGACC TCGTGCTGTA CGCCGAGTCT

9241 CCCACCATGC CAAACTACCA CTGGTGGGTT GAACATCTGA ACCTGATGCT GGGTTTTCAG

9301 ACGGACCCAA AGAAGACAGC TATAACAGAC TCGCCATCAT TTTTGGGTTG TAGGATAATA

9361 AATGGACGCC AGTTAGTCCC CAACCGTGAC AGGATCCTCG CGGCCCTCGC CTACCATATG

9421 AAGGCAAACA ATGTTTCTGA ATACTACGCC TCGGCGGCTG CAATACTCAT GGACAGTTGT

9481 GCTTGTTTGG AGTACGATCC TGAGTGGTTT GAAGAGCTCG TGGTTGGGAT GGCGCAGTGC

9541 GCCCGCAAGG ACGGCTACAG TTTTCCTGGC CCGCCGTTCT TCTTGTCCAT GTGGGAAAAA

9601 CTCAGGTCCA ATCATGAGGG GAAGAAGTCT AGAATGTGCG GTTACTGTGG GGCCCCAGCT

9661 CCGTATGCCA CTGCCTGTGG CCTTGATGTT TGTATTTATC ACACCCACTT CCACCAGCAT

9721 TGTCCAGTCA TAATCTGGTG TGGCCATCCG GCGGGTTCTG GCTCTTGTAG TGAGTGCAAA

9781 CCCCCCCTAG GGAAAGGCAC AAGCCCTCTA GATGTGGTGT TAGAACAAGT CCCGTACAAG

9841 CCTCCACGAA CTGTAATCAT GCATGTGGAG CAGGGTCTCA CCCCTCTTGA CCCAGGCAGA

9901 TACCAGACTC GCCGCGGATT AGTCTCCGTT AGGCGTGGCA TCAGGGAAA CGAAATCGAC

9961 CTACCAGACG GTGATTATGC TAGTACCGCC TTGCTCCCCA CTTGTAAAGA TATCAACATG

10021 GTCGCTGTCG CTTCCAATGT GTTGCGCAGC AGGTTCATCA TCGGTCCACC CGGTGCTGGT
```

-continued

```
10081 AAAACATACT GGCTCCTTCA ACAGGTCCAG GATGGTGATG TCATTTACAC GCCAACTCAT

10141 CAGACCATGC TTGACATGAT CAAGGCTTTG GGGACGTGCC GGTTCAACGC CCCAGCAGGC

10201 ACAACGCTGC AATTCCCTGC TCCCTCCCGT ACCGGCCCGT GGGTTCGCAT CCTGGCCGGC

10261 GGTTGGTGTC CTGGCAAGAA TTCCTTCCTG GATGAAGCAG CGTATTGTAA TCACCTTGAT

10321 GTCTTGAGGC TTCTTAGCAA AACTACCCTC ACCTGTCTGG GAGATTTCAA ACAACTCCAC

10381 CCAGTGGGTT TTGATTCTCA TTGCTATGTT TTTGACATCA TGCCTCAGAC TCAACTGAAG

10441 ACCATCTGGA GGTTTGGACA GAATATCTGT GATGCCATTC AGCCAGATTA CAGGGACAAA

10501 CTTGTGTCCA TGGTCAACAC AACCCGTGTA ACCTACGTGG AAAGACCTGT CAAGCATGGG

10561 CAGGTCCTCA CCCCTTACCA CAGGGACCGA GAGGACGGCG CCATCACAAT TGACTCCAGT

10621 CAAGGCGCCA CATTTGATGT GGTTACATTG CATTTGCCCA CTAAAGATTC ACTCAACAGG

10681 CAAAGAGCCC TTGTTGCTAT CACCAGGGCG AGACATGCTA TCTTTGTGTA TGACCCACAT

10741 AGGCAACTGC AGAGCATGTT TGATCTTCCT GCAAAAGGCA CACCCGTCAA CCTTGCCGTG

10801 CACCGTGACG AGCAGCTGAT CGTACTAGAT AGAAATAACA AAGAGTGCAC GGTTGCTCAG

10861 GCTCTAGGCA ATGGGACAA ATTCAGGGCC ACAGACAAGC GCGTTGTAGA TTCTCTCCGC

10921 GCCATTTGTG CAGATCTTGA AGGGTCGAGC TCCCCGCTCC CCAAGGTCGC ACATAACTTG

10981 GGATTTTATT TCTCACCTGA TTTGACACAG TTTGCTAAAC TCCCGGCAGA ACTTGCACCC

11041 CACTGGCCCG TGGTGACAAC CCAGAACAAT GAAAAGTGGC CAGACAGGCT GGTTGCCAGC

11101 CTCCGCCCTA TCCATAAATA TAGCCGCGCA TGCATTGGAG CCGGCTATAT GGTGGGCCCT

11161 TCGGTGTTTC TAGGCACCCC TGGGGTTGTG TCATACTATC TCACAAAATT TGTTAAGGGG

11221 GAGGCTCAGG TGCTTCCGGA GACAGTCTTC AGCACCGGCC GAATTGAGGT AGATTGCCGG

11281 GAGTATCTTG ATGATCGGGA ACGAGAAGTT GCTGAGTCCC TCCCACATGC CTTCATTGGC

11341 GACGTCAAAG GCACTACCGT TGGGGGATGT CACCATGTCA CCTCTAAATA CCTTCCGCGC

11401 TTCCTTCCTA AGGAATCAGT TGCGGTGGTT GGGGTTTCGA GCCCCGGGAA AGCCGCAAAA

11461 GCAGTCTGCA CATTAACAGA TGTGTATCTC CCAGACCTTG AAGTTTACCT CCACCCAGAG

11521 ACCCAATCCA AGTGCTGGAA ATAATGTTG GACTTCAAGG AAGTCCGACT GATGGTCTGG

11581 AAAGACAAAA CGGCCTATTT TCAACTTGAA GGCCGCCATT TCACCTGGTA TCAGCTTGCA

11641 AGCTATGCCT CGTACATCCG AGTTCCTGTT AACTCTACGG TGTATTTGGA CCCCTGCATG

11701 GGCCCTGCCC TTTGCAACAG AAGAGTTGTC GGGTCCACTC ATTGGGGGC TGACCTCGCA

11761 GTCACCCCTT ATGATTATGG TGCCAAAATC ATTCTGTCTA GTGCATACCA TGGTGAAATG

11821 CCTCCTGGGT ACAAAATCCT GGCGTGCGCG GAGTTCTCGC TTGACGACCC AGTGAGGTAC

11881 AAACACACCT GGGGGTTTGA ATCGGACACA GCGTATCTGT ACGAGTTCAC CGGAAACGGT

11941 GAGGACTGGG AGGATTACAA TGACGCATTT CGTGCGCGCC AGAAAGGGAA AATTTATAAG

12001 GCCACTGCCA CCAGCATGAG GTTTCATTTT CCCCCGGGCC CCATCATTGA ACCAACTTTA

12061 GGCCTGAACT GAAATGAGAT GGGGGCTATG CAAAGCCTTT TCTACAAAAT TGGCCAACTT

12121 TTTGTGGATG CTTTCACGGA ATTTTTGGTG TCCATTGTTG ATATCATCAT ATTTTTGGCC

12181 ATTTTGTTTG GCTTCACCAT CGCCGGTTGG CTGGTGGTCT TCTGCATCCG ATTGGTTTGC

12241 TCCGCGGTAC TCCGTGCGCG CCCTACCATT CACCCTGAGC AATTACAGAA GATCCTATGA

12301 GGCCTTTCTT TCTCAGTGCC GGGTGGACAT TCCCACCTGG GAACCAAAC ATCCCTTGGG

12361 GATACTTTGG CACCATAAGG TGTCAACCCT GATTGATGAA ATGGTGTCGC GTCGAATGTA

12421 CCGCATCATG GAAAAATCAG GACAGGCTGC CTGGAAACAG GTTGTGAGCG AGGCTACGCT

12481 GTCTCGCATC AGTGGTTTGG ATGTGGTGGC TCATTTTCAG CATCTTGCCG CCATTGAAGC
```

```
12541 CGAGACCTGT AAATATTTGG CCTCTCGGAT GCCCATGCTA CACAACCTGC GCATGACAGG
12601 GTCAAATGTA ACCATAGTGT ATAATAGTAC TTTGAATCAG GTGTTAGCAA TCTTCCCGAC
12661 CTCTGAATCC CGGCCAAAGC TTCATGATTT TCAACAATGG TTAATAACTG TACATTCCTC
12721 CATATTTTCC TCCGTTGTGT CTTCCTGTAC TCTTTTTGTT GTGCTGTGGT TGCGAATTCC
12781 AATGCTACGT ACTGTTTTTG GTTTCCACTG GTTAGGGGCA ATTTTTCTTT CGAACTCACA
12841 GTGAATTACA CGGTGTGCCC ACCTTGCCTC ACCCGGCAAG CAGCCGCTGA GATCTACGAA
12901 CCCGGCAGGT CTCTTTGGTG CAGGATAGGG CATGATCGAT GTAGCGAGGA CGATCATGAC
12961 GAACTAGGGT TCTTGGTTCC GCCTGGCCTC TCCAGCGAAG GCCACTTGAC CAGTGTTTAC
13021 GCCTGGTTGG CGTTCCTGTC CTTCAGCTAT ACAGCCCAGT TCCATCCCGA GATATTTGGG
13081 ATAGGGAATG TGAGTAAAAT TTATGTTGAC ATCAAGCACC AATTCATCTG CGCCGAACAC
13141 GACGGGCAGA ACGCCACCCT GCCTCGCCAT GACAACATTT CAGCCGTGTT TCAGACCTAC
13201 TACCAACATC AGGTCGATGG CGGCAATTGG TTTCACCTGG AATGGCTGCG CCCCTTCTTT
13261 TCCTCTTGGT TGGTTTTAAA TGTTTCGTGG TTTCTCAGGC GTTCGCCTGC AAGCCATGTT
13321 TCAGTTCGAG TCTTTCAGAC ATCAAAACCA ACACCACCGC AGCACCAAAT TTTGTTGTCC
13381 TCCAGGACAT CAGCTGCCTT AGGCATGGCG ACCCGTCCTC TCCGGCGATT CGCAAAAGCT
13441 CTCAGTGCCG CACGGCGATA GGAACACCCG TGTATATCAC CATCACAGCC AATGTGACAG
13501 ATGAGAATTA TTTACATTCT TCTGATCTCC TCATGCTTTC TTCTTGCCTT TTCTATGCTT
13561 CTGAGATGAG TGAAAAGGGG TTCAAGGTGG TATTCGGCAA TGTGTCAGGC ATCGTGGCTG
13621 TGTGTGTCAA CTTTACCAGT TACGTCCAAC ATGTCAAGGA GTTTACCCAA CGCTCCTTGG
13681 TGGTCGAGCA TGTGCGACTG CTTCATTTCA TGACACCTGA AACCATGAGG TGGGCAACCG
13741 TTTTAGCCTG TCTTTTTGCC ATTCTGTTGG CAATTTGAAT GTTTAAGTAT GTTGGGGAAA
13801 TGCTTGACCG CGGGCTGTTG CTCGCCGTTG CTTTTTTTGT GGTGTATCGT GCCGTCTTGC
13861 TTTGTTGCGC CCGTCAACGT CGACGGGAAC GACAGCTCAA AGTTACAGCT GATTTACAAC
13921 TTGACGCTAT GTGAGCTGAA TGGCACAGAT TGGCTGGCTG GTAGATTTGA CTGGGCAGTG
13981 GAGTGTTTTG TCATTTTTCC CGTGTTGACT CACATTGTCT CCTATGGTGC CCTCACTACT
14041 AGCCATTTCC TTGACACAGT CGGTCTGGTC ACTGTGTCTG CCGCCGGGTT CCTTCATGAA
14101 CGGTATGTTT TGAGTAGCAT CTACGCGGTC TGTGCCCTGG CTGCGTTGAT TTGCTTCGTC
14161 ATTAGGCTTG CGAAGAACTG CATGTCCTGG CGCTACTCGT GTACCAGATA TACCAACTTC
14221 CTTTTGGACA CCAAGGGGAG ACTCTATCGT TGGCGATCGC CGTCATCAT AGAGAAAAAG
14281 GGTAAAGTTG AGGTTGAAGG TCATTTGATC GACCTCAAAA GAGTTGTGCT TGATGGTTCC
14341 GTGGCAACCC CTATAACCAA AATTTCAGCG GAACAATGGG GTCGTCCTTA GATGACTTCT
14401 GCCATGATAG CACGGCTCCA CAAAAGGTGC TTTTGGCGTT TTCCATTACC TATACACCAG
14461 TGATGATATA TGCCCTAAAG GTAAGTCGCG GCCGACTGCT AGGGCTTTTG CACCTTTTGA
14521 TCTTTCTGAA CTGTGCTTTC ACCTTCGGGT ATATGACATT CACGCACTTT CAGAGTACAA
14581 ACAAGGTCGC GCTCACTATG GGAGCAGTAG TTGCACTCCT TGGGGGGTG TACTCAGCCA
14641 TAGAAACCTG GAAATTCATC ACCTCCAGAT GCCGTTTGTG CTTGCTAGGC CGCAAGTACA
14701 TTCTGGCCCC TGCCCACCAC GTTGAGAGTG CCGCAGGCTT TCATCCGATT GCGGCAAATG
14761 ATAACCACGC ATTTGTCGTC CGGCGTCCCG GTTCCACTAC GGTCAACGGC ACATTGGTCC
14821 CCGGGTTGAA AAGCCTCGTG TTGGGTGGCA GAAAAGCTGT CAAACAGGGA GTGGTAAACC
14881 TTGTTAAATA TGCCAAGTAA CAACGGCAGG CAGCAGAAAA AAGAAAGGG GGATGGCCAG
```

-continued

14941 CCAGTCAATC AGCTGTGTCA GATGCTGGGT AAAATTATTG CCCAGCAAAA TCAGTCCAGG

15001 GGCAAGGGAC CGGGAAAGAA AAATAACAAG AAAAACCCGG AGAAGCCCCA TTTTCCTCTA

15061 GCGACTGAAG ATGATGTCAG ACATCACTTT ACCCCGAGTG AGCGACAATT GTGTCTGTCG

15121 TCAATCCAGA CTGCCTTCAA TCAGGGCGCT GGAACTTGTA CCCTGTCAGA TTCAGGCAGG

15181 ATAAGTTACA CTGTGGAGTT TAGTTTGCCG ACGCATCACA CTGTGCGCCT GATCCGCGCT

15241 ACAGCATCAC CCTCAGCATG ATGAGCTGGC ATTCCTGGGT ATCCCAGTGT TTGAATTGGA

15301 AGAATGTGTG GTGAATGGCA CTGATTGACA TTGTGCTTCT AAGTCACCTA TTCAATTAGG

15361 GCGACCGTGT GGGAGTAGAA TTTAATTGGC GAGAACCACG CGGCCGAAAT TAAAAAAAAA

15421 AAAAAAAAAA AAAAAAAAAA AAAA

The cDNA consensus sequence of PRRS strain SD 02-10 at P83 has been assigned GenBank Accession number KU131561 (SEQ. ID. NO:5). The cDNA consensus sequence designated SEQ. ID. NO:5 is:

1 CGCCCGGGCA TGTGTTGGCT CCATGCCACG ACATTTGTAT TGTCAGGAGC TGTGACCACT

61 GGCACAGCCC AAAGCTTGCT GCACAGAAAC ACCCTTCTGT GACAGCCTCC TTCAGGGGAG

121 TTTAGGGGTC TGTCCCTAAC ACCTTGCTTC CGGAGTTGCA CTGCTTTACG GTCTCTCCAC

181 CCTTTAACCA TGTCTGGGAT ACTTGATCGG TGCACGTGCA CCCCCAATGC CAGGGTGTTT

241 ATGGCGGAGG GCCAAGTCTA CTGCACACGA TGTCTCAGTG CACGGTCTCT CCTTCCTCTG

301 AATCTCCAAG TTTCTGAACT AGGGGTGCTA GGCCTATTTT ACAGGCCCGA AGAGCCACTC

361 CGGTGGACGT TGCCACGTGC ATTCCCCACT GTTGAGTGCT CCCCCGCCGG GGCCTGCTGG

421 CTTTCTGCAA TTTTTCCAAT TGCACGAATG ACTAGTGGAA ATCTGAACTT CCAACAAAGA

481 ATGGTACGGG TCGCAGCTGA GCTTTACAGA GCCGGCCAGC TCACCCCTGC AGTCTTAAAG

541 GCTCTACAAG TTTATGAACG GGGCTGCCGC TGGTACCCCA TTGTAGGACC TGTCCCTGGA

601 GTGGCCGTTT ACGCCAACTC CTTACATGTG AGTGATAAAC CTTTCCCGGG AGCAACTCAC

661 GTGTTAACCA ACCTACCGCT CCCGCAAAGA CCAAAACCTG AAGACTTTTG CCCCTTTGAG

721 TGTGCCATGG CTACCGTCTA TGACATCGGT CGTGACGCCG TCATGTATGT AACCGAGGGA

781 AAAGTCTCCT GGGCCCCTCG TGGTGGGGAT GAAACAAGAT TTGAAACTGT CCCCGGTGGG

841 TTGAAGTTGA TTGCGGACCA ACTCTACTCC TCCTTCCCGC CCCATCACAC GGTGGACATA

901 TCTAAGTTCG CCCTCACAGC CCCTGGGCGC GGTGTATCCA TGCGGGTTGA ACGCCAGTGT

961 GGCTGCCTCC CCGCTGACAC TGTCCCTGAA GGCAACTGTT GGTGGAGCTT ATTCGATTCA

1021 CTCCCACTGG AAGTCCAGAA CAAAGAAATT CGCCATGCTA ACCAATTTGG CTACCAAACC

1081 AAGCATGGCG TCTCCGGCAA GTACCTTCAG CGGAGGCTGC AAGTTAATGG CCTCCGAGCA

1141 GTAACTGACT TGAATGGACC TATTGTCATA CAGTACTTCT CCGTTAGAGA GAGTTGGATC

1201 CGCCACTTGA AACTGGCGGA AGAACCCGGC CTCCCTGGGT TTGAGGACCT CCTCAGAATA

1261 AGGGTTGAAC CCAACACATC GCCATTGGCT AACGAGGATG AGAAAATCTT CCGATTTGGC

1321 AGCCATAAGT GGTACGGCGC TGGGAGGAGA GCAAGGAAAG CACGCCACAG TGCAATTGCT

1381 GCGGTCGCAG GCCGCGCTTC GTCTGCTCGT GAAATCCAGC AGGCCAAGAA GCATGAGGCT

1441 GCTGACGCCA ATAAGGTTGA GCACCTCAAA CGCTACTCCC CGCCCGCCGA AGGGAATTGC

1501 GGTTGGCACT GTATTTCTGC CATCGCCAAT CGAATGGTGA ATTCTAAATT TAAAACCACC

1561 CTTCCCGAAA GAGTGAGGCC TTCAGATGAC TGGGCCACTG ATGAGGATCT TGTGAATGTC

1621 ATCCAAATCC TCAGGCTCCC TGCGGCCTTG GACAGGAACG GTGCTTGTGC CAGCGCCAAG

1681 TACGTACTTA AGCTAGAAGG TGAGCATTGG ACTGTCACTG TGACCCCTGG GATGTCCCCT

-continued

```
1741 TCTTTGCTCC CTCTTGAATG TGTTCAGGGC TGTTGTGAGC ATAAGGGCGG TCTAGGTACC
1801 CCAGATGCAG TCGAGGTTTT CGGATTTGAC CCTGCCTGCC TCAACTGGTT GGCTGAGGTG
1861 ATGCACCTGC CTAGCAGTGC TATCCCAGCC GCTCTGGCCG AAATGTCCGG TGATTCCGGT
1921 CGTTCGGCTT CCCCGGTCAC CACCGTGTGG ACCGTTTCGC AGTTCTTTGC CCGCCACAAT
1981 GGAGGGAGTC ACCCTGACCA AGTGCGTTTA GGGAAAATTA TTAGCCTTTG TCAGGTGATT
2041 GAGGACTGCT GCTGTTCCCA GAACAAAACC AACCGGGTTA CCCCGGAGGA GGTCGCAGCA
2101 AAGATTGACT TGTACCTCCG TGGAGCGACA AGTCTTGAAG AATGCTTGGC CAGGCTTGAG
2161 AAAGCTCGCC CGCCACGCGT AATGGACACC TCCTTTGATT GGGATGTTGT GCTCCCTGGG
2221 GTTGAGGCGG CAACTCAGAC GACCGAATTG CCCCAGGTCA ACCAGTGTCG TGCTTTGGTC
2281 CCTGTTGTAA CTCAAAAGTC CTTGGACAAC AACTCGGTTC CCTTGACCGC CTTTTCACTG
2341 GCTAACTACT ACTACCGTGC GCAAGGTGAA GAAGTTCGTC ACCGTGAAAG ACTAACCGCC
2401 GTGCTCTCCA AATTGGAAGG GGTTGTCCGA GAGGAATATG GGCTCATGCC AACCGGGCCT
2461 GGTCCACGGC CCACATTGCC ACGCGGGCTC GACGAACTCA AGATCAGAT GGAAGAGGAC
2521 TTGCTGAAAC TGGCTAACGC CCAGACGACT TCGGAGATGA TGGCCTGGGC AGTCGAGCAG
2581 GTCGACCTAA AAACTTGGGT CAAGAACTAC CCGCGGTGGA CACCACCACC CCCTCCGCCA
2641 AAAGTTCAGC CTCGAAAAAC GAAGTCTGCC AAGAGCTTGC TAGAGAGAAA GCCTGTCCCC
2701 GCCCCGCGCA GGAAGGTTGG GACCAATTGT GGCAGCCCGA TTTCATTGGG CGACAATATC
2761 CCTAACAGTT GGGAAGATTT GGCTGTTGGT GGCCCCTATG ATCCCCCGAC CCCACCTGAG
2821 CCGGCAACAC CTTCAGGTGA GCTGGTGGTT GTGTCCACAC CGCAATGCAT CTTCAGGCCG
2881 GCGACACCCT CGAGTGAGCC GGCTCTAATT CCCGCATCCC GCGGGCTGT GTCTCGACCG
2941 GTGACACCCT TGAGTGAGCC GATCCCTGTG CCCGCACCGC GGCGTAAGTT TCAGCAGGTG
3001 AAAAGATTGA GTTCGGCAGC GGTAACCCCG CCGTACCAGG ACGAGCCCCT AAATTTGTCT
3061 GCTTCCTCTC AAACTGAATT TGAGGCCCCC TCCCTAGCAC CGCCGCAGAG CGAGGGTGTT
3121 TTGGGAGTGA AGGGGCAGGA AGCTGAGGAG GCCCTGAGTG AAATCTCGGA CATGTCGGGC
3181 GGCATTAAAC CTGCGTCCGT ATCATCAAGC AGCTCCTTGT CCAGCGTGAG AGTCACACGC
3241 CCAAAATACT CAGCTCAAGC CATCATAGAC TTGGGCGGGC CCTGCAGTGG GCATCTCCAA
3301 GAGGTAAAGG AAGCATGCCT CGGAATCATG CGCGAGGCAT GTGATGCGAC TAAGCTTGAT
3361 GACCCTGCTA CGCAGGAATG GCTTTCCCGC ATGTGGGACC GGGTGGACAT GCTGACTTGG
3421 CGCAACACGT CTGCCTACCA GGCGTTTCGT ACCTTAGATG GCAGGTTAAA GTTCCTCCCA
3481 AAAATGATAC TCGAGACACC GCCGCCCTAT CCGTGTGAGT TTGTGATGAT GCCTCACTCG
3541 CCTGCACCTT CCGTAGGTGC GGAGAGTGAC CTTACCATTG GCTCAGTCGC TACTGAAGAT
3601 GTTCCACGTA TCCTCGAGAA AATAGAAAAT GTCGGCGAGA TGACCAACCA GGGACCCTTG
3661 GCCTTCTCCG AGGATAAACC GGTGGATGAC CAGCTTGCCA AGACCCCCG GATATCGTCG
3721 CAGAGTCCTG ACGAGAGCAC ATCAGCTCCG CCCACAGGCA CAGGAGGCGC CGGTTCATTT
3781 ACCGATTTGC CGCCTTCAGA CGGCGCGGAT GCGGACGGGG GGGGCCGTT TCGGACGATA
3841 AAAAGAAAAG CTGAAGGGCT CTTTGACCGA CTGAGCCGAC AGGTTTTTAA CCTCGTCTCC
3901 CATCTCCCTG TTTTCTTCTC ACGCCTTTTC AACCCGGGCG GTAGTTATTC TCCGGGTGAT
3961 TGGGGTTTTG CAGCTTTTAC TCTATTGTGC CTCCTTTTAT GCTACAGTTA TCCAGCATTT
4021 GGTATTGCTC CCCTCTTGGG TGTGTTTTCT GGGTCTTCTC GGCGCGTCCG AATGGGGGTT
4081 TTTGGCTGCT GGTTGGCTTT TGCTGTTGGT CTGTTCAAGC CTGTGTCCGA CCCAGTCGGC
```

```
-continued
4141  GCTGCTTGTG AGTTTGATTC GCCAGAGTGT AGAAACATCC TTCATTCTTT TGAGCTTCTC

4201  AAACCTTGGG ACCCTGTTCG CGGCCTTGTT GTGGGCCCCG TCGGTCTCGG TCTTGCCATT

4261  CTTGGCAGGT TACTGGGCGG GGCACGCTGC ATCTGGCACT TTTTGCTTAG CTTGGCATT

4321  GTTGCAGACT GTGTCTTGGC TGGAGCTTAT GTGCTTTCTC AAGGCAGGTG TAAAAAGTGC

4381  TGGGGATCTT GTATAAGAAC TGCTCCTAGT GAGGTCGCTT TTAATGTGTT TCCTTTTACA

4441  CGTGCGACCA GGTCGTCGCT TACTGACCTG TGCGATCGGT TTTGTGCGCC AAAAGGCATG

4501  GACCCCATTT TTCTCGCCAC TGGGTGGCGC GGGTGCTGGG CCGGCCGAAG CCCCATTGAG

4561  CAACCCTCTG AAAAACCCAT CGCGTTTGCC CAGTTGGATG AAAAGAAGAT TACGGCTAGG

4621  ACTGTCGTCG CCCAGCCTTA TGACCCTAAC CAAGCCGTAA AGTGCTTGCG GGTATTGCAG

4681  GCGGGTGGGG CAATGGTAGC TGAGGCAGTC CCAAAAGTTG TCAAGGTTTC CGCTGTCCCA

4741  TTCCGAGCCC CCTTCTTTCC CACCGGAGTG AAAGTTGACC CAGAATGCAG GGTTGTGGTT

4801  GACCCCGACA CTTTCACCGC AGCTCTCCGG TCTGGCTACT CCACCACAAA CCTCGTCCTT

4861  GGTACAGGGG ACTTTGCCCA GCTGAATGGA TTGAAAATCA GGCAGATTTC CAAGCCTTCA

4921  GGAGGAGGCC CACACCTCAC GGCTGCCCTG CATGTTGCTT GCTCGATGGC TTTGCACATG

4981  CTTGTTGGGA TTTATGTGAC TGCGGTGGGT TCTTGCGGCA CCGGCACCAA CGACCCGTGG

5041  TGCGCTAACC CGTTTGCCGT CCCTGGCTAC GGACCTGGCT CTCTTTGCAC GTCCAGGTTG

5101  TGCATTTCCC AACATGGCCT TACCCTGCCC TTGACAGCAC TCGTGGCGGG ATTCGGCATT

5161  CAAGAAATTG CCTTGGTCGT TTTGATTTTT GTTTCCATCG GAGGCATGGC TCACAGGTTA

5221  AGTTGCAAGG CTGACATGCT GTGTGTTTTG CTTGCAATTG CCAGCTATGT TTGGGTACCT

5281  CTTACCTGGT TGCTTTGTGT GTTTCCTTGC TGGTTGCGCT GTTTTTCTTT GCATCCCCTC

5341  ACCATCCTAT GGTTGGTTTT TTTCTTGATT TCTGTGAATA TGCCTTCAGG AATCTTGGCC

5401  ATGGTGCTGT TGGTTTCTCT TTGGCTTCTT GGTCGTTATA CTAATGTTGC TGGTCTTGTT

5461  ACCCCCTACG ACATTCATCA TTACACTAGT GGCCCCCGCG GTGTTGCCGC CTTGGCTACC

5521  GCACCAGATG GGACCTACTT GGCCGCTGTC CGCCGTGCTG CGTTAACCGG CCGTACCATG

5581  CTGTTTACCC CGTCCCAGCT TGGGTCTCTT CTTGAGGGTG CTTTCAGAAC TCGAAAACCC

5641  TCACTGAACA CCGTCAATGT GGTCGGGTCC TCCATGGGCT CTGGCGGGGT GTTCACCATT

5701  GACGAAAAA TTAAGTGCGT AACTGCCGCA CATGTCCTTA CGGGCAATTC AGCTAGGATT

5761  TCCGGGGTCG GCTTCAATCA AATGCTTGAC TTTGACGTAA AGGGAGATTT CGCCATAGCT

5821  GATTGCCCGA ATTGGCAAGG GGTTGCCCCC AAGACCCAAT TCTGCAAGGA TGGATGGACT

5881  GGCCGTGCCT ATTGGCTGAC ATCCTCTGGC GTCGAACCCG GCGTCATTGG AAAAGGATTC

5941  GCCTTCTGCT TCACTGCGTG CGGCGATTCC GGGTCCCAG TGATCACCGA GGCCGGTGAG

6001  CTTGTCGGCG TTCACACGGG ATCAAATAAA CAAGGAGGAG GCATCGTTAC GCGCCCCTCA

6061  GGCCAGTTTT GTAATGTGGC ACCCATCAAA CTAAGCGAAT TAAGTGAATT CTTTGCTGGG

6121  CCTAAGGTCC CGCTCGGTGA TGTAAAGGTT GGCAGCCACA TAATTAAAGA CATAGGCGAG

6181  GTGCCCTCAG ATCTTTGTGC CTTGCTTGCT GCCAAACCTG AACTGGAAGG GGGCCTCTCC

6241  ACCGTCCAAC TTCTTTGTGT GTTTTTCCTC CTGTGGAGGA TGATGGGACA TGCCTGGACG

6301  CCCTTGGTTG CTGTGGGTTT CTTTATCCTG AATGAGGTTC TCCCAGCCGT CCTGGTCCGG

6361  AGTGTTTTCT CCTTTGGAAT GTTTGTGCTA TCCTGGCTCA CGCCATGGTC TGCGCAAGTT

6421  CTGATGATCA GACTTCTAAC AGCAGCCCTT AACAGGAACA GATGGTCACT TGCCTTTTTC

6481  AGTCTTGGTG CAGTGACCGG TTTTGTCGCA GAATTTGCGG CTACTCAGGG GCATCCGTTG

6541  CAGGCTGTGA TGAATTTGAG CACCTATGCA TTCCTGCCTC GGATGATGGT TGTGACCTCA
```

-continued

```
6601 CCGGCCCCAG TGATCGCGTG TGGTGTCGTG CACCTACTTG CCATCATTTT GTACTTGTTT

6661 AAGTACCGCG GCCTGCACCA AATCCTTGTT GGCGACGGAG TGTTCTCTGC GGCTTTCTTC

6721 TTGCGATACT TTGCCGAGGG TAAGTTAAGG GAAGGGGTGT CGCAATCCTG TGGGATGGAT

6781 CATGAGTCTC TGACTGGTGC CCTCGCTATG AGACTCAGTG ACGAGGACTT GGATTTCCTT

6841 GCGAAATGGA CTGATTTTAA GTGCTTTGTT TCTGCGTCCA ACATGAGGAA TGCAGCGGGT

6901 CAATTTATTG AGGCTGCCTA TGCTAAAGCA CTTAGAATGG AGCTTGCCCA GTTGGTGCAG

6961 GTTGACAAAG TTCGAGGTAC TTTGGCCAAA CTCGAAGCTT TTGCTGATAC CGTGGCACCC

7021 CAGCTCTCGC CCGGTGACAT TGTTGTTGCT CTCGGCCATA CGCCTGTTGG CAGTATCTTC

7081 GACCTAAAGG TTGGTAGCAC CAAGCATACT CTCCAAGCCA TTGAGACCAG AGTCCTTGCT

7141 GGGTCCAAAA TGACCGTGGC GCGCGTCGTC AACCCGACCC CCACGCCACC ACCCGCACCC

7201 GTGCCCATCC CCCTCCCACC GAAAGTCCTG GAGAATGGCC CCAACGCTTG GGGGATGAG

7261 GACCGTTTGA ATAAGAAGAA GAGGCGCAGG ATGGAAGCCC TCGGCATCTA CGTCATGGGC

7321 GGGAAAAAGT ACCAGAAATT CTGGGACAAG AATTCCGGTG ATGTGTTTTA TGAGGAGGTC

7381 CATAATAACA TAGATGAGTG GGAGTGTCTC AGAGTTGGCG ATCCTGCCGA CTTTGACCCT

7441 GAGAAGGGAA CTCTGTGTGG ACATGTCACC ATTGAAGACA AGGCTTACCG TGTTTACGCC

7501 TCCCCATCTG GTAAGAGGTT CTTGGTCCCC GTCAACCCAG AAAATGGAAG AGTCCAATGG

7561 GAAGCTGCAA AGCTTTCTGT GGAGCAGGCC CTTGGCATGA TGAACGTCGA CGGTGAGTTG

7621 ACTGCCAAAG AACTGGAGAA ACTAAAAAGA ATAATTGACA AACTCCAGAG CCTGACTAAG

7681 GAGCAGTGTT TAAACTGCTA GCCGCCAGCG GCTTGACCCG CTGTGGTCGC GGCGGCTTGG

7741 TTGTTACTGA AACAGCGGTA AAAATAGTCA AATTTCACAA CCGGACCTTC ACCCTGGGAC

7801 CTGTGAATTT AAAAGTGGCC AGTGAGGTTG AGCTAAAAGA CGCGATTGAG CACAATCAAC

7861 ACCCGGTTGC GAGACCGGTC GATGGTGGTG TTGTGCTTCT GCGTTCCGCG GTTCCTTCGC

7921 TTATAGACGT CTTGATCTCC GGTGCTGATG CATCTCCCAA GTTACTTGCC CACCACGGGC

7981 CGGGAAACAC TGGGATCGAT GGCACGCTCT GGGATTTTGA GTCCGAAGCC ACTAAAGAGG

8041 AAGTCGCACT TAGTGCGCAA ATAATACAGG CTTGTGACAT TAGGCGCGGC GACGCCCCTG

8101 AAATTGGTCT TCCTTACAAG CTGTACCCTG TTAGGGGTAA CCCTGAGCGA GTAAAAGGGG

8161 TTCTACAAAA TACAAGGTTT GGAGACATAC CTTACAAAAC CCCCAGTGAT ACTGGAAACC

8221 CAGTGCACGC GGCTGCCTGC CTTACGCCCA ATGCCACTCC GGTGACTGAT GGGCGCTCCG

8281 TTTTGGCCAC GACCATGCCC TCCGGGTTTG AGTTGTATGT ACCAACCATA CCAGCGTCTG

8341 TCCTTGATTA CCTTGATTCC AGACCTGACT GCCCTAAACA GCTGACAGAG CACGGCTGTG

8401 AAGATGCCGC ACTAAGAGAC CTCTCCAAAT ATGACTTGTC CACCCAAGGC TTTGTTTTAC

8461 CTGGGGTTCT TCGCCTTGTA CGGAAATACC TGTTTGCCCA TGTAGGTAAG TGCCCACCCG

8521 TTCATCGGCC TTCCACTTAC CCTGCTAAGA ATTCTATGGC TGGAATAAAT GGGAACAGGT

8581 TCCCAACCAA GGATATTCAG AGCGTCCCTG AGATCGACGT TCTGTGCGCA CAGGCTGTGC

8641 GGGAAAACTG GCAAACTGTT ACCCCTTGTA CTCTTAAGAA ACAGTATTGT GGGAAGAAGA

8701 AGACTAGGAC CATACTCGGC ACAAATAACT TCATCGCGCT AGCCCACCGA GCAGCGTTGA

8761 GTGGTGTTAC CCAGGGCTTC ATGAAGAAGG CGTTTAACTC GCCCATCGCC CTCGGAAAAA

8821 ACAAGTTTAA GGAGCTACAG ACTCCGGTCC TGGGCAGGTG TCTAGAAGCT GATCTTGCAT

8881 CCTGCGACCG ATCCACACCC GCAATTGTCC GCTGGTTTGC CGCCAACCTC CTTTATGAGC

8941 TTGCCTGCGC TGAAGAGCAT CTACCGTCGT ACGTGCTAAA CTGCTGCCAC GACTTACTGG
```

-continued

```
 9001 TCACGCAGTC CGGCGCAGTG ACTAAGAGAG GTGGCCTGTC GTCTGGCGAC CCGATCACCT

9061 CTGTGTCTAA CACCATTTAC AGTTTGGTGA TCTACGCACA GCATATGGTG CTCAGTTACT

9121 TCAAAAGTGG TCACCCCCAT GGCCTCTTAT TCTTACAGGA CCAGCTAAAG TTTGAGGACA

9181 TGCTTAAGGT TCAACCCCTG ATCGTCTATT CGGACGACCT CGTGCTGTAT GCCGAGTCTC

9241 CCACTATGCC AAACTACCAC TGGTGGGTTG AGCATCTGAA TTTGATGCTG GGGTTTCAGA

9301 CGGACCCAAA GAAGACAGCC ATAACAGACT CGCCATCATT TTTGGGCTGT AGAATAATAA

9361 ATGGACGCCA GCTAGTCCCC AACCGTGACA GGATTCTCGC GGCCCTCGCC TACCACATGA

9421 AGGCGAGTAA TGTTTCTGAA TACTACGCCT CTGCGGCTGC AATACTCATG GACAGCTGTG

9481 CTTGTTTGGA GTATGATCCT GAATGGTTCG AAGAACTTGT AGTTGGAATA GCGCAATGCG

9541 CCCGCAAGGA TGGCTACAGC TTTCCCGGCC CGCCGTTCTA TATATCCATG TGGGAAAAAC

9601 TCAGATCCAA TTATGAGGGG AAGAAGTCGA GAGTGTGCGG GTACTGCGGG GCCCCGGCCC

9661 CGTATGCTAC CGCCTGTGGT CTCGACGTCT GCATTTACCA CACTCACTTC CACCAGCATT

9721 GTCCAGTCAT AATCTGGTGT GGCCATCCAG CCGGTTCTGG TTCTTGTAGT GAGTGCAGAT

9781 CCCCTGTGGG GAAAGGCACA AGCCCTTTAG ACGAGGTGCT GGAACAAGTC CCGTACAAGC

9841 CCCCACGGAC CGTTATCATG CATGTGGAGC AGGGTCTTAC CCCCCTTGAC CCAGGCAGAT

9901 ATCAGACTCG CCGCGGGTTA GTCTCCGTCA GGCGCGGGAT CAGGGGAAAT GAGGTTGAGC

9961 TACCAGACGG TGATTATGCC AGTACCGCCT TGCTCCCTAC CTGCAAAGAG ATCAACATGG

10021 TCGCTGTCGC TTCTAATGTA TTGCGCAGCA GGTTCATCAT TGGTCCACCC GGTGCGGGGA

10081 AAACATACTG GCTACTTCAA CAGGTCCAGG ATGGTGATGT TATTTACACA CCAACTCACC

10141 AGACCATGCT TGACATGATT AGAGCTTTGG GACGTGCCG GTTCAACGTC CCGGCAGGCA

10201 CAACGCTGCA ATTCCCGGTC CCCTCCCGCA CCGGTCCGTG GGTTCGCATC CTAGCCGGCG

10261 GTTGGTGTCC TGGCAAGAAT TCCTTCCTGG ATGAAGCAGC GTATTGCAAT CACCTTGATG

10321 TCTTAAGGCT TCTTAGCAAA ACTACCCTCA CCTGTCTGGG AGACTTTAAA CAACTCCACC

10381 CAGTGGGTTT TGATTCTCAT TGCTATGTTT TTGACATCAT GCCTCAAACT CAACTGAAGA

10441 CCATCTGGAG GTTTGGACAA AATATCTGTG ATGCCATCCA ACCAGATTAC AGGGACAAAC

10501 TCATGTCCAT GGTCAACATG ACCCGTGTAA CCTACGTGGA AAAACCTGTC AGGTATGGGC

10561 AAGTCCTCAC CCCCTACCAC AGGGACCGAG AGGACGACGC CATCACCATT GACTCCAGTC

10621 AAGGCGCCAC ATTTGATGTG GTTACACTGC ATTTGCCCAC TAAAGATTCA CTCAACAGGC

10681 AAAGAGCCCT TGTTGCTATC ACCAGGGCAA GACATGCTAT CTTTGCGTAT GATCCACACA

10741 GGCAGCTGCA GAGCCTGTTT GATCTTCCTG CAAAAGGTAC ACCCGTCAAC CTTGCAGTGC

10801 ACCGCGATGG GCAGCTGATC GTGCTAGATA GAAATAACAA TGAATGCACG GTTGCTCAGG

10861 CTCTAGGTAA CGGGGATAAA TTTAGGGCCA CAGACAAGCG CGTTGTAGAT TCTCTCCGCG

10921 CCATTTGTGC TGATCTAGAA GGTACGAGCT CTCCGCTCCC CAAGGTCGCA CACAACTTGG

10981 GATTTTATTT CTCACCTGAT TTAACACAGT TTGCTAAACT CCCAGCAGAA CTTGCACCTC

11041 ACTGGCCCGT GGTGACAGCC CAGAACAATG AAAAGTGGCC AGATCGGCTG GTTACTAGCC

11101 TTCGCCCTAT CCATAAATAT AGCCGCGCGT GCATCGGTGC CGGCTATATG GTGGGCCCCT

11161 CGGTGTTTCT AGGCACTCCT GGGGTCGTGT CATACTATCT CACAAAATTT GTTAAGGGCG

11221 AGGCTCAAGT GCTTCCGGAG ACGGTTTTCA GCACCGGCCG AATTGAGGTA GACTGCCGGG

11281 AATATCTTGA TGACCAGGAG CGAGAAGTTG CTGCGTCCCT CCCACATGCC TTCATTGGCG

11341 ACGTCAAAGG CACTACCGTT GGAGGGTGCC ACCATGTCAC TTCCAGATAC CTCCCGCGCT

11401 TCCTTCCCAA GGAATCAGTT GCGGTAGTCG GGGTTTCAAG TCCCGGAAAA GCCGCGAAAG
```

```
11461 CATTGTGCAC ACTAACAGAT GTGTACCTCC CAGACCTTGA AGCCTATCTC CACCCGGAGA

11521 CCCCGTCCAA GTGCTGGAGA ATGATGTTGG ACTTCAAGGA AGTTCGACTA ATGGTCTGGA

11581 AAGACAAAAC AGCCTATTTC CAACTTGAAG GTCGCTATTT CACCTGGTAT CAGCTTGCCA

11641 GCTATGCCTC GTACATCCGT GTTCCTGTCA ACTCTACGGT GTACTTGGAC CCCTGCATGG

11701 GCCCCGCCCT TTGCAACAGG AGAGTCGTCG GGTCCACTCA TTGGGGGCT GACCTTGCGG

11761 TCACCCCTTA TGATTACGGC GCTAAAATCA TCCTGTCTAG CGCGTACCAT GGTGAAATGC

11821 CCCCCGGATA CAAGATTCTG GCGTGCGCGG AATTCTCGGT GGACGACCCA GTCAAGTACA

11881 AACATACCTG GGGGTTTGAA TCGGATACAG CGTATCTGTA TGAGTTCACC GGAAACGGTG

11941 AGGACTGGGA GGATTACAAT GATGCGTTTC GTGCGCGCCA GGAAGGGAAA ATTTATAAGG

12001 CTACTGCCAC CAGCATGAAG TTTTATTTTC CCCCGGGCCC TGTCATTGAA CCAACTTTAG

12061 GCCTGAATTG AAATGAAATG GGGTCCATGC AAAGCCTTTT TAGCAAAATT GGCCAACTTT

12121 TTGTGGATGC TTTCACGGAG TTCTTGGTGT CTATTGTTGA TATCATTATA TTTTTGGCCA

12181 TCTTGTTTGG CTTCACCATC GCCGGTTGGC TGGTGGTCTT TTGCATCAGA TTGGTTTGCT

12241 CCGCGATACT CCGTGCGCGC CCTGCCATTC ACCCTGAGCA ATTACAGAAG ATCTTATGAG

12301 GCCTTTCTTT CCCAGTGCCA AGTGGACATT CCCACCTGGG GAACTAAACA CCCTTTGGGG

12361 ATGTTTTGGC ACCATAAGGT GTCAACCCTG ATTGATGAGA TGGTGTCGCG TCGAATGTAC

12421 CGCACCATGG AAAAAGCAGG ACAGGCTGCC TGGAAACAGG TGGTGAGCGA GGCTACGCTG

12481 TCTCGCATTA GTAGTTTGGA TGTGGTGGCT CATTTTCAGC ATCTTGCCGC CATTGAAGCC

12541 GAGACCTGTA AATATTTGGC CTCCCGGCTG CCCATGCTAC ATAACCTGCG CATGACAGGG

12601 TCAAATGTAA CCATAGTGTA TAATAGTACT TTAAATCAGG TGTTTGCTAT TTTCCCGACC

12661 CCTGGTTCCC GGCCAAAGCT TCATGATTTT CAGCAATGGC TAATCGCTGT ACACTCCTCC

12721 ATATTCTCCT CTGTTGCAGC TTCTTGTACT CTTTTTGTTG TGCTGTGGTT GCGGATGCCG

12781 ATGCTACGTA CTGTTTTTGG TTTCCGCTGG TTAGGGGCAA CTTTTCCTTC GAGCTCACGG

12841 TGAATTACAC GGTGTGCCCA CCTTGCCTCA CCCGGCAGGC GGCCGCACAG GCCTACGAAC

12901 CCGGTAGGTC TCTTTGGTGC AGGATAGGGT ACGATCGGTG TGGAGAGGAC GACCATGACG

12961 AGCTAGGGTT TATGGTACCG TCTGGCCTCT CCAGCGAAGG CCACTTGACC AGTGTTTACG

13021 CCTGGTTGGC GTTCTTGTCC TTCAGCTACA CAGCCCAGTT CCACCCCGAG ATATTCGGGA

13081 TAGGGAATGT GAGTCAAGTT TATGTTGACA CCAAACATCA ACTCATCTGC GCCAAACATG

13141 ACGGGCAGAA CACCACCTTG CCTCGTCATG ACAATATTTC AGCTGTGTTT CAGACCTATT

13201 ACCAACATCA AGTCGACGGC GGCAATTGGT TTCACCTAGA ATGGCTGCGT CCCTTCTTTT

13261 CCTCATGGTT GGTTTTAAAT GTCTCTTGGT TTCTCAGGCG TTCGCCTGCA AACCATGTTT

13321 CAGTTCGAGT CTTGCAGACA TTAAGACCAA CACCACCGCA GCGGCAGGCT TTGCTGTCCT

13381 CCAAGACATC AGTTGCCTTA GGCATCGCAA CTCGGCCCCT GAGGCGCTTC GCAAAATCCC

13441 TCAGTGCCGT ACGGCGATAG GGACACCTGT GTATATTACC ATCACAGCCA ATGTGACAGA

13501 TGAGAATTAT TTACATTCTT CTGATCTCCT CATGCTCTCT CTTGCCTTT TCTACGCTTC

13561 TGAGATGAGT GAAAAGGGAT TTAAGGTGGT TTTTGGCAAT GTGTCAGGCA TCGTGGCTGT

13621 GTGTGTCAAT TTTACCAGCT ACGTCCAACA TGTCAGGGAG TTTACCCAAC GCTCCTTGAT

13681 GGTCGACCAT GTGCGGCTGC TCCATTTCAT GACACCTGAG ACCATGAGGT GGGCAACCGT

13741 TTTAGCCTGT CTTGTTGCCA TTCTGTTGGC AATTTGAATG TTTAAGTATG TTGGGGAAAT

13801 GCTTGACCGC GGGCTGTTGC TCGCGATTGC TTTCTTTGTG GTGTATCGTG CCGTTCTGTT
```

-continued

```
13861 CCACTGTGCT CGTCGACGCC AACGGCAACA GCAGCTCTCA TCTGCAATTG ATTTACAACT
13921 TGACGCTATG TGAGCTGAAT GGCACGGATT GGCTAGCTAA TAGATTTGAT TGGGCAGTGG
13981 AGAGCTTTGT CATCTTTCCT GTTTTGACTC ACATAGTCTC CTATGTTGCC CTCACCACCA
14041 GCCATTTCCT TGACACAATT GCTTTAGTCA CTGTATCTAC CGCCGGTTTT CTTCACGGGC
14101 GGTATGTCCT GAGTAGCATC TACGCGGTCT GTGCCCTGGC TGCGTTGACT TGCTTCGTCA
14161 TTAGGTTTGT AAAGAATTGC ATGTCTTGGC GCTACTCATG TACCAGATAT ACCAATTTTC
14221 TTCTGGACAC TAAGGGCAGA CTCTATCGTT GGCGGTCGCC TGTCATCATA GAGAAGAGGG
14281 GCAAAGTTGA GGTCGAAGGT CATCTGATCG ATCTCAAAAG AGTTGTGCTT GATGGTTCCG
14341 TGGCAACCCC TATAACCAGA GTTTCAGCGG AACAATGGGG TCGTCCTTAG ATGACTTTTG
14401 TCATGATAGT GCGGCTCCAC AAAAGGTGCT TTTGGCATTT TCTATTACCT ACACGCCAGT
14461 GATGATATAT GCCCTAAAGG TGAGTCGCGG CCGACTGCTA GGGCTGCTGC ACCTTTTGAT
14521 TTTCCTGAAC TGTGCTTTCA CCTTTGGGTA CATGACATTC ACGCACTTTC AGAGTACAAA
14581 TAAGGTCGCG CTCACTATGG GAGCAGTAGT TGCACTCCTT TGGGGGGTGT ACTCAGCCAT
14641 AGAAACCTGG AAATTCATCA CCTCCAGATG CCGTTTGTGC TTGCTAGGCC GCAAGTACAT
14701 TCTGGCCCCT GCCCACCACG TTGAAAGTGC CGCAGGCTTT CATCCGATTG CGGCAAATGA
14761 TAACCACGCA TTTGTCGTCC GGCGTCCCGG CTCCACTACG GTCAACGGCA CATTGGTGCC
14821 CGGGTTGAAA AGCCTCGTGT TGGGTGGCAG AAAAGCTGTT AAACAGGGAG TGGTAAACCT
14881 TGTCAAATAT GCCAAATAAC AACGGCAAGC AGCAGAAGAG AAAGAAGGGG GATGGCCAGC
14941 CAGTCAATCA GCTGTGCCAG ATGCTGGGTA AGATCATCGC CCAGCAAAAC CAGTCTAGAG
15001 GCAAGGGACC GGGGAAGAAA AATAAGAAGA AAAACCCGGA GAAGCCCCAT TTTCCTCTAG
15061 CTACTGAAGA TGATGTCAGA CATCACTTTA CCCCTAGTGA GCGGCAATTG TGTCTGTCGT
15121 CAATCCAGAC TGCCTTTAAT CAAGGCGCTG GGACTTGCAC CCTGTCAGAT TCAGGGAGGA
15181 TAAGTTACAC TGTGGAGTTT AGTTTGCCTA CGCATCATAC TGTGCGCTTG ATCCGCGTCA
15241 CAGCATCACC CTCAGCATGA TGGGCTGGCA TTCTGAGGCA TCCCAGTGTT TGAATTGGAA
15301 GAATGTGTGG TGAATGGCAC TGATTGACAT TGTGCCTCTA AGTCACCTAT TCAATTAGGG
15361 CGACCGTGTG GGGGTAATAT TTAATTGGCG AGAACCACAC GGCCGAAATT AAA
```

The cDNA consensus sequence of PRRS strain SD 03-15 at P83 has been assigned GenBank Accession number KU131560 (SEQ. ID. NO:6). The cDNA consensus sequence designated SEQ. ID. NO:6 is:

```
  1 ATGATGTGTA GGGTATTCCC CCTACATACA CGACACTTCT GGTGTTTGTG TACCTTGGAG
 61 GCGTGGGTAC AGCCCCGCCC CACCCCTTGG CCCCTGTTCT AGCCCAACAG GTATCCTTCT
121 CCCTCGGGGC GAGCGCGCCG CCTACTGCTC CCTTGCAGTA GGAAGGACCT CCCGAGTATT
181 TCCGGAGAGC ACCTGCTTTA CGGGATCTCC ACCCTTTAAC CATGTCTGGG ACGTTCTCCC
241 GGTGCATGTG CACCCCGGCT GCCCGGGTAT TTTGGAACGC CGGCCAAGTC TTTTGCACAC
301 GGTGTCTCAG TGCGCGGTCT CTTCTCTCTT CAGAACTTCA GGACACTGAC CTCGGTGCAA
361 TTGGATTGTT CCACAAGCCT AGGGACAAGC TTCACTGGAA AGTCCCCATC GGCATCCCTC
421 AGGTGGAATG TACTCCATCC GGGTGCTGTT GGCTCTCAGC TATATTCCCT ATAGCACGTA
481 TGACCTCTGG CAATCATAAC TTCCTCCAAC GACTTGTTAA GGTTGCTGAT GTTTTGTACC
541 GCGACGGTTG CTTGGCACCT CGACACCTTC GTGAACTCCA AGTTTACGAG CGCGGCTGCA
601 ACTGGTACCC GATCACGGGG CCCGTACCCG GGATGGGTTT GTTTGCGAAC TCCATGCACG
661 TATCCGACCA GCCGTTCCCT GGAGCCACCC ATGTGTTGAC TAACTCGCCT CTGCCTCAAC
```

-continued

```
 721 GGGCGTGCCG GCAACCGTTC TGTCCATTTG AGGAAGCTCA TTCTAACGTG TATAGGTGGA
 781 ATAAATTTGT GATTTTCACG GACTCCACTC TCAACGGCCA ATCTCGCATG ATGTGGACGC
 841 CGGGATCCGA TGATTCAGCC GCCTTGGAGG CGCTACCGCC TGAATTAGAA CGTCAGGTCG
 901 GAATCCTCAT TCGGAGTTTC CCTGCTCATC ACCCCGTTAA CCTGGCCGAC TGGGAGCTCA
 961 CTGAGACCCC TGAGAATGGC TTCTCCTTCA GCACGTCTCA TTCTTGTGGT TATCTTGTCC
1021 AAAACCCCGA TGTGTTTGAT AGCAAGTGCT GGCTCACTTG CTTTTCGGGC CAGTCGGTCG
1081 AAGTGCGCCG CTGTGAAGAA CATTTAGCCA ACGCCCTTGG TTACCAAACC AAGTGGGGCG
1141 TGCACGGTAA GTACCTTCAG CGCAGGCTCC AAGTTCGCGG CATTCGTGCT GTAGTCGATC
1201 CTGATGGCCC CATTCACGTT GAAGCGCTGT CTTGCTCCCA GTCTTGGATC AGGCACCTGA
1261 CTCTGAATAA TGGTGTTACC CCAGGATTCG TTCGCCTGAC ATCCATTCGC ATTGTGCCGA
1321 ACACAGAGCC TACCACTTTC CGGATCTTTC GGTTTGGAGC GCATAAGTGG TATGGCGCTG
1381 CTGGCAAACG GGCTCGTGCC AAGCGTGCCG CTAAAAGTGG GAAAGATTCG GCTTCCACTC
1441 CCAAGGTTGC CCAGCCGGCC CTTACCTGTG GAGTCACCAC CTACTCTCCA CCAACAGACG
1501 GGTCTTGCGG TTGGCATGTC CTTGCCGCCA TAATGAACCG GATGATGAAC GGTGACTTCA
1561 CGTCCCCACT GCCTCAGTAC AATAGACCAG AAGACGATTG GGCTTCTGAT TATGATCTTG
1621 CTCAGGCGAT TCAATGTCTA CAACTGCCTG CAACCGTGGT TCGGAATCGT GCCTGTCCTA
1681 ACGCCAAGTA CCTTGTAAGA CTTAACGGGG TTCACTGGGA GGTAGAGGTG AGATCTGGAA
1741 TGGCTCCCCG CTCCCTTTCT CGTGAATGTG TAGTTGGCGT TTGCTCTGAA GGTTGTGTTG
1801 CTCCGCCTTA TCCAGCGGAC GGGCTTCCTA AACGCGCACT AGAGGCCTTG GCGTCTGCTT
1861 ACAGACTACC CTCCGATTGT GTTAGCTCTG GCATTGATGA CTTTCTTGCT AATCCACCCC
1921 CTCAGGAATT TTGGACTCTT GACAAAATGC TGACCTCCCC GTCACCAGAA CGGTCCGGCT
1981 TCTCTAGTTT GTATAAGTTA CTGTTAGAGG TTGTTCCGCA AAAGTGTGGT GCCACGGAAG
2041 GGGCTTTCAC CTATGCTGTT GAGAGGATGT TAAAGGATTG TCCGAGCTCT GAACAGGCCA
2101 TGGCCCTTCT GGCAAAAATT AAAGTTCCAT CCTCAAAGGC CCCGTCTGTG TCCCTGGACG
2161 GGTGTTTCCC TGCGGATATT CCGGCTGATT TCGAGCCAGC GTCTCGGGAA AGGCCCCGAA
2221 GTTCCAGCGT TGCTGTTGCC CTGTGTTCAC CGGATGCAGA AAGGTTCGAG GAAGTACCCC
2281 CAGAAGAAGT TCAAGAGAGA GGCTACAAGG CCGTCAACTC TGCACTCCTT GCCGAAAACC
2341 CCAATGATGA ACAGGCACAG GTGGTTGCCG GTGAACAACT GAAGCTCGGC GGTTGTAGTT
2401 TGGCAATCGG GAATGCTCAG TCCACTCCAG GCTCCATGGA AGAGAACATG CGCAATAGCC
2461 GGGAAGACGA ACCACTAGAT TTGTCCCTAC CAGCACTAGC TACCACGACG ACCCTTGTGA
2521 GAGAGCGAAT ACTCGACAAC CCAGGTCCTG ATGCCGGTAC CCTCCCTGCC ACCGTTCGAG
2581 AATTTGTCTC GACAGGGCCT ATGCTCCGTC ATGTTGAGCA TTGTGGCACG GAGTCTGGCG
2641 ACAGCAGTTC ACCTTTGGAT CTGTCTTATG CGCAAACTCC GGACCAGCCT TTAAATCTGT
2701 CCCTGGCCGC TTGGCCGGTG AAGACCACCG CGTCTGACCC TGGCTGGGTC CACGGTAGGT
2761 GCGAGCCTGT CTTTGTAAAG CCTCGAAAAG CTTTTTCTGA TGGCGATTCA GCCTTTCAGT
2821 TCGGGGGGCT TTCTGAGTCC AGCTCTGTCA TCGAGTTTGA CCGAACAAAA GATGCATCGG
2881 AGGTTGACGC TCCTGTCGGC TTGACGACTT CGAACGAGGC CCTCTCTGTG GTCGACCCTT
2941 TCGAATTTGC CGAACTCAAG CGCCCGCGTT TCTCCGCACA AGCCTTAATT GACCGAGGCG
3001 GCCCGCTTGC CGATGTCCAT GCAAAAATAA AGCACCGGGT GTATGAACAA TGCCTTCAAG
3061 CTTGTGAGCC TGGTAGCCGT GCAACCCCAG CCACCAAGAA GTGGCTCGAC AAAATGTGGG
```

-continued

```
3121 ACAGGGTGGA CATGAAAACT TGGCGCTGCA CCTCGCAGTT CCAAGCTGGT CGCATCCTTG

3181 CATCCCTCAA ATTCCTTCCT GACATGATTC AAGACGCACC GCCTCCTGTT CCCAGGAAGA

3241 ACCGAGCTAG TGACAACGCC GGTTTGAAGC AACTGGTGGC ACAGTGGGAT AGGAAATTGA

3301 GTGGAACCCC CCCCCCAAAA CCGGCTGGGT CAGTGCTTGA CCAGGCCGTC CCTCCACCCA

3361 CGGACGTCCA GCAAGAAGAT GTCACTCCTT CCGGCGGGCC ACTCCATGCG CCGGATTTCC

3421 CTAGTCGAGT TAGCACGAGC GGGGGTTGGA AAAGCCTTAT ACTTTCCGGG ACCCGTCTCG

3481 CAGGGTCTGT CAGTCAGCGC CTCATGACAC GGGTTTTTGA AGTTTTCTCC CATCTCCCAG

3541 CTTTTGCGCT CACACTTTTC TCGCCGCGGG GCTCTATGGC TCCAGGCGAT TGGTTGTTTG

3601 CAGGTATTGT TTTACTTGCT CTCTTGTTCT GTCGTTTTTA CCCGATACTC GGATGCCTTC

3661 CCTTATTGGG TGTCTTTTCT GGGTCTGTGC GGCGTGTTCG TCTGGGTGTT TTTGGTTCTT

3721 GGATGGCTTT TGCTGTATTT CTATTCTCGA CTCCATCCAA CCCAGTCGGT TCTTCTTGTG

3781 ACCACGATTC GCCGGAGTGT CATGCTGAGC TTTTGGTTCT TGAGCAGCGC CAACTTTGGG

3841 AACCTGTGCG CGGCCTTGTG GTCGGCCCCT CGGGCCTCCT ATGTGTCATT CTTGGCAAGT

3901 TACTCGGTGG GTCACGTTAT CTCTGGCATG TTCTCCTACG TTTATGCATG CTTACAGATT

3961 TGGCCCTTTC TCTTGTTTAT GTGGTGTCCC AGGGGCGTTG TCACAAGTGT TGGGGAAAGT

4021 GTATAAGGAC GGCTCCTGCT GAGGTAGCAC TTAATGTATT TCCTTTCTCG CGCGCCACCC

4081 GTAGCTCTCT TGTATCCTTG TGTGATCGGT TCCAAGCGCC TAAAGGAGTT GATCCTGTGC

4141 ACTTGGCAAC GGGTTGGCAC GGGTGTTGGT GTGGCGAGAG CCCCGTTCAT CAATCACACC

4201 AAAAGCCAAT AACCTATGCC AATTTGGATG AAAAGAAAAT ATCTGCCCAA ACGGTGGTTG

4261 CTGTCCCATA CGACCCCAGC CAGGCTATCA AATGCCTGAA AGTTCTGCAG GCGGGAGGGG

4321 CTATCGTAGA CCAGCCTACA CCTGAAGTTG TTCGCGTGTC CGAGGTCCCC TTCTCAGCCC

4381 CATTTTTCCC AAAAGTTCCT GTCAACCCGG ATTGCAGGAT TGTGGTGGAT TCGGACACTT

4441 TTGTGGCTGC GGTCCGCTGC GGTTACTCGA CAGCACAACT GGTCCTGGGC CGGGGCAATT

4501 TTGCCAAGCT AAATCAGACC CCCCTCAGGA GCTCTACCTC CACCAAAACG ACTGGGGGGG

4561 CCTCTTACAC CCTTGCTGTA GCTCAAGTGT CTGCGTGGAC TCTTGCCCAT TCATCCTCG

4621 GCCTTTGGTT CACATCACCT CAAGTGTGTG GCCGAGGGAC CGCTGATCCA TGGTGTTCAA

4681 ATCCCTTTTC ATACCCTGCC TATGGCCCTG GAGTTGTATG CTCCTCTCGA CTTTGTGTGT

4741 CTGCCGATGG GGTCACCCTG CCATTGTTTT CAGCTGTGGC ACAACTCTCC GGCAGAGAGG

4801 TGGGGATTTT TATTTTGGTG CTTGTCTCCC TGATAGCTTT GGCCCATCGC TTGGCTCTTA

4861 AGGCAGACTT GTTAGTGGTC TTTTTGGCTT TTTGTGCTTA CGCCTGGCCC ATGAGTTCCT

4921 GGCTAATCTG CTTCTTTCCT ATACTCTTAA AGTGGATCAC CCTCCACCCT CTCACCATGC

4981 TTTGGGTGCA CTCATTCTTG GTGTTTTGCC TGCCAGCAGC CGGCGTCCTC TCACTAGGGA

5041 TAACTGGCCT TCTTTGGGCA ATCGGCCGCT TTACCCAGGT TGCCGGGATT ATTACACCTT

5101 ATGACATCCA CCAGTACACC TCCGGCCGCC GTGGTGCAGC TGCTGTGGCC ACAGCCCCAG

5161 AAGGCACTTA TATGGCCGCC GTCCGGAGAG CTGCTTTAAC TGGGCGATCT TTAATATTCA

5221 CCCCGTCAGC AGTTGGATCC CTCCTCGAAG GTGCTTTCAG GACTCATAAA CCCTGTCTTA

5281 ATACTGTGAA TGTTGTGGGC TCTTCCCTTG GTTCCGGAGG CGTTTTCACC ATTGATGGCA

5341 GAAGAACTGT TGTCACTGCT GCTCATGTGT TGAATGGCGA CACAGCTAGA GTTACCGGCG

5401 ACTCCTACAA CCGCATGCAC ACTTTCAAGA CCAATGGTGA TTATGCCTGG TCCCATGCTG

5461 ATGACTGGCA GGGCATTGCC CCCGTGGTCA AGGTAGTGAA GGGGTACCGC GGTCGTGCTT

5521 ATTGGCAAAC ATCAACTGGT GTCGAACCCG GCATCATTGG AGAAGGGTTT GCCTTCTGTT
```

```
                           -continued
5581  TCACTAATTG TGGTGATTCG GGGTCACCCG TCATCTCAGA ATCCGGTGAT CTCATCGGAA

5641  TTCACACCGG TTCAAACAAA CTCGGTTCTG GTCTTGTGAC GACCCCTGAA GGGGAGACCT

5701  GTACCATCAA AGAAACCAAG CTCTCCGACC TTTCCAGACA TTTTGCAGGC CCTAGTGTTC

5761  CTCTTGGTGA CATTAAATTA AGCCCGGCCA TCATCCCTGA TGTAACATCT ATTCCGAGTG

5821  ACTTGGCATC GCTCCTAGCC TCTGTCCCTG TGGTGGAAGG CGGCCTCTCG ACCGTTCAAC

5881  TTCTGTGTGT CTTTTTCCTT CTCTGGCGCA TGATGGGCCA TGCCTGGACA CCCATTGTTG

5941  CCGTGGGCTT CTTTCTGCTG AATGAAATCC TCCCAGCAGT TTTGGTCCGA GCCGTGTTTT

6001  CTTTTGCACT CTTTGTGCTT GCATGGGTCA CCCCCTGGTC CGCACAGGTG TTGATGATTA

6061  GACTCCTCAC GGCATCTCTC AACCGCAACA AGCTCTCTCT GGTGTTCTAC GCACTCGGGG

6121  GTATCGTCGG TTTGGCCGCT GAAATCGGGA CTTTCGCTGG CAGATTGCCT GAATTGTCTC

6181  AAGCCCTTTC GACCTACTGT TTCTTGCCTA GGGCCCTTGC CATGGCCAGT TGTGTCCCCA

6241  TCGTCATTAT TGGCGGACTT CATGCCCTCG GTGTAATTCT GTGGTTGTTC AAATACCGGT

6301  GCCTCCACAA CACGCTGGTT GGTGATGGGT GTTTTTCAAG TGCCTTCTTC CTGCGCTATT

6361  TTGCGGAGGG CAATCTGAGG AAAGGTGTTT CACAGTCCTG TGGCATGAAT AACGAGTCTC

6421  TGACGGCTGC TCTGGCTTGC AAGCTGTCGC AGGCTGATCT TGAATTTTTG TCCAGTTTAA

6481  CGAACTTCAA GTGCTTTGTG TCTGCTTCAA ATATGAAAAA TGCCGCCGGC CAGTACATTG

6541  AAGCAGCTTA TGCCAAGGCC TTGCGCCAAG AGTTGGCCTC TCTAGTTCAG GTTGATAAAA

6601  TGAAAGGAGT TTTGTCCAAG CTCGAGGCCT TTGCTGAAAC AGCCACCCCG TCCCTTGACA

6661  CAGGTGACGT GGTTGTTTTG CTTGGGCAGC ATCCTCACGG GTCTATCCTC GATATTAATG

6721  TGGGGACTGA AAGGAAAACT GTGTCCGTGC AAGAGACCCG GAACCTAGGC GGCTCCAAAT

6781  TCAGTGTTTG CACTGTCGTG TCCAACACAC CCGTGGACGC CTTAACCGGC ATCCCACTCC

6841  GGACACCAAC CCCTCTTTTT GAGAATGGTC CGCGTCATCG CGGTGAGGAA GACGATCTCA

6901  AAGTCGAGAG GATGAAGAAA CACTGTGTAT CCCTCGGCTT CCACAACATC AATGGCAAAG

6961  TCTACTGTAA GATCTGGGAT AAGTCTACCG GTGACACCTT TTACACCGAC GATTCCCGGT

7021  ATACCCACGA CCATGCTTTT CAGGACAGGT CAGCCGACTA CAGAGACAGG GACTACGAAG

7081  GTGTGCAAAC CGCCCCCCAA CAAGGCTTTG ATCCAAAGTC TGAAACCCCT GTTGGCACTG

7141  TAGTGATCGG CGGTATCACG TATAACAGGT ACCTGATTAA AGGTAAGGAG GTCCTGGTCC

7201  CCAAGCCTGA CAACTGCCTC GAAGCTGCCA AGCTGTCCCT TGAGCAGGCT CTCGCTGGGA

7261  TGGGCCAAAC TTGCGACCTT ACGGCTGCCG AGGTGGAAAA GCTGAAGCGC ATCATTAGTC

7321  AACTCCAAGG TTTGACCACT GAACAGGCTT TAAACTGTTA GCCGCCAGCG GCTTGACCCG

7381  CTGTGGCCGC GGCGGCTTAG TAGTGACTGA AACGGCGGTA AAAATTGTAA AATATCACAA

7441  CAGAACTTTC ACCTTAGGCC CTTTTGACCT GAAAGTCACT ACCGAGGCAG AGGTCAAGAA

7501  ATCAGCTGAG CAGGGCCACG CTGTTGTGGC AAATTTATGT TCTGGTGTCG TCTTGATGAG

7561  ACCTCACCCA CCGTCTCTTG TTGACGTTCT TTTGAAACCC GGACTTGACA CAAAACCCGG

7621  CATTCAGCCA GGGCATGGGG CCGGGAATAT GGGCGTGGAA GGTTCTATTT GGGATTTCGA

7681  AACCGCACCT ACAAAGGCAG AACTCGAGTT ATCCAAGCAA ATAATTCAAG CATGTGAAGT

7741  TAGGCGCGGG GACGCCCCGA ACCTCCAACT CCCTTACAAG CTCTATCCTG TTAGGGGGGA

7801  TCCTGAGCGG CATGAGGGCC GCCTTATCAA CACCAGGTTT GGAGATTTAT CTTACAAAAC

7861  TCCTCAAGAC ACCAAGTCCG CAATCCACGC GGCTTGTTGC CTGCACCCCA ACGGGGCCCC

7921  CGTGTCTGAT GGTAAATCAA CACTAGGTAC CACTCTTCAA CATGGTTTTG AGCTTTACGT
```

-continued

```
7981  CCCTACTGTG CCTTATAGTG TCATGGAGTA CCTCGATTCA CGCCCTGACA CCCCTTTTAT
8041  GTGCACCAAA CATGGCACTT CCAAGGCTGC TGCAGAGGAC CTTCAAAAAT ACGACCTGTC
8101  CACTCAAGGC TTCGTCCTGC CTGGGGTCCT ACGCCTAGTA CGTAGATACA TTTTTGGCCA
8161  TATTGGTAAG GCGCCGCCAT TGTTCCTCCC ATCAACCTAT CCCGCCAAGA ACTCTATGGC
8221  AGGGATCAAT GGCCAGAGAT TCCCAACAAA GGACGTTCAG AGCATACCTG AAATTGATGA
8281  AATGTGTGCC CGCGCCGTCA AAGAGAATTG GCAAACTGTG ACACCTTGTA CCCTCAAGAA
8341  ACAGTATTGT TCCAAGCCCA AAACCAGGAC CATCCTAGGC ACTAACAACT TTATTGCCTT
8401  GGCTCACAGA TCGGCGCTCA GTGGTGTTAC CCAGGCATTC ATGAAGAAGG CTTGGAAGTC
8461  CCCAATTGCC TTGGGAAAAA ACAAATTCAA GGAGCTGCAT TGCACCGTCG CCGGCAGGTG
8521  TCTTGAGGCT GACTTGGCCT CCTGTGACCG CAGCACCCCC GCCATTGTGA GATGGTTCGT
8581  CGCCAACCTC CTGTATGAAC TTGCGGGATG TGAAGAGTAC TTGCCTAGCT ATGTACTTAA
8641  TTGCTGCCAT GACCTTGTGG CAACACAGGA TGGTGCCTTC ACAAAACGCG GTGGCCTGTC
8701  GTCCGGGGAC CCCGTCACCA GTGTGTCTAA CACCGTATAT TCGCTGGTAA TCTATGCCCA
8761  GCACATGGTG TTGTCAGCCT TGAAAATGGG TCATGAAATC GGTCTTAAGT TCCTCGAGGA
8821  ACAGCTCAGA TTCGAGGACC TCCTCGAAAT TCAGCCTATG TTGGTATACT CTGATGACCT
8881  CGTTTTGTAC GCTGAAAGAC CCACTTTTCC TAATTATCAC TGGTGGGTCG AGCACCTTGA
8941  CCTAATGCTG GGTTTTAAAA CGGACCCAAA GAAGACCGTC ATAACTGATA AACCCAGCTT
9001  CCTCGGCTGC AGAATTGAGG CAGGGCGGCA GCTGGTCCCC AATCGCGACC GCATCCTGGC
9061  TGCTCTCGCA TATCACATGA AGGCGCAGAA TGCCTCAGAG TATTATGCGT CTGCTGCCGC
9121  AATCCTGATG GATTCATGCG CTTGCATTGA TCATGACCCC GAGTGGTATG AGGACCTCAT
9181  CTGCGGTATT GCCCGATGCG CCCGCCAAGA TGGTTATAGC TTCCCAGGTC CGGCGTTTTT
9241  CATGTCTATG TGGGAGAGGC TGAGAAGTCA CAATGAAGGG AAGAAATTCC GCCACTGCGG
9301  CATCTGTGAC GCCAAAGCCG ACTATGCATC CGCCTGTGGG CTCGATCTAT GTTTGTTCCA
9361  CTCGCACTTT CATCAACACT GTCCCGTCAC TCTGAGCTGC GGTCACCATG CCGGTTCAAG
9421  GGAATGTTCG CAGTGTCAGT CACCTGTTGG GGCTGGCAGA TCCCCTCTTG ATGCTGTGTT
9481  GAAACAAATT CCATACAAAC CTCCCCGCAC TGTCATCATG AAGGTGAGTA ACAAAACAAC
9541  GGCCCTCGAT CCGGGGAGGT ACCAGTCCCG TCGAGGCCTC GTTGCAGTCA AGAGAGGTAT
9601  CGCCGGCAAT GAAGTTGATC TTTCTGATGG AGACTACCAA GTGGTACCTC TTTTGCCGAC
9661  TTGCAAAGAC ATAAACATGG TGAAAGTGGC TTGCAATGTA CTACTCAGTA AGTTCATAGT
9721  GGGGCCACCA GGTTCCGGAA AGACCACCTG GCTACTAGAT CAAGTCCAAG ACGATGATGT
9781  CATTTACACA CCAACCCATC AGACTATGTT TGATATAGTT AGTGCTCTCA AAGTTTGCAG
9841  GTACTCTATT CCAGGAGCCT CAGGACTCCC TTTCCCACCA TCTGCCAGAT CCGGGCCGTG
9901  GGTTAGGCTT ATAGCCAGTG GGCACGTCCC TGGCCGCGTA TCTTACCTCG ATGAGGCCGG
9961  ATACTGTAAT CATCTGGACA TTCTCAGATT GCTCTCCAAA ACGCCCCTTG TGTGTTTGGG
10021 TGACCTTCAA CAGCTACACC CTGTCGGCTT TGATTCCTAC TGTTATGTGT TTGATCAGAT
10081 GCCCCAGAAG CAACTGACCG TTATTTACAG ATTTGGCCCT AACATCTGCG CGGCCATTCA
10141 GCCTTGTTAC AGAGAGAAGC TTGAATCCAA GGCTAGAAAC ACCAGGGTGG TTTTTGTCAA
10201 CCGGCCTGTG GCCTTTGGTC AGGTCCTGAC ACCATACCAT AAAGATCGCA TCGGCTCTGC
10261 GGTAACCATA GACTCATCCC AGGGAGCCAC CTTTGATATT GTGACACTGC ATCTACCGTC
10321 ACCAAAGTCC CTAACCAAAT CCCGAGCACT TGTGGCCATC ACTCGGGCAA GACACGGGTT
10381 GTTCATTTAT GACCCACATG ACCAGCTCCA GGAGTTTTTC AACTTAATCC CTGAGCTCAC
```

```
10441 AGATTGCAAC CTTGTGTTTA ACCGCGGGA TGAGCTGGTA GTTCTGGATT CGGATAATGC

10501 AGTCACAACT GTAGCAAAGG CCCTAGAAAC AGGTCAATCT CGATTCCGAG TGTCAGACCC

10561 GAGGTGCAAG TCTCTCTTGG CCGCTTGTTC GGCCAGTCTG GAAGGGAGCT GTATGCCACT

10621 ACCGCAAGTA GCACATAATC TGGGGTTTTA CTTTTCCCCA GACAGTCCAG TATTTGCACC

10681 TCTGCCAAGA GAGTTGGCGT CACATTGGCC AGTGGTTACC CACCAGAATA ATCGGGCGTG

10741 GCCTGATCGA CTTGTCGCTA GTATGCGCCC AATCGATGCC CGCTACAGCA AGCCGATGGT

10801 CGGTGCAGGG TACGTAGTCG GGCCGTCCAC TTTTCTTGGT ACTCCCGGTG TGGTGTCATA

10861 CTACCTCACG CTATACATCA GGGGTGAGCC CCAGGCCCTG CCAGAAACAC TCGTTTCAAC

10921 GGGGCGTATA GCAACAGATT GTCGGGAGTA TCTCGATGCG GCTGAGGAGG AGGCAGCAAA

10981 AGAACTCCCC CACGCATTCA TTGGCGATGT CAAAGGTACC ACGGTGGGGG GTTGTCATCA

11041 CATCACGTCA AAATACTTAC CTAGGTCCCT GCCTAAAGAC TCTGTTGCCG TAGTTGGAGT

11101 GAGTTCACCC GGCAGGGCTG CTAAAGCCAT GTGCACCGTC ACCGATGTGT ATCTCCCTGA

11161 ACTCCGGCCG TATCTGCAAC CTGAGACGGC ATCAAAGTGC TGGAAACTTA AATTAGACTT

11221 CAGGGACGTC CGACTAATGG TCTGGAAAGG AGCTACCGCC TATTTCCAGT TGGAAGGGTT

11281 TACATGGTCG GCGCTGCCCG ACTATGCCAG GTTCATTCAG CTGCCCAAGG ATGCCGTTGT

11341 ATACATCGAT CCGTGTATAG GACCGGCAAC AGCCAACCGC AAGGTCGTGC GAACCACAGA

11401 CTGGCGGGCC GACCTGGCAG TGACACCGTA TGACTACGGT GCCCAGACTA TTTTAACAAC

11461 AGCCTGGTTC GAGGACCTCG GGCCACAGTG GAAGATTTTG GGGTTGCAGC CCTTTAGGCG

11521 AGCACTTGGT CTGGAAAACA CTGAGGATTG GGCAATTCTT GCACGCCGTA TGAATGACGG

11581 CAAAGACTAC ACTGACTATA ACTGGAATTG TGTTCGAGGA CGCCCACAAG CCATCTACGG

11641 GCGTGCTCGT GACCATACGT ATCATTTCGC CCCCGGCACG GAACTGCAGG TAGAGCTAGG

11701 TAAACCCCGG CTATCGCCTG AGCAGGTGCC GTGAATTTGG AGTGATGCAA TGGGGTCACT

11761 GTGGAGTAAA ATCAGCCAGC TGTTCGTGGA TGCCTTCACT GAGTTCTTGG TTAGTGTGGT

11821 TGATATTGTC ATCTTCCTTG CTATATTGTT TGGGTTCACC GTCGCAGGAT GGTTATTGGT

11881 CTTCCTTCTC AGAGTGGTTT GCTCCGCGTT TCTCCGTTCG CGCTCTGCCA TTCACTCTCC

11941 CGAACTATCG AAGATCCTAT GAAGGCTTGT TGCCCAACTG CAGACCGGAT GTCCCACAAT

12001 TTGCATTCAA GCACCCTTTG GGTATGTTGT GGCATATGCG AGTTTCCCAC CTGATTGATG

12061 AGATGGTCTC TCGCCGCATT TACCAGACCA TGGAACATTC AGGTCAAGCG GCCTGGAAGC

12121 AAGTAGTTGG TGAGGCCACT CTCACGAAGC TGTCAGGGCT CGATATAGTC ACTCACTTCC

12181 AACACCTGGC CGCAGTGGAG GCGGATTCTT GCCGCTTTCT CAGCTCACGA CTCGTGATGC

12241 TAAAAAATCT TGCCGTTGGC AATGTGAGCC TACAGTACAA CACCACGCTG GACCGCGTTG

12301 AGCTCATTTT TCCCACGTCA GGTACGAGGC CCAAGTTAAC CGACTTCAGA CAATGGCTCA

12361 TCAGTGTGCA CGCTTCCATT TTTTCCTCTG TGGCTTCATC TATCACCTTG TTTGTAGTGC

12421 TTTGGCTTCG AATTCCAGCT CTACGCTATG TTTTTGGTTT CCACTGGCCC ACGGCAACAC

12481 ATCATTGAG CTGACCATCA ACTATACCAT ATGCAAGCCT TGTCTTACCA GTCAAGCAGC

12541 TCACCAAAGG CTTGAGCCCG GTCGCAATGT GTGGTGCAGA ATAGGGCATG AGACGTGTGA

12601 GGAGCGTGAC CATGATGAGT TGTTCATGCC CATCCCGTCC GGATACGATA ACATCAAACT

12661 TAAGGGTTAT TATGCCTGGC TGGCTTTTTT GTCCTTTTCC TACGCGGCCC AATTCCACCC

12721 GGAGTTGTTC GGGATTGGGA ATGTGTCGCG TGTCTTTGTG GACAAACATC ACCAGTTCAT

12781 TTGTGCCGAG CATGATGGAC AGAATTCGAC CGTATCTACT GGACACAACA TCTCTGCACT
```

```
12841 ATATGCGGCA TACTACCACC ACCAAATAGA CGGGGGTAAT TGGTTCCATT TGGAATGGCT

12901 GCGACCACTC TTTTCCTCCT GGTTGGTGCT CAATATATCA TGGTTTCTGA GGCGTTCGCC

12961 TGCAAGCCCT GTTTCTCGAC GCATCTATCA GATATTAAGA CCAACACGAC CGCGGCTGCC

13021 GGTTTCATGG TCCTTCAGGA CATCAATTGT TTCCAACCCC ACAGGGTCCC AGCAACGCAA

13081 AATGGAGCCC CCTTCAAAAA GTCGTCCCAA TGCCGTGAAG CTGTCGGCAC TCCCCAATAC

13141 ATCACAATAA CAGCTAATGT GACCGACGAA TCGTACTTGT ACAACGCGGA CTTGCTGATG

13201 CTTTCTGCGT GCCTTTTCTA CGCTTCAGAA ATGAGTGAGA AAGGCTTTAA AGTCATCTTC

13261 GGGAATGTCT CTGGCGTTGT TTCCGCTTGT GTCAATTTTA CAGATTATGT GGCCCATGTG

13321 ACCCAACACA CCCAGCAGCA TCACCTGGTA ATTGATCACA TTCGGCTGCT GCATTTCCTG

13381 ACACCATCTG CAATGAGGTG GGCTACAACC ATTGCTTGTT TGCTCGCCAT TCTCTTGGCG

13441 ATATGAGATG TTCTCACAAG TTGGGGCGTT CCTTGACTCC GCACTCTTGC TTCTGGTGGC

13501 TTTTTTTGCT GTGTACCGGC TTGTCTTGGT CCTTTGCCGA TGGCAACGGC AACAACTCGA

13561 CATACCAATA CATATATAAT TTGACGATAT GCGAGTTGAA TGGGACCGCG TGGCTGTCCG

13621 GCCATTTTGA TTGGGCAGTT GAGACTTTTG TGCTTTACCC GGTTGCCACT CACATCCTCT

13681 CACTGGGTTT TCTCACAACA AGTCATTTTT TTGACGCGCT CGGTCTCGGT GTTGTATCCA

13741 CTGCTGGATT TGTTGGCGGG CGGTATGTAC TCAGCAGCGT CTACGGCGCT TGTGCTTTCG

13801 CAGCGTTCGT GTGTTTTGCC ATCCGTATTG CGAAAAATTG CATGGCCTGC CGCTACGCCC

13861 GCACCCGGTT TACCAACTTC ATTGTGGACG ACCGGGGAGG AGTTCATCGA TGGAAGTCCC

13921 CAATAGTGGT GGAAAAATTG GGCAAAGCCG AAGTCGACGG CAGCCTTGTC ACCATCAAAC

13981 ATGTCGTCCT CGAAGGGGTT AAAGCTCAAC CTTTAACGAG GACTTCGGCC GAGCAATGGG

14041 AGGCCTAGAT GATTTTTGCA ACGATTCTAC CGCTGCACAA AAGCTCGTGC TGGCTTTCAG

14101 CATCACATAC ACACCTATAA TGATATATGC CCTTAAGGTG TCACGCGGCC GACTCCTGGG

14161 GCTGTTGCAC ATCCTAATAT TTCTGAACTG TTCCTTTACA TTCGGATACA TGACATATGT

14221 GCATTTTCAA TCCACCAACC GTGTCGCACT CACTCTGGGG CTGTCGTCG CCCTTTTATG

14281 GGGTGCTTAC AGCCTCACAG AGTCATGGAA GTTTATCACT TCCAGATGCA GATTGTGTTG

14341 CCTTGGCCGG CGATACATTC TGGCCCCTGC CCATCACGTA GAAAGTGCTG CAGGTCTCCA

14401 TCCAATCTCA GCGTCTGGTA ACCGAGCATA CGCTGTGAGA AAGCCAGGAC TAACATCAGT

14461 GAACGGCACT CTAGTACCAG GACTTCGGAG CCTCGTGCTG GGCGGCAAAC GAGCTGTTAA

14521 ACGAGGAGTG GTTAACCTCG TCAAGTATGG CCGGTAGAAA CCAGAGCCAG AAGAAAAAGA

14581 AAAACACAGC TCCAATGGGG AATGGCCAGC CAGTCAATCA ACTGTGCCAG TTGCTGGGTG

14641 CAATGATAAA GTCCCAGCGC CAGCAACCTA GGGGAGGACA GGCCAAAAAG AAAAAGCCTG

14701 AGAAGCCACA TTTTCCCTTG GCTGCAGAAG ATGACATCCG GCACCACCTC ACCCAGACTG

14761 AACGCTCCCT CTGCTTGCAA TCGATCCAGA CGGCTTTCAA TCAAGGCGCG GGAACTGCGT

14821 TGCTTTCATC CAGCGGGAAG GTCAGTTTTC AAGTTGAGTT TATGCTGCCG GTTGCTCATA

14881 CAGTGCGCCT GATTCGCGTG ACTTCTACAT CCGCTAGTCA GGGTGCAAGT TAATTTGATG

14941 GTCAGGTGAA TGGTCGCGAT TGGCGTGTGG CCTTTGAGTC ACCTATTCAA TTAGGGCGAT

15001 CACATGGGGG TCATACTTAA TCAGGCAGGA ACCATGTGAC CGAAATTAAA AAAAAAAAA

15061 AAAAAAAAAA AAAAAAA
```

The cDNA consensus sequence of PRRS strain SD 04-89 at P83 has been assigned GenBank Accession number KU131559 (SEQ. ID. NO:7). The cDNA consensus sequence designated SEQ. ID. NO:7 is:

```
   1 TATGACGTAT AGGTGTTGGC TCTATGCCTT GGCATTTGTA TTGTCAGGAG CTGTGACCAT
  61 TGGCACAGCC CAAAACTTGC TGCACAGAAA CACCCTTCTG TGATAGCCTC CTTCAGGGGA
 121 GCTTAGGGTT TGTCCCTAGC ACCTTGCTTC GGAGTTGCA CTGCTTTACG GTCTCTCCAC
 181 CCCTTTAACC ATGTCTGGGA TACTTGATCG GTGCACGTGT ACCCCCAATG CCAGGGTGTT
 241 TATGGCGGAG GGCCAAGTCT ACTGCACACG ATGCCTCAGT GCACGGTCTC TCCTTCCCCT
 301 GAACCTCCAA GTTTCTGAGC TCGGGGTGCT AGGCCTATTC TACAGGCCCG AAGAGCCACT
 361 CCGGTGGACG TTGCCACGTG CATTCCCCAC TGTTGAGTGC TCCCCCGCCG GGGCCTGCTG
 421 GCTTTCTGCA ATCTTTCCAA TCGCACGAAT GACCAGTGGA AACCTGAACT TCCAACAAAG
 481 AATGGTACGG GTCGCAGCTG AGCTTTACAG AGCCGGCCAG CTCACCCCTG CAGTCTTGAA
 541 GGCTCTACAA GTTTATGAAC GGGGTTGCCG CTGGTACCCC ATTGTTGGAC CTGTCCCTGG
 601 AGTGGCCGTT TTCGCCAATT CCCTACATGT GAGTGATAAA CCTTTCCCGG GAGCTACTCA
 661 CGTGTTGACC AACCTGCCGC TCCCGCAGAG ACCCAAGCCT GAAGACTTTT GCCCCTTTGA
 721 GTGTGCTATG GCTACTGTCT ATGACATTGG TCATGACGCC GTCATGTATG TGGCCGAAAG
 781 GAAAATCTCC TGGGCCCCTC GTGGCGGGGA TGAAGTGAAA TTTGAAGCTG TCCCCGGGGA
 841 GTTGAAGTTG ATTGCGAACC AGCTCCGCAC CTCCTTCCCG CCCCACCACA CAGTGGACAT
 901 GTCTAAGTTC GCCTTCACAG CCCCTGGGTG TGGTGTTTCT ATGCGGGTCG AACGCCAACA
 961 CGGCTGCCTT CCCGCTGACA CTGTCCCTGA AGGCAACTGC TGGTGGAGCT TGTTTGACTT
1021 GCTTCCACTG GAAGTTCAGA ACAAGAAAT TCGCCATGCT AACCAATTTG GCTACCAGAC
1081 CAAGCATGGT GTCTCTGGCA AGTACCTACA GCGGAGGCTG CAAGTTAATG GTCTCCGAGC
1141 AGTAACTGAC CTAAACGGAC CTATCGTCGT ACAGTACTTC TCCGTTAAGG AGAGTTGGAT
1201 CCGCCATTTG AAACTGGCGG GAGAACCCAG CTACTCTGGG TTTGAGGACC TCCTCAGAAT
1261 AAGGGTTGAG CCTAACACGT CGCCATTGGC TGACAAGGAA GAAAAAATTT TCCGGTTTGG
1321 CAGTCACAAG TGGTACGGCG CTGGAAAGAG AGCAAGAAAA GCACGCTCTT GTGCGACTGC
1381 TACAGTCGCT GGCCGCGCCT TGTCCGTTCG TGAAACCCGG CAGGCCAAGG AGCACGAGGT
1441 TGCCGGCGCC AACAAGGCTG AGCACCTCAA ACACTACTCC CCGCCTGCCG AAGGGAATTG
1501 TGGTTGGCAC TGCATTTCCG CCATCGCCAA CCGGATGGTG AATTCCAAAT TTGAAACCAC
1561 CCTTCCCGAA AGAGTGAGAC CTTCAGATGA CTGGGCTACT GACGAGGATC TTGTGAATGC
1621 CATCCAAATC CTCAGACTCC CTGCGGCCTT AGACAGGAAC GGTGCTTGTA CTAGCGCCAA
1681 GTACGTACTT AAGCTGGAAG GTGAGCATTG GACTGTCACT GTGACCCCTG GGATGTCCCC
1741 TTCTTTGCTC CCTCTTGAAT GTGTTCAGGG CTGTTGTGGG CACAAGGGCG GTCTTGGTTC
1801 CCCAGATGCA GTCGAGGTCT CCGGGTTTGA CCCTGCCTGC CTTGACCGGC TGGCTGAGGT
1861 GATGCACCTG CCTAGCAGTG CTATCCCAGC CGCTCTGGCC GAAATGTCTG GCGATTCCGA
1921 TCGTTCGGCT TCTCTGGTCA CCACCGTGTG GACTGTTTCG CAGTTCTTTG CCCGTCACAG
1981 CGGAGGGAAT CACCCTGACC AAGTGCGCTT AGGGAAAATT ATCAGCCTTT GTCAGGTGAT
2041 TGAGGACTGC TGCTGTTCCC AGAACAAAAC CAACCGGGTC ACCCCGGAGG AGTCGCAGC
2101 AAAGATTGAC CTGTACCTCC GTGGTGCAAC AAATCTTGAA GAATGCTTGG CCAGGCTTGA
2161 GAAAGCGCGC CCGCCACGCG TAATCGACAC CTCCTTTGAT TGGGGTGTTG TGCTCCCTGG
2221 GGTTGAGGCG GTAACCCAGA CGACCAAGCT GCCCCAGGTC AACCAGTGTC GTGCTCTGGT
2281 CCCTGTTGTG ACTCAAAAGT CCTTGGACAA CAACTCGGTC CCCCTGACCG CCTTTTCACT
```

```
2341 GGCTAACTAC TACTACCGTG CGCAAGGTGA CGAAGTTCGT CACCGTGAAA GACTAACCGC

2401 CGTGCTCTCC AAGTTGGAAA AGGTTGTTCG AGAAGAATAT GGGCTCATGC CAACCGAGCC

2461 TGGTTCACGG CCCACACTGC CACGCGGGCT CGACGAACTC AAAGACCAGA TGGAGGAGGA

2521 CTTGCTGAAA CTGGCTAACG CCCAGACGAC TTCGGACATG ATGGCCTGGG CGGTCGAGCA

2581 GGTTGACCTA AAAACTTGGG TCAAGAACTA CCCGCGGTGG ACACCACCAC CCCCTCCGCC

2641 AAAAGTTCAG CCTCGAAAAA CGAAGCCTGT CAAGAGCTTC CGGAGAGAA AGCCTGTCCC

2701 CGCCCCGCGC AGGAAGGTTG GGTCCGATTG TGGCAGCCCG GTTTCATTAG GCGGCGATGT

2761 CCCTAACAGT TGGGAAGATT TGGCTGTTAG TAGCCCCTTT GATCTCCCGA CCCCACCTGA

2821 GCCGGCAACA CCTTCAAGTG AGCTGGTGAT TGTGTCCTCA CCGCAATGCA TCTTCAGGCC

2881 GGCGACACCC TTGAGTGAGC CGGCTCCAAT TCCCGCACCT CGCGGAACTG TGTCTCGACC

2941 GGTGACACCC TTGAGTGAGC CGATCCCTGT GCCCGCACCG CGGCGTAAGT TTCAGCAGGT

3001 GAAAAGATTG AGTTCGGCGG CGGCAATCCC ACCGTACCAG AACGAGCCCC TGGATTTGTC

3061 TGCTTCCTCA CAGACTGAAT ATGAGGCCTC TCCCCCAGCA CCGCCGCACC AGGGACCCTT

3121 GGCCTTCTCC GAGGATAAAC CGGTAGACGA CCAACTTGTC AACGACTCCC GGATATCGTC

3181 GCGGAGGCCT GACGAGAGCA CATCAGCTCC GTCCGCAGGC ACAGGTGGCG CCGGCTCTCT

3241 TACCGATTTG CCGCCTTCAG ATGGCGCGGA TGCGGACGGG GGGGGCCGT TTCGGACGGT

3301 AAAAGAAAA GCTGAAAGGC TCTTTGACCA ACTGAGCCGT CAGGTTTTTG ACCTCGTCTC

3361 CCATCTCCCT GTTTTCTTCT CACGCCTTTT CCACCCTGGC GGTGGTTATT CTCCGGGTGA

3421 TTGGGGTTTT GCAGCTTTTA CTCTATTGTG CCTCTTTTTA TGTTACAGTT ACCCAGCCTT

3481 TGGTATTGCT CCCCTCTTGG GTGTGTTTTC TGGGTCTTCT CGGCGCGTTC GAATGGGGGT

3541 TTTTGGCTGC TGGTTGGCTT TTGCTGTTGG TCTGTTCAAA CCTGTGTCCG ACCCAGTCGG

3601 CGCTGCTTGT GAGTTTGACT CGCCAGAGTG TAGAAACATC CTTCATTCTT TTGAGCTTCT

3661 CAAACCTTGG GACCCTGTTC GCAGCCTTGT TGTGGGCCCC GTCGGTCTCG GTCTTGCCAT

3721 TCTTGGCAGG TTACTGGGCG GGGCACGCTG CATCTGGCAC TTTTTGCTTA GGCTTGGCAT

3781 TGTTGCAGAC TGTATCTTGG CTGGAGCTTA CGTGCTTTCT CAAGGTAGGT GTAAAAAGTG

3841 CTGGGGATCT TGTATAAGAA CTGCTCCTAA TGAGGTCGCT TTTAACGTGT TTCCTTTCAC

3901 ACGTGCGACC AGGTCGTCAC TTATCGACCT GTGCGATCGG TTTTGTGCGC CAAAAGGAAT

3961 GGACCCCATT TTTCTCGCCA CTGGGTGGCG CGGGTGCTGG GCCGGCCGAA GCCCCATTGA

4021 GCAACCCTCT GAAAACCCA TCGCGTTTGC CAATTGGAT GAAAAGAAGA TTACGGCTAG

4081 GACTGTGGTC GCCCAGCCTT ATGACCCCAA CCAAGCCGTA AAGTGCTTGC GGGTATTGCA

4141 GGCGGGTGGG GCGATGGTGG CTGAGGCGGT CCCAAAAGTG GTCAAGGTTT CCGCTGTTCC

4201 ATTCCGAGCC CCCTTCTTTC CCACTGGAGT GAAAGTTGAC CCTGATTGCA GGGTCGTGGT

4261 TGACCCTGAC ACTTTCACTG CAGCTCTCCG GTCTGGCTAC TCCACCACAA ACCTCGTCCT

4321 TGGTGTAGGG GACTTTGCCC AGCTGAATGG ATTAAAAATC AGGCAAATTT CCAAGCCTTC

4381 AGGGGGAGGC CCACATCTCA TGGCTGCCCT GCATGTTGCC TGCTCGATGG CTCTGCACAT

4441 GCTTGTTGGG ATTTATGTGA CTGCGGTGGG TTCTTGCGGC ACCGGCACCA ACGACCCGTG

4501 GTGCGCTAAC CCGTTTGCCG TCCCTGGCTA CGGACCTGGC TCTCTCTGCA CGTCCAGATT

4561 GTGCATTTCC CAACACGGCC TTACCCTGCC CTTGACAGCA CTTGTGGCGG GATTCGGTAT

4621 TCAAGAAATT GCCTTGGTCG TTTTGATTTT TGTTCCATC GGAGGCATGG CTCATAGGTT

4681 GAGCTGTAAG GCTGACATGC TGTTTGTTTT GCTTGCAATT GCCAGCTATG TTTGGGTACC

4741 TCTTACCTGG TTGCTTTGTG TGTTTCCTTG CTGGTTGCGC TGTTTTTCTT TGCACCCCCT
```

-continued

```
4801 CACCATCCTA TGGTTGGTGT TTTTCTTGAT TTCTGTGAAT ATGCCTTCAG GAATCTTGGC

4861 CATGGTGTTG TTGGTTTCTT TTTGGCTTCT TGGTCGTTAT ACTAATGTTG CTGGCCTTGT

4921 CACCCCCTAC GACATTCATC ATTACACCAG TGGCCCCCGC GGTGTTGCCG CCTTGGCTAC

4981 CGCACCAGAT GGGACCTACT TGGCCGCTGT CCGCCGCGCT GCGTTGACTG GCCGCACCAT

5041 GCTGTTTACC CCGTCCCAGC TTGGGTCTCT TCTTGAGGGT GCTTTCAGAA CTCGAAAGCC

5101 CTCACTGAAC ACCGTCAATG TGATCGGGTC CTCCATGGGC TCTGGCGGGG TGTTTACCAT

5161 CGACGGGAAA GTCAAGTGCG TAACTGCCGC ACATGTCCTT ACGGGCAATT CAGCTCGGGT

5221 TTCCGGGGTC GGCTTCAATC AAATGCTTGA CTTTGACGTA AAGGGAGATT TCGCTATAGC

5281 TGATTGCCCG AATTGGCAAG GGGCTGCCCC CAAGACCCAA TTCTGCACGG ATGGATGGAC

5341 TGGCCGTGCC TATTGGCTAA CATCCTCTGG CGTCGAACCC GGCGTCATTG GAAAAGGATT

5401 CGCCTTCTGC TTCACCGCAT GTGGCGATTC CGGGTCCCCA GTGATCACCG AGGCCGGTGA

5461 GCTTGTCGGC GTTCACACGG GATCGAATAA ACAAGGGGGG GGCATTGTTA CGCGCCCCTC

5521 AGGCCAGTTT TGTAATGTGG CACCCATCAA GCTAAGCGAA TTAAGTGAAT TCTTTGCTGG

5581 GCCTAAGGTC CCGCTCGGTG ATGTGAAGGT CGGCAGCCAC ATAATTAAAG ACATAAGCGA

5641 GGTGCCTTCA GATCTTTGTG CCTTGCTTGC TGCCAAACCT GAACTGGAAG GAGGCCTCTC

5701 CACCGTCCAA CTTCTTTGTG TGTTTTTTCT CCTGTGGAGA ATGATGGGAC ATGCCTGGAC

5761 GCCCTTGGTT GCTGTGAGTT TCTTTATTTT GAATGAGGTT CTCCCAGCCG TCCTGGTCCG

5821 GAGTGTTTTC TCCTTTGGAA TGTTTGTGCT ATCCTGGCTC ACGCCATGGT CTGCGCAAGT

5881 TCTGATGATC AGGCTTCTGA CAGCAGCTCT TAACAGGAAC AGATGGTCAC TTGCCTTTTT

5941 CAGCCTCGGT GCAGTGACCG GTTTTGTCGC AGATCTTGCG GCCACTCAGG GGCATCCGCT

6001 GCAGGCAGTG ATGAATTTGA GCACCTATGC ATTCCTGCCT CGGATGATGG TTGTGACCTC

6061 ACCAGTCCCA GTGATCACGT GTGGTGTCGT GCACCTACTT GCCATCATTT TGTACTTGTT

6121 TAAGTACCGT GGCCTGCACC ATATCCTTGT TGGCGATGGA GTGTTCTCTG CGGCTTTCTT

6181 CTTGAGATAC TTTGCCGAGG GAAAGTTGAG GGAAGGGGTG TCGCAATCCT GCGGAATGAA

6241 TCATGAGTCT CTGACTGGTG CCCTCGCTAT GAGACTCAAT GACGAGGACT GGATTTCCT

6301 TATAAAATGG ACTGATTTTA AGTGCTTTGT TTCTGCGTCC AACATGAGGA ATGCAGCGGG

6361 TCAATTTATC GAGGCTGCCT ATGCTAAAGC ACTTAGAGTA GAACTGGCCC AGTTGGTGCA

6421 GGTTGATAAA GTTCGAGGTA CTTTGGCCAA ACTTGAAGCT TTTGCTGATA CCGTGGCACC

6481 TCAACTCTCG CCCGGTGACA TTGTTGTCGC TCTCGGCCAC ACGCCTGTTG GCAGTATCTT

6541 CGACCTAAAG GTTGGTAGCA CCAAGCATAC CCTCCAAGCC ATTGAGACCA GAGTCCTTGC

6601 TGGGTCCAAA ATGACCGTGG CGCGCGTCGT CGACCCGACC CCCACGCCCC CACCCGCACC

6661 CGTGCCCATC CCCCTCCCAC CGAAAGTTCT GGAGAATGGC CCCAACGCTT GGGGGGATGA

6721 GGACCGTTTG AATAAGAAGA AGAGGCGCAG GATGGAAGCC CTCGGCATCT ATGTTATGGG

6781 CGGGAAAAAG TACCAGAAAT TTTGGGACAA GAATTCCGGT GATGTGTTTT ATGAGGAGGT

6841 CCATAATAAC ACAGATGAGT GGGAGTGTCT CAGAGTTGGC GACCCTGCCG ACTTTGACCC

6901 TGAGAAGGGA ACTCTGTGTG GACATGTCAC CATTGAAAAC AAGGCTTACC ATGTTTACAC

6961 CTCCCCATCT GGTAAGAAGT TCTTGGTCCC CGTCAACCCA GAGAATGGAA GAGTTCAATG

7021 GGAAGCTGCA AAGCTTTCCG TGGAGCAGGC CCTAGGTATG ATGAATGTCG ACGGCGAACT

7081 GACTGCCAAA GAACTGGAGA AACTGAAAAG AATAATTGAC AAACTCCAGG GCCTGACTAA

7141 GGAGCAGTGT TTAAACTGCT AGCCGCCAGC GACTTGACCC GCTGTGGTCG CGGCGGCTTG
```

-continued

```
7201 GTTGTTACTG AAACAGCGGT AAAAATAGTC AAATTTCACA ACCGGACCTT CACCCTGGGA

7261 CCTGTGAATT TAAAAGTGGC CAGTGAGGTT GAGCTAAAAG ACGCGGTTGA GCACAACCAA

7321 CACCCGGTTG CGAGACCGAT CGATGGTGGA GTTGTGCTCC TGCGCTCCGC GGTTCCTTCG

7381 CTTATAGACG TCTTGATCTC CGGTGCTGAT GCATCTCCCA AGTTACTTGC CCATCACGGG

7441 CCGGGAAACA CTGGGATCGA TGGCACGCTC TGGGATTTTG AGTCCGAAGC CACTAAAGAG

7501 GAAGTCGCAC TCAGTGCGCA AATAATACAG GCTTGTGACA TTAGGCGCGG CGACGCTCCT

7561 GAAATTGGTC TCCCTTACAA GCTGTACCCT GTTAGGGGTA ACCCTGAGCG GGTGAAAGGA

7621 GTTTTGCAGA ATACAAGGTT TGGAGACATA CCTTACAAAA CCCCCAGTGA CACTGGAAGC

7681 CCAGTGCACG CGGCTGCTTG CCTTACGCCC AACGCCACTC CGGTGACTGA TGGGCGCTCC

7741 GTCTTGGCCA CGACCATGCC CCCCGGGTTT GAGTTATATG TACCGACCAT ACCAGCGTCT

7801 GTCCTTGATT ACCTTGACTC TAGGCCTGAC TGCCCTAAGC AGCTGACAGA GCACGGCTGC

7861 GAAGATGCCG CACTGAAAGA CCTCTCTAAA TATGACTTGT CCACCCAAGG CTTTGTTTTA

7921 CCTGGAGTTC TTCGCCTTGT GCGGAAATAC CTGTTTGCCC ATGTAGGTAA GTGCCCACCC

7981 GTTCATCGGC CTTCTACTTA CCCTGCTAAG AATTCTATGG CTGGAATAAA TGGGAACAGG

8041 TTCCCAACCA AGGACATTCA GAGCGTCCCT GAAATCGACG TTCTGTGCGC ACAGGCTGTG

8101 CGAGAAAACT GGCAAACTGT CACCCCTTGT ACTCTTAAGA ACAGTATTG CGGGAAGAAG

8161 AAGACTAGGA CCATACTCGG CACCAATAAC TTCATCGCAC TAGCCCACCG AGCAGTGTTG

8221 AGTGGTGTTA CCCAGGGCTT CATGAAAAAG GCGTTTAACT CGCCCATCGC CCTCGGAAAG

8281 AACAAGTTTA AGGAGCTACA GACTCCGGTC CTGGGCAGGT GCCTTGAAGC TGATCTCGCA

8341 TCCTGCGATC GATCCACGCC TGCAATTGTC CGCTGGTTTG CCGCCAACCT TCTTTATGAA

8401 CTTGCCTGTG CTGAAGAGTA TCTACCGTCG TACGTGCTGA ACTGCTGCCA CGACTTACTG

8461 GTCACGCAGT CCGGCGCAGT GACTAAGAGA GGTGGCCTGT CGTCTGGCGA CCCGATCACC

8521 TCTGTGTCTA ACACCATTTA TAGTTTGGTG ATCTATGCAC AGCATATGGT GCTTAGTTAC

8581 TTCAAAAGTG GTCACCCCCA TGGCCTTCTG TTCTTACAAG ACCAGCTAAA GTTTGAGGAC

8641 ATGCTCAAGG TTCAACCCCT GATCGTCTAT TCGGACGACC TCGTGCTGTA TGCCGAGTCT

8701 CCCACCATGC CAAACTATCA CTGGTGGGTT GAACATCTGA ATTTGATGCT GGGGTTTCAG

8761 ACGGACCCAA AGAAGACTGC AATAACAGAC TCGCCATCAT TTCTAGGCTG TAGAATAATA

8821 AATGGGCGCC AGCTGGTCCC CAACCGTGAC AGGATCCTCG CGGCCCTCGC CTATCACATG

8881 AAGGCGAGTA ATGTTTCTGA ATACTATGCC TCAGCGGCTG CAATACTCAT GGACAGCTGT

8941 GCTTGTTTGG AGTATGATCC TGAATGGTTT GAAGAACTTG TAGTTGGAAT AGCGCAGTGC

9001 GCCCGCAAGG ACGGCTATAG CTTTCCCGGC ACGCCGTTCT TCATGTCCAT GTGGGAAAAA

9061 CTCAGGTCCA ATTATGAGGG GAAGAAGTCG AGAGTGTGCG GGTACTGCGG GGCCCCGGCT

9121 CCGTACGCTA CTGCCTGTGG CCTCGACGTC TGCATTTACC ACACCCACTT CCACCAGCAT

9181 TGTCCAGTCA CAATCTGGTG TGGCCATCCA GCGGGTTCTG GTTCTTGTAG TGAGTGCAAA

9241 TCCCCTGTAG GGAAAGGCAC AAGCCCTTTA GACGAGGTGC TGGAACAAGT CCCGTATAAG

9301 CCCCCACGGA CCGTTATCAT GCATGTGGAG CAGGGTCTCA CCCCCCTTGA TCCAGGTAGA

9361 TACCAAACTC GCCGCGGACT AGTCTCTGTC AGGCGTGGAA TTAGGGGAAA TGAAGTTGAA

9421 CTACCAGACG GTGATTATGC TAGCACCGCC TTGCTCCCTA CCTGCAAAGA GATCAACATG

9481 GTCGCTGTCG CTTCCAATGT ATTGCGCAGC AGGTTCATCA TCGGCCCACC CGGTGCTGGG

9541 AAAACATACT GGCTCCTTCA ACAGGTCCAG GATGGTGATG TTATTTACAC ACCAACTCAC

9601 CAGACCATGC TTGACATGAT TAGGGCTTTG GGGACGTGCC GGTTCAACGT CCCGGCAGGT
```

-continued

```
 9661 ACAACGCTGC AATTCCCCGT CCCCTCCCGC ACCGGTTCGT GGGTTCGCAT CCTAGCCGGC

9721 GGTTGGTGTC CTGGCAAGAA TTCCTTCCTA GATGAAGCAG CGTATTGCAA TCACCTTGAT

9781 GTTTTGAGGC TTCTTAGTAA AACTACCCTC ACCTGTCTAG GAGACTTCAA GCAACTCCAC

9841 CCAGTGGGTT TTGATTCTCA TTGCTATGTT TTTGACATCA TGCCTCAAAC TCAACTGAAG

9901 ACCATCTGGA GGTTTGGACA GAATATCTGT GATGCCATTC AGCCAGATTA CAGGGACAAA

9961 CTCATGTCCA TGGTCAACAC AACCCGTGTG ACCTACGTGG AAAAACCTGT TAGGTATGGG

10021 CAGGTCCTCA CCCCCTACCA TAGGGACCGA GAGGACGACG CCATCACTAT TGACTCCAGT

10081 CAAGGCGCCA CATTCGATGT GGTTACATTG CATTTGCCCA CTAAAGATTC ACTCAACAGG

10141 CAAAGAGCCC TTGTTGCCAT CACCAGGGCA AGACACGCTA TCTTTGCGTA TGACCCACAC

10201 AGGCAGCTGC AGGGCTTGTT TGATCTTCCT GCAAAAGGCA CACCCGTCAA CCTCGCAGTG

10261 CACCGCGACG GGCAGCTGAT CGTGCTGGAT AGAAATAACA AAGAATGCAC GGTTGCTCAG

10321 GCTCTAGGCA ACGGGGATAA ATTTAGGGCC ACAGACAAGT GTGTTGTAGA TTCTCTCCGC

10381 GCCATTTGTG CTGATCTAGA AGGGTCGAGC TCTCCGCTCC CCAAGGTCGC ACACAACTTG

10441 GGATTTTATT TCTCACCTGA TTTAACACAG TTTGCTAAAC TCCCAGTAGA ACTTGCACCT

10501 CACTGGCCCG TGGTGACAAC CCAGAACAAT GAAAAGTGGC CAGATCGGCT GGTTGCCAGC

10561 CTTCGCCCTA TCCATAAATA CAGCCGCGCG TGCATCGGTG CCGGCTATAT GGTGGGCCCT

10621 TCGGTGTTTC TAGGCACTCC TGGGGTCGTG TCATACTATC TCACAAAATT TGTTAAGGGC

10681 GAGGCTCAAT TGCTTCCGGA GACGGTTTTC AGCACCGGCC GAATTGAGGT AGACTGCCGG

10741 GAATATCTTG ATGATCGGGA GCGAGAAGTT GCTGCGTCCC TCCCACACGC TTTCATTGGC

10801 GACGTCAAAG GCACTACCGT TGGAGGATGT CATCATGTCA CCTCCAGATA CCTCCCGCGC

10861 GTCCTTCCCA AGGAATCAGT TGCGGTAGTC GGGGTTTCAA GCCCCGGAAA AGCCGCAAAA

10921 GCATTGTGCA CACTGACAGA TGTGTACCTC CCAGATCTTG AAGCCTATCT CCACCCGGAG

10981 ACCCAGTCCA AGTGCTGGAG AATGATGTTG GACTTCAAAG AAGTTCGACT AATGGTCTGG

11041 AAAGACAAAA CAGCCTATTT CCAACTTGAA GGTCGCTATT TCACCTGGTA TCAGCTTGCC

11101 AGCTATGCCT CGTACATCCG TGTTCCTGTC AACTCTACGG TGTACTTGGA CCCCTGCATG

11161 GGCCCCGCCC TTTGCAACAG GAGAGTCGTC GGGTCCACCC ACTGGGGGC TGACCTCGCG

11221 GTCACCCCTT ATGATTACGG CGCTAAAATT ATCCTGTCTA GCGCGTACCA TGGTGAAATG

11281 CCCCCCGGAT ACAAAATTCT GGCGTGCGCG GAGTTCTCGT TGGATGACCC AGTTAAGTAC

11341 AAACATACCT GGGGGTTTGA ATCGGATACA GCGTATCTGT ATGAGTTCAC CGGAAACGGT

11401 GAGGACTGGG AGGATTACAA TGATGCGTTT CGTGCGCGCC AGGAAGGGAA AATTTATAAG

11461 GCCACTGCCA CCAGCTTGAA GTTTTATTTT CCCCCGGGCC CTGTCATTGA ACCAACTTTA

11521 GGCCTGAATT GAAATGAAAT GGGGTCCATG CAAAGCCTTT TTTACAAAGT TGGCCAACTT

11581 TTTGTGGATG CTTTCACGGA GTTCTTGGTG TCCATTGTTG ATATCATTAT ATTTTTGGCC

11641 ATTTTGTTTG GCTTCACCAT CGCCGGTTGG CTGGTGGTCT TTTGCATCAG ATTGGTTTGC

11701 TCCGCGATAC TCCGTGCGCG CCCTGCCATT CACTCTGAGC AATTACAGAA GATCTTATGA

11761 GGCCTTTCTT TCCCAGTGCC AAGTGGACAT TCCCACCTGG GGAACTAAAC ATCCTTTGGG

11821 GATACTTTGG CACCATAAGG TGTCAACCCT GATTGATGAA ATGGTGTCGC GTCGAATGTA

11881 CCGCATCATG GAAAAGCAG GGCAGGCTGC CTGGAAACAG GTGGTGAGCG AGGCTACGCT

11941 GTCTCGCATT AGTAGTTTGG ATGTGGTGGC TCATTTTCAG CATCTAGCCG CCATTGAAGC

12001 CGAGACCTGT AAATATTTGG CCTCCCGGCT GCCCATGCTA CACAACCTGC GCATGACAGG
```

```
                          -continued
12061 TTCAAATGTA ACCATAGTGT ATAATAGCAC TTTGAATCAG GTGTTTGCTA TTTTTCCAAC

12121 CCCTGGTTCC CGGCCAAAGC GTCATGATTT TCAGCAATGG TTAATAGCTG TACATTCCTC

12181 CATATTTTCC TCTGTTGCAG CTTCTTGTAC TCTTTTTGTT GTGCTGTGGT TGCGGGTTCC

12241 AATACTACGT ACTGTTTTTG GTTCCGCTG GTTAGGGCA ATTTTTCTTT CGAACTCACA

12301 GTGAATTACA CGGTGTGTCC ACCTTGCCTC ACCCGGCAAG CAGCCGCAGA GATCTACGAA

12361 CCCGGTAGGT CTCTTTGGTG CAGGATAGGG TATGACCGAT GTGAGGAGGA TGATCATGAC

12421 GAGCTAGGGT TTATGGTACC GCCTGGCCTC TCCAGCGAAG GCCACTTGAC TAGTGTTTAC

12481 GCCTGGTTGG CGTTCTTGTC CTTCAGTTAC ACGGCCCAGT TCCATCCCGA GATATTCGGG

12541 ATAGGGAATG TAAGTCGAGT TTATGTTGAC ATCAAACATC AACTCATCTG CGCCGAACAT

12601 GACGGGCAGA ACACCACCTT GCCTCGTCAT GACAACATTT CAGCCGTGTT TCAGACCTAT

12661 TACCAACATC AAGTCGACGG CGGCAATTGG TTTCACCTAG AATGGCTTCG TCCCTTCTTT

12721 TCCTCGTGGT TGGTTTTAAA TGTCTCTTGG TTTCTCAGGC GTTCGCCTGC AAACCATGTT

12781 TCAGTTCGAG TCTTGCAGAC ATTAAGACCA ACACCACCGC AGCGGCAAGC TTTGCTGTCC

12841 TCCAAGACAT CAGTTGCCTT AGGCATCGCG ACTCGGCCTC TGAGGCGATT CGCAAAATCC

12901 CTCAGTGCCG TACGGCGATA GGGACACCTG TGTATGTTAC CATCACAGCC AATGTGACAG

12961 ATGAGAATTA TTTACATTCT TCTGATCTCC TCATGCTTTC TTCTTGCCTT TTCTATGCTT

13021 CTGAGATGAG TGAAAAGGGA TTTAAGGTGG TATTTGGCAA TGTGTCAGGC ATCGTGGCTG

13081 TGTGTGTCAA TTTTACCAGC TACGTCCAAC ATGTCAAGGA GTTTACCCAA CGCTCCCTGG

13141 TGGTCGACCA TGTGCGGTTG CTCCATTTCA TGACACCTGA GACCATGAGG TGGGCAACTG

13201 TTTTAGCCTG TCTTTTTGCC ATTCTGTTGG CAATTTGAAT GTTTAAGTAT GTTGGAGAAA

13261 TGCTTGACCG CGGGCTGTTG CTCGCAATTG CTTTCTTTGT GGTGTATCGT GCCGTTCTGT

13321 TTTGCTGTGC TCGTCAACGC CAGCAACGAC AGCAGCTCCC ATCTACAGCT GATTTACAAC

13381 TTGACGCTAT GTGAGCTGAA TGGCACAGAT TGGCTAGCTA AAAAATTTGA TTGGGCAGTG

13441 GAGAGTTTTG TTATCTTTCC CGTTTTGACT CACATTGTCT CCTATGGTGC CCTCACTGCC

13501 AGCCATTTCT TTGACACAGT CGCTTTAGTC ACTGTGTCTA CCGCCGGGTT TGTTCACGGG

13561 CGGTATGTCC TAAGTAGCAT CTACGCGGTC TGTGCCCTGG CTGCGTTGAC TTGCTTCGTC

13621 ATTAGGTTTG CAAAGAATTG CATGTCCTGG CGCTACGCGT GTACCAGATA TACCAACTTT

13681 CTTCTGGACA CTAAGGGCAG ACTCTATCGT TGGCGGTCGC CTGTCATCAT AGAGAAAAGG

13741 GGCAAAGTTG AGGTCGAAGG TCATCTGATC GACCTCAAAA GAGTTGTGCT TGATGGTTCC

13801 GTGGCAACCC CTATAACCAG AGTTTCAGCG GAACAATGGG GTCGTCCTTA GATGACTTCT

13861 GTCATGATAG CACGGCTCCA GGAAAGGTGC TTTTGGCGTT TTCTATTACC TACACGCCAG

13921 TGATGATATA TGCCCTAAAG GTGAGTCGCG GCCGACTGCT AGGGCTTCTG CACCTTTTGA

13981 TCTTCCTGAA TTGTGCTTTC ACCTTCGGGT ACATGACTTT CGCGCACTTT CAGAGTACAA

14041 ATAAGGTCGC GCTCACTATG GGAGCAGTAG TTGCACTCCT TTGGGGGGTG TACTCAGCCA

14101 TAGAAACCTG GAAATTCATC ACCTCCAGAT GCCGTTTGTG CTTGCTAGGC CGCAAGTACA

14161 TTCTGGCCCC TGCCCACCAC GTTGAAAGTG CCGCAGGCTT TCATCCGATT GCGGCAAATG

14221 ATAACCACGC ATTTGTCGTC CGGCGTCCCG GCTCCACTAC GGTCAACGGC ACATTGGTGC

14281 CCGGGTTAAA AAGCCTCGTG TTGGGTGGCA GAAAAGCTGT TAAACAGGGA GTGGTAAACC

14341 TTGTCAAATA TGCCAAATAA CAACGGCAAG CAGCAGAAGA GAAAGAAGGG GGATGGCCAG

14401 CCAGTCAATC AGCTGTGCCA GATGCTGGGT AAGATCATCG CTCAGCAAAA CCAGTCCAGA

14461 GGCAAGGGAC CGGGAAAGAA AAATAAGAAG AAAAACCCGG AGAAGCCCCA TTTTCCTCTA
```

-continued

14521 GCGACTGAAG ATGATGTCAG ACATCACTTT ACCCCTAGTG AGCGGCAATT GTGTCTGTCG

14581 TCAATCCAGA CCGCCTTTAA TCAAGGCGCT GGGACTTGCA CCCTGTCAGA TTCAGGGAGG

14641 ATAAGTTACA CTGTGGAGTT TAGTTTGCCT ACGCATCATA CTGTGCGCCT GATCCGCGTC

14701 ACAGCATCAC CCTCAGCATG ATGGGCTGGC ATTCTTGAGG CATCTCAGTG TTTGAATTGG

14761 AAGAATGTGT GGTGAATGGC ACTGATTGAC ATTGTGCCTC TAAGTCACCT ATTCAATTAG

14821 GGCGACCGTG TGGGGGTGAG ATTTAATTGG CGAGAACCAT GCGGCCGAAA TTAAAAAAAA

14881 AAAAA

The cDNA consensus sequence of PRRS strain MN 05-68 at P83 has been assigned GenBank Accession number KU131558 (SEQ. ID. NO:8). The cDNA consensus sequence designated SEQ. ID. NO:8 is:

1 ATGACGTATA GGTGTTGGCT CTATGCCGTG ACATTTGTAT AGTCAGGAGC TGCGACCATT

61 GGTACAGCCC AAAACTTGCT GCACGGGAAC GCCCTTCCGT GACAGCCTTC TTCAGGGGAG

121 TTTAGGGATC TATCCCTAGC ACCTTGCTTC CGGAGTTGCA CTGCTTTACG GTCTCTCCAA

181 CCCTTTAACC ATGTCTGGGA TACTTGATCG GTGCACGTGC ACCCCCAATG CCAGGGTGTT

241 TATGGCGGAG GGCCAAGTCT ACTGCACACG ATGTCTCAGT GCACGGTCTC TCCTTCCTCT

301 GAATCTCCAA GTCCCTGAGC TTGGGGTGCT GGGCCTATTT TACAGGCCCG AAGAGCCACT

361 CCGGTGGACA TTGCCGCGTG CATTCCCCAC TGTCGAGTGC TCCCCCGCCG GGGCCTGCTG

421 GCTTTCTGCG ATCTTCCCAA TTGCACGAAT GACCAGTGGA AACCTGAACT TTCAACAAAG

481 AATGGTGCGG GTCGCAGCTG AGATTTACAG AGCCGGTCAG CTCACTCCCA CAGTCTTGAA

541 GAATCTACAA GTTTATGAGC GGGGTTGCCG TTGGTACCCT ATTGTCGGGC CTGTCCCCGG

601 AGTGGCCGTT TACGCCAACT CCCTACATGT GAGTGACAAA CCCTTTCCGG GAGCAACTCA

661 TGTGTTAACT AATCTACCGC TCCCGCAGAG GCCCAAGCTT GAAGATTTTT GCCCCTTTGA

721 GTGTGCTATG GCTGACGTCT ATGATATCGG TCATGACGCC GTCATGTACG TGGCCAAAGG

781 GAAAGTCTCC TGGGCTCCTC GTGGTGGGGA CAAGACAAAA TTTGAAACTG TCCCTAGGGA

841 GTTGAAGTTG ATCGCGAACC GACTCCATGT CTCCTTCCCG CCCCACCACG CAGTGGACAT

901 GTCCCAGTTT GCGTTCATAA CCTTCGGGAG CGGTGTCTCT ATGCGGGTCG AGTGCCCACA

961 TGGCTGTCTC CCCGCCAATA CCGTCCCTGA AGGCAACTGC TGGTGGCGCT TGTTTGACAT

1021 GCTTCCACCG GAGGTTCAGA ACGATGAAAT TCGCCGTGCC TGCCAATTCG GTTATCAAAC

1081 CAAGCATGGT GTCGCTGGCA AGTACCTACA ACGGAGGTTG CAAGCTAATG GCCTCCGAGC

1141 GGTGACTGAT ACAAGTGGGC CTATCGTTGT GCAGTTTTTC TCCGTTAAGG AGAGTTGGAT

1201 CCGCCACTTA AGGCTGGCGG ACGAACCTAG CCTTCCTGGT TTTGAGGACC TCCTCAGAAT

1261 AAGGGTTGAG CCCAACACGT CACCATTGGT TAGCAAGGAT GTGAAAATCT TCCGGTTCGG

1321 CAGTCACAAA TGGTACGGTG CTGGAAAGAG GGCAAAGAAA GCACGCTCTG GTGCGGCTGC

1381 CACGGTCATT CACCGCGCTT TGCCTGTTCG CGAAGCCCAG CAGACCAAGA CGCACAAGGT

1441 TGCTAGCGCT AACAGGGCTG AGTGTCTCAA GCGCTATTCT CCGCCTGCCG ATGGGAACTG

1501 TGGTTGGCAC TGCATTTCCG CCATCGCCAA CCGGATGGTG AATTCGAAAT TTGAGACCAC

1561 CCTTCCCGAA AGAGTGAGAC CTTCTGATGA TTGGGCTACC GACGAGGATC TTGTGAACGC

1621 CATTCAAATC CTCAAGCTCC CTGCGGCCTT GGACAGGAAC GGAGCTTGTG GTAGCGCCAA

1681 GTACGTGCTT AAGCTGGAAG GCGTGCATTG GACTGTCTCT GTGACCCCTG GGATGTCCCC

1741 CTCTTTGCTC CCCCTTGAAT GTGTTCAGGG CTGTTGTGAG CATAAGGACG GTTCTGGCCC

```
1801 CCCAGATGCG GTCGAGGTTT CCGGATTTGA CCCTGCCTGC CTTGACCGAC TGGCTGGGGT

1861 GATGCATTTA CCTAGCAGTG CTATCCCAGC CGCTCTGGCT GAAATGTCCG GCAACTCCAA

1921 TCGCCCGGCT TCCCCGGTCA ACACTGTGTG GACTGTTTCG CAATTCTATG CCCGTCACTT

1981 AGGAGGAGTT CATCCTGACC AGGTGTGCTT AGGGAAAATT ATTAGCCTCT GTCAAGTCAT

2041 TGAGGATTGC TGCTGCCATC AAAACAAAAC CAACCGGGCC ACCCCGGAAG AGGTCGCGGC

2101 AAAGATTGAT CAGTACCTCC GTGGTGCAAC AAGTCTTGAG GAATGCTTGA CTAGGCTTGA

2161 AAGGGTTTGC CCTCCGAGCG CTGCGGACAC CTCCTTTGAT TGGAATGTTG TGCTCCCTGG

2221 GGTTGAGGCT GCAACCCAGA CAACTAAACA GCTCCATGTC AACCGGTGCC GCGTTTTGGC

2281 TCCTGTCGTG ACTCAAGAGC CTTCGGACAA AGACTCGGTC CCTCTGACCG CCTTCTCGTT

2341 GTCCAATTAC TACTACCCGG CACAAGGTGA CGAGATTCAT CACCGTGAGA GGCTGAACTC

2401 CGTACTCTCT AAGTTGGAGG GGGTTGTTCG CGAGGAATAT GGGCTCACGC CAACTGAACC

2461 TGGTCCGCGA CCCGCACTAC CGAACGGGCT CGACGAGCTC AGAGACCAGA TGGAGATGGA

2521 TCTGCTGAGA CTAGTCAACG ATCAGGCAAC TTCAGAAATG ATGGCCCGGG CAGCTGAGCA

2581 GGTTGATCTA AAAGCTTGGG TCAAAAACTA CCCACGGTGG ACACCGCCGC CCACTCCACC

2641 AAGAGTTCAG CCTCGAAAAA CGAGGTCTGT CAAGAGCTTG CCAGGGGATA AGCCTGTCCC

2701 GGCTCCGCGT AGGAAGGTCA GATCTGATTG TGGCAGCCCG ATTTTGATGG GCGACAATGT

2761 TCCTAACGAT CGGGAAGATT TGACTGTTAA TGGGCCCCTT GACCTTTCGA CACCATCCGA

2821 GTCGATGACA CCTCTGAGTG AGCCTGCACT TATGCCCGCG TTGCAACATG TTTCTAGGTC

2881 GGCGACATCT TTGAGTGTGC CGACCCCAGT TCCTGTACCG CGCAGAGCTG TGTCCCGACC

2941 GGTGGCACCC TTGAGTGAGC CAACCTTTGA GTCTTCACCG CGACACAAAT TTCAAGAGGT

3001 GAAAGAAGTG AATCTGGCGG CAACAACGCC GACGCACCAA GACGAACCTC TAGATTTGTC

3061 TGCATCCTCA CAGACTGTAT GTGAGGCCTC TCCCCTAGCA CCGCCTCAGA ACATAGGTAT

3121 TCTGGGGGTG GAGGGGCAAG AAACTGAGGA AGTCCTGAGT GAAGTCTCGG ATATACCGTA

3181 TGACATTAAC CTTGCACCTG TGTCATCAAG CAGCTCCCTG TCAAGTGTAA AGATCACACG

3241 TCCGAAATAC TCAGCTCAAG CCATTATTGA CTCAGGCGGG CCCTGCAGTG GCATCTTCG

3301 AAAGGGAAAA GAAGCATGCC TCAGCATCAT GCGCAGGGCT TGTGATGCGG CTAAGCTTAG

3361 TGACCCTGCC ACGCAAGAAT GGCTTTCTCG TATGTGGGAT AGGGTTGACA TGCTGACTTG

3421 GCGCAACACG TCTGCTTACC AGGCGTTGCG CATCTTAGAT GGCAGGTTTG GGTTCCTCCC

3481 GAAAATGATA CTCGAGACAC CACCGCCCTA TCCGTGTGGG TTTGTGATGC TGCCTCACAC

3541 GCCTGCACCT TCCGTGAGTG CAGAGAGCGA CATTACCATT GGTTCAGTTG CCTCTGAAGA

3601 TGTTCCACGC ATCCTCGGGA AAATAGAAAA CGCCGGCGAG ATGCCCAACC AGGGGCTCTT

3661 GGCGTCCCTT GAGGAAAAAC CGGTGCACGA CCAACCTGCC GAAGACTCCC GGATGCCGTT

3721 GCGGGGGTTT GACGAGAGCG TAACGGCTCC GTCCGCTGGT ACAGGTTGCG CTGACTCACC

3781 CACTGATTTG TCGCCTTCAG GTGGTGTGGA CGTGGACGGG GGGGGGCGT TACGGGCGGT

3841 AAGAAAGAAA GCTGAAAGGC TCTTCGATCA ATTGAGCCGC CAGGTTTTTA ACCTCGTCTC

3901 CCATCTCCCT GTTTTCTTCT CACACCTCTT CAAATCTGAC AGTGGTTATT CTCCGGGTGA

3961 TTGGGGTTTT GCAGCTTTTA CTCTATTTTG TCTCTTTTTA TGTTACAACT ACCCATTTTT

4021 TGGGTTTGCT CCCCTCTTGG GTGTGTTTTC TGGGTCTTCT CGGCGTGTGC GCATGGGGGT

4081 TTTTGGCTGC TGGTTGGCTT TTGCTGTTGG CCTGTTCAAA CCTGTGTCCG ACCCAGTCGG

4141 CACTGCTTGT GAATTTGACT CGCCAGAGTG TAGGAACGTC CTTCATTCTT TTGAGCTTCT

4201 CAAACCTTGG GACCCTGTTC GCAGCCTTGT TGTGGGCCCC GTCGGTCTCG GTCTTGCCAT
```

```
4261  TCTTGGCAGG TTACTGGGCG GGGCACGCTA CATCTGGCAT TTTTTGCTTA GGCTTGGCAT
4321  TGTTGCAGAT TGTGTCTTGG CTGGAGCTTA TGTGCTTTCT CAAGGTAGGT GTAAAAAGTG
4381  CTGGGGATCT TGTGTAAGAA CTGCTCCCAA TGAAATTGCC TTCAACGTGT TCCCTTTTAC
4441  GCGTGCGACC AGGTCGTCAC TCATCGACCT GTGCAACCGG TTTCGTGCGC CGAAAGGCAT
4501  GGACCCCATT TTTCTCGCTA CTGGGTGGCG CGGGTGCTGG ACCGGCCAAA GTCCCATTGA
4561  GCAACCCTCC GAAAACCCA TCGCGTTCGC CCAGTTGGAT GAAAAGAGGA TCACGGCCAG
4621  AACTGTAGTT GCTCAGCCTT ATGATCCTAA CCAAGCCGTA AAGTGCCTGC GGGTGTTACA
4681  GGCGGGTGGG GCGATGGTGG CCGAGGCAGT CCCGAAAGTT GTCAAAGTTT CCGCTATCCC
4741  ATTCCGAGCC CCTTTTTTTC CCACCGGAGT GAAGGTTGAT CCTGAGTGCA GGATCGTAGT
4801  CGACCCCGAC ACTTTCACTA CTGCTCTTCG GTCTGGTTAC TCCACCACAA ACCTCGTCCT
4861  TGGTGTGGGG GACTTTGCCC AACTGAATGG ATTAAAAATC AGGCAAATTT CCAAGCCTTC
4921  GGGAGGAGGC CCACACCTCA TTGCTGCCCT GCATGTTGCT TGCTCGATGG CGTTGCACAT
4981  GCTTGCTGGG GTTTACGTAA CTGCAGTGGG GTCTTGCGGT ACCGGCACCA ACGATCCGTG
5041  GTGCACCAAC CCATTCGCCG TCCCTGGCTA CGGACCTGGC TCTCTCTGCA CGTCCAGGTT
5101  GTGCATCTCC CAACATGGCC TTACCTTGCC CTTGACAGCA CTTGTGGCAG GCTTCGGTCT
5161  TCAGGAAATT GCCTTGGTCG TTCTGATTTT TGTTTCCATC GGAGGCATGG CTCATAGGTT
5221  GAGTTGTAAG GCTGATATGC TGTGCGTCTT GCTCGCAATC GCCAGCTATG TTTGGGTACC
5281  CCTTACCTGG TTGCTCTGCG TGTTTCCTTG CTGGTTGCGC TGGTTCTCTT GCACCCCCT
5341  CACCATCCTA TGGTTGGTGT TTTTCTTGAT TTCTGTAAAT ATGCCTTCAG GAACCTTAGC
5401  CGTGGTGTTA TTGGTCGCTC TTTGGCTTCT AGGCCGTTAC ACTAATGTTG TTGGTCTTGT
5461  CACCCCCTAC GATATCCATC ATTACACCAG CGGCCCTCGC GGTGTTGCCG CCTTGGCTAC
5521  CGCACCAGAT GGAACTTATT TGGCCGCTGT CCGCCGCGCT GCGTTGACTG GCCGTACCGT
5581  TCTGTTTACC CCGTCTCAGC TTGGGTCCCT TCTTGAGGGC GCTTTCAGGA CTCGAAAGCC
5641  CTCATTGAAC ACCGTTAATG TGGTCGGGTC CTCCATGGGC TCTGGCGGAG TGTTCACTAT
5701  CGATGGGAAA ATTAAGTGTG TGACTGCCGC ACATGTCCTT ACGGGCAACT CAGCCAGGGT
5761  TTCCGGGGTC GGCTTCAATC AGATGCTTGA CTTTGATGTA AAAGGAGATT TCGCCATAGC
5821  TGATTGCCCG AATTGGCAAG GGACTGCTCC TAAGACCCAA TTCTGCAAGG ACGGGTGGAC
5881  TGGCCGTGCC TATTGGCTAA CATCTTCTGG TGTCGAACCC GGTGTCATTG GAAATGGGTT
5941  CGCCTTCTGC TTCACCGCGT GCGGTGACTC CGGGTCTCCA GTGATCACCG AAGCCGGTGA
6001  GCTTGTCGGC GTTCACACAG GATCAAACAA ACAAGGAGGA GGCATTGTTA CGCGCCCCTC
6061  AGGCCAGTTT TGTAATGTGG CACCCATCAA GCTGAGCGAA TTAAGTGAGT TCTTTGCTGG
6121  ACCTAAGGTC CCGCTCGGTG ATGTGAAGGT TGGTAGCCAC ATAATTAAAG ACATATGCGA
6181  GGTACCTTCA GATCTTTGTG CCTTGCTTGC TGCCAAACCC GAATTGGAAG GAGGCCTCTC
6241  CACCGTCCAA CTTCTATGTG TATTTTTCCT CCTGTGGAGA ATGATGGGAC ATGCCTGGAC
6301  ACCCTTGGTT GCCGTGGGTT TTTTTATTTT GAATGAGATT CTTCCAGCTG TACTGGTCCG
6361  GAGTGTTTTC TCCTTCGGAA TGTTTGTGTT ATCTTGGCTC ACACCATGGT CTGCACAAGT
6421  TCTGATGATC AGGCTCCTCA CAGCAGCTCT TAATAGGAAC AGATTGTCAC TCGCCTTCTA
6481  CAGCCTTGGT GCGGCAACCG GTTTTGTCGC AGACCTAGCG GCGACCCAAG GCATCCGTT
6541  GCACGCAGTA ATGAATTTGA GTACCTATGC CTTCCTGCCT CGGGTGATGG TTGTGACCTC
6601  ACCAGTCCCA GTAATCGCGT GTGGTGTTGT GCACCTCCTT GCCATAATTT TGTACTTGTT
```

-continued

```
6661 TAGGTACCGC TGCCTGCATG GTGTTCTTGT TGGCGATGGG GCGTTCTCTG CGGCTTTTTT

6721 TTTGCGATAC TTTGCTGAGG GGAAATTGAG GGAAGGGGTG TCGCAATCCT GCGGGATGAA

6781 TCATGAGTCG CTGACTGGTG CCCTCGCCAT GAGACTCAAT AACGAGGATT GGATTTCCT

6841 CACTAAGTGG ACTGATTTTA AGTGCTTTGT TTCTGCTTCC AACATGAGGA ATGCAGCGGG

6901 CCAATTCATT GAGGCTGCCT ATGCCAAAGC ACTTAGAATA GAACTTGCCC AGCTGGTGCA

6961 GGTCGACAAG GTCCGAGGCA CTTTGGCCAA ACTTGAAGCT TTTGCCGACA CCGTGGCACC

7021 CCAACTCTCG CCCGGTGACA TTGTTGTCGC TCTTGGCCAT ACGCCTGTTG GCAGTGTCTT

7081 CGACCTGAAG GTTGGTAACA CCAAGCACAC TCTCCAAGCC ATTGAGACCA GGGTCCTTGC

7141 TGGGTCCAAA ATGACCGTGG CGCGCGTCGT CGACCCGACC CCCACGCCCC CACCCGCACC

7201 CGTACCCATC CCCCTCCCAC CGAAGGTTTT GGAGAACGGT CCAAACGCTT GGGGGATGA

7261 AGATCGTTTG AATAAAAAGA AGAGGCGCAG GATGGAAGCT GTCGGCATCT TTGTTATGGG

7321 CGGAAAGAAA TACCAGAAAT TTTGGGACAA GAATTCCGGT GATGTGTTTT ATGAGGAGGT

7381 CCATGACAAT ACAGACGCGT GGGAGTGCCT CAGGGTTGAT AACTCTGCCG ACTTTGATCC

7441 CGAGAAGGGA ACTCTGTGTG GCATACTAC CATTGAGAAT AAAACCTACA ATATCTACGC

7501 CTCCCCATCC GGCAAGAAGT TCCTGGTCCC TGCCAACTCA GAGGGCGGAA AAGTCCAGTG

7561 GGAAGCTGCA AAGCTCTCCG TGGAGCAGGC CCTTGGCATG ATGAATGTCG ACGGTGAACT

7621 GACAGCCAGA GAACTGGAGA AACTAAAAAA AATAATTGAC AAACTCCAGG ACCTGACCAA

7681 GGAGCAGTGT TTAAACTGCT AGCCGCCAGC GGCCTGACCC GCTGTGGTCG CGGCGGCTTA

7741 GTTGTTACTG AGACAGCGGT AAAAATAGTC AAATATCACA GCCGGACCTT CACCCTAGGA

7801 CCTGTAAATT TAAAAGTGGC TAGTGAGGTT GAGCTAAAAG ACGCGGTCGA GCATAACCAG

7861 CACCCGGTCG CAAGACCGGT TGATGGTGGT GTTGTGCTTC TGCGCTCCGC AGTTCCTTCG

7921 CTTATAGACG TCTTGATCTC CGGCGCTGAT GCATCTCCTA AGTTACTCGC TCGCCACGGG

7981 CCGGGAAATA CTGGGATCGA CGGCACGCTT TGGGATTTTG AGGCCGAGGC CACCAAAGAG

8041 GAGATCGCAC TCAGTGCGCA GATAATACAG GCTTGTGACA TTAGGCGCGG CGACGCACCC

8101 GAAATTGGTC TCCCTTATAA GCTGTACCCT GTTAGGGGCA ATCCCGAGCG GGTAAAAGGA

8161 GTTTTACAGA ATACAAGGTT CGGGGACATT CCTTATAAAA CCCCCAGTGA CACTGGAAGC

8221 CCAGTGCACG CGGCTGCCTG CCTCACGCCC AATGCCACTC CGGTGACTGA TGGGCGCTCC

8281 GTCTTGGCTA CAACCATGCC CTCCGGTTTT GAGTTGTACG TGCCGACCAT TCCAGCATCT

8341 GTCCTTGATT ACCTTGACTC CAGGCCTGAC TGCCCTAAAC AGTTGACAGA GCACGGCTGT

8401 GAGGATGCCG CATTAAGAGA CCTTTCCAAG TATGACTTGT CCACTCAAGG CTTTGTTTTG

8461 CCAGGAGTTC TTCGCCTTGT GCGTAAGTAC CTATTTGCTC ATGTGGGCAA GTGCCCGCCT

8521 ATTCATCGGC CTTCCACCTA CCCTGCCAAG AATTCTATGG CTGGAATAAA TGGGAACAGG

8581 TTTCCAACCA AGGACATCCA GGGCGTCCCT GAAATCGACG TCCTGTGCGC TCAGGCCGTG

8641 CGGGAAAACT GGCAGACTGT CACCCCTTGT ACCCTCAAGA AACAGTATTG TGGGAAGAAG

8701 AAGACTAGGA CAATACTCGG CACCAATAAT TTCATTGCAT TGGCCCACCG GGCAGCGTTG

8761 AGTGGCGTCA CCCAGGGCTT TATGAAAAAG GCGTTCAATT CGCCCATCGC CCTCGGAAAA

8821 AACAAATTTA AGGAGCTACA AACTCCGGTC TTAGGCAGGT GCCTAGAGGC TGACCTTGCA

8881 TCCTGCGATC GATCCACACC TGCGATTGTC CGCTGGTTTG CCGCCAATCT TCTTTATGAA

8941 CTTGCCTGTG CTGAGGAACA TCTACCATCG TACGTGCTGA ACTGCTGCCA CGACTTACTG

9001 GTCACGCAAT CCGGCGCGGT GACTAAGAGA GGTGGCCTGT CGTCTGGCGA CCCGATTACT

9061 TCTGTGTCAA ACACCATTTA TAGTTTGGTG ATATATGCAC AGCACATGGT GCTCAGTTAC
```

```
9121 TTTAAAAGTG GTCACCCTCA CGGCCTTCTG TTTCTGCAAG ACCAGCTAAA GTTTGAGGAC

9181 ATGCTCAAGG TTCAACCCCT GATCGTCTAT TCGGACGACC TCGTGTTGTA TGCCGAGTCT

9241 CCCACTATGC CAAACTACCA CTGGTGGGTT GAACATCTGA ATCTTATGTT GGGTTTTCAG

9301 ACGGACCCAA GAAAGACAGC CATAACAGAC TCACCATCTT TTCTAGGCTG TAGAATAATA

9361 AATGGGCGCC AGCTAGTCCC CCACCGTGAC AGGATTCTCG CGGCCCTTGC CTACCATATG

9421 AAGGCAAGCA ATGTTTCTGA ATACTACGCT TCGGCGGCCG CGATACTCAT GGACAGCTGT

9481 GCTTGTCTAG AGCATGATCC TGAATGGTTT GAAGAACTTG TGGTCGGAAT GGCGCAGTGT

9541 GCCCGCAAGG ACGGCTACAG CTTTCCCGGC CCGCCGTTCT TCTTGTCTAT GTGGGAAAAA

9601 CTCAGGTCTA ATTATGAGGG GAAGAAGTCG AGAGCGTGCG GATACTGCGG GGCCCCGGCT

9661 CCGTACGCTA CCGCCTGTGG CCTCGACGTC TGCATTTATC ACACCCATTT CCACCAGCAT

9721 TGTCCGGTCA TAATCTGGTG TGGTCATCCG GCGGGTTCTG GTTCTTGTAG TGAGTGCAAA

9781 CCCCCCCTTG GGAAAGGTAC AAGCCCTCTA GATGAGGTGT TGGAACAAGT CCCGTACAAG

9841 CCTCCGCGGA CCGTGATCAT GCACGTAGAG CAGGGTCTTA CTCCACTCGA CCCAGGTAGA

9901 TACCAAACCC GCCGCGGATT AGTCTCCGTT AGGCGTGGCA TTAGGGGAAA CGAAGTTGAA

9961 CTACCAGACG GTGATTATGC TAGTACCGCC TTGCTCCCCA CTTGTAAAGA GATCAACATG

10021 GTTGCTGTTG CTTCTAACGT GTTACGCAGC AGGTTCATCA TCGGTCCACC TGGTGCTGGT

10081 AAAACATACT GGCTCCTTCA ACAGGTCCAG GATGGTGATG TCATTTACAC GCCAACTCAT

10141 CAGACTATGC TTGACATGAT TAAGGCTTTG GGACGTGCC GGTTCAACGT TCCAGCAGGC

10201 ACAACGCTGC AATTCCCTGC CCCCTCCCGC ACCGGCCCGT GGGTTCGCAT CCTGGCCGGC

10261 GGTTGGTGTC CTGGCAAGAA TTCCTTCCTG GATGAAGCAG CGTATTGCAA TCATCTTGAC

10321 GTCTTGAGGC TTCTTAGCAA AACTACCCTC ACCTGCCTGG GAGATTTCAA ACAACTCCAC

10381 CCGGTGGGTT TTGATTCCCA TTGCTATGTT TTTGACATTA TGCCTCAGAC TCAACTGAAG

10441 ACCATCTGGA GGTTTGGGCA GAACATCTGT GACGCCATTC AACCAGATTA TAGAGACAAA

10501 CTTGTGTCCA TGGTCAACAC AACCCGTGTA ACCTACGTGG AAAAACCTGT CAAGTATGGG

10561 CAAGTCCTCA CCCCCTACCA CAGGGACCGA GAGGACGGCG CCGTCACAAT TGACTCAAGT

10621 CAAGGCGCCA CATTTGATGT GGTTACACTG CATTTGCCCA CTAAAGATTC ACTCAACAGG

10681 CAAAGGGCCC TTGTTGCTAT CACCAGGGCA AGACATGCTA TCTTTGTGTA TGACCCACAC

10741 AGGCAATTGC AGAGCTTGTT TGATCTTCCT GCAAAAGCA CACCCGTCAA TCTCGCAGTG

10801 CACCGTGACG AGCAGCTGAC CGTGTTAGAT AGAAATAACA AAGAGTGCAC GGTTGCTCAG

10861 GCTCTAGGCA ATGGGGATAA ATTTAGGGCC ACAGACAAGC GCGTTGTAGA TTCTCTCCGC

10921 GCCGTTTGTG CAGACCTGGA AGGGTCTAGC TCCCCGCTCC CAAGGTTGC ACACAACTTG

10981 GGATTTTATT TCTCGCCTGA TTTGACACAG TTTGCTAAGC TTCCGGTAGA ACTTGCACCT

11041 CACTGGCCCG TGGTGACAAC CCAGAACAAT GAAAAGTGGC CAGACCGGTT GGTTGCTAGC

11101 CTTCGCCCTG TCCATGAGTA TAGCCGTGCG TGTGTCGGTG CCGGCTATAT GGTGGGCCCC

11161 TCAGTGTTCC TAGGCACTCC TGGGGTTGTG TCATACTATC TCACAAAATT TGTTAGAGGC

11221 GAGGCTCAAA TGCTTCCGGA GACAGTCTTC AGCACCGGCC GAATTGAGGT AGATTGCCGG

11281 GAGTACCTTG ATGATCGGGA GCGAGAAGTT GCTGAGTCCC TCCCACACGC CTTCATTGGC

11341 GACGTCAAAG GCACTACCGT TGGGGGATGT CACCATGTCA CCTCTAAATA CCTCCCGCGT

11401 TTCCTCCCCA AGGAATCGGT TGCGGTAGTT GGGGTTTCGA GCCCCGGGAA AGCCGCAAAA

11461 GCAGTTTGCA CATTGACAGA TGTGTACCTC CCAGACCTTG AAGCTTATCT CCACCCAGAG
```

-continued

```
11521 ACCCAGTCTA AGTGCTGGAA AATGATGTTG GACTTCAAGG AGGTTCGACT GATGGTCTGG

11581 AAAGATAAGA CGGCCTATTT TCAACTTGAA GGCCGCCATT TCACCTGGTA CCAGCTTGCA

11641 AGCTATGCCT CGTACATCCG AGTTCCTGTT AATTCTACGG TATATCTGGA CCCTTGCATG

11701 GGCCCTGCCC TTTGCAACAG GAGGGTTGTC GGGTCCACCC ATTGGGAAGC TGACCTCGCA

11761 GTCACCCCTT ATGATTATGG TGCCAAAATC ATTTTGTCTT GTGCATACCA TGGTGAAATG

11821 CCTCCCGGGT ACAAGATTCT GGCGTGCGCG GAGTTCTCGC TTGACGACCC AGTCAGGTAC

11881 AAACACACCT GGGGATTTGC ATCGGATATA GCGTATTTGT ACGAGTTCAC CGGAAACGGT

11941 GAGGACTGGG AGGATTACAA TGATGCGTTT CGTGCGCGCC AGAAAGGGAA AATTTACAAA

12001 GCCACTGCCG CCAGCATGAG GTTTTATTTT CCCCCGGGCC CTATCGTTGA ACCAACTTTG

12061 GGCCTAGACT GAAATGAAAT GGGGTCTATG CAAAGCCTCT TTGACAAAAT CGGCCAACTT

12121 TTTGTGGATG CCTTCACGGA ATTTTTGGTG TCCATTGTTG ATATCATCAT ATTTCTGGCC

12181 ATTTTGTTTG GCTTTACCAT CGCTGGCTGG CTGGTGGTCT TCTGCATCCG ACTGGTTTGC

12241 TCCGCGGTAC TCCGTGCGCG CCCTACCATT CACTCTGAGC AATTACAGAA GATCCTATGA

12301 GGCCTTTCTT TCTCAGTGCC AGGTGGACAT TCCCGCCTGG GGAACTAAAC ACCCCTTGGG

12361 GATGTTTTGG CACCATAAGG TGTCGACCCT GATTGATGAA ATGGTGTCGC GTCGAATGTA

12421 CCGCACCATG GAAAAGCAG GACAGGCTGC CTGGAGACAG GTGGTAAGCG AGGCTACGTT

12481 GTCTCGCATT AGTGGTTTGG ATGTGGTGGC TCATTTTCAG CATCTTGCCG CCATTGAAGC

12541 TGAGACCTGC AAATACTTGG CCTCTCGGCT TCCCATGCTG CACAATCTGC GCATGACAGG

12601 GTCAAATGTA ACCATAGTGT ATAATAGCAC TTTGAATCAG GTGTTTGCTA TTTTTCCAAC

12661 CCCTGAATCC CGGCCGAAGC TTCATGATTT TCAGCAATGG CTAATAGCTG TGCATTCCTC

12721 CATATTTTCC TCCGTTGCAG CTTCTTGCAC TCTTTTTGTT GTGCTGTGGT TGCGGATTCC

12781 AACACTACGT ATTGTTTTTG GTTTCCACTG GTAAGGGGCA ATTTTTCCTT CGAGCTCACG

12841 GTGAATTACA CGGTGTGCCC GCTTTGCCTC ACCCGACAAG CAGCCTATGA GATCTATGAA

12901 TCACGCAGGT CTTTTTGGTG CAGGATAGGG CATGACCGAT GCAGTGAGGT CGACCACGAC

12961 GAGCTAGGGT TCATGGTTCC GTCTGGCCTC TCCAGCGAAG GCCACCTGAC CAGTGTTTAC

13021 GCCTGGTTGG CGTTCCTGTC CTTCAGCTAC ACGGCCCAGT TCCATCCCGA GATATTTGGG

13081 ATAGGGAATG TGAGTCGAGT TTATGTTGAC ATCAAGCACC AACTCATCTG CGCCGTTCAC

13141 GACGGGGAGA ACACCACCTT GCCTCGTCAT GACAACATTT CAGCCGTATT TCAGACCTAC

13201 TACCAGCATC AAGTCGACGG CGGCAATTGG TTTCACCTAG AATGGCTGCG TCCCTTCTTT

13261 TCCTCCTGGT TGGTTTTAAA TGTCTCGTGG TTTCTCAGGC GTTCGCCTGC AAGCCATGTT

13321 TCAGTTCAAG TCTTTCGGAC ATCAAAACCA ACACTACCGC AGCATCAGGC TTTGTTACCC

13381 TCCAGGACAT CAGCTGTCTT AGGCATGGCG ACTCGCCCTC TCAGACGATT CGCAAAAGCC

13441 CTCCGTGCCG CACGGCGCTA GGGACACCCG TGTACATCAC TGTTACAGCC AATGTCACGG

13501 ATGAGAATTA TTTACACTCC TCTGATCTCC TCATGCTTTC TTCTTGCCTT TTCTATGCTT

13561 CTGAGATGAG TGAAAAGGGA TTCAAGGTGA TATTTGGCAA TGTGTCAGGC ATCGTGGCCG

13621 TGTGTGTTAA TTTTACCAGC TACGTCCAAC ATGTCAAAGA GTTCACCCAA CGCTCTTTGG

13681 TGGTCGACCA TGTGCGGCTG CTCCATTTCA TGACACCTGA AACCATGAGG TGGGCAACCG

13741 TTTTAGCCTG TCTTGTTGCC ATCTTGCTGG CAATTTGAAT GTTTCAGTAT GTTGGGGAGA

13801 TGCTTGACCG CGGGCTGCTG CTTGCGATTG CTTTCTTTGT GGTGTATCGT GCCGTTCTGG

13861 TTTGCTGCAC TCGTCAGCGC CAACCAGAAC CACAGCTCTC ATCTTCAATT GATTTACAAC

13921 TTGACGCTAT GTGAGCTGAA TGGCACAGAA TGGCTGGGAG ACAAATTTAA TTGGGCAGTG
```

```
13981 GAGACCTTTG TCATCTTTCC CGTGTTAACT CACATTGTCT CATATGGTGC ACTCACCACT

14041 AGCCATTTCC TTGACACAGT CGGTCTGGTT ACTGTGTCTA CCGCCGGGTA TTATCACGGG

14101 CGGTATGTTT TGAGTAGTAT CTACGCGGTC TGCGCTCTGG CCGCGTTAAT TTGCTTCGTC

14161 ATTCGGCTTG CGAAGAACTG CATGTCCTGG CGCTACTCTT GTACCAGATA TACCAATTTC

14221 CTTCTGGACA CTAAGGGCAG ACTCTATCGC TGGCGGTCGC CCGTTATCAT AGAGAAAAGG

14281 GGTAAGGTTG AGGTCGGAAG TCACCTGATC GATCTCAAGA GAGTTGTGCT TGATGGTTCT

14341 GCGGCAACCC CTTTAACCAG AGTTTCAGCG GAACAATGGG GTCGTCTCTA GACGACTTTT

14401 GCTATGATAG CACGGCTCCA CAAAAGGTGT TTTTGGCGTT TTCCATTACC TACACGCCAG

14461 TAATGATTTA TGCCCTGAAG GTAAGTCGCG GCCGACTGTT AGGGCTTCTG CACCTTTTGA

14521 TCTTTCTGAA TTGTGCTTTT ACCTTCGGGT ACATGACATT TGTGCACTTT GATAGCACAA

14581 ATAAGGTCGC GCTCACTATG GGAGCAGTGG TTGCACTCCT TTGGGGGGTG TACTCGGCCA

14641 TAGAAACCTG GAAATTCATC ACCTCCAGAT GCCGTTTGTG CTTGCTAGGC CGCAAGTACA

14701 TTCTGGCCCC TGCCCACCAC GTCGAAAGTG CCGCGGGCTT TCATCCGATT GCGGCAAATG

14761 ATAACCACGC ATTTGTCGTC CGGCGTCCCG GCTCCACTAC GGTTAACGGC ACATTGGTGC

14821 CCGGGTTGAA AAGCCTCGTG TTGGGTGGCA GAAAAGCTGT AAAACAGGGA GTGGTAAACC

14881 TTGTCAAATA TGCCAAATAA CAACGGCAAG CAGCAAAAGA AAAAAAGGG GAATGGCCAG

14941 CCAGTCAACC AGCTGTGCCA AATGTTGGGC AAAATCATCG CCCAGCAGAA CCAGTCCAGA

15001 GGTAAGGGAC CGGGAAAGAA AATTAAAAAG AAAAGCCCGG AGAAGCCCCA TTTTCCTCTA

15061 GCGACTGAGG ATGACGTCAG GCATCACTTT ACCCCTGGTG AGCGGCAATT GTGTCTGTCG

15121 TCAATCCAGA CTGCCTTTAA TCAAGGCGCT GGAACTTGCA CCCTGTCAGA TTCAGGGAGG

15181 ATAAGTTACG CTGTGGAGTT TAGTTTGCCG ACGCATCATA CTGTGCGCCT GATTCGCGTC

15241 ACAGCACCAC CTTCAGCGTG ATGGGCTGGC ATTCTTGAGA CATCCCGGCG TTAGAATTGG

15301 AAGAATGCGT GGTGAATGGC ACTGATTGAC ACTGTGCCTC TAAGTCACCT ATTCAGTTAG

15361 GGCGACCGTG TGGGGGTAGA GTTTAATTGG CGAGAACCAC ACGGCCGAAA TTAAAAAAAA

15421 AAAAAAAAAA AAAA
```

The cDNA consensus sequence of PRRS strain SD 11-21 at P83 has been assigned GenBank Accession number KU131557 (SEQ. ID. NO:9). The cDNA consensus sequence designated SEQ. ID. NO:9 is:

1 ATGACGTATA GGTGTTTGCT TTATGCCGCG GCATTTGTAT TGTCAGGAGC TGTGACCACT
61 GGCACAGCCC GAAACTTGCT GCACAGAAAC ACCCTTCTGT GACAGCCTCC TTCAGGGGAG
121 TTTAGGGGTT TCTCCCTAAC GCCCTGCTTC CGGAGTTGCA CTGCTTTACG GTCTCTCCAT
181 CCTTTTAACC ATGTCTGGGA TTCTTGATCG GTGCACGTGC ACCCCCAATG CCAGGGTGTT
241 TGTGGCAGAG GGCCAAGTCT ACTGCACACG ATGTCTCAGT GCACGGTCCC TCCTTCCCCT
301 AAATCTCCAA GTTTCTGAGC TTGGGGTACT TGGTTTATTC TACAGGCCCG AAGAGCCATT
361 ACGGTGGACG TTGCCACACG CATTCCCCAC TGTCGAGTGT GCTCCTGCTG GCGCTTGTTG
421 GCTTTCTGCA ATTTTTCCAA TTGCGCGAAT GACCAGTGGA AACCTGAATT TCCAGCAAAG
481 GCTGGTACGT GTCGCAGCCG AGCTTTACAG AGCCGGCCAG CTCACCCCTA CAAGCCTGAA
541 AACCTTACAG GTCTATGAAA GGGGTTGCCG TTGGTACCCC ATTGTTGGAC CTGTTCCTGG
601 AGTGGCCGTT TACGCCAACT CCCTACATGT GAGTGACAAA CCCTTCCCAG GAGCGACTCA
661 CGTGCTGACC AACTTACCAC TCCCGCAGAG ACCAAAATCT GAAGATTTCT GCCCCTTCGA

```
 721 GTGCGCCACG GCCGCCGTCT ATGACATCGG CCATGACGCC GTCATGTATG TAACCGAGGA

781 AAAGGTTTCC TGGGCTCCTC GTGGCGGGGA TAAAGGGAAA TTTGAGACTG TTCCTGAGGG

841 GTTGAAGTTG ACTGCGGAAC GACTCTACAC CTCCTTCCCG CCTCACCATG CGGTGGACAT

901 GTCCCTTTTC ATCTTCACAG ACCTTGAGTG CGGCGCTTCC ATGCGGGTCG AACGCCAATA

961 TGGTTGCCTC TCTGCTGGCA CTGTCCCTGA AGGCAACTGC TGGTGGAGTC TGTTTGGCTC

1021 GCTTTCGTTA GAAGCTCAGT ATAAAGAAAT CCGCTACGCC GCCCAATTTG CTATCAGAC

1081 CAAACATGGC GTTACTGGCA AGTACCTGCA GCGGAGGCTG CAAATTAATG GTCTCCGAGC

1141 AGTGGTTGAC CCGAATGGGC CTCTTGTCGT ACAGTATTTC TCCGTTAAGG AGAGCTGGAT

1201 GCGCCACGTG AGACTGGCGG AAGAGCCAGG CTATCCTGGG TTTGAGGATC TCCTCAGGAT

1261 AAGAGTCGAG CCCAACACGT TGCCTTTGTC AACAAGGAC GAGAAAATCT TCCGTTTCGG

1321 CGGTTACAAG TGGTACGGTG CTGGGCGGAG GGCAAGGAGA ACACGTGCAA GAGCAGTCAC

1381 CGCAGTTGCT AGTCATGCTC CGCCCGCTCG TGGGGCCCAG CAGGCCGAGA AGCACGAAGT

1441 TGCTAGTGCC AACAAGACTG AGCTCCTTAC GCACTACTCC CCACCTGCTG AAGGGAATTG

1501 CGGCTGGCAC TGCATCTCCG CCATCATGAA CCGGATGGTG CATTCCAAGT TTGAAACCGC

1561 CCTTTCCGAA AGAGTGAGAT CCCCGGAAGA CTGGGCGACT GATGAGGATC TTGTGAATAC

1621 TATTCAAATC CTCAGGCTCC CTGCGGCCTT AGACAGGAAC GGCGCCTGTA AAAACGCCAA

1681 GTACATCCTT AAGCTGGAAG GTGAGCACTG GACTGTTTCA GTGACCCCCG AATGCCCCC

1741 CTCTTCACTT CCTCTTGAAT GCGTTCAGGG TTGTTGCGAG CATAAGGGCA ATTTTGACTC

1801 TCAAAACGCG GTCGGTTTCT TTGGGTTCGA CCCTGCCAGC CTTGACCGAC TCGCTGGGGT

1861 AATGCATCTG CCCAGCAGCG CCATCCCTGC CGCCCTGGCC GAGTTGTCTG GTGAACTTGA

1921 TTGTTCAACT CCCCCGGCCA CCACTGTGTG GACTACCTTG CAGTTTTATG CTCGTCTTGG

1981 TGGGGGGGAG CATCCTGATC AAGAGTGCTT GAGAAAAATC ATCAGCCTCT GTGAGGTGCT

2041 CGGGAGTTGC TGCTGTTCTC AGAGTAGGGT CAACCGGGTC ACCCCGGAAG AGGTCGCAGC

2101 AAAGATTGAC CTGTATCTTC GTGACGCAGC GAGTCTTGAA GAGTGCTTGG CTAGGCTTGA

2161 GAAAGCTCGC CCGCCAAGCA TGCTGGACAC CTCCTTTGAC TGGGATGTTG TACTCCCTGG

2221 TGTTGGGACG GCTGCTCGGG CAGCAGAACT ACCCCCCACC GATGAGTGTC GCGCTCTAGT

2281 CACTGCTGTG GCCCAAAGGC CTTCGCCGAA AGTTCAGCCT CGAAAGGCGG GGTCTGTTAA

2341 GAGTCTACCA GAGATCAGGC CTGTCCCTGC CCCACGCAGG AAGGTTAAGT CTAGTTGTGG

2401 TGATCTGGCC CCGTTGGGCG GCAATTTCCC TGATAGCTGG AAGATTTGG CTGGTGGCTC

2461 CCTTAATCTC CAGATCTTAC CTGAGCCGGT GGCACAATCC TTTGAACCTG TGCCTGTCCC

2521 TGCACCGCGC AAGACTGCGC CTCGATTAGT GTCGTCATCA TTGGCGTCGA CCCCCGTACC

2581 TACACCACGA TGTGGGTTTC GGCAGTTTGA GGGAATGAAT TTGACAGCTG TGACCCTAGC

2641 ATGCCAGGAT GAGTCCCTCA ATTTGTCTGC ATCCTCGCAG ACTGAATATG AGGCTTCTCC

2701 TTTGGCATTG CAGCAGGGTG AGGATGTCCT TGCGGTGGGG GGACGAGAAG CCGAAGAAGT

2761 CCTGAGCGGA ATCTCGGGAA TGTCAGGTGG CATTAGATTA GCGCCCGCAT CATCAAGTAG

2821 CTCCTTGTCA AGCGTGGAGA TCACACGCCC GAAGTACTCA GCTCAAGCCA TCATTGACTC

2881 AGGTGGACCC TGTTGCGGGC ACCTTCAAGA GGTGAAAGAG AAATACCTTA ATGTCATGCG

2941 TGAGGCATGT GATGCGACTA AGCTCGATGA CCCTGCCACG CAAGAATGGC TCTCTCGCAT

3001 GTGGGAGAGG GTAGACATGC TAACCTGGCG CAACACGTCC ATCTTTCAAG CGCCTTTTAC

3061 CTTAGCTGAC AAGTTTAAGT CCCTCCCGAA GATGATACTC GAAACGCCGC CACCCTACCC

3121 TTGCGGGTTT GTGATGATGC CCCGCACGCC CGCACCTTCT GTGGGTGCGG AAAGCGACAT
```

```
-continued
3181 CACCGTTGGT TCAGTTGCTA CTGAAGATGT CCCGCGTATA CTCGGGGAGG TGGGAGATGT
3241 TGGCAAGATG ACCGGCCAGG AACCCTTAGA ATCCTTCGCA GATGAACTGG CAGATGACCA
3301 ACCTGCTAGG GAGTCCCGAA CACAAGCTCC TCCTGCAAGC ACAGGTAGCG CTGGTTTAGT
3361 TTTGGATTCT GGAGGGTCGC TGGGGCTCAC TGACCTGCCG CTCCCAAACA ATATAGACGC
3421 GGGCGGGAAA GGACCGTTTC ACGCGGTCAA GAAAAAAGCT GTAGGGTGCT TTGACCAACT
3481 GAGCCGCCGG GTTTTTGACA TCGTCTCCCA TCTCCCTGTT TTTTTTTCAC GCCTTTTCGC
3541 GCCCGGTGGT TTTTACTCTT CGGGTGACTG GAGTTTTGCA GCTTTTACTT TATTGTGTCT
3601 CTTTTTATGT TACAGTTATC CGGCCTTTGG TTTTGCTCCC CTCGTGGGTG TATTTTCTGG
3661 GTCTTCTCGG CGCGTGCGCA TGGGGGTTTT TGGCTGCTGG CTGGCTTTTG CTGTTGGTTT
3721 GTTCAAGCCT GCACCCGACC CAGTCGGTGC TGCTTGTGAG TTTGACTCGC CAGAGTGTAG
3781 AGACATCCTT CATTCTTTTG AGCTCCTGCA ACCTTGGGAC CCTGTTCGCA GCCTTGTGGT
3841 GGGCCCCGTC GGTCTCGGCC TTGCCATTTT TGGCAGGTTA CTGGGCGGGG CACGCTACGT
3901 CTGGCTGCTT TTGCTTAGGC TTGGCATCGT TTCAGACTGT ATCCTGGCTG GAGCCTATGT
3961 GCTTTCGCAA GGCAGGTGTA AAAAGTGTTG GGGATCTTGT ATAAGAACAG CCCCCAGTGA
4021 AGTTGCCTTC AATGTGTTTC CCTTTACACG CGCAACTAGA TCGTCACTTG TCAACCTGTG
4081 CGACCGGTTC TGTGCACCCA AGGGCATGGA CCCCATCTTC CTTGCCACAG GATGGCGCGG
4141 ATGCTGGTCC GGCCAGAGCC CCATTGAGCA ACCCTCTGAA AAACCCATAG CGTTCGCCCA
4201 GTTGGACGAA AAGAAAATCA CGGCTAGGAC TGTGGTTGCC CAGCCTTATG ACCCCAACCA
4261 AGCTGTGAAG TGCCTGCGAG TCCTCCAGGC GGGTGGAGCG ATGGTAGCCG AGGCAGTTCC
4321 AAAAGTAGTC AAAGTTTCTG CTGTCCCGTT TCGAGCCCCT TTTTTTCCTG CCGGAGTGAA
4381 AGTTGACCCT GAATGCAGGG TCGTGGTTGA CCCTGACACC TTTACAACCG CTCTCCGGAC
4441 CGGCTACTCC ACCACAAACC TCATTCTTGG TGTTGGGGAC TTTGCCCAGC TGAATGGGTT
4501 GAAGATCAGA CAAATTTCCA AGTCCCCAGG AGGGGGCCCT CACCTCATGG CGGCTTTACA
4561 TGTTGCTTGC TCGATGACTT TGCACATGCT TGTTGGGATT TATGTCACCA TGGTGGGTTC
4621 TTGTGGCTCT GGCACTAACG ATCCGTGGTG CACTAACCCG TTTGCCGTCC CTGTCTATGG
4681 GCCTGGCTCT CTCTGCACGT CCAGGTTGTG CATTTCCCAG CGTGGCCTGA CCCTGCCCTT
4741 AACAGCGCTT GTGGCAGGGT TTGGCGTTCA GGAAATCGCT TTGGTTGTTT TAATCTTTGT
4801 CTCCATCGGG GGTATGGCCC ACAGGTTGAG TTGCAAGGCT GACGTGCTGT GTATCCTGCT
4861 TGCTATTGTC AGCTATGTTT GGCCACCCCT TACCTGGTTG CTTTGTGTGT TTCCTTGCTG
4921 GTTGCGCTGG TTTTCTTTAC ATCCCCTTAC TATTCTATGG TTAGTGTTTT TCTTGATTTC
4981 TGTAAATACG CCCTCGGGAA TCTTGGCCTT GGTCCTGTTA ATCTCTCTTT GGCTCCTTGG
5041 TCGCTATACC AATGTTGCCG GCCTTGTCAC CCCTTATGAC ATTCACCATT ACACCAACGG
5101 CCCTCGCGGC GTTGCCGCCT TGGCCACTGC CCCGGATGGG ACCTACCTGG CTGCTGTCCG
5161 CCGTGCTGCG TTGACTGGCC GTACCATGCT GTTCACCCCG TCCCAACTTG GCTCGCTCCT
5221 TGAGGGCGCT TTTAGAACCC AAAAGCCTTC ACTGAACACT GTCAATGTAG TTGGGTCCTC
5281 CATGGGCTCC GGCGGGGTGT TCACCATTGA TGGGAAGATC AAATGTGTGA CCGCTGCTCA
5341 TGTCCTCACG GGTAACTCTG CCAGGGTTTC CGGGGTTGGC TTCAATCAAA TGTTGGACTT
5401 TGATGTTAAA GGGGATTTTG CCATAGCCGA TTGTCCGAAT TGGCAAGGAG TCGCCCCCAA
5461 GTCCCGGTTC TGCAAGGATG ATTGGACTGG CCGTGCTTAT TGGCTCACGT CCTCCGGCGT
5521 CGAACCCGGC GTCATTGGGC AAGGATTCGC CTTTTGTTTC ACCGCGTGCG GCGATTCCGG
```

```
-continued
5581  GTCCCCAGTG ATCACCGAGG CCGGGGAGCT TGTCGGTGTC CACACGGGAT CAAACAAACA

5641  AGGAGGAGGC ATTGTTACGC GCCCTTCAGG CCGGTTTTGT AATGTGACAC CCACCAAATT

5701  AAGTGAATTG AGTGAATTCT TCGCTGGACC TAGGGTCCCG CTTGGTGACG TGAAGGTTGG

5761  CAATCACATA ATCAAAGATA TAAATGAGGT GCCCTCAGAT CTCTGCGCCT TACTCGCTGC

5821  CAAACCCGAA TTGGAAGGAG GCCTCTCCAC CGTTCAACTT CTGTGCGTGT TTTTTCTCCT

5881  ATGGAGAATG ATGGGACATG CCTGGACACC CTTGGTTGCC GTTGGTTTTT TCATCTTGAA

5941  TGAAGTTCTC CCAGCAGTCC TGGTCCGGAG TGTCTTCTCC TTTGGAATGT TCGCACTGTC

6001  TTGGTTCACG CCGTGGTCTG CACAAATTCT AATGATCAGG CTCTTGACAG CAGCCCTAAA

6061  CAGAAACAGA TCGTCACTTG CCTTTTACAG CCTGGGCGCA CTAACCGGTT TTGTTGCAGA

6121  TCTTGCAACC AATCAGGGGT ATTTATTGCA CGCGGTCATG AATGTGAGCA CCTATGCATT

6181  CCTGCCTCGT GCAATGGCCG TGACCTCACC AGTCCCAATA GTTGCGTGTG GCGTTGTGCA

6241  CTTGCTTGCC ATCATTCTGT ACTTGTTCAA GTACCGTAGC CTGCATGCCG TCCTGGTCGG

6301  CGATGGTGCG TTTTCCGCGG CTTTCTTCTT GCGATACTTT GCGGAGGGAA AGTTGAGGGA

6361  AGGGGTGTCG CAGTCTTGCG GCATGAATCA TGAGTCACTA ACCGGTGCCC TCGCCATGAA

6421  ACTCAGCGAC GAAGACTTGG ACTTCCTCAC AAAATTGACT GATTTTAAGT GCTTTGTTTC

6481  TGCATCCAAC ATGAGGAATG CGGCGGGTCA ATTTATAGAG GCCGCCTACG CCAAAGCACT

6541  GAGGGTGGAA CTTGCCCAGT TGGTTCAAGT CGATAAAGTT CGAGGTGTCC TGGCCAAACT

6601  TGAAGCTTTC GCTGACACCG TGGCGCCTCA ACTTTCACCC GGTGACATTG TTGTCGCCCT

6661  TGGACACACA CCTGTCGGCA GCATTTTTGA CCTGAAGGTC GGCAATGTTA AGCACACTCT

6721  CCAGTCCATT GAGACCAGAA CCCTTGCCGG GTCTAAAATG ACTGTGGCGC GCGTCGTAGA

6781  CCCAACCCCC ACACCCCCGC CCGCACCTGT GCCCATTTCC CTCCCACCAA AGGTTTTGGA

6841  GAACGGTCCC AACGCCTGGG GGGATGAGAA CGGTTTGAAC AAAAAAAAGC GGCGCAAGAT

6901  GGAGGCCGTT GGCATTTACG TTATGGGCGG GAAAAAGTAT CAAAAATTTT GGGATAAGAA

6961  TTCTGGTGAT GTGTTCTATG AAGAAGTCCA CGACAACACA GACGCGTGGG AATGCCTCAG

7021  AGTTGACAAC CCTGCCGACT TGGATCCTGA GAGGGGAACC TTGTGTGGAC ACACCACCAT

7081  AGACAACAGG CCTTACCATG TTTATGCTTC TCCGTCTGGT AGGAAGTTTC TAGTCCCTGT

7141  CAACCCGGAG AGCGGAAAAG CTCAGTGGGA AGCTGCTAAG CTTTCTTTAG ATCAGGCCCT

7201  CAGTATGATG AATGTCGACG GCGAACTGAC CGCCAAAGAA GTGGAAAAAT TGAAGAGAAT

7261  AATTGACAAA CTCCAGGGCC TGACTAAGGA GCAGTGTTTA AACTGCTAGC CGCCAGCGGC

7321  TTGACCCGCT GTGGTCGCGG CGGCTTGGTT GTTACTGAGA CAGCGGTAAA GATAGTCAGG

7381  TTCCACAACC GGACCTTTAC CCTAGGGCCT GTGAATTTGA AAGTAGCTAG CGAAGTTGAG

7441  TTGAAGGACG CGGTCGAGCA CGGCCAACAC CCGGTCGCGA TACCAGCCGA TGGTGGCGTC

7501  GTGCTCCTGC GTTCCGCTGT TCCTTCGCTT ATAGACGTCC TGATCTCCGG TGCTGACGCA

7561  TCTCCCAGGT TGCTCGCCCG TCACGGACCG GGAAATACTG GGGTCAATGG CGCGCTTTGG

7621  GATTTTGAGT CTGAAGCTAC CAAAGAGGAA GTAGCACTTA GTGCGCAAAT AATACAGGCC

7681  TGTGACATTA GACGCGGCGA TGCACCTGAG ATTGGCCTTC CTTACAAGTT GTACCCTGTT

7741  AGGGGCAACC CTGAACGGGC AAGAGGGGTT CTAATGAACA CAAGATTTGG AGACATACCT

7801  TACAAGACCC CCAGCGACAC CGGGAGCCCG GTGCACGCGG CCGCCTGCCT TACGCCCAAC

7861  GCCACTCCAG TAACTGATGG CGCGCTCCATC CTGGCCACGA CCATGCCCTC CGGGTTTGAA

7921  CTATATGTGC CGACCATTCC AGCGTCTGTC CTTGATTACC TTGACTCCAG ACCAGACTGT

7981  CCTAAACAGT TGACTGAGCA CGGGTGTGAA GATGCCGCGT TGAAGGACCT TTCTAAATAT
```

```
8041 GACCTGTCCA CCCAAGGCTT TGTGTTACCT GGAGTTCTAC GCCTCGTGCG AAAATATCTG

8101 TTTGCTCATG TAGGTAAGTG CCCGCCTGTC CACCGGCCCT CTACCTATCC TGCCAAGAAC

8161 TCCATGGCCG GAATAAATGG GAACAGGTTC CCAACCAAGG ATATTCAAAG CATCCCTGAG

8221 ATCGACGTTT TGTGTGCACA AGCTGTGCGA GAAAACTGGC AAACTGTTAC ACCCTGCACT

8281 CTTAAGAAGC AGTATTGCGG TAAAAAGAAG ACCAGGACCA TACTTGGCAC CAACAACTTC

8341 GTTGCGCTGG CCCACCGGGC GGCGCTGAGT GGTGTCACCC AGGGTTTCAT GAAGAAGGCG

8401 TTTAACTCAC CCATCGCCCT TGGGAAAAAT AAATTTAAGG AGCTACAGAC TCCAGTCTTG

8461 GGTAGGTGTC TTGAGGCTGA TCTCGCTTCC TGCGATCGAT CCACGCCTGC AATCGTTCGC

8521 TGGTTTGCCG CCAACCTTCT TTATGAACTT GCCTGTGCTG AGGAGCATTT ACCGTCGTAC

8581 GTGCTGAACT GTTGTCACGA CCTATTGGTC ACGCAGTCCG GCGCAGTGAC TAAGAGAGGT

8641 GGCCTGTCGT CCGGTGACCC AATCACCTCT GTGTCCAACA CCATTTATAG CTTGGTGATC

8701 TATGCACAGC ATATGGTGCT TAGTTACTTC AAAAGTGGTC ACCCCATGG CCTTCTGTTT

8761 TTACAAGACC AGCTAAAGTT TGAAGACATG CTCAAAGTTC AACCCCTAAT CGTCTATTCG

8821 GACGACCTCG TGTTGTATGC CGAGTCTCCC ACCATGCCAA ACTATCACTG GTGGGTTGAA

8881 CACCTGAATT TGATGTTGGG ATTTCAGACG GACCCAAAGA AGACTGCAAT AACAGACTCA

8941 CCTTCATTCC TAGGTTGTAG AATAATAAAT GGCCGCCAGT TAGTACCCAA CCGTGACAGA

9001 ATTCTCGCGG CCCTTGCCTA TCACATGAAG GCGAGTAATG TTTCTGAGTA CTACGCCTCC

9061 GCAGCCGCAA TACTCATGGA CAGTTGTGCT TGTCTAGAGT ATGATCCTGA GTGGTTTGAA

9121 GAACTTGTGG TTGGAATGGC GCAGTGCGCC CGTAAGGACG GCTATAGTTT CCCCGGCCCG

9181 CCGTTCTTCT TGTCCATGTG GGAAAAGCTC AGGTCAAATT ATGAGGGGAA GAAGTTGAGA

9241 GTGTGTGGTT ATTGCGGAGC TTCAGCCCCG TATGCTACTG CCTGTGGCCT TGACGTTTGT

9301 GTTTACCACA CCCACTTTCA CCAGCATTGT CCAGTCATAA TATGGTGTGG CCACCCGGCG

9361 GGTTCTGGGT CCTGCGATGA GTGCAAATCC CCTACAGGGA AGGGTACAAG CCCTCTGGAT

9421 GAGGTCTTAA GACAAGTCCC TTATAAGCCT CCACGGACTA TTCTTATGCA TGTGGAGCAG

9481 GGCCTCACCC CCCTTGACCC AGGCAGATAC CAGACCCGCC GTGGGTTGGT TGCTGTCAGG

9541 CGCGGGATAA GGGGAAATGA AGTTGACCTG CCAGATGGTG ATTATGCCAG TACTGCCCTA

9601 CTCCCCACCT GCAAAGACAT AGACATGGTT GCTGTGGCCT CCAATGTGTT GCGCAGTAGG

9661 TTCATCATCG GCCCACCTGG CGCAGGGAAA ACACACTGGC TTCTTCAACA GGTTCAGGAT

9721 AGTGATGTCA TTTACACGCC AACCCATCAG ACCATGCTTG ACATGATCAA GGCTTTGGGG

9781 ACGTGCCGGT TCAATGTCCC GGCAGGCACA ACGCTGCAAT TCCCTGCCCC CTCCCGTACC

9841 GGCCCGTGGG TTCGCATCCT TGCCGGCGGT TGGTGTCCAG GTAAGAATTC CTTCCTGGAT

9901 GAAGCAGCGT ATTGCAATCA CCTTGACGTC TTGAGGCTTC TCAGCAAAAC TACCCTCACC

9961 TGTCTGGGGG ATTTCAAACA ACTCCACCCG GTGGGTTTTG ATTCTCATTG CTATGTTTTT

10021 GATATCATGC CTCAGACTCA ACTGAAGACC ATCTGGAGGT TTGGACAGAA TATCTGTGAC

10081 GCCATTCAGC CAGATTACAG GGACAAACTC GTGTCCATGG TCAACACAAC CCGTGTAACC

10141 TATGTGGAAA GACCTGTCAA GTATGGGCAA GTCCTCACCC CCTACCACAG AGACCGAGAG

10201 GATGGTGCTA TCACTATTGA CTCCAGTCAA GGCGCCACAT TTGATGTGGT CACATTGCAT

10261 TTGCCCACTA AAGATTCACT CAACAGGCAA AGAGCCCTTG TTGCTATCAC CAGGGCAAGG

10321 CATGCAATCT TTGTGTATGA CCCACACAGG CAACTGCAGA GCATGTTTCG TCTTCCTGCA

10381 AAAGGCACAC CTGTCAACCT TGCCGTGCAC CGTGACGAGC AGCTCATCGT ATTAGATAGA
```

```
10441 AATAACAAAG AGTGCACGGT TGTTCAGGCT TTAGGCAATG GGGACAAATT CAGGGCCAGT
10501 GACAAGCGCG TTGTAGATTC TCTTCGCGCC ATTTGTGCAG ATCTTGAAGG GTCGAGCTCC
10561 CCGCTCCCCA AGGTCGCACA CAACTTGGGA TTTTATTTCT CACCTGATTT GACACAGTTT
10621 GCTAAACTCC CGGCGGAACT TGCACCCCAC TGGCCCGTGG TGACAACTCA GAACAACGAA
10681 AATTGGCCAG ACCGGCTGGT TGCTAGCCTC CGCCCTATCC ACAAATATAG CCGCGCGTGC
10741 ATCGGAGCCG GCTATATGGT GGGCCCCTCA GTGTTTCTAG GCACTCCTGG GGTTGTGTCA
10801 TACTATCTCA CACAATTTGT CAAAGGGGAG GCTCAGGTGC TTCCGGAGAC GGTCTTCAGC
10861 ACCGGCCGAA TTGAGGTAGA TTGTCGAGAG TATCTTGATG ATCGGGAACG AGAAGTTGCT
10921 GAGTCCCTCC CACATGCCTT TATTGGCGAC GTCAAAGGCA CTACCGTTGG GGGATGTCAC
10981 CATGTCACTT CTAAATATCT CCCACGCTTC CTTCCCAAGG AATCAGTTGC GGTGGTTGGG
11041 GTTTCAAGCC CCGGGAAAGC CGCAAAAGCA GTTTGCACAT TAACAGATGT GTACCTCCCA
11101 GATCTTGAGG CTTACCTCCA TCCAGAGACC CAGTCTAAGT GCTGGAAAGT GATGTTGGAC
11161 TTCAAGGAAG TTCGACTGAT GGTCTGGAGA GATAAGACGG CCTACTTTCA ACTTGAAGGC
11221 CGCCATTTCA CCTGGTACCA GCTTGCAAGT TATGCCTCGT ACATCCGAGT TCCCGTTAAC
11281 TCTACGGTGT ACCTGGACCC CTGTATGGGC CCTGCCCTTT GCAACAGAAG AGTCGTTGGG
11341 TCTGCACATT GGGGAGCTGA CCTTGCAGTT ACCCCTTATG ATTATGGTGC CAAAATCATT
11401 CTGTCTAGTG CGCACCATGG TGAAATGCCT CCTGGGTACA GAATTCTAGC GTGCGCGGAG
11461 TTCTCGCTTG ATGACCCAGT GAGGTACAAA CACACTTGGG GGTTTGAATC GGATACAGCG
11521 TATCTGTACG AGTTCACCGG AAACGGTGAG GACTGGGAGG ATTACAATGA TGCGTTTCGT
11581 GCACGCCAGA AAGGGAAAAT TTATAAGGCC ACTGCCACCA GCATGAGATT TCATTTTCCC
11641 CCGGGTCCTG CCATTGAACC AACATTGGGC CTGAACTGAA ATGAAATGGG GGCTGTGCAG
11701 AGCCTTTTCG ACAAAATTTG CCAACTTTTT GTGGATGCTT TCACGGAATT TTTGGTGTCC
11761 ATTGTTGATA TCATCATATT TTTGGCCATT TTGTTTGGCT TCACCATCGC AGGCTGGCTG
11821 GTTGTCTTCT GTATCCGACT GGTTTGCTCC ACGGTACTCC GTGCGCGCTC TACCATTCAC
11881 CCTGAGCAAT TACAGAAGAT CCTATGAGGC CTTCCTTTCC CAGTGCCAAG TGGACATTCC
11941 CGCCTGGGGA ACTAAGCATC CCTTGGGGGT GCTTTGGCAC CACAAGGTGT CAACTCTGAT
12001 TGATGAAATG GTGTCGCGTC GAATGTACCG CATCATGGAA AAAGCAGGAC AGGCTGCCTG
12061 GAAACAGGTT GTGAGCGAAG CTACATTGTC TCGCATAAGT GGCTTGGATG TGGTGGCTCA
12121 TTTTCAGCAT CTTGCTGCCA TTGAAGCCGA GACTTGCAAA TATTTGGCCT CTCGGCTGCC
12181 CATGCTACAC AACCTAGTCA TGTCAGGGTC GAATGTAACC ATAGTGTATA ATAGCACTTT
12241 GGGTCAAGTG TTTGCCATTT TCCCAACCCC TGGTTCCCGG CCAAAACTTT CTGATTTTCA
12301 ACAATGGCTC ATAGCTGTGC ATTCTTCCAT ATTTTCTTCT GTTGCGGCTT CTTGTACTCT
12361 TTTTGTTGTG CTGTGGCTGC GAATTCCAAT ACTACGTACT GTTTTTGGTT TCCGCTGGTT
12421 AGGGGCAACT TTTCTTTCGA ACTCACAGTG AATTACACGG TGTGCCCACC CTGCCTCACC
12481 CGGCAAGCAG CCGCTGAGAT CTACGAACAC AGCGGGTCTC TTTGGTGCAG GATAGGGCAT
12541 GACCGATGTA GCCAGAGTGA TCATGACGAA CTAGGGTTCT TGGTTCCACC TGGCCTTTCC
12601 AGCGAGGGCC ACTTGACCAG TGTTTACGCC TGGCTGGCGT TCTTGTCTTT CAGCTACACA
12661 GCCCAGTTCC ACCCCGAGAT ATTTGGAATA GGGAATGTGA GTAGAGTTTA TGTTGACGTC
12721 ACTCACCAAC TCATCTGCGC CGAACACGAC GGGCAGAACA CCACCCTGCG TCGCCATGAC
12781 AATATCTCAG CCGTGTTTCA GACCTATTAC CAACATCAGG TCGATGGCGG CAATTGGTTT
12841 CACCTAGAAT GGCTGCGTCC CTTCTTTTCC TCTTGGCTGG TTTTGAATGT CTCGTGGTTT
```

```
12901 CTCAGGCGTT CGCCTGCAAA CCGTGTTTCA GTTCGAGTCT TTCAGACATC AAAACCAACA

12961 CCACCGCAGC TGCAGGCTTT GCTGTCCTCC AAGACATCAG CTGTCTTAGG CATGGCTACT

13021 CGTCCATTGA GGCGATTCGC AAAAGCCGTC AATGCCGCAC GGCGATAGGA ACGCCCGTGT

13081 ACATCACTGT CACGGCCAAT GTAACAGATG AGAATTACTT GCATTCCTCT GATCTCCTCA

13141 TGCTTTCCTC TTGCCTCTTC TATGCTTCTG AGATGAGTGA AAAGGGATTC AATGTGGTCT

13201 TCGGCAACGT GTCAGGCATT GTGGCTGTGT GTGTCAACTT TACCAGCTAT GTCCAACATG

13261 TTAAGGAGTT TACTCAGCGC TCTTTGGTGG TCGACCACGT GCGACTGCTT CATTTCATGA

13321 CACCTGCGAC CATGAGGTGG GCAACAGTTT TAGCCTGTCT TTTCGCCATC TTGTTGGCGA

13381 TTTGAATGTT TAAGTATGTT GGGGAAATGC TTGACCGCGG GCTACTGCTC GCAATTGCTT

13441 TTTTTCTGGT GTATCGTGCC GTTCTGTTTT GCTGCGCTCG TCAACGCCGC CAGCAACAGC

13501 AGCTCCCATT TACAGTTGAT TTATAACCTG ACGATATGCG AGCTGAATGG CACAGATTGG

13561 TTGAATCAAA AGTTTGATTG GGCAGTGGAG ACTTTTGTCA TTTTTCCTGT GTTGACCCAC

13621 ATTGTCTCCT ACGGTGCCCT TACCACCAGC CATTTCCTTG ACACGGCCGG CCTAATCACT

13681 GTGTCTACCG CCGGATATTA CCATGGGCGG TATGTGTTGA GTAGCATCTA CGCCGTCTTT

13741 GCCCTGGCTG CGTTGATTTG TTTTGTCATT AGGTTGACAA AAAACTGTAT GTCCTGGCGC

13801 TACTCATGTA CCAGATATAC CAACTTTCTT CTGGACACCA AAGGCAATCT CTATCGTTGG

13861 CGGTCACCCG TCGTTATAGA GAGAAGGGGT AAAGTTGAGG TTGGAGACCA CCTAATCGAC

13921 CTCAAAAGAG TTGTGCTTGA TGGTTCCGCG GCAACCCCTA TAACCAAGAT TTCAGCGGAA

13981 CAATGGGGTC GTCCCTAGAC GACTTCTGCA ATGACAGCAC AGCTGCACAA AAGGTGCTTT

14041 TGGCGTTTTC CATCACCTAT ACGCCAATAA TGATATATGC CCTGAAGGTA AGTCGCGGCC

14101 GACTGTTAGG GCTTTTGCAT CTTTTAATTT TCTTGAATTG TGCTTTCACC TTCGGGTACA

14161 TGACATTTGT TCATTTTCAG AGTACAAACA AGGTCGCGCT CACTATGGGA GCAGTTGTTG

14221 CACTCCTTTG GGGGGTGTAC TCAGCCATAG AAACCTGGAA ATTCATCACT TCCAGATGCC

14281 GTTTGTGCTT GCTAGGCCGC AGGTACATTC TGGCCCCTGC CCACCACGTT GAAAGTGCCG

14341 CGGGCTTTCA TCCGATTGCG GCAAGTGATA ACCACGCATT TGTCGTCCGG CGTCCCGGCT

14401 CCACTACTGT TAACGGCACA TTGGTGCCCG GGTTGAAAAG CCTCGTGTTG GGTGGCAGAA

14461 AAGCTGTTAA GCGGGGAGTG GTAAACCTCG TTAAATATGC CAAATAACAA CGGCAGGCAG

14521 CAAAAAAATA AGAAGGGGAG TGGCCAGCCA GTCAATCAGC TGTGCCAAAT GCTGGGCAAG

14581 ATCATCGCCC AGCAAAATCA GTCCAGAGGC AAGGGACCGG GTAAGAAAAA TAAGAAGAGA

14641 AACCCGGAGA AGCCCCATTT TCCTCTTGCG ACCGAAGATG ACGTCAGGCA TCACTTCACC

14701 CCCAGTGAAC GGCAATTGTG TCTGTCGTCG ATCCAGACTG CCTTCAACCA GGGCGCTGGA

14761 ACTTGCACCC TGTCAGATTC AGGGAGGATA AGTTACACTG TGGAGTTTAG TTTGCCGACG

14821 CACCACACTG TGCGCCTTAT TCGCGCCACA GCATCACCTC CATCGTGATG GGCTTACATT

14881 CTTGGAGCTC CTCAGTTTCA CAATTGGAAG AATGTGTGGT GAATGGCACT GATTGGCACT

14941 GTGCCTCTAA GTCACCTATT CAATTAGGGC GACCGTGTGG GGGTAGAGTT TAATTGGCGA

15001 GAACCATACG GCCGAAATTA AAAAAAAAAA AAAAAAAAAA AAAAAA
```

A person skilled in the art would recognize the polyadenosine tails of each of the genomic consensus sequences could vary in length from the above reported sequences.

EXAMPLE 2

The objective of this study is to evaluate the efficacy of experimental PRRSV vaccines in growing swine following heterologous challenge with a virulent PRRS virus. The efficacy of a test vaccine is based on the effectiveness of the vaccine to reduce lung lesions and viremia compared to a non-vaccinated control. The design of this study is given in Table 1.

TABLE 1

Study design.

| Treatment Group | PRRSV strain | FFU[1] titer/mL | Dose Volume | Route | Vaccination Day | Number of Animals |
|---|---|---|---|---|---|---|
| T01 | None[2] | N/A | 0.5 mL | IM[3] | Day 0 | 16 |
| T02 | SD 04-89 | $1.1 \times 10^7$ | 0.5 mL | IM | Day 0 | 10 |
| T03 | SD 03-15 | $3.8 \times 10^6$ | 0.5 mL | IM | Day 0 | 10 |
| T04 | SD 95-10 | $1.3 \times 10^7$ | 0.5 mL | IM | Day 0 | 10 |
| T05 | SD 11-21 | $4.0 \times 10^6$ | 0.5 mL | IM | Day 0 | 10 |
| T06 | SD 02-10 | $1.1 \times 10^7$ | 0.5 mL | IM | Day 0 | 10 |
| T07 | SD 95-47 | $2.4 \times 10^7$ | 0.5 mL | IM | Day 0 | 10 |
| T08 | ND 99-14 | $2.1 \times 10^7$ | 0.5 mL | IM | Day 0 | 10 |
| T09 | MN 05-68 | $1.6 \times 10^7$ | 0.5 mL | IM | Day 0 | 10 |

[1]Flourescent foci unit (FFU).
[2]Placebo control animals received phosphate-buffered saline (PBS).
[3]IM = Intramuscular.

The pre-challenge phase was from the day of arrival at the study site (Day −1) through day of challenge (Day 35). Blood samples for PRRSV serum antibody determination using fluorescent foci neutralization (FFN) testing were collected on Days 0, 14, 28 and 35. Blood samples for determination of PRRSV viremia were collected on Days 0 and 35. Nasal swabs to assess viral load were collected on Days 0 and 35. A body weight measurement (lbs) was taken on Day 0 and prior to the challenge on Day 35.

On Day 35, a 3 mL non-luer lock syringe was used to deliver a 2 mL dose intranasally, with approximately 1 mL per nostril. The post-challenge phase was from Day 35 to Day 49. All pigs were individually assessed for depression, body condition and respiratory distress on Days 35-49 and scored for each clinical sign. Blood samples for PRRSV serum antibody determination (FFN) were collected on Days 42 and 49. Blood samples for determination of PRRSV viremia were collected on Days 38, 42, 45, and 49. Nasal swabs to assess viral load were collected on Days 38, 42, 45, and 49. A body weight measurement was obtained at the time of necropsy on Day 49. On Day 49, animals were humanely euthanized as per the site standard operating procedure and lungs were scored by the Study Investigator who was blinded to treatment. Each of the seven pulmonary lobes was examined both visually and by palpation for gross characteristic lesions attributed to PRRSV. The amount of lesion/consolidation in each pulmonary lobe was scored as an actual between 0 and 100% of the lobe. The score for each lobe was entered into a weighted formula to calculate the percentage of lung with lesions.

Ninety-six weaned crossbred gilts and barrows approximately 3 weeks of age that were sero-negative to PRRSV and assessed to be in good health were utilized for this study. Upon arrival at the study site, selected study animal were randomly assigned to treatment groups (T01-T09) and study pen. Upon arrival all candidate animal that met the following inclusion criteria were included in the study and those that did not meet criteria were excluded: 1) seronegative for PRRSV by serum neutralization testing (FFN) on Day 0; and 2) animals clinically assessed to be in good health based on physical examination conducted on Day O.

After arrival at the study site, the pigs were housed by treatment group in five BSL-2 environmentally-controlled containment rooms. Each containment room contained five pens capable of holding five pigs per pen. Within each of the vaccinate rooms, the two treatment groups were separated by a plastic sheeting barrier and groups did not share the same airspace. Biosecurity was strictly maintained between the two areas separating the vaccinate groups within the room. The pigs were fed production-appropriate, standard swine grower ration (NRC, 2012) ad libitum. The pigs had access to clean drinking water ad libitum.

General health observations were conducted once daily from time of arrival at the study site until the day prior to challenge (Day −1 through 34). All pigs were individually assessed for depression, body condition and respiratory distress on Days 35-49 and scored for each clinical sign as defined in the scoring system.

Animals that developed clinically significant concurrent disease prior to Day 35 were removed from the study. Any data collected from the pig prior to exclusion was not included in data analysis. Following challenge on Day 35, any pig found dead or sacrificed in extremis was necropsied to determine cause of death, if possible. Due to a death attributable to *S. suis* and a confirmed illness in the same pen (T08), EXCEDE® antibiotic (Zoetis Animal Health) was administered to individual study animals as needed and all animals on Day 30.

All candidate PRRSV strains were passed 83 times on MARC-145 cells. Titers for each of the eight (8) vaccines were determined, as shown in Table I. Sterility testing per USDA 9 C.F.R. requirements was successfully completed at Benchmark BioLabs, Lincoln, Nebraska. Vaccines comprised the PRRSV in a pharmaceutically-acceptable excipient, i.e. physiological saline.

Immediately prior to use, three 1 mL stock vials of the PRRSV NADC-20 challenge strain were thawed at room temperature and 3 mLs of the stock was added to 297 mLs of Minimum Essential Medium Eagle with Earle's salts and L-glutamine (MEM) from Mediatech, Inc. in a sterile container. The inoculum (consisting of the viral stock and medium) was hand mixed and retained on wet ice during administration to animals. Prior to challenge, five (5) mLs of the challenge inoculum was aliquoted directly into a sterile container for submission to the diagnostic laboratory for titer determination. Titer results were $10^{2.75}$ $TCID_{50}/mL$.

Animal were the experimental unit. Differences between groups were assessed using two-sided tests at alpha=0.05.

Percentage of total lung with lesions was calculated according to the following formula:

Percentage of total lung with lesions={(0.10×left apical)+(0.10×left cardiac)+(0.25×left diaphragmatic)+(0.10×right apical)+(0.10×right cardiac)+(0.25×right diaphragmatic)+(0.10×intermediate)}.

The influence of vaccination on the percentage of total lung lesions was evaluated by calculating the mitigated fraction and the associated 95% confidence interval (MF; CI; the FREQ procedure in SAS® software, SAS Institute, Cary N.C.) for each placebo/vaccinated pair. In addition, the percentage of total lung with lesions was transformed using the arcsine square root, prior to further analysis. The transformed data was analyzed by a mixed linear model that includes the fixed effect of treatment (the MIXED procedure in SAS® software) as the only factor. If the effect of treatment was statistically significant, pair-wise comparisons between the placebo and vaccinated groups were made using linear contrasts and an unadjusted alpha=0.05. The vaccine complied with the test if the vaccinated pigs, when compared with controls, showed a significant reduction in the lung lesion score.

Methods appropriate for repeated measures were used to evaluate the effect of vaccination on viremia values (the MIXED procedure in SAS® software, SAS Institute, Cary N.C.) under the assumption of a normal distribution. Data was transformed prior to analysis to stabilize the residuals. The statistical model included treatment, time, and treatment by time interaction as fixed effects. If the treatment by time interaction was significant, the effects of the vaccine within that time treatment were evaluated. Within time, comparisons were made between vaccinated and non-vaccinated animals. If the interaction was not significant, the main effect of treatment was assessed. Comparisons were made between vaccinated and non-vaccinated animals. Least squares means, standard errors, 95% confidence intervals of the mean, and ranges were presented as appropriate.

Methods appropriate for repeated measures of continuous or binomial data were used to evaluate the effect of vaccination on serum antibody and nasal swab values (the MIXED or GLIMMIX procedure in SAS® software, SAS Institute, Cary N.C.) under the assumption of a normal/binomial distribution. Data was transformed prior to analysis to stabilize the residuals. The statistical model included treatment, time, and treatment by time interaction as fixed effects. If the treatment by time interaction was significant, the effects of within time treatment were evaluated. Within time, comparisons were made between vaccinated and non-vaccinated animals. If the interaction was not significant, the main effect of treatment was assessed. Comparisons were made between vaccinated and non-vaccinated animals. Least squares means, standard errors, 95% confidence intervals of the mean, and ranges were presented as appropriate.

Body weight (Days 35 and 49), depression score, respiratory score and body condition scores (Days 35-49) were statistically analyzed using an ANCOVA appropriate for repeated measures (the MIXED procedure). Day 0 values were included as a covariate, if appropriate. Treatment group, time and the group by time interaction were included in the model as fixed effects. If the interaction term was significant, within time group effects were evaluated by comparing each vaccination group to the control using an unadjusted alpha=0.05. If the interaction was not significant, the main effect of group was evaluated, and if significant, group effects were evaluated by comparing each vaccination group to the control using an unadjusted alpha=0.05. Mortality was not assessed since there was only one death during the study.

The mean percent lung involvement in the control group was 37.9% (Table 2) which was in agreement with the expected pathology for this PRRSV challenge model (range 30 to 50%, L. Kesl of Veterinary Resources, Inc., personal communication) using Type-2 strain NADC-20. It was concluded that the PRRS viral challenge was adequate to assess the vaccine strain candidates.

Mean lung lesion scores are presented in Table 2. With the exception of the vaccine containing PRRSV EU-like (i.e. Type 1 PRRSV) strain SD 03-15, all experimental vaccines reduced (P<0.05) lung lesions compared to the control group. Notably, strains SD 95-10, SD 11-21 and ND 99-14 induced a high degree of protection resulting in very low lung involvement (2.7%, 1.0% and 1.6%, respectively). Strains SD 95-47 and MN 05-68 also performed well, while strains SD 04-89 and SD 02-10 were acceptable. The mitigated fraction of each vaccine versus the control group is shown in Table 3. These results indicated that pigs vaccinated with attenuated PRRSV strains SD 95-10 (T04), SD 11-21 (T05) and ND 99-14 (T08) had at least a 90% probability of having less severe lung lesions than pigs in the control group.

TABLE 2

Mean Lung Lesion Scores.

| Treatment Group | Vaccine | Estimate[1] | Standard Error | Mean[2] |
|---|---|---|---|---|
| T01 | None (PBS only) | 0.6633 | 0.05594 | 37.91% |
| T02 | Strain SD 04-89 | 0.3861* | 0.07075 | 14.14% |
| T03 | Strain SD 03-15 | 0.4885 | 0.07075 | 22.02% |
| T04 | Strain SD 95-10 | 0.1662* | 0.07075 | 2.74% |
| T05 | Strain SD 11-21 | 0.0988* | 0.07075 | 0.97% |
| T06 | Strain SD 02-10 | 0.3642* | 0.07075 | 12.69% |
| T07 | Strain SD 95-47 | 0.2073* | 0.07075 | 4.24% |
| T08 | Strain ND 99-14 | 0.1252* | 0.07458 | 1.56% |
| T09 | Strain MN 05-68 | 0.2316* | 0.07075 | 5.27% |

[1]Untransformed means.
[2]Back transformed means.
*Versus T01, significantly different at $P < 0.05$.

TABLE 3

Lung Lesion Scores.

| Treatment Group Comparison | Mitigated Fraction[1] | 95% confidence interval |
|---|---|---|
| Control (T01) versus SD 04-89 (T02) | 0.5875 | 0.2266, 0.9484 |
| Control (T01) versus SD 03-15 (T03) | 0.3125 | −0.1838, 0.8088 |
| Control (T01) versus SD 95-10 (T04) | 0.9000 | 0.7077, 1.0000 |
| Control (T01) versus SD 11-21 (T05) | 0.9688 | 0.9017, 1.0000 |
| Control (T01) versus SD 02-10 (T06) | 0.7000 | 0.3092, 1.0000 |
| Control (T01) versus SD 95-47 (T07) | 0.8000 | 0.5290, 1.0000 |
| Control (T01) versus ND 99-14 (T08) | 0.9028 | 0.7152, 1.0000 |
| Control (T01) versus MN 05-68 (T09) | 0.7875 | 0.4986, 1.0000 |

[1]Mitigated fraction means the relative increase in the probability that the lung lesions of vaccinates (T02-T09) will be less severe than the lung lesions of non-vaccinates (T01).

Geometric means of PRRSV enumerated by qtRT-PCR from nasal secretions are presented in Table 4, as an indication of viral shedding. With the exception of pigs vaccinated with strain SD 02-10, vaccine virus was detected in the nasal swabs of all vaccinated groups at Day 35. Pigs vaccinated with strains SD 03-15, SD 95-10 and SD 95-47 had statistically greater (P<0.05) genomic copies/mL than the pigs of the control group with mean values of 277, 337 and 7 genomic copies/mL, respectively. Upon challenge on Day 35, all groups shed some virus at Day 38, 42, 45 and 49 (3, 7, 10 and 14 days post challenge (DPC), respectively). Pigs vaccinated with strains SD 95-10, SD 95-47 and ND 99-14 had a lower (P<0.05) level of shedding than controls at all time-points post challenge. By 10 and 14 DPC, all vaccine strains induced a reduction (P<0.05) in shedding compared to the controls, with the exception of strains SD 04-89 and SD 03-15.

TABLE 4

Geometric Means of PRRSV Genomic Copies/mL in Nasal Swab.

| Treatment Group | Vaccine | Day 0 | Day 35 | Day 38 | Day 42 | Day 45 | Day 49 |
|---|---|---|---|---|---|---|---|
| T01 | None (PBS only) | 0 | 0 | 285500 | 66956 | 8805 | 1375 |
| T02 | Strain SD 04-89 | 0 | 1 | 776071 | 26115 | 3157 | 1360 |
| T03 | Strain SD 03-15 | 0 | 277* | 3200* | 3200* | 3871 | 2201 |
| T04 | Strain SD 95-10 | 0 | 337* | 158* | 368* | 28* | 89* |
| T05 | Strain SD 11-21 | 0 | 1 | 529399 | 5521* | 75* | 16* |
| T06 | Strain SD 02-10 | 0 | 0 | 215539 | 14541 | 158* | 3* |
| T07 | Strain SD 95-47 | 0 | 7* | 4193* | 3544* | 38* | 26* |
| T08 | Strain ND 99-14 | 0 | 3 | 343* | 710* | 159* | 30* |
| T09 | Strain MN 05-68 | 0 | 5 | 105* | 38680 | 459* | 12* |

*Within day versus T01, significantly different at P < 0.05.

Geometric means of PRRSV enumerated by qtRT-PCR (genomic copies/mL) from serum are presented in Table 5. All vaccinated groups had some measurable viremia attributable to the vaccination on Day 35, although the levels in the groups vaccinated with SD 04-89 and SD 11-21 were not statistically different from the control (P>0.05, which were negative. Upon challenge on Day 35, all groups were viremic at 3, 7, 10 and 14 DPC. Pigs vaccinated with strains SD 95-10 and ND 99-14 had lower (P<0.05) levels of viremia than controls at all time-points post challenge. By 10 and 14 DPC, all vaccine strains induced a reduction (P<0.05) in viremia compared to the controls, with the exception of strains SD 04-89 and SD 03-15.

TABLE 5

Geometric Means of PRRSV Genomic Copies/mL in Serum.

| Treatment Group | Vaccine Strain | Day 0 | Day 35 | Day 38 | Day 42 | Day 45 | Day 49 |
|---|---|---|---|---|---|---|---|
| T01 | None | 0 | 0 | 2903710 | 17470074 | 5039915 | 429509 |
| T02 | SD 04-89 | 0 | 51 | 1616541 | 25183510 | 2328418 | 95654 |
| T03 | SD 03-15 | 0 | 3840* | 206281* | 591903* | 813498* | 217313 |
| T04 | SD 95-10 | 0 | 20528 | 5122* | 7787* | 5176* | 377* |
| T05 | SD 11-21 | 0 | 5 | 2782331 | 1590087* | 45034* | 2835* |
| T06 | SD 02-10 | 2 | 2617* | 611028 | 3408898 | 647775* | 30347* |
| T07 | SD 95-47 | 0 | 5711* | 504891 | 1407041* | 44550* | 9692* |
| T08 | ND 99-14 | 0 | 357* | 21432* | 95434* | 3358* | 1177* |
| T09 | MN 05-68 | 0 | 1578* | 47685* | 2888361 | 183890* | 10337* |

*Within day versus T01, significantly different at P < 0.05.

Seroconversion was determined by measuring geometric mean fluorescent foci neutralization (FFN) titers, as shown in Table 6. Control animals remained seronegative through Day 35 (day of challenge), began to seroconvert by Day 42 (7 DPC) and had seroconverted by Day 49 (14 DPC). All vaccinate groups had seroconverted by Day 14 after vaccination, with the exception of SD 03-15. Geometric mean titers in all vaccinate groups exceeded (P<0.05) the one of the controls on Days 28, 35 and 42 and were similar to or less than the one of the controls on Day 49. Peak FFN titer response in the vaccinate groups occurred on Days 35 and 42. Strains SD 95-10, SD 11-21, SD 95-47 and ND 99-14 appeared to elicit the most robust serological response.

TABLE 6

Geometric Means of Fluorescent Foci Neutralization (FFN) Titers.

| Treatment Group | Vaccine Strain | Day 0 | Day 35 | Day 38 | Day 42 | Day 45 | Day 49 |
|---|---|---|---|---|---|---|---|
| T01 | None | 0 | 0.00 | 0.00 | 0.11 | 1.26 | 122.59 |
| T02 | SD 04-89 | 0 | 1.20* | 4.75* | 12.13* | 78.38* | 74.94 |
| T03 | SD 03-15 | 0 | 0.67 | 3.83* | 15.87* | 21.43* | 17.11* |
| T04 | SD 95-10 | 0 | 27.90* | 3.42* | 119.51* | 104.10* | 52.54* |
| T05 | SD 11-21 | 0 | 26.04* | 48.56* | 137.26* | 147.18* | 84.57 |
| T06 | SD 02-10 | 0 | 10.16* | 30.10* | 52.59* | 97.29* | 69.91 |
| T07 | SD 95-47 | 0 | 11.66* | 34.62* | 111.85* | 121.79* | 35.73* |

TABLE 6-continued

Geometric Means of Fluorescent Foci Neutralization (FFN) Titers.

| Treatment Group | Vaccine Strain | Day 0 | Day 35 | Day 38 | Day 42 | Day 45 | Day 49 |
|---|---|---|---|---|---|---|---|
| T08 | ND 99-14 | 0 | 15.89* | 5.92* | 125.04* | 107.19* | 73.05 |
| T09 | MN 05-68 | 0 | 19.86* | 16.14* | 97.92* | 97.40* | 43.27* |

*Within day versus T01, significantly different at $P < 0.05$.

Least square mean body weights are included in Table 7. The Day 0 body weight was used as a covariate in the analysis. On day of challenge (Day 35), the four groups vaccinated with strains SD 03-15, SD 95-10, ND 99-14 and MN 05-68, respectively had lower mean body weights ($P<0.05$) than the ones of the control. All other groups had mean body weights similar ($P>0.05$) to the one of the control group. On day of necropsy (Day 49), at 14 DPC, the three groups vaccinated with strains SD 11-21, SD 95-47 and ND 99-14 had mean body weights that exceeded ($P<0.05$) the one of the control. Body weights of all other groups were similar ($P>0.05$) to the one of the control.

TABLE 7

Least Square Mean Body Weights (lbs).

| Treatment Group | Vaccine Strain | Day 35 LS Mean ± SEM | Day 49 LS Mean ± SEM |
|---|---|---|---|
| T01 | None | 51.2967 ± 1.2386 | 57.7779 ± 1.8550 |
| T02 | SD 04-89 | 49.5986 ± 1.5763 | 58.6786 ± 2.3529 |
| T03 | SD 03-15 | 46.6000* ± 1.5601 | 63.3200 ± 2.3420 |
| T04 | SD 95-10 | 42.2323* ± 1.5604 | 60.1423 ± 2.3422 |
| T05 | SD 11-21 | 51.4161 ± 1.5695 | 65.7061* ± 2.3483 |
| T06 | SD 02-10 | 50.6237 ± 1.5651 | 62.2837 ± 2.3454 |
| T07 | SD 95-47 | 51.0636 ± 1.5614 | 66.3136* ± 2.3429 |
| T08 | ND 99-14 | 45.2815* ± 1.6536 | 63.9593* ± 2.4748 |
| T09 | MN 05-68 | 44.4676* ± 1.5620 | 60.4576 ± 2.3433 |

*Within day versus T01, significantly different at $P < 0.05$.

Means of the summed clinical scores (respiratory+depression+body condition) were collected for each animal and averaged for each group. Clinical signs were not apparent in any group for up to 7 days after challenge. On Days 42 and 43, clinical signs were evident in some of the vaccine groups but their mean score did not differ ($P<0.05$) from the one of controls. From Day 44 to 49, all vaccine groups had a lower ($P<0.05$) summed score than controls, except for groups vaccinated with strains SD 04-89 and SD 02-10 on Day 44.

In conclusion, eight attenuated PRRSV vaccine strains have been successfully evaluated in a viral challenge model. With the exception of the EU-like strain SD 03-15, all strains elicit some protection against challenge with the virulent NADC-20 Type-2 PRRSV. Four strains, SD 11-21, SD 95-10, SD 95-47, and ND 99-14, confer the greatest protection as demonstrated by higher reduction of lung lesions and viremia.

EXAMPLE 3

The objective of this study is to evaluate the cross-protective efficacy of four experimental PRRSV vaccines in growing swine following a challenge with two distinct virulent PRRSV Type-2 strains. Efficacy is evaluated by the extent of lung lesions and viremia. The study was conducted in BSL-2 facilities at Veterinary Resources, Inc. (VRI), Cambridge, Iowa. The study design is presented in Table 8.

TABLE 8

Study design.

| Treatment Group | PRRSV strain | FFU[1] titer/mL | PRRSV Challenge | Vaccination Day/Challenge | Number of Animals |
|---|---|---|---|---|---|
| T01 | None[2] | N/A | MN-184 | Day 0/35 | 10 |
| T02 | SD 95-10 | $1.3 \times 10^7$ | MN-184 | Day 0/35 | 10 |
| T03 | SD 11-21 | $4.0 \times 10^6$ | MN-184 | Day 0/35 | 10 |
| T04 | ND 99-14 | $2.1 \times 10^7$ | MN-184 | Day 0/35 | 10 |
| T05 | MN 05-68 | $1.6 \times 10^7$ | MN-184 | Day 0/35 | 10 |
| T06 | None[2] | N/A | KS-11 | Day 0/35 | 10 |
| T07 | SD 95-10 | $1.3 \times 10^7$ | KS-11 | Day 0/35 | 10 |
| T08 | SD 11-21 | $4.0 \times 10^6$ | KS-11 | Day 0/35 | 10 |
| T09 | ND 99-14 | $2.1 \times 10^7$ | KS-11 | Day 0/35 | 10 |
| T10 | MN 05-68 | $1.6 \times 10^7$ | KS-11 | Day 0/35 | 10 |

[1]Flourescent foci unit (FFU).
[2]Placebo control animals received phosphate-buffered saline (PBS).

Study personnel who conducted health observations or collected samples were blinded to the treatment identity as well as to assignment of pigs to the treatment groups. One hundred (100) crossbred gilts and barrows approximately 3 weeks of age that were seronegative to PRSSV by virus neutralizing testing (FFN) and assessed to be in good health were utilized for this study. Pigs were sourced from Wilson Prairie View Farms, Burlington, Wis. On Day −1, pigs were allotted to treatment and pen and housed by treatment group within pens in three BSL-2 containment rooms. Within each room the four vaccinate groups were separated by an empty pen or alley way and a solid pen partition to prevent any direct contact and waste contamination into other pens. Pigs were fed standard commercial medicated (CTC/DENAGARD® antibiotic) starter diets (NRC, 2012) ad libitum. Pigs had access to clean drinking water ad libitum.

General health observations were conducted once daily from time of arrival at the study site until the day prior to challenge (Day −3 through 34). All pigs were individually assessed for depression, body condition and respiratory distress on Days 35-49 and scored for each clinical sign.

Prior to weaning and shipment to VRI, each pig was treated with a single dose of VITAL E-500 (Vitamin E), a single dose of EXCEDE® antibiotic (ceftiofur cystalline, Zoetis Animal Health), and was vaccinated with INGELVAC CIRCOFLEX® vaccine (Boehringer Ingelheim Vetmedica). In addition, all pigs were administered a single dose of EXCEDE® antibiotic on either Day 13 or Day 14.

Any pig which exhibited signs of clinical illness or injury was removed from the study. Pertinent samples were submitted to the Iowa State University Veterinary Diagnostics Laboratory (VDL) for diagnostic evaluation. The date, reason, and disposition of the animal removed from the study post-challenge were recorded. Data collected on pigs removed from the study were excluded from the statistical analyses.

All candidate PRRSV strains were passed 83 times on MARC-145 cells. Titers for each of the four (4) vaccines were determined. Sterility testing per USDA 9 CFR requirements was successfully completed at Benchmark BioLabs, Lincoln, Nebr. Vaccines were prepared as in Example 2.

Each of the 100 pigs enrolled in the study were vaccinated on Day 0. Pigs were injected with their assigned treatment as a 0.5 mL intramuscular dose in the right side of the neck. Within one hour following the injections, the Study Investigator examined each pig for any adverse event.

The post-vaccination phase was from Day 1 through Day 35. Blood samples for PRRSV serum antibody determination using fluorescent foci neutralization (FFN) testing were collected on Days −1, 14, 28, and 35. For the FFN assay, twofold dilutions of serum (1:4 to 1:512) were mixed each with an equal volume of culture medium containing 100 focus forming units (FFU) of the test PRRSV strain (MN-184). The mixture was incubated at 37° C. for 1 h and then added to confluent cultures of MARC-145 cells in 96-well tissue culture plates. After about 1 day the plates were fixed in 80% (v/v) acetone in water and infected cells (foci) detected by incubation with fluorescein isothiocyanate conjugated (FITC) anti-N-protein monoclonal antibody SDOW17. The serum neutralization FFN titer was expressed as the reciprocal of the highest dilution that reduced focus formation by about 90% as compared to a serum control. Blood samples for determination of PRRSV viremia were collected on Days −1, 14 and 35. Nasal swabs to assess viral shedding were collected on Days −1, 14 and 35. A body weight measurement (lb) was taken on Day −1 and prior to the challenge on Day 35 using a scale calibrated with certified weights.

The MN-184 PRRSV challenge strain (obtained from Iowa State University VDL) was isolated in 2001 from a swine herd experiencing severe reproductive disease and sow mortality in southern Minnesota. The KS-11 PRRSV challenge strain (obtained from Kansas State University VDL) was isolated in 2011 from a swine herd experiencing severe reproductive disease in northeast Kansas. On Day 35, the challenge material was prepared by thawing the frozen aliquots of MN-184 and KS-11 immediately prior to challenge. Challenge material was in a ready-to-use form requiring no dilution. A sample of each inoculum (MN-184 and KS-11) was submitted to the ISUVDL for titer determination. Day 0 titers for MN-184 and KS-11 strain were determined to be $4.2 \times 10^5$ and $6.7 \times 10^3$ TCID$_{50}$/ml, respectively. A 3 mL non-luer lock syringe was used to deliver a 2 mL dose intranasally, with approximately 1 mL per nostril.

The post-challenge phase was from Day 35 to Day 49. All pigs were individually assessed for depression, body condition and respiratory distress on Days 35 to 49 and scored for each clinical sign. Rectal temperature (° F.) was also recorded during this same time period using a calibrated thermometer. Blood samples for PRRSV neutralizing antibody determination (FFN) were collected on Days 42 and 49. Blood samples for determination of PRRSV viremia were collected on Days 38, 42, 45, and 49. Nasal swabs to assess viral shedding were collected on Days 38, 42, 45, and 49. A body weight measurement (lb) was obtained at the time of necropsy on Day 49 using a scale calibrated with certified weights. On Day 49, animals were humanely euthanized, and lungs were excised and scored by the Study Investigator who was blinded to treatment. Each of the seven pulmonary lobes was examined both visually and by palpation for gross characteristic lesions attributed to PRRSV. The amount of lesion/consolidation in each pulmonary lobe was scored as an actual value between 0 and 100% of the lobe. The score for each lobe was entered into a weighted formula to calculate the percentage of lung with lesions.

Percentage of total lung with lesions was calculated according to the formula and procedure given in Example 2.

Rectal temperature, depression score, respiratory score and body condition scores (Days 35 to 49) were statistically analyzed using methods appropriate for repeated measures (the MIXED procedure). Clinical scores were summed within a day for each animal. The summed scores were statistically analyzed as described above for the individual scores.

Average daily weight gain (ADWG) was determined for the following periods: Day −1 to 35; Day −1 to 49; and Day 35 to Day 49. Average daily weight gain (ADWG) for each period was analyzed using ANOVA (the MIXED procedure). Treatment was included in the model as a fixed effect and block was included as a random effect. If the main effect of treatment was significant, treatment effects were evaluated by comparing each vaccination group to the control using an unadjusted alpha=0.05.

One pig (T09) died on Day 28 from a suspected *S. suis* infection. Two pigs, one from T03 and another from T09, were removed from the study due to bronchopneumonia associated with *Bordetella bronchiseptica*. None of the adverse events were attributed to the vaccines.

The mean percent of lung lesions in the control group challenged with MN-184 was 52.4% which was in agreement with the expected pathology for this PRRSV challenge strain. The mean percent of lung lesions in the control group challenged with KS-11 was 22.5%. This PRRSV strain had not been previously used as challenge material thus the expected degree of lung pathology was unknown. The level achieved in this study was considered adequate to evaluate the vaccine candidates.

For prevention of disease associated with PRRSV, the post-challenge lung lesions and viremia were the primary outcome variables. The vaccine was considered effective if the mean lung lesion score and viremia levels of the vaccinated group was significantly less (P<0.05) than that of the control group.

The mean lung lesion scores (back-transformed means) are shown in Table 9. All vaccinated pigs had significantly less (P<0.05) lung lesions compared to the non-vaccinated control pigs when challenged with MN-184. Pigs challenged with the KS-11 strain and vaccinated with the SD 95-10, SD 11-21, and ND 99-14 strains had significantly less (P<0.05) lung lesions when compared to the non-vaccinated control pigs. Pigs vaccinated with the MN 05-68 strain and challenged with the KS-11 strain had similar (P>0.05) lung lesions to the non-vaccinated control pigs.

The effect of vaccination on lung lesion score was evaluated by calculating the mitigated fraction and the associated 95% confidence interval from the un-transformed data. As shown in Table 10, the mitigated fraction ranged from −0.06 to 0.98. The 95% confidence interval included 0 for pigs vaccinated with the MN 05-68 strain and challenged with the KS-11 strain, indicating no effect of vaccination on lung lesion scores. All other vaccines, regardless of challenge strain, indicated an effect of vaccination on reducing lung lesion scores.

TABLE 9

Mean Lung Score—Percent of Lung Involvement.

| Treatment Group | Vaccine strain | Challenge Strain | Estimate[1] | Standard Error | Mean[2] |
|---|---|---|---|---|---|
| T01 | Control | MN-184 | 0.8090 | 0.1026 | 52.4% |
| T02 | SD 95-10 | MN-184 | 0.2551* | 0.1026 | 6.4% |
| T03 | SD 11-21 | MN-184 | 0.2478* | 0.1043 | 6.0% |
| T04 | ND 99-14 | MN-184 | 0.1575* | 0.1026 | 2.5% |
| T05 | MN 05-68 | MN-184 | 0.3039* | 0.1026 | 8.9% |
| T06 | Control | KS-11 | 0.4937 | 0.08280 | 22.5% |
| T07 | SD 95-10 | KS-11 | 0.1142* | 0.08280 | 1.3% |
| T08 | SD 11-21 | KS-11 | 0.1651* | 0.08280 | 2.7% |
| T09 | ND 99-14 | KS-11 | 0.0873* | 0.09257 | 0.8% |
| T10 | MN 05-68 | KS-11 | 0.4936 | 0.08280 | 22.5% |

[1]Untransformed mean.
[2]Back-transformed mean.
*Within a challenge strain versus the control, significantly different at P < 0.05.

TABLE 10

Lung Lesion Scores.

| Treatment Group Comparison | Mitigated Fraction[1] | 95% confidence interval |
|---|---|---|
| Control (T01) versus SD95-10 (T02) | 0.90 | 0.74, 1.00 |
| Control (T01) versus SD 11-21 (T03) | 0.91 | 0.76, 1.00 |
| Control (T01) versus ND 99-14 (T04) | 0.98 | 0.93, 1.00 |
| Control (T01) versus MN 05-68 (T05) | 0.88 | 0.69, 1.00 |
| Control (T06) versus SD95-10 (T07) | 0.77 | 0.49, 1.00 |
| Control (T06) versus SD 11-21 (T08) | 0.58 | 0.16, 1.00 |
| Control (T06) versus ND 99-14 (T09) | 0.78 | 0.48, 1.00 |
| Control (T06) versus MN 05-68 (T10) | −0.06 | −0.58, 0.46 |

[1]Mitigated fraction means the relative increase in the probability that the lung lesions of vaccinates (T02-T05, T07-T10) will be less severe than the lung lesions of non-vaccinates (T01, T06).

Results of the analysis for nasal shedding data are summarized in Table 11. The treatment by time interaction for the vaccinated groups was highly significant (P<0.0001) compared to challenge controls. Vaccine virus shedding was detected in all vaccine groups on Day 14. By Day 35, only pigs vaccinated with the MN 05-68 strain in the MN-184 challenge room were shedding vaccine virus at levels greater (P<0.05) than the control pigs.

Upon challenge with the MN-184 strain, pigs vaccinated with the ND 99-14 strain had reduced (P<0.05) shedding compared to control pigs at each post-challenge time point (Days 38, 42, 45, and 49). Pigs vaccinated with the SD 95-10 and MN 05-68 strains showed significantly reduced (P<0.05) shedding on Days 42, 45, and 49 compared to control pigs. Pigs vaccinated with the SD 11-21 strain had higher shedding compared to the control pigs on Day 38, but lower (P<0.05) shedding on Days 42, 45, and 49.

Upon challenge with the KS-11 strain, pigs vaccinated with the SD 95-10 and ND 99-14 strains had reduced (P<0.05) nasal shedding on Days 38, 42, and 45 when compared to control pigs. Pigs vaccinated with the SD 11-21 strain demonstrated significantly less nasal shedding on Days 38, 42, and 49 when compared to control pigs. Pigs vaccinated with the MN 05-68 strain had reduced (P<0.05) shedding on Day 38 when compared to control pigs but the two treatment groups were not different (P>0.05) on Days 42, 45, and 49.

TABLE 11

Geometric Means of PRRSV Genomic Copies/mL in Nasal Swabs.

| Vaccine strain | Day −1 | Day 14 | Day 35 | Day 38 | Day 42 | Day 45 | Day 49 |
|---|---|---|---|---|---|---|---|
| Challenge strain MN-184 | | | | | | | |
| T01: Control | 0.34 | 0.34 | 0.34 | 1336.82 | 44675.37 | 19723.17 | 1092.89 |
| T02: SD 95-10 | 0.34 | 14042.29* | 4.62 | 162.56 | 72.39* | 19.18* | 1.05* |
| T03: SD 11-21 | 0.34 | 322.05* | 0.34 | 87613.34* | 778.30* | 79.82* | 5.04* |
| T04: ND 99-14 | 0.34 | 6417.89* | 6.51 | 21.66* | 45.01* | 484.22* | 21.34* |
| T05: MN 05-68 | 0.34 | 1924.61* | 11.20* | 165.58 | 1846.89* | 1098.49* | 44.52* |
| Challenge strain KS-11 | | | | | | | |
| T06: Control | 0.08 | 0.08 | 0.08 | 1940.27 | 8247.61 | 1451.58 | 28.76 |
| T07: SD 95-10 | 0.08 | 2874.26* | 1.12 | 3.38* | 103.92* | 6.75* | 9.87 |
| T08: SD 11-21 | 0.08 | 67.94* | 1.20 | 39.59* | 734.61* | 389.33 | 0.78* |
| T09: ND 99-14 | 0.06 | 468.14* | 1.94 | 23.25* | 309.32* | 22.99* | 21.70 |
| T10: MN 05-68 | 0.08 | 55.84* | 4.15 | 1.95* | 2345.55 | 840.51 | 41.01 |

*Within a challenge strain versus the control, significantly different at P < 0.05.

The results of the analysis for viremia are summarized in Table 12. The treatment by time interaction was highly significant (P<0.0001) for the vaccinated groups compared to challenge controls. As expected, all vaccinated groups had higher (P<0.05) viremia levels compared to their respective control group at Days 14 and 35 post-vaccination due to the presence of the vaccine virus.

TABLE 12

Geometric Means of PRRSV Genomic Copies/mL in Serum.

| Vaccine strain | Day −1 | Day 14 | Day 35 | Day 38 | Day 42 | Day 45 | Day 49 |
|---|---|---|---|---|---|---|---|
| Challenge strain MN-184 | | | | | | | |
| T01: Control | 1 | 1 | 1 | 1268568 | 12755842 | 8025222 | 4958926 |
| T02: SD 95-10 | 1 | 117788357* | 9817* | 26175* | 10984* | 29315* | 225* |
| T03: SD 11-21 | 1 | 58407* | 105* | 421636* | 295462* | 140786* | 2225* |
| T04: ND 99-14 | 1 | 24935423* | 5065* | 3810* | 3988* | 117277* | 49706* |
| T05: MN 05-68 | 1 | 5581677* | 24552* | 7305* | 763523* | 497076* | 58676* |
| Challenge strain KS-11 | | | | | | | |
| T06: Control | 0 | 0 | 1 | 128142 | 626622 | 865358 | 705737 |
| T07: SD 95-10 | 0 | 11960258* | 745* | 1756* | 9635* | 618* | 17* |
| T08: SD 11-21 | 0 | 104036* | 394* | 714* | 45674 | 120113 | 3492* |
| T09: ND 99-14 | 0 | 4049078* | 742* | 193* | 527* | 480* | 288* |
| T10: MN 05-68 | 0 | 2252609* | 353* | 91* | 1686* | 256349 | 40242* |

*Within a challenge strain versus the control, significantly different at P < 0.05.

Upon challenge with the MN-184 strain, all vaccinated groups had lower (P<0.05) viremia levels when compared to the control group at each time point post-challenge (Days 38, 42, 45, and 49). Upon challenge with the KS-11 strain, pigs vaccinated with the SD 95-10 and ND 99-14 strains had lower (P<0.05) viremia levels at each time point post-challenge (Days 38, 42, 45, and 49). Pigs vaccinated with the MN 05-68 strain had lower (P<0.05) viremia levels when compared to the control pigs on Days 38, 42, and 49 and pigs vaccinated with the SD 11-21 strain had reduced (P<0.05) viremia levels on Day 38, and 49 when compared to the control pigs.

The results of the analysis for serology are summarized in Table 13. The treatment by time interaction was highly significant (P<0.0001) for the vaccinated groups compared to the challenge controls. All pigs were seronegative on Day −1 prior to vaccination. Virus neutralizing antibodies were detected in pigs vaccinated with the SD 95-10 and ND 99-14 strains, regardless of the challenge strain, starting on Day 28 and remained present throughout the duration of the study. Virus neutralizing antibodies were higher (P<0.05) in pigs vaccinated with the SD 95-10 and ND 99-14 strains compared to the control pigs at Days 28, 35, 42, and 49.

TABLE 13

Geometric Means of Fluorescent Foci Neutralization (FFN) Titers.

| Treatment Group | Vaccine strain | Day −1 | Day 14 | Day 28 | Day 35 | Day 42 | Day 49 |
|---|---|---|---|---|---|---|---|
| Challenge strain MN-184 | | | | | | | |
| T01 | Control | 0 | 0 | 0 | 0 | 0 | 0 |
| T02 | SD 95-10 | 0 | 0 | 4* | 3* | 2* | 10* |
| T03 | SD 11-21 | 0 | 0 | 0 | 0 | 2* | 4* |
| T04 | ND 99-14 | 0 | 0 | 6* | 12* | 12* | 13* |
| T05 | MN 05-68 | 0 | 0 | 0 | 0 | 0 | 1* |
| Challenge strain KS-11 | | | | | | | |
| T06 | Control | 0 | 0 | 0 | 0 | 0 | 0 |
| T07 | SD 95-10 | 0 | 0 | 2* | 3* | 4* | 12* |
| T08 | SD 11-21 | 0 | 0 | 0 | 0 | 0 | 2* |
| T09 | ND 99-14 | 0 | 0 | 24* | 14* | 19* | 22* |
| T10 | MN 05-68 | 0 | 0 | 0 | 0 | 0 | 1* |

*Within a challenge strain versus the control, significantly different at P < 0.05.

Upon challenge with the MN-184 strain, virus neutralizing antibodies did not appear in pigs vaccinated with the SD 11-21 strain until Day 42 and remained thru Day 49. Virus neutralizing antibodies were higher (P<0.05) than control pigs at both time points. Pigs vaccinated with the MN 05-68 strain did not have detectable virus neutralizing antibody levels until Day 49, however, levels were greater (P<0.05) than the ones of the pigs in the control group.

Upon challenge with the KS-11 strain, pigs vaccinated with the SD 11-21 and MN 05-68 strain did not have detectable virus neutralizing antibody levels until Day 49, but levels for both vaccine strains were greater (P<0.05) compared to control pigs.

No virus neutralizing antibodies were detected in either of the control groups throughout the duration of the study. This is not unexpected, as virus neutralizing antibodies are often not detected until 28-35 days post-exposure.

The analysis for rectal temperature and summed clinical scores (respiratory+depression+body condition) was performed as described above. A highly significant (P<0.0005) treatment by time interaction was observed for both challenge groups.

Upon challenge with the MN-184 strain, pigs vaccinated with the SD 95-10, ND 99-14 and MN 05-68 strains had consistently lower (P<0.05) body temperatures and clinical scores when compared to control pigs starting around six days post challenge (Day 41). Pigs vaccinated with the SD 11-21 strain had consistently lower (P<0.05) body temperatures and fewer (P<0.05) clinical signs starting around eight days post-challenge (Day 43) compared to control pigs. Significant reductions (P<0.05) in body temperatures were noted as early as two days post-challenge in pigs vaccinated with the SD 95-10, ND 99-14 and MN 05-68 strains.

Upon challenge with the KS-11 strain, pigs vaccinated with either of the four vaccine strains had a significant reduction (P<0.05) in clinical scores starting nine days post-challenge (Day 44) when compared to control pigs and continued to have fewer (P<0.05) clinical signs thru the completion of the study. Body temperatures were reduced (P<0.05) in the SD 95-10, SD 11-21, and ND 99-14 groups beginning around six days post-challenge. Pigs vaccinated with the MN 05-68 strain only had lower (P<0.05) body temperatures when compared to control pigs on Days 37 and 46.

The analysis of the body weight gain data is shown in Table 14 given as least square means of body weight gain by period. There was a vaccine effect for body weight gain during the post-challenge period of Day 35-49. This resulted in a vaccine effect for the overall treatment period from Day −1 to Day 49. There were no body weight gain differences (P>0.05) between groups during the pre-challenge period (Days −1 to 35). During the post-challenge period (Day 35-49), all vaccinated groups, regardless of the vaccine strain, had improved (P<0.05) ADWG when compared to control pigs for both the MN-184 and KS-11 challenges. Vaccination with the SD 95-10, ND 99-14, and MN 05-68 strains improved (P<0.05) overall ADWG (Day −1 to 49) compared to control pigs in the MN-184 challenge room. Overall ADWG was not different (P>0.05) compared to control pigs in pigs vaccinated with SD 11-21 and challenged with MN-184. Vaccination with all strains improved (P<0.05) overall ADWG (Days −1 to 49) compared to control pigs in the KS-11 challenge room.

TABLE 14

Least Square Mean Body Weight Gain (lb).

| Treatment Group | Vaccine strain | Days −1 to 35 | Days −1 to 49 | Days 35 to 49 |
|---|---|---|---|---|
| Challenge strain MN-184 | | | | |
| T01 | Control | 1.1734 | 1.0024 | 0.5637 |
| T02 | SD 95-10 | 1.0445 | 1.1741* | 1.4865* |
| T03 | SD 11-21 | 1.1092 | 1.1166 | 1.1235* |
| T04 | ND 99-14 | 1.1485 | 1.2016* | 1.3229* |
| T05 | MN 05-68 | 1.1008 | 1.1608* | 1.2994* |
| Challenge strain KS-11 | | | | |
| T06 | Control | 1.2081 | 1.0754 | 0.7707 |
| T07 | SD 95-10 | 1.2153 | 1.3028* | 1.5486* |
| T08 | SD 11-21 | 1.1967 | 1.2150* | 1.2879* |
| T09 | ND 99-14 | 1.2452 | 1.2569* | 1.3080* |
| T10 | MN 05-68 | 1.2233 | 1.2383* | 1.3029* |

*Within a challenge strain versus the control, significantly different at P < 0.05.

In conclusion, all vaccinated groups were viremic and were shedding vaccine virus at 14 and 35 days post-vaccination.

Upon challenge with the MN-184 strain, all vaccines reduce (P<0.05) lung lesions, viremia, nasal shedding, clinical signs and rectal temperature during the post-challenge period. In addition, all vaccines improve (P<0.05) ADWG during the post-challenge period.

Upon challenge with the KS-11 strain, pigs vaccinated with the SD 95-10, SD 11-21, and ND 99-14 strains have reduced (P<0.05) lung lesions, viremia, nasal shedding, clinical signs and rectal temperature during the post-challenge period. In addition, all vaccine strains significantly improve (P<0.05) ADWG during the post-challenge period.

Three of the four vaccine strains are effective in reducing lung lesions and viremia following challenges with both strains of PRRSV. The SD 95-10, SD 11-21, and ND 99-14 strains are effective against both challenge strains. The MN 05-68 strain was only effective in reducing lung lesions upon MN-184 challenge and did not reduce lung lesions in pigs challenged with the KS-11 strain.

EXAMPLE 4

The objective of this study is to prepare the master seed virus (MSV) of Porcine Reproductive and Respiratory Syndrome Virus (PRRSV) strain ND 99-14. This seed will be used for PRRSV vaccine development.

PRRSV ND 99-14 strain has been modified by passing in the MARC-145 cells 83 times (P83) including two rounds of plaque purification and one round of sucrose gradient purification, prior to the initial characterization and sequencing as described in Example 1. The ND 99-14 strain has been further attenuated by passing 12 times (P95) in MARC-145 cells in the growth medium OPTI-MEM® I (Life Technologies) supplemented with 5% fetal bovine serum (PBS; Sigma Aldrich) and 50 µg gentamicin/mL (Life Technologies), and an additional 5 passages have been performed in the same growth medium supplemented with 2% FBS without gentamicin. The $100^{th}$ passage (P100) of PRRSV ND 99-14 has been used as the Pre-Master Seed Virus (Pre-MSV).

The following procedure is used to determine the titer of PRRSV MSV ND 99-14. MARC-145 cells are seeded into 96-well plates at a density of $0.75$-$1.5 \times 10^4$ cells in 100 µL of growth medium (OPTI-MEM® I media supplemented with 5% FBS and 50 µg/mL gentamycin). Cells are incubated in $37 \pm 2°$ C. and $5 \pm 1\%$ $CO_2$ incubator for 48-72 hours until cells are over 95% confluent. On the day of titration, all media is removed from the 96-well plate and replaced with 100 µL of fresh growth media.

Ten-fold serial dilutions of the MSV are prepared with diluent (OPTI-MEM® I media, 50 µg/mL gentamycin) and transferred to corresponding wells on the plates prepared as above along with a negative control consisting of diluent alone. Titration plates are incubated in $37 \pm 2°$ C. with $5 \pm 1\%$ $CO_2$ incubator for 4 days. At the end of the incubation period, each plate is observed for the presence of virus-induced cytopathic effect (CPE) in each sample well using an inverted microscope. The 50% tissue culture infectious dose ($TCID_{50}$) is calculated using the Reed-Muench method and titer is recorded as $\log_{10} TCID_{50}/mL$. The mean titer of the PRRSV MSV ND 99-14 is $3.50 \log_{10} TCID_{50}/mL$. There have been no distinguishable differences in the titers over the course of MSV preparation.

The PRRS ND 99-14 MLV strain has been denoted as a "master seed virus (MSV)," and has been deposited under conditions that assure that access to the cultures will be available during the pendency of this patent application to one determined by the Commissioner of Patents and Trademarks to be entitled thereto under 37 C.F.R. § 1.14 and 35 U.S.C. § 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action. The subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the deposited culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it. A deposit of PRRSV MSV ND 99-14 was entered into the permanent collection of the Patent Depository of the American Type Culture Laboratory, located at 10801 University Blvd., Manassas, Va., 20110-2209, USA, on Dec. 2, 2015 under the terms of the Budapest Treaty, whereupon it was assigned accession number ATCC PTA-122675 by the repository.

EXAMPLE 5

The objective of this study is to use next generation sequencing to establish genetic identity, obtain a consensus sequence, and assess genomic variants (subpopulations) that exist within PRRSV Strain ND 99-14 passage 84 and passage 100 preparations, both described in Example 4.

Sequence characterization using the massive parallel sequencing (MP-Sep) system is a standard procedure comprised of several steps which include: nucleic acid extraction from the virus preparations, cDNA library synthesis and quantitation, clonal amplification and enrichment of DNA library by PCR and sequencing of the library by the Roche/454 next generation sequencing platform. Sequencing by synthesis is used to simultaneously determine the nucleotide order of the fragments in the cDNA library. Genome identification and characterization were performed using bioinformatics analyses of the resulting fragments by mapping each data set to the reference sequence. The reference sequence used in this analysis by BioReliance consisted of the full length sequence PRRSV ND 99-14 passage 83 (P83) disclosed in Example 1 (SEQ ID NO:4).

Sequencing of the PRRSV ND 99-14 genome resulted in the complete genome coverage for both P84 and P100 samples. The complete consensus genomes for P84 and P100 can be found in SEQ ID NO: 10 and SEQ ID NO: 11, respectively. The cDNA consensus sequences have also been deposited with GenBank. The cDNA consensus sequence of PRRS strain ND 99-14 at P84 has been assigned GenBank Accession number KU131567 (SEQ. ID. NO:10). The cDNA consensus sequence designated SEQ. ID. NO:10 is:

```
   1 ATGACGTATA GTTGTTGGCT CTATGTCGTG ACATTTGTAT AGTCAGGAGC TGCGACCATT
  61 GGTACAGCCC AAAACTTGCT GCGCGGGAAC GCCCTTCCGT GACAGCCTTC TTCAGGGGAG
 121 TTTAGGGGTC TATCCCTAGC ACCTTGCTTC CGGAGTTGCA CTGCTTTACG GTCTCTCCAC
 181 CCCTTTAACC ATGTCTGGGA TACTTGATCG GTGCACGTGT ACCCCCAATG CCAGGGTGTT
 241 TGTGGCGGAG GGCCAAGTCT ACTGCACACG ATGTCTCAGT GCACGGTCTC TCCTTCCTTT
 301 GAATCTCCAA GTTTCTGAGC TTGGGGTGCT GGGCTTATTT TATAGGCCCG AAGAGCCGCT
 361 CCGGTGGACG TTGCCACGTG CATTCCCCAC TGTCGAGTGC TCCCCCGCCG GGGCCTGCTG
 421 GCTTTCTGCG ATTTTTCCAA TTGCACGAAT GACCAGTGGA AACCTGAACT TTCAACAAAG
 481 AATAGTGCGG GTCGCAGCTG AGCTCTACAG AGCCGGTCAG CTCACCCCCG TAGTCTTGAA
 541 GAATCTACAG GTTTATGAAC GGGGTTGCCG TTGGTACCCC ATCGTTGGAC CTGTTCCTGG
 601 AGTGGCTGTT TATGCCAATT CCTTACACGT GAGTGACAAA CCTTTCCCGG GAGCAACTCA
 661 TGTGTTAACC AACCTACCGC TCCCGCAGAG GCCCAAGCCT GAAGACTTTT GCCCCTTTGA
 721 GTGTGCTATG GCTGACGTCT ATGACATTGG TCATGACGCT GTCATGTATG TGGCCGGAGG
 781 GAGAGTCTCC TGGGCCCCTC GTGGCGGGGA CAAAGGAAAA TTTGAAATAG TTCCCAAGGA
 841 GTTGAAGTTG ATTGCGAATC GACTCCACAT TTCCTTCCCG CCCCACCACG CAGTGGACAT
 901 GTCCAAGTTT GCCTTTATAA GCCCTGGGAG TGGTGTTTCC ATGCGGGTCG AGTACCAACA
 961 TGGCTGTCTC CCCGCTGATA CTGTCCCTGA AGGAAACTGT TGGTGGCGCT TGTTTGACTT
1021 GCTTCCACCG GAAGTTCAGA ACAAAGAGAT TCGCCATGCT AACCAACTCG GCTATCAGAC
1081 CAAGCATGGT GTCGCTGGCA AGTACCTACA GCGGAGGCTG CAAGTTAATG GACTCCGAGC
1141 AGTAACTGAC GCGAATGGAC CTATCGTCAT ACAGTATTTT TGTGATAGGG AAAGCTGGAT
1201 CCGCCACTTA AGACTGGTAG AAGAACCTAG CCTCCCTGGG TTTGAGGACC TCCTCAGAAT
1261 AAGAGTTGAG CCCAATACGT TGCCATTGGT TGGCGAGGAT GAGAAAATCT TCCGATTTGG
1321 CAATCACAAA TGGTACGGTG CTGGAAAGAG GGCAAGGAAA GCACGCTTTG GTGCGGCTGC
1381 CACGGTCGCT CACCGCGCTT TGCCCGCTCA CGAAACCCAG CAGGCCAAGA AGCACGAAGT
1441 TACCAGCGCC AACAGGGCTG AGCATCTCGA GCACTATTCC CCGCCTACCG ACGGGAACTG
1501 TGGTTGGCAC TGCGTTTCCG CCATTGTCAA CCGGATTGTG AATTCCAAAT TTGAAACCAC
1561 CCTTCCCGAG AGAGTGAGAC CTTTAGATGA CTGGGCTACT GACGAGGATC TTGTGAATAC
1621 TATCCAAATC CTCAGGCTCC CTGCGGCCTT GGACAGGAAC GGTGCTTGTG TCGGCGCCAA
1681 GTACGTGCTC AAGCTGGAAG GTGTGCACTG GACAGTCTCT GTGGCCCCTG GGATGACCCC
1741 TTCTCTGCTC CCCCTTGAAT GTGTTCAGGG CTGTTGTGAG CATAAGAGCG GTCTTGGTCC
1801 CCCAGATGTG GCTGAAGTTT CCGGATTTGA CCCTGCCTGC CTTAACCGAC TGGCTGAGGT
1861 AATGCACTTG CCTAGTTGTG TCATCCCAGC TGCTCTGGCT GAAATGTCCG ACGACCCCAA
```

-continued

```
1921  TCGCCCGGCT TCCCCAGTCA CCACTGTGTG GACTATTTCG CAATTCTTTG CCCATTATAG
1981  AGGAGGAGAG CACCCTGATC AGGTGTGCTT AGGGAAAATC ATCAGCCTTT GTCAGGTGAT
2041  TGAGGAATGC TGTTGTTCCC AGAACAAAAC CAACCGGGCC ACCCCGGAAG AGGTCGCGGC
2101  AAAAATTGAC CAGTACCTCC GTGATGCAGC AAGCCTTGGA GAATGCTTAG CCAAGCTTGA
2161  GAGGGCTCGC CCGCCGAGCG CGATGGACAC CTCCTTTGAT TGGAATGTTG TGCTTCCTGG
2221  GGTTGAGGCG GCGAACCAGA CGACCAAACA GCTCCATGTC AACCAGCACC GTGCTTCGGT
2281  TCCTGCCATG ACTCAGGAGC CTTTGGACAA AGACTCGGTC CCTTTGACCG CCTTCTCGCT
2341  GTCTAATTGC TACTACCCTG CACAAGGTGA CGAGGTTCGT CACCGTGAGA GGCTGATCTC
2401  CGTGCTCTCT AAGTTGGAGG AGGTTGTTCG TGAGGAATAT GGGCTCACGC CAACTGGATC
2461  TGGCCCGCGA CCCGCACTGC CGAACGGGCT CGACGAGCTC AAAGACCAGA TGGAAGAGGA
2521  TCTGTTGAAA CTGGTCAACG CCCAGGCAAC TTCAGAAATG ATGGCCCGGG CAGCTGAGCA
2581  GGTTGATCTA AAAGTTTGGG TCAAAAATTA CCCACGGTGG ACACCGCCAC CCCCTCCACC
2641  AAGAGTTCAG CCTCGAAAAA CAAAGTCTGC TAAGAGCCTG CCAGAGAACA AGCCTGTCCC
2701  TGCTCCGCGC AGGAAAGTCA GATCTGATTG TGGCAGCCCG ACTTTGAGGG GCAACAATGT
2761  TCCTAACGGT TGGGAAGACT TGGCCGTTGG TGGTCCTCTT GATCTTTCGA CACCATCCGA
2821  GCCGATGACA CCTCTGAGTG AGCCTGCACT TATGCCCGTG TTGCAACATA TTTCTGGACC
2881  AGTGACGCCT TTGAGCGTGC CGGCCCCTAT TCCTGCACCG CGTAAAGCTG TGTCCCGACC
2941  GATGGCGCCC TCGAGTGAGC CAATTTTTGT GTCTGCACCG CGGCAAAAAT TTCAGCAGGT
3001  GGAAGAAGCA AATCTGGCGG CAACAACGCT GACATACCAG GACGAACCTA TAGATCTGTC
3061  AGCATCCTCA CAGACTGAAT ATGAGGCTCC TTCCCTAGCA CCACTGCAGA ACATAGGTAC
3121  TCTGGAGGTG GGGGGGCAAG AAGCTGAGGA AATTCTGAGT GAAACCTCGG ATATACCGAA
3181  TGACATCAAC CCTGTGCCTG TATCATCAAG CAGCTCCTTG TCAAGCGTTA AGATCACACG
3241  CCCAAGACAC TCAGCTCAAG CCATCATCGA CTCGGGCGGG CCCTGCAGTG GCATCTCCA
3301  AAGGGAGAAA GAAGCGTGCC TCCGCATCAT GCGTGAGGCT TGTGATGCGA CTAAGCTTAG
3361  TGACCCTGCC ACGCAGGAAT GGCTTTCTCG CATGTGGGAT AGGGTGGACA TGCTGACTTG
3421  GCGCAACACG TCTGCTTTCC AGGCGTTTCG CATCTTAGAC GGCAGGCTTG AGTTTCTTCC
3481  AAAGATGATA CTCGAGACGC CGCCGCCCTA CCCGTGTGGG TTTGTGATGC TGCCTCACAC
3541  CCCTGCACCT TCCGTGAGTG CAGAGAGCGA CCTTACCATC GGTTCAGTCG CCACTGAAGA
3601  TATTCCACGC ATCCTCGGGA AAATAGAAAA CACCAGTGAG ATGATCAACC AGGGACCCTT
3661  GGCATCCTCT GAGGAAAAAC CGGCATACAA CCAACCCGCT AAGGACTCCC TGATATCGTC
3721  GCGGGGGTTT GACGAGAGCA CAGCAGCTCC GTCCGCAGGT ACGGGTGGCG CCGGCTTGTT
3781  TACTGATTTG CCACCTTCAG ACGGTGTAGA TGCGGACGGG GGGGGCCGC TGCAGACGGT
3841  GAAAAAGAAC GCTGAAAGGC TCCTCGACCG ATTGAGCCGT CAGGTTTTTA ACCTCGTCTC
3901  CCATCTCCCT GTTTTCCTCT CACACCTCTT CAAATCTGAC AGTGGTTATT CTCCGGGTGA
3961  TTGGGGTTTT GCAGCTTTTA CTCTATTTTG CCTCTTTTTA TGTTACAGCT ACCCATTCTT
4021  TGGTTTCGCT CCCCTTTTGG GTGTGTTTTC TGGGTCTTCT CGGCGCGTGC GCATGGGGGT
4081  TTTTGGCTGC TGGTTGGCTT TTGCTGTTGG TTTGTTCAAG CCTGTGTCCG ACCCAGTCGG
4141  CACTGCTTGT GAGTTTGATT CGCCAGAGTG TAGGAATGTC CTTCATTCTT TTGAGCTTCT
4201  CAAACCTTGG GACCCTGTTC GCAGCCTTGT TGTGGGCCCC GTCGGTCTCG GTCTTGCCAT
4261  TCTTGGCAGG TTACTGGGCG GGGCACGCTA CATCTGGCAT TTTCTGCTTA GGCTTGGCAT
```

-continued

```
4321 TGTTACAGAC TGTATCCTGG CTGGAGCTTA TGTGCTTTCT CAAGGTAGGT GTAAAAGTG

4381 CTGGGGATCT TGCATAAGAA CAGCTCCTAA TGAGATTGCC TTTAACGTGT TCCCTTTTAC

4441 ACGTGCGACT AGGTCGTCAC TCATCGACCT GTGCAATCGG TTTTGTGCGC CAAAGGGCAT

4501 GGACCCTATT CTCCTCGCCA CTGGGTGGCG TGGGTGCTGG ACCGGCCGAA GCCCCATTGA

4561 ACAACCCTCT GAAAACCCA TCGCGTTTGC CCAGTTGGAC GAAAAGAGGA TTACGGCCAG

4621 GACCGTGGTC GCCCAGCCTT ATGACCCCAA CCAAGCCGTA AAGTGCTTGC GGGTGTTACA

4681 GGCGGGCGGG GCGATGGTGG CTGAGGCAGT CCCAAAAGTG GTCAAAGTTT CCGCTATTCC

4741 ATTCCGAGCC CCCTTTTTTC CCACCGGAGT GAAAGTTGAC CCTGAGTGTA GGATCGTGGT

4801 TGACCCCGAC ACTTTTACTA CAGCCCTCCG GTCCGGCTAT TCCACCACAA ACCTCGTTCT

4861 TGGTGTGGGG GACTTTGCCC AGCTGAATGG ATTAAAAATC AGGCAAATTT CCAAGCCTTC

4921 GGGAGGAGGC CCGCACCTCA TTGCTGCCCT ACATGTTGCC TGCTCGATGG CGTTGCACAT

4981 GCTTGCTGGG GTTTATGTAA CTGCAGTGGG GTCTTGCGGT ACCGGCACCA ACGATCCGTG

5041 GTGCACCAAC CCGTTTGCCG TCCCTGGCTA CGGGCCTGGT ACTCTTTGCA CGTCCAGATT

5101 GTGCATCTCC CAACATGGCC TTACCCTGCC CTTGACAGCA CTTGTGGCAG GATTCGGTCT

5161 TCAGGAAATT GCCTTGGTTG TTTTGATTTT CGTTTCCATC GGAGGCATGG CTCACAGGTT

5221 GAGTTGCAAG GCTGACATGC TGTGCGTTTT ACTTGCAATC GCCAGCTATG TTTGGGTGCC

5281 CCTTACCTGG TTTCTTTGTG TGTTTCCTTG CTGGTTGCGC TGGTTCTCTT TGCATCCCCT

5341 CACCATCCTA TGGTTGGTGT TTTTCTTGAT TTCTGTAAAT GTGCCTTCGG GAATCTTGGC

5401 TGTGGTGTTG TTAGTTTCTC TTTGGCTCTT AGGTCGTTAC ACTAATGTTG CTGGTCTTGT

5461 CACCCCATAT GACATTCATC ATCACACCAG TGGCCCCCGA GGTGTTGCCG CCTTGGCTAC

5521 TGCACCGGAT GGGACCTACT TGGCCGCCGT TCGCCGTGCT GCGTTGACCG TCGTACCAT

5581 GCTGTTTACC CCGTCTCAGC TTGGGTCCCT TCTTGAGGGT GCTTTCAGAA CTCAAAAGCC

5641 CTCACTGAAC ACCGTCAATG TGGTCGGATC CTCTATGGGC TCCGGCGGGG TGTTCACCAT

5701 CGACGGGAAA ATTAAGTGCG TAACAGCCGC ACATGTCCTT ACGGGTAATT CAGCTAGGGT

5761 TTCCGGGGTC GGCTTCAACC AAATGCTTGA TTTTGATGTG AAAGGGGACT TCGCCATAGC

5821 TGATTGCCCG AATTGGCAAG GAGCTGCCCC CAAGACCCAA TTCTGCGAGG ATGGATGGAC

5881 TGGCCGTGCC TATTGGCTGA CATCCTCTGG AGTCGAACCC GGTGTCATTG GAATGGATT

5941 CGCCTTCTGC TTCACCGCGT GCGGCGATTC TGGATCCCCG GTGATTACCG AAGCCGGTGA

6001 GCTTGTCGGC GTTCACACAG GATCAAACAA ACAAGGAGGA GGCATAGTCA CACGCCCCTC

6061 AGGCCAGTTT TGTAATGTGG CGCCCATCAA GCTGAGCGAA TTGAGTGAAT TCTTCGCTGG

6121 ACCTAAGGTC CCGCTCGGTG ATGTGAAGAT TGGCAGCCAC ATAATTAAAG ACGTATGCGA

6181 GGTACCTTCA GATCTTTGCG CCTTGCTCGC TGCCAAACCC GAACTGGAAG GAGGCCTCTC

6241 CACCGTCCAA TTCTGTGTG TGTTTTTCCT CCTGTGGAGA ATGATGGGAC ATGCCTGGAC

6301 GCCCTTGGTT GCTGTGGGGT TTTTTATCTT GAATGAGGTT CTCCCAGCTG TCCTGGTCCG

6361 GAGTGTCTTC TCCTTTGGTA TGTTTGTGCT ATCTTGGCTT ACACCATGGT CTGCGCAAGT

6421 CCTGATGATC AGGCTTCTAA CAGCAGCTCT TAACAGGAAC AGGGGGTCAC TCGCCTTCTA

6481 CAGCCTCGGT GCAGTGACCG GATTTATCGC AGATCTTGCA GCAACTCAGG GCATCCGCT

6541 GCAGGCAGTG ATGAACTTAA GCACCTATGC CTTCCTGCCT CGGATGATGG TTGTGACCTC

6601 ACCAGTCCCA GTGCTTGCTT GTGGTGTTGT GCACCTCCTT GCCATAATTT TGTACCTGTT

6661 TAAGCACCGT TGCCTGCATT ATGTCCTTGT TGGCGATGGA GTGTTCTCTA AAGCCTTCTT

6721 CTTGCGATAC TTTGCCGAAG GGAAGTTGAG GGAAGGGGTG TCGCAGTCCT GCGGGATGAA
```

```
6781  TCACGAGTCA CTGACTGGTG CCCTCGCTAT GAGACTCAAT GACGAAGACT TGGACTTCCT

6841  TACGAAATGG ACTGATTTTA AGTGCTTTGT TTCTGCGTCC AACATGAGGA ATGCAGCGGG

6901  CCAATTCATC GAGGCTGCCT ATGCAAAAGC ACTTAGAATT GAGCTTGCCC AGTTAGTACA

6961  GGTTGATAAG GTTCGAGGTA CTTTGGCCAA ACTTGAAGCC TTTGCTGATA CCGTGGCACC

7021  CCAGCTCTCG CCCGGTGACA TTGTTGTTGC TCTTGGCCAC ACGCCTGTTG GCAGTATCTT

7081  CGACCTAAAG GTTGGCAGTA CCAAGCATAC CCTCCAGGCC ATTGAGACCA GAGTCCTTGC

7141  CGGGTCCAAA ATGACCGTGG CGCGTGTCGT TGATCCAACC CCCACGCCCC CACCCGCACC

7201  CGTGCCCATC CCCCTCCCAC CGAAAGTCCT GGAGAACGGC CCCAACGCCT GGGGGGATGA

7261  GGACCGGTTG AATAAGAGGA AGAGACGCAG GATGGAAGCC GTCGGCATCT TTGTTATGGG

7321  TGGGAAGAAG TACCAAAAAT TTTGGGACAA GAATTCCGGT GATGTGTTTT ACGAGGAGGT

7381  CCATGATAAC ACAGATGCGT GGGAGTGCCT CAGAGTTGGT GACCCTGCCG ACTTTGACCC

7441  TGAGAAGGGA ACTCTGTGTG GCATACTAC CATTGAAGAC AAGGCTTATA ATGTCTACAC

7501  CTCCCCATCT GGCAGGAAGT TCCTGGTCCC CGTCAACCCA GAGAGCGGAA GAGCCCAATG

7561  GGAAGCTGCA AAGCTTTCCG TAGAGCAGGC CCTTAGCATG ATGAATGTCG ACGGTGAGCT

7621  GACAGCCAAA GAACTGGAGA AACTGAAAAG AATAATTGAC AAACTCCAGG GCCTAACTAA

7681  GGAGCAGTGT TTAAACTGCT AGCCGCCAGC GGCTTGACCC GCTGTGGTCG CGGCGGCTTG

7741  GTTGTTACTG AGACAGCGGT GAAAATAGTT AAATTTCACA ACCGGACCTT CACCCTAGGA

7801  CCTGTGAATT TAAAAGTGGC CAGTGAGGTT GAGCTAAAAG ACGCAGTCGA GCATAACCAA

7861  CACCCGGTTG CAAGACCGGT TGATGGTGGT GTTGTGCTCC TGCGCTCCGC AGTTCCTTCG

7921  CTTATAGACG TCTTGATCTC TGGCGCTGAT GCATCTCCTA AGTTACTCGC CCACCACGGG

7981  CCGGGAAACA CTGGGATCGA TGGTTCGCTT TGGGATTTTG AGGCCGAGGC CACCAAAGAG

8041  GAAATTGCAC TCAGTGCGCA AATAATACAG GCTTGTGACA TTAGGCGCGG CGACGCACCC

8101  GAAATTGGTC TTCCTTATAA GCTGCACCCT GTTAGGGGCA ACCCTGAGCG GGTAAAAGGG

8161  GTTTTACAGA ATACAAGGTT TGGAGACATA CCTTATAAAA CCCCCAGTGA CACTGGGAGC

8221  CCAGTGCACG CGGCTGCCTG CCTCACGCCC AATGCCACTC CGGTGACTGA CGGTCGTTCC

8281  GTCTTGGCTA CGACCATGCC CTCCGGTTTT GAGTTGTATG TACCGACCAT TCCAGCGTCT

8341  GTCCTTGATT ATCTTGATTC CAGGCCTGAT TGCCCCAAAC AGTTGACAGA GCACGGCTGT

8401  GAGGATGCCG CATTAAGAGA CCTCTCCAAG TATGACTTGT CCACCCAAGG CTTTGTCTTG

8461  CCTGGAGTTC TTCGCCTTGT GCGTAAGTAC CTGTTTGCTC ATGTGGGTAA GTGCCCGCCT

8521  ATTCATCGGC CTTCCACTTA CCCTGCCAAG AATTCCATGG CTGGAATAAA TGGGAACAGG

8581  TTTCCAACCA AGGACATTCA GAGCGTCCCT GAAATCGACG TTTTGTGCGC ACAGGCCGTG

8641  CGAGAAAACT GGCAAACTGT TACTCCTTGT ACCCTCAAGA AGCAGTATTG CGGGAAGAAG

8701  AAGACTAGGA CAATACTCGG CACTAATAAC TTCATTGCGC TGGCCCACCG GGCAGCATTG

8761  AGTGGTGTCA CCCAGGGCTT CATGAAAAAA GCGTTTAACT CGCCCATCGC ACTCGGGAAA

8821  AACAAATTCA AGGAGCTGCA GACTCCGGTC TTGGGCAGAT GTCTTGAAGC TGACCTTGCA

8881  TCCTGTGACC GATCCACACC CGCAATTGTC CGCTGGTTTG CCGCCAATCT TCTTTATGAA

8941  CTTGCCTGTG CTGAGGAGCA TATACCATCG TACGTGTTGA ACTGCTGCCA CGACTTACTG

9001  GTCACGCAGT CCGGCGCGGT GACTAAGAGA GGTGGCCTAT CGTCTGGCGA CCCGATTACT

9061  TCTGTATCAA ACACCATTTA CAGCTTGGTG ATATATGCAC AGCACATGGT ACTCAGTTAT

9121  TTTAAAAGTG GTCACCCCCA TGGCCTTCTG TTTCTACAAG ACCAGCTAAA GTTTGAGGAC
```

-continued

```
9181  ATGCTCAAGG TTCAGCCCCT GATCGTCTAT TCGGACGACC TCGTGCTGTA CGCCGAGTCT

9241  CCCACCATGC CAAACTACCA CTGGTGGGTT GAACATCTGA ACCTGATGCT GGGTTTTCAG

9301  ACGGACCCAA AGAAGACAGC TATAACAGAC TCGCCATCAT TTTTGGGTTG TAGGATAATA

9361  AATGGACGCC AGTTAGTCCC CAACCGTGAC AGGATCCTCG CGGCCCTCGC CTACCATATG

9421  AAGGCAAACA ATGTTTCTGA ATACTACGCC TCGGCGGCTG CAATACTCAT GGACAGTTGT

9481  GCTTGTTTGG AGTACGATCC TGAGTGGTTT GAAGAGCTCG TGGTTGGGAT GGCGCAGTGC

9541  GCCCGCAAGG ACGGCTACAG TTTTCCTGGC CCGCCGTTCT TCTTGTCCAT GTGGGAAAAA

9601  CTCAGGTCCA ATCATGAGGG GAAGAAGTCT AGAATGTGCG GTACTGTGG GGCCCCAGCT

9661  CCGTATGCCA CTGCCTGTGG CCTTGATGTT TGTATTTATC ACACCCACTT CCACCAGCAT

9721  TGTCCAGTCA TAATCTGGTG TGGCCATCCG GCGGGTTCTG GCTCTTGTAG TGAGTGCAAA

9781  CCCCCCCTAG GGAAAGGCAC AAGCCCTCTA GATGTGGTGT TAGAACAAGT CCCGTACAAG

9841  CCTCCACGAA CTGTAATCAT GCATGTGGAG CAGGGTCTCA CCCCTCTTGA CCCAGGCAGA

9901  TACCAGACTC GCCGCGGATT AGTCTCCGTT AGGCGTGGCA TCAGGGAAA CGAAATCGAC

9961  CTACCAGACG GTGATTATGC TAGTACCGCC TTGCTCCCCA CTTGTAAAGA TATCAACATG

10021 GTCGCTGTCG CTTCCAATGT GTTGCGCAGC AGGTTCATCA TCGGTCCACC CGGTGCTGGT

10081 AAAACATACT GGCTCCTTCA ACAGGTCCAG GATGGTGATG TCATTTACAC GCCAACTCAT

10141 CAGACCATGC TTGACATGAT CAAGGCTTTG GGGACGTGCC GGTTCAACGC CCCAGCAGGC

10201 ACAACGCTGC AATTCCCTGC TCCCTCCCGT ACCGGCCCGT GGGTTCGCAT CCTGGCCGGC

10261 GGTTGGTGTC CTGGCAAGAA TTCCTTCCTG GATGAAGCAG CGTATTGTAA TCACCTTGAT

10321 GTCTTGAGGC TTCTTAGCAA AACTACCCTC ACCTGTCTGG GAGATTTCAA ACAACTCCAC

10381 CCAGTGGGTT TTGATTCTCA TTGCTATGTT TTTGACATCA TGCCTCAGAC TCAACTGAAG

10441 ACCATCTGGA GGTTTGGACA GAATATCTGT GATGCCATTC AGCCAGATTA CAGGGACAAA

10501 CTTGTGTCCA TGGTCAACAC AACCCGTGTA ACCTACGTGG AAAGACCTGT CAAGCATGGG

10561 CAGGTCCTCA CCCCTTACCA CAGGGACCGA GAGGACGGCG CCATCACAAT TGACTCCAGT

10621 CAAGGCGCCA CATTTGATGT GGTTACATTG CATTTGCCCA CTAAAGATTC ACTCAACAGG

10681 CAAAGAGCCC TTGTTGCTAT CACCAGGGCG AGACATGCTA TCTTTGTGTA TGACCCACAT

10741 AGGCAACTGC AGAGCATGTT TGATCTTCCT GCAAAAGGCA CACCCGTCAA CCTTGCCGTG

10801 CACCGTGACG AGCAGCTGAT CGTACTAGAT AGAAATAACA AAGAGTGCAC GGTTGCTCAG

10861 GCTCTAGGCA ATGGGGACAA ATTCAGGGCC ACAGACAAGC GCGTTGTAGA TTCTCTCCGC

10921 GCCATTTGTG CAGATCTTGA AGGGTCGAGC TCCCCGCTCC CCAAGGTCGC ACATAACTTG

10981 GGATTTTATT TCTCACCTGA TTTGACACAG TTTGCTAAAC TCCCGGCAGA ACTTGCACCC

11041 CACTGGCCCG TGGTGACAAC CCAGAACAAT GAAAAGTGGC CAGACAGGCT GGTTGCCAGC

11101 CTCCGCCCTA TCCATAAATA TAGCCGCGCA TGCATTGGAG CCGGCTATAT GGTGGGCCCT

11161 TCGGTGTTTC TAGGCACCCC TGGGGTTGTG TCATACTATC TCACAAAATT TGTTAAGGGG

11221 GAGGCTCAGG TGCTTCCGGA GACAGTCTTC AGCACCGGCC GAATTGAGGT AGATTGCCGG

11281 GAGTATCTTG ATGATCGGGA ACGAGAAGTT GCTGAGTCCC TCCCACATGC CTTCATTGGC

11341 GACGTCAAAG GCACTACCGT TGGGGGATGT CACCATGTCA CCTCTAAATA CCTTCCGCGC

11401 TTCCTTCCTA AGGAATCAGT TGCGGTGGTT GGGGTTTCGA GCCCGGGAA AGCCGCAAAA

11461 GCAGTCTGCA CATTAACAGA TGTGTATCTC CCAGACCTTG AAGTTTACCT CCACCCAGAG

11521 ACCCAATCCA AGTGCTGGAA AATAATGTTG GACTTCAAGG AAGTCCGACT GATGGTCTGG

11581 AAAGACAAAA CGGCCTATTT TCAACTTGAA GGCCGCCATT TCACCTGGTA TCAGCTTGCA
```

```
-continued

11641 AGCTATGCCT CGTACATCCG AGTTCCTGTT AACTCTACGG TGTATTTGGA CCCCTGCATG

11701 GGCCCTGCCC TTTGCAACAG AAGAGTTGTC GGGTCCACTC ATTGGGGGGC TGACCTCGCA

11761 GTCACCCCTT ATGATTATGG TGCCAAAATC ATTCTGTCTA GTGCATACCA TGGTGAAATG

11821 CCTCCTGGGT ACAAAATCCT GGCGTGCGCG GAGTTCTCGC TTGACGACCC AGTGAGGTAC

11881 AAACACACCT GGGGGTTTGA ATCGGACACA GCGTATCTGT ACGAGTTCAC CGGAAACGGT

11941 GAGGACTGGG AGGATTACAA TGACGCATTT CGTGCGCGCC AGAAAGGGAA AATTTATAAG

12001 GCCACTGCCA CCAGCATGAG GTTTCATTTT CCCCCGGGCC CCATCATTGA ACCAACTTTA

12061 GGCCTGAACT GAAATGAGAT GGGGGCTATG CAAAGCCTTT TCTACAAAAT TGGCCAACTT

12121 TTTGTGGATG CTTTCACGGA ATTTTTGGTG TCCATTGTTG ATATCATCAT ATTTTTGGCC

12181 ATTTTGTTTG GCTTCACCAT CGCCGGTTGG CTGGTGGTCT TCTGCATCCG ATTGGTTTGC

12241 TCCGCGGTAC TCCGTGCGCG CCCTACCATT CACCCTGAGC AATTACAGAA GATCCTATGA

12301 GGCCTTTCTT TCTCAGTGCC GGGTGGACAT TCCCACCTGG GGAACCAAAC ATCCCTTGGG

12361 GATACTTTGG CACCATAAGG TGTCAACCCT GATTGATGAA ATGGTGTCGC GTCGAATGTA

12421 CCGCATCATG GAAAATCAG GACAGGCTGC CTGGAAACAG GTTGTGAGCG AGGCTACGCT

12481 GTCTCGCATC AGTGGTTTGG ATGTGGTGGC TCATTTTCAG CATCTTGCCG CCATTGAAGC

12541 CGAGACCTGT AAATATTTGG CCTCTCGGAT GCCCATGCTA CACAACCTGC GCATGACAGG

12601 GTCAAATGTA ACCATAGTGT ATAATAGTAC TTTGAATCAG GTGTTAGCAA TCTTCCCGAC

12661 CTCTGAATCC CGGCCAAAGC TTCATGATTT TCAACAATGG TTAATAACTG TACATTCCTC

12721 CATATTTTCC TCCGTTGTGG CTTCCTGTAC TCTTTTTGTT GTGCTGTGGT TGCGAATTCC

12781 AATGCTACGT ACTGTTTTTG GTTCCACTG GTTAGGGGCA ATTTTTCTTT CGAACTCACA

12841 GTGAATTACA CGGTGTGCCC ACCTTGCCTC ACCCGGCAAG CAGCCGCTGA GATCTACGAA

12901 CCCGGCAGGT CTCTTTGGTG CAGGATAGGG CATGATCGAT GTAGCGAGGA CGATCATGAC

12961 GAACTAGGGT TCTTGGTTCC GCCTGGCCTC TCCAGCGAAG GCCACTTGAC CAGTGTTTAC

13021 GCCTGGTTGG CGTTCCTGTC CTTCAGCTAT ACAGCCCAGT TCCATCCCGA GATATTTGGG

13081 ATAGGGAATG TGAGTAAAAT TTATGTTGAC ATCAAGCACC AATTCATCTG CGCCGAACAC

13141 GACGGGCAGA ACGCCACCCT GCCTCGCCAT GACAACATTT CAGCCGTGTT TCAGACCTAC

13201 TACCAACATC AGGTCGATGG CGGCAATTGG TTTCACCTGG AATGGCTGCG CCCCTTCTTT

13261 TCCTCTTGGT TGGTTTTAAA TGTTTCGTGG TTTCTCAGGC GTTCGCCTGC AAGCCATGTT

13321 TCAGTTCGAG TCTTTCAGAC ATCAAAACCA ACACCACCGC AGCACCAAAT TTTGTTGTCC

13381 TCCAGGACAT CAGCTGCCTT AGGCATGGCG ACCCGTCCTC TCCGGCGATT CGCAAAAGCT

13441 CTCAGTGCCG CACGGCGATA GGAACACCCG TGTATATCAC CATCACAGCC AATGTGACAG

13501 ATGAGAATTA TTTACATTCT TCTGATCTCC TCATGCTTTC TTCTTGCCTT TTCTATGCTT

13561 CTGAGATGAG TGAAAAGGGG TTCAAGGTGG TATTCGGCAA TGTGTCAGGC ATCGTGGCTG

13621 TGTGTGTCAA CTTTACCAGT TACGTCCAAC ATGTCAAGGA GTTTACCCAA CGCTCCTTGG

13681 TGGTCGAGCA TGTGCGACTG CTTCATTTCA TGACACCTGA AACCATGAGG TGGGCAACCG

13741 TTTTAGCCTG TCTTTTTGCC ATTCTGTTGG CAATTTGAAT GTTTAAGTAT GTTGGGGAAA

13801 TGCTTGACCG CGGGCTGTTG CTCGCCGTTG CTTTTTTTGT GGTGTATCGT GCCGTCTTGC

13861 TTTGTTGCGC CCGTCAACGT CGACGGGAAC GACAGCTCAA AGTTACAGCT GATTTACAAC

13921 TTGACGCTAT GTGAGCTGAA TGGCACAGAT TGGCTGGCTG GTAGATTTGA CTGGGCAGTG

13981 GAGTGTTTTG TCATTTTTCC CGTGTTGACT CACATTGTCT CCTATGGTGC CCTCACTACT
```

```
14041 AGCCATTTCC TTGACACAGT CGGTCTGGTC ACTGTGTCTG CCGCCGGGTT CCTTCATGAA
14101 CGGTATGTTT TGAGTAGCAT CTACGCGGTC TGTGCCCTGG CTGCGTTGAT TTGCTTCGTC
14161 ATTAGGCTTG CGAAGAACTG CATGTCCTGG CGCTACTCGT GTACCAGATA TACCAACTTC
14221 CTTTTGGACA CCAAGGGGAG ACTCTATCGT TGGCGATCGC CCGTCATCAT AGAGAAAAAG
14281 GGTAAAGTTG AGGTTGAAGG TCATTTGATC GACCTCAAAA GAGTTGTGCT TGATGGTTCC
14341 GTGGCAACCC CTATAACCAA AATTTCAGCG GAACAATGGG GTCGTCCTTA GATGACTTCT
14401 GCCATGATAG CACGGCTCCA CAAAAGGTGC TTTTGGCGTT TTCCATTACC TATACACCAG
14461 TGATGATATA TGCCCTAAAG GTAAGTCGCG GCCGACTGCT AGGGCTTTTG CACCTTTTGA
14521 TCTTTCTGAA CTGTGCTTTC ACCTTCGGGT ATATGACATT CACGCACTTT CAGAGTACAA
14581 ACAAGGTCGC GCTCACTATG GGAGCAGTAG TTGCACTCCT TTGGGGGGTG TACTCAGCCA
14641 TAGAAACCTG GAAATTCATC ACCTCCAGAT GCCGTTTGTG CTTGCTAGGC CGCAAGTACA
14701 TTCTGGCCCC TGCCCACCAC GTTGAGAGTG CCGCAGGCTT TCATCCGATT GCGGCAAATG
14761 ATAACCACGC ATTTGTCGTC CGGCGTCCCG GTTCCACTAC GGTCAACGGC ACATTGGTCC
14821 CCGGGTTGAA AAGCCTCGTG TTGGGTGGCA GAAAAGCTGT CAAACAGGGA GTGGTAAACC
14881 TTGTTAAATA TGCCAAGTAA CAACGGCAGG CAGCAGAAAA AAAGAAAGGG GGATGGCCAG
14941 CCAGTCAATC AGCTGTGTCA GATGCTGGGT AAAATTATTG CCCAGCAAAA TCAGTCCAGG
15001 GGCAAGGGAC CGGGAAAGAA AAATAACAAG AAAAACCCGG AGAAGCCCCA TTTTCCTCTA
15061 GCGACTGAAG ATGATGTCAG ACATCACTTT ACCCCGAGTG AGCGACAATT GTGTCTGTCG
15121 TCAATCCAGA CTGCCTTCAA TCAGGGCGCT GGAACTTGTA CCCTGTCAGA TTCAGGCAGG
15181 ATAAGTTACA CTGTGGAGTT TAGTTTGCCG ACGCATCACA CTGTGCGCCT GATCCGCGCT
15241 ACAGCATCAC CCTCAGCATG ATGAGCTGGC ATTCCTGGGT ATCCCAGTGT TTGAATTGGA
15301 AGAATGTGTG GTGAATGGCA CTGATTGACA TTGTGCTTCT AAGTCACCTA TTCAATTAGG
15361 GCGACCGTGT GGGAGTAGAA TTTAATTGGC GAGAACCACG CGGCCGAAAT TAAAAAAAAA
15421 AAAAAAAAAA AAAAAAAAAA AAAA
```

The cDNA consensus sequence of PRRS strain ND 99-14 at P100 has been assigned GenBank Accession number KU131569 (SEQ. ID. NO:11). The cDNA consensus sequence designated SEQ. ID. NO:11 is:

1 ATGACGTATA GTTGTTGGCT CTATGTCGTG ACATTTGTAT AGTCAGGAGC TGCGACCATT

61 GGTACAGCCC AAAACTTGCT GCGCGGGAAC GCCCTTCCGT GACAGCCTTC TTCAGGGGAG

121 TTTAGGGGTC TATCCCTAGC ACCTTGCTTC CGGAGTTGCA CTGCTTTACG GTCTCTCCAC

181 CCCTTTAACC ATGTCTGGGA TACTTGATCG GTGCACGTGT ACCCCCAATG CCAGGGTGTT

241 TGTGGCGGAG GGCCAAGTCT ACTGCACACG ATGTCTCAGT GCACGGTCTC TCCTTCCTTT

301 GAATCTCCAA GTTTCTGAGC TTGGGGTGCT GGGCTTATTT TATAGGCCCG AAGAGCCGCT

361 CCGGTGGACG TTGCCACGTG CATTCCCCAC TGTCGAGTGC TCCCCCGCCG GGGCCTGCTG

421 GCTTTCTGCG ATTTTTCCAA TTGCACGAAT GACCAGTGGA AACCTGAACT TTCAACAAAG

481 AATAGTGCGG GTCGCAGCTG AGCTCTACAG AGCCGGTCAG CTCACCCCCG TAGTCTTGAA

541 GAATCTACAG GTTTATGAAC GGGGTTGCCG TTGGTACCCC ATCGTTGGAC CTGTTCCTGG

601 AGTGGCTGTT TATGCCAATT CCTTACACGT GAGTGACAAA CCTTTCCCGG GAGCAACTCA

661 TGTGTTAACC AACCTACCGC TCCCGCAGAG GCCCAAGCCT GAAGACTTTT GCCCCTTTGA

721 GTGTGCTATG GCTGACGTCT ATGACATTGG TCATGACGCT GTCATGTATG TGGCCGGAGG

781 GAGAGTCTCC TGGGCCCCTC GTGGCGGGGA CAAAGGAAAA TTTGAAATAG TTCCCAAGGA

-continued

```
 841 GTTGAAGTTG ATTGCGAATC GACTCCACAT TTCCTTCCCG CCCCACCACG CAGTGGACAT
 901 GTCCAAGTTT GCCTTTATAA GCCCTGGGAG TGGTGTTTCC ATGCGGGTCG AGTACCAACA
 961 TGGCTGTCTC CCCGCTGATA CTGTCCCTGA AGGAAACTGT TGGTGGCGCT TGTTTGACTT
1021 GCTTCCACCG GAAGTTCAGA ACAAAGAGAT TCGCCATGCT AACCAACTCG GCTATCAGAC
1081 CAAGCATGGT GTCGCTGGCA AGTACCTACA GCGGAGGCTG CAAGTTAATG GACTCCGAGC
1141 AGTAACTGAC GCGAATGGAC CTATCGTCAT ACAGTATTTT TGTGATAGGG AAAGCTGGAT
1201 CCGCCACTTA AGACTGGTAG AAGAACCTAG CCTCCCTGGG TTTGAGGACC TCCTCAGAAT
1261 AAGAGTTGAG CCCAATACGT TGCCATTGGT TGGCGAGGAT GAGAAAATCT TCCGATTTGG
1321 CAATCACAAA TGGTACGGTG CTGGAAAGAG GGCAAGGAAA GCACGCTTTG GTGCGGCTGC
1381 CACGGTCGCT CACCGCGCTT TGCCCGCTCA CGAAACCCAG CAGGCCAAGA AGCACGAAGT
1441 TACCAGCGCC AACAGGGCTG AGCATCTCGA GCACTATTCC CCGCCTACCG ACGGGAACTG
1501 TGGTTGGCAC TGCGTTTCCG CCATTGTCAA CCGGATTGTG AATTCCAAAT TTGAAACCAC
1561 CCTTCCCGAG AGAGTGAGAC CTTTAGATGA CTGGGCTACT GACGAGGATC TTGTGAATAC
1621 TATCCAAATC CTCAGGCTCC CTGCGGCCTT GGACAGGAAC GGTGCTTGTG TCGGCGCCAA
1681 GTACGTGCTC AAGCTGGAAG GTGTGCACTG GACAGTCTCT GTGGCCCCTG GGATGACCCC
1741 TTCTCTGCTC CCCCTTGAAT GTGTTCAGGG CTGTTGTGAG CATAAGAGCG TCTTGGTCC
1801 CCCAGATGTG GCTGAAGTTT CCGGATTTGA CCCTGCCTGC CTTAACCGAC TGGCTGAGGT
1861 AATGCACTTG CCTAGTTGTG TCATCCCAGC TGCTCTGGCT GAAATGTCCG ACGACCCCAA
1921 TCGCCCGGCT TCCCCAGTCA CCACTGTGTG GACTATTTCG CAATTCTTTG CCCATTATAG
1981 AGGAGGAGAG CACCCTGATC AGGTGTGCTT AGGGAAAATC ATCAGCCTTT GTCAGGTGAT
2041 TGAGGAATGC TGTTGTTCCC AGAACAAAAC CAACCGGGCC ACCCCGGAAG AGGTCGCGGC
2101 AAAAATTGAC CAGTACCTCC GTGATGCAGC AAGCCTTGGA GAATGCTTAG CCAAGCTTGA
2161 GAGGGCTCGC CCGCCGAGCG CGATGGACAC CTCCTTTGAT TGGAATGTTG TGCTTCCTGG
2221 GGTTGAGGCG GCGAACCAGA CGACCAAACA GCTCCATGTC AACCAGCACC GTGCTTCGGT
2281 TCCTGCCATG ACTCAGGAGC CTTTGGACAA AGACTCGGTC CCTTTGACCG CCTTCTCGCT
2341 GTCTAATTGC TACTACCCTG CACAAGGTGA CGAGGTTCGT CACCGTGAGA GGCTGATCTC
2401 CGTGCTCTCT AAGTTGGAGG AGGTTGTTCG TGAGGAATAT GGGCTCACGC CAACTGGATC
2461 TGGCCCGCGA CCCGCACTGC CGAACGGGCT CGACGAGCTC AAAGACCAGA TGGAAGAGGA
2521 TCTGTTGAAA CTGGTCAACG CCCAGGCAAC TTCAGAAATG ATGGCCCGGG CAGCTGAGCA
2581 GGTTGATCTA AAAGTTTGGG TCAAAAATTA CCCACGGTGG ACACCGCCAC CCCCTCCACC
2641 AAGAGTTCAG CCTCGAAAAA CAAAGTCTGC TAAGAGCCTG CCAGAGAACA AGCCTGTCCC
2701 TGCTCCGCGC AGGAAAGTCA GATCTGATTG TGGCAGCCCG ACTTTGAGGG GCAACAATGT
2761 TCCTAACGGT TGGGAAGACT TGGCCGTTGG TGGTCCTCTT GATCTTTCGA CACCATCCGA
2821 GCCGATGACA CCTCTGAGTG AGCCTGCACT TATGCCCGTG TTGCAACATA TTTCTGGACC
2881 AGTGACGCCT TTGAGCGTGC CGGCCCCTAT TCCTGCACCG CGTAAAGCTG TGTCCCGACC
2941 GATGGCGCCC TCGAGTGAGC CAATTTTTGT GTCTGCACCG CGGCAAAAAT TCAGCAGGT
3001 GGAAGAAGCA AATCGGCGG CAACAACGCT GACATACCAG GACGAACCTA TAGATCTGTC
3061 AGCATCCTCA CAGACTGAAT ATGAGGCTCC TTCCCTAGCA CCACTGCAGA ACATAGGTAC
3121 TCTGGAGGTG GGGGGGCAAG AAGCTGAGGA AATTCTGAGT GAAACCTCGG ATATACCGAA
3181 TGACATCAAC CCTGTGCCTG TATCATCAAG CAGCTCCTTG TCAAGCGTTA AGATCACACG
```

```
3241  CCCAAGACAC TCAGCTCAAG CCATCATCGA CTCGGGCGGG CCCTGCAGTG GGCATCTCCA

3301  AAGGGAGAAA GAAGCGTGCC TCCGCATCAT GCGTGAGGCT TGTGATGCGA CTAAGCTTAG

3361  TGACCCTGCC ACGCAGGAAT GGCTTTCTCG CATGTGGGAT AGGGTGGACA TGCTGACTTG

3421  GCGCAACACG TCTGCTTTCC AGGCGTTTCG CATCTTAGAC GGCAGGCTTG AGTTTCTTCC

3481  AAAGATGATA CTCGAGACGC CGCCGCCCTA CCCGTGTGGG TTTGTGATGC TGCCTCACAC

3541  CCCTGCACCT TCCGTGAGTG CAGAGAGCGA CCTTACCATC GGTTCAGTCG CCACTGAAGA

3601  TATTCCACGC ATCCTCGGGA AAATAGAAAA CACCAGTGAG ATGATCAACC AGGGACCCTT

3661  GGCATCCTCT GAGGAAAAAC CGGCATACAA CCAACCCGCT AAGGACTCCC TGATATCGTC

3721  GCGGGGGTTT GACGAGAGCA CAGCAGCTCC GTCCGCAGGT ACGGGTGGCG CCGGCTTGTT

3781  TACTGATTTG CCACCTTCAG ACGGTGTAGA TGCGGACGGG GGGGGGCCGC TGCAGACGGT

3841  GAAAAGAAC GCTGAAAGGC TCCTCGACCG ATTGAGCCGT CAGGTTTTTA ACCTCGTCTC

3901  CCATCTCCCT GTTTTCCTCT CACACCTCTT CAAATCTGAC AGTGGTTATT CTCCGGGTGA

3961  TTGGGGTTTT GCAGCTTTTA CTCTATTTTG CCTCTTTTTA TGTTACAGCT ACCCATTCTT

4021  TGGTTTCGCT CCCCTTTTGG GTGTGTTTTC TGGGTCTTCT CGGCGCGTGC GCATGGGGGT

4081  TTTTGGCTGC TGGTTGGCTT TTGCTGTTGG TTTGTTCAAG CCTGTGTCCG ACCCAGTCGG

4141  CACTGCTTGT GAGTTTGATT CGCCAGAGTG TAGGAATGTC CTTCATTCTT TTGAGCTTCT

4201  CAAACCTTGG GACCCTGTTC GCAGCCTTGT TGTGGGCCCC GTCGGTCTCG GTCTTGCCAT

4261  TCTTGGCAGG TTACTGGGCG GGGCACGCTA CATCTGGCAT TTTCTGCTTA GGCTTGGCAT

4321  TGTTACAGAC TGTATCCTGG CTGGAGCTTA TGTGCTTTCT CAAGGTAGGT GTAAAAAGTG

4381  CTGGGGATCT TGCATAAGAA CAGCTCCTAA TGAGATTGCC TTTAACGTGT TCCCTTTTAC

4441  ACGTGCGACT AGGTCGTCAC TCATCGACCT GTGCAATCGG TTTTGTGCGC CAAAGGGCAT

4501  GGACCCTATT CTCCTCGCCA CTGGGTGGCG TGGGTGCTGG ACCGGCCGAA GCCCCATTGA

4561  ACAACCCTCT GAAAAACCCA TCGCGTTTGC CCAGTTGGAC GAAAAGAGGA TTACGGCCAG

4621  GACCGTGGTC GCCCAGCCTT ATGACCCCAA CCAAGCCGTA AAGTGCTTGC GGGTGTTACA

4681  GGCGGGCGGG GCGATGGTGG CTGAGGCAGT CCCAAAAGTG GTCAAAGTTT CCGCTATTCC

4741  ATTCCGAGCC CCCTTTTTTC CCACCGGAGT GAAAGTTGAC CCTGAGTGTA GGATCGTGGT

4801  TGACCCCGAC ACTTTTACTA CAGCCCTCCG GTCCGGCTAT TCCACCACAA ACCTCGTTCT

4861  TGGTGTGGGG GACTTTGCCC AGCTGAATGG ATTAAAAATC AGGCAAATTT CCAAGCCTTC

4921  GGGAGGAGGC CCGCACCTCA TTGCTGCCCT ACATGTTGCC TGCTCGATGG CGTTGACAT

4981  GCTTGCTGGG GTTTATGTAA CTGCAGTGGG GTCTTGCGGT ACCGGCACCA ACGATCCGTG

5041  GTGCACCAAC CCGTTTGCCG TCCCTGGCTA CGGGCCTGGT ACTCTTTGCA CGTCCAGATT

5101  GTGCATCTCC CAACATGGCC TTACCCTGCC CTTGACAGCA CTTGTGGCAG GATTCGGTCT

5161  TCAGGAAATT GCCTTGGTTG TTTTGATTTT CGTTTCCATC GGAGGCATGG CTCACAGGTT

5221  GAGTTGCAAG GCTGACATGC TGTGCGTTTT ACTTGCAATC GCCAGCTATG TTTGGGTGCC

5281  CCTTACCTGG TTTCTTTGTG TGTTTCCTTG CTGGTTGCGC TGGTTCTCTT TGCATCCCCT

5341  CACCATCCTA TGGTTGGTGT TTTTCTTGAT TTCTGTAAAT GTGCCTTCGG GAATCTTGGC

5401  TGTGGTGTTG TTAGTTTCTC TTTGGCTCTT AGGTCGTTAC ACTAATGTTG CTGGTCTTGT

5461  CACCCCATAT GACATTCATC ATCACACCAG TGGCCCCCGA GGTGTTGCCG CCTTGGCTAC

5521  TGCACCGGAT GGGACCTACT TGGCCGCCGT TCGCCGTGCT GCGTTGACCG GTCGTACCAT

5581  GCTGTTTACC CCGTCTCAGC TTGGGTCCCT TCTTGAGGGT GCTTTCAGAA CTCAAAAGCC

5641  CTCACTGAAC ACCGTCAATG TGGTCGGATC CTCTATGGGC TCCGGCGGGG TGTTCACCAT
```

-continued

```
5701  CGACGGGAAA ATTAAGTGCG TAACAGCCGC ACATGTCCTT ACGGGTAATT CAGCTAGGGT
5761  TTCCGGGGTC GGCTTCAACC AAATGCTTGA TTTTGATGTG AAAGGGGACT TCGCCATAGC
5821  TGATTGCCCG AATTGGCAAG GAGCTGCCCC CAAGACCCAA TTCTGCGAGG ATGGATGGAC
5881  TGGCCGTGCC TATTGGCTGA CATCCTCTGG AGTCGAACCC GGTGTCATTG GAATGGATT
5941  CGCCTTCTGC TTCACCGCGT GCGGCGATTC TGGATCCCCG GTGATTACCG AAGCCGGTGA
6001  GCTTGTCGGC GTTCACACAG GATCAAACAA ACAAGGAGGA GGCATAGTCA CACGCCCCTC
6061  AGGCCAGTTT TGTAATGTGG CGCCCATCAA GCTGAGCGAA TTGAGTGAAT TCTTCGCTGG
6121  ACCTAAGGTC CCGCTCGGTG ATGTGAAGAT TGGCAGCCAC ATAATTAAAG ACGTATGCGA
6181  GGTACCTTCA GATCTTTGCG CCTTGCTCGC TGCCAAACCC GAACTGGAAG GAGGCCTCTC
6241  CACCGTCCAA CTTCTGTGTG TGTTTTTCCT CCTGTGGAGA ATGATGGGAC ATGCCTGGAC
6301  GCCCTTGGTT GCTGTGGGGT TTTTTATCTT GAATGAGGTT CTCCCAGCTG TCCTGGTCCG
6361  GAGTGTCTTC TCCTTTGGTA TGTTTGTGCT ATCTTGGCTT ACACCATGGT CTGCGCAAGT
6421  CCTGATGATC AGGCTTCTAA CAGCAGCTCT TAACAGGAAC AGGGGGTCAC TCGCCTTCTA
6481  CAGCCTCGGT GCAGTGACCG GATTTATCGC AGATCTTGCA GCAACTCAGG GGCATCCGCT
6541  GCAGGCAGTG ATGAACTTAA GCACCTATGC CTTCCTGCCT CGGATGATGG TTGTGACCTC
6601  ACCAGTCCCA GTGCTTGCTT GTGGTGTTGT GCACCTCCTT GCCATAATTT TGTACCTGTT
6661  TAAGCACCGT TGCCTGCATT ATGTCCTTGT TGGCGATGGA GTGTTCTCTA AAGCCTTCTT
6721  CTTGCGATAC TTTGCCGAAG GGAAGTTGAG GGAAGGGGTG TCGCAGTCCT GCGGGATGAA
6781  TCACGAGTCA CTGACTGGTG CCCTCGCTAT GAGACTCAAT GACGAAGACT TGGACTTCCT
6841  TACGAAATGG ACTGATTTTA AGTGCTTTGT TTCTGCGTCC AACATGAGGA ATGCAGCGGG
6901  CCAATTCATC GAGGCTGCCT ATGCAAAAGC ACTTAGAATT GAGCTTGCCC AGTTAGTACA
6961  GGTTGATAAG GTTCGAGGTA CTTTGGCCAA ACTTGAAGCC TTTGCTGATA CCGTGGCACC
7021  CCAGCTCTCG CCCGGTGACA TTGTTGTTGC TCTTGGCCAC ACGCCTGTTG GCAGTATCTT
7081  CGACCTAAAG GTTGGCAGTA CCAAGCATAC CCTCCAGGCC ATTGAGACCA GAGTCCTTGC
7141  CGGGTCCAAA ATGACCGTGG CGCGTGTCGT TGATCCAACC CCCACGCCCC CACCCGCACC
7201  CGTGCCCATC CCCCTCCCAC CGAAAGTCCT GGAGAACGGC CCCAACGCCT GGGGGGATGA
7261  GGACCGGTTG AATAAGAGGA AGAGACGCAG GATGGAAGCC GTCGGCATCT TTGTTATGGG
7321  TGGGAAGAAG TACCAAAAAT TTTGGGACAA GAATTCCGGT GATGTGTTTT ACGAGGAGGT
7381  CCATGATAAC ACAGATGCGT GGGAGTGCCT CAGAGTTGGT GACCCTGCCG ACTTTGACCC
7441  TGAGAAGGGA ACTCTGTGTG GCATACTAC CATTGAAGAC AAGGCTTATA ATGTCTACAC
7501  CTCCCCATCT GGCAGGAAGT TCCTGGTCCC CGTCAACCCA GAGAGCGGAA GAGCCCAATG
7561  GGAAGCTGCA AAGCTTTCCG TAGAGCAGGC CCTTAGCATG ATGAATGTCG ACGGTGAGCT
7621  GACAGCCAAA GAACTGGAGA AACTGAAAAG AATAATTGAC AAACTCCAGG GCCTAACTAA
7681  GGAGCAGTGT TTAAACTGCT AGCCGCCAGC GGCTTGACCC GCTGTGGTCG CGGCGGCTTG
7741  GTTGTTACTG AGACAGCGGT GAAAATAGTT AAATTTCACA ACCGGACCTT CACCCTAGGA
7801  CCTGTGAATT TAAAAGTGGC CAGTGAGGTT GAGCTAAAAG ACGCAGTCGA GCATAACCAA
7861  CACCCGGTTG CAAGACCGGT TGATGGTGGT GTTGTGCTCC TGCGCTCCGC AGTTCCTTCG
7921  CTTATAGACG TCTTGATCTC TGGCGCTGAT GCATCTCCTA AGTTACTCGC CCACCACGGG
7981  CCGGGAAACA CTGGGATCGA TGGTTCGCTT TGGGATTTTG AGGCCGAGGC CACCAAAGAG
8041  GAAATTGCAC TCAGTGCGCA AATAATACAG GCTTGTGACA TTAGGCGCGG CGACGCACCC
```

```
-continued
8101 GAAATTGGTC TTCCTTATAA GCTGCACCCT GTTAGGGGCA ACCCTGAGCG GGTAAAAGGG

8161 GTTTTACAGA ATACAAGGTT TGGAGACATA CCTTATAAAA CCCCCAGTGA CACTGGGAGC

8221 CCAGTGCACG CGGCTGCCTG CCTCACGCCC AATGCCACTC CGGTGACTGA CGGTCGTTCC

8281 GTCTTGGCTA CGACCATGCC CTCCGGTTTT GAGTTGTATG TACCGACCAT TCCAGCGTCT

8341 GTCCTTGATT ATCTTGATTC CAGGCCTGAT TGCCCCAAAC AGTTGACAGA GCACGGCTGT

8401 GAGGATGCCG CATTAAGAGA CCTCTCCAAG TATGACTTGT CCACCCAAGG CTTTGTCTTG

8461 CCTGGAGTTC TTCGCCTTGT GCGTAAGTAC CTGTTTGCTC ATGTGGGTAA GTGCCCGCCT

8521 ATTCATCGGC CTTCCACTTA CCCTGCCAAG AATTCCATGG CTGGAATAAA TGGGAACAGG

8581 TTTCCAACCA AGGACATTCA GAGCGTCCCT GAAATCGACG TTTTGTGCGC ACAGGCCGTG

8641 CGAGAAAACT GGCAAACTGT TACTCCTTGT ACCCTCAAGA AGCAGTATTG CGGGAAGAAG

8701 AAGACTAGGA CAATACTCGG CACTAATAAC TTCATTGCGC TGGCCCACCG GGCAGCATTG

8761 AGTGGTGTCA CCCAGGGCTT CATGAAAAAA GCGTTTAACT CGCCCATCGC ACTCGGGAAA

8821 AACAAATTCA AGGAGCTGCA GACTCCGGTC TTGGGCAGAT GTCTTGAAGC TGACCTTGCA

8881 TCCTGTGACC GATCCACACC CGCAATTGTC CGCTGGTTTG CCGCCAATCT TCTTTATGAA

8941 CTTGCCTGTG CTGAGGAGCA TATACCATCG TACGTGTTGA ACTGCTGCCA CGACTTACTG

9001 GTCACGCAGT CCGGCGCGGT GACTAAGAGA GGTGGCCTAT CGTCTGGCGA CCCGATTACT

9061 TCTGTATCAA ACACCATTTA CAGCTTGGTG ATATATGCAC AGCACATGGT ACTCAGTTAT

9121 TTTAAAAGTG GTCACCCCCA TGGCCTTCTG TTTCTACAAG ACCAGCTAAA GTTTGAGGAC

9181 ATGCTCAAGG TTCAGCCCCT GATCGTCTAT TCGGACGACC TCGTGCTGTA CGCCGAGTCT

9241 CCCACCATGC CAAACTACCA CTGGTGGGTT GAACATCTGA ACCTGATGCT GGGTTTTCAG

9301 ACGGACCCAA AGAAGACAGC TATAACAGAC TCGCCATCAT TTTTGGGTTG TAGGATAATA

9361 AATGGACGCC AGTTAGTCCC CAACCGTGAC AGGATCCTCG CGGCCCTCGC CTACCATATG

9421 AAGGCAAACA ATGTTTCTGA ATACTACGCC TCGGCGGCTG CAATACTCAT GGACAGTTGT

9481 GCTTGTTTGG AGTACGATCC TGAGTGGTTT GAAGAGCTCG TGGTTGGGAT GGCGCAGTGC

9541 GCCCGCAAGG ACGGCTACAG TTTTCCTGGC CGCCGTTCT TCTTGTCCAT GTGGGAAAAA

9601 CTCAGGTCCA ATCATGAGGG GAAGAAGTCT AGAATGTGCG GGTACTGTGG GGCCCCAGCT

9661 CCGTATGCCA CTGCCTGTGG CCTTGATGTT TGTATTTATC ACACCCACTT CCACCAGCAT

9721 TGTCCAGTCA TAATCTGGTG TGGCCATCCG GCGGGTTCTG GCTCTTGTAG TGAGTGCAAA

9781 CCCCCCCTAG GGAAAGGCAC AAGCCCTCTA GATGTGGTGT TAGAACAAGT CCCGTACAAG

9841 CCTCCACGAA CTGTAATCAT GCATGTGGAG CAGGGTCTCA CCCCTCTTGA CCCAGGCAGA

9901 TACCAGACTC GCCGCGGATT AGTCTCCGTT AGGCGTGGCA TCAGGGGAAA CGAAATCGAC

9961 CTACCAGACG GTGATTATGC TAGTACCGCC TTGCTCCCCA CTTGTAAAGA TATCAACATG

10021 GTCGCTGTCG CTTCCAATGT GTTGCGCAGC AGGTTCATCA TCGGTCCACC CGGTGCTGGT

10081 AAAACATACT GGCTCCTTCA ACAGGTCCAG GATGGTGATG TCATTTACAC GCCAACTCAT

10141 CAGACCATGC TTGACATGAT CAAGGCTTTG GGGACGTGCC GGTTCAACGC CCCAGCAGGC

10201 ACAACGCTGC AATTCCCTGC TCCCTCCCGT ACCGGCCCGT GGGTTCGCAT CCTGGCCGGC

10261 GGTTGGTGTC CTGGCAAGAA TTCCTTCCTG GATGAAGCAG CGTATTGTAA TCACCTTGAT

10321 GTCTTGAGGC TTCTTAGCAA AACTACCCTC ACCTGTCTGG GAGATTTCAA ACAACTCCAC

10381 CCAGTGGGTT TTGATTCTCA TTGCTATGTT TTTGACATCA TGCCTCAGAC TCAACTGAAG

10441 ACCATCTGGA GGTTTGGACA GAATATCTGT GATGCCATTC AGCCAGATTA CAGGGACAAA

10501 CTTGTGTCCA TGGTCAACAC AACCCGTGTA ACCTACGTGG AAAGACCTGT CAAGCATGGG
```

```
-continued

10561 CAGGTCCTCA CCCCTTACCA CAGGGACCGA GAGGACGGCG CCATCACAAT TGACTCCAGT

10621 CAAGGCGCCA CATTTGATGT GGTTACATTG CATTTGCCCA CTAAAGATTC ACTCAACAGG

10681 CAAAGAGCCC TTGTTGCTAT CACCAGGGCG AGACATGCTA TCTTTGTGTA TGACCCACAT

10741 AGGCAACTGC AGAGCATGTT TGATCTTCCT GCAAAAGGCA CACCCGTCAA CCTTGCCGTG

10801 CACCGTGACG AGCAGCTGAT CGTACTAGAT AGAAATAACA AAGAGTGCAC GGTTGCTCAG

10861 GCTCTAGGCA ATGGGGACAA ATTCAGGGCC ACAGACAAGC GCGTTGTAGA TTCTCTCCGC

10921 GCCATTTGTG CAGATCTTGA AGGGTCGAGC TCCCCGCTCC CCAAGGTCGC ACATAACTTG

10981 GGATTTTATT TCTCACCTGA TTTGACACAG TTTGCTAAAC TCCCGGCAGA ACTTGCACCC

11041 CACTGGCCCG TGGTGACAAC CCAGAACAAT GAAAAGTGGC CAGACAGGCT GGTTGCCAGC

11101 CTCCGCCCTA TCCATAAATA TAGCCGCGCA TGCATTGGAG CCGGCTATAT GGTGGGCCCT

11161 TCGGTGTTTC TAGGCACCCC TGGGGTTGTG TCATACTATC TCACAAAATT TGTTAAGGGG

11221 GAGGCTCAGG TGCTTCCGGA GACAGTCTTC AGCACCGGCC GAATTGAGGT AGATTGCCGG

11281 GAGTATCTTG ATGATCGGGA ACGAGAAGTT GCTGAGTCCC TCCCACATGC CTTCATTGGC

11341 GACGTCAAAG GCACTACCGT TGGGGGATGT CACCATGTCA CCTCTAAATA CCTTCCGCGC

11401 TTCCTTCCTA AGGAATCAGT TGCGGTGGTT GGGGTTTCGA GCCCCGGGAA AGCCGCAAAA

11461 GCAGTCTGCA CATTAACAGA TGTGTATCTC CCAGACCTTG AAGTTTACCT CCACCCAGAG

11521 ACCCAATCCA AGTGCTGGAA ATAATGTTG GACTTCAAGG AAGTCCGACT GATGGTCTGG

11581 AAAGACAAAA CGGCCTATTT TCAACTTGAA GGCCGCCATT TCACCTGGTA TCAGCTTGCA

11641 AGCTATGCCT CGTACATCCG AGTTCCTGTT AACTCTACGG TGTATTTGGA CCCCTGCATG

11701 GGCCCTGCCC TTTGCAACAG AAGAGTTGTC GGGTCCACTC ATTGGGGGC TGACCTCGCA

11761 GTCACCCCTT ATGATTATGG TGCCAAAATC ATTCTGTCTA GTGCATACCA TGGTGAAATG

11821 CCTCCTGGGT ACAAAATCCT GGCGTGCGCG GAGTTCTCGC TTGACGACCC AGTGAGGTAC

11881 AAACACACCT GGGGGTTTGA ATCGGACACA GCGTATCTGT ACGAGTTCAC CGGAAACGGT

11941 GAGGACTGGG AGGATTACAA TGACGCATTT CGTGCGCGCC AGAAAGGGAA AATTTATAAG

12001 GCCACTGCCA CCAGCATGAG GTTTCATTTT CCCCCGGGCC CCATCATTGA ACCAACTTTA

12061 GGCCTGAACT GAAATGAGAT GGGGGCTATG CAAAGCCTTT TCTACAAAAT TGGCCAACTT

12121 TTTGTGGATG CTTTCACGGA ATTTTTGGTG TCCATTGTTG ATATCATCAT ATTTTTGGCC

12181 ATTTTGTTTG GCTTCACCAT CGCCGGTTGG CTGGTGGTCT TCTGCATCCG ATTGGTTTGC

12241 TCCGCGGTAC TCCGTGCGCG CCCTACCATT CACCCTGAGC AATTACAGAA GATCCTATGA

12301 GGCCTTTCTT TCTCAGTGCC GGGTGGACAT TCCCACCTGG GGAACCAAAC ATCCCTTGGG

12361 GATACTTTGG CACCATAAGG TGTCAACCCT GATTGATGAA ATGGTGTCGC GTCGAATGTA

12421 CCGCATCATG GAAAAATCAG ACAGGCTGC CTGGAAACAG TTGTGAGCG AGGCTACGCT

12481 GTCTCGCATC AGTGGTTTGG ATGTGGTGGC TCATTTTCAG CATCTTGCCG CCATTGAAGC

12541 CGAGACCTGT AAATATTTGG CCTCTCGGAT GCCCATGCTA CACAACCTGC GCATGACAGG

12601 GTCAAATGTA ACCATAGTGT ATAATAGTAC TTTGAATCAG GTGTTAGCAA TCTTCCCGAC

12661 CTCTGAATCC CGGCCAAAGC TTCATGATTT TCAACAATGG TTAATAACTG TACATTCCTC

12721 CATATTTTCC TCCGTTGTGG CTTCCTGTAC TCTTTTTGTT GTGCTGTGGT TGCGAATTCC

12781 AATGCTACGT ACTGTTTTTG GTTTCCACTG GTTAGGGGCA ATTTTTCTTT CGAACTCACA

12841 GTGAATTACA CGGTGTGCCC ACCTTGCCTC ACCCGGCAAG CAGCCGCTGA GATCTACGAA

12901 CCCGGCAGGT CTCTTTGGTG CAGGATAGGG CATGATCGAT GTAGCGAGGA CGATCATGAC
```

```
                    -continued
12961 GAACTAGGGT TCTTGGTTCC GCCTGGCCTC TCCAGCGAAG GCCACTTGAC CAGTGTTTAC

13021 GCCTGGTTGG CGTTCCTGTC CTTCAGCTAT ACAGCCCAGT TCCATCCCGA GATATTTGGG

13081 ATAGGGAATG TGAGTAAAAT TTATGTTGAC ATCAAGCACC AATTCATCTG CGCCGAACAC

13141 GACGGGCAGA ACGCCACCCT GCCTCGCCAT GACAACATTT CAGCCGTGTT TCAGACCTAC

13201 TACCAACATC AGGTCGATGG CGGCAATTGG TTTCACCTGG AATGGCTGCG CCCCTTCTTT

13261 TCCTCTTGGT TGGTTTTAAA TGTTTCGTGG TTTCTCAGGC GTTCGCCTGC AAGCCATGTT

13321 TCAGTTCGAG TCTTTCAGAC ATCAAAACCA ACACCACCGC AGCACCAAAT TTTGTTGTCC

13381 TCCAGGACAT CAGCTGCCTT AGGCATGGCG ACCCGTCCTC TCCGGCGATT CGCAAAAGCT

13441 CTCAGTGCCG CACGGCGATA GGAACACCCG TGTATATCAC CATCACAGCC AATGTGACAG

13501 ATGAGAATTA TTTACATTCT TCTGATCTCC TCATGCTTTC TTCTTGCCTT TTCTATGCTT

13561 CTGAGATGAG TGAAAAGGGG TTCAAGGTGG TATTCGGCAA TGTGTCAGGC ATCGTGGCTG

13621 TGTGTGTCAA CTTTACCAGT TACGTCCAAC ATGTCAAGGA GTTTACCCAA CGCTCCTTGG

13681 TGGTCGAGCA TGTGCGACTG CTTCATTTCA TGACACCTGA AACCATGAGG TGGGCAACCG

13741 TTTTAGCCTG TCTTTTTGCC ATTCTGTTGG CAATTTGAAT GTTTAAGTAT GTTGGGGAAA

13801 TGCTTGACCG CGGGCTGTTG CTCGCCGTTG CTTTTTTTGT GGTGTATCGT GCCGTCTTGC

13861 TTTGTTGCGC CCGTCAACGT CGACGGGAAC GACAGCTCAA AGTTACAGCT GATTTACAAC

13921 TTGACGCTAT GTGAGCTGAA TGGCACAGAT TGGCTGGCTG GTAGATTTGA CTGGGCAGTG

13981 GAGTGTTTTG TCATTTTTCC CGTGTTGACT CACATTGTCT CCTATGGTGC CCTCACTACT

14041 AGCCATTTCC TTGACACAGT CGGTCTGGTC ACTGTGTCTG CCGCCGGGTT CCTTCATGAA

14101 CGGTATGTTT TGAGTAGCAT CTACGCGGTC TGTGCCCTGG CTGCGTTGAT TTGCTTCGTC

14161 ATTAGGCTTG CGAAGAACTG CATGTCCTGG CGCTACTCGT GTACCAGATA TACCAACTTC

14221 CTTTTGGACA CCAAGGGGAG ACTCTATCGT TGGCGATCGC CGTCATCAT AGAGAAAAAG

14281 GGTAAAGTTG AGGTTGAAGG TCATTTGATC GACCTCAAAA GAGTTGTGCT TGATGGTTCC

14341 GTGGCAACCC CTATAACCAA AATTTCAGCG GAACAATGGG GTCGTCCTTA GATGACTTCT

14401 GCCATGATAG CACGGCTCCA CAAAAGGTGC TTTTGGCGTT TTCCATTACC TATACACCAG

14461 TGATGATATA TGCCCTAAAG GTAAGTCGCG GCCGACTGCT AGGGCTTTTG CACCTTTTGA

14521 TCTTTCTGAA CTGTGCTTTC ACCTTCGGGT ATATGACATT CACGCACTTT CAGAGTACAA

14581 ACAAGGTCGC GCTCACTATG GGAGCAGTAG TTGCACTCCT TTGGGGGGTG TACTCAGCCA

14641 TAGAAACCTG GAAATTCATC ACCTCCAGAT GCCGTTTGTG CTTGCTAGGC CGCAAGTACA

14701 TTCTGGCCCC TGCCCACCAC GTTGAGAGTG CCGCAGGCTT TCATCCGATT GCGGCAAATG

14761 ATAACCACGC ATTTGTCGTC CGGCGTCCCG GTTCCACTAC GGTCAACGGC ACATTGGTCC

14821 CCGGGTTGAA AAGCCTCGTG TTGGGTGGCA GAAAAGCTGT CAAACAGGGA GTGGTAAACC

14881 TTGTTAAATA TGCCAAGTAA CAACGGCAGG CAGCAGAAAA AAGAAAGGG GATGGCCAG

14941 CCAGTCAATC AGCTGTGTCA GATGCTGGGT AAAATTATTG CCCAGCAAAA TCAGTCCAGG

15001 GGCAAGGGAC CGGGAAAGAA AAATAACAAG AAAAACCCGG AGAAGCCCCA TTTTCCTCTA

15061 GCGACTGAAG ATGATGTCAG ACATCACTTT ACCCCGAGTG AGCGACAATT GTGTCTGTCG

15121 TCAATCCAGA CTGCCTTCAA TCAGGGCGCT GGAACTTGTA CCCTGTCAGA TTCAGGCAGG

15181 ATAAGTTACA CTGTGGAGTT TAGTTTGCCG ACGCATCACA CTGTGCGCCT GATCCGCGCT

15241 ACAGCATCAC CCTCAGCATG ATGAGCTGGC ATTCCTGGGT ATCCCAGTGT TTGAATTGGA

15301 AGAATGTGTG GTGAATGGCA CTGATTGACA TTGTGCTTCT AAGTCACCTA TTCAATTAGG
```

```
15361 GCGACCGTGT GGGAGTAGAA TTTAATTGGC GAGAACCACG CGGCCGAAAT TAAAAAAAAA

15421 AAAAAAAAAA AAAAAAAAAA AAAA
```

A person skilled in the art would recognize the polyadenosine tails of each of the genomic consensus sequences could vary in length from the above reported sequences.

Variant identification was also performed to determine the number and frequency of nucleotide changes in the virus population for both passages. Table 15 shows the 7 nucleotide changes found in P84 and P100 compared to the reference sequence. Overall the variant positions were consistent between the passages with the exception of 2 nucleotide changes in P84 which were not present in P100. Furthermore, the frequencies of each variant were similar between the passages and were detected at relatively low frequencies suggesting that similar sub-populations are found in both P84 and P100 of ND 99-14.

TABLE 15

PRRSV ND 99-14 Sequence Variants.

| | | | Frequency (% of Population) | |
| --- | --- | --- | --- | --- |
| Position | Reference Base | Variant Base | P84 | P100 |
| 1,120 | G | T | 19.73% | 17.27% |
| 2,276 | C | T | 77.41% | 73.92% |
| 2,680 | G | A | 26.39% | 19.42% |
| 6,001 | G | A | 19.57% | 7.26% |
| 8,745 | C | T | 31.18% | 29.78% |
| 13,699 | T | C | 15.68% | ND |
| 14,005 | T | C | 5.12% | ND |

ND = not detected.

EXAMPLE 6

The objective of this study is to prepare the master seed virus (MSV) of Porcine Reproductive and Respiratory Syndrome Virus (PRRSV) strain SD 11-21. This seed will be used for PRRSV vaccine development.

PRRSV SD 11-21 strain has been modified by passing in the MARC-145 cells 83 times (P83) including two rounds of plaque purification and one round of sucrose gradient purification, prior to the initial characterization and sequencing as described in Example 1. The SD 11-21 strain has been further attenuated by passing 12 times (P95) in MARC-145 cells in the growth medium Opti-MEM® I (Life Technologies) supplemented with 5% fetal bovine serum (FBS; Sigma Aldrich) and 50 µg gentamicin/mL (Life Technologies), and an additional 5 passages have been performed in the same growth medium supplemented with 2% FBS without gentamicin. The 100$^{th}$ passage (P100) of PRRSV SD 11-21 has been used to prepare the Pre-Master Seed Virus (Pre-MSV).

The following procedure is used to determine the titer of PRRSV MSV SD 11-21. MARC-145 cells are seeded into 96-well plates at a density of 0.75-1.5×10$^4$ cells in 100 µL of growth medium (OPTI-MEM® I media supplemented with 5% FBS and 50 µg/mL gentamycin). Cells are incubated in 37±2° C. and 5±1% $CO_2$ incubator for 48-72 hours until cells are over 95% confluent. On the day of titration, all media is removed from the 96-well plate and was replaced with 100 µL of fresh growth media.

Ten-fold serial dilutions of the MSV are prepared with diluent (OPTI-MEM® I media, 50 µg/mL gentamycin) and transferred to corresponding wells on the plates prepared as above along with a negative control consisting of diluent alone. Titration plates are incubated in 37±2° C. with 5±1% $CO_2$ incubator for 4 days. At the end of the incubation period, each plate is observed for the presence of virus-induced cytopathic effect (CPE) in each sample well using an inverted microscope. The 50% tissue culture infectious dose ($TCID_{50}$) was calculated using the Reed-Muench method and titer is recorded as $\log_{10} TCID_{50}/mL$. The mean titer of the PRRSV MSV SD 11-21 is 3.25 $\log_{10} TCID_{50}/mL$. There were no distinguishable differences in the titers over the course of MSV preparation.

The PRRS SD 11-21 MLV strain has been denoted as a "master seed virus (MSV)," and has been deposited under conditions that assure that access to the cultures will be available during the pendency of this patent application to one determined by the Commissioner of Patents and Trademarks to be entitled thereto under 37 C.F.R. § 1.14 and 35 U.S.C. § 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action. The subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the deposited culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it. A deposit of PRRSV MSV SD 11-21 was entered into the permanent collection of the Patent Depository of the American Type Culture Laboratory, located at 10801 University Blvd., Manassas, Va., 20110-2209, USA, on Dec. 2, 2015 under the terms of the Budapest Treaty, whereupon it was assigned accession number ATCC PTA-122674 by the repository.

EXAMPLE 7

The objective of this study is to use next generation sequencing to establish genetic identity, obtain a consensus sequence, and assess genomic variants (subpopulations) that exist within PRRSV Strain SD 11-21 passage 84 and passage 100 preparations, both described in Example 6.

Sequence characterization using the massive parallel sequencing (MP-Sep) system is a standard procedure comprised of several steps which include: nucleic acid extraction from the virus preparations, cDNA library synthesis and quantitation, clonal amplification and enrichment of DNA library by PCR and sequencing of the library by the Roche/

454 next generation sequencing platform. Sequencing by synthesis is used to simultaneously determine the nucleotide order of the fragments in the cDNA library. Genome identification and characterization were performed using bioinformatics analyses of the resulting fragments by mapping each data set to the reference sequence. The reference sequence used in this analysis by BioReliance consisted of the full length sequence PRRSV SD 11-21 passage 83 (P83) disclosed in Example 1 (SEQ ID NO:9).

Sequencing of the PRRSV SD 11-21 genome resulted in the complete genome coverage for both P84 and P100 samples. The complete consensus genomes for P84 and P100 can be found in SEQ ID NO: 12 and SEQ ID NO: 13, respectively. The cDNA consensus sequences have also been deposited with GenBank. The cDNA consensus sequence of PRRS strain SD 11-21 at P84 was assigned GenBank Accession number KU131566 (SEQ. ID. NO:12). The cDNA consensus sequence designated SEQ. ID. NO:12 is:

```
   1 ATGACGTATA GGTGTTTGCT TTATGCCGCG GCATTTGTAT TGTCAGGAGC TGTGACCACT
  61 GGCACAGCCC GAAACTTGCT GCACAGAAAC ACCCTTCTGT GACAGCCTCC TTCAGGGGAG
 121 TTTAGGGGTT TCTCCCTAAC GCCCTGCTTC CGGAGTTGCA CTGCTTTACG GTCTCTCCAT
 181 CCTTTTAACC ATGTCTGGGA TTCTTGATCG GTGCACGTGC ACCCCCAATG CCAGGGTGTT
 241 TGTGGCAGAG GGCCAAGTCT ACTGCACACG ATGTCTCAGT GCACGGTCCC TCCTTCCCCT
 301 AAATCTCCAA GTTTCTGAGC TTGGGGTACT TGGTTTATTC TACAGGCCCG AAGAGCCATT
 361 ACGGTGGACG TTGCCACACG CATTCCCCAC TGTCGAGTGT GCTCCTGCTG GCGCTTGTTG
 421 GCTTTCTGCA ATTTTTCCAA TTGCGCGAAT GACCAGTGGA AACCTGAATT CCAGCAAAG
 481 GCTGGTACGT GTCGCAGCCG AGCTTTACAG AGCCGGCCAG CTCACCCCTA CAAGCCTGAA
 541 AACCTTACAG GTCTATGAAA GGGGTTGCCG TTGGTACCCC ATTGTTGGAC CTGTTCCTGG
 601 AGTGGCCGTT TACGCCAACT CCCTACATGT GAGTGACAAA CCCTTCCCAG GAGCGACTCA
 661 CGTGCTGACC AACTTACCAC TCCCGCAGAG ACCAAAATCT GAAGATTTCT GCCCCTTCGA
 721 GTGCGCCACG GCCGCCGTCT ATGACATCGG CCATGACGCC GTCATGTATG TAACCGAGGA
 781 AAAGGTTTCC TGGGCTCCTC GTGGCGGGGA TAAAGGGAAA TTTGAGACTG TTCCTGAGGG
 841 GTTGAAGTTG ACTGCGGAAC GACTCTACAC CTCCTTCCCG CCTCACCATG CGGTGGACAT
 901 GTCCCTTTTC ATCTTCACAG ACCTTGAGTG CGGCGCTTCC ATGCGGGTCG AACGCCAATA
 961 TGGTTGCCTC TCTGCTGGCA CTGTCCCTGA AGGCAACTGC TGGTGGAGTC TGTTTGGCTC
1021 GCTTTCGTTA GAAGCTCAGT ATAAAGAAAT CCGCTACGCC GCCCAATTTG GCTATCAGAC
1081 CAAACATGGC GTTACTGGCA AGTACCTGCA GCGGAGGCTG CAAATTAATG GTCTCCGAGC
1141 AGTGGTTGAC CCGAATGGGC CTCTTGTCGT ACAGTATTTC TCCGTTAAGG AGAGCTGGAT
1201 GCGCCACGTG AGACTGGCGG AAGAGCCAGG CTATCCTGGG TTTGAGGATC TCCTCAGGAT
1261 AAGAGTCGAG CCCAACACGT TGCCTTTGTC CAACAAGGAC GAGAAAATCT TCCGTTTCGG
1321 CGGTTACAAG TGGTACGGTG CTGGGCGGAG GGCAAGGAGA ACACGTGCAA GAGCAGTCAC
1381 CGCAGTTGCT AGTCATGCTC CGCCCGCTCG TGGGCCCAG CAGGCCGAGA AGCACGAAGT
1441 TGCTAGTGCC AACAAGACTG AGCTCCTTAC GCACTACTCC CCACCTGCTG AAGGGAATTG
1501 CGGCTGGCAC TGCATCTCCG CCATCATGAA CCGGATGGTG CATTCCAAGT TTGAAACCGC
1561 CCTTTCCGAA AGAGTGAGAT CCCCGGAAGA CTGGGCGACT GATGAGGATC TTGTGAATAC
1621 TATTCAAATC CTCAGGCTCC CTGCGGCCTT AGACAGGAAC GGCGCCTGTA AAACGCCAA
1681 GTACATCCTT AAGCTGGAAG GTGAGCACTG GACTGTTTCA GTGACCCCCG GAATGCCCCC
1741 CTCTTCACTT CCTCTTGAAT GCGTTCAGGG TTGTTGCGAG CATAAGGGCA ATTTTGACTC
1801 TCAAACGCG GTCGGTTTCT TTGGGTTCGA CCCTGCCAGC CTTGACCGAC TCGCTGGGGT
1861 AATGCATCTG CCCAGCAGCG CCATCCCTGC CGCCCTGGCC GAGTTGTCTG GTGAACTTGA
1921 TTGTTCAACT CCCCCGGCCA CCACTGTGTG GACTACCTTG CAGTTTTATG CTCGTCTTGG
1981 TGGGGGGGAG CATCCTGATC AAGAGTGCTT GAGAAAAATC ATCAGCCTCT GTGAGGTGCT
2041 CGGGAGTTGC TGCTGTTCTC AGAGTAGGGT CAACCGGGTC ACCCCGGAAG AGGTCGCAGC
```

```
2101  AAAGATTGAC CTGTATCTTC GTGACGCAGC GAGTCTTGAA GAGTGCTTGG CTAGGCTTGA

2161  GAAAGCTCGC CCGCCAAGCA TGCTGGACAC CTCCTTTGAC TGGGATGTTG TACTCCCTGG

2221  TGTTGGGACG GCTGCTCGGG CAGCAGAACT ACCCCCCACC GATGAGTGTC GCGCTCTAGT

2281  CACTGCTGTG GCCCAAAGGC CTTCGCCGAA AGTTCAGCCT CGAAAGGCGG GGTCTGTTAA

2341  GAGTCTACCA GAGATCAGGC CTGTCCCTGC CCCACGCAGG AAGGTTAAGT CTAGTTGTGG

2401  TGATCTGGCC CCGTTGGGCG GCAATTTCCC TGATAGCTGG AAGATTTGG CTGGTGGCTC

2461  CCTTAATCTC CAGATCTTAC CTGAGCCGGT GGCACAATCC TTTGAACCTG TGCCTGTCCC

2521  TGCACCGCGC AAGACTGCGC CTCGATTAGT GTCGTCATCA TTGGCGTCGA CCCCCGTACC

2581  TACACCACGA TGTGGGTTTC GGCAGTTTGA GGGAATGAAT TTGACAGCTG TGACCCTAGC

2641  ATGCCAGGAT GAGTCCCTCA ATTTGTCTGC ATCCTCGCAG ACTGAATATG AGGCTTCTCC

2701  TTTGGCATTG CAGCAGGGTG AGGATGTCCT TGCGGTGGGG GGACGAGAAG CCGAAGAAGT

2761  CCTGAGCGGA ATCTCGGGAA TGTCAGGTGG CATTAGATTA GCGCCCGCAT CATCAAGTAG

2821  CTCCTTGTCA AGCGTGGAGA TCACACGCCC GAAGTACTCA GCTCAAGCCA TCATTGACTC

2881  AGGTGGACCC TGTTGCGGGC ACCTTCAAGA GGTGAAAGAG AAATACCTTA ATGTCATGCG

2941  TGAGGCATGT GATGCGACTA AGCTCGATGA CCCTGCCACG CAAGAATGGC TCTCTCGCAT

3001  GTGGGAGAGG GTAGACATGC TAACCTGGCG CAACACGTCC ATCTTTCAAG CGCCTTTTAC

3061  CTTAGCTGAC AAGTTTAAGT CCCTCCCGAA GATGATACTC GAAACGCCGC CACCCTACCC

3121  TTGCGGGTTT GTGATGATGC CCCGCACGCC CGCACCTTCT GTGGGTGCGG AAAGCGACAT

3181  CACCGTTGGT TCAGTTGCTA CTGAAGATGT CCCGCGTATA CTCGGGGAGG TGGGAGATGT

3241  TGGCAAGATG ACCGGCCAGG AACCCTTAGA ATCCTTCGCA GATGAACTGG CAGATGACCA

3301  ACCTGCTAGG GAGTCCCGAA CACAAGCTCC TCCTGCAAGC ACAGGTAGCG CTGGTTTAGT

3361  TTTGGATTCT GGAGGGTCGC TGGGGCTCAC TGACCTGCCG CTCCCAAACA ATATAGACGC

3421  GGGCGGGAAA GGACCGTTTC ACGCGGTCAA GAAAAAAGCT GTAGGGTGCT TTGACCAACT

3481  GAGCCGCCGG GTTTTTGACA TCGTCTCCCA TCTCCCTGTT TTTTTTTCAC GCCTTTTCGC

3541  GCCCGGTGGT TTTTACTCTT CGGGTGACTG GAGTTTTGCA GCTTTTACTT TATTGTGTCT

3601  CTTTTTATGT TACAGTTATC CGGCCTTTGG TTTTGCTCCC CTCGTGGGTG TATTTTCTGG

3661  GTCTTCTCGG CGCGTGCGCA TGGGGGTTTT TGGCTGCTGG CTGGCTTTTG CTGTTGGTTT

3721  GTTCAAGCCT GCACCCGACC CAGTCGGTGC TGCTTGTGAG TTTGACTCGC CAGAGTGTAG

3781  AGACATCCTT CATTCTTTTG AGCTCCTGCA ACCTTGGGAC CCTGTTCGCA GCCTTGTGGT

3841  GGGCCCCGTC GGTCTCGGCC TTGCCATTTT TGGCAGGTTA CTGGGCGGGG CACGCTACGT

3901  CTGGCTGCTT TTGCTTAGGC TTGGCATCGT TTCAGACTGT ATCCTGGCTG GAGCCTATGT

3961  GCTTTCGCAA GGCAGGTGTA AAAAGTGTTG GGGATCTTGT ATAAGAACAG CCCCCAGTGA

4021  AGTTGCCTTC AATGTGTTTC CCTTTACACG CGCAACTAGA TCGTCACTTG TCAACCTGTG

4081  CGACCGGTTC TGTGCACCCA AGGGCATGGA CCCCATCTTC CTTGCCACAG GATGGCGCGG

4141  ATGCTGGTCC GGCCAGAGCC CCATTGAGCA ACCCTCTGAA AAACCCATAG CGTTCGCCCA

4201  GTTGGACGAA AAGAAAATCA CGGCTAGGAC TGTGGTTGCC CAGCCTTATG ACCCCAACCA

4261  AGCTGTGAAG TGCCTGCGAG TCCTCCAGGC GGGTGGAGCG ATGGTAGCCG AGGCAGTTCC

4321  AAAAGTAGTC AAAGTTTCTG CTGTCCCGTT TCGAGCCCCT TTTTTTCCTG CCGGAGTGAA

4381  AGTTGACCCT GAATGCAGGG TCGTGGTTGA CCCTGACACC TTTACAACCG CTCTCCGGAC

4441  CGGCTACTCC ACCACAAACC TCATTCTTGG TGTTGGGGAC TTTGCCCAGC TGAATGGGTT
```

```
4501  GAAGATCAGA CAAATTTCCA AGTCCCCAGG AGGGGGCCCT CACCTCATGG CGGCTTTACA

4561  TGTTGCTTGC TCGATGACTT TGCACATGCT TGTTGGGATT TATGTCACCA TGGTGGGTTC

4621  TTGTGGCTCT GGCACTAACG ATCCGTGGTG CACTAACCCG TTTGCCGTCC CTGTCTATGG

4681  GCCTGGCTCT CTCTGCACGT CCAGGTTGTG CATTTCCCAG CGTGGCCTGA CCCTGCCCTT

4741  AACAGCGCTT GTGGCAGGGT TTGGCGTTCA GGAAATCGCT TTGGTTGTTT TAATCTTTGT

4801  CTCCATCGGG GGTATGGCCC ACAGGTTGAG TTGCAAGGCT GACGTGCTGT GTATCCTGCT

4861  TGCTATTGTC AGCTATGTTT GGCCACCCCT TACCTGGTTG CTTTGTGTGT TTCCTTGCTG

4921  GTTGCGCTGG TTTTCTTTAC ATCCCCTTAC TATTCTATGG TTAGTGTTTT TCTTGATTTC

4981  TGTAAATACG CCCTCGGGAA TCTTGGCCTT GGTCCTGTTA ATCTCTCTTT GGCTCCTTGG

5041  TCGCTATACC AATGTTGCCG GCCTTGTCAC CCCTTATGAC ATTCACCATT ACACCAACGG

5101  CCCTCGCGGC GTTGCCGCCT TGGCCACTGC CCCGGATGGG ACCTACCTGG CTGCTGTCCG

5161  CCGTGCTGCG TTGACTGGCC GTACCATGCT GTTCACCCCG TCCCAACTTG GCTCGCTCCT

5221  TGAGGGCGCT TTTAGAACCC AAAAGCCTTC ACTGAACACT GTCAATGTAG TTGGGTCCTC

5281  CATGGGCTCC GGCGGGGTGT TCACCATTGA TGGGAAGATC AAATGTGTGA CCGCTGCTCA

5341  TGTCCTCACG GGTAACTCTG CCAGGGTTTC CGGGGTTGGC TTCAATCAAA TGTTGGACTT

5401  TGATGTTAAA GGGGATTTTG CCATAGCCGA TTGTCCGAAT TGGCAAGGAG TCGCCCCCAA

5461  GTCCCGGTTC TGCAAGGATG ATTGGACTGG CCGTGCTTAT TGGCTCACGT CCTCCGGCGT

5521  CGAACCCGGC GTCATTGGGC AAGGATTCGC CTTTTGTTTC ACCGCGTGCG GCGATTCCGG

5581  GTCCCCAGTG ATCACCGAGG CCGGGGAGCT TGTCGGTGTC CACACGGGAT CAAACAAACA

5641  AGGAGGAGGC ATTGTTACGC GCCCTTCAGG CCGGTTTTGT AATGTGACAC CCACCAAATT

5701  AAGTGAATTG AGTGAATTCT TCGCTGGACC TAGGGTCCCG CTTGGTGACG TGAAGGTTGG

5761  CAATCACATA ATCAAAGATA TAAATGAGGT GCCCTCAGAT CTCTGCGCCT TACTCGCTGC

5821  CAAACCCGAA TTGGAAGGAG GCCTCTCCAC CGTTCAACTT CTGTGCGTGT TTTTTCTCCT

5881  ATGGAGAATG ATGGGACATG CCTGGACACC CTTGGTTGCC GTTGGTTTTT TCATCTTGAA

5941  TGAAGTTCTC CCAGCAGTCC TGGTCCGGAG TGTCTTCTCC TTTGGAATGT TCGCACTGTC

6001  TTGGTTCACG CCGTGGTCTG CACAAATTCT AATGATCAGG CTCTTGACAG CAGCCCTAAA

6061  CAGAAACAGA TCGTCACTTG CCTTTTACAG CCTGGGCGCA CTAACCGGTT TGTTGCAGA

6121  TCTTGCAACC AATCAGGGGT ATTTATTGCA CGCGGTCATG AATGTGAGCA CCTATGCATT

6181  CCTGCCTCGT GCAATGGCCG TGACCTCACC AGTCCCAATA GTTGCGTGTG GCGTTGTGCA

6241  CTTGCTTGCC ATCATTCTGT ACTTGTTCAA GTACCGTAGC CTGCATGCCG TCCTGGTCGG

6301  CGATGGTGCG TTTTCCGCGG CTTTCTTCTT GCGATACTTT GCGGAGGGAA AGTTGAGGGA

6361  AGGGGTGTCG CAGTCTTGCG GCATGAATCA TGAGTCACTA ACCGGTGCCC TCGCCATGAA

6421  ACTCAGCGAC GAAGACTTGG ACTTCCTCAC AAAATTGACT GATTTAAGT GCTTTGTTTC

6481  TGCATCCAAC ATGAGGAATG CGGCGGGTCA ATTTATAGAG GCCGCCTACG CCAAAGCACT

6541  GAGGGTGGAA CTTGCCCAGT TGGTTCAAGT CGATAAAGTT CGAGGTGTCC TGGCCAAACT

6601  TGAAGCTTTC GCTGACACCG TGGCGCCTCA ACTTTCACCC GGTGACATTG TTGTCGCCCT

6661  TGGACACACA CCTGTCGGCA GCATTTTTGA CCTGAAGGTC GGCAATGTTA AGCACACTCT

6721  CCAGTCCATT GAGACCAGAA CCCTTGCCGG GTCTAAAATG ACTGTGGCGC GCGTCGTAGA

6781  CCCAACCCCC ACACCCCCGC CCGCACCTGT GCCCATTTCC CTCCCACCAA AGGTTTTGGA

6841  GAACGGTCCC AACGCCTGGG GGATGAGAA CGGTTTGAAC AAAAAAAGC GGCGCAAGAT

6901  GGAGGCCGTT GGCATTTACG TTATGGGCGG GAAAAAGTAT CAAAAATTTT GGGATAAGAA
```

```
-continued
6961  TTCTGGTGAT GTGTTCTATG AAGAAGTCCA CGACAACACA GACGCGTGGG AATGCCTCAG
7021  AGTTGACAAC CCTGCCGACT TGGATCCTGA GAGGGGAACC TTGTGTGGAC ACACCACCAT
7081  AGACAACAGG CCTTACCATG TTTATGCTTC TCCGTCTGGT AGGAAGTTTC TAGTCCCTGT
7141  CAACCCGGAG AGCGGAAAAG CTCAGTGGGA AGCTGCTAAG CTTTCTTTAG ATCAGGCCCT
7201  CAGTATGATG AATGTCGACG GCGAACTGAC CGCCAAAGAA GTGGAAAAAT TGAAGAGAAT
7261  AATTGACAAA CTCCAGGGCC TGACTAAGGA GCAGTGTTTA AACTGCTAGC CGCCAGCGGC
7321  TTGACCCGCT GTGGTCGCGG CGGCTTGGTT GTTACTGAGA CAGCGGTAAA GATAGTCAGG
7381  TTCCACAACC GGACCTTTAC CCTAGGGCCT GTGAATTTGA AAGTAGCTAG CGAAGTTGAG
7441  TTGAAGGACG CGGTCGAGCA CGGCCAACAC CCGGTCGCGA TACCAGCCGA TGGTGGCGTC
7501  GTGCTCCTGC GTTCCGCTGT TCCTTCGCTT ATAGACGTCC TGATCTCCGG TGCTGACGCA
7561  TCCCCCAGGT TGCTCGCCCG TCACGGACCG GGAAATACTG GGTCAATGG CGCGCTTTGG
7621  GATTTTGAGT CTGAAGCTAC CAAAGAGGAA GTAGCACTTA GTGCGCAAAT AATACAGGCC
7681  TGTGACATTA GACGCGGCGA TGCACCTGAG ATTGGCCTTC CTTACAAGTT GTACCCTGTT
7741  AGGGGCAACC CTGAACGGGA AGAGGGGTT CTAATGAACA CAAGATTTGG AGACATACCT
7801  TACAAGACCC CCAGCGACAC CGGGAGCCCG GTGCACGCGG CCGCCTGCCT TACGCCCAAC
7861  GCCACTCCAG TAACTGATGG GCGCTCCATC CTGGCCACGA CCATGCCCTC CGGGTTTGAA
7921  CTATATGTGC CGACCATTCC AGCGTCTGTC CTTGATTACC TTGACTCCAG ACCAGACTGT
7981  CCTAAACAGT TGACTGAGCA CGGGTGTGAA GATGCCGCGT TGAAGGACCT TTCTAAATAT
8041  GACCTGTCCA CCCAAGGCTT TGTGTTACCT GGAGTTCTAC GCCTCGTGCG AAAATATCTG
8101  TTTGCTCATG TAGGTAAGTG CCCGCCTGTC CACCGGCCCT CTACCTATCC TGCCAAGAAC
8161  TCCATGGCCG GAATAAATGG GAACAGGTTC CCAACCAAGG ATATTCAAAG CATCCCTGAG
8221  ATCGACGTTT TGTGTGCACA AGCTGTGCGA GAAAACTGGC AAACTGTTAC ACCCTGCACT
8281  CTTAAGAAGC AGTATTGCGG TAAAAAGAAG ACCAGGACCA TACTTGGCAC CAACAACTTC
8341  GTTGCGCTGG CCCACCGGGC GGCGCTGAGT GGTGTCACCC AGGGTTTCAT GAAGAAGGCG
8401  TTTAACTCAC CCATCGCCCT TGGGAAAAAT AAATTTAAGG AGCTACAGAC TCCAGTCTTG
8461  GGTAGGTGTC TTGAGGCTGA TCTCGCTTCC TGCGATCGAT CCACGCCTGC AATCGTTCGC
8521  TGGTTTGCCG CCAACCTTCT TTATGAACTT GCCTGTGCTG AGGAGCATTT ACCGTCGTAC
8581  GTGCTGAACT GTTGTCACGA CCTATTGGTC ACGCAGTCCG GCGCAGTGAC TAAGAGAGGT
8641  GGCCTGTCGT CCGGTGACCC AATCACCTCT GTGTCCAACA CCATTTATAG CTTGGTGATC
8701  TATGCACAGC ATATGGTGCT TAGTTACTTC AAAAGTGGTC ACCCCCATGG CCTTCTGTTT
8761  TTACAAGACC AGCTAAAGTT TGAAGACATG CTCAAAGTTC AACCCCTAAT CGTCTATTCG
8821  GACGACCTCG TGTTGTATGC CGAGTCTCCC ACCATGCCAA ACTATCACTG GTGGGTTGAA
8881  CACCTGAATT TGATGTTGGG ATTTCAGACG GACCCAAAGA AGACTGCAAT AACAGACTCA
8941  CCTTCATTCC TAGGTTGTAG AATAATAAAT GGCCGCCAGT TAGTACCCAA CCGTGACAGA
9001  ATTCTCGCGG CCCTTGCCTA TCACATGAAG GCGAGTAATG TTTCTGAGTA CTACGCCTCC
9061  GCAGCCGCAA TACTCATGGA CAGTTGTGCT TGTCTAGAGT ATGATCCTGA GTGGTTTGAA
9121  GAACTTGTGG TTGGAATGGC GCAGTGCGCC CGTAAGGACG GCTATAGTTT CCCCGGCCCG
9181  CCGTTCTTCT TGTCCATGTG GGAAAAGCTC AGGTCAAATT ATGAGGGGAA GAAGTTGAGA
9241  GTGTGTGGTT ATTGCGGAGC TTCAGCCCCG TATGCTACTG CCTGTGGCCT TGACGTTTGT
9301  GTTTACCACA CCCACTTTCA CCAGCATTGT CCAGTCATAA TATGGTGTGG CCACCCGGCG
```

```
9361 GGTTCTGGGT CCTGCGATGA GTGCAAATCC CCTACAGGGA AGGGTACAAG CCCTCTGGAT

9421 GAGGTCTTAA GACAAGTCCC TTATAAGCCT CCACGGACTA TTCTTATGCA TGTGGAGCAG

9481 GGCCTCACCC CCCTTGACCC AGGCAGATAC CAGACCCGCC GTGGGTTGGT TGCTGTCAGG

9541 CGCGGGATAA GGGGAAATGA AGTTGACCTG CCAGATGGTG ATTATGCCAG TACTGCCCTA

9601 CTCCCCACCT GCAAAGACAT AGACATGGTT GCTGTGGCCT CCAATGTGTT GCGCAGTAGG

9661 TTCATCATCG GCCCACCTGG CGCAGGGAAA ACACACTGGC TTCTTCAACA GGTTCAGGAT

9721 AGTGATGTCA TTTACACGCC AACCCATCAG ACCATGCTTG ACATGATCAA GGCTTTGGGG

9781 ACGTGCCGGT TCAATGTCCC GGCAGGCACA ACGCTGCAAT TCCCTGCCCC CTCCCGTACC

9841 GGCCCGTGGG TTCGCATCCT TGCCGGCGGT TGGTGTCCAG GTAAGAATTC CTTCCTGGAT

9901 GAAGCAGCGT ATTGCAATCA CCTTGACGTC TTGAGGCTTC TCAGCAAAAC TACCCTCACC

9961 TGTCTGGGGG ATTTCAAACA ACTCCACCCG GTGGGTTTTG ATTCTCATTG CTATGTTTTT

10021 GATATCATGC CTCAGACTCA ACTGAAGACC ATCTGGAGGT TTGGACAGAA TATCTGTGAC

10081 GCCATTCAGC CAGATTACAG GGACAAACTC GTGTCCATGG TCAACACAAC CCGTGTAACC

10141 TATGTGGAAA GACCTGTCAA GTATGGGCAA GTCCTCACCC CCTACCACAG AGACCGAGAG

10201 GATGGTGCTA TCACTATTGA CTCCAGTCAA GGCGCCACAT TTGATGTGGT CACATTGCAT

10261 TTGCCCACTA AAGATTCACT CAACAGGCAA AGAGCCCTTG TTGCTATCAC CAGGGCAAGG

10321 CATGCAATCT TTGTGTATGA CCCACACAGG CAACTGCAGA GCATGTTTCG TCTTCCTGCA

10381 AAAGGCACAC CTGTCAACCT TGCCGTGCAC CGTGACGAGC AGCTCATCGT ATTAGATAGA

10441 AATAACAAAG AGTGCACGGT TGTTCAGGCT TTAGGCAATG GGACAAATT CAGGGCCAGT

10501 GACAAGCGCG TTGTAGATTC TCTTCGCGCC ATTTGTGCAG ATCTTGAAGG GTCGAGCTCC

10561 CCGCTCCCCA AGGTCGCACA CAACTTGGGA TTTTATTTCT CACCTGATTT GACACAGTTT

10621 GCTAAACTCC CGGCGGAACT TGCACCCCAC TGGCCCGTGG TGACAACTCA GAACAACGAA

10681 AATTGGCCAG ACCGGCTGGT TGCTAGCCTC CGCCCTATCC ACAAATATAG CCGCGCGTGC

10741 ATCGGAGCCG GCTATATGGT GGGCCCCTCA GTGTTTCTAG GCACTCCTGG GGTTGTGTCA

10801 TACTATCTCA CACAATTTGT CAAAGGGGAG GCTCAGGTGC TTCCGGAGAC GGTCTTCAGC

10861 ACCGGCCGAA TTGAGGTAGA TTGTCGAGAG TATCTTGATG ATCGGGAACG AGAAGTTGCT

10921 GAGTCCCTCC CACATGCCTT TATTGGCGAC GTCAAAGGCA CTACCGTTGG GGGATGTCAC

10981 CATGTCACTT CTAAATATCT CCCACGCTTC CTTCCCAAGG AATCAGTTGC GGTGGTTGGG

11041 GTTTCAAGCC CCGGGAAAGC CGCAAAAGCA GTTTGCACAT TAACAGATGT GTACCTCCCA

11101 GATCTTGAGG CTTACCTCCA TCCAGAGACC CAGTCTAAGT GCTGGAAAGT GATGTTGGAC

11161 TTCAAGGAAG TTCGACTGAT GGTCTGGAGA GATAAGACGG CCTACTTTCA ACTTGAAGGC

11221 CGCCATTTCA CCTGGTACCA GCTTGCAAGT TATGCCTCGT ACATCCGAGT TCCCGTTAAC

11281 TCTACGGTGT ACCTGGACCC CTGTATGGGC CCTGCCCTTT GCAACAGAAG AGTCGTTGGG

11341 TCTGCACATT GGGGAGCTGA CCTTGCAGTT ACCCCTTATG ATTATGGTGC CAAAATCATT

11401 CTGTCTAGTG CGCACCATGG TGAAATGCCT CCTGGGTACA GAATTCTAGC GTGCGCGGAG

11461 TTCTCGCTTG ATGACCCAGT GAGGTACAAA CACACTTGGG GGTTTGAATC GGATACAGCG

11521 TATCTGTACG AGTTCACCGG AAACGGTGAG GACTGGGAGG ATTACAATGA TGCGTTTCGT

11581 GCACGCCAGA AAGGGAAAAT TTATAAGGCC ACTGCCACCA GCATGAGATT TCATTTTCCC

11641 CCGGGTCCTG CCATTGAACC AACATTGGGC CTGAACTGAA ATGAAATGGG GGCTGTGCAG

11701 AGCCTTTTCG ACAAAATTTG CCAACTTTTT GTGGATGCTT TCACGGAATT TTTGGTGTCC

11761 ATTGTTGATA TCATCATATT TTTGGCCATT TGTTTGGCT TCACCATCGC AGGCTGGCTG
```

```
11821 GTTGTCTTCT GTATCCGACT GGTTTGCTCC ACGGTACTCC GTGCGCGCTC TACCATTCAC

11881 CCTGAGCAAT TACAGAAGAT CCTATGAGGC CTTCCTTTCC CAGTGCCAAG TGGACATTCC

11941 CGCCTGGGGA ACTAAGCATC CCTTGGGGGT GCTTTGGCAC CACAAGGTGT CAACTCTGAT

12001 TGATGAAATG GTGTCGCGTC GAATGTACCG CATCATGAAA AAAGCAGGAC AGGCTGCCTG

12061 GAAACAGGTT GTGAGCGAAG CTACATTGTC TCGCATAAGT GGCTTGGATG TGGTGGCTCA

12121 TTTTCAGCAT CTTGCTGCCA TTGAAGCCGA GACTTGCAAA TATTTGGCCT CTCGGCTGCC

12181 CATGCTACAC AACCTAGTCA TGTCAGGGTC GAATGTAACC ATAGTGTATA ATAGCACTTT

12241 GGGTCAAGTG TTTGCCATTT TCCCAACCCC TGGTTCCCGG CCAAAACTTT CTGATTTTCA

12301 ACAATGGCTC ATAGCTGTGC ATTCTTCCAT ATTTTCTTCT GTTGCGGCTT CTTGTACTCT

12361 TTTTGTTGTG CTGTGGCTGC GAATTCCAAT ACTACGTACT GTTTTTGGTT TCCGCTGGTT

12421 AGGGGCAACT TTTCTTTCGA ACTCACAGTG AATTACACGG TGTGCCCACC CTGCCTCACC

12481 CGGCAAGCAG CCGCTGAGAT CTACGAACAC AGCGGGTCTC TTTGGTGCAG GATAGGGCAT

12541 GACCGATGTA GCCAGAGTGA TCATGACGAA CTAGGGTTCT TGGTTCCACC TGGCCTTTCC

12601 AGCGAGGGCC ACTTGACCAG TGTTTACGCC TGGCTGGCGT TCTTGTCTTT CAGCTACACA

12661 GCCCAGTTCC ACCCCGAGAT ATTTGGAATA GGGAATGTGA GTAGAGTTTA TGTTGACGTC

12721 ACTCACCAAC TCATCTGCGC CGAACACGAC GGGCAGAACA CCACCCTGCG TCGCCATGAC

12781 AATATCTCAG CCGTGTTTCA GACCTATTAC CAACATCAGG TCGATGGCGG CAATTGGTTT

12841 CACCTAGAAT GGCTGCGTCC CTTCTTTTCC TCTTGGCTGG TTTTGAATGT CTCGTGGTTT

12901 CTCAGGCGTT CGCCTGCAAA CCGTGTTTCA GTTCGAGTCT TTCAGACATC AAAACCAACA

12961 CCACCGCAGC TGCAGGCTTT GCTGTCCTCC AAGACATCAG CTGTCTTAGG CATGGCTACT

13021 CGTCCATTGA GGCGATTCGC AAAAGCCGTC AATGCCGCAC GGCGATAGGA ACGCCCGTGT

13081 ACATCACTGT CACGGCCAAT GTAACAGATG AGAATTACTT GCATTCCTCT GATCTCCTCA

13141 TGCTTTCCTC TTGCCTCTTC TATGCTTCTG AGATGAGTGA AAAGGGATTC AATGTGGTCT

13201 TCGGCAACGT GTCAGGCATT GTGGCTGTGT GTGTCAACTT TACCAGCTAT GTCCAACATG

13261 TTAAGGAGTT TACTCAGCGC TCTTTGGTGG TCGACCACGT GCGACTGCTT CATTTCATGA

13321 CACCTGCGAC CATGAGGTGG GCAACAGTTT TAGCCTGTCT TTTCGCCATC TTGTTGGCGA

13381 TTTGAATGTT TAAGTATGTT GGGGAAATGC TTGACCGCGG GCTACTGCTC GCAATTGCTT

13441 TTTTTCTGGT GTATCGTGCC GTTCTGTTTT GCTGCGCTCG TCAACGCCGC CAGCAACAGC

13501 AGCTCCCATT TACAGTTGAT TTATAACCTG ACGATATGCG AGCTGAATGG CACAGATTGG

13561 TTGAATCAAA AGTTTGATTG GGCAGTGGAG ACTTTTGTCA TTTTTCCTGT GTTGACCCAC

13621 ATTGTCTCCT ACGGTGCCCT TACCACCAGC CATTTCCTTG ACACGGCCGG CCTAATCACT

13681 GTGTCTACCG CCGGATATTA CCATGGGCGG TATGTGTTGA GTAGCATCTA CGCCGTCTTT

13741 GCCCTGGCTG CGTTGATTTG TTTTGTCATT AGGTTGACAA AAAACTGTAT GTCCTGGCGC

13801 TACTCATGTA CCAGATATAC CAACTTTCTT CTGGACACCA AAGGCAATCT CTATCGTTGG

13861 CGGTCACCCG TCGTTATAGA GAGAAGGGGT AAAGTTGAGG TTGGAGACCA CCTAATCGAC

13921 CTCAAAAGAG TTGTGCTTGA TGGTTCCGCG GCAACCCCTA TAACCAAGAT TTCAGCGGAA

13981 CAATGGGTC GTCCCTAGAC GACTTCTGCA ATGACAGCAC AGCTGCACAA AAGGTGCTTT

14041 TGGCGTTTTC CATCACCTAT ACGCCAATAA TGATATATGC CCTGAAGGTA AGTCGCGGCC

14101 GACTGTTAGG GCTTTTGCAT CTTTTAATTT TCTTGAATTG TGCTTTCACC TTCGGGTACA

14161 TGACATTTGT TCATTTTCAG AGTACAAACA AGGTCGCGCT CACTATGGGA GCAGTTGTTG
```

```
14221 CACTCCTTTG GGGGGTGTAC TCAGCCATAG AAACCTGGAA ATTCATCACT TCCAGATGCC
14281 GTTTGTGCTT GCTAGGCCGC AGGTACATTC TGGCCCCTGC CCACCACGTT GAAAGTGCCG
14341 CGGGCTTTCA TCCGATTGCG GCAAGTGATA ACCACGCATT TGTCGTCCGG CGTCCCGGCT
14401 CCACTACTGT TAACGGCACA TTGGTGCCCG GGTTGAAAAG CCTCGTGTTG GGTGGCAGAA
14461 AAGCTGTTAA GCGGGGAGTG GTAAACCTCG TTAAATATGC CAAATAACAA CGGCAGGCAG
14521 CAAAAAAATA AGAAGGGGAG TGGCCAGCCA GTCAATCAGC TGTGCCAAAT GCTGGGCAAG
14581 ATCATCGCCC AGCAAAATCA GTCCAGAGGC AAGGGACCGG GTAAGAAAAA TAAGAAGAGA
14641 AACCCGGAGA AGCCCCATTT TCCTCTTGCG ACCGAAGATG ACGTCAGGCA TCACTTCACC
14701 CCCAGTGAAC GGCAATTGTG TCTGTCGTCG ATCCAGACTG CCTTCAACCA GGGCGCTGGA
14761 ACTTGCACCC TGTCAGATTC AGGGAGGATA AGTTACACTG TGGAGTTTAG TTTGCCGACG
14821 CACCACACTG TGCGCCTTAT TCGCGCCACA GCATCACCTC CATCGTGATG GGCTTACATT
14881 CTTGGAGCTC CTCAGTTTCA CAATTGGAAG AATGTGTGGT GAATGGCACT GATTGGCACT
14941 GTGCCTCTAA GTCACCTATT CAATTAGGGC GACCGTGTGG GGGTTTAGTT TAATTGGCGA
15001 GAACCACGCG GCCGAAATTA AAAAAAAAAA AAAAAAAAAA AAAAAA
```

The cDNA consensus sequence of PRRS strain SD 11-21 at P100 was assigned GenBank Accession number KU131568 (SEQ. ID. NO:13). The cDNA consensus sequence designated SEQ. ID. NO:13 is:

1 ATGACGTATA GGTGTTTGCT TTATGCCGCG GCATTTGTAT TGTCAGGAGC TGTGACCACT

61 GGCACAGCCC GAAACTTGCT GCACAGAAAC ACCCTTCTGT GACAGCCTCC TTCAGGGGAG

121 TTTAGGGGTT TCTCCCTAAC GCCCTGCTTC CGGAGTTGCA CTGCTTTACG GTCTCTCCAT

181 CCTTTTAACC ATGTCTGGGA TTCTTGATCG GTGCACGTGC ACCCCCAATG CCAGGGTGTT

241 TGTGGCAGAG GGCCAAGTCT ACTGCACACG ATGTCTCAGT GCACGGTCCC TCCTTCCCCT

301 AAATCTCCAA GTTTCTGAGC TTGGGGTACT TGGTTTATTC TACAGGCCCG AAGAGCCATT

361 ACGGTGGACG TTGCCACACG CATTCCCCAC TGTCGAGTGT GCTCCTGCTG GCGCTTGTTG

421 GCTTTCTGCA ATTTTTCCAA TTGCGCGAAT GACCAGTGGA AACCTGAATT TCCAGCAAAG

481 GCTGGTACGT GTCGCAGCCG AGCTTTACAG AGCCGGCCAG CTCACCCCTA CAAGCCTGAA

541 AACCTTACAG GTCTATGAAA GGGGTTGCCG TTGGTACCCC ATTGTTGGAC CTGTTCCTGG

601 AGTGGCCGTT TACGCCAACT CCCTACATGT GAGTGACAAA CCCTTCCCAG GAGCGACTCA

661 CGTGCTGACC AACTTACCAC TCCCGCAGAG ACCAAAATCT GAAGATTTCT GCCCCTTCGA

721 GTGCGCCACG GCCGCCGTCT ATGACATCGG CCATGACGCC GTCATGTATG TAACCGAGGA

781 AAAGGTTTCC TGGGCTCCTC GTGGCGGGGA TAAAGGGAAA TTTGAGACTG TTCCTGAGGG

841 GTTGAAGTTG ACTGCGGAAC GACTCTACAC CTCCTTCCCG CCTCACCATG CGGTGGACAT

901 GTCCCTTTTC ATCTTCACAG ACCTTGAGTG CGGCGCTTCC ATGCGGGTCG AACGCCAATA

961 TGGTTGCCTC TCTGCTGGCA CTGTCCCTGA AGGCAACTGC TGGTGGAGTC TGTTTGGCTC

1021 GCTTTCGTTA GAAGCTCAGT ATAAAGAAAT CCGCTACGCC GCCCAATTTG GCTATCAGAC

1081 CAAACATGGC GTTACTGGCA AGTACCTGCA GCGGAGGCTG CAAATTAATG GTCTCCGAGC

1141 AGTGGTTGAC CCGAATGGGC CTCTTGTCGT ACAGTATTTC TCCGTTAAGG AGAGCTGGAT

1201 GCGCCACGTG AGACTGGCGG AAGAGCCAGG CTATCCTGGG TTTGAGGATC TCCTCAGGAT

1261 AAGAGTCGAG CCCAACACGT TGCCTTTGTC CAACAAGGAC GAGAAAATCT TCCGTTTCGG

1321 CGGTTACAAG TGGTACGGTG CTGGGCGGAG GGCAAGGAGA ACACGTGCAA GAGCAGTCAC

1381 CGCAGTTGCT AGTCATGCTC CGCCCGCTCG TGGGGCCCAG CAGGCCGAGA AGCACGAAGT

```
1441 TGCTAGTGCC AACAAGACTG AGCTCCTTAC GCACTACTCC CCACCTGCTG AAGGGAATTG

1501 CGGCTGGCAC TGCATCTCCG CCATCATGAA CCGGATGGTG CATTCCAAGT TTGAAACCGC

1561 CCTTTCCGAA AGAGTGAGAT CCCCGGAAGA CTGGGCGACT GATGAGGATC TTGTGAATAC

1621 TATTCAAATC CTCAGGCTCC CTGCGGCCTT AGACAGGAAC GGCGCCTGTA AAAACGCCAA

1681 GTACATCCTT AAGCTGGAAG GTGAGCACTG GACTGTTTCA GTGACCCCCG GAATGCCCCC

1741 CTCTTCACTT CCTCTTGAAT GCGTTCAGGG TTGTTGCGAG CATAAGGGCA ATTTTGACTC

1801 TCAAAACGCG GTCGGTTTCT TTGGGTTCGA CCCTGCCAGC CTTGACCGAC TCGCTGGGGT

1861 AATGCATCTG CCCAGCAGCG CCATCCCTGC CGCCCTGGCC GAGTTGTCTG GTGAACTTGA

1921 TTGTTCAACT CCCCCGGCCA CCACTGTGTG GACTACCTTG CAGTTTTATG CTCGTCTTGG

1981 TGGGGGGGAG CATCCTGATC AAGAGTGCTT GAGAAAAATC ATCAGCCTCT GTGAGGTGCT

2041 CGGGAGTTGC TGCTGTTCTC AGAGTAGGGT CAACCGGGTC ACCCCGGAAG AGGTCGCAGC

2101 AAAGATTGAC CTGTATCTTC GTGACGCAGC GAGTCTTGAA GAGTGCTTGG CTAGGCTTGA

2161 GAAAGCTCGC CCGCCAAGCA TGCTGGACAC CTCCTTTGAC TGGGATGTTG TACTCCCTGG

2221 TGTTGGGACG GCTGCTCGGG CAGCAGAACT ACCCCCCACC GATGAGTGTC GCGCTCTAGT

2281 CACTGCTGTG GCCCAAAGGC CTTCGCCGAA AGTTCAGCCT CGAAAGGCGG GGTCTGTTAA

2341 GAGTCTACCA GAGATCAGGC CTGTCCCTGC CCCACGCAGG AAGGTTAAGT CTAGTTGTGG

2401 TGATCTGGCC CCGTTGGGCG GCAATTTCCC TGATAGCTGG GAAGATTTGG CTGGTGGCTC

2461 CCTTAATCTC CAGATCTTAC CTGAGCCGGT GGCACAATCC TTTGAACCTG TGCCTGTCCC

2521 TGCACCGCGC AAGACTGCGC CTCGATTAGT GTCGTCATCA TTGGCGTCGA CCCCCGTACC

2581 TACACCACGA TGTGGGTTTC GGCAGTTTGA GGGAATGAAT TTGACAGCTG TGACCCTAGC

2641 ATGCCAGGAT GAGTCCCTCA ATTTGTCTGC ATCCTCGCAG ACTGAATATG AGGCTTCTCC

2701 TTTGGCATTG CAGCAGGGTG AGGATGTCCT TGCGGTGGGG GGACGAGAAG CCGAAGAAGT

2761 CCTGAGCGGA ATCTCGGGAA TGTCAGGTGG CATTAGATTA GCGCCCGCAT CATCAAGTAG

2821 CTCCTTGTCA AGCGTGGAGA TCACACGCCC GAAGTACTCA GCTCAAGCCA TCATTGACTC

2881 AGGTGGACCC TGTTGCGGGC ACCTTCAAGA GGTGAAAGAG AAATACCTTA ATGTCATGCG

2941 TGAGGCATGT GATGCGACTA AGCTCGATGA CCCTGCCACG CAAGAATGGC TCTCTCGCAT

3001 GTGGGAGAGG GTAGACATGC TAACCTGGCG CAACACGTCC ATCTTTCAAG CGCCTTTTAC

3061 CTTAGCTGAC AAGTTTAAGT CCCTCCCGAA GATGATACTC GAAACGCCGC CACCCTACCC

3121 TTGCGGGTTT GTGATGATGC CCCGCACGCC CGCACCTTCT GTGGGTGCGG AAAGCGACAT

3181 CACCGTTGGT TCAGTTGCTA CTGAAGATGT CCCGCGTATA CTCGGGGAGG TGGGAGATGT

3241 TGGCAAGATG ACCGGCCAGG AACCCTTAGA ATCCTTCGCA GATGAACTGG CAGATGACCA

3301 ACCTGCTAGG GAGTCCCGAA CACAAGCTCC TCCTGCAAGC ACAGGTAGCG CTGGTTTAGT

3361 TTTGGATTCT GGAGGGTCGC TGGGGCTCAC TGACCTGCCG CTCCCAAACA ATATAGACGC

3421 GGGCGGGAAA GGACCGTTTC ACGCGGTCAA GAAAAAGCT GTAGGGTGCT TGACCAACT

3481 GAGCCGCCGG GTTTTTGACA TCGTCTCCCA TCTCCCTGTT TTTTTTCAC GCCTTTTCGC

3541 GCCCGGTGGT TTTTACTCTT CGGGTGACTG GAGTTTTGCA GCTTTTACTT TATTGTGTCT

3601 CTTTTTATGT TACAGTTATC CGGCCTTTGG TTTTGCTCCC CTCGTGGGTG TATTTTCTGG

3661 GTCTTCTCGG CGCGTGCGCA TGGGGGTTTT TGGCTGCTGG CTGGCTTTTG CTGTTGGTTT

3721 GTTCAAGCCT GCACCCGACC CAGTCGGTGC TGCTTGTGAG TTTGACTCGC CAGAGTGTAG

3781 AGACATCCTT CATTCTTTTG AGCTCCTGCA ACCTTGGGAC CCTGTTCGCA GCCTTGTGGT
```

-continued

```
3841 GGGCCCCGTC GGTCTCGGCC TTGCCATTTT TGGCAGGTTA CTGGGCGGGG CACGCTACGT

3901 CTGGCTGCTT TTGCTTAGGC TTGGCATCGT TTCAGACTGT ATCCTGGCTG GAGCCTATGT

3961 GCTTTCGCAA GGCAGGTGTA AAAGTGTTG GGGATCTTGT ATAAGAACAG CCCCCAGTGA

4021 AGTTGCCTTC AATGTGTTTC CCTTTACACG CGCAACTAGA TCGTCACTTG TCAACCTGTG

4081 CGACCGGTTC TGTGCACCCA AGGGCATGGA CCCCATCTTC CTTGCCACAG GATGGCGCGG

4141 ATGCTGGTCC GGCCAGAGCC CCATTGAGCA ACCCTCTGAA AAACCCATAG CGTTCGCCCA

4201 GTTGGACGAA AAGAAAATCA CGGCTAGGAC TGTGGTTGCC CAGCCTTATG ACCCCAACCA

4261 AGCTGTGAAG TGCCTGCGAG TCCTCCAGGC GGGTGGAGCG ATGGTAGCCG AGGCAGTTCC

4321 AAAAGTAGTC AAAGTTTCTG CTGTCCCGTT TCGAGCCCCT TTTTTTCCTG CCGGAGTGAA

4381 AGTTGACCCT GAATGCAGGG TCGTGGTTGA CCCTGACACC TTTACAACCG CTCTCCGGAC

4441 CGGCTACTCC ACCACAAACC TCATTCTTGG TGTTGGGGAC TTTGCCCAGC TGAATGGGTT

4501 GAAGATCAGA CAAATTTCCA AGTCCCCAGG AGGGGGCCCT CACCTCATGG CGGCTTTACA

4561 TGTTGCTTGC TCGATGACTT TGCACATGCT TGTTGGGATT TATGTCACCA TGGTGGGTTC

4621 TTGTGGCTCT GGCACTAACG ATCCGTGGTG CACTAACCCG TTTGCCGTCC CTGTCTATGG

4681 GCCTGGCTCT CTCTGCACGT CCAGGTTGTG CATTTCCCAG CGTGGCCTGA CCCTGCCCTT

4741 AACAGCGCTT GTGGCAGGGT TTGGCGTTCA GGAAATCGCT TTGGTTGTTT TAATCTTTGT

4801 CTCCATCGGG GGTATGGCCC ACAGGTTGAG TTGCAAGGCT GACGTGCTGT GTATCCTGCT

4861 TGCTATTGTC AGCTATGTTT GGCCACCCCT TACCTGGTTG CTTTGTGTGT TTCCTTGCTG

4921 GTTGCGCTGG TTTTCTTTAC ATCCCCTTAC TATTCTATGG TTAGTGTTTT TCTTGATTTC

4981 TGTAAATACG CCCTCGGGAA TCTTGGCCTT GGTCCTGTTA ATCTCTCTTT GGCTCCTTGG

5041 TCGCTATACC AATGTTGCCG GCCTTGTCAC CCCTTATGAC ATTCACCATT ACACCAACGG

5101 CCCTCGCGGC GTTGCCGCCT TGGCCACTGC CCCGGATGGG ACCTACCTGG CTGCTGTCCG

5161 CCGTGCTGCG TTGACTGGCC GTACCATGCT GTTCACCCCG TCCCAACTTG GCTCGCTCCT

5221 TGAGGGCGCT TTTAGAACCC AAAAGCCTTC ACTGAACACT GTCAATGTAG TTGGGTCCTC

5281 CATGGGCTCC GGCGGGGTGT TCACCATTGA TGGGAAGATC AAATGTGTGA CCGCTGCTCA

5341 TGTCCTCACG GGTAACTCTG CCAGGGTTTC CGGGGTTGGC TTCAATCAAA TGTTGGACTT

5401 TGATGTTAAA GGGGATTTTG CCATAGCCGA TTGTCCGAAT TGGCAAGGAG TCGCCCCCAA

5461 GTCCCGGTTC TGCAAGGATG ATTGGACTGG CCGTGCTTAT TGGCTCACGT CCTCCGGCGT

5521 CGAACCCGGC GTCATTGGGC AAGGATTCGC CTTTTGTTTC ACCGCGTGCG GCGATTCCGG

5581 GTCCCCAGTG ATCACCGAGG CCGGGGAGCT TGTCGGTGTC CACACGGGAT CAAACAAACA

5641 AGGAGGAGGC ATTGTTACGC GCCCTTCAGG CCGGTTTTGT AATGTGACAC CCACCAAATT

5701 AAGTGAATTG AGTGAATTCT TCGCTGGACC TAGGGTCCCG CTTGGTGACG TGAAGGTTGG

5761 CAATCACATA ATCAAAGATA TAAATGAGGT GCCCTCAGAT CTCTGCGCCT TACTCGCTGC

5821 CAAACCCGAA TTGGAAGGAG GCCTCTCCAC CGTTCAACTT CTGTGCGTGT TTTTTCTCCT

5881 ATGGAGAATG ATGGGACATG CCTGGACACC CTTGGTTGCC GTTGGTTTTT TCATCTTGAA

5941 TGAAGTTCTC CCAGCAGTCC TGGTCCGGAG TGTCTTCTCC TTTGGAATGT TCGCACTGTC

6001 TTGGTTCACG CCGTGGTCTG CACAAATTCT AATGATCAGG CTCTTGACAG CAGCCCTAAA

6061 CAGAAACAGA TCGTCACTTG CCTTTTACAG CCTGGGCGCA CTAACCGGTT TGTTGCAGA

6121 TCTTGCAACC AATCAGGGGT ATTTATTGCA CGCGGTCATG AATGTGAGCA CCTATGCATT

6181 CCTGCCTCGT GCAATGGCCG TGACCTCACC AGTCCCAATA GTTGCGTGTG GCGTTGTGCA

6241 CTTGCTTGCC ATCATTCTGT ACTTGTTCAA GTACCGTAGC CTGCATGCCG TCCTGGTCGG
```

```
6301  CGATGGTGCG TTTTCCGCGG CTTTCTTCTT GCGATACTTT GCGGAGGGAA AGTTGAGGGA

6361  AGGGGTGTCG CAGTCTTGCG GCATGAATCA TGAGTCACTA ACCGGTGCCC TCGCCATGAA

6421  ACTCAGCGAC GAAGACTTGG ACTTCCTCAC AAAATTGACT GATTTTAAGT GCTTTGTTTC

6481  TGCATCCAAC ATGAGGAATG CGGCGGGTCA ATTTATAGAG GCCGCCTACG CCAAAGCACT

6541  GAGGGTGGAA CTTGCCCAGT TGGTTCAAGT CGATAAAGTT CGAGGTGTCC TGGCCAAACT

6601  TGAAGCTTTC GCTGACACCG TGGCGCCTCA ACTTTCACCC GGTGACATTG TTGTCGCCCT

6661  TGGACACACA CCTGTCGGCA GCATTTTTGA CCTGAAGGTC GGCAATGTTA AGCACACTCT

6721  CCAGTCCATT GAGACCAGAA CCCTTGCCGG GTCTAAAATG ACTGTGGCGC GCGTCGTAGA

6781  CCCAACCCCC ACACCCCCGC CCGCACCTGT GCCCATTTCC CTCCCACCAA AGGTTTTGGA

6841  GAACGGTCCC AACGCCTGGG GGGATGAGAA CGGTTTGAAC AAAAAAAAGC GGCGCAAGAT

6901  GGAGGCCGTT GGCATTTACG TTATGGGCGG GAAAAAGTAT CAAAAATTTT GGGATAAGAA

6961  TTCTGGTGAT GTGTTCTATG AAGAAGTCCA CGACAACACA GACGCGTGGG AATGCCTCAG

7021  AGTTGACAAC CCTGCCGACT TGGATCCTGA GAGGGGAACC TTGTGTGGAC ACACCACCAT

7081  AGACAACAGG CCTTACCATG TTTATGCTTC TCCGTCTGGT AGGAAGTTTC TAGTCCCTGT

7141  CAACCCGGAG AGCGGAAAAG CTCAGTGGGA AGCTGCTAAG CTTTCTTTAG ATCAGGCCCT

7201  CAGTATGATG AATGTCGACG GCGAACTGAC CGCCAAAGAA GTGGAAAAAT TGAAGAGAAT

7261  AATTGACAAA CTCCAGGGCC TGACTAAGGA GCAGTGTTTA AACTGCTAGC CGCCAGCGGC

7321  TTGACCCGCT GTGGTCGCGG CGGCTTGGTT GTTACTGAGA CAGCGGTAAA GATAGTCAGG

7381  TTCCACAACC GGACCTTTAC CCTAGGGCCT GTGAATTTGA AAGTAGCTAG CGAAGTTGAG

7441  TTGAAGGACG CGGTCGAGCA CGGCCAACAC CCGGTCGCGA TACCAGCCGA TGGTGGCGTC

7501  GTGCTCCTGC GTTCCGCTGT TCCTTCGCTT ATAGACGTCC TGATCTCCGG TGCTGACGCA

7561  TCCCCCAGGT TGCTCGCCCG TCACGGACCG GGAAATACTG GGGTCAATGG CGCGCTTTGG

7621  GATTTTGAGT CTGAAGCTAC CAAAGAGGAA GTAGCACTTA GTGCGCAAAT AATACAGGCC

7681  TGTGACATTA GACGCGGCGA TGCACCTGAG ATTGGCCTTC CTTACAAGTT GTACCCTGTT

7741  AGGGGCAACC CTGAACGGGC AAGAGGGGTT CTAATGAACA CAAGATTTGG AGACATACCT

7801  TACAAGACCC CCAGCGACAC CGGGAGCCCG GTGCACGCGG CCGCCTGCCT TACGCCCAAC

7861  GCCACTCCAG TAACTGATGG GCGCTCCATC CTGGCCACGA CCATGCCCTC CGGGTTTGAA

7921  CTATATGTGC CGACCATTCC AGCGTCTGTC CTTGATTACC TTGACTCCAG ACCAGACTGT

7981  CCTAAACAGT TGACTGAGCA CGGGTGTGAA GATGCCGCGT GAAGGACCT TTCTAAATAT

8041  GACCTGTCCA CCCAAGGCTT TGTGTTACCT GGAGTTCTAC GCCTCGTGCG AAAATATCTG

8101  TTTGCTCATG TAGGTAAGTG CCCGCCTGTC CACCGGCCCT CTACCTATCC TGCCAAGAAC

8161  TCCATGGCCG GAATAAATGG GAACAGGTTC CCAACCAAGG ATATTCAAAG CATCCCTGAG

8221  ATCGACGTTT TGTGTGCACA AGCTGTGCGA GAAAACTGGC AAACTGTTAC ACCCTGCACT

8281  CTTAAGAAGC AGTATTGCGG TAAAAAGAAG ACCAGGACCA TACTTGGCAC CAACAACTTC

8341  GTTGCGCTGG CCCACCGGGC GGCGCTGAGT GGTGTCACCC AGGGTTTCAT GAAGAAGGCG

8401  TTTAACTCAC CCATCGCCCT TGGGAAAAAT AAATTTAAGG AGCTACAGAC TCCAGTCTTG

8461  GGTAGGTGTC TTGAGGCTGA TCTCGCTTCC TGCGATCGAT CCACGCCTGC AATCGTTCGC

8521  TGGTTTGCCG CCAACCTTCT TTATGAACTT GCCTGTGCTG AGGAGCATTT ACCGTCGTAC

8581  GTGCTGAACT GTTGTCACGA CCTATTGGTC ACGCAGTCCG GCGCAGTGAC TAAGAGAGGT

8641  GGCCTGTCGT CCGGTGACCC AATCACCTCT GTGTCCAACA CCATTTATAG CTTGGTGATC
```

```
-continued
 8701 TATGCACAGC ATATGGTGCT TAGTTACTTC AAAAGTGGTC ACCCCCATGG CCTTCTGTTT

8761 TTACAAGACC AGCTAAAGTT TGAAGACATG CTCAAAGTTC AACCCCTAAT CGTCTATTCG

8821 GACGACCTCG TGTTGTATGC CGAGTCTCCC ACCATGCCAA ACTATCACTG GTGGGTTGAA

8881 CACCTGAATT TGATGTTGGG ATTTCAGACG GACCCAAAGA AGACTGCAAT AACAGACTCA

8941 CCTTCATTCC TAGGTTGTAG AATAATAAAT GGCCGCCAGT TAGTACCCAA CCGTGACAGA

9001 ATTCTCGCGG CCCTTGCCTA TCACATGAAG GCGAGTAATG TTTCTGAGTA CTACGCCTCC

9061 GCAGCCGCAA TACTCATGGA CAGTTGTGCT TGTCTAGAGT ATGATCCTGA GTGGTTTGAA

9121 GAACTTGTGG TTGGAATGGC GCAGTGCGCC CGTAAGGACG GCTATAGTTT CCCCGGCCCG

9181 CCGTTCTTCT TGTCCATGTG GGAAAAGCTC AGGTCAAATT ATGAGGGGAA GAAGTTGAGA

9241 GTGTGTGGTT ATTGCGGAGC TTCAGCCCCG TATGCTACTG CCTGTGGCCT TGACGTTTGT

9301 GTTTACCACA CCCACTTTCA CCAGCATTGT CCAGTCATAA TATGGTGTGG CCACCCGGCG

9361 GGTTCTGGGT CCTGCGATGA GTGCAAATCC CCTACAGGGA AGGGTACAAG CCCTCTGGAT

9421 GAGGTCTTAA GACAAGTCCC TTATAAGCCT CCACGGACTA TTCTTATGCA TGTGGAGCAG

9481 GGCCTCACCC CCCTTGACCC AGGCAGATAC CAGACCCGCC GTGGGTTGGT TGCTGTCAGG

9541 CGCGGGATAA GGGGAAATGA AGTTGACCTG CCAGATGGTG ATTATGCCAG TACTGCCCTA

9601 CTCCCCACCT GCAAAGACAT AGACATGGTT GCTGTGGCCT CCAATGTGTT GCGCAGTAGG

9661 TTCATCATCG GCCCACCTGG CGCAGGGAAA ACACACTGGC TTCTTCAACA GGTTCAGGAT

9721 AGTGATGTCA TTTACACGCC AACCCATCAG ACCATGCTTG ACATGATCAA GGCTTTGGGG

9781 ACGTGCCGGT TCAATGTCCC GGCAGGCACA ACGCTGCAAT TCCCTGCCCC CTCCCGTACC

9841 GGCCCGTGGG TTCGCATCCT TGCCGGCGGT TGGTGTCCAG GTAAGAATTC CTTCCTGGAT

9901 GAAGCAGCGT ATTGCAATCA CCTTGACGTC TTGAGGCTTC TCAGCAAAAC TACCCTCACC

9961 TGTCTGGGGG ATTTCAAACA ACTCCACCCG GTGGGTTTTG ATTCTCATTG CTATGTTTTT

10021 GATATCATGC CTCAGACTCA ACTGAAGACC ATCTGGAGGT TTGGACAGAA TATCTGTGAC

10081 GCCATTCAGC CAGATTACAG GGACAAACTC GTGTCCATGG TCAACACAAC CCGTGTAACC

10141 TATGTGGAAA GACCTGTCAA GTATGGGCAA GTCCTCACCC CCTACCACAG AGACCGAGAG

10201 GATGGTGCTA TCACTATTGA CTCCAGTCAA GGCGCCACAT TTGATGTGGT CACATTGCAT

10261 TTGCCCACTA AAGATTCACT CAACAGGCAA AGAGCCCTTG TTGCTATCAC CAGGGCAAGG

10321 CATGCAATCT TTGTGTATGA CCCACACAGG CAACTGCAGA GCATGTTTCG TCTTCCTGCA

10381 AAAGGCACAC CTGTCAACCT TGCCGTGCAC CGTGACGAGC AGCTCATCGT ATTAGATAGA

10441 AATAACAAAG AGTGCACGGT TGTTCAGGCT TTAGGCAATG GGACAAATT CAGGGCCAGT

10501 GACAAGCGCG TTGTAGATTC TCTTCGCGCC ATTTGTCAG ATCTTGAAGG GTCGAGCTCC

10561 CCGCTCCCCA AGGTCGCACA CAACTTGGGA TTTTATTTCT CACCTGATTT GACACAGTTT

10621 GCTAAACTCC CGGCGGAACT TGCACCCCAC TGGCCCGTGG TGCAACTCA GAACAACGAA

10681 AATTGGCCAG ACCGGCTGGT TGCTAGCCTC CGCCCTATCC ACAAATATAG CCGCGCGTGC

10741 ATCGGAGCCG GCTATATGGT GGGCCCCTCA GTGTTTCTAG GCACTCCTGG GGTTGTGTCA

10801 TACTATCTCA CACAATTTGT CAAAGGGGAG GCTCAGGTGC TTCCGGAGAC GGTCTTCAGC

10861 ACCGGCCGAA TTGAGGTAGA TTGTCGAGAG TATCTTGATG ATCGGGAACG AGAAGTTGCT

10921 GAGTCCCTCC CACATGCCTT TATTGGCGAC GTCAAAGGCA CTACCGTTGG GGGATGTCAC

10981 CATGTCACTT CTAAATATCT CCCACGCTTC CTTCCCAAGG AATCAGTTGC GGTGGTTGGG

11041 GTTTCAAGCC CCGGGAAAGC CGCAAAAGCA GTTTGCACAT TAACAGATGT GTACCTCCCA

11101 GATCTTGAGG CTTACCTCCA TCCAGAGACC CAGTCTAAGT GCTGGAAAGT GATGTTGGAC
```

```
11161 TTCAAGGAAG TTCGACTGAT GGTCTGGAGA GATAAGACGG CCTACTTTCA ACTTGAAGGC

11221 CGCCATTTCA CCTGGTACCA GCTTGCAAGT TATGCCTCGT ACATCCGAGT TCCCGTTAAC

11281 TCTACGGTGT ACCTGGACCC CTGTATGGGC CCTGCCCTTT GCAACAGAAG AGTCGTTGGG

11341 TCTGCACATT GGGGAGCTGA CCTTGCAGTT ACCCCTTATG ATTATGGTGC CAAAATCATT

11401 CTGTCTAGTG CGCACCATGG TGAAATGCCT CCTGGGTACA GAATTCTAGC GTGCGCGGAG

11461 TTCTCGCTTG ATGACCCAGT GAGGTACAAA CACACTTGGG GGTTTGAATC GGATACAGCG

11521 TATCTGTACG AGTTCACCGG AAACGGTGAG GACTGGGAGG ATTACAATGA TGCGTTTCGT

11581 GCACGCCAGA AAGGGAAAAT TTATAAGGCC ACTGCCACCA GCATGAGATT TCATTTTCCC

11641 CCGGGTCCTG CCATTGAACC AACATTGGGC CTGAACTGAA ATGAAATGGG GGCTGTGCAG

11701 AGCCTTTTCG ACAAAATTTG CCAACTTTTT GTGGATGCTT TCACGGAATT TTTGGTGTCC

11761 ATTGTTGATA TCATCATATT TTTGGCCATT TTGTTTGGCT TCACCATCGC AGGCTGGCTG

11821 GTTGTCTTCT GTATCCGACT GGTTTGCTCC ACGGTACTCC GTGCGCGCTC TACCATTCAC

11881 CCTGAGCAAT TACAGAAGAT CCTATGAGGC CTTCCTTTCC CAGTGCCAAG TGGACATTCC

11941 CGCCTGGGGA ACTAAGCATC CCTTGGGGGT GCTTTGGCAC ACAAGGTGT CAACTCTGAT

12001 TGATGAAATG GTGTCGCGTC GAATGTACCG CATCATGGAA AAAGCAGGAC AGGCTGCCTG

12061 GAAACAGGTT GTGAGCGAAG CTACATTGTC TCGCATAAGT GGCTTGGATG TGGTGGCTCA

12121 TTTTCAGCAT CTTGCTGCCA TTGAAGCCGA GACTTGCAAA TATTTGGCCT CTCGGCTGCC

12181 CATGCTACAC AACCTAGTCA TGTCAGGGTC GAATGTAACC ATAGTGTATA ATAGCACTTT

12241 GGGTCAAGTG TTTGCCATTT TCCCAACCCC TGGTTCCCGG CCAAAACTTT CTGATTTTCA

12301 ACAATGGCTC ATAGCTGTGC ATTCTTCCAT ATTTCTTCT GTTGCGGCTT CTTGTACTCT

12361 TTTTGTTGTG CTGTGGCTGC GAATTCCAAT ACTACGTACT GTTTTTGGTT TCCGCTGGTT

12421 AGGGGCAACT TTTCTTTCGA ACTCACAGTG AATTACACGG TGTGCCCACC CTGCCTCACC

12481 CGGCAAGCAG CCGCTGAGAT CTACGAACAC AGCGGGTCTC TTTGGTGCAG GATAGGGCAT

12541 GACCGATGTA GCCAGAGTGA TCATGACGAA CTAGGGTTCT TGGTTCCACC TGGCCTTTCC

12601 AGCGAGGGCC ACTTGACCAG TGTTTACGCC TGGCTGGCGT TCTTGTCTTT CAGCTACACA

12661 GCCCAGTTCC ACCCCGAGAT ATTTGGAATA GGGAATGTGA GTAGAGTTTA TGTTGACGTC

12721 ACTCACCAAC TCATCTGCGC CGAACACGAC GGGCAGAACA CCACCCTGCG TCGCCATGAC

12781 AATATCTCAG CCGTGTTTCA GACCTATTAC CAACATCAGG TCGATGGCGG CAATTGGTTT

12841 CACCTAGAAT GGCTGCGTCC CTTCTTTTCC TCTTGGCTGG TTTTGAATGT CTCGTGGTTT

12901 CTCAGGCGTT CGCCTGCAAA CCGTGTTTCA GTTCGAGTCT TTCAGACATC AAAACCAACA

12961 CCACCGCAGC TGCAGGCTTT GCTGTCCTCC AAGACATCAG CTGTCTTAGG CATGGCTACT

13021 CGTCCATTGA GGCGATTCGC AAAAGCCGTC AATGCCGCAC GGCGATAGGA ACGCCCGTGT

13081 ACATCACTGT CACGGCCAAT GTAACAGATG AGAATTACTT GCATTCCTCT GATCTCCTCA

13141 TGCTTTCCTC TTGCCTCTTC TATGCTTCTG AGATGAGTGA AAAGGGATTC AATGTGGTCT

13201 TCGGCAACGT GTCAGGCATT GTGGCTGTGT GTGTCAACTT TACCAGCTAT GTCCAACATG

13261 TTAAGGAGTT TACTCAGCGC TCTTTGGTGG TCGACCACGT GCGACTGCTT CATTTCATGA

13321 CACCTGCGAC CATGAGGTGG GCAACAGTTT TAGCCTGTCT TTTCGCCATC TTGTTGGCGA

13381 TTTGAATGTT TAAGTATGTT GGGGAAATGC TTGACCGCGG GCTACTGCTC GCAATTGCTT

13441 TTTTTCTGGT GTATCGTGCC GTTCTGTTTT GCTGCGCTCG TCAACGCCGC CAGCAACAGC

13501 AGCTCCCATT TACAGTTGAT TTATAACCTG ACGATATGCG AGCTGAATGG CACAGATTGG
```

-continued

```
13561 TTGAATCAAA AGTTTGATTG GGCAGTGGAG ACTTTTGTCA TTTTTCCTGT GTTGACCCAC

13621 ATTGTCTCCT ACGGTGCCCT TACCACCAGC CATTTCCTTG ACACGGCCGG CCTAATCACT

13681 GTGTCTACCG CCGGATATTA CCATGGGCGG TATGTGTTGA GTAGCATCTA CGCCGTCTTT

13741 GCCCTGGCTG CGTTGATTTG TTTTGTCATT AGGTTGACAA AAAACTGTAT GTCCTGGCGC

13801 TACTCATGTA CCAGATATAC CAACTTTCTT CTGGACACCA AAGGCAATCT CTATCGTTGG

13861 CGGTCACCCG TCGTTATAGA GAGAAGGGGT AAAGTTGAGG TTGGAGACCA CCTAATCGAC

13921 CTCAAAAGAG TTGTGCTTGA TGGTTCCGCG GCAACCCCTA TAACCAAGAT TTCAGCGGAA

13981 CAATGGGGTC GTCCCTAGAC GACTTCTGCA ATGACAGCAC AGCTGCACAA AAGGTGCTTT

14041 TGGCGTTTTC CATCACCTAT ACGCCAATAA TGATATATGC CCTGAAGGTA AGTCGCGGCC

14101 GACTGTTAGG GCTTTTGCAT CTTTTAATTT TCTTGAATTG TGCTTTCACC TTCGGGTACA

14161 TGACATTTGT TCATTTTCAG AGTACAAACA AGGTCGCGCT CACTATGGGA GCAGTTGTTG

14221 CACTCCTTTG GGGGGTGTAC TCAGCCATAG AAACCTGGAA ATTCATCACT TCCAGATGCC

14281 GTTTGTGCTT GCTAGGCCGC AGGTACATTC TGGCCCCTGC CCACCACGTT GAAAGTGCCG

14341 CGGGCTTTCA TCCGATTGCG GCAAGTGATA ACCACGCATT TGTCGTCCGG CGTCCCGGCT

14401 CCACTACTGT TAACGGCACA TTGGTGCCCG GGTTGAAAAG CCTCGTGTTG GGTGGCAGAA

14461 AAGCTGTTAA GCGGGGAGTG GTAAACCTCG TTAAATATGC CAAATAACAA CGGCAGGCAG

14521 CAAAAAAATA AGAAGGGGAG TGGCCAGCCA GTCAATCAGC TGTGCCAAAT GCTGGGCAAG

14581 ATCATCGCCC AGCAAAATCA GTCCAGAGGC AAGGGACCGG GTAAGAAAAA TAAGAAGAGA

14641 AACCCGGAGA AGCCCCATTT TCCTCTTGCG ACCGAAGATG ACGTCAGGCA TCACTTCACC

14701 CCCAGTGAAC GGCAATTGTG TCTGTCGTCG ATCCAGACTG CCTTCAACCA GGGCGCTGGA

14761 ACTTGCACCC TGTCAGATTC AGGGAGGATA AGTTACACTG TGGAGTTTAG TTTGCCGACG

14821 CACCACACTG TGCGCCTTAT TCGCGCCACA GCATCACCTC CATCGTGATG GGCTTACATT

14881 CTTGGAGCTC CTCAGTTTCA CAATTGGAAG AATGTGTGGT GAATGGCACT GATTGGCACT

14941 GTGCCTCTAA GTCACCTATT CAATTAGGGC GACCGTGTGG GGGTTTAGTT TAATTGGCGA

15001 GAACCACGCG GCCGAAATTA AAAAAAAAAA AAAAAAAAAA AAAAAA
```

A person skilled in the art would recognize the polyadenosine tails of each of the genomic consensus sequences could vary in length from the above reported sequences.

Variant identification has been performed to determine the number and frequency of nucleotide changes in the virus population for both passages. Table 16 shows the 11 nucleotide changes found in P84 and P 100 compared to the reference sequence. Six of the 11 variant positions are consistent between the passages with the exception of 5 nucleotide changes in P100 which were not present in P84. These changes suggest that a little less roughly half of the subpopulation variants arose during the passage of the virus from 84 to 100.

TABLE 16

PRRSV SD 11-21 Sequence Variants.

| | | | Frequency (% of Population) | |
|---|---|---|---|---|
| Position | Reference Base | Variant Base | P84 | P100 |
| 811 | T | C | 11.85% | 11.90% |
| 1,469 | A | G | 8.45% | 5.29% |
| 3,235 | A | T | 5.21% | 5.71% |
| 7,563 | T | C | 97.46% | 96.73% |

TABLE 16-continued

PRRSV SD 11-21 Sequence Variants.

| | | | Frequency (% of Population) | |
|---|---|---|---|---|
| Position | Reference Base | Variant Base | P84 | P100 |
| 7,760 | C | T | ND | 13.07% |
| 12,314 | G | A | ND | 22.39% |
| 12,911 | C | T | ND | 22.39% |
| 12,914 | C | T | ND | 8.53% |
| 14,039 | T | A | ND | 5.00% |
| 14,985 | AG | TT | 100.00% | 99.03% |
| 15,007 | TA | CG | 97.73% | 96.38% |

ND = not detected.

EXAMPLE 8

The objective of this study is to evaluate the dose response and onset-of-immunity (OOI) of an experimental modified live PRRSV vaccine in a vaccination-challenge study. Vaccines are evaluated on their ability to reduce lung lesions, viral load in the lungs and blood, and clinical signs. The study was conducted in BSL-2 facilities at Veterinary Resources, Inc., Cambridge, Iowa, using similar procedures and conditions as described in Examples 2 and 3. Laboratory assays were conducted at the Iowa State University Veterinary Diagnostic Laboratory, Ames, Iowa, as described in Examples 2 and 3. Eighty (80) clinically healthy, 14 or 15 day old weaned pigs that were seronegative to PRRSV were enrolled in the study. Pigs were randomly assigned to one of four treatment groups (n=20/group). Treatment groups included a placebo-matched control group and three PRRSV vaccine dose groups (2.7, 4.1 or 5.1 $\log_{10}$ TCID$_{50}$/mL).

Pigs received their respective vaccine or placebo intramuscularly (1.0 mL) in the right side of the neck on Day 0. Vaccines are formulated to include the SD 11-21 PRRSV strain, a stabilizer and a preservative (gentamicin). OPTI-MEM® I Reduced Serum Medium is used as the blending diluent. Vaccines are prepared using master seed virus (MSV) at the highest passage level intended for production (MSV+5) grown on master cell stock (MCS) at the highest passage level (MCS+20). The median tissue culture infective dose (TCID$_{50}$) for each vaccine was determined by infecting MARC-145 cells. No local or systemic adverse reactions were observed following vaccination. Compared to the placebo control group, a transient increase in rectal temperature was observed by Day 2 post-vaccination in all vaccine groups, but remained within the normal physiological range and was not observed thereafter.

At Day 28 post vaccination, all pigs were challenged with 4 mL (1 mL/nostril and 2 mL IM) of PRRSV strain NADC-20 (passage 3) at $3.98\times10^4$ TCID$_{50}$/mL. The mean percent of lung lesion involvement in the placebo group was 54%. The level achieved in this study was considered adequate to evaluate the vaccine candidates.

Results of the statistical analysis of the lung lesion scores are summarized in Tables 17 and 18. The main effect of treatment was statistically significant (P<0.0001). Vaccinated pigs in all dose groups had significantly lower (P<0.05) lung lesion scores than control pigs (Table 17). Linear and quadratic contrasts were not statistically significant. The mitigated fractions are provided in Table 18. The mitigated fraction for groups T02 (2.7 logs), T03 (4.1 logs) and T04 (5.1 logs) compared to group T01 (placebo) was significant. Vaccination with T02, T03 and T04 increased the probability by 0.9200, 0.9450 and 0.9789, respectively, that a vaccinated animal would have less lung lesions than a non-vaccinated control animal.

TABLE 17

Mean Lung Lesion Score[1]

| Treatment Group | Estimate[2] | Standard Error | Mean[3] |
|---|---|---|---|
| T01: Placebo | 0.8288 | 0.04258 | 54.33 |
| T02: 2.7 $\log_{10}$ TCID$_{50}$/mL | 0.1804 | 0.04183 | 3.22* |
| T03: 4.1 $\log_{10}$ TCID$_{50}$/mL | 0.1650 | 0.04243 | 2.70* |
| T04: 5.1 $\log_{10}$ TCID$_{50}$/mL | 0.1662 | 0.04308 | 2.74* |

[1]Arcsine Transformed Percent Lung Involvement.
[2]Untransformed means.
[3]Back transformed means.
*T01 versus T02, T03 or T04 significantly different at P < 0.05.

TABLE 18

Mitigated Fraction—Lung Lesion Scores

| Group Comparison | Mitigated Fraction | 95% Confidence Interval |
|---|---|---|
| Placebo versus 2.7 $\log_{10}$ TCID$_{50}$/mL | 0.9200 | 0.7834, 1.0000 |
| Placebo versus 4.1 $\log_{10}$ TCID$_{50}$/mL | 0.9450 | 0.8461, 1.0000 |
| Placebo versus 5.1 $\log_{10}$ TCID$_{50}$/mL | 0.9789 | 0.9347, 1.0000 |

On Day 42, BAL fluid was obtained aseptically from excised lungs. An aliquot of the BAL fluid was submitted to ISUVDL for qRT-PCR analysis of the presence of PRRSV nucleic acids. Results are summarized in Table 19. Vaccinated pigs in all three dose groups had significantly lower (P<0.05) viral loads in the lungs when compared to control pigs. The main effect of treatment was significant (P<0.0001).

TABLE 19

Geometric Means of PRRSV Genomic Copies/mL in BAL Fluid

| Treatment Group | Estimate[1] | Standard Error | Geometric Mean[2] | 95% confidence interval[2] | |
|---|---|---|---|---|---|
| | | | | Lower Bound | Upper Bound |
| T01: Placebo | 8.9071 | 0.2545 | 807351537 | 250619135 | 2600824971 |
| T02: 2.7 logs | 6.1271 | 0.2545 | 1340130* | 416005 | 4317131 |
| T03: 4.1 logs | 6.2598 | 0.2545 | 1818858* | 564612 | 5859320 |
| T04: 5.1 logs | 6.3339 | 0.2611 | 2157074* | 649559 | 7163277 |

*T01 versus T02, T03 or T04 significantly different at P < 0.05.
[1]Untransformed means.
[2]Back transformed means.

Blood samples for determination of PRRSV antibody levels and PRRSV viremia were collected from all study animals on Days −1, 28 (prior to challenge) and 42. Serology and viremia were determined by ELISA and qRT-PCR methodology, respectively. As determined by ELISA antibody titer, all pigs were seronegative on Day −1. ELISA values in all vaccinated groups were significantly higher (P<0.05) than values in the placebo group on both Days 28 and 42.

No pigs were positive for viremia on Day −1. At time of challenge (Day 28), all pigs in the placebo control group were negative, whereas 95%, 75% and 89% of pigs in groups T02, T03 and T04 were positive due to the presence of the vaccine virus. All pigs in all groups were positive post-challenge on Day 42, but values in the vaccinated groups (T02, T03 and T04) were significantly lower (P<0.05) than values in the placebo control group (T01).

All study animals were weighed individually in pounds on day of challenge (Day 28) and day of necropsy (Day 42) and their weight recorded. Average daily weight gain (ADWG) was determined for the following periods: day prior to vaccination to day of challenge (Day −1 to Day 28); day prior to vaccination to day of necropsy (Day −1 to Day 42); and day of challenge to day of necropsy (Day 28 to Day 42). The main effect of treatment was not significant (P=0.2304) prior to challenge (Day −1 to 28). During the challenge period (Day 28 to 42) and for the entire 42 day study period, the main effect of treatment was significant (P<0.0001). For each of these two periods, pigs in the vaccinated groups gained more weight (P<0.05) than those pigs in the placebo control group.

All animals were evaluated for depression, body condition, and respiratory distress on a daily basis for 14 days post-challenge (Days 28-42) and scored for each clinical sign. Depression score, respiratory score and body condition scores were summarized by time. Clinical scores were also summed within a day for each animal. On Day 8, values in T02 and T04 were significantly lower (P<0.05) than values in the placebo control group (T01). On Day 9, values in T02 were significantly lower (P<0.05) than values in T01. On Days 10-14, values in all vaccinated groups (T02, T03, and T04) were significantly lower (P<0.05) than values in T01. There was no effect of dose on clinical signs.

In conclusion, all dose levels of vaccine are effective in reducing (P<0.05) lung lesions, viral load in the lungs, viremia, and clinical signs. No local or systemic adverse reaction to the vaccine at any dose level has been observed. A derived benefit of vaccine efficacy is a significant improvement (P<0.05) in average daily weight gain compared to control animals. Thus, a 28-day onset of immunity (OOI) is achievable in pigs vaccinated as early as 14-15 days of age.

As a summary, Table 20 lists the various PRRS virus vaccine strains and references to their consensus genomic cDNA sequences.

TABLE 20

PRRS virus vaccine strains.

| Strain | Passage | ATCC Accession Number | GenBank Accession Number | SEQ ID Number | cDNA length (number of bases) |
|---|---|---|---|---|---|
| SD 95-10 | P83 | none | KU131565 | SEQ. ID NO: 1 | 15386 |
| SD 95-47 | P83 | none | KU131564 | SEQ. ID NO: 2 | 15444 |
| SD 98-163 | P83 | none | KU131563 | SEQ. ID. NO: 3 | 15013 |
| ND 99-14 | P83 | none | KU131562 | SEQ. ID. NO: 4 | 15444 |
|  | P84 | none | KU131567 | SEQ. ID. NO: 10 | 15444 |
|  | P100 | PTA-122675 | KU131569 | SEQ. ID. NO: 11 | 15444 |
| SD 02-10 | P83 | none | KU131561 | SEQ. ID. NO: 5 | 15423 |
| SD 03-15 | P83 | none | KU131560 | SEQ. ID. NO: 6 | 15078 |
| SD 04-89 | P83 | none | KU131559 | SEQ. ID. NO: 7 | 14885 |
| MN 05-68 | P83 | none | KU131558 | SEQ. ID. NO: 8 | 15434 |
| SD 11-21 | P83 | none | KU131557 | SEQ. ID. NO: 9 | 15047 |
|  | P84 | none | KU131566 | SEQ. ID. NO: 12 | 15047 |
|  | P100 | PTA-122674 | KU131568 | SEQ. ID. NO: 13 | 15047 |

EXAMPLE 9

The objective of this study was to demonstrate the lack of reversion-to-virulence of Master Seed Virus (MSV) SD 11-21 X+1 of Porcine Reproductive and Respiratory Syndrome Virus (PRRSV) vaccine, modified live virus in pigs.

A total of eighty (80) clinically healthy, 14-15 day old weaned pigs, seronegative to PRRSV and negative for PRRSV by RT-qPCR were enrolled over four separate backpassages. Each backpassage contained twenty pigs, with 10 pigs in the control group and 10 pigs in the Investigational Veterinary Product (IVP) group. Pigs were randomly allocated to treatment group on either D-2 or D-1. In backpassage 1 (BP), the IVP consisted of SD 11-21 MSV X+1. In BP 2-4, the IVP consisted of PRRSV isolated from broncho-alveolar lavage (BAL) fluid from pigs in the previous backpassage. The control product was phosphate buffered saline (PBS). An animal was considered clinically affected by PRRSV if it exhibited pyrexia and clinical signs typical of PRRSV infection; it died or was removed due to PRRSV based on the diagnostic report; or it had gross lung lesions attributable to PRRSV.

Titer of the PRRSV SD 11-21 MSV was 3.3 $\log_{10}$ TCID$_{50}$(796-70-23Sep14). The MSV X+1 was generated in order to achieve a titer level of a typical vaccine dose, including overage. In order to generate the X+1, confluent MARC-145 cells were infected with PRRSV Master Seed Virus (MSV) SD 11-21 (796-70-23Sep14) and PRRSV SD 11-21 X+1 was harvested when over 95% of cytopathic effect (CPE) was observed.

On Day 0, pigs in the IVP group were administered 1.0 ml of the IVP intranasally (IN; 0.5 ml/nare). Pigs were observed daily for clinical signs (depression, respiratory, and body condition) and pyrexia for 14 day in BP 1-3 and for 21 days in BP 4. Pigs were euthanized on D14 in BP 1-3 and on D21 in BP 4. Lungs were excised, and evaluated for the presence of gross lung lesions. Broncho-alveolar lavage (BAL) fluid was collected and analyzed for PRRSV by RT-qPCR and virus isolation was conducted. (Table 21). RT-qPCR was conducted using the EZ-PRRSV MPX 4.0 RT-PCR kit (Tetracore). BAL fluids positive for PRRSV by RT-qPCR were concentrated with a sucrose cushion and pooled. The pooled material was tested for PRRSV by RT-qPCR and the titer was determined by cytopathic effect (CPE) prior to administration to the next group of animals. The inability to isolate the virus in animals following a backpassage deemed the MSV stable and free from reversion to virulence. PRRSV present in the pooled BAL fluid from the last backpassage that tested positive by RT-qPCR was compared both phenotypically and genotypically to the PRRSV in the original MSV X+1. Phenotypic comparison was conducted by IFA testing, using a PRRSV specific antibody, and the genotypic comparison was conducted by comparing genomic sequencing of the ORF5 gene.

Virus titer for the MSV X+1 was 8.2 $\log_{10}$ TCID$_{50}$/ml. The median tissue culture infective dose (TCID$_{50}$) for each virus was determined by infecting MARC-145 cells with 10-fold serial dilutions of the virus and incubating the infected cells for 4 days. At the end of the incubation period each infection was examined for the presence or absence of virus induced cytopathic effect (CPE) and scored as positive or negative. The data collected was then used to calculate the titer of the virus using the Reed-Muench method for TCID$_{50}$ calculation and reported as $\log_{10}$ TCID$_{50}$/ml. Potency of the MSV X+1 exceeded the expected targeted release dose of the product. Virus titers of the material administered in BP 2 and 3 were 2.1 and 2.6 $\log_{10}$TCID$_{50}$/ml, respectively. Material administered in BP 4 was negative for CPE. No pig administered the IVP in any of the four backpassages was positive for the case definition of a pig clinically affected with PRRSV. Additionally, virus from pooled BAL fluid from the last positive backpassage was shown to be phenotypically similar to the MSV X+1 and a genotypic match to the MSV X+1 when comparing the ORF5 gene.

This study demonstrates the lack of reversion-to-virulence and confirms the genetic stability of a Master Seed Virus SD 11-21 X+1 of Porcine Reproductive and Respiratory Syndrome Virus Vaccine, Modified Live Virus administered to 14-15 day old pigs.

TABLE 21

BAL fluid virus isolation results by backpassage

| | Individual BAL fluid Samples | | Pooled Positive BAL fluid Samples | |
|---|---|---|---|---|
| Backpassage | Number of Positive RT-qPCR samples | Number of Positive Virus Isolation samples | RT-qPCR (+/−) | Titer of Pooled Material ($\log_{10}$ TCID$_{50}$) |
| 1 | 5/10 | 3/10 | Positive | 2.1 |
| 2 | 3/10 | 2/10 | Positive | 2.6 |

TABLE 21-continued

BAL fluid virus isolation results by backpassage

| Back-passage | Individual BAL fluid Samples | | Pooled Positive BAL fluid Samples | |
|---|---|---|---|---|
| | Number of Positive RT-qPCR samples | Number of Positive Virus Isolation samples | RT-qPCR (+/−) | Titer of Pooled Material ($\log_{10}$ $TCID_{50}$) |
| 3 | 3/10 | 0/10 | Negative | Negative |
| 4 | 0/10 | 0/10 | NA | NA |

NA-Not applicable; all individual BAL fluids were by both PCR and immunofluorescence so no pool was generated.

EXAMPLE 10

The objective of this study was to assess the shedding and transmission of a porcine reproductive and respiratory syndrome virus (PRRSV) SD 11-21 Master Seed Virus (MSV) from vaccinated to sentinel animals. Twenty (20) clinically healthy, 14 day old, weaned pigs, seronegative to PRRSV and negative for PRRSV by RT-qPCR were enrolled. On D-1, pigs were physically examined, and randomly allocated to either the sentinel/control group or the PRRSV SD 11-21 MSV X+1 treatment group. The PRRSV SD 11-21 MSV X+1 was generated as in Example 9. Pigs were housed in pens with 4 pigs/pen, with each pen containing two pigs/treatment group.

On D0, pigs in the MSV X+1 treatment group were vaccinated with 1.0 ml intramuscularly (IM) in the right side of the neck while sentinel pigs were left untreated. Nasal swabs and serum samples were collected on D-1, D3, D5, D7, D10, D14, D17, and D21 and were tested for PRRSV by RT-qPCR. On D21, pigs were humanely euthanized and lungs were excised. Broncho-alveolar lavage (BAL) fluid was aseptically collected and tested for PRRSV by RT-qPCR. In addition, tissue samples were collected from the lung, spleen, tonsil, thymus, and the right and left tracheo-bronchial lymph nodes and were tested for PRRSV by RT-qPCR. If a tissue sample tested positive for PRRSV by RT-qPCR, the sample was identity tested by genomic sequencing using the ORF5 region and compared to the ORF5 region of the MSV X+1. Body weights were collected on D-1 and D21.

Nine out of ten vaccinated pigs (90%) had at least one nasal swab positive for PRRSV during the 21 day study period. Some pigs (4/9) were still shedding vaccine at the end of the 21 day study period. All vaccinated pigs were viremic from D3-D21. Additionally, all BAL fluids and tissue samples from the vaccinated pigs were positive for PRRSV by RT-qPCR on D21. The nucleotide sequences of the RNA isolated from tissue samples showed 99.67-100% similarities to the MSV X+1, indicating the only virus present in the pigs originated from the vaccine virus. One out of ten sentinel pigs (10%) was considered positive for vaccine virus. A single nasal swab was positive during the 21 day sampling period. No serum sample, BAL fluid sample, or tissue sampled, tested positive for PRRSV by RT-qPCR in any of the sentinel pigs.

The MSV X+1 is shed from vaccinated animals for at least 21 days following administration. Transmission of the MSV X+1 from vaccinated to sentinel animals is limited, as no vaccine virus was detected in any of the sentinel animals outside of a single positive nasal swab.

EXAMPLE 11

The objective of this study was to evaluate the efficacy of an experimental modified-live PRRSV vaccine containing a type-2 PRRSV strain (SD 11-21) at 4.45 $\log_{10}$ $TCID_{50}$/mL when administered to PRRSV seronegative 14-day old piglets that were subsequently challenged with a contemporary virulent type-2 PRRSV strain (NC-174). The NC-174 PRRS virus was isolated from serum samples of 9 week old pigs experiencing respiratory symptoms on a swine farm in Harrells, N.C. Detailed symptomatic observations from the farm were anorexia, lethargy, hyperpnea, dyspnea, 15% morbidity and 5% mortality. The vaccine was evaluated on its ability to reduce lung lesions, viral load in the lungs and blood, and clinical signs.

Forty (40) clinically healthy, 14 day old weaned pigs that were seronegative to PRRSV were enrolled in the study. Pigs were ranked by decreasing body weight and randomly assigned to one of two treatment groups (n=20/group). Treatment groups included the experimental vaccine and a placebo-matched control group. Pigs were housed by treatment group to prevent exposure due to shedding of the vaccine virus up to time of challenge. At challenge, pigs were commingled such that there were two pigs from each treatment group in a pen.

Pigs received the vaccine or placebo intramuscularly (1.0 mL) in the right side of the neck on Day 0. Blood samples were collected on Days −1, 28, 35 and 42 and the serum tested for PRRSV antibody levels by ELISA and for viral load by quantitative PCR (qRT-PCR). At Day 28, all pigs were challenged with 4 mL (1 mL/nostril and 2 mL IM) of PRRSV strain NC-174 (lineage 1, passage 3) at $1.3 \times 10^6$ $TCID_{50}$/mL. Clinical scores representing respiratory distress, depression and body condition were recorded daily from Day 28 to 42. Pigs were weighed on Day −1, 28 and 42 to evaluate weight gain. Pigs were euthanized on Day 42, lungs were excised, and the extent of lung lesions was determined. Broncho-alveolar lavage (BAL) fluids were collected on Day 42 and tested for PRRSV by qRT-PCR.

No local or systemic adverse reactions were observed following vaccination. The experimental vaccine was effective in reducing ($P<0.05$) percent lung lesions (45.9% in controls vs 4.0% in vaccinates), viral load in the lungs (decreased 95%), viremia (at 14 days post challenge), and clinical signs. Mitigated fraction evaluation of the lung lesion data indicated that vaccination increased the probability by 0.9368 that a vaccinated animal would have less lung lesions than a non-vaccinated control animal.

A derived benefit of vaccine efficacy was a significant improvement ($P<0.05$) in average daily weight gain compared to control animals (0.43 vs 0.25 kg/day) during the 14-day challenge period.

In conclusion, administration of an experimental PRRSV vaccine containing strain SD 11-21 as a single 1.0 mL dose to naïve 14-day old pigs was safe and effective against challenge with the contemporary PRRSV field strain NC-174.

EXAMPLE 12

The objective of this study was to confirm a minimum of 26 weeks (182 day) duration of immunity of an experimental modified-live PRRSV vaccine containing a type-2 PRRSV strain (SD 11-21) at 4.45 $\log_{10}$ $TCID_{50}$/mL when administered to PRRSV seronegative 14-day old piglets that were subsequently challenged with a virulent type-2 PRRSV strain (NADC-20). The vaccine was evaluated on its ability to reduce lung lesions, viral load in the lungs and blood, and clinical signs. Sixty-four (64) clinically healthy, 14-day old weaned pigs that were seronegative to PRRSV were enrolled in the study. Pigs were blocked by litter and randomly assigned to one of two treatment groups (n=32/group). Treatment groups included the experimental vaccine (T02) and a placebo-matched control group (T01). Pigs were housed by treatment group to prevent exposure due to shedding of the vaccine virus up to time of challenge. At challenge, pigs were commingled such that there were two pigs from each treatment group in a pen.

Pigs received the vaccine or placebo intramuscularly (1.0 mL) in the right side of the neck on Day 0. Blood samples were collected on Days −1, 28, 112, 168, 181, 189 and 196 and the serum tested for PRRSV antibody levels by ELISA and for viral load by quantitative PCR (qRT-PCR). At Day 182, all pigs were challenged with 10 mL (4 mL/nostril and 2 mL IM) of PRRSV strain NADC-20 at $10^{6.7}$ TCID$_{50}$/mL. Clinical scores representing respiratory distress, depression and body condition were recorded daily from Day 182 to 196. Pigs were euthanized on Day 196 (14 days post-challenge), lungs were excised, and the extent of lung lesions was determined. Broncho-alveolar lavage (BAL) fluids were collected and tested for PRRSV by qRT-PCR.

The experimental vaccine was effective in reducing (P<0.05) percent lung lesions (12.3% in controls vs 1.1% in vaccinates). Mitigated fraction evaluation of the lung lesion data indicated that vaccination increased the probability by 0.6566 that a vaccinated animal would have less lung lesions than a non-vaccinated control animal.

Results from this study confirmed that the administration of an experimental PRRSV vaccine containing strain SD 11-21 as a single 1.0 mL dose to naïve 14-day old pigs was effective against a virulent PRRSV challenge given 26 weeks later.

What is claimed is:

1. A modified, live Porcine Reproductive and Respiratory Syndrome (PRRS) virus strain, wherein the consensus complementary DNA sequence of said PRRS strain is at least 95% identical to a sequence selected from the group of SEQ ID NO: 9, SEQ ID NO: 12, and SEQ ID NO: 13.

2. The modified, live PRRS virus strain of claim 1, wherein the consensus complementary DNA sequence of said PRRS strain is at least 98% identical to a sequence selected from the group of SEQ ID NO: 9, SEQ ID NO: 12, and SEQ ID NO: 13.

3. The modified, live PRRS virus strain of claim 1, wherein said PRRS strain is SD 11-21.

4. The PRRS strain of claim 1, wherein said PRRS virus strain is passaged at least 80 times in tissue culture cells.

5. The PRRS strain of claim 1, wherein said PRRS virus strain is passaged 100 times in tissue culture cells.

6. An immunogenic composition comprising a modified, live PRRS virus strain having a consensus complementary DNA sequence at least 95% identical to a sequence selected from the group of SEQ ID NO: 9, SEQ ID NO: 12, and SEQ ID NO: 13; and
a pharmaceutically-acceptable excipient, stabilizer, solubilizer, or diluent.

7. The immunogenic composition of claim 6, wherein the consensus complementary DNA sequence is at least 98% identical to a sequence selected from the group of SEQ ID NO: 9, SEQ ID NO: 12, and SEQ ID NO: 13.

8. The immunogenic composition of claim 6, wherein the modified, live PRRS virus strain is SD 11-21.

9. The immunogenic composition of claim 6, further comprising an adjuvant.

10. A method of treating or preventing a symptom caused by type 2 Porcine Reproductive and Respiratory Syndrome (PRRS) virus infection in a porcine animal, comprising administering to said porcine animal an immunogenic composition comprising a modified, live PRRS virus strain having a consensus complementary DNA sequence at least 98% identical to a sequence selected from the group of SEQ ID NO: 9, SEQ ID NO: 12, and SEQ ID NO: 13; and a pharmaceutically-acceptable excipient, stabilizer, solubilizer, or diluent.

11. A vaccine comprising a modified, live PRRS virus strain, wherein said PRRS virus strain is SD 11-21.

12. A method of treating or preventing a symptom caused by type 2 Porcine Reproductive and Respiratory Syndrome (PRRS) virus infection in a porcine animal, comprising administering to said porcine animal a vaccine comprising a modified, live PRRS virus strain, wherein said PRRS virus strain is SD 11-21.

13. The method of claim 12, wherein the PRRS virus infection is caused by a virulent type 2 PRRS virus heterologous to the modified, live PRRS virus strain in the vaccine.

* * * * *

SEQUENCE LISTING

<160> NUMBER OF SEQ ID NOS: 13

<210> SEQ ID NO 1
<211> LENGTH: 15386
<212> TYPE: DNA
<213> ORGANISM: Artificial Sequence
<220> FEATURE:
<223> OTHER INFORMATION: Synthetic Construct

<400> SEQUENCE: 1

```
atgacgtata ggtgttggct ctatgccatg acatttgtat agtcaggagc tgcgaccatt      60
ggtacagccc aaaacttgct gcacggaaac gcccttccgt gacagccctc ttcaggggag     120
tttaggggtc tatccctagc accttgcttc cggagttgca ctgctttacg gtctctccaa     180 cccttaacc atgtctggga tacttgatcg gtgcacgtgt acccccaatg ccagggtgtt      240
catggcggag ggccaagtct actgcacacg atgtctcagt gcacggtctc tccttcctct     300
gaatctccaa gttcccgagc ttggagtgct gggcctatt tacaggcccg aagagccgct      360
ccggtggacg ttgccacgtg cattccccac tgtcgagtgc tcccccgccg gggcttgctg     420
gctttctgcg atcttcccaa ttgcacgaat gaccagtgga aacctgaact ttcaacaaag     480
aatggtgcgg gtcgctgccg agatttacag agccggccag ctcaccctg cagtcttgaa     540 ggctctacaa gtttatgaac ggggttgccg ctggtacccc attgtcggac ctgtccctgg     600
agtggccgtt ttcgccaact ccctacatgt gagtgacaaa ccttttccgg gagcaactca     660
tgtgttaacc aatctaccgc tcccgcagag gcccaagcct gaagacttt gcccttttga     720 gtgtgctatg gctgacatct atgacatcgg tcatgacgcc gtcatgtatg tggccggaga     780
gaaagtctcc tgggcccctc gtggcgggga tgaagtgaaa tttgaaaatg ttcccaagga     840
gttgaagttg attgcgaacc gactccacat ctccttcccg ccccaccacg tagtggacat     900
gtccaagttt accttcatag cccccgggag tggtgtctcc atgcgggttg agtgccaaca     960
cggctgcctc cccgctgata ctgttcctga aggaaactgc tggtggcgct tgttcgactc    1020
gctcccgccg gaagtccagc acaaagaaat tcgctatgct aaccaatttg gttatcaaac    1080
caagcatggt gtctctggca agtacctaca gcggaggctg caagttaacg gtctccgagc    1140
agtgaccgac gtacatggac ctatcgtcat acagtacttc tctgttaagg agagttggat    1200
ccgccacttc aggctggcgg aagaacctag cctccctggg ttcgaagacc tcctcagaat    1260
tagggttgag cccaatacat caccactggc tggcgaggat ggaagatct tccggtttgg    1320
```

```
cagtcacaag tggtacggtg ctggaaggag agcaaggaaa gcacgttctg gtgcgaccac    1380
catggtcgct catcgcgctt tgtccgctcg tgaaacccag caggcaaaga aggacgaggg    1440
tgccgacgct aacaaggctg agcatctcaa gcactactct ccgcccgccg aagggaactg    1500
tggttggcac tgtatttccg ccatcgccaa ccggatgata aattccaaat ttgaaactac    1560
ccttcccgaa agagtaaggc ctctggatga ctgggctact gacgaggatc ttgtgaatac    1620
catccaaatc ctcaggctcc ccgcggcctt ggataggaac ggtgcttgta gtagcgccaa    1680
gtacgtgctt aagctggaag gtgtgcattg gactgtctct gtgacccctg ggatgtcccc    1740
ttccttgctc ccccttgaat gtgttcaggg ctgttgcgag cataagggcg ttttggctc     1800 cccagatgcg gtcgaagttt ccggatttga ccctgcctgc cttgaccgac tggctgaggt    1860
aatgcacttg cctagcagtg ccatcccagc cgctctggcc gaaatgtccg gcgactccaa    1920
tcgtccggct tccccggtca acactgtgtg gactgtttcg caattctatg cccgtcatac    1980
aggaggaaat catcctgacc aggtgtgctt agagcagatc attaatctct gtcaggttat    2040
tgaggtttgt tgctgccatc aaaacaaaac caaccgggcc accccggaag aggtcgcggc    2100
aaagattgat cagtacctcc gtggtgcaac aaatcttgaa gaatgcttga ccaggcttga    2160
gagggtttgc ccgccgagcg ctgcggacac ctcctttgat tggaatgttg tgctccctgg    2220
ggttgaggct gcaactcaga caaccaaaca gccccacgtc aaccagtgct gcgctctggt    2280
tcctgtcgtg actcaagagc cttttggacaa agactcggtc cctctgaccg ccttctcgct    2340
gtccaattgc tactaccctg cacaaggtga agaggttcgt caccgtgaga gactaaactc    2400
cgtactctcg aagttggagg gggctgttcg tgaggaatat gggctcacgc caactgaacc    2460
tggcctgcaa cccgcactac cgaacgggct cgacgaactt aaagaccgga tggaggagga    2520
tctgctgaaa ctagtcaacg ctcaggcaac ttcagaaatg atggcctggg cagccgagca    2580
gattgattta aaagcttggg tcaaaaacta cccacggtgg acaccgccac cccctccacc    2640
aagagctcag cctcggaaaa cgaagtctgt taagagcttg ccagggaaca agcctatccc    2700
tgctccacgc aggaaggtca gatctgattt gactgttaat ggccccttg atctttcgac     2760 accatccgag ccgatgacac ccctgagtga gcctgcactt atgcccgcgt tgcaacatat    2820
ttctaggcca gtgacatctt tgagtgagcc ggtcccagtt cctgcaccgc gtagagctgt    2880
gtcccgaccg gtgacgccct tgagtgggcc aacttttgag tttgcgccgc gacacaaatt    2940
tcagcaggtg ggagaagtga atctggcggc aacaacgctg acgcaccagg acgaacctct    3000
agatttgtct gcatcctcac agactgaata tgaggcttct cccctagtac caccgcagaa    3060
catgggtatc ctgggggtgg ggggcaaga ggctgaagaa gttctgagtg aaatctcgga     3120
tatactgagt gacattaacc ctgcacctgt gtcattaagc agctccctgt caagtgttaa    3180
gatcacacgc ccaaaatact cagctcaagc catcattgac tcgggcgggc cctgcagtgg    3240
gcatctccga agggaaaaag aagcatgcct cagcgtcatg cgtgaggctt gtgatgcggc    3300
taaacttagc gaccctgcca cgcaggaatg ctttctcgc atgtgggata gggttgacat     3360
gctgacctgg cgcaataagt ctgcttacca ggcgtttcgc atcttggatg caggtttga    3420 gtttctccca aagatgatac tcgagacacc gccgcctat ccgtgtgggt ttgtgatgct     3480
gcctcacacg cctgcacctt ccgtgagtgc agagagtgac cttaccattg gttcagtcgc    3540
cactgaagat gttccacgca tcctcgggaa aatagaaaac gccggcgagg tgcccaacca    3600
ggggctctcg gcatcctccg gggaagaacc gatgtatgca caacctgcca aagactcccg    3660
gatgtcgtcg cggggggttg acgagagcat aacggctccg tccgtaggta caggtggcgc    3720
```

```
tgacttactc actgatttgc caccttcagg tggtgtggat gtggacgggg ggggccgtt    3780
acggacggta agaaagaaaa ttgaaaggct cttcgaccaa tttagccgtc aggttttaa    3840
cctcgtctcc catctccctg ttttcttctc acacctcttc aaacctgaca gtggttattc    3900
tccgggtgat tggggttttg cagctttcac tctactttgc ctcttttgt gttatagcta    3960
cccattcttt ggcttcgctc ccctcttggg tgtatttct gggtcttctc ggagggtgcg    4020
catggggtt tttggctgct ggttggcttt tgcttgttggc ctgttcaagc ctgtgtccga    4080
cccagtcggc actgcttgtg aatttgactc gccagagtgt aggaacgtcc ttcattcttt    4140
tgagcttctc aaaccttggg accctgttcg cagccttgtt gtgggccccg caggtctcgg    4200
tcttgccatt cttggcaggt tactgggcgg ggcacgctac atctggcatt ttttgcttag    4260
gcttggcatt gttgcagatt gtgtcttggc tggagcttat gtgctttctc aaggtaggtg    4320
taaaaagtgc tggggatctt gtataagaac tgctcctaat gaaatcgcct tcaacgtgtt    4380
cccttttcacg cgtgcgacca ggtcgtcact catcgacctg tgcgaccggt ttcgtgcgcc    4440
aaaaggcatg gaccctgttt tcctcgctac tgggtggcgc gggtgctgga ccggtcaaag    4500
tcccattgag caaccctctg aaaaacccat cgcgttcgcc cagttggatg aaaagaggat    4560
cacggctaga actgtggtcg ctcagcctta tgatcctaac caagccgtaa agtgcttgcg    4620
ggtgctacag gcgggtgggg cgatggtggc cgaggcagtc ccaaaagtgg tcaaggtttc    4680
cgctattcca ttccgagccc cctttttcc caccggagtg aaggttgatc ctgagtgcag    4740
gatcgtggtc gaccccgaca cttttactac agctctccgg tctggttact ccaccacaaa    4800
cctcgtcctt ggtgtggggg actttgccca attgaatgga ttgaaaatca ggcaaatttc    4860
caagccttcg ggaggaggcc cacacctcat tgctgccctg catgttgcgt gctctatggc    4920
gttgcacatg cttgctgggg tttatgtaac tgcagtgggg tcttgcggta ccggcaccaa    4980
cgatccgtgg tgcactaacc cattcgccgt ccctggctac ggacctggct ctctctgcac    5040
gtccagattg tgcatctccc aacatggcct caccctgccc ttgacagcac ttgtggcagg    5100
attcggtctt caggaaattg ccttagtcgt tttgattttc gtttccatcg gaggcatggc    5160
tcataggttg agttgtaagg ctgacatgct gtgcatctta cttgcaatcg ccagctatgt    5220
ttgggtaccc cttacctggt tgctctgtgt gtttccttgc tggttgcgct ggttcacttt    5280
gcaccctctc accatcctat ggttggtgtt tttcctgatt tctgtaaata tgccttcggg    5340
aatcttggcc atggtgttat tggttgctct ttggcttttta ggccgttata ctaatgttgt    5400
tggtcttgtt accccctatg atattcacca ttacaccagt ggccccgcg gtgtagccgc    5460
cttggccacc gcaccagatg ggacttactt ggccgctgtc cgccgcgctg cgttgactgg    5520
ccgcaccgtg ctgtttaccc cgtctcagct tgggtccctt cttgagggcg ctttcaggac    5580
tcgaaagccc tcattgaaca ccgtcaatgt ggtcgggtcc tccatgggct ctggcggagt    5640
gttcactatc gacggaaaaa tcaagtgcgt gactgccgca catgtcctta cgggtaattc    5700
agccagggtt tccggggtcg gcttcaatca aatgcttgac tttaatgtaa agggggactt    5760
cgccatagct gattgcccga attggcaagg ggctgctccc aagacccaat ctgcgagga    5820
tggatggact ggtcgtgcct attggctgac atcctctggt gtcgaacccg gtatcattgg    5880
gaatggattt gccttctgct tcaccgcgtg cggcgattct ggatcccag tgattaccga    5940
agccggtgag cttgtcggcg ttcacacagg atcgaacaaa caaggaggag cattgtcac    6000
gcgcccctcg ggccagtttt gtaatgtggc gcccatcaag ctgagcgaat tgagtgaatt    6060
```

```
cttcgctgga cctaaggtcc cgctcggtga tgtgaaggtt ggcagccaca taattaaaga    6120
catatgcgag gtaccttcag acctttgcgc cttgcttgct gccaaacccg aactggaagg    6180
aggcctctct accgtccaac ttctgtgtgt gttttttcctc ctgtggagaa tgatggggca   6240
tgcctggacg cccttggttg ctgtgggggtt ttttatcttg aatgaggtcc tcccagctgt   6300
cctggtccgg agtgttttct cctttggaat gtttgtgcta tcttggctca cgccatggtc   6360
tgcgcaagtt ctgatgatca ggcttctaac agcagctctt aacaggaaca gattttcact   6420
cgccttttac agccttggtg cagcgaccgg ttttgtcgca gatctggcga caactcaagg   6480
gcatccgttg caggcagtaa tgaatttaag tacctatgcc ttcctgcctc ggatgatggt   6540
tgtgacatca ccagtcccag tgattgcgtg tggtgttgtg cacctccttg ccataatttt   6600
gtacttgttc aagtaccgtt gcctgcacaa tgtccttgtt ggcgacgag cgttctctgc    6660
ggcttttttc ttgcgatact ttgccgaggg aaagttgaga aagggggtgt cgcagtcctg   6720
cgggatgaat cacgagtcac tgactggagc cctcgctatg agactcaatg acgaggactt   6780
ggacttcctt acgaaatgga ctgattttaa gtgcttgtt tctgcttcca atatgaggaa    6840
tgcagcgggc caattcatcg aggcagccta tgctaaagca cttagaatag aacttgccca   6900
gttggtgcag gtcgacaagg ttcgaggtgt tttggccaaa cttgaagctt ttgctgatac   6960
tgtggcaccc caactctcgc ccggtgacat tgtcgttgct cttggccata cgcctgttgg   7020
tagtatcttc gacctaaagg ttggtagcac caagcatact ctccaagcca ttgagaccag   7080
agtccttgcc gggtccaaga tgaccgtggc gcgcgtcgtt gacccaaccc ccacgccccc   7140
acccgcaccc gtgcctatcc ccctcccgcc aaaaattctg gagaatggtc caacgcctg    7200
gggggatgag gaccgtttga ataagaagaa gaggcgcagg atggaagccg ttggcatctt   7260
tgttatgggc gggaagaagt accagaaatt ttgggacaag agctccggtg atgtgtttta   7320
cgaggaagtc catgataaca cagatgcatg ggagtgcttc agagttgaca accctgccga   7380
ctttgaccct gagaagggaa ctctgtgtgg gcataccacc attgaaaata aggcttacaa   7440
tgtctacgtc tccccatctg gcaggaagtt tctagtccct gtcaacccag agagtggaaa   7500
agcccaatgg gaagctgcaa ggcttttccgt ggagcaggcc cttggcatga tgaatgtcaa   7560
cggtgaactg acagccaaag aactggagaa actgaaaaga ataattgaca aactccagga   7620
cctgactaag gagcagtgtt taaactgcta gccgccagcg gcttgacccg ctgtggtcgc   7680
ggcggcttag ttgttactga gacagcggta aaaatagtca aatttcacaa ccggaccttc   7740
accctaggac ccgtaaactt aaaagtggcc agtgaggttg agctaaaaga cgcggtcgag   7800
cataaccaac acccggttgc aagaccggtt gatggcggtg ttgtgctcct gcgctccgca   7860
gttccttcgc ttatagacgt cttgatctcc ggcgctgatg catctcctaa gttactcgcc   7920
cgccacgggc cgggaaacac tgggatcgat ggcacgcttt ggactttga ggccgaggcc    7980
actagagagg aaattgcact cagtgcgcaa ataatacagg cttgtgacat taggcgcggc   8040
gacgcgcccg aaattggtct tccttataag ctgtaccctg ttaggggcaa ccctgagcgg   8100
gtaaaaggag ttttacagaa cacaaggttt ggagacatac cttacaaaac ccccagtgac   8160
actggaagcc cagtacacgc ggctgcctgc ctcacgccca tgccactcc ggtgactgat    8220
gggcgctccg tcttggctac gactatgccc tccggttttg agttgtatgt accgaccatt   8280
ccagcgtctg tccttgatta tcttgattct aggcctgact gccctaaaca gttgacagag   8340
cacgttgtgt aggatgccgc attgagagac ctctccaagt atgacttgtc cacccaaggt   8400
tttgtttgc ctggagttct tcgccttgtg cggaagtacc tgtttgccca tgtgggtaag    8460
```

-continued

```
tgcccgtccg ttcatcggcc ttccacttac cctgccaaga attctatggc tggaataaat   8520
gggaacaggt ttccaaccaa ggacattcag agcgtccctg aaatcgacgt tctgtgcgca   8580
caggccgtgc gagagaactg gcaaactgtc accccttgta ccctcaagaa acagtattgt   8640
gggaagaaga agactaggac aatactcggc accaataact tcattgcgtt ggcccaccga   8700
gcagcgttga gtggtgtcac ccagggcttc atgaaaaagg cgtttaactc gcccatcgcc   8760
ctcgggaaaa acaaatttaa ggagctgcag actccggtct taggcaggtg ccttgaagct   8820
gatcttgcat cctgcgatcg atccacacca gcaattgttc gctggtttgc cgccaatctt   8880
ctttatgaac ttgcctgtgc tgaggagcat ctgccatcgt acgtgctgaa ctgctgccac   8940
gacttactgg tcacgcagtc cggcgcggtg actaagagag gtggcctgtc gtctggcgac   9000
ccgattactg ctgtgtcaaa caccatttac agcttggtga tatatgcaca gcacatggtg   9060
ctcagttact ttaaaagtgg tcaccctcat ggccttctgt ttctgcaaga ccagctgaag   9120
tttgaggaca tgctcaaggt tcaacccctg atcgtctatt cggacgacct cgtgctgtat   9180
gccgagtctc ccaccatgcc aaactaccac tggtgggtgg aacatctgaa tcttatgctg   9240
ggttttcaga cggacccaag gaagacagcc ataacagatt cgccatcatt tctaggctgt   9300
aggataataa atggacgcca actagtcccc aaccgtgaca ggatcctcgc ggccctcgct   9360
taccatatga aggcaagcaa tgtttctgaa tactacgcct cggcggctgc aatactcatg   9420
gacagctgtg cttgtttaga gtatgatcct gaatggtttg aagagctcgt ggttgggatg   9480
gcgcagtgcg cccgcaagga cggctatagt ttccctggcc cgccgttctt cttgtccatg   9540
tgggaaaaac tcaggtccaa tcatgaaggg aagaagtcca gaatgtgcgg gtactgcggg   9600
gccccggctc cgtacgccac tgcctgtggc ctcgacgtct gtgtttatca cacccacttt   9660
caccagcatt gtccagtcat aatctggtgt ggccatccgg ctggttctgg ttcttgcagt   9720
gagtgcaaac ccccttagg gaaaggcaca agccctctag atgaggtgtt agaacaagtc   9780
ccgtacaagc ctccacggac tgtaatcatg catgtggagc agggtctcac ccctcttgac   9840
ccaggtagat accagactcg ccgcggatta gtctccgtta ggcgtggcat caggggaaat   9900
gaagttgacc taccagacgg tgattatgct agtaccgccc tgctccccac ttgtaaagag   9960
atcaacatgg tcgctgtcgc ctctaacgtg ttgcgcagca ggttcatcat cggtccgcct  10020
ggtgctggga aaacatactg gctccttcaa caggtccaag atggtgatgt catttacacg  10080
ccgactcacc agaccatgct cgacatgatt agggctttgg ggacgtgccg gttcaacgtc  10140
ccggcaggta caacgctgca attccccgcc cctcccgta ccggcccgtg ggttcgcatc  10200
ctagccggcg gttggtgtcc tggtaagaat tccttcctgg atgaagcagc gtattgcaat  10260
caccttgatg tcttgaggct tcttagcaaa actacccctta cctgcctagg agacttcaaa  10320
caactccacc cggtgggttt tgactctcat tgctatgttt ttgacatcat gcctcagacc  10380
caactgaaga ccatctggag gtttggacag aacatctgtg atgccatcca accagattac  10440
agggacaaac ttgtatccat ggtcaacaca acccgtgtaa cctacgtgga aagacctgtc  10500
aattatgggc aagtcctcac cccttaccac agggaccgag aggacggcgc catcacaatt  10560
gactccagtc aaggcgccac atttgatgtg gttacactgc atctgcccac taaagactca  10620
ctcaacaggc aaagagccct tgttgctatc accagggcaa acatgctat ctttgtgtat  10680
gacccacaca ggcaactgca gagcatgttt gatcttcctg cgaaaggcac accccgtcaac  10740
ctcgctgtgc accgtgacga gcagctgatc gtactagata gaaataacaa agaatgcacg  10800
```

```
gttgctcagg ctctaggcaa tgggdataaa ttcagggcca cagacaagcg cgttgtagat   10860
tctctctgcg ccatttgtgc agatctggaa gggtcgagct ctccgctccc caaggtcgca   10920
cacaacttgg ggttttattt ctcacctgat ttgacacagt ttgctaaact cccggtagaa   10980
cttgcacccc actggcccgt ggtgacaacc cagaacaatg aaaagtggcc agaccggctg   11040
gttgccagtc ttcgccctgt ccataagtat agccgtgcgt gcatcggtgc cggctacatg   11100
gtgggcccct cagtgtttct aggcacccct ggggttgtgt catactatct cacaaaattt   11160
gtcaagggcg aggctcaaat gcttccggag acagttttca gcaccggccg aattgaggta   11220
gattgccggg agtatcttga tgaccgggaa cgagaaattg ctgagtccct cccccatgcc   11280
ttcattggcg acgtcaaagg cactaccgtt ggaggatgtc accatgtcac ctccaaatac   11340
cttccgcgct tccttcccaa ggaatcagtc gcggtagtcg gggtttcaag ccccgggaaa   11400
gccgcaaaag cagtttgcac attaacagat gtgtacctcc cagaccttga ggcttacctc   11460
cacccagaga cccagtccag gtgctggaaa atgatgttgg acttcaagga agttcgactg   11520
atggtctgga aagacaagac ggcctatttt caacttgaag ccgccatttt cacctggtat   11580
cagcttgcga gctatgcctc gtacatccga gttcctgtta actctacggt gtatttggac   11640
ccatgcatgg gccctgccct ttgcaataga agggttgtcg ggtccaccca ttggggagct   11700
gacctcgcag tcactcctta tgattatggt gccaagatca ttttgtctag tgcataccat   11760
ggtgaaatgc ctcctgggta caaaatccta gcgtgtgcgg agttctcgct tgatgatcca   11820
gtgaggtaca agcacacctg gggatttgaa tcggatacag cgtatctgta cgagttcacc   11880
ggaaacggtg aggactggga ggattacaat gatgcgtttc gtgcgcgcca gaaagggaaa   11940
atttataagg ccactgccac cagcatgagg tttcattttc ccccgggccc tgtcattgaa   12000
ccaactttgg gcctgaactg aaatgaaatg ggggctatgc aaagccttt ctacaaaatt   12060
ggccaacttt ttgtggatgc tttcacggag tttttggtgt ccattgttga tatcatcata   12120
tttctggcca ttttgtttgg cttcaccatc gccggctggc tggtggtctt ctgcatccga   12180
ttggtttgct ccgcggtact ccgtgcgcgc cctaccgttc accctgagca attacagaag   12240
atcttatgag gcctttcttt ctcagtgcca ggtggacatt cccacctggg gaaccaaaca   12300
tcccttgggg atgctttggc accataaggt gtcaaccctg attgatgaaa tggtgtcgcg   12360
tcgaatgtac cgcatcatgg aaaaagcagg acaggctgcc tggaaacagg tggtgagcga   12420
ggccacgctg tctcgtatta gtggtttgga tgtggtggct cattttcagc atcttgctgc   12480
cattgaagcc gagaactgta aatatttggc ctctcggctg cccatgctac acaacctgcg   12540
catgacaggg tcaaatgtaa ccttagtgta taatagcact ttgaatcagg tgttcgctat   12600
cttttccaacc cctggttccc ggccaaagct tcatgatttt cagcaatggc taatagctgt   12660
acattcctct atattttcct ccgttgcggc ttcttgtact cttttttgttg tgctgtggtt   12720
gcgaatccca attctacgta ctgttttttgg tttccactgg ttaggggcaa tttctcttc   12780
gaactcacag tgaattacac ggtgtgccca ccttgcctca cccgacaagc agccgctgag   12840
atctatgaac ccggcaggtc tctttggtgc aggatagga atgaccgatg tagtgagagc   12900
gatcatgacg aactagggtt catggttccg tctggcctct ccagcgaagg ccacttgacc   12960
agtgtttacg cttggttggc gtttctgtcc ttcagctaca cggcccagtt ccatcccgag   13020
atatttggga tagggaatgt gagtaaagtt tatgttgaca tcaagcacca attaatctgc   13080
gccgttcatg acgggcagaa caccaccttg cctcgccatg acaatatttc agccgtattt   13140
cagacctatt atcaacatca ggtcgacggc ggcaactggt ttcacctaga atggctgcgt   13200
```

```
cccttcttttt cctcttggtt ggttttaaat gtttcgtggt ttctcaggcg ttcgcctgca    13260
agccatgttt cagttcgagt ctttcggaca tcaagaccaa cactaccgca gcatcaggct    13320
ttgtcgtcct ccaggacatc agctgcctta ggcatggcga ctcgtcctct cagacgattc    13380
gcaaaagctc tcagtgccgc acggcgatag ggacgcccgt gtacatcacc atgcagcca    13440 atgtcacaga tgagaattat ttgcattctt ctgatctcct catgctttct tcttgccttt    13500
tctatgcttc tgagatgagt gaaaagggat tcaaggtggt gtttggcaat gtgtcaggca    13560
tcgtggctgt gtgtgtcaac tttaccagct acgtccaaca cgtcaaggag ttcacccaac    13620
gctccttggt agtcgatcat gtgcggctgc ttcacttcat gacacctgag accatgaggt    13680
gggcaaccgt tttagcctgt cttttttgcca tcttgctggc aatttgaatg ttcaagtatg    13740
ttggggaaat gcttgaccgc gggctgttgc tcgcgattgc cttttttgtg gtgtatcgtg    13800
ccgttctgtt ttgctgtgat cgtcgacgcc aacagcaaca gcagctctca tttccagttg    13860
atttataact tgacgttatg cgagctgaat ggcacagatt ggctggttga taaatttgat    13920
tgggcagtgg agacttttgt cattttttccc gtgttgactc acattgtttc ttatggtgca    13980
ctcaccacca gccatttcct tgacacagtt ggtctggtta ctgtatccgc cgccgggttt    14040
tgtcacgggc ggtatgtctt gagtagcatc tacgcggtct gtgccctggc tgcgttggtt    14100
tgctttgtca tcagatttgc gaagaactgc atgtcctggc gctactcatg tactagatac    14160
accaacttcc ttctagacac taagggcaga ctctatcgtt ggcggtcgcc tgtcatcata    14220
gagaaagggg gcaaggttga ggtcgaaggc catctgatcg acctcaaaaa agttgtgctt    14280
gatggttccg cggcaacccc tttaaccaga atttcagcgg aacaatggtg tcgtccctag    14340
acgacttttg caatgatagc acagctccac ggaaggtgct cttggcgttt tctatcacct    14400
acacgccagt gatgatatat gctctaaagg taagtcgcgg ccgactgttg gggcttctgc    14460 acctttttgat ttttctgaac tgtgcccttta ccttcgggta catgacattc acgcactttc    14520
agagcacaaa tagggtcgcg ctcactatgg gagcagtagt cgcactcctt tgggggtgt    14580 actcagccat agaaacctgg aaattcatca cctccagatg ccgtttgtgc ttgctaggcc    14640
gcaagtacat tttggcccct gcccaccacg tcgaaagtgc cgcgggcttt catccgattg    14700
cggcaaatga taaccacgca tttgtcgtcc ggcgtcccgg ctccactacg gtcaacggca    14760
cattggtgcc cgggttgaaa agcctcgtgt tgggtggcag aaaagctgtt aaacaggag    14820 tggtaaaccct tgtcaaatat gccaaataac aacggcaagc agcaaaagaa aaagaagggg    14880
aatggccagc cagtcaatca gctgtgccag atgctgggta agatcatcgc ccagcaaaac    14940
cagtccagag gtaagggacc ggggaagaaa aataagaaga aaacccggga gaagcccat    15000 tttcctctag cgaccgaaga tgacgtcagg catcacttta cccctagtga gcggcaattg    15060
tgtctgtcgt cgatccagac tgcctttaac cagggcgctg gaacttgcac cctgtcagac    15120
tcagggagga taagttacac tgtggagttt agtttgccga cgcatcatac tgtgcgcctg    15180
attcgcgcca cagcatcaac ctcagcatga tgggctggca ttcttgaagc accacagtgt    15240
taggattgga agaatgtgtg gtgaatggca ctgattgaca ctgtgcctct aagtcaccta    15300
ttcaattagg gcgaccgtgt gggggtaaag tttaattggc gagaaccatg cggccgcaat    15360
taaaaaaaaa aaaaaaaaa aaaaaa                                          15386

<210> SEQ ID NO 2
<211> LENGTH: 15444
<212> TYPE: DNA
```

<213> ORGANISM: Artificial Sequence
<220> FEATURE:
<223> OTHER INFORMATION: Synthetic Construct

<400> SEQUENCE: 2

```
tatgtacgta taggtgttgg ctctatgcct ttggcatttg tattgtcagg agctgtgacc      60
attggcacag cccaaaactt gctacacaga aacacccttc tgtgatagcc tccttcaggg     120
gagcttaggg tttgtcccta gcaccttgct tccggagttg cactgcttta cggtctctcc     180
accccttaa ccatgtctgg gatacttgat cggtgcacgt gtaccccaa tgccagggtg       240
tttatggcgg agggccaagt ctactgcaca cgatgcctca gtgcacggtc tctccttccc     300
ctgaacctcc aagtttctga gctcggggtg ctaggcctat tctacaggcc cgaagagcca     360
ctccggtgga cgttgccacg tgcattcccc actgttgagt gctcccccgc cggggcctgc     420
tggctttctg caatctttcc aatcgcacga atgaccagtg gaaacctgaa cttccaacaa     480
agaatggtac gggtcgcagc tgagctttac agagccggcc agctcacccc tgcagtcttg     540
aaggctctac aagtttatga acggggttgc cgctggtacc ccattgttgg acctgtccct     600
ggagtggccg ttttcgccaa ttccctacat gtgagtgata aaccttcc gggagcaact       660
cacgtgttga ccaacctgcc gctcccgcag agacccaagc tgaagacttt tgccccttt     720
gagtgtgcta tggctactgt ctatgacatt ggtcatgacg ccgtcatgta tgtggccgaa     780
aggaaaatct cctgggcccc tcgtggcgag gatgaagtga aatttgaagc tgtccccggg     840
gagttgaagt tgattgcgaa ccggctccgc acctccttcc cgccccacca cacagtggac     900
atgtctaagt tcgccttcac agcccctggg tgtggtgttt ctatgcgggt cgaatgccaa     960
cacggctgcc ttcccgctga cactgtccct gaaggcaact gctggtggag cttgtttgac    1020
ttgcttccac tggaagttca gaacaaagaa attcgccatg ctaaccaatt tggctaccag    1080
accaagcatg gtgtctctgg caaataccta cagcgtaggc tgcaagttaa tggtctccga    1140
gcagtaactg acctaaacgg acctatcgtc gtacagtact tctccgttaa ggagagttgg    1200
atccgccatt tgaaactggc gggagaaccc agctactctg ggtttgagga cctcctcaga    1260
ataagggttg agcctaacac gtcgccattg gctgacaagg aagaaaaat ttttccggttt    1320
ggcagtcaca agtggtacgg cgctggaaag agagcaagaa aagcgcgctc ttgtgcgact    1380
gctacagtcg ctggccgcgc tttgtccgtt tgtgaaaccc ggcaggccaa ggagcacgag    1440
gttgccggcg ccaacaaggc tgagcacctc aaacactact ccccgcctgc cgaagggaat    1500
tgtggttggc actgcatttc cgccatcgcc aaccggatgg tgaattccaa atttgaaacc    1560
accctttccg aaagagtgag accttcagat gactgggcta ctgacgagga tcttgtgaat    1620
gccatccaaa tcctcagact ccctgcggcc ttagacagga acggtgcttg tactagcgcc    1680
aagtacgtac ttaagctgga aggtgagcat tggactgtca ctgtgacccc tgggatgtcc    1740
ccttctttgc tccctcttga atgtgttcag ggctgttgtg gcacaaggg cggtcttggt    1800
accccagatg cagtcgaggt ctccggattt gaccctgcct gccttgaccg gctggctgag    1860
gtgatgcacc tgcctagcag tgctatccca gccgctctgg ccgaaatgtc tggcgattcc    1920
gatcgttcgg cttctccggt caccaccgtg tggactgttt cgcagttctt tgcccgtcac    1980
agcggaggga atcaccctga ccaagtgcgc ttagggaaaa ttatcagtct tgtcaggtg    2040
attgaggact gctgctgttc ccagaacaaa ccaaccgggg tcaccccgga ggaggtcgca    2100
gcaaagattg acctgtacct ccgtggtgca acaaatcttg aagaatgctt ggccaggctt    2160
gagaaagcgc gcccgccgcg cgtaatcgac accttctttg attgggatgt tgtgctccct    2220
```

```
gggggttgagg cggcaaccca gacgatcaag ctgccccagg tcaaccagtg tcgtgctctg    2280
gtccctgttg tgactcaaaa gtccttggac aacaactcgg tcccctgac cgccttttca     2340 ctggctaact actactaccg tgcgcaaggt gacgaagttc gtcaccgtga aagactaacc    2400
gccgtgctct ccaagttgga aaaggttgtt cgagaagaat atgggctcat gccaaccgag    2460
cctggtccac ggcccacact gccacgcggg ctcgacgaac tcaaagacca gatggaggag    2520
gacttgctga aactggctaa cgcccagacg acttcggaca tgatggcctg ggcagtcgag    2580
caggttgact taaaaacttg ggtcaagaac tacccgcggt ggacaccacc acccctccg     2640 ccaaaagttc agcctcgaaa aacgaagcct gtcaagagct gccggagag aaagcctgtc    2700 cccgccccgc gcaggaaggt tgggtccgat tgtggcagcc cggtttcatt aggcggcgat    2760
gtccctaaca gttgggaaga tttgctgtt agtagcccct ttgatctccc gacctcacct    2820
gagccggcaa caccttcaag tgagctggtg attgtgtcct caccgcaatg catcttcagg    2880
ccggcgacac ccttgagtga gccggctcca attcccgcac ctcgcggaac tgtgtctcga    2940
ccggtgacac ccttgagtga gccgatccct gtgcccgcac cgcggcgtaa gtttcagcag    3000
gtgaaaagat tgagttcggc ggcggcaatc ccaccgtacc agaacgagcc cctggatttg    3060
tctgcttcct cacagactga atatgaggcc tctccccag caccgccgca gagcgggggc    3120
gttctgggag tagaggggca tgaagctgag gaaaccccga gtgaaatctc ggacatgtcg    3180
ggtaacatta aacctgcgtc cgtgtcatca agcagctcct tgtccagcgt gagaatcaca    3240
cgcccaaaat actcagctca agccatcatc gactcgggcg ggccctgcag tgggcatctc    3300
caagaggtaa aggaaacatg ccttagtgtc atgcgcgagg catgtgatgc gactaagctt    3360
gatgaccctg ctacgcagga atggctttct cgcatgtggg atcgggtgga catgctgact    3420
tggcgcaata cgtctgctta ccaggcgatt tgcaccttag atggcaggtt aaagttcctc    3480
ccaaaaatga tactcgagac accgccgccc tatccgtgtg agtttgtgat gatgcctcac    3540
acgcctgcac cttccgtagg tgcggagagc gaccttacca ttggctcagt tgctactgaa    3600
gatgttccac gcatcctcga gaaaatagaa aatgtcggcg agatggccaa ccagggaccc    3660
ttggccttct ccgaggataa accggtagat gaccaacttg tcaacgaccc ccggataccg    3720
tcgcggaggc ctgacgagag cacatcagct ccgtccgcag gcacaggtgg cgccggctct    3780
tttaccgatt tgccgccttc agatggcgcg gatgcggacg ggggggggcc gtttcggacg    3840 gtaaaagaa aagctgaaag gctctttgac caactgagcc gtcaggtttt tgacctcgtc    3900
tcccatctcc ctgttttctt ctcacgcctt ttctaccctg gcggtggtta ttctccgggt    3960
gattggggtt ttgcagcttt tactctattg tgcctctttt tatgttacag ttacccagcc    4020
tttggtattg ctccctctt gggtgtgttt tctgggtctt ctcggcgcgt tcgaatgggg    4080 gttttttggct gctggttggc ttttgctgtt ggtctgttca agcctgtgtc cgacccagtc    4140
ggcgctgctt gtgagtttga ctcgccagag tgtagaaaca tccttcattc ttttgagctt    4200
ctcaaacctt gggaccctgt tcgcagcctt gttgtgggcc ccgtcggtct cggtcttgcc    4260
attcttggca ggctactggg cggggcacgc tgtatctggc acttttttgct taggcttggc    4320 attgttgcag actgtatctt ggctggagct tacgtgcttt ctcaaggtag gtgtaaaaag    4380
tgctggggat cttgtataag aactgctcct aatgaggtcg cttttaacgt gtttccttcc    4440
acacgtgcga ccaggtcgtc acttatcgac ctgtgcgatc ggttttgtgc accaaaagga    4500
atggacccca ttttctcgc cactgggtgg cgcgggtgct gggccggccg aagccccatt    4560
```

```
gagcaaccct ctgaaaaacc catcgcgttt gcccaattgg atgaaaagaa gattacggct    4620
aggactgtgg tcgcccagcc ttatgacccc aaccaagccg taaagtgctt gcgggtgttg    4680
caggcgggtg gggcgatggt ggctgaggcg gtcccaaaag tggtcaaggt ttccgctgtt    4740
ccattccgag cccccttctt tcccactgga gtgaaagttg atcctgattg cagggtcgtg    4800
gttgaccctg atactttcac tgcagctctc cggtctggct actccaccac aaacctcgtc    4860
cttggtgtag gggactttgc ccagctgaat ggattaaaaa tcaggcaaat ttccaagcct    4920
tcaggggag gcccacatct catggctgcc ctgcatgttg cctgctcgat ggctctgcac    4980
atgcttgctg ggatctatgt gactgcgtgt ggttcttgcg gcaccggcac caacgacccg    5040
tggtgcgcta acccgtttgc cgtccctggc tacggacctg gctctctctg cacgtccaga    5100
ttgtgcattt cccaacacgg cctaccctg cccttgacag cacttgtggc gggattcggt    5160
attcaagaaa ttgccttagt cgttttgatt tttgtttcca tcggaggcat ggctcatagg    5220
ttgagctgta aggctgacat gctgtttgtt ttgcttgcaa tcgccagcta tgtttgggta    5280
cctcttacct ggttgctttg tgtgtttcct tgctggttgc gctgttttc tttgcacccc    5340
ctcaccgtcc tatggttggt gttttttcttg atttctgtga atatgccttc aggaatcttg    5400
gccatggtgt tgttggtttc tctttggctt cttggtcgtt atactaatgt tgctggcctt    5460
gtcaccccct acgacattca ccattacacc agcggccccc gcggtgttgc cgccttggct    5520
accgctccag atgggaccta cttggccgct gtccgccgcg ctgcgttgac tggccgcacc    5580
atgctgttta ccccgtccca gcttgggtct cttcttgagg gtgcttcag aactcgaaag    5640
ccctcactga acaccgtcaa tgtgatcggg tcctccatgg gctctggcgg ggtgtttacc    5700
atcgacggga aagtcaagtg cgtaactgcc gcacatgtcc ttacgggcaa ttcagctcgg    5760
gttttccggg tcggcttcaa tcaaatgctt gactttgacg taagggaga ttttgctata    5820
gctgattgcc cgaattggca aggggctgcc cccaagaccc aattctgcac ggatggatgg    5880
actgccgtg cctattggct aacatcctct ggcgtcgaac ccggcgtcat tggaaaagga    5940
ttcgccttct gcttcaccgc atgtggcgat tccgggtccc cagtgatcac cgaggccggt    6000
gagcttgtcg gcgttcacac gggatcgaat aaacaagggg ggggcattgt tacgcgcccc    6060
tcaggccagt tttgtaatgt ggcacccatc aagctaagcg aattaagtga attctttgct    6120
gggcctaagg tcccgctcgg tgatgtgaag gtcggcagcc acataattat agacataagc    6180
gaggtgcctt cagatctttg tgccttgctt gctgccaaac ctgaactgga aggaggcctc    6240
tccaccgtcc aacttctttg tgtgttttt ctcctgtgga gaatgatggg acatgcctgg    6300
acgcccttgg ttgctgtgag tttctttatt ctgaatgagg ttctcccctgc cgtcctggtc    6360
cggagtgttt tctcctttgg aatgtttgtg ctatcctggc tcacgccatg gtctgcgcaa    6420
gttctgatga tcaggcttct gacagcagct cttaacagga acagatggtc acttgccttt    6480
ttcagcctcg gtgcagtgac cggttttgtc gcagatcttg cggccactca ggggcatccg    6540
ttgcaggcag tgatgaattt gagcacctat gcattcctgc ctcggatgat ggttgtgacc    6600
tcaccagtcc cagtgatcac gtgtggtgtc gtgcacctac ttgccatcat tttgtacttg    6660
tttaagtacc gtgccctgca ccatatcctt gttggcgatg agtgttctc tgcggctttc    6720
ttcttgagat actttgccga gggaaagttg agggaagggg tgtcgcaatc ctgcggaatg    6780
aatcatgagt ctctgactgg tgccctcgct atgagactca atgacgagga cttggatttc    6840
cttatgaaat ggactgattt taagtgcttt gtttctgcgt ccaacatgag gaatgcagcg    6900
ggtcaatta tcgaggctgc ctatgctaaa gcacttagag tagaactggc ccagttggtg    6960
```

```
caggttgata aagttcgagg tactttggcc aaacttgaag cttttgctga taccgtggca   7020
cctcaactct cgcccggtga cattgttgtc gctctcggcc acacgcctgt tggcagtatc   7080
ttcgacctaa aggttggtag caccaagcat accctccaag ccattgagac cagagtcctt   7140
gctgggtcca aaatgaccgt ggcgcgcgtc gtcgacccga cccccacgcc cccgcccgca   7200
cccgtgccca tcccccctccc accgaaagtt ctggagaatg ccccaacgc ttgggggat    7260 gaggaccgtt tgaataagaa gaagaggcgc aggatgaag ccctcggcat ctatgttatg    7320
ggcgggaaaa agtaccagaa attttgggac aagaattccg gtgatgtgtt ttatgaggag   7380
gtccataata acacagatga ttgggagtgt ctcagagttg gcgaccctgc cgactttgac   7440
cctgagaagg gaactctgtg tggacatgtc accattgaaa acaaggctta ccatgtttac   7500
acctccccat ctggtaagaa gttcttggtc cccgtcaacc cagagaatgg aagagttcaa   7560
tgggaagctg caaagctttc cgtggagcag gccctaggta tgatgaatgt cgacggcgaa   7620
ctgactgcca aagaactgga gaaactgaaa agaataattg acaaactcca gggcctgact   7680
aaggagcagt gttaaactg ctagccgcta gcgacttgac ccgctgtggt cgcggcggct    7740
tggttgttac tgaaacagcg gtaaaaatag tcaaatttca caaccggacc ttcaccctgg   7800
gacctgtgaa tttaaaagtg gccagtgagg ttgagctaaa agacgcggtt gagcacaacc   7860
aacacccggt tgcgagaccg atcgatggtg gagttgtgct cctgcgttcc gcggttcctt   7920
cgcttataga cgtcttgatc tccggtgctg atgcatctcc caagttactt gcccatcacg   7980
ggccgggaaa cactgggatc gatggcacgc tctgggattt tgagtccgaa gccactaaag   8040
aggaagtcgc actcagtgcg caaataatac aggcttgtga cattaggcgc ggcgacgctc   8100
ctgaaattgg tctcccttac aagctgtacc ctgttagggg taaccctgag cgggtgaaag   8160
gagttctgca gaatacaagg tttggagaca taccttacaa aaccccagt gacactggaa    8220 gcccagtgca cgcggctgcc tgccttacgc ccaacgccac tccggtgact gatgggcgct   8280
ccgtcttggc cacgaccatg cccccgggt ttgagttata tgtaccgacc ataccctgcgt   8340 ctgtccttga ttaccttgac tctaggcctg actgccctaa acagctgaca gagcacggct   8400
gcgaagatgc cgcactgaaa gacctctcca aatatgactt gtccacccaa ggctttgttt   8460
tacctggagt tcttcgcctt gtgcggaaat acctgtttgc ccatgtaggt aagtgcccac   8520
ccgttcatcg gccttctact tacccctgcta agaattctat ggctggaata aatgggaata   8580
ggttcccaac caaggacatt cagagcgtcc ctgaaatcga cgttctgtgc gcacaggctg   8640
tgcgagaaaa ctggcaaact gtcacccctt gcactcttaa gaaacagtat tgcgggaaga   8700
agaagactag gaccatactc ggcaccaata acttcatcgc actagcccac cgagcagtgt   8760
tgagtggtgt tacccagggc ttcatgaaaa aggcgtttaa ctcgcccatc gccctcggaa   8820
agaacaagtt taaggagcta cagactccgg tcctgggcag gtgccttgaa gctgatctcg   8880
catcctgcga tcgatccacg cctgcaattg tccgctggtt tgccgccaac cttctttatg   8940
aacttgcctg tgctgaagag catctaccgt cgtacgtgct gaactgctgc cacgacttac   9000
tggtcacgca gtccggcgca gtgactaaga gaggtggcct gtcgtctggc gacccgatca   9060
cctctgtgtc taacaccatt tatagttttgg tgatctatgc acagcatatg gtgcttagtt   9120
acttcaaaag tggtcacccc catggccttc tgttcttaca agaccagcta agtttgagg    9180 acatgctcaa ggttcaaccc ctgatcgtct attcggacga cctcgtgctg tatgccgagt   9240
ctcccaccat gccaaactat cactggtggg ttgaacatct gaatttgatg ctggggtttc   9300
```

```
agacggaccc aaagaagaca gcaataacag actcgccatc atttctaggc tgtagaataa    9360
taaatgggcg ccagctagtc cccaaccgtg acaggatcct cgcggccctc gcctatcaca    9420
tgaaggcgag taatgtttct gaatactatg cctcagcggc tgcaatactc atggacagct    9480
gtgcttgttt ggagtatgat cctgaatggt ttgaagaact tgtagttgga atagcgcagt    9540
gcgcccgcaa ggacggctac agctttcccg gcacgccgtt cttcatgtcc atgtgggaaa    9600
aactcaggtc caattatgag gggaagaagt cgagagtgtg cgggtactgc ggggccccgg    9660
ccccgtacgc tactgcctgt ggcctcgacg tctgcattta ccacacccac ttccaccagc    9720
attgtccagt cacaatctgg tgtggccatc agcgggttc tggttcttgt agtgagtgca     9780
aatcccctgt agggaaaggc acaagccctt tagacgaggt gctggaacaa gtcccgtata    9840
agcccccacg gaccgttatc atgcatgtgg agcagggtct cacccccctt gatccaggta    9900
gataccaaac tcgccgcgga ctggtctctg tcaggcgtgg aattagggga aatgaagttg    9960
aactaccaga cggtgattat gctagcaccg ccttgctccc tacctgcaaa gagatcaaca   10020
tggtcgctgt cgcttccaat gtattgcgca gcaggttcat catcggccca cccggtgctg   10080
ggaaaacata ctggctcctt caacaggtcc aggatggtga tgttatttac acaccaactc   10140
accagaccat gcttgacatg attagggctt tggggacgtg ccggttcaac gtcccggcag   10200
gcacaacgct gcaattcccc gtcccctccc gcaccggtcc gtgggttcgc atcctagccg   10260
gcggttggtg tcctggcaag aattccttcc tagatgaagc agcgtattgc aaccaccttg   10320
atgttttgag gcttctcagt aaaactaccc tcacctgtct aggagacttc aagcaactcc   10380
acccagtggg ttttgattct cattgctatg ttttttgacat catgcctcaa actcaactga   10440
agaccatctg gaggtttgga cagaatatct gtgatgccat tcagccagat tacagggaca   10500
aactcatgtc catggtcaac acaacccgtg tgacctacgg gaaaaacct gtcaggtatg    10560
ggcaggtcct cacccctac acagggacc gagaggacga cgccatcact attgactcca     10620
gtcaaggcgc cacattcgat gtggttacgt tgcatttgcc cactaaagat tcactcaaca   10680
ggcaaagagc ccttgttgcc atcaccaggg caagacacgc tatctttgcg tatgacccac   10740
acaggcagct gcagggctta tttgatcttc ctgcaaaagg cacacccgtc aacctcgcag   10800
tgcaccgcga cgggcagctg atcgtgctgg atagaaataa caaagaatgc acggttgctc   10860
aggctctagg caacggggat aaatttaggg ccacagataa gcgtgttgta gattctctcc   10920
gcgccatttg tgctgatcta gaagggtcga gctctccgct cccaaggtc gcacacaact    10980
tgggatttta tttctcacct gatttaacac agtttgctaa actcccagta gaacttgcac   11040
ctcactggcc cgtggtgaca acccagaaca atgaaaagtg gccagatcgg ctggttgcca   11100
gccttcgccc tatccataaa tacagccgcg cgtgcatcgg tgccggctat atggtgggcc   11160
cttcggtgtt tctaggcact cctggggtcg tgtcatacta tctcacaaaa tttgttaagg   11220
gcgaggctca attgcttcca gagacggttt tcagcaccgg ccgaattgag gtagactgcc   11280
gggaatatct tgatgatcgg gagcgagaag ttgctgcgtc cctcccacac gctttcattg   11340
gcgacgtcaa aggcactacc gttggaggat gtcatcatgt cacctccaga tacctcccgc   11400
gcgtccttcc caaggaatca gttgcggtag tcggggtttc aagccccgga aaagccgcga   11460
aagcattgtg cacactgaca gatgtgtacc tcccagatct tgaagcctat ctccacccgg   11520
agacccagtc caagtgctgg aaaatgatgt tggacttcaa agaagttcga ctaatggtct   11580
ggaaagacaa aacagcctat ttccaacttg aaggtcgcta tttcacctgg tatcagcttg   11640
ccagctatgc ctcgtacatc cgtgttcctg tcaactctac ggtgtacttg gacccctgca   11700
```

```
tgggccccgc cctttgcaac aggagagtcg tcgggtccac ccattggggg gctgacctcg   11760
cggtcacccc ttatgattac ggcgctaaaa ttatcctgtc tagcgcgtac catggtgaaa   11820
tgccccccgg atacaaaatt ctggcgtgcg cggagttctc gttggatgac ccagttaagt   11880
acaaacatac ctgggggttt gaatcggata cagcgtatct gtatgagttc accggaaacg   11940
gtgaggactg ggaggattac aatgatgcgt ttcgtgcgcg ccaggaaggg aaaatttaca   12000
aggccactgc caccagcttg aagtttcatt ttccccgggg ccctgtcatt gaaccaactt   12060
taggcctgaa ttgaaatgaa atggggtcca tgcaaagcct ttttcacaaa attggccaac   12120
tttttgtgga tgctttcacg gagttcttgg tgtccattgt tgatatcatc atattttttgg  12180 ccatttttgtt tggcttcacc atcgccggtt ggctggtggt cttttgcatc agattggttt   12240
gctccgcgat actccgtacg cgctctgcca ttcactctga gcaattacag aagatcttat   12300
gaggcctttc tttcccagtg ccaagtggac attcccacct ggggaactaa acatcctttg   12360
gggattctct ggcaccataa ggtgtcaacc ctgattgatg aaatggtgtc gcgtcgaatg   12420
taccgcatca tggaaaaatc agggcaggct gcctggaaac aggtggtgag cgaggctacg   12480
ctgtctcgca ttagtagttt ggatgtggtg gctcattttc agcatctagc cgccattgaa   12540
gccgagacct gtaaatattt ggcctcccgg ctgcccatgc tacacaacct gcgcatgaca   12600
ggttcaaatg taaccatagt gtataatagc actttgaatc aggtgtttgc tatttttcca   12660
acctctggtt cccggccaaa gcttcatgat tttcagcaat ggttaatagc tgtacattcc   12720
tccatatttt cctctgttgc agcttcttgt actcttttttg ttgtgctgtg gttgcgtgtt  12780
ccaatactac gtactgtttt tggtttccgc tggttagggg caattttttct ttcgaactca   12840 cagtgaatta cacggtgtgt ccaccttgcc tcacccggca agcagccgca gagatctacg   12900
aacccggtag gtctctttgg tgcaggatag ggtatgaccg atgtgaggag gatgatcatg   12960
acgagctagg gtttatggta ccgcctggcc tctccagcga aggccacttg actagtgttt   13020
acgcctggtt ggcgttcttg tccttcagct acacggccca gttccatccc gagatattcg   13080
ggatagggaa tgtgagtcga gtttatgttg acatcaaaca tcaactcatc tgcgccgaac   13140
atgacgggca gaacaccacc ttgcctcgtc atgacaacat ttcagccgtg tttcagacct   13200
attaccaaca tcaagtcgat ggcggcaatt ggtttcacct agaatggctt cgtcccttct   13260
tttcctcgtg gctggtttta atgtctcttg gtttctcag gcgttcgcct gcaaccatg    13320 tttcagttcg agtctcgcag atattgagac caacaccacc gcagcggcaa gctttgctgt   13380
cctccaagac atcagttgcc ttaggcatcg cgactcggcc tctgaggcga ttcgcaaaat   13440
ccctcagtgc cgtacggcga tagggacacc cgtgtatatt actatcacag ccaatgtgac   13500
agatgagaat tatttacatt cttctgatct cctcatgctt tcttcttgcc ttttctatgc   13560
ttctgagatg agtgaaaagg gatttaaggt ggtatttggc aatgtgtcag gcatcgtggc   13620
tgtgtgtgtc aattttacca gctacgtcca acatgtcaag gagttcaccc aacgctccct   13680
ggtggtcgac catgtgcggt tgctccattt catgacacct gagaccatga ggtgggcaac   13740
tgttttagcc tgtcttgttg ccattctgtt ggcaatttga atgtttaagt atgttggaga   13800
aatgcttgac cgcgggctgt tgctcgcaat tgctttcttt tgtggtgtatc gtgccgttct   13860 gtttttgctgt gctcgccaac gccagcagcg acagcagctc ccatctacag ctgatttaca   13920
acttgacgct atgtgagctg aatggcacag attggctagc tgacaaattt gattgggcag   13980
cggagagttt tgtcatcttt cccgttttga ctcacattgt ctcctatggt gccctcacta   14040
```

```
ctagccattt ccttgacacg gtcgctttag ccactgtgtc taccgccggg tttgttcacg    14100
ggcggtatgt cctaagtagc atctacgcgg tctgtgccct ggctgcgttg acttgcttcg    14160
tcattaggtt tgcaaagaat tgcatgtcct ggcgctacgc gtgtaccaga tataccaact    14220
ttcttctgga cactaagggc agactctatc gttggcggtc gcctgtcatc atagagaaaa    14280
ggggcaaagt tgaggtcgaa ggtcatctga tcgacctcaa aagagttgtg cttgatggtt    14340
ccgtggcaac ccctataacc agagtttcag cggaacaatg gggtcgtcct tagatgactt    14400
ctgtcatgat agcacggctc cagaaaaggt gcttttggcg ttttctatta cctacacgcc    14460
agtgatgata tatgccctaa aggtgagtcg cggccgactg ctagggcttc tgcacctttt    14520
gatcttcctg aattgtgctt tcaccttcgg gtacatgact ttcgcgcact ttcagagtac    14580
aaataaggtc gcgctcacta tgggagcagt agttgcactc ctttgggggg tgtactcagc    14640
catagaaacc tggaaattca tcacctccag atgccgtttg tgcttgctag gccgcaagta    14700
cattctggcc cctgcccacc acgttgaaag tgccgcaggc tttcatccga ttgcggcaaa    14760
tgataaccac gcatttgtcg tccggcgtcc cggctccact acggtcaacg gcacattggt    14820
gcccgggtta aaaagcctcg tgttgggtgg cagaaaagct gttaaacagg gagtggtaaa    14880
ccttgtcaaa tatgccaaat aacaacggca agcagcagaa gagaaagaag ggggatggcc    14940
agccagtcaa tcagctgtgc cagatgctgg gtaagatcat cgctcagcaa aaccagtcca    15000
gaggcaaggg accgggaaag aaaaataaga agaaaaaccc ggagaagccc catttcctc     15060 tagcgactga agatgatgtc agacatcact ttaccctag tgagcggcaa ttgtgtctgt      15120
cgtcaatcca gaccgccttt aatcaaggcg ctgggacttg caccctgtca gattcaggga    15180
ggataagtta cactgtggag tttagtttgc ctacgcatca tactgtgcgc ctgatccgcg    15240
tcacagcatc accctcagca tgatgggctg gcattcttga gacatctcag tgtttgaatt    15300
ggaagaatgt gtggtgaatg gcactgattg acattgtgcc tctaagtcac ctattcaatt    15360
agggcgaccg tgtgggggtg agatttaatt ggcgagaacc atgcggccga aattaaaaaa    15420
aaaaaaaaaa aaaaaaaaaa aaaa                                           15444
```

<210> SEQ ID NO 3
<211> LENGTH: 15013
<212> TYPE: DNA
<213> ORGANISM: Artificial Sequence
<220> FEATURE:
<223> OTHER INFORMATION: Synthetic Construct

<400> SEQUENCE: 3

```
atgacgtata ggtgttggct ctatgccacg gcatttgtat tgtcaggagc tgtgaccatt       60
ggcacagccc aaaacttgct gcacggaaaa cgcccttccg tgacagcctt cttcagggga     120 gcttagggt ctgtccctaa caccttgctt ctggagttgc actgctttac ggtctctcca      180 acccttaac catgtctggg atacttgatc ggtgcacgtg cacccccaat gccagggtgt      240
ttatggcgga gggccaagtc tactgcacac gatgtctcag tgcacggtct ctccttcctc      300
tgaatctcca agtttctgag cttggagtgc tgggcctatt ttataggccc gaagagccac      360
tccggtggac gttgccacgt gcatacccca ctgtcgagtg ctcccccgcc ggggcctgct      420
ggctttctgc gatctttcca attgcacgaa tgaccagtgg gaacctgaac tttcaacaaa      480
gaatggtgcg ggtcgcagct gagatttaca gagtcggtca gctcaccccc acagtcttga      540
agaatctaca agtttatgaa cggggttgcc gctggtaccc cattgtcgga cctgtccctg      600
gagtggccgt tttcgccaat tccctacatg tgagtgacaa accttttccg ggagcaactc      660
```

-continued

```
atgtgttaac taatctaccg ctcccgcaga ggcccaagcc tgaagacttt tgtccttttg     720
agtgtgctat ggctgacatc tatgacattg gtcatgacgc cgtcatgtat gtggccggag     780
ggaaagtctc ctgggcccct cgtggcgggg atgaagggaa atttgaaact gtccccgagg     840
agttgaagtt aattgcgaac cgacttcaca tctccttccc gccccaccac gtagtggaca     900
tatctaagtt tgcctttata gcccccggga gtggtgtctc catgcgggtt gagtgccaac     960
atggctgcct ccccgctgat actgttcctg gagggaactg ctggtggcgc ttgttcgact    1020
cgctcccacc ggaagttcag aataaagaaa ttcgctatgc taaccaattt ggttatcaaa    1080
ccaagcatgg tgtctctggc aagtacctac agcggaggct gcaagttaat ggtctccgag    1140
cagtgactga tacaagtggg cctatcgtcg tacagtattt ctctgttaag gagagttgga    1200
tccgccactt aaggctggcg gaagaaccta gcctccctgg gtttgaggac ctcctcagaa    1260
taagggttga gcccaatacg tcaccattgg ttggcaagga tgtgaaaatc ttccggtttg    1320
gcaatcacaa atggtacggc gctggaaaga gagcaaggaa atcacgctct ggtgcgactg    1380
ccacggtcgc tcaccgcgct ttacccgttc gtgaaaccct gcaggctaag aggcgcgagg    1440
ttgccagcgc caacagggct gagcatatca agcactatta tccgccagcc gacgaaaact    1500
gtggttggca ctgcatttcc gctattgtca accggatggt gaattctaaa tttgaaactg    1560
ctcttcccga gagagcgaga ccttctgatg actgggctac tgacgaggac cttgtgaata    1620
ccatccaaat cctcagactc cctgcggcct tggacaggga cggtgcttgt gttagcgcca    1680
agtacgtgct taaactagaa ggcgagcatt ggactgtctc tgtgaccccct gggatgtccc    1740 cttctttgct ccccccttgaa tgtgttcagg gctgttgtga acataagaac ggccttggtc    1800
ccccagatgc ggtcgaaagt tttggatttg accctgcctg ccttgaccga ctggctgagg    1860
taatgcactt gcctagtagt gtcatcccag ctgctctggc cgaaatgtcc ggtgaccccca    1920 attgtccggc atccccggtc accactgtgt ggactgtttc acaattcttt gcccgccaca    1980
gaggaggaga gcaccctgat caggtgcgct taggaaagat catcagcctt tgtcaagttg    2040
ttgaggaatg ctgttgccat cagaataaaa ccaaccgggc caccccgaa gaggtcgcgg     2100 caaagattaa tcagtacctc catggtgcaa caagtcttga agactgcttg actaggcttg    2160
agagggcttg cccgccgagt gctgcggaca ccttctttga ttggaacgtt gtgctccctg    2220
gggttgaggc tgcaactccg ccaccccctc caccaagagt tcagcctcga aaacaaagt     2280 ctgtcaagag cttgccggga acaatcctg tccccgctcc acgcaggaag gttagatctg      2340
actgtggcag cccgattttg acgggcgaca atgatctttc gacgccatcc gagccgatga    2400
catctctgaa tgagcctgcg cttatgcctg cgttgcaatg tatctctagg ccagtgacat    2460
ctttgagtgt gccggcccca gttcctgcac cgcgtagagc tgtgtcccga ccggtgacgc    2520
ccttgagtga gccagttttt tgtctgcac cgcgacacaa atttcagcag gtgaaagaag      2580
cgaatctggt ggcaacaacg ctgatgtgcc aggacgaacc tctagatttg tctgcatcct    2640
cacagactga atatgaagct tcccccccag caccactgca gaacatgggt attctggagg    2700 tgggggggaca agaagctgtg gaagttctga gtgaaatctc ggatacactg aatgacacca    2760
accctgcacc tgtgtcatca agcagctccc tgtcaagtgt taagatcaca cgcccaaaat    2820
actcagctca agccatcatt gattcggccg ggccctgcag tgggcacctc cgaaggggaa    2880
aagaagcatg cctcagcctc atgcgtgagg cttgtgatgc ggctaagctt agtgaccctg    2940
ccacgcaaga atggctttct cgcatgtggg atagggttga catgctgacc tggcgcaaca    3000
```

```
cgtctgccta ccaggcgttt cgcatcttag atggtaggtt tgagtttctc ccaaagatga    3060
tactcgagac accgccgccc tacccgtgtg ggtttgtgat gctgcctcac acgcctgcac    3120
cttccgtgag tgcagagagc gaccttacca ttggttcagt cgccactgaa gatgttccac    3180
gcattctcgg gaaaatagaa aacgccggcg agacgcccaa ccaggggctc ttggcaccct    3240
tcggggaaga accggtgtgc gaccaacctg tcaaagactc ccggatgttg tcgcggggt    3300 ttgacgagag cacgacggct ccgtccgcag gtacaggtgg cgctgactta cccactgatt    3360
tgccaccttc agatggtgtg gatgcggacg gggtggggct gttacggacg gtaagaaaga    3420
aagctgaaag gctcttcgac caattgagcc gtcaggtttt taacctcgtc tcccatctcc    3480 ctgtttttctt ctcacacctc ttcaaatctg acagtggtta ttctccgggt gattggggtt    3540
ttgcagcttt tactttattt tgcctctttt tatgttacag ctacccattc ttcggtttcg    3600
ctcccctctt gggtgtgttt tctgggtctt ctcggcgcgt gcgcatgggg gttttttggct    3660 gctggttggc ttttgctgtt ggcctgttca agcctgtgtc cgaccagtc ggcactgctt    3720 gtgagtttga ctcgccagag tgtaggaacg tccttcattc ttttgagctt ctcaaacctt    3780
gggaccctgt ccgcagcctt gttgtgggcc ccgtcggtct cggtcttgcc attcttggca    3840
ggttactggg cggggcacgc tacatctggc atttttttcct taggcttggc attgttgcag    3900
attgcttctt ggctggagct tatgtgcttt ctcaaggtag gtgtaaaaaa tgctggggat    3960
cttgtgtaag aactgctcct aatgaaatcg ccttcaacgt gttccctttt acgcgtgcga    4020
ccaggtcgtc actcatcgac ctgtgcgatc ggttttgtgc gccaaaaggc atggacccca    4080
ttttcctcgc tactgggtgg cgtgggtgct ggaccggccg gagtcccatt gagcaaccct    4140
ctgaaaaacc tatcgcgttc gcccagttgg atgagaagag gattacggct agaactgtgg    4200
tcgttcagcc ttatgatcct aaccaagccg taaagtgctt gcgggtgtta caggcgggtg    4260
gggcgatggt ggccgaggca gtcccaaaag tggtcaaggt ttccgccatt ccattccgag    4320
ctcccttttt tcccaccgga gtgaaggttg atcctgagtg caggatcgtg gtcgaccccg    4380
acacttttac tacagctctc cggtctggtt actccaccac aaacctcgtc cttggtgtgg    4440
gggactttgc ccaactgaat ggattaaaaa tcaggcaaat ttccaagtct tcgggggag    4500 gcccacacct cattgctgcc ctgcatgttg cttgctcgat ggcgttgcac atgcttgctg    4560
gggtttatgt aactgcagtg gggtcttgcg gtaccggcac caatgatccg tggtgcacta    4620
acccattcgc cgtccctggc tacggacctg gctctctctg cacgtccaga ttgtgcatct    4680
cccaacatgg ccttaccctg cccttgacag cacttgtggc aggattcggt cttcaggaaa    4740
ttgccttagt cgttttgatt tttgtttcca tcggaggcat ggctcatagg ttgagttgca    4800
aggctgatat gctgtgcgtc ttacttgcaa tcgcaagcta tgtttgggta cccttacct    4860 ggttgctctg tgtgtttcct tgctggttgc gctggttctc tttgcaccct ctcaccatcc    4920
tatggttggt gttttcttta atttccgtaa atatgccttc gggaatcttg gccgtggtgt    4980
tattggttgc tctttggctt ctaggccgtt atactaatgt tgttggtctt gttacccct    5040 atgatattca tcatcacacc agtggccccc gcggtgttgc cgccttggct accgcaccgg    5100
atgggactta tttggccgct gtccgccgcg ctgcgttgac tggccgcacc gtgttgttta    5160
ccccgtccca gcttgggtcc ctccttgagg gcgctttcag aactcgaaag ccctcactga    5220
acaccgtcaa tgtggtcggg tcctctatgg gctctgccgg agtgttcact atcgatggga    5280
aaattaagtg cgtgactgcc gcacatgtcc ttacgggtaa ttcagctagg gtttccgggg    5340
ttggcttcaa tcaaatgctt gactttgatg taaaagggga cttcgccata gctgattgcc    5400
```

```
cgaattggca aggggctgct cctaagaccc aattctgcga ggatgggtgg actggccgtg   5460
cctattggct gacatcctct ggtgtcgaac ccggcgtcat tgggaatgga ttcgccttct   5520
gcttcaccgc gtgcggcgat tctgggtccc cagtgatcac cgaagccggt gagcttgtcg   5580
gcgttcacac aggatcaaat aaacaaggag gaggcattgt tacgcgcccc tcaggccagt   5640
tttgtaatgt ggcacccatc aagctgagcg aattaagtga gttctttgct ggacctaagg   5700
tcccgctcgg tgatgtgaag gttggcagcc acataattaa agatatatgc gaggtacctt   5760
cagacctttg cgccttgctt gccgccaaac ccgaattgga aggaggcctc tccaccgtcc   5820
aacttttatg tgtgttttt ctcctgtgga gaatgatggg acatgcctgg acacccttgg   5880
ttgctgtggg ttttttttatc ttgaatgaag tcctcccagc tgtcctggtc cggagtgttt   5940
tctcctttgg aatgtttgtg ctatcttggc tcacaccatg gtctgcgcaa gttctgatga   6000
tcaggcttct aacagcagct ctcaacagga acagattgtc actcgccttt tacagccttg   6060
gtgcggcgac cggctttgtc gcagatctgg cggcaactca agggcatccg ttgcaagcag   6120
taatgaattt aagtacctat gccttcctgc ctcggatgat ggttgtgacc tcaccagtcc   6180
cagttattgc gtgtggtgtc gtgcacctcc ttgccataat tttgtacttg tttaagtacc   6240
gctgcctgca caatgttctt gttggcgatg gagcgttctc tgcggctttc ttttttgcgat   6300 actttgccga ggggaaattg agggaagggg tgtcgcaatc ctgcgggatg aatcatgagt   6360
cgctgactgg tgccctcgct atgagactca atgacgagga cttggatttc cttacgaaat   6420
ggactgattt taagtgcttt gtttctgcgt ccaacatgag gaatgcggcg ggccagttca   6480
tcgaggctgc ctatgcaaaa gcacttagaa ttgaacttgc ccagttggtg caggttgata   6540
aggttcgagg tactatggcc aaacttgaag cttttgctga taccgtggca ccccaactct   6600
cgcccggtga cattgttgtt gctcttggcc atacacctgt tggcggtatc ttcgacctaa   6660
aggttggtag caccaagcac accctccaat ccattgagac cagagtcctt gccgggtcca   6720
aaatgaccgt ggcgcgtgtc gttgacccaa cccccacacc cccaccccgca cccgtgccca   6780 tcccctccc accgaaagtt ctggagaatg gtcctaacgc ctgggggggat gaggatcgtt   6840 tgaacaagaa gaagaggcgc aggatggaag ccgtcggcat ctttgttatg ggtggaaaga   6900
aataccagaa attttgggac aagaattccg gtgatgtgtt ttatgaggag gtccatgata   6960
acacagacgc gtgggagtgc tcagagttga caaccctgc cgactttgac cctgagaagg   7020
gaactctgtg tgggcatact accattgaag gtaaggctta caatgtctac gcctccccat   7080
ctggcaagaa gtttctggtc cccgtcaacc cagagagtgg aagagcccaa tgggaagctg   7140
caaagctttc cgtggagcag gcccttggca tgatgaatgt cgacggtgag ctgacagcca   7200
aagaactgga gaaactgaaa agaataattg acaaactcca gggtctgact aaggagcagt   7260
gtttaaactg ttagccgcca gcggcttgac ccgctgtggt cgcggcggct tggttgttac   7320
tgagacagcg gtaaaaatag tcaaatttca caaccggacc ttcaccctag acctgtgaa   7380 cttaaaagtg gccagtgagg ttgagctaaa agacgcggtc gagcacaacc aacacccggt   7440
tgcaagaccg gttgatggtg gcgttgtact cctgcgcccc gcagttcctt cgcttgtaga   7500
tgtcttgatc tctggcgctg atgcatcccc taagttactc gcccgccatg ggccgggaaa   7560
cactgggatc gatggcacgc tttgggattt tgagaccgaa gccaccaaag aggaaattac   7620
acttagtgcg caaataatac aggcttgtga cattaggcgc ggcgacgcac ctgaaattgg   7680
tctcccttat aagctgcacc ctgttagggg caaccctgag cggataaaag gagttttaca   7740
```

```
gaatacaagg tttggggaca taccttacaa aacccccagt gacactggca gcccagtgca   7800
tgcggctgcc tgcctcacgc ccaatgccac tccggtgacc gatgggcgct ccgtcttggc   7860
tacgactatg ccctccggtt ttgagttgta tataccgacc attccatcgt ctgtccttga   7920
ttatcttgat tctaggcctg actgcccaa acagttaaca gagcacggct gtgaggatgc   7980
cgcattgaga gacctctcca agtatgactt gtccacccaa ggctttgttt tgcctggagt   8040
tcttcgccta gtgcgtaagt acctgttgc tcatgtgggt aagtgcccgc ccgttcatcg   8100
gccttccact tatcctgcca agaactctat ggctggaata aatgggaaca ggtttccaac   8160
caaggacatt cagagcatcc ctgaaatcga cgttctgtgc gcacaggctg tgcgagaaaa   8220
ctggcaaact gttacccctt gcaccctcaa gaaacaatat tgtgggaaga agaagactag   8280
gacaatactc ggcaccaata acttcgttgc gttggcccac cgggcagcgt tgagtggtgt   8340
cacccagggc tttatgaaaa aggcgtttaa ctcgcccatt gccctcggga aaacaaatt   8400
taaagagcta cagactccgg tcttaggcag gtgccttgaa gctgatcttg catcctgcga   8460
tcggtccaca cctgcaattg tccgctggtt tgccgccaat cttctttatg aacttgcctg   8520
tactgaagaa catctaccgt cgtacgtgct gaactgctgc cacgacctac tggtcacgca   8580
gtccggcgcg gtgactaaga gaggtggcct gtcgtctggc gacccgatta cctctgtgtc   8640
aaacaccatt tacagcttag tgatatatgc acagcacatg gtgctcagtt actttaaaag   8700
tggtcaccct cacggccttc tgtttctgca agaccagcta aagttgagg acatgctcaa   8760
ggttcaaccc ctgatcgtct attcggacga cctcgtgctg tatgccgagt ctcccaccat   8820
gccaaactac cactggtggg ttgaacatct gaatcttatg ttgggttttc aaacggaccc   8880
aaggaagaca gccataacag actcaccatc ttttctaggc tgtagaataa taaatgggcg   8940
ccagctagtc ccccaccgtg acaggattct cgcggccctt gcctaccata tgaaagcaag   9000
caatgtttct gaatattacg cctcggcggc tgcaatactc atggacagct gtgcttgttt   9060
agagtatgat cctgaatggt ttgaagagct cgtggttggg atggcgcagt gcgcccgcaa   9120
ggacggctac agttttcctg gcccgccgtt cttcttgtcc atgtgggaaa aactcaggtc   9180
caaccacgag ggaaagaagt ccagaatgtg cgggtactgc ggggcccgg ctccgtacgc   9240
cactgcctgt ggcctcgatg tctgtgttta ccacacccac ttccaccagc attgtccagt   9300
cataatctgg tgtggccatc cggcgggttc tggttcttgt agtgagtgca aacccccct   9360
agggaaaggc acaagccctc tggatgaggt gttggaacaa gtcccgtaca agcctccgcg   9420
gactgtaatc atgcatgtgg agcagggtct caccctctt gacccaggta gataccaaac   9480
tcgccgcgga ttagtctccg ttaggcgtgg catcagggga aatgaagttg acctaccaga   9540
cggtgattat gccagtaccg ccctgctccc tacttgtaaa gagatcaaca tggtcgctgt   9600
cgcctctaat gtgttgcgca gcaggttcat catcggtccg cccggtgctg ggaaaacata   9660
ctggctcctt caacaggtcc aggatggtga tgtcatttac acaccaactc accagaccat   9720
gcttgacatg attagggctt tgggggcgtg ccggttcaac gtcccagcag gcacaacgct   9780
gcaattccct gcccctccc ataccggccc gtgggttcgc atcctagccg gcggttggtg   9840
tcctggtaag aattccttcc tggatgaagc agcgtattgt aatcacccttg atgtcttgag   9900
gctccttagc aaaactaccc tcacctgtct aggagatttc aaacaactcc acccagtggg   9960
ttttgattct cattgctatg ttttttgacat tatgcctcag actcaactga agaccatctg   10020
gagatttgga cagaatatct gcgatgccat tcagccagat tacagggaca aacttgtatc   10080
catggtcaac acaacccgtg taacctactt ggaaaaacct gtcaagtatg ggcaagtcct   10140
```

```
caccccttac cacagggacc gagaggacgg cgccatcaca attgactcta gtcaaggcgc    10200
cacatttgat gtggttacac tgtatttgcc cactaaagat tcactcaaca ggcaaagagc    10260
ccttgttgct atcaccaggg caagacatgc tatctttgtg tatgacccac acaggcaact    10320
gcagagcatg tttgatcttc ccgcgaaagg cacacccgtc aacctcgctg tgcaccgtga    10380
cgagcagctg atcgtactag atagaaacaa caaagaatgc tcggttgctc aggctctagg    10440
caatggggat aaattcaggg ccacagacaa gcgcgttgta gattctctcc gcgccatttg    10500
tgcagatctt gaagggtcga gctccccgct tcccaaggtc gcacacaact gggattttta    10560
tttctcgcct gatttgacac agtttgccaa actcccggta gaacttgcac cccactggcc    10620
cgtggtgaca acacagaaca atgaaaagtg gccagaccgg ttggttgcta gccttcgccc    10680
tgtccataag tatagccgcg cgtgcatcgg tgccggctac atggtgggcc cctcagtgtt    10740
tctaggcacc cctggggttg tgtcatacta tctcacaaaa tttgtcaggg gcgaggctca    10800
aatgcttccg gagacagtct tcagcaccgg ccgaattgag gtagattgcc gggagtacct    10860
tgatgaccgg gagcgagaaa ttgctgagtc cctcccccat gctttcattg gtgacgtcaa    10920
aggtactacc gttggaggat gtcaccatgt caccttccaaa taccttccgc gcttccttcc    10980
caaggaatca gtcgcggtag tcggggtttc aagccccggg aaagccgcaa aagcagtttg    11040
cacattaaca gatgtgtatc tcccagacct tgaagcttac ctccacccag agcccagtc     11100 caagtgctgg aaaatgatgt tggacttcaa ggaagttcga ctgatggtct ggaaaggcaa    11160
gacggcctat tttcaacttg aaggccgcca tttcacctgg tatcagcttg caagctacgc    11220
ctcgtacatc cgagtacctg ttaattctac ggtgtatttg dacccctgca tgggccctgc    11280
cctttgcaac agaagagttg tcgggtccac ccattgggga gccgacctcg cagtcacccc    11340
ttatgattac ggtgccaaag tcattctgtc tagtgcatac catggtgaaa tgcctcctgg    11400
gtacaaaatc ctggcgtgcg cggagttctc gcttgacgat ccagttaggt acaaacgcac    11460
ctgggggttt gaatcggata cagcgtatct gtatgagttc accggaaacg gtgaggactg    11520
ggaagactac aatgatgcgt ttcgtgcgcg ccagaaaggg aaaatttata aggccactgc    11580
caccagcatg aggtttcatt ttcccccggg ccctgttatt gaaccaactt taggcctgaa    11640
ttgagatgaa atggggtcta tgcaaagcct ctttaacaaa attggccaac tttttgtgga    11700
tgctttcacg gaattttttgg tgtccattgt tgatatcatc atattttttgg ccattttgtt    11760 tggcttcacc atcgcaggtt ggctggtggt cttctgcatc agattggttt gctccgcggt    11820
actccgtgcg cgccctgcca ttcaccctga gcaattacag aagatcctat gaggcctttc    11880
tttctcagtg ccgggtggac attcccacct ggggaactaa acatcctttg gggatattgt    11940
ggcaccataa ggtgtcaacc ctgattgatg aaatggtgtc gcgtcgaatg taccgcacca    12000
tggaaaaagc aggacaggct gcctggaaac aggtggtgag cgaggccacg ttgtctcgca    12060
ttagtggttt ggatgtggtg gctcattttc agcatcttgc cgccattgaa gccgagacct    12120
gtaaatattt ggtttctcgg ctgcccatgc tacacaacct gcgcatgaca gggtcaaatg    12180
taaccatagt gtataatagc acttttaaatc aggtgtttgc catttttcca accccctggtt    12240 cccggccaag gcctcatgat tttcagcaat ggctaatagc tgtgcattcc tccatatttt    12300
cctctgttgc ggcttcttgt actctttttg ttgtgctgtg gttgcggatc ccaatgctac    12360
gtactgtttt tggtttccac tggtcagggg caatttttct ttcgaactca cggtgaatta    12420
cacggtgtgc ccaccttgcc tcacccggca agcagccgct gagatctacg aatccggcag    12480
```

```
gtctctttgg tgcaggatag ggcatgaccg atgtagtgag gacgatcacg acgaactagg   12540
gttcatggtt ccgcctggcc tctccagcga aggccactta accagtgttt atgcctggtt   12600
ggcgttcctg tctttcagct cacggccca attccatccc gagatatttg ggatagggaa    12660
tgtgagtaaa gttatgttg acgtcaagca ccaattcatc tgcgccgttc atgacggaca    12720
aaacaccacc ttgccccgcc atgacaacat ttcagccgta tttcagacct actatcaaca   12780
tcaggtcgac ggcggcaatt ggttccacct agaatggctg cgtcccttct tttcctcttg   12840
gttagtttta aatgtttcgt ggtttctcag gcgttcgcct gcaagccatg tttcagttca   12900
agtctttcag acatcaaaac caacaccact gcagcatcag gcttcgttgt cctccaggac   12960
atcagctgcc ttaggtatgg cgactcgtcc tctccgacga ttcgcaaaag ctctcaatgc   13020
cgcacggcga tagggacacc cgtgtatatt accatcacag ccaatgtgtc agacgagaat   13080
tacttacatt cttcagatct cctcatgctt tcttcttgcc ttttctatgc ctctgagatg   13140
agtgaaaagg ggttcaaggt gatatttggc aatgtttcag gcattgtggc tgtgtgtgtc   13200
aactttacca gctacgtcca acatgttagg gagttcaccc aacgctctct ggcggtcgat   13260
catgtgcggc tgcttcattt catgacacct gagaccatga ggtgggcaac cgttttagcc   13320
tgtcttgttg ccatccttt ggcaatttga atgtttaagt atgttgggga aatgcttgac    13380
cgcgggctat tgctcgcgat tgccttttt gtggtgtatc gtgccgttct gttttgctgt    13440
gatcgtcaac gccagcagca acagcagctc tcattttcag tcgatttata acttgacgct   13500
atgtgagctg aatggcacag attggctggc tggtaaattt gattgggcag tggagacttt   13560
tgttatcttt cccgtgttga ctcacattgt ttcctatggt gcacttacca ccagccattt   13620
ccttgacaca gttggtctgg ttattgtgtc caccgccggg ttttatcatg gcggtatgt    13680
cttgagtagc gtctacgcag tctgtgccct ggctgcgttg attcgctttg tcattagatt   13740
tgcgaagaac tgcatgtcct ggcgctactc atgtaccaga tataccaact tccttctaga   13800
taccaagggc aaactctatc gttggcggtc gcctgttatc atagagaaag ggggtaaggt   13860
tgaggtcgaa ggtcacctga tcgacctcaa aagagttgtg cttgatggtt ccgtggcaac   13920
tcctttaacc agagtttcag ctgaacaatg gggtcgtccc tagacgactt ttgcaatgat   13980
agcacggctc cgcaaaaggt gcttctggcg ttttccatta cctacacgcc agtgatgata   14040
tatgctctga aggtaagtcg cggccgcctg ctagggcttc tgcaccttt aatctttctg    14100
aattgtgctt tcaccttcgg gtacatgaca ttcgcgaact ttcagagcac aaacagggtt   14160
gcgctcacta tgggagcagt agttgcactt ctttgggggg tgtactcagc catagaaacc   14220
tggaaattca tcacctccag atgccgtttg tgcttgctag gccgcaggta cattctggcc   14280
cctgcccacc acgtcgaaag tgtcgcaggc tttcatccga ttgcggcaag tgataaccac   14340
gcatttgtcg tccggcgtcc cggctccact acggttaacg gcacattggt gcccgggttg   14400
aaaagcctcg tgttgggtgg cagaaaagct gttaaacagg gagtggtaaa ccttgtcaaa   14460
tatgccaaat aacaatggca ggcagcaaaa aagaaataag ggggacggcc agccagtcaa   14520
tcagctgtgt cagatgctgg gtaagatcat cgcccagcaa aatcagtcca gaggcagggg   14580
accggggaag aaaaataaaa agaaaaaccc ggagaagccc cattttcctc tagcgaccga   14640
agatgacgtc aggcatcact tcaccccctag tgagcggcaa ttgtgtctgt cgtcgatcca   14700
gactgccttt aaccagggcg ctggaacttg taccctgtca gattcaggga ggataagtta   14760
cactgtggag tttagtttgc cgacgcatca cactgtgcgc ctgattcgcg ccacagcatc   14820
accctcagcg tgatgggctg gcattcttga agcacctcag tgttagaatt ggaagaatgt   14880
```

```
gtggtggatg gcactgattg acactgtgcc tctaagtcac ctattcaatt agggcgaccg    14940
tgtgggggta aagtttaatt ggcgagaacc atgcggccga aattaaaaaa aaaaaaaaaa    15000
aaaaaaaaaa aaa                                                       15013

<210> SEQ ID NO 4
<211> LENGTH: 15444
<212> TYPE: DNA
<213> ORGANISM: Artificial Sequence
<220> FEATURE:
<223> OTHER INFORMATION: Artificial Construct

<400> SEQUENCE: 4
atgacgtata gttgttggct ctatgtcgtg acatttgtat agtcaggagc tgcgaccatt      60
ggtacagccc aaaacttgct gcgcgggaac gcccttccgt gacagccttc ttcaggggag     120
tttaggggtc tatccctagc accttgcttc cggagttgca ctgctttacg gtctctccac     180
ccctttaacc atgtctggga tacttgatcg gtgcacgtgt accccaatg ccagggtgtt      240 tgtggcggag ggccaagtct actgcacacg atgtctcagt gcacggtctc tccttccttt     300
gaatctccaa gttctgagc ttggggtgct gggcttattt tataggcccg aagagccgct      360
ccggtggacg ttgccacgtg cattccccac tgtcgagtgc tcccccgccg gggcctgctg     420
gctttctgcg attttccaa ttgcacgaat gaccagtgga aacctgaact ttcaacaaag      480
aatagtgcgg gtcgcagctg agctctacag agccggtcag ctcaccccg tagtcttgaa      540 gaatctacag gtttatgaac ggggttgccg ttggtacccc atcgttggac ctgttcctgg     600
agtggctgtt tatgccaatt ccttacacgt gagtgacaaa cctttcccgg gagcaactca     660
tgtgttaacc aacctaccgc tcccgcagag gcccaagcct gaagactttt gccccttga     720 gtgtgctatg gctgacgtct atgacattgg tcatgacgct gtcatgtatg tggccggagg     780
gagagtctcc tgggcccctc gtggcgggga caaaggaaaa tttgaaatag ttcccaagga     840
gttgaagttg attgcgaatc gactccacat ttccttcccg ccccaccacg cagtggacat     900
gtccaagttt gcctttataa gccctgggag tggtgtttcc atgcgggtcg agtaccaaca     960
tggctgtctc cccgctgata ctgtccctga aggaaactgt tggtggcgct tgtttgactt    1020
gcttccaccg gaagttcaga acaaagagat tcgccatgct aaccaactcg gctatcagac    1080
caagcatggt gtcgctggca agtacctaca gcggaggctg caagttaatg gactccgagc    1140
agtaactgac gcgaatggac ctatcgtcat acagtatttt tgtgataggg aaagctggat    1200
ccgccactta agactggtag aagaacctag cctccctggg tttgaggacc tcctcagaat    1260
aagagttgag cccaatacgt tgccattggt tggcgaggat gagaaaatct tccgatttgg    1320
caatcacaaa tggtacggtg ctggaaagag ggcaaggaaa gcacgctttg gtgcggctgc    1380
cacggtcgct caccgcgctt tgcccgctca cgaaacccag caggccaaga agcacgaagt    1440
taccagcgcc aacagggctg agcatctcga gcactattcc ccgcctaccg acgggaactg    1500
tggttggcac tgcgtttccg ccattgtcaa ccggattgtg aattccaaat ttgaaaccac    1560
ccttcccgag agagtgagac ctttagatga ctgggctact gacgaggatc ttgtgaatac    1620
tatccaaatc ctcaggctcc ctgcggcctt ggacaggaac ggtgcttgtg tcggcgccaa    1680
gtacgtgctc aagctggaag gtgtgcactg gacagtctct gtggcccctg ggatgacccc    1740
ttctctgctc cccccttgaat gtgttcaggg ctgttgtgag cataagagcg gtcttggtcc    1800
cccagatgtg gctgaagttt ccggatttga ccctgcctgc cttaaccgac tggctgaggt    1860
```

```
aatgcacttg cctagttgtg tcatcccagc tgctctggct gaaatgtccg acgacccaa    1920 tcgcccggct tccccagtca ccactgtgtg gactatttcg caattctttg cccattatag    1980
aggaggagag caccctgatc aggtgtgctt agggaaaatc atcagccttt gtcaggtgat    2040
tgaggaatgc tgttgttccc agaacaaaac caaccgggcc accccggaag aggtcgcggc    2100
aaaaattgac cagtacctcc gtgatgcagc aagccttgga gaatgcttag ccaagcttga    2160
gagggctcgc ccgccgagcg cgatggacac ctcctttgat tggaatgttg tgcttcctgg    2220
ggttgaggcg gcgaaccaga cgaccaaaca gctccatgtc aaccagcacc gtgctccggt    2280
tcctgccatg actcaggagc ctttggacaa agactcggtc cctttgaccg ccttctcgct    2340
gtctaattgc tactaccctg cacaaggtga cgaggttcgt caccgtgaga ggctgatctc    2400
cgtgctctct aagttggagg aggttgttcg tgaggaatat gggctcacgc caactggatc    2460
tggcccgcga cccgcactgc cgaacgggct cgacgagctc aaagaccaga tggaagagga    2520
tctgttgaaa ctggtcaacg cccaggcaac ttcagaaatg atggcccggg cagctgagca    2580
ggttgatcta aaagtttggg tcaaaaatta cccacggtgg acaccgccac ccctccacc    2640 aagagttcag cctcgaaaaa caaagtctgc taagagcctg ccagagaaca agcctgtccc    2700
tgctccgcgc aggaaagtca gatctgattg tggcagcccg actttgaggg gcaacaatgt    2760
tcctaacggt tgggaagact tggccgttgg tggtcctctt gatctttcga caccatccga    2820
gccgatgaca cctctgagtg agcctgcact tatgcccgtg ttgcaacata tttctggacc    2880
agtgacgcct ttgagcgtgc cggcccctat tcctgcaccg cgtaaagctg tgtcccgacc    2940
gatgcgcccc tcgagtgagc caattttttgt gtctgcaccg cggcaaaaat ttcagcaggt    3000
ggaagaagca aatctggcgg caacaacgct gacataccag gacgaaccta tagatctgtc    3060
agcatcctca cagactgaat atgaggctcc ttccctagca ccactgcaga acataggtac    3120
tctggaggtg gggggggcaag aagctgagga aattctgagt gaaacctcgg atataccgaa    3180
tgacatcaac cctgtgcctg tatcatcaag cagctccttg tcaagcgtta agatcacacg    3240
cccaagacac tcagctcaag ccatcatcga ctcgggcggg ccctgcagtg ggcatctcca    3300
aagggagaaa gaagcgtgcc tccgcatcat gcgtgaggct tgtgatgcga ctaagcttag    3360
tgaccctgcc acgcaggaat ggctttctcg catgtgggat agggtggaca tgctgacttg    3420
gcgcaacacg tctgctttcc aggcgttttcg catcttagac ggcaggcttg agtttcttcc    3480
aaagatgata ctcgagacgc cgccgcccta cccgtgtggg tttgtgatgc tgcctcacac    3540
ccctgcacct tccgtgagtg cagagagcga ccttaccatc ggttcagtcg ccactgaaga    3600
tattccacgc atcctcggga aaatagaaaa caccagtgag atgatcaacc agggacccctt    3660 ggcatcctct gaggaaaaac cggcatacaa ccaacccgct aaggactccc tgatatcgtc    3720
gcggggtttt gacgagagca cagcagctcc gtccgcaggt acgggtggcg ccggcttgtt    3780
tactgatttg ccaccttcag acggtgtaga tgcggacggg ggggggccgc tgcagacggt    3840
gaaaaagaac gctgaaaggc tcctcgaccg attgagccgt caggttttta acctcgtctc    3900
ccatctccct gttttcctct cacacctctt caaatctgac agtggttatt ctccgggtga    3960 ttgggggtttt gcagctttta ctctattttg cctcttttta tgttacagct acccattctt    4020
tggtttcgct cccctttttgg gtgtgttttc tgggtcttct cggcgcgtgc gcatgggggt    4080
ttttggctgc tggttggctt ttgctgttgg tttgttcaag cctgtgtccg acccagtcgg    4140
cactgcttgt gagtttgatt cgccagagtg taggaatgtc cttcattctt ttgagcttct    4200
caaaccttgg gaccctgttc gcagccttgt tgtgggcccc gtcggtctcg gtcttgccat    4260
```

```
tcttggcagg ttactgggcg gggcacgcta catctggcat tttctgctta ggcttggcat    4320
tgttacagac tgtatcctgg ctggagctta tgtgctttct caaggtaggt gtaaaaagtg    4380
ctggggatct tgcataagaa cagctcctaa tgagattgcc tttaacgtgt tcccttttac    4440
acgtgcgact aggtcgtcac tcatcgacct gtgcaatcgg ttttgtgcgc caaagggcat    4500
ggaccctatt ctcctcgcca ctgggtggcg tgggtgctgg accggccgaa gccccattga    4560
acaaccctct gaaaaaccca tcgcgtttgc ccagttggac gaaaagagga ttacggccag    4620
gaccgtggtc gcccagcctt atgaccccaa ccaagccgta aagtgcttgc gggtgttaca    4680
ggcgggcggg gcgatggtgg ctgaggcagt cccaaaagtg gtcaaagttt ccgctattcc    4740
attccgagcc ccctttttc ccaccggagt gaaagttgac cctgagtgta ggatcgtggt     4800 tgacccgac acttttacta cagccctccg gtccggctat tccaccacaa acctcgttct     4860
tggtgtgggg gactttgccc agctgaatgg attaaaaatc aggcaaattt ccaagccttc    4920
gggaggaggc ccgcacctca ttgctgccct acatgttgcc tgctcgatgg cgttgcacat    4980
gcttgctggg gtttatgtaa ctgcagtggg gtcttgcggt accggcacca acgatccgtg    5040
gtgcaccaac ccgtttgccg tccctggcta cgggcctgg  actctttgca cgtccagatt    5100
gtgcatctcc caacatggcc ttaccctgcc cttgacagca cttgtggcag gattcggtct    5160
tcaggaaatt gccttggttg ttttgatttt cgtttccatc ggaggcatgg ctcacaggtt    5220
gagttgcaag gctgacatgc tgtgcgtttt acttgcaatc gccagctatg tttgggtgcc    5280
ccttacctgg tttctttgtg tgtttccttg ctggttgcgc tggttctctt tgcatcccct    5340
caccatccta tggttggtgt ttttcttgat ttctgtaaat gtgccttcgg gaatcttggc    5400
tgtggtgttg ttagtttctc tttggctctt aggtcgttac actaatgttg ctggtcttgt    5460 cacccccatat gacattcatc atcacaccag tggccccga  ggtgttgccg ccttggctac    5520
tgcaccggat gggacctact ggccgccgt  tcgccgtgct gcgttgaccg gtcgtaccat    5580
gctgtttacc ccgtctcagc ttgggtccct tcttgagggt gctttcagaa ctcaaaagcc    5640
ctcactgaac accgtcaatg tggtcggatc ctctatgggc tccggcgggg tgttcaccat    5700
cgacgggaaa attaagtgcg taacagccgc acatgtcctt acgggtaatt cagctagggt    5760
ttccggggtc ggcttcaacc aaatgcttga ttttgatgtg aaaggggact tcgccatagc    5820
tgattgcccg aattggcaag gagctgcccc caagacccaa ttctgcgagg atggatggac    5880
tggccgtgcc tattggctga catcctctgg agtcgaaccc ggtgtcattg ggaatggatt    5940
cgccttctgc ttcaccgcgt gcggcgattc tggatcccg  gtgattaccg aagccggtga    6000
gcttgtcggc gttcacacag gatcaaacaa acaaggagga ggcatagtca cacgcccctc    6060
aggccagttt tgtaatgtgg cgcccatcaa gctgagcgaa ttgagtgaat tcttcgctgg    6120
acctaaggtc ccgctcggtg atgtgaagat tggcagccac ataattaaag acgtatgcga    6180
ggtaccttca gatctttgcg ccttgctcgc tgccaaaccc gaactggaag gaggcctctc    6240
caccgtccaa cttctgtgtg tgttttttcct cctgtggaga atgatgggac atgcctggac    6300
gcccttggtt gctgtggggt tttttatctt gaatgaggtt ctcccagctg tcctggtccg    6360
gagtgtcttc tcctttggta tgtttgtgct atccttggctt acaccatggt ctgcgcaagt    6420
cctgatgatc aggcttctaa cagcagctct taacaggaac agggggtcac tcgccttcta    6480 cagccttcggt gcagtgaccg gatttatcgc agatcttgca gcaactcagg gcatccgctt    6540
gcaggcagtg atgaacttaa gcacctatgc cttcctgcct cggatgatgg ttgtgacctc    6600
```

```
accagtccca gtgcttgctt gtggtgttgt gcacctcctt gccataattt tgtacctgtt    6660
taagcaccgt tgcctgcatt atgtccttgt tggcgatgga gtgttctcta aagcccttctt   6720 cttgcgatac tttgccgaag ggaagttgag ggaaggggtg tcgcagtcct gcgggatgaa    6780
tcacgagtca ctgactggtg ccctcgctat gagactcaat gacgaagact tggacttcct    6840
tacgaaatgg actgatttta agtgctttgt ttctgcgtcc aacatgagga atgcagcggg    6900
ccaattcatc gaggctgcct atgcaaaagc acttagaatt gagcttgccc agttagtaca    6960
ggttgataag gttcgaggta ctttggccaa acttgaagcc tttgctgata ccgtggcacc    7020
ccagctctcg cccggtgaca ttgttgttgc tcttggccac acgcctgttg gcagtatctt    7080
cgacctaaag gttggcagta ccaagcatac cctccaggcc attgagacca gagtccttgc    7140
cgggtccaaa atgaccgtgg cgcgtgtcgt tgatccaacc cccacgcccc cacccgcacc    7200
cgtgcccatc ccctcccac cgaaagtcct ggagaacggc cccaacgcct gggggatga     7260 ggaccggttg aataagagga agagacgcag gatggaagcc gtcggcatct ttgttatggg    7320
tgggaagaag taccaaaaat tttgggacaa gaattccggt gatgtgtttt acgaggaggt    7380
ccatgataac acagatgcgt gggagtgcct cagagttggt gaccctgccg actttgaccc    7440
tgagaaggga actctgtgtg gcatactac cattgaagac aaggcttata atgtctacac     7500
ctccccatct ggcaggaagt tcctggtccc cgtcaaccca gagagcggaa gagcccaatg    7560
ggaagctgca aagctttccg tagagcaggc ccttagcatg atgaatgtcg acggtgagct    7620
gacagccaaa gaactggaga aactgaaaag aataattgac aaactccagg gcctaactaa    7680
ggagcagtgt ttaaactgct agccgccagc ggcttgaccc gctgtggtcg cggcggcttg    7740
gttgttactg agacagcggt gaaaatagtt aaatttcaca accggacctt caccctagga    7800
cctgtgaatt taaagtggc cagtgaggtt gagctaaaag acgcagtcga gcataaccaa     7860 caccggttg caagaccggt tgatggtggt gttgtgctcc tgcgctccgc agttccttcg     7920
cttatagacg tcttgatctc tggcgctgat gcatctccta agttactcgc ccaccacggg    7980
ccgggaaaca ctgggatcga tggttcgctt tgggattttg aggccgaggc caccaaagag    8040
gaaattgcac tcagtgcgca aataatacag gcttgtgaca ttaggcgcgg cgacgcaccc    8100
gaaattggtc ttccttataa gctgcaccct gttaggggca accctgagcg gtaaaaggg     8160 gtttacaga atacaaggtt tggagacata ccttataaaa cccccagtga cactgggagc    8220
ccagtgcacg cggctgcctg cctcacgccc aatgccactc cggtgactga cggtcgttcc    8280
gtcttggcta cgaccatgcc ctccggtttt gagttgtatg taccgaccat tccagcgtct    8340
gtccttgatt atcttgattc caggcctgat tgccccaaac agttgacaga gcacggctgt    8400
gaggatgccg cattaagaga cctctccaag tatgacttgt ccacccaagg ctttgtcttg    8460
cctggagttc ttcgccttgt gcgtaagtac ctgtttgctc atgtgggtaa gtgcccgcct    8520
attcatcggc cttccactta ccctgccaag aattccatgg ctggaataaa tgggaacagg    8580
tttccaacca aggacattca gagcgtccct gaaatcgacg ttttgtgcgc acaggccgtg    8640
cgagaaaact ggcaaactgt tactccttgt acccctcaaga agcagtattg cgggaagaag    8700
aagactagga caatactcgg cactaataac ttcattgcgc tggcccaccg gcagcattg     8760 agtggtgtca cccagggctt catgaaaaaa gcgtttaact cgcccatcgc actcgggaaa    8820
aacaaattca aggagctgca gactccggtc ttgggcagat gtcttgaagc tgaccttgca    8880
tcctgtgacc gatccacacc cgcaattgtc cgctggtttg ccgccaatct tctttatgaa    8940
cttgcctgtg ctgaggagca tatccatcg tacgtgttga actgctgcca cgacttactg    9000
```

```
gtcacgcagt ccggcgcggt gactaagaga ggtggcctat cgtctggcga cccgattact   9060
tctgtatcaa acaccattta cagcttggtg atatatgcac agcacatggt actcagttat   9120
tttaaaagtg gtcaccccca tggccttctg tttctacaag accagctaaa gtttgaggac   9180
atgctcaagg ttcagcccct gatcgtctat tcggacgacc tcgtgctgta cgccgagtct   9240
cccaccatgc caaactacca ctggtgggtt gaacatctga acctgatgct gggttttcag   9300
acggacccaa agaagacagc tataacagac tcgccatcat tttgggttg taggataata   9360 aatggacgcc agttagtccc caaccgtgac aggatcctcg cggccctcgc ctaccatatg   9420
aaggcaaaca atgtttctga atactacgcc tcggcggctg caatactcat ggacagttgt   9480
gcttgtttgg agtacgatcc tgagtggttt gaagagctcg tggttgggat ggcgcagtgc   9540
gcccgcaagg acggctacag ttttcctggc ccgccgttct tcttgtccat gtgggaaaaa   9600
ctcaggtcca atcatgaggg gaagaagtct agaatgtgcg ggtactgtgg ggccccagct   9660
ccgtatgcca ctgcctgtgg ccttgatgtt tgtatttatc acaccccactt ccaccagcat   9720 tgtccagtca taatctggtg tggccatccg gcgggttctg gctcttgtag tgagtgcaaa   9780
ccccccctag ggaaaggcac aagccctcta gatgtggtgt tagaacaagt cccgtacaag   9840
cctccacgaa ctgtaatcat gcatgtggag cagggtctca cccctcttga cccaggcaga   9900
taccagactc gccgcggatt agtctccgtt aggcgtggca tcaggggaaa cgaaatcgac   9960
ctaccagacg gtgattatgc tagtaccgcc ttgctcccca cttgtaaaga tatcaacatg  10020
gtcgctgtcg cttccaatgt gttgcgcagc aggttcatca tcggtccacc cggtgctggt  10080
aaaacatact ggctccttca acaggtccag gatggtgatg tcatttacac gccaactcat  10140
cagaccatgc ttgacatgat caaggctttg gggacgtgcc ggttcaacgc cccagcaggc  10200
acaacgctgc aattccctgc tcctccccgt accggcccgt gggttcgcat cctggccggc  10260
ggttggtgtc ctggcaagaa ttccttcctg gatgaagcag cgtattgtaa tcaccttgat  10320
gtcttgaggc ttcttagcaa aactaccctc acctgtctgg gagatttcaa acaactccac  10380
ccagtgggtt ttgattctca ttgctatgtt tttgacatca tgcctcagac tcaactgaag  10440
accatctgga ggtttggaca gaatatctgt gatgccattc agccagatta cagggacaaa  10500
cttgtgtcca tggtcaacac aacccgtgta acctacgtgg aaagacctgt caagcatggg  10560
caggtcctca ccccttacca cagggaccga gaggacggcg ccatcacaat tgactccagt  10620
caaggcgcca catttgatgt ggttacattg catttgccca ctaaagattc actcaacagg  10680
caaagagccc ttgttgctat caccagggcg agacatgcta tctttgtgta tgacccacat  10740
aggcaactgc agagcatgtt tgatcttcct gcaaaaggca cacccgtcaa ccttgccgtg  10800
caccgtgacg agcagctgat cgtactagat agaaataaca aagagtgcac ggttgctcag  10860
gctctaggca tggggacaa attcagggcc acagacaagc gcgttgtaga ttctctccgc  10920
gccatttgtg cagatcttga agggtcgagc tccccgctcc caaggtcgc acataacttg  10980 ggattttatt tctcacctga tttgacacag tttgctaaac tcccggcaga acttgcaccc  11040
cactggcccg tggtgacaac ccagaacaat gaaaagtggc cagacaggct ggttgccagc  11100
ctccgcccta tccataaata tagccgcgca tgcattggag ccggctatat ggtgggccct  11160
tcggtgtttc taggcacccc tggggttgtg tcatactatc tcacaaaatt tgttaagggg  11220
gaggctcagg tgcttccgga gacagtcttc agcaccggcc gaattgaggt agattgccgg  11280
gagtatcttg atgatcggga acgagaagtt gctgagtccc tcccacatgc cttcattggc  11340
```

```
gacgtcaaag gcactaccgt tgggggatgt caccatgtca cctctaaata ccttccgcgc  11400
ttccttccta aggaatcagt tgcggtggtt ggggtttcga gccccgggaa agccgcaaaa  11460
gcagtctgca cattaacaga tgtgtatctc ccagaccttg aagtttacct ccacccagag  11520
acccaatcca agtgctggaa ataatgttg gacttcaagg aagtccgact gatggtctgg    11580
aaagacaaaa cggcctattt tcaacttgaa ggccgccatt tcacctggta tcagcttgca  11640
agctatgcct cgtacatccg agttcctgtt aactctacgg tgtatttgga ccctgcatg   11700
ggccctgccc tttgcaacag aagagttgtc gggtccactc attgggggc tgacctcgca   11760
gtcaccccctt atgattatgg tgccaaaatc attctgtcta gtgcatacca tggtgaaatg  11820
cctcctgggt acaaaatcct ggcgtgcgcg gagttctcgc ttgacgaccc agtgaggtac  11880
aaacacacct gggggtttga atcggacaca gcgtatctgt acgagttcac cggaaacggt  11940
gaggactggg aggattacaa tgacgcattt cgtgcgcgcc agaaagggaa aatttataag  12000
gccactgcca ccagcatgag gtttcatttt cccccgggcc ccatcattga accaacttta  12060
ggcctgaact gaaatgagat gggggctatg caaagccttt tctacaaaat tggccaactt  12120
tttgtggatg ctttcacgga attttttggtg tccattgttg atatcatcat atttttggcc  12180
atttttgtttg gcttcaccat cgccggttgg ctggtggtct tctgcatccg attggtttgc  12240
tccgcggtac tccgtgcgcg ccctaccatt caccctgagc aattacagaa gatcctatga  12300
ggcctttctt tctcagtgcc gggtggacat tcccacctgg ggaaccaaac atcccttggg  12360
gatactttgg caccataagg tgtcaacccct gattgatgaa atggtgtcgc gtcgaatgta  12420
ccgcatcatg gaaaaatcag gacaggctgc ctggaaacag gttgtgagcg aggctacgct  12480
gtctcgcatc agtggtttgg atgtggtggc tcatttttcag catcttgccg ccattgaagc  12540
cgagacctgt aaatatttgg cctctcggat gcccatgcta cacaacctgc gcatgacagg  12600
gtcaaatgta accatagtgt ataatagtac tttgaatcag gtgttagcaa tcttcccgac  12660
ctctgaatcc cggccaaagc ttcatgattt tcaacaatgg ttaataactg tacattcctc  12720
catattttcc tccgttgtgg cttcctgtac tctttttgtt gtgctgtggt tgcgaattcc  12780
aatgctacgt actgtttttg gtttccactg gttaggggca atttttcttt cgaactcaca  12840
gtgaattaca cggtgtgccc accttgcctc acccggcaag cagccgctga gatctacgaa  12900
cccggcaggt ctcttttggtg caggataggg catgatcgat gtagcgagga cgatcatgac  12960
gaactagggt tcttggttcc gcctggcctc tccagcgaag gccacttgac cagtgtttac  13020
gcctggttgg cgttcctgtc cttcagctat acagcccagt tccatcccga gatatttggg  13080
atagggaatg tgagtaaaat ttatgttgac atcaagcacc aattcatctg cgccgaacac  13140
gacgggcaga acgccaccct gcctcgccat gacaacattt cagccgtgtt tcagacctac  13200
taccaacatc aggtcgatgg cggcaattgg tttcacctgg aatggctgcg ccccttcttt  13260
tcctcttggt tggttttaaa tgtttcgtgg tttctcaggc gttcgcctgc aagccatgtt  13320
tcagttcgag tctttcagac atcaaaacca acaccaccgc agcaccaaat tttgttgtcc  13380
tccaggacat cagctgcctt aggcatggcg accgtcctc tccggcgatt cgcaaaagct  13440
ctcagtgccg cacggcgata ggaacacccg tgtatatcac catcacagcc aatgtgcag   13500
atgagaatta tttacattct tctgatctcc tcatgctttc ttcttgcctt ttctatgctt  13560
ctgagatgag tgaaaagggg ttcaaggtgg tattcggcaa tgtgtcaggc atcgtggctg  13620
tgtgtgtcaa ctttaccagt tacgtccaac atgtcaagga gttacccaa cgctccttgg   13680
tggtcgagca tgtgcgactg cttcatttca tgacacctga aaccatgagg tgggcaaccg  13740
```

```
ttttagcctg tcttttttgcc attctgttgg caatttgaat gtttaagtat gttgggaaa    13800 tgcttgaccg cgggctgttg ctcgccgttg cttttttgt ggtgtatcgt gccgtcttgc     13860
tttgttgcgc ccgtcaacgt cgacgggaac gacagctcaa agttacagct gatttacaac    13920
ttgacgctat gtgagctgaa tggcacagat tggctggctg gtagatttga ctgggcagtg    13980
gagtgttttg tcattttcc cgtgttgact cacattgtct cctatggtgc cctcactact     14040
agccatttcc ttgacacagt cggtctggtc actgtgtctg ccgccgggtt ccttcatgaa    14100
cggtatgttt tgagtagcat ctacgcggtc tgtgccctgg ctgcgttgat ttgcttcgtc    14160
attaggcttg cgaagaactg catgtcctgg cgctactcgt gtaccagata taccaacttc    14220
cttttggaca ccaaggggag actctatcgt tggcgatcgc ccgtcatcat agagaaaaag    14280
ggtaaagttg aggttgaagg tcatttgatc gacctcaaaa gagttgtgct tgatggttcc    14340
gtggcaaccc ctataaccaa aatttcagcg gaacaatggg gtcgtcctta gatgacttct    14400
gccatgatag cacggctcca caaaggtgc ttttggcgtt ttccattacc tatacaccag     14460
tgatgatata tgccctaaag gtaagtcgcg gccgactgct agggcttttg cacctttga    14520 tctttctgaa ctgtgctttc accttcgggt atatgacatt cacgcacttt cagagtacaa    14580
acaaggtcgc gctcactatg ggagcagtag ttgcactcct ttgggggtg tactcagcca     14640 tagaaacctg gaaattcatc acctccagat gccgtttgtg cttgctaggc cgcaagtaca    14700
ttctggcccc tgcccaccac gttgagagtg ccgcaggctt tcatccgatt gcggcaaatg    14760
ataaccacgc atttgtcgtc cggcgtcccg gttccactac ggtcaacggc acattggtcc    14820
ccgggttgaa aagcctcgtg ttgggtggca gaaaagctgt caaacaggga gtggtaaacc    14880
ttgttaaata tgccaagtaa caacggcagg cagcagaaaa aaagaaaggg ggatggccag    14940
ccagtcaatc agctgtgtca gatgctgggt aaaattattg cccagcaaaa tcagtccagg    15000
ggcaagggac cgggaaagaa aaataacaag aaaaacccgg agaagcccca ttttcctcta    15060
gcgactgaag atgatgtcag acatcacttt accccgagtg agcgacaatt gtgtctgtcg    15120
tcaatccaga ctgccttcaa tcagggcgct ggaacttgta ccctgtcaga ttcaggcagg    15180
ataagttaca ctgtggagtt tagtttgccg acgcatcaca ctgtgcgcct gatccgcgct    15240
acagcatcac cctcagcatg atgagctggc attcctgggt atcccagtgt ttgaattgga    15300
agaatgtgtg gtgaatggca ctgattgaca ttgtgcttct aagtcaccta ttcaattagg    15360
gcgaccgtgt gggagtagaa tttaattggc gagaaccacg cggccgaaat taaaaaaaaa    15420 aaaaaaaaa aaaaaaaaa aaaa                                             15444
```

<210> SEQ ID NO 5
<211> LENGTH: 15413
<212> TYPE: DNA
<213> ORGANISM: Artificial Sequence
<220> FEATURE:
<223> OTHER INFORMATION: Artificial Construct

<400> SEQUENCE: 5

```
cgcccgggca tgtgttggct ccatgccacg acatttgtat tgtcaggagc tgtgaccact      60
ggcacagccc aaagcttgct gcacagaaac acccttctgt gacagcctcc ttcagggag     120 tttaggggtc tgtccctaac accttgcttc cggagttgca ctgctttacg gtctctccac    180
cctttaacca tgtctgggat acttgatcgg tgcacgtgca cccccaatgc cagggtgttt    240
atggcggagg gccaagtcta ctgcacacga tgtctcagtg cacggtctct ccttcctctg    300
```

```
aatctccaag tttctgaact aggggtgcta ggcctatttt acaggcccga agagccactc    360
cggtggacgt tgccacgtgc attcccact  gttgagtgct ccccgccgg  ggcctgctgg    420
cttctgcaa  tttttccaat tgcacgaatg actagtggaa atctgaactt ccaacaaaga    480
atggtacggg tcgcagctga gctttacaga gccggccagc tcacccctgc agtcttaaag    540
gctctacaag tttatgaacg gggctgccgc tggtacccca ttgtaggacc tgtccctgga    600
gtggccgttt acgccaactc cttacatgtg agtgataaac ctttcccggg agcaactcac    660
gtgttaacca acctaccgct cccgcaaaga ccaaaacctg aagacttttg ccccttgag    720
tgtgccatgg ctaccgtcta tgacatcggt cgtgacgccg tcatgtatgt aaccgaggga    780
aaagtctcct gggcccctcg tggtggggat gaaacaagat ttgaaactgt ccccggtggg    840
ttgaagttga ttgcggacca actctactcc tccttcccgc cccatcacac ggtggacata    900
tctaagttcg ccctcacagc ccctgggcgc ggtgtatcca tgcgggttga acgccagtgt    960
ggctgcctcc ccgctgacac tgtccctgaa ggcaactgtt ggtggagctt attcgattca   1020
ctcccactgg aagtccagaa caaagaaatt cgccatgcta accaatttgg ctaccaaacc   1080
aagcatggcg tctccggcaa gtaccttcag cggaggctgc aagttaatgg cctccgagca   1140
gtaactgact tgaatggacc tattgtcata cagtacttct ccgttagaga gagttggatc   1200
cgccacttga aactggcgga agaacccggc ctccctgggt ttgaggacct cctcagaata   1260
agggttgaac ccaacacatc gccattggct aacgaggatg agaaaatctt ccgatttggc   1320
agccataagt ggtacggcgc tgggaggaga gcaaggaaag cacgccacag tgcaattgct   1380
gcggtcgcag gccgcgcttc gtctgctcgt gaaatccagc aggccaagaa gcatgaggct   1440
gctgacgcca ataaggttga gcacctcaaa cgctactccc cgcccgccga agggaattgc   1500
ggttggcact gtatttctgc catcgccaat cgaatggtga attctaaatt taaaaccacc   1560
cttcccgaaa gagtgaggcc ttcagatgac tgggccactg atgaggatct tgtgaatgtc   1620
atccaaatcc tcaggctccc tgcggccttg acaggaacg  gtgcttgtgc cagcgccaag   1680
tacgtactta agctagaagg tgagcattgg actgtcactg tgaccctgg  gatgtcccct   1740
tctttgctcc ctcttgaatg tgttcagggc tgttgtgagc ataagggcgg tctaggtacc   1800
ccagatgcag tcgaggtttt cggatttgac cctgcctgcc tcaactggtt ggctgaggtg   1860
atgcacctgc ctagcagtgc tatcccagcc gctctggccg aaatgtccgg tgattccggt   1920
cgttcggctt ccccggtcac caccgtgtgg accgtttcgc agttctttgc ccgccacaat   1980
ggagggagtc accctgacca agtgcgttta gggaaaatta ttagcctttg tcaggtgatt   2040
gaggactgct gctgttccca gaacaaaacc aaccgggtta ccccggagga ggtcgcagca   2100
aagattgact tgtacctccg tggagcgaca agtcttgaag aatgcttggc caggcttgag   2160
aaagctcgcc cgccacgcgt aatggacacc tcctttgatt gggatgttgt gctccctggg   2220
gttgaggcgg caactcagac gaccgaattg ccccaggtca accagtgtcg tgctttggtc   2280
cctgttgtaa ctcaaaagtc cttggacaac aactcggttc ccttgaccgc ctttcactg    2340
gctaactact actaccgtgc gcaaggtgaa gaagttcgtc accgtgaaag actaaccgcc   2400
gtgctctcca aattggaagg ggttgtccga gaggaatatg gctcatgcc  aaccgggcct   2460
ggtccacggc ccacattgcc acgcgggctc gacgaactca agatcagat  ggaagaggac   2520
ttgctgaaac tggctaacgc ccagacgact tcggagatga tggcctgggc agtcgagcag   2580
gtcgacctaa aaacttgggt caagaactac ccgcggtgga caccaccacc ccctccgcca   2640
aaagttcagc ctcgaaaaac gaagtctgcc aagagcttgc tagagagaaa gcctgtcccc   2700
```

```
gccccgcgca ggaaggttgg gaccaattgt ggcagcccga tttcattggg cgacaatatc    2760
cctaacagtt gggaagattt ggctgttggt ggccccctatg atcccccgac cccacctgag   2820
ccggcaacac cttcaggtga gctggtggtt gtgtccacac cgcaatgcat cttcaggccg    2880
gcgacaccct cgagtgagcc ggctctaatt cccgcatccc gcggggctgt gtctcgaccg    2940
gtgacaccct tgagtgagcc gatccctgtg cccgcaccgc ggcgtaagtt tcagcaggtg    3000
aaaagattga gttcggcagc ggtaacccccg ccgtaccagg acgagcccct aaatttgtct   3060
gcttcctctc aaactgaatt tgaggccccc tccctagcac cgccgcagag cgagggtgtt   3120
ttgggagtga aggggcagga agctgaggag gccctgagtg aaatctcgga catgtcgggc   3180
ggcattaaac ctgcgtccgt atcatcaagc agctccttgt ccagcgtgag agtcacacgc    3240
ccaaaatact cagctcaagc catcatagac ttgggcgggc cctgcagtgg gcatctccaa   3300
gaggtaaagg aagcatgcct cggaatcatg cgcgaggcat gtgatgcgac taagcttgat    3360
gaccctgcta cgcaggaatg gctttcccgc atgtgggacc gggtggacat gctgacttgg   3420
cgcaacacgt ctgcctacca ggcgtttcgt accttagatg gcaggttaaa gttcctccca   3480
aaaatgatac tcgagacacc gccgcccctat ccgtgtgagt ttgtgatgat gcctcactcg   3540
cctgcacctt ccgtaggtgc ggagagtgac cttaccattg gctcagtcgc tactgaagat    3600
gttccacgta tcctcgagaa aatagaaaat gtcggcgaga tgaccaacca gggacccttg    3660
gccttctccg aggataaacc ggtggatgac cagcttgcca agacccccg gatatcgtcg     3720 cagagtcctg acgagagcac atcagctccg cccacaggca caggaggcgc cggttcattt    3780
accgatttgc cgccttcaga cggcgcggat gcggacgggg gggggccgtt tcggacgata    3840
aaaagaaaag ctgaagggct ctttgaccga ctgagccgac aggtttttaa cctcgtctcc    3900
catctccctg ttttcttctc acgccttttc aacccgggcg gtagttattc tccgggtgat   3960
tggggttttg cagcttttac tctattgtgc ctccttttat gctacagtta ccagcatttc   4020
ggtattgctc ccctcttggg tgtgttttct gggtcttctc ggcgcgtccg aatgggggtt    4080
tttggctgct ggttggcttt tgctgttggt ctgttcaagc ctgtgtccga cccagtcggc    4140
gctgcttgtg agtttgattc gccagagtgt agaaacatcc ttcattcttt tgagcttctc    4200
aaaccttggg accctgttcg cggccttgtt gtgggccccg tcggtctcgg tcttgccatt    4260
cttggcaggt tactgggcgg ggcacgctgc atctggcact ttttgcttag gcttggcatt   4320
gttgcagact gtgtcttggc tggagcttat gtgctttctc aaggcaggtg taaaaagtgc    4380
tggggatctt gtataagaac tgctcctagt gaggtcgctt ttaatgtgtt ccttttttaca   4440 cgtgcgacca ggtcgtcgct tactgacctg tgcgatcggt tttgtgcgcc aaaaggcatg    4500
gaccccattt ttctcgccac tgggtggcgc gggtgctggg ccggccgaag ccccattgag   4560
caaccctctg aaaaacccat cgcgtttgcc cagttggatg aaaagaagat tacggctagg    4620
actgtcgtcg cccagcctta tgaccctaac caagccgtaa agtgcttgcg ggtattgcag    4680
gcgggtgggg caatggtagc tgaggcagtc ccaaaagttg tcaaggtttc cgctgtccca    4740
ttccgagccc ccttctttcc caccggagtg aaagttgacc cagaatgcag ggttgtggtt    4800
gaccccgaca ctttcaccgc agctctccgg tctggctact ccaccacaaa cctcgtcctt   4860
ggtacagggg actttgccca gctgaatgga ttgaaaatca ggcagatttc caagccttca    4920
ggaggaggcc cacacctcac ggctgccctg catgttgctt gctcgatggc tttgcacatg   4980
cttgttggga tttatgtgac tgcggtgggt tcttgcggca ccggcaccaa cgacccgtgg    5040
```

```
tgcgctaacc cgtttgccgt ccctggctac ggacctggct ctctttgcac gtccaggttg   5100
tgcatttccc aacatggcct taccctgccc ttgacagcac tcgtggcggg attcggcatt   5160
caagaaattg ccttggtcgt tttgattttt gtttccatcg gaggcatggc tcacaggtta   5220
agttgcaagg ctgacatgct gtgtgttttg cttgcaattg ccagctatgt ttgggtacct   5280
cttacctggt tgctttgtgt gtttccttgc tggttgcgct gttttctttt gcatcccctc   5340
accatcctat ggtggttttt tttcttgatt tctgtgaata tgccttcagg aatcttggcc   5400
atggtgctgt tggtttctct ttggcttctt ggtcgttata ctaatgttgc tggtcttgtt   5460 acccccctacg acattcatca ttacactagt ggccccgcg gtgttgccgc cttggctacc   5520
gcaccagatg ggacctactt ggccgctgtc cgccgtgctg cgttaaccgg ccgtaccatg   5580
ctgtttaccc cgtcccagct tgggtctctt cttgagggtg cttcagaac tcgaaaccc    5640 tcactgaaca ccgtcaatgt ggtcgggtcc tccatgggct ctggcggggt gttcaccatt   5700
gacgaaaaaa ttaagtgcgt aactgccgca catgtcctta cggcaattc agctaggatt   5760 tccgggtcg gcttcaatca aatgcttgac tttgacgtaa agggagattt cgccatagct   5820
gattgcccga attggcaagg ggttgccccc aagacccaat tctgcaagga tggatggact   5880
ggccgtgcct attggctgac atcctctggc gtcgaacccg cgtcattgg aaaaggattc   5940 gccttctgct tcactgcgtg cggcgattcc gggtccccag tgatcaccga ggccggtgag   6000
cttgtcggcg ttcacacggg atcaaataaa caaggaggag gcatcgttac gcgcccctca   6060
ggccagtttt gtaatgtggc acccatcaaa ctaagcgaat taagtgaatt ctttgctggg   6120
cctaaggtcc cgctcggtga tgtaaaggtt ggcagccaca taattaaaga cataggcgag   6180
gtgccctcag atctttgtgc cttgcttgct gccaaacctg aactggaagg gggcctctcc   6240
accgtccaac ttctttgtgt gttttttcctc ctgtggagga tgatgggaca tgcctggacg   6300
cccttggttg ctgtgggttt ctttatcctg aatgaggttc tcccagccgt cctggtccgg   6360 agtgtttttct cctttggaat gtttgtgcta tcctggctca cgccatggtc tgcgcaagtt   6420
ctgatgatca gacttctaac agcagccctt aacaggaaca gatggtcact tgcctttttc   6480
agtcttggtg cagtgaccgg ttttgtcgca gaatttgcgg ctactcaggg gcatccgttg   6540
caggctgtga tgaatttgag cacctatgca ttcctgcctc ggatgatggt tgtgacctca   6600
ccggccccag tgatcgcgtg tggtgtcgtg cacctacttg ccatcatttt gtacttgttt   6660
aagtaccgcg gcctgcacca aatccttgtt ggcgacggag tgttctctgc ggctttcttc   6720
ttgcgatact ttgccgaggg taagttaagg gaaggggtgt cgcaatcctg tgggatggat   6780
catgagtctc tgactggtgc cctcgctatg agactcagtg acgaggactt ggatttcctt   6840
gcgaaatgga ctgattttaa gtgctttgtt tctgcgtcca acatgaggaa tgcagcgggt   6900
caatttattg aggctgccta tgctaaagca cttagaatgg agcttgccca gttggtgcag   6960
gttgacaaag ttcgaggtac tttggccaaa ctcgaagctt ttgctgatac cgtggcaccc   7020
cagctctcgc ccggtgacat tgttgttgct ctcggccata cgcctgttgg cagtatcttc   7080
gacctaaagg ttggtagcac caagcatact ctccaagcca ttgagaccag agtccttgct   7140
gggtccaaaa tgaccgtggc gcgcgtcgtc aacccgaccc ccacgccacc acccgcaccc   7200
gtgcccatcc ccctcccacc gaaagtcctg gagaatggcc caacgcttg gggggatgag   7260 gaccgtttga ataagaagaa gaggcgcagg atgaagccc tcggcatcta cgtcatgggc   7320
gggaaaaagt accagaaatt ctgggacaag aattccggtg atgtgtttta tgaggaggtc   7380
cataataaca tagatgagtg ggagtgtctc agagttggcg atcctgccga ctttgaccct   7440
```

```
gagaagggaa ctctgtgtgg acatgtcacc attgaagaca aggcttaccg tgtttacgcc   7500
tccccatctg gtaagaggtt cttggtcccc gtcaacccag aaaatggaag agtccaatgg   7560
gaagctgcaa agctttctgt ggagcaggcc cttggcatga tgaacgtcga cggtgagttg   7620
actgccaaag aactggagaa actaaaaaga ataattgaca aactccagag cctgactaag   7680
gagcagtgtt taaactgcta gccgccagcg gcttgacccg ctgtggtcgc ggcggcttgg   7740
ttgttactga aacagcggta aaatagtca aatttcacaa ccggaccttc accctgggac    7800
ctgtgaattt aaaagtggcc agtgaggttg agctaaaaga cgcgattgag cacaatcaac   7860
acccggttgc gagaccggtc gatggtggtg ttgtgcttct gcgttccgcg gttccttcgc   7920
ttatagacgt cttgatctcc ggtgctgatg catctcccaa gttacttgcc caccacgggc   7980
cgggaaacac tgggatcgat ggcacgctct gggattttga gtccgaagcc actaaagagg   8040
aagtcgcact tagtgcgcaa ataatacagg cttgtgacat taggcgcggc gacgcccctg   8100
aaattggtct tccttacaag ctgtaccctg ttaggggtaa ccctgagcga gtaaaagggg   8160
ttctacaaaa tacaaggttt ggagacatac cttacaaaac ccccagtgat actggaaacc   8220
cagtgcacgc ggctgcctgc cttacgccca atgccactcc ggtgactgat gggcgctccg   8280
ttttggccac gaccatgccc tccgggtttg agttgtatgt accaaccata ccagcgtctg   8340
tccttgatta ccttgattcc agacctgact gccctaaaca gctgacagag cacggctgtg   8400
aagatgccgc actaagagac ctctccaaat atgacttgtc cacccaaggc tttgttttac   8460 ctgggggttct tcgccttgta cggaaatacc tgtttgccca tgtaggtaag tgcccacccg   8520
ttcatcggcc ttccacttac cctgctaaga attctatggc tggaataaat gggaacaggt   8580
tcccaaccaa ggatattcag agcgtccctg agatcgacgt tctgtgcgca caggctgtgc   8640
gggaaaactg gcaaactgtt acccctttgta ctcttaagaa acagtattgt gggaagaaga   8700
agactaggac catactcggc acaaataact tcatcgcgct agcccaccga gcagcgttga   8760
gtggtgttac ccagggcttc atgaagaagg cgtttaactc gcccatcgcc ctcggaaaaa   8820
acaagtttaa ggagctacag actccggtcc tgggcaggtg tctagaagct gatcttgcat   8880
cctgcgaccg atccacaccc gcaattgtcc gctggtttgc cgccaacctc ctttatgagc   8940
ttgcctgcgc tgaagagcat ctaccgtcgt acgtgctaaa ctgctgccac gacttactgg   9000
tcacgcagtc cggcgcagtg actaagagag gtggcctgtc gtctggcgac ccgatcacct   9060
ctgtgtctaa caccatttac agtttggtga tctacgcaca gcatatggtg ctcagttact   9120
tcaaaagtgg tcaccccccat ggcctcttat tcttacagga ccagctaaag tttgaggaca   9180
tgcttaaggt tcaaccctg atcgtctatt cggacgacct cgtgctgtat gccgagtctc    9240
ccactatgcc aaaactaccac tggtgggttg agcatctgaa tttgatgctg gggttcaga    9300 cggacccaaa gaagacagcc ataacagact cgccatcatt tttgggctgt agaataataa   9360
atggacgcca gctagtcccc aaccgtgaca ggattctcgc ggccctcgcc taccacatga   9420
aggcgagtaa tgtttctgaa tactacgcct ctgcggctgc aatactcatg gacagctgtg   9480 cttgttttgga gtatgatcct gaatggttcg aagaacttgt agttggaata gcgcaatgcg   9540
cccgcaagga tggctacagc tttcccggcc cgccgttcta tatatccatg tgggaaaaac   9600
tcagatccaa ttatgagggg aagaagtcga gagtgtgcgg gtactgcggg gccccggccc   9660
cgtatgctac cgcctgtggt ctcgacgtct gcatttacca cactcacttc caccagcatt   9720
gtccagtcat aatctggtgt ggccatccag ccggttctgg ttcttgtagt gagtgcagat   9780
```

```
ccctgtgggg gaaaggcaca agcccttttag acgaggtgct ggaacaagtc ccgtacaagc    9840
ccccacggac cgttatcatg catgtggagc agggtcttac cccccttgac ccaggcagat    9900
atcagactcg ccgcgggtta gtctccgtca ggcgcgggat caggggaaat gaggttgagc    9960
taccagacgg tgattatgcc agtaccgcct tgctccctac ctgcaaagag atcaacatgg   10020
tcgctgtcgc ttctaatgta ttgcgcagca ggttcatcat tggtccaccc ggtgcgggga   10080
aaacatactg gctacttcaa caggtccagg atggtgatgt tatttacaca ccaactcacc   10140
agaccatgct tgacatgatt agagctttgg ggacgtgccg gttcaacgtc ccggcaggca   10200
caacgctgca attcccggtc ccctcccgca ccggtccgtg ggttcgcatc ctagccggcg   10260
gttggtgtcc tggcaagaat tccttcctgg atgaagcagc gtattgcaat caccttgatg   10320
tcttaaggct tcttagcaaa actaccctca cctgtctggg agactttaaa caactccacc   10380
cagtgggttt tgattctcat tgctatgttt ttgacatcat gcctcaaact caactgaaga   10440
ccatctggag gtttggacaa atatctgtg atgccatcca accagattac agggacaaac   10500
tcatgtccat ggtcaacatg acccgtgtaa cctacgtgga aaaacctgtc aggtatgggc   10560
aagtcctcac ccctaccac agggaccgag aggacgacgc catcaccatt gactccagtc   10620
aaggcgccac atttgatgtg gttacactgc atttgcccac taaagattca ctcaacaggc   10680
aaagagccct tgttgctatc accagggcaa gacatgctat ctttgcgtat gatccacaca   10740
ggcagctgca gagcctgttt gatcttcctg caaaaggtac acccgtcaac cttgcagtgc   10800
accgcgatgg gcagctgatc gtgctagata gaaataacaa tgaatgcacg gttgctcagg   10860
ctctaggtaa cggggataaa tttagggcca cagacaagcg cgttgtagat tctctccgcg   10920
ccatttgtgc tgatctagaa ggtacgagct ctccgctccc caaggtcgca cacaacttgg   10980
gattttattt ctcacctgat ttaacacagt ttgctaaact cccagcagaa cttgcacctc   11040
actggcccgt ggtgacagcc cagaacaatg aaaagtggcc agatcggctg gttactagcc   11100
ttcgccctat ccataaatat agccgcgcgt gcatcggtgc cggctatatg gtgggccct   11160
cggtgtttct aggcactcct ggggtcgtgt catactatct cacaaaattt gttaagggcg   11220
aggctcaagt gcttccggag acggttttca gcaccggccg aattgaggta gactgccggg   11280
aatatcttga tgaccaggag cgagaagttg ctgcgtccct cccacatgcc ttcattggcg   11340
acgtcaaagg cactaccgtt ggagggtgcc accatgtcac ttccagatac ctcccgcgct   11400
tccttcccaa ggaatcagtt gcggtagtcg gggtttcaag tcccggaaaa gccgcgaaag   11460
cattgtgcac actaacagat gtgtacctcc cagaccttga agcctatctc cacccggaga   11520
ccccgtccaa gtgctggaga atgatgttgg acttcaagga agttcgacta atggtctgga   11580
aagacaaaac agcctatttc caacttgaag gtcgctattt cacctggtat cagcttgcca   11640
gctatgcctc gtacatccgt gttcctgtca actctacggt gtacttggac ccctgcatgg   11700
gccccgccct ttgcaacagg agagtcgtcg ggtccactca ttgggggggct gaccttgcgg   11760
tcacccctta tgattacggc gctaaaatca tcctgtctag cgcgtaccat ggtgaaatgc   11820
cccccggata caagattctg gcgtgcgcgg aattctcggt ggacgaccca gtcaagtaca   11880
aacatacctg ggggtttgaa tcggatacag cgtatctgta tgagttcacc ggaaacggtt   11940
aggactggga ggattacaat gatgcgtttc gtgcgcgcca ggaagggaaa atttataagg   12000
ctactgccac cagcatgaag ttttattttc ccccgggccc tgtcattgaa ccaactttag   12060
gcctgaattg aaatgaaatg gggtccatgc aaagcctttt tagcaaaatt ggccaacttt   12120
ttgtggatgc tttcacggag ttcttggtgt ctattgttga tatcattata tttttggcca   12180
```

```
tcttgtttgg cttcaccatc gccggttggc tggtggtctt ttgcatcaga ttggtttgct   12240
ccgcgatact ccgtgcgcgc cctgccattc accctgagca attacagaag atcttatgag   12300
gcctttcttt cccagtgcca agtggacatt cccacctggg gaactaaaca cccttgggg    12360
atgttttggc accataaggt gtcaaccctg attgatgaga tggtgtcgcg tcgaatgtac   12420
cgcaccatgg aaaaagcagg acaggctgcc tggaaacagg tggtgagcga ggctacgctg   12480
tctcgcatta gtagtttgga tgtggtggct cattttcagc atcttgccgc cattgaagcc   12540
gagacctgta atatttggc ctcccggctg cccatgctac ataacctgcg catgacaggg     12600
tcaaatgtaa ccatagtgta taatagtact ttaaatcagg tgtttgctat tttcccgacc   12660
cctggttccc ggccaaagct tcatgatttt cagcaatggc taatcgctgt acactcctcc   12720
atattctcct ctgttgcagc ttcttgtact ctttttgttg tgctgtggtt gcggatgccg   12780
atgctacgta ctgttttgg tttccgctgg ttaggggcaa cttttccttc gagctcacgg     12840
tgaattacac ggtgtgccca ccttgcctca cccggcaggc ggccgcacag gcctacgaac   12900
ccggtaggtc tctttggtgc aggatagggt acgatcggtg tggagaggac gaccatgacg   12960
agctagggtt tatggtaccg tctggcctct ccagcgaagg ccacttgacc agtgtttacg   13020
cctggttggc gttcttgtcc ttcagctaca cagcccagtt ccaccccgag atattcggga   13080
tagggaatgt gagtcaagtt tatgttgaca ccaaacatca actcatctgc gccaaacatg   13140
acgggcagaa caccaccttg cctcgtcatg acaatatttc agctgtgttt cagacctatt   13200
accaacatca agtcgacggc ggcaattggt ttcacctaga atggctgcgt cccttctttt   13260
cctcatggtt ggttttaaat gtctcttggt ttctcaggcg ttcgcctgca aaccatgttt   13320
cagttcgagt cttgcagaca ttaagaccaa caccaccgca gcggcaggct ttgctgtcct   13380
ccaagacatc agttgcctta ggcatcgcaa ctcggcccct gaggcgcttc gcaaaatccc   13440
tcagtgccgt acggcgatag ggacaccgt gtatattacc atcacagcca atgtgacaga     13500
tgagaattat ttacattctt ctgatctcct catgctctct tcttgccttt tctacgcttc   13560
tgagatgagt gaaaagggat ttaaggtggt ttttggcaat gtgtcaggca tcgtggctgt   13620
gtgtgtcaat tttaccagct acgtccaaca tgtcagggag tttacccaac gctccttgat   13680
ggtcgaccat gtgcggctgc tccatttcat gacacctgag accatgaggt gggcaaccgt   13740
tttagcctgt cttgttgcca ttctgttggc aatttgaatg tttaagtatg ttggggaaat   13800
gcttgaccgc gggctgttgc tcgcgattgc tttctttgtg gtgtatcgtg ccgttctgtt   13860
ccactgtgct cgtcgacgcc aacggcaaca gcagctctca tctgcaattg atttacaact   13920
tgacgctatg tgagctgaat ggcacggatt ggctagctaa tagatttgat tgggcagtgg   13980
agagctttgt catctttcct gttttgactc acatagtctc ctatgttgcc ctcaccacca   14040
gccatttcct tgacacaatt gctttagtca ctgtatctac cgccggtttt cttcacgggc   14100
ggtatgtcct gagtagcatc tacgcggtct gtgccctggc tgcgttgact tgcttcgtca   14160
ttaggtttgt aaagaattgc atgtcttggc gctactcatg taccagatat accaattttc   14220
ttctggacac taagggcaga ctctatcgtt ggcggtcgcc tgtcatcata gagaagaggg   14280
gcaaagttga ggtcgaaggt catctgatcg atctcaaaag agttgtgctt gatggttccg   14340
tggcaacccc tataaccaga gtttcagcgg aacaatgggg tcgtccttag atgacttttg   14400
tcatgatagt gcggctccac aaaaggtgct tttggcattt tctattacct acacgccagt   14460
gatgatatat gccctaaagg tgagtcgcgg ccgactgcta gggctgctgc acctttgat    14520
```

| | |
|---|---:|
| tttcctgaac tgtgctttca cctttgggta catgacattc acgcactttc agagtacaaa | 14580 |
| taaggtcgcg ctcactatgg gagcagtagt tgcactcctt tgggggggtgt actcagccat | 14640 |
| agaaacctgg aaattcatca cctccagatg ccgtttgtgc ttgctaggcc gcaagtacat | 14700 |
| tctggcccct gcccaccacg ttgaaagtgc cgcaggcttt catccgattg cggcaaatga | 14760 |
| taaccacgca tttgtcgtcc ggcgtcccgg ctccactacg gtcaacggca cattggtgcc | 14820 |
| cgggttgaaa agcctcgtgt tgggtggcag aaaagctgtt aaacagggag tggtaaacct | 14880 |
| tgtcaaatat gccaaataac aacggcaagc agcagaagag aaagaagggg gatggccagc | 14940 |
| cagtcaatca gctgtgccag atgctgggta agatcatcgc ccagcaaaac cagtctagag | 15000 |
| gcaagggacc ggggaagaaa aataagaaga aaaacccgga gaagcccat tttcctctag | 15060 |
| ctactgaaga tgatgtcaga catcacttta cccctagtga gcggcaattg tgtctgtcgt | 15120 |
| caatccagac tgccttaat caaggcgctg ggacttgcac cctgtcagat tcagggagga | 15180 |
| taagttacac tgtggagttt agtttgccta cgcatcatac tgtgcgcttg atccgcgtca | 15240 |
| cagcatcacc ctcagcatga tgggctggca ttctgaggca tcccagtgtt tgaattggaa | 15300 |
| gaatgtgtgg tgaatggcac tgattgacat tgtgcctcta agtcacctat tcaattaggg | 15360 |
| cgaccgtgtg ggggtaatat ttaattggcg agaaccacac ggccgaaatt aaa | 15413 |

<210> SEQ ID NO 6
<211> LENGTH: 15078
<212> TYPE: DNA
<213> ORGANISM: Artificial Sequence
<220> FEATURE:
<223> OTHER INFORMATION: Synthetic Construct

<400> SEQUENCE: 6

| | |
|---|---:|
| atgatgtgta gggtattccc cctacataca cgacacttct ggtgtttgtg taccttggag | 60 |
| gcgtgggtac agccccgccc cacccccttgg ccctgttct agcccaacag gtatccttct | 120 |
| ccctcggggc gagcgcgccg cctactgctc ccttgcagta ggaaggacct cccgagtatt | 180 |
| tccggagagc acctgcttta cgggatctcc accctttaac catgtctggg acgttctccc | 240 |
| ggtgcatgtg cacccccggct gcccgggtat tttggaacgc cggccaagtc ttttgcacac | 300 |
| ggtgtctcag tgcgcggtct cttctctctt cagaacttca ggacactgac ctcggtgcaa | 360 |
| ttggattgtt ccacaagcct agggacaagc ttcactggaa agtccccatc ggcatccctc | 420 |
| aggtggaatg tactccatcc gggtgctgtt ggctctcagc tatattccct atagcacgta | 480 |
| tgacctctgg caatcataac ttcctccaac gacttgttaa ggttgctgat gttttgtacc | 540 |
| gcgacggttg cttggcacct cgacaccttc gtgaactcca agtttacgag cgcggctgca | 600 |
| actggtaccc gatcacgggg cccgtacccg ggatgggttt gtttgcgaac tccatgcacg | 660 |
| tatccgacca gccgttccct ggagccaccc atgtgttgac taactcgcct ctgcctcaac | 720 |
| gggcgtgccg gcaaccgttc tgtccatttg aggaagctca ttctaacgtg tataggtgga | 780 |
| ataaatttgt gattttcacg gactccactc tcaacggcca atctcgcatg atgtggacgc | 840 |
| cgggatccga tgattcagcc gccttggagg cgctaccgcc tgaattagaa cgtcaggtcg | 900 |
| gaatcctcat tcggagtttc cctgctcatc accccgttaa cctggccgac tgggagctca | 960 |
| ctgagacccc tgagaatggc ttctccttca gcacgtctca ttcttgtggt tatcttgtcc | 1020 |
| aaaaccccga tgtgtttgat agcaagtgct ggctcacttg cttttcgggc cagtcggtcg | 1080 |
| aagtgcgccg ctgtgaagaa catttagcca acgcccttgg ttaccaaacc aagtggggcg | 1140 |
| tgcacggtaa gtaccttcag cgcaggctcc aagttcgcgg cattcgtgct gtagtcgatc | 1200 |

```
ctgatggccc cattcacgtt gaagcgctgt cttgctccca gtcttggatc aggcacctga    1260
ctctgaataa tggtgttacc ccaggattcg ttcgcctgac atccattcgc attgtgccga    1320
acacagagcc taccactttc cggatctttc ggtttggagc gcataagtgg tatggcgctg    1380
ctggcaaacg ggctcgtgcc aagcgtgccg ctaaaagtgg gaaagattcg gcttccactc    1440
ccaaggttgc ccagccggcc cttacctgtg gagtcaccac ctactctcca ccaacagacg    1500
ggtcttgcgg ttggcatgtc cttgccgcca taatgaaccg gatgatgaac ggtgacttca    1560
cgtccccact gcctcagtac aatagaccag aagacgattg gcttctgat tatgatcttg     1620 ctcaggcgat tcaatgtcta caactgcctg caaccgtggt tcggaatcgt gcctgtccta    1680
acgccaagta ccttgtaaga cttaacgggg ttcactggga ggtagaggtg agatctggaa    1740
tggctccccg ctccctttct cgtgaatgtg tagttggcgt ttgctctgaa ggttgtgttg    1800
ctccgcctta tccagcggac gggcttccta aacgcgcact agaggccttg gcgtctgctt    1860
acagactacc ctccgattgt gttagctctg gcattgatga cttctcttgct aatccacccc    1920 ctcaggaatt ttggactctt gacaaaatgc tgacctcccc gtcaccagaa cggtccggct    1980
tctctagttt gtataagtta ctgttagagg ttgttccgca aaagtgtggt gccacggaag    2040
gggctttcac ctatgctgtt gagaggatgt taaaggattg tccgagctct gaacaggcca    2100
tggcccttct ggcaaaaatt aaagttccat cctcaaaggc cccgtctgtg tcctggacg     2160 ggtgtttccc tgcggatatt ccggctgatt tcgagccagc gtctcgggaa aggccccgaa    2220
gttccagcgt tgctgttgcc ctgtgttcac cggatgcaga aaggttcgag gaagtacccc    2280
cagaagaagt tcaagagaga ggctacaagg ccgtcaactc tgcactcctt gccgaaaacc    2340
ccaatgatga acaggcacag gtggttgccg gtgaacaact gaagctcggc ggttgtagtt    2400
tggcaatcgg gaatgctcag tccactccag gctccatgga agagaacatg cgcaatagcc    2460
gggaagacga accactagat ttgtccctac cagcactagc taccacgacg acccttgtga    2520
gagagcgaat actcgacaac ccaggtcctg atgccggtac cctccctgcc accgttcgag    2580
aatttgtctc gacagggcct atgctccgtc atgttgagca ttgtggcacg gagtctggcg    2640
acagcagttc acctttggat ctgtcttatg cgcaaactcc ggaccagcct ttaaatctgt    2700
ccctggccgc ttggccggtg aagaccaccg cgtctgaccc tggctgggtc cacggtaggt    2760
gcgagcctgt cttttgtaaag cctcgaaaag cttttttctga tggcgattca gcctttcagt    2820 tcgggggct ttctgagtcc agctctgtca tcgagtttga ccgaacaaaa gatgcatcgg     2880
aggttgacgc tcctgtcggc ttgacgactt cgaacgaggc cctctctgtg gtcgacccctt    2940 tcgaatttgc cgaactcaag cgcccgcgtt tctccgcaca agccttaatt gaccgaggcg    3000
gcccgcttgc cgatgtccat gcaaaaataa agcaccgggt gtatgaacaa tgccttcaag    3060
cttgtgagcc tggtagccgt gcaaccccag ccaccaagaa gtggctcgac aaaatgtggg    3120
acagggtgga catgaaaact tggcgctgca cctcgcagtt ccaagctggt cgcatccttg    3180
catccctcaa attccttcct gacatgattc aagacgcacc gcctcctgtt cccaggaaga    3240
accgagctag tgacaacgcc ggtttgaagc aactggtggc acagtgggat aggaaattga    3300
gtggaacccc cccccaaaa ccggctgggt cagtgcttga ccaggccgtc cctccaccca     3360
cggacgtcca gcaagaagat gtcactcctt ccggcgggcc actccatgcg ccggatttcc    3420
ctagtcgagt tagcacgagc gggggttgga aaagccttat actttccggg acccgtctcg    3480
cagggtctgt cagtcagcgc ctcatgacac gggttttga agttttctcc catctcccag      3540
```

```
cttttgcgct cacactttc tcgccgcggg gctctatggc tccaggcgat tggttgtttg    3600
caggtattgt tttacttgct ctcttgttct gtcgttttta cccgatactc ggatgccttc    3660
ccttattggg tgtcttttct gggtctgtgc ggcgtgttcg tctgggtgtt tttggttctt    3720
ggatggcttt tgctgtattt ctattctcga ctccatccaa cccagtcggt tcttcttgtg    3780
accacgattc gccggagtgt catgctgagc ttttggttct tgagcagcgc caactttggg    3840
aacctgtgcg cggccttgtg gtcggcccct cgggcctcct atgtgtcatt cttggcaagt    3900
tactcggtgg gtcacgttat ctctggcatg ttctcctacg tttatgcatg cttacagatt    3960
tggccctttc tcttgtttat gtggtgtccc aggggcgttg tcacaagtgt tggggaaagt    4020
gtataaggac ggctcctgct gaggtagcac ttaatgtatt tcctttctcg cgcgccaccc    4080
gtagctctct tgtatccttg tgtgatcggt tccaagcgcc taaaggagtt gatcctgtgc    4140
acttggcaac gggttggcac gggtgttggt gtggcgagag ccccgttcat caatcacacc    4200
aaaagccaat aacctatgcc aatttggatg aaagaaaat atctgcccaa acggtggttg    4260
ctgtcccata cgaccccagc caggctatca aatgcctgaa agttctgcag gcggaggggg    4320
ctatcgtaga ccagcctaca cctgaagttg ttcgcgtgtc cgaggtcccc ttctcagccc    4380
cattttcccc aaaagttcct gtcaacccgg attgcaggat tgtggtggat cggacacttt    4440
ttgtggctgc ggtccgctgc ggttactcga cagcacaact ggtcctgggc cggggcaatt    4500
ttgccaagct aaatcagacc ccctcagga gctctacctc caccaaaacg actgggggg      4560
cctcttacac ccttgctgta gctcaagtgt ctgcgtggac tcttgcccat ttcatcctcg    4620
gcctttggtt cacatcacct caagtgtgtg gccgagggac cgctgatcca tggtgttcaa    4680
atccctttc ataccctgcc tatggccctg gagttgtatg ctcctctcga ctttgtgtgt     4740
ctgccgatgg ggtcaccctg ccattgtttt cagctgtggc acaactctcc ggcagagagg    4800
tggggatttt tattttggtg cttgtctccc tgatagcttt ggcccatcgc ttggctctta    4860
aggcagactg gttagtggtc tttttggctt tttgtgctta cgcctggccc atgagttcct    4920
ggctaatctg cttctttcct atactcttaa agtggatcac cctccaccct ctcaccatgc    4980
tttgggtgca ctcattcttg gtgtttttgcc tgccagcagc cggcgtcctc tcactaggga    5040
taactggcct tctttgggca atcggccgct ttacccaggt tgccgggatt attacacctt    5100
atgcatcca ccagtacacc tccgggccgc gtggtcagc tgctgtggcc acagccccag      5160
aaggcactta tatggccgcc gtccggagag ctgctttaac tgggcgatct ttaatattca    5220
ccccgtcagc agttggatcc ctcctcgaag gtgctttcag gactcataaa ccctgtctta    5280
atactgtgaa tgttgtgggc tcttcccttg gttccggagg cgttttcacc attgatggca    5340
gaagaactgt tgtcactgct gctcatgtgt tgaatggcga cacagctaga gttaccggcg    5400
actcctacaa ccgcatgcac actttcaaga ccaatggtga ttatgcctgg tcccatgctg    5460
atgactggca gggcattgcc cccgtggtca aggtagtgaa ggggtaccgc ggtcgtgctt    5520
attggcaaac atcaactggt gtcgaacccg gcatcattgg agaagggttt gccttctgtt    5580
tcactaattg tggtgattcg gggtcacccg tcatctcaga atccggtgat ctcatcggaa    5640
ttcacaccgg ttcaaacaaa ctcggttctg gtcttgtgac gaccctgaa ggggagacct     5700
gtaccatcaa agaaaccaag ctctccgacc tttccagaca ttttgcaggc cctagtgttc    5760
ctcttggtga cattaaatta gcccggcca tcatccctga tgtaacatct attccgagtg     5820
acttggcatc gctcctagcc tctgtccctg tggtggaagg cggcctctcg accgttcaac    5880
ttctgtgtgt ctttttcctt ctctggcgca tgatgggcca tgcctggaca cccattgttg    5940
```

```
ccgtgggctt ctttctgctg aatgaaatcc tcccagcagt tttggtccga gccgtgtttt   6000
cttttgcact ctttgtgctt gcatgggtca cccctggtc cgcacaggtg ttgatgatta     6060
gactcctcac ggcatctctc aaccgcaaca agctctctct ggtgttctac gcactcgggg    6120
gtatcgtcgg tttggccgct gaaatcggga ctttcgctgg cagattgcct gaattgtctc    6180
aagccctttc gacctactgt ttcttgccta gggcccttgc catggccagt tgtgtcccca    6240
tcgtcattat tggcggactt catgcccctcg gtgtaattct gtggttgttc aaataccggt   6300
gcctccacaa cacgctggtt ggtgatgggt gttttcaag tgccttcttc ctgcgctatt     6360
ttgcggaggg caatctgagg aaaggtgttt cacagtcctg tggcatgaat aacgagtctc    6420
tgacggctgc tctggcttgc aagctgtcgc aggctgatct tgaattttg tccagtttaa     6480 cgaacttcaa gtgctttgtg tctgcttcaa atatgaaaaa tgccgccggc cagtacattg    6540
aagcagctta tgccaaggcc ttgcgccaag agttggcctc tctagttcag gttgataaaa    6600
tgaaaggagt tttgtccaag ctcgaggcct ttgctgaaac agccaccccg tcccttgaca    6660
caggtgacgt ggttgttttg cttgggcagc atcctcacgg gtctatcctc gatattaatg    6720
tggggactga aggaaaaact gtgtccgtgc aagagacccg gaacctaggc ggctccaaat    6780
tcagtgtttg cactgtcgtg tccaacacac ccgtggacgc cttaaccggc atcccactcc    6840
ggacaccaac ccctcttttt gagaatggtc cgcgtcatcg cggtgaggaa gacgatctca    6900
aagtcgagag gatgaagaaa cactgtgtat ccctcggctt ccacaacatc aatggcaaag    6960
tctactgtaa gatctgggat aagtctaccg gtgacacctt ttacaccgac gattcccggt    7020 atcccacga ccatgctttt caggacaggt cagccgacta cagagacagg gactacgaag      7080
gtgtgcaaac cgcccccaa caaggctttg atccaaagtc tgaaacccct gttggcactg     7140
tagtgatcgg cggtatcacg tataacaggt acctgattaa aggtaaggag gtcctggtcc    7200
ccaagcctga caactgcctc gaagctgcca agctgtccct tgagcaggct ctcgctggga    7260
tgggccaaac ttgcgacctt acggctgccg aggtggaaaa gctgaagcgc atcattagtc    7320
aactccaagg tttgaccact gaacaggctt taaactgtta gccgccagcg gcttgacccg    7380
ctgtggccgc ggcggcttag tagtgactga acggcggta aaaattgtaa aatatcacaa      7440
cagaactttc accttaggcc cttttgacct gaaagtcact accgaggcag aggtcaagaa    7500
atcagctgag cagggccacg ctgttgtggc aaatttatgt tctggtgtcg tcttgatgag    7560
acctcaccca ccgtctcttg ttgacgttct tttgaaaccc ggacttgaca caaaacccgg    7620
cattcagcca gggcatgggg ccgggaatat gggcgtggaa ggttctattt gggatttcga    7680
aaccgcacct acaaaggcag aactcgagtt atccaagcaa ataattcaag catgtgaagt    7740
taggcgcggg gacgccccga acctccaact cccttacaag ctctatcctg ttagggggga    7800
tcctgagcgg catgagggcc gccttatcaa caccaggttt ggagatttat cttacaaaac    7860
tcctcaagac accaagtccg caatccacgc ggcttgttgc ctgcacccca acggggcccc    7920
cgtgtctgat ggtaaatcaa cactaggtac cactcttcaa catggttttg agctttacgt    7980
ccctactgtg ccttatagtg tcatggagta cctcgattca cgccctgaca ccccttttat    8040
gtgcaccaaa catggcactt ccaaggctgc tgcagaggac cttcaaaaat acgacctgtc    8100
cactcaaggc ttcgtcctgc ctggggtcct acgcctagta cgtagataca ttttggcca     8160 tattggtaag cgcgccgccat tgttcctccc atcaacctat cccgccaaga actctatggc    8220
agggatcaat ggccagagat tcccaacaaa ggacgttcag agcatacctg aaattgatga    8280
```

```
aatgtgtgcc cgcgccgtca aagagaattg gcaaactgtg acaccttgta ccctcaagaa    8340
acagtattgt tccaagccca aaaccaggac catcctaggc actaacaact ttattgcctt    8400
ggctcacaga tcggcgctca gtggtgttac ccaggcattc atgaagaagg cttggaagtc    8460
cccaattgcc ttgggaaaaa acaaattcaa ggagctgcat tgcaccgtcg ccggcaggtg    8520
tcttgaggct gacttggcct cctgtgaccg cagcacccc gccattgtga gatggttcgt     8580
cgccaacctc ctgtatgaac ttgcgggatg tgaagagtac ttgcctagct atgtacttaa    8640
ttgctgccat gaccttgtgg caacacagga tggtgccttc acaaacgcg gtggcctgtc     8700
gtccggggac cccgtcacca gtgtgtctaa caccgtatat tcgctggtaa tctatgccca    8760
gcacatggtg ttgtcagcct tgaaaatggg tcatgaaatc ggtcttaagt tcctcgagga    8820
acagctcaga ttcgaggacc tcctcgaaat tcagcctatg ttggtatact ctgatgacct    8880
cgttttgtac gctgaaagac ccactttcc taattatcac tggtgggtcg agcaccttga     8940
cctaatgctg ggttttaaaa cggacccaaa gaagaccgtc ataactgata aacccagctt    9000
cctcggctgc agaattgagg cagggcggca gctggtcccc aatcgcgacc gcatcctggc    9060
tgctctcgca tatcacatga aggcgcagaa tgcctcagag tattatgcgt ctgctgccgc    9120
aatcctgatg gattcatgcg cttgcattga tcatgacccc gagtggtatg aggacctcat    9180
ctgcggtatt gcccgatgcg cccgccaaga tggttatagc ttcccaggtc ggcgttttt    9240
catgtctatg tgggagaggc tgagaagtca caatgaaggg aagaaattcc gccactgcgg    9300
catctgtgac gccaaagccg actatgcatc cgcctgtggg ctcgatctat gtttgttcca    9360
ctcgcacttt catcaacact gtcccgtcac tctgagctgc ggtcaccatg ccggttcaag    9420
ggaatgttcg cagtgtcagt cacctgttgg ggctggcaga tcccctcttg atgctgtgtt    9480
gaaacaaatt ccatacaaac ctccccgcac tgtcatcatg aaggtgagta acaaaacaac    9540
ggccctcgat ccggggaggt accagtcccg tcgaggcctc gttgcagtca agagaggtat    9600
cgccggcaat gaagttgatc tttctgatgg agactaccaa gtggtacctc ttttgccgac    9660
ttgcaaagac ataaacatgg tgaaagtggc ttgcaatgta ctactcagta agttcatagt    9720
ggggccacca ggttccggaa agaccacctg gctactagat caagtccaag acgatgatgt    9780
catttacaca ccaacccatc agactatgtt tgatatagtt agtgctctca agtttgcag    9840
gtactctatt ccaggagcct caggactccc tttcccacca tctgccagat ccggccgtg    9900
ggttaggctt atagccagtg ggcacgtccc tggccgcgta tcttacctcg atgaggccgg    9960
atactgtaat catctggaca ttctcagatt gctctccaaa acgccctg tgtgtttggg     10020
tgaccttcaa cagctacacc ctgtcggctt tgattcctac tgttatgtgt tgatcagat    10080
gccccagaag caactgaccg ttatttacag atttggccct aacatctgcg cggccattca    10140
gccttgttac agagagaagc ttgaatccaa ggctagaaac accagggtgg ttttgtcaa    10200
ccggcctgtg gcctttggtc aggtcctgac accataccat aaagatcgca tcggctctgc    10260
ggtaaccata gactcatccc agggagccac ctttgatatt gtgacactgc atctaccgtc    10320
accaaagtcc ctaaccaaat cccgagcact tgtggccatc actcgggcaa gacacgggtt    10380
gttcatttat gacccacatg accagctcca ggagtttttc aacttaatcc ctgagctcac    10440
agattgcaac cttgtgttta ccgcgggga tgagctggta gttctggatt cggataatgc    10500
agtcacaact gtagcaaagg ccctagaaac aggtcaatct cgattccgag tgtcagaccc    10560
gaggtgcaag tctctcttgg ccgcttgttc ggccagtctg aagggagct gtatgccact    10620
accgcaagta gcacataatc tggggtttta ctttccccca gacagtccag tatttgcacc    10680
```

```
tctgccaaga gagttggcgt cacattggcc agtggttacc caccagaata atcgggcgtg    10740
gcctgatcga cttgtcgcta gtatgcgccc aatcgatgcc cgctacagca agccgatggt    10800
cggtgcaggg tacgtagtcg ggccgtccac ttttcttggt actcccggtg tggtgtcata    10860
ctacctcacg ctatacatca ggggtgagcc ccaggccctg ccagaaacac tcgtttcaac    10920
ggggcgtata gcaacagatt gtcgggagta tctcgatgcg gctgaggagg aggcagcaaa    10980
agaactcccc cacgcattca ttggcgatgt caaaggtacc acggtggggg gttgtcatca    11040
catcacgtca aaatacttac ctaggtccct gcctaaagac tctgttgccg tagttggagt    11100
gagttcaccc ggcagggctg ctaaagccat gtgcaccgtc accgatgtgt atctccctga    11160
actccggccg tatctgcaac ctgagacggc atcaaagtgc tggaaactta aattagactt    11220
cagggacgtc cgactaatgg tctggaaagg agctaccgcc tatttccagt tggaagggtt    11280
tacatggtcg gcgctgcccg actatgccag gttcattcag ctgcccaagg atgccgttgt    11340
atacatcgat ccgtgtatag gaccggcaac agccaaccgc aaggtcgtgc gaaccacaga    11400
ctggcgggcc gacctggcag tgacaccgta tgactacggt gcccagacta ttttaacaac    11460
agcctggttc gaggacctcg ggccacagtg aagattttg ggttgcagc ctttaggcg    11520 agcacttggt ctggaaaaca ctgaggattg gcaattctt gcacgccgta tgaatgacgg    11580
caaagactac actgactata actggaattg tgttcgagga cgcccacaag ccatctacgg    11640
gcgtgctcgt gaccatacgt atcatttcgc ccccggcacg gaactgcagg tagagctagg    11700
taaaccccgg ctatcgcctg agcaggtgcc gtgaatttgg agtgatgcaa tggggtcact    11760
gtggagtaaa atcagccagc tgttcgtgga tgccttcact gagttcttgg ttagtgtggt    11820
tgatattgtc atcttccttg ctatattgtt tgggttcacc gtcgcaggat ggttattggt    11880
cttccttctc agagtggttt gctccgcgtt tctccgttcg cgctctgcca ttcactctcc    11940
cgaactatcg aagatcctat gaaggcttgt tgcccaactg cagaccggat gtcccacaat    12000
ttgcattcaa gcacccttg ggtatgttgt ggcatatgcg agtttcccac ctgattgatg    12060
agatggtctc tcgccgcatt taccagacca tggaacattc aggtcaagcg gcctggaagc    12120
aagtagttgg tgaggccact ctcacgaagc tgtcagggct cgatatagtc actcacttcc    12180
aacacctggc cgcagtggag gcggattctt gccgctttct cagctcacga ctcgtgatgc    12240
taaaaaatct tgccgttggc aatgtgagcc tacagtacaa caccacgctg gaccgcgttg    12300
agctcatttt tcccacgtca ggtacgaggc ccaagttaac cgacttcaga caatggctca    12360
tcagtgtgca cgcttccatt ttttcctctg tggcttcatc tatcacctg tttgtagtgc    12420 tttggcttcg aattccagct ctacgctatg ttttggttt ccactggccc acggcaacac    12480
atcattcgag ctgaccatca actataccat atgcaagcct tgtcttacca gtcaagcagc    12540
tcaccaaagg cttgagcccg tcgcaatgt gtggtgcaga tagggcatg agacgtgtga    12600 ggagcgtgac catgatgagt tgttcatgcc catcccgtcc ggatacgata acatcaaaact    12660 taagggttat tatgcctggc tggctttttt gtccttttcc tacgcggccc aattccaccc    12720
ggagttgttc gggattggga atgtgtcgcg tgtctttgtg gacaaacatc accagttcat    12780
ttgtgccgag catgatggac agaattcgac cgtatctact ggacacaaca tctctgcact    12840
atatgcggca tactaccacc accaaataga cgggggtaat tggttccatt tggaatggct    12900
gcgaccactc ttttcctcct ggttggtgct caatatatca tggtttctga ggcgttcgcc    12960
tgcaagccct gtttctcgac gcatctatca gatattaaga ccaacacgac cgcggctgcc    13020
```

| | | | | | |
|---|---|---|---|---|---|
| ggtttcatgg | tccttcagga | catcaattgt | ttccaacccc | acagggtccc | agcaacgcaa | 13080 |
| aatggagccc | ccttcaaaaa | gtcgtcccaa | tgccgtgaag | ctgtcggcac | tccccaatac | 13140 |
| atcacaataa | cagctaatgt | gaccgacgaa | tcgtacttgt | acaacgcgga | cttgctgatg | 13200 |
| ctttctgcgt | gccttttcta | cgcttcagaa | atgagtgaga | aaggctttaa | agtcatcttc | 13260 |
| gggaatgtct | ctggcgttgt | ttccgcttgt | gtcaatttta | cagattatgt | ggcccatgtg | 13320 |
| acccaacaca | cccagcagca | tcacctggta | attgatcaca | ttcggctgct | gcatttcctg | 13380 |
| acaccatctg | caatgaggtg | ggctacaacc | attgcttgtt | tgctcgccat | tctcttggcg | 13440 |
| atatgagatg | ttctcacaag | ttggggcgtt | ccttgactcc | gcactcttgc | ttctggtggc | 13500 |
| ttttttgct | gtgtaccggc | ttgtcttggt | cctttgccga | tggcaacggc | aacaactcga | 13560 |
| cataccaata | catatataat | ttgacgatat | gcgagttgaa | tgggaccgcg | tggctgtccg | 13620 |
| gccattttga | ttgggcagtt | gagactttg | tgctttaccc | ggttgccact | cacatcctct | 13680 |
| cactgggttt | tctcacaaca | agtcattttt | ttgacgcgct | cggtctcggt | gttgtatcca | 13740 |
| ctgctggatt | tgttggcggg | cggtatgtac | tcagcagcgt | ctacgcgct | tgtgctttcg | 13800 |
| cagcgttcgt | gtgttttgcc | atccgtattg | cgaaaaattg | catggcctgc | cgctacgccc | 13860 |
| gcacccggtt | taccaacttc | attgtggacg | accggggagg | agttcatcga | tggaagtccc | 13920 |
| caatagtggt | ggaaaaattg | ggcaaagccg | aagtcgacgg | cagccttgtc | accatcaaac | 13980 |
| atgtcgtcct | cgaaggggtt | aaagctcaac | ctttaacgag | gacttcggcc | gagcaatggg | 14040 |
| aggcctagat | gatttttgca | acgattctac | cgctgcacaa | aagctcgtgc | tggctttcag | 14100 |
| catcacatac | acacctataa | tgatatatgc | ccttaaggtg | tcacgcggcc | gactcctggg | 14160 |
| gctgttgcac | atcctaatat | ttctgaactg | ttcctttaca | ttcggataca | tgacatatgt | 14220 |
| gcattttcaa | tccaccaacc | gtgtcgcact | cactctgggg | gctgtcgtcg | ccctttatg | 14280 |
| gggtgcttac | agcctcacag | agtcatggaa | gtttatcact | tccagatgca | gattgtgttg | 14340 |
| ccttggccgg | cgatacattc | tggcccctgc | ccatcacgta | gaaagtgctg | caggtctcca | 14400 |
| tccaatctca | gcgtctggta | accgagcata | cgctgtgaga | aagccaggac | taacatcagt | 14460 |
| gaacggcact | ctagtaccag | gacttcggag | cctcgtgctg | ggcggcaaac | gagctgttaa | 14520 |
| acgaggagtg | gttaacctcg | tcaagtatgg | ccggtagaaa | ccagagccag | aagaaaaaga | 14580 |
| aaaacacagc | tccaatgggg | aatggccagc | cagtcaatca | actgtgccag | ttgctgggtg | 14640 |
| caatgataaa | gtcccagcgc | cagcaaccta | ggggaggaca | ggccaaaaag | aaaaagcctg | 14700 |
| agaagccaca | ttttcccttg | gctgcagaag | atgacatccg | gcaccacctc | acccagactg | 14760 |
| aacgctccct | ctgcttgcaa | tcgatccaga | cggctttcaa | tcaaggcgcg | ggaactgcgt | 14820 |
| tgctttcatc | cagcgggaag | gtcagttttc | aagttgagtt | tatgctgccg | gttgctcata | 14880 |
| cagtgcgcct | gattcgcgtg | acttctacat | ccgctagtca | gggtgcaagt | taatttgatg | 14940 |
| gtcaggtgaa | tggtcgcgat | tggcgtgtgg | cctttgagtc | acctattcaa | ttagggcgat | 15000 |
| cacatggggg | tcatacttaa | tcaggcagga | accatgtgac | cgaaattaaa | aaaaaaaaa | 15060 |
| aaaaaaaaaa | aaaaaaaa | | | | | 15078 |

<210> SEQ ID NO 7
<211> LENGTH: 14885
<212> TYPE: DNA
<213> ORGANISM: Artificial Sequence
<220> FEATURE:
<223> OTHER INFORMATION: Synthetic Construct

<400> SEQUENCE: 7

```
tatgacgtat aggtgttggc tctatgcctt ggcatttgta ttgtcaggag ctgtgaccat    60
tggcacagcc caaaacttgc tgcacagaaa caccccttctg tgatagcctc cttcagggga   120
gcttagggtt tgtccctagc accttgcttc cggagttgca ctgctttacg gtctctccac   180 cccctttaacc atgtctggga tacttgatcg gtgcacgtgt accccccaatg ccagggtgtt   240 tatggcggag ggccaagtct actgcacacg atgcctcagt gcacggtctc tccttcccct   300
gaacctccaa gtttctgagc tcggggtgct aggcctattc tacaggcccg aagagccact   360
ccggtggacg ttgccacgtg cattccccac tgttgagtgc tccccgccg gggcctgctg   420 gctttctgca atctttccaa tcgcacgaat gaccagtgga aacctgaact tccaacaaag   480
aatggtacgg gtcgcagctg agctttacag agccggccag ctcacccctg cagtcttgaa   540
ggctctacaa gtttatgaac ggggttgccg ctggtacccc attgttggac ctgtccctgg   600
agtggccgtt ttcgccaatt ccctacatgt gagtgataaa cctttcccgg gagctactca   660
cgtgttgacc aacctgccgc tcccgcagag acccaagcct gaagacttttt gccccttgta   720 gtgtgctatg gctactgtct atgacattgg tcatgacgcc gtcatgtatg tggccgaaag   780
gaaaatctcc tgggccctc gtggcgggga tgaagtgaaa tttgaagctg tccccgggga   840
gttgaagttg attgcgaacc agctccgcac ctccttcccg ccccaccaca cagtggacat   900
gtctaagttc gccttcacag cccctgggtg tggtgtttct atgcgggtcg aacgccaaca   960
cggctgcctt cccgctgaca ctgtccctga aggcaactgc tggtggagct tgtttgactt  1020
gcttccactg gaagttcaga acaaagaaat tcgccatgct aaccaatttg ctaccagac   1080 caagcatggt gtctctggca agtacctaca gcggaggctg caagttaatg gtctccgagc  1140
agtaactgac ctaaacggac ctatcgtcgt acagtacttc tccgttaagg agagttggat  1200
ccgccatttg aaactggcgg gagaacccag ctactctggg tttgaggacc tcctcagaat  1260
aagggttgag cctaacacgt cgccattggc tgacaaggaa gaaaaatttt ccggtttgg  1320 cagtcacaag tggtacggcg ctggaaagag agcaagaaaa gcacgctctt gtgcgactgc  1380
tacagtcgct ggccgcgcct tgtccgttcg tgaaacccgg caggccaagg agcacgaggt  1440
tgccggcgcc aacaaggctg agcacctcaa acactactcc ccgcctgccg aagggaattg  1500
tggttggcac tgcatttccg ccatcgccaa ccggatggtg aattccaaat ttgaaaccac  1560
ccttcccgaa agagtgagac cttcagatga ctgggctact gacgaggatc ttgtgaatgc  1620
catccaaatc ctcagactcc ctgcggcctt agacaggaac ggtgcttgta ctagcgccaa  1680
gtacgtactt aagctggaag gtgagcattg gactgtcact gtgaccccctg ggatgtcccc  1740 ttctttgctc cctcttgaat gtgttcaggg ctgttgtggg cacaagggcg tcttggttc   1800 cccagatgca gtcgaggtct ccgggtttga ccctgcctgc cttgaccggc tggctgaggt  1860
gatgcacctg cctagcagtg ctatcccagc cgctctggcc gaaatgtctg gcgattccga  1920
tcgttcggct tctctggtca ccaccgtgtg gactgtttcg cagttctttg cccgtcacag  1980
cggagggaat caccctgacc aagtgcgctt agggaaaatt atcagccttt gtcaggtgat  2040
tgaggactgc tgctgttccc agaacaaaac caaccgggtc accccggagg aggtcgcagc  2100
aaagattgac ctgtacctcc gtggtgcaac aaatcttgaa gaatgcttgg ccaggcttga  2160
gaaagcgcgc ccgccacgcg taatcgacac ctcctttgat tggggtgttg tgctccctgg  2220
ggttgaggcg gtaacccaga cgaccaagct gccccaggtc aacagtgtc gtgctctggt  2280 ccctgttgtg actcaaaagt ccttggacaa caactcggtc cccctgaccg cctttttcact  2340
```

```
ggctaactac tactaccgtg cgcaaggtga cgaagttcgt caccgtgaaa gactaaccgc    2400
cgtgctctcc aagttggaaa aggttgttcg agaagaatat gggctcatgc caaccgagcc    2460
tggttcacgg cccacactgc cacgcgggct cgacgaactc aaagaccaga tggaggagga    2520
cttgctgaaa ctggctaacg cccagacgac ttcggacatg atggcctggg cggtcgagca    2580
ggttgaccta aaaacttggg tcaagaacta cccgcggtgg acaccaccac ccctccgcc     2640 aaaagttcag cctcgaaaaa cgaagcctgt caagagcttg ccggagagaa agcctgtccc    2700
cgccccgcgc aggaaggttg ggtccgattg tggcagcccg gtttcattag gcggcgatgt    2760
ccctaacagt tgggaagatt tggctgttag tagccccttt gatctcccga ccccacctga    2820
gccggcaaca ccttcaagtg agctggtgat tgtgtcctca ccgcaatgca tcttcaggcc    2880
ggcgacaccc ttgagtgagc cggctccaat tcccgcacct cgcggaactg tgtctcgacc    2940
ggtgacaccc ttgagtgagc cgatccctgt gcccgcaccg cggcgtaagt ttcagcaggt    3000
gaaaagattg agttcggcgg cggcaatccc accgtaccag aacgagcccc tggatttgtc    3060
tgcttcctca cagactgaat atgaggcctc tcccccagca ccgccgcacc agggacccctt   3120 ggccttctcc gaggataaac cggtagacga ccaacttgtc aacgactccc ggatatcgtc    3180
gcggaggcct gacgagagca catcagctcc gtccgcagga caggtggcg ccggctctct     3240 taccgatttg ccgccttcag atggcgcgga tgcggacggg gggggccgt ttcggacggt     3300 aaaaagaaaa gctgaaaggc tctttgacca actgagccgt caggttttg acctcgtctc     3360 ccatctccct gttttcttct cacgcctttt ccaccctggc ggtggttatt ctccgggtga    3420
ttggggtttt gcagctttta ctctattgtg cctcttttta tgttacagtt acccagcctt    3480
tggtattgct cccctcttgg gtgtgttttc tgggtcttct cggcgcgttc gaatgggggt    3540
ttttggctgc tggttggctt ttgctgttgg tctgttcaaa cctgtgtccg acccagtcgg    3600
cgctgcttgt gagtttgact cgccagagtg tagaaacatc cttcattctt ttgagcttct    3660
caaaccttgg gaccctgttc gcagccttgt tgtgggcccc gtcggtctcg gtcttgccat    3720
tcttggcagg ttactgggcg gggcacgctg catctggcac ttttttgctta ggcttggcat    3780 tgttgcagac tgtatcttgg ctggagctta cgtgctttct caaggtaggt gtaaaaagtg    3840
ctggggatct tgtataagaa ctgctcctaa tgaggtcgct tttaacgtgt ttccttttcac   3900 acgtgcgacc aggtcgtcac ttatcgacct gtgcgatcgg ttttgtgcgc caaaaggaat    3960
ggaccccatt tttctcgcca ctgggtggcg cgggtgctgg gccggccgaa gccccattga    4020
gcaaccctct gaaaaaccca tcgcgtttgc ccaattggat gaaaagaaga ttacggctag    4080
gactgtggtc gcccagcctt atgaccccaa ccaagccgta aagtgcttgc gggtattgca    4140
ggcgggtggg gcgatggtgg ctgaggcggt cccaaaagtg gtcaaggttt ccgctgttcc    4200
attccgagcc cccttctttc ccactggagt gaaagttgac cctgattgca gggtcgtggt    4260
tgaccctgac actttcactg cagctctccg gtctggctac tccaccacaa acctcgtcct    4320
tggtgtaggg gactttgccc agctgaatgg attaaaaatc aggcaaattt ccaagccttc    4380
agggggaggc ccacatctca tggctgccct gcatgttgcc tgctcgatgg ctctgcacat    4440
gcttgttggg atttatgtga ctgcggtggg ttcttgcggc accggcacca acgacccgtg    4500
gtgcgctaac ccgtttgccg tccctggcta cggacctggc tctctctgca cgtccagatt    4560
gtgcatttcc caaacgcc ttaccctgcc cttgacagca cttgtggcgg gattcggtat      4620
tcaagaaatt gccttggtcg ttttgatttt tgtttccatc ggaggcatgg ctcataggtt    4680
gagctgtaag gctgacatgc tgtttgtttt gcttgcaatt gccagctatg tttgggtacc    4740
```

```
tcttacctgg ttgctttgtg tgtttccttg ctggttgcgc tgttttttctt tgcaccccct    4800 caccatccta tggttggtgt ttttcttgat ttctgtgaat atgccttcag gaatcttggc    4860
catggtgttg ttggtttctt tttggcttct tggtcgttat actaatgttg ctggccttgt    4920
caccccctac gacattcatc attacaccag tggcccccgc ggtgttgccg ccttggctac    4980
cgcaccagat gggacctact tggccgctgt ccgccgcgct cgttgactg gccgcaccat    5040 gctgtttacc ccgtcccagc ttgggtctct tcttgagggt gctttcagaa ctcgaaagcc    5100
ctcactgaac accgtcaatg tgatcgggtc ctccatgggc tctggcgggg tgtttaccat    5160
cgacgggaaa gtcaagtgcg taactgccgc acatgtcctt acgggcaatt cagctcgggt    5220
ttccggggtc ggcttcaatc aaatgcttga ctttgacgta aagggagatt cgctatagc     5280 tgattgcccg aattggcaag gggctgcccc caagacccaa ttctgcacgg atggatggac    5340
tggccgtgcc tattggctaa catcctctgg cgtcgaaccc ggcgtcattg gaaaaggatt    5400
cgccttctgc ttcaccgcat gtggcgattc cgggtcccca gtgatcaccg aggccggtga    5460
gcttgtcggc gttcacacgg gatcgaataa acaagggggg ggcattgtta cgcgcccctc    5520
aggccagttt tgtaatgtgg cacccatcaa gctaagcgaa ttaagtgaat ctttgctgg     5580 gcctaaggtc ccgctcggtg atgtgaaggt cggcagccac ataattaaag acataagcga    5640
ggtgccttca gatctttgtg ccttgcttgc tgccaaacct gaactggaag gaggcctctc    5700
caccgtccaa cttctttgtg tgttttttct cctgtggaga atgatgggac atgcctggac    5760
gcccttggtt gctgtgagtt tctttatttt gaatgaggtt ctcccagccg tcctggtccg    5820
gagtgttttc tcctttggaa tgtttgtgct atcctggctc acgccatggt ctgcgcaagt    5880
tctgatgatc aggcttctga cagcagctct taacaggaac agatggtcac ttgccttttt    5940
cagcctcggt gcagtgaccg ttttgtcgc agatcttgcg gccactcagg ggcatccgct    6000
gcaggcagtg atgaatttga gcacctatgc attcctgcct cggatgatgg ttgtgacctc    6060
accagtccca gtgatcacgt gtggtgtcgt gcacctactt gccatcattt tgtacttgtt    6120
taagtaccgt ggcctgcacc atatccttgt tggcgatgga gtgttctctg cggctttctt    6180
cttgagatac tttgccgagg gaaagttgag ggaaggggtg tcgcaatcct gcggaatgaa    6240
tcatgagtct ctgactggtg ccctcgctat gagactcaat gacgaggact tggatttcct    6300
tataaaatgg actgattta agtgcttgtt ttctgcgtcc aacatgagga atgcagcggg    6360
tcaatttatc gaggctgcct atgctaaagc acttagagta gaactggccc agttggtgca    6420
ggttgataaa gttcgaggta cttttggccaa acttgaagct tttgctgata ccgtggcacc    6480
tcaactctcg cccggtgaca ttgttgtcgc ctcggccac acgcctgttg cagtatctt     6540 cgacctaaag gttggtagca ccaagcatac cctccaagcc attgagacca gagtccttgc    6600
tgggtccaaa atgaccgtgg cgcgcgtcgt cgacccgacc cccacgcccc cacccgcacc    6660
cgtgcccatc cccctcccac cgaaagttct ggagaatggc cccaacgctt ggggggatga    6720
ggaccgtttg aataagaaga agaggcgcag gatggaagcc ctcggcatct atgttatggg    6780
cgggaaaaag taccagaaat tttgggacaa gaattccggt gatgtgtttt atgaggaggt    6840
ccataataac acagatgagt gggagtgtct cagagttggc gaccctgccg actttgaccc    6900
tgagaaggga actctgtgtg gacatgtcac cattgaaaac aaggcttacc atgtttacac    6960
ctccccatct ggtaagaagt tcttggtccc cgtcaaccca gagaatggaa gagttcaatg    7020
ggaagctgca aagctttccg tggagcaggc cctaggtatg atgaatgtcg acggcgaact    7080
```

```
gactgccaaa gaactggaga aactgaaaag aataattgac aaactccagg gcctgactaa    7140
ggagcagtgt ttaaactgct agccgccagc gacttgaccc gctgtggtcg cggcggcttg    7200
gttgttactg aaacagcggt aaaaatagtc aaatttcaca accggacctt caccctggga    7260
cctgtgaatt taaagtggc cagtgaggtt gagctaaaag acgcggttga gcacaaccaa    7320
cacccggttg cgagaccgat cgatggtgga gttgtgctcc tgcgctccgc ggttccttcg    7380
cttatagacg tcttgatctc cggtgctgat gcatctccca agttacttgc ccatcacggg    7440
ccgggaaaca ctgggatcga tggcacgctc tgggattttg agtccgaagc cactaaagag    7500
gaagtcgcac tcagtgcgca aataatacag gcttgtgaca ttaggcgcgg cgacgctcct    7560
gaaattggtc tcccttacaa gctgtaccct gttaggggta accctgagcg ggtgaaagga    7620
gttttgcaga atacaaggtt tggagacata ccttacaaaa cccccagtga cactggaagc    7680
ccagtgcacg cggctgcttg ccttacgccc aacgccactc cggtgactga tgggcgctcc    7740
gtcttggcca cgaccatgcc ccccgggttt gagttatatg taccgaccat accagcgtct    7800
gtccttgatt accttgactc taggcctgac tgccctaagc agctgacaga gcacggctgc    7860
gaagatgccg cactgaaaga cctctctaaa tatgacttgt ccacccaagg ctttgtttta    7920
cctggagttc ttcgccttgt gcggaaatac ctgtttgccc atgtaggtaa gtgcccaccc    7980
gttcatcggc cttctactta ccctgctaag aattctatgg ctggaataaa tgggaacagg    8040
ttcccaacca aggacattca gagcgtccct gaaatcgacg ttctgtgcgc acaggctgtg    8100
cgagaaaact ggcaaactgt caccccttgt actcttaaga acagtattg cgggaagaag    8160 aagactagga ccatactcgg caccaataac ttcatcgcac tagcccaccg agcagtgttg    8220
agtggtgtta cccagggctt catgaaaaag gcgtttaact cgcccatcgc cctcggaaag    8280
aacaagttta aggagctaca gactccggtc ctgggcaggt gccttgaagc tgatctcgca    8340
tcctgcgatc gatccacgcc tgcaattgtc cgctggtttg ccgccaacct tctttatgaa    8400
cttgcctgtg ctgaagagta tctaccgtcg tacgtgctga actgctgcca cgacttactg    8460
gtcacgcagt ccggcgcagt gactaagaga ggtggcctgt cgtctggcga cccgatcacc    8520
tctgtgtcta acaccattta tagttttgtg atctatgcac agcatatggt gcttagttac    8580
ttcaaaagtg gtcaccccca tggccttctg ttcttacaag accagctaaa gtttgaggac    8640
atgctcaagg ttcaaccccct gatcgtctat tcggacgacc tcgtgctgta tgccgagtct    8700
cccaccatgc caaactatca ctggtgggtt gaacatctga atttgatgct ggggtttcag    8760
acggacccaa agaagactgc aataacagac tcgccatcat ttctaggctg tagaataata    8820
aatgggcgcc agctggtccc caaccgtgac aggatcctcg cggccctcgc ctatcacatg    8880
aaggcgagta atgtttctga atactatgcc tcagcggctg caatactcat ggacagctgt    8940
gcttgtttgg agtatgatcc tgaatggttt gaagaacttg tagttggaat agcgcagtgc    9000
gcccgcaagg acggctatag ctttcccggc acgccgttct tcatgtccat gtgggaaaaa    9060
ctcaggtcca attatgaggg gaagaagtcg agagtgtgcg ggtactgcgg ggccccggct    9120
ccgtacgcta ctgcctgtgg cctcgacgtc tgcatttacc acacccactt ccaccagcat    9180
tgtccagtca caatcggtg tggccatcca gcgggtctg gttcttgtag tgagtgcaaa    9240
tcccctgtag ggaaaggcac aagcccttta gacgaggtgc tggaacaagt cccgtataag    9300
cccccacgga ccgttatcat gcatgtggag cagggtctca ccccccttga tccaggtaga    9360
taccaaactc gccgcggact agtctctgtc aggcgtggaa ttaggggaaa tgaagttgaa    9420
ctaccagacg gtgattatgc tagcaccgcc ttgctcccta cctgcaaaga gatcaacatg    9480
```

```
gtcgctgtcg cttccaatgt attgcgcagc aggttcatca tcggcccacc cggtgctggg   9540
aaaacatact ggctccttca acaggtccag gatggtgatg ttatttacac accaactcac   9600
cagaccatgc ttgacatgat tagggctttg gggacgtgcc ggttcaacgt cccggcaggt   9660
acaacgctgc aattccccgt ccctcccgc accggtccgt gggttcgcat cctagccgga   9720
ggttggtgtc ctggcaagaa ttccttccta gatgaagcag cgtattgcaa tcaccttgat   9780
gttttgaggc ttcttagtaa aactaccctc acctgtctag gagacttcaa gcaactccac   9840
ccagtgggtt ttgattctca ttgctatgtt tttgacatca tgcctcaaac tcaactgaag   9900
accatctgga ggtttggaca gaatatctgt gatgccattc agccagatta cagggacaaa   9960
ctcatgtcca tggtcaacac aacccgtgtg acctacgtgg aaaaacctgt taggtatggg  10020
caggtcctca cccctacca tagggaccga gaggacgacg ccatcactat tgactccagt  10080
caaggcgcca cattcgatgt ggttacattg catttgccca ctaaagattc actcaacagg  10140
caaagagccc ttgttgccat caccagggca agacacgcta tctttgcgta tgacccacac  10200
aggcagctgc agggcttgtt tgatcttcct gcaaaaggca cacccgtcaa cctcgcagtg  10260
caccgcgacg ggcagctgat cgtgctggat agaaataaca aagaatgcac ggttgctcag  10320
gctctaggca acggggataa atttagggcc acagacaagt gtgttgtaga ttctctccgc  10380
gccatttgtg ctgatctaga agggtcgagc tctccgctcc ccaaggtcgc acacaacttg  10440
ggattttatt tctcacctga tttaacacag tttgctaaac tcccagtaga acttgcacct  10500
cactggcccg tggtgacaac ccagaacaat gaaaagtggc cagatcggct ggttgccagc  10560
cttcgcccta tccataaata cagccgcgcg tgcatcggtg ccggctatat ggtgggccct  10620
tcggtgtttc taggcactcc tggggtcgtg tcatactatc tcacaaaatt tgttaagggc  10680
gaggctcaat tgcttccgga gacggttttc agcaccggcc gaattgaggt agactgccgg  10740
gaatatcttg atgatcggga gcgagaagtt gctgcgtccc tcccacacgc tttcattggc  10800
gacgtcaaag gcactaccgt tggaggatgt catcatgtca cctccagata cctcccgcgc  10860
gtccttccca aggaatcagt tgcggtagtc ggggtttcaa gccccggaaa agccgcaaaa  10920
gcattgtgca cactgacaga tgtgtacctc ccagatcttg aagcctatct ccacccggag  10980
acccagtcca agtgctggag aatgatgttg gacttcaaag aagttcgact aatggtctgg  11040
aaagacaaaa cagcctattt ccaacttgaa ggtcgctatt tcacctggta tcagcttgcc  11100
agctatgcct cgtacatccg tgttcctgtc aactctacgg tgtacttgga cccctgcatg  11160
ggccccgccc tttgcaacag gagagtcgtc gggtccaccc actgggggc tgacctcgcg  11220 gtcacccctt atgattacgg cgctaaaatt atcctgtcta gcgcgtacca tggtgaaatg  11280
ccccccggat acaaaattct ggcgtgcgcg gagttctcgt tggatgaccc agttaagtac  11340
aaacatacct gggggtttga atcggataca gcgtatctgt atgagttcac cggaaacggt  11400
gaggactggg aggattacaa tgatgcgttt cgtgcgcgcc aggaagggaa aatttataag  11460
gccactgcca ccagcttgaa gttttatttt ccccgggcc ctgtcattga accaacttta  11520
ggcctgaatt gaaatgaaat ggggtccatg caaagccttt tttacaaagt tggccaactt  11580
tttgtggatg ctttcacgga gttccttggt gtccattgttg atatcattat atttttggcc  11640
attttgtttg gcttcaccat cgccggttgg ctggtggtct tttgcatcag attggttttgc  11700 tccgcgatac tccgtgcgcg ccctgccatt cactctgagc aattacagaa gatcttatga  11760 ggccttttctt tcccagtgcc aagtggacat tcccacctgg ggaactaaac atcctttggg  11820
```

```
gatactttgg caccataagg tgtcaaccct gattgatgaa atggtgtcgc gtcgaatgta    11880
ccgcatcatg gaaaaagcag ggcaggctgc ctggaaacag gtggtgagcg aggctacgct    11940
gtctcgcatt agtagtttgg atgtggtggc tcattttcag catctagccg ccattgaagc    12000
cgagacctgt aaatatttgg cctcccggct gcccatgcta cacaacctgc gcatgacagg    12060
ttcaaatgta accatagtgt ataatagcac tttgaatcag gtgtttgcta ttttccaac    12120 ccctggttcc cggccaaagc gtcatgattt tcagcaatgg ttaatagctg tacattcctc    12180
catattttcc tctgttgcag cttcttgtac tcttttgtt gtgctgtggt tgcgggttcc     12240
aatactacgt actgttttg gtttccgctg gttaggggca attttctttt cgaactcaca    12300
gtgaattaca cggtgtgtcc accttgcctc acccggcaag cagccgcaga gatctacgaa    12360
cccggtaggc tctttggtg caggataggg tatgaccgat gtgaggagga tgatcatgac    12420
gagctagggt ttatggtacc gcctggcctc tccagcgaag gccacttgac tagtgtttac    12480
gcctggttgg cgttcttgtc cttcagttac acggcccagt ccatcccga gatattcggg    12540 atagggaatg taagtcgagt ttatgttgac atcaaacatc aactcatctg cgccgaacat    12600
gacgggcaga acaccacctt gcctcgtcat gacaacattt cagccgtgtt tcagacctat    12660
taccaacatc aagtcgacgg cggcaattgg tttcacctag aatggcttcg tcccttcttt    12720
tcctcgtggt tggttttaaa tgtctcttgg tttctcaggc gttcgcctgc aaaccatgtt    12780
tcagttcgag tcttgcagac attaagacca acaccaccgc agcggcaagc tttgctgtcc    12840
tccaagacat cagttgcctt aggcatcgcg actcggcctc tgaggcgatt cgcaaaatcc    12900
ctcagtgccg tacggcgata gggacacctg tgtatgttac catcacagcc aatgtgacag    12960
atgagaatta tttacattct tctgatctcc tcatgctttc ttcttgcctt ttctatgctt    13020
ctgagatgag tgaaaaggga tttaaggtgg tatttggcaa tgtgtcaggc atcgtggctg    13080
tgtgtgtcaa ttttaccagc tacgtccaac atgtcaagga gtttacccaa cgctccctgg    13140
tggtcgacca tgtgcggttg ctccatttca tgacacctga gaccatgagg tgggcaactg    13200
ttttagcctg tctttttgcc attctgttgg caatttgaat gtttaagtat gttggagaaa    13260
tgcttgaccg cgggctgttg ctcgcaattg ctttctttgt ggtgtatcgt gccgttctgt    13320
tttgctgtgc tcgtcaacgc cagcaacgac agcagctccc atctacagct gatttacaac    13380
ttgacgctat gtgagctgaa tggcacagat tggctagcta aaaaatttga ttgggcagtg    13440
gagagttttg ttatctttcc cgttttgact cacattgtct cctatggtgc cctcactgcc    13500
agccatttct ttgacacagt cgctttagtc actgtgtcta ccgccgggtt tgttcacggg    13560
cggtatgtcc taagtagcat ctacgcggtc tgtgccctgg ctgcgttgac ttgcttcgtc    13620
attaggtttg caaagaattg catgtcctgg cgctacgcgt gtaccagata taccaacttt    13680
cttctggaca ctaagggcag actctatcgt tggcggtcgc ctgtcatcat agagaaaagg    13740
ggcaaagttg aggtcgaagg tcatctgatc gacctcaaaa gagttgtgct tgatggttcc    13800
gtggcaaccc ctataaccag agtttcagcg gaacaatggg gtcgtcctta gatgacttct    13860
gtcatgatag cacggctcca ggaaaggtgc ttttggcgtt ttctattacc tacacgccag    13920
tgatgatata tgccctaaag gtgagtcgcg gccgactgct agggcttctg cacctttttga    13980 tcttcctgaa ttgtgctttc accttcgggt acatgacttt cgcgcacttt cagagtacaa    14040
ataaggtcgc gctcactatg ggagcagtag ttgcactcct ttgggggggtg tactcagcca    14100 tagaaacctg gaaattcatc acctccagat gccgttgtg cttgctaggc cgcaagtaca    14160
ttctggcccc tgcccaccac gttgaaagtg ccgcaggctt tcatccgatt gcggcaaatg    14220
```

```
ataaccacgc atttgtcgtc cggcgtcccg gctccactac ggtcaacggc acattggtgc   14280
ccgggttaaa aagcctcgtg ttgggtggca gaaaagctgt taaacaggga gtggtaaacc   14340
ttgtcaaata tgccaaataa caacggcaag cagcagaaga gaaagaaggg ggatggccag   14400
ccagtcaatc agctgtgcca gatgctgggt aagatcatcg ctcagcaaaa ccagtccaga   14460
ggcaagggac cgggaaagaa aaataagaag aaaaacccgg agaagcccca ttttcctcta   14520
gcgactgaag atgatgtcag acatcacttt accctagtg agcggcaatt gtgtctgtcg   14580
tcaatccaga ccgcctttaa tcaaggcgct gggacttgca ccctgtcaga ttcagggagg   14640
ataagttaca ctgtggagtt tagtttgcct acgcatcata ctgtgcgcct gatccgcgtc   14700
acagcatcac cctcagcatg atgggctggc attcttgagg catctcagtg tttgaattgg   14760
aagaatgtgt ggtgaatggc actgattgac attgtgcctc taagtcacct attcaattag   14820
ggcgaccgtg tggggtgag atttaattgg cgagaaccat gcggccgaaa ttaaaaaaaa   14880
aaaaa                                                              14885
```

<210> SEQ ID NO 8
<211> LENGTH: 15434
<212> TYPE: DNA
<213> ORGANISM: Artificial Sequence
<220> FEATURE:
<223> OTHER INFORMATION: Synthetic Construct

<400> SEQUENCE: 8

```
atgacgtata ggtgttggct ctatgccgtg acatttgtat agtcaggagc tgcgaccatt     60
ggtacagccc aaaacttgct gcacgggaac gcccttccgt gacagccttc ttcagggag    120 tttagggatc tatccctagc accttgcttc cggagttgca ctgctttacg gtctctccaa    180 cccctttaacc atgtctggga tacttgatcg gtgcacgtgc accccaatg ccagggtgtt    240 tatggcggag ggccaagtct actgcacacg atgtctcagt gcacggtctc tccttcctct    300
gaatctccaa gtccctgagc ttggggtgct gggcctattt tacaggcccg aagagccact    360
ccggtggaca ttgccgcgtg cattcccac tgtcgagtgc tcccccgccg gggcctgctg    420
gctttctgcg atcttcccaa ttgcacgaat gaccagtgga aacctgaact tcaacaaag    480 aatggtgcgg gtcgcagctg agatttacag agccggtcag ctcactccca cagtcttgaa    540
gaatctacaa gtttatgagc ggggttgccg ttggtaccct attgtcgggc ctgtccccgg    600
agtggccgtt tacgccaact ccctacatgt gagtgacaaa cccttccgg gagcaactca    660 tgtgttaact aatctaccgc tcccgcagag gcccaagctt gaagattttt gcccccttga    720
gtgtgctatg gctgacgtct atgatatcgg tcatgacgcc gtcatgtacg tggccaaagg    780
gaaagtctcc tgggctcctc gtggtgggga caagacaaaa tttgaaactg tccctaggga    840
gttgaagttg atcgcgaacc gactccatgt ctccttcccg ccccaccacg cagtggacat    900
gtcccagttt gcgttcataa ccttcggag cggtgtctct atgcgggtcg agtgcccaca    960
tggctgtctc cccgccaata ccgtccctga aggcaactgc tggtggcgct tgtttgacat   1020
gcttccaccg gaggttcaga acgatgaaat tcgccgtgcc tgccaattcg gttatcaaac   1080
caagcatggt gtcgctggca agtacctaca acggaggttg caagctaatg gcctccgagc   1140
ggtgactgat acaagtgggc ctatcgttgt gcagtttttc tccgttaagg agagttggat   1200
ccgccactta aggctggcgg acgaacctag ccttcctggt tttgaggacc tcctcagaat   1260
aagggttgag cccaacacgt caccattggt tagcaaggat gtgaaaatct tccggttcgg   1320
```

```
cagtcacaaa tggtacggtg ctggaaagag ggcaaagaaa gcacgctctg gtgcggctgc    1380
cacggtcatt caccgcgctt tgcctgttcg cgaagcccag cagaccaaga cgcacaaggt    1440
tgctagcgct aacagggctg agtgtctcaa gcgctattct ccgcctgccg atgggaactg    1500
tggttggcac tgcatttccg ccatcgccaa ccggatggtg aattcgaaat ttgagaccac    1560
ccttcccgaa agagtgagac cttctgatga ttgggctacc gacgaggatc ttgtgaacgc    1620
cattcaaatc ctcaagctcc ctgcggcctt ggacaggaac ggagcttgtg gtagcgccaa    1680
gtacgtgctt aagctggaag gcgtgcattg gactgtctct gtgacccctg ggatgtcccc    1740
ctctttgctc ccccttgaat gtgttcaggg ctgttgtgag cataaggacg gttctggccc    1800
cccagatgcg gtcgaggttt ccggatttga ccctgcctgc cttgaccgac tggctggggt    1860
gatgcattta cctagcagtg ctatcccagc cgctctggct gaaatgtccg gcaactccaa    1920
tcgcccggct tccccggtca acactgtgtg gactgtttcg caattctatg cccgtcactt    1980
aggaggagtt catcctgacc aggtgtgctt agggaaaatt attagcctct gtcaagtcat    2040
tgaggattgc tgctgccatc aaaacaaaac caaccgggcc accccggaag aggtcgcggc    2100
aaagattgat cagtacctcc gtggtgcaac aagtcttgag gaatgcttga ctaggcttga    2160
aagggttttgc cctccgagcg ctgcggacac ctcctttgat tggaatgttg tgctccctgg    2220
ggttgaggct gcaacccaga caactaaaca gctccatgtc aaccggtgcc gcgttttggc    2280
tcctgtcgtg actcaagagc cttggacaa agactcggtc cctctgaccg ccttctcgtt    2340
gtccaattac tactacccgg cacaaggtga cgagattcat caccgtgaga ggctgaactc    2400
cgtactctct aagttggagg gggttgttcg cgaggaatat gggctcacgc caactgaacc    2460
tggtccgcga cccgcactac cgaacgggct cgacgagctc agagaccaga tggagatgga    2520
tctgctgaga ctagtcaacg atcaggcaac ttcagaaatg atggcccggg cagctgagca    2580
ggttgatcta aaagcttggg tcaaaaacta cccacggtgg acaccgccgc ccactccacc    2640
aagagttcag cctcgaaaaa cgaggtctgt caagagcttg ccaggggata gcctgtccc    2700
ggctccgcgt aggaaggtca gatctgattg tggcagcccg attttgatgg cgacaatgt    2760
tcctaacgat cggaagatt tgactgttaa tgggccccctt gacctttcga caccatccga    2820
gtcgatgaca cctctgagtg agcctgcact tatgcccgcg ttgcaacatg tttctaggtc    2880
ggcgacatct ttgagtgtgc cgaccccagt tcctgtaccg cgcagagctg tgtcccgacc    2940
ggtggcaccc ttgagtgagc caacctttga gtcttcaccg cgacacaaat ttcaagaggt    3000
gaaagaagtg aatctggcgg caacaacgcc gacgcaccaa gacgaacctc tagatttgtc    3060
tgcatcctca cagactgtat gtgaggcctc tcccctagca ccgcctcaga acataggtat    3120
tctgggggtg gaggggcaag aaactgagga agtcctgagt gaagtctcgg atataccgta    3180
tgacattaac cttgcacctg tgtcatcaag cagctccctg tcaagtgtaa agatcacacg    3240
tccgaaatac tcagctcaag ccattattga ctcaggcggg ccctgcagtg ggcatcttcg    3300
aaagggaaaa gaagcatgcc tcagcatcat gcgcagggct tgtgatgcgg ctaagcttag    3360
tgaccctgcc acgcaagaat ggctttctcg tatgtgggat agggttgaca tgctgacttg    3420
gcgcaacacg tctgcttacc aggcgttgcg catcttagat ggcaggttg ggttcctccc    3480
gaaaatgata ctcgagacac caccgcccta tccgtgtggg tttgtgatgc tgcctcacac    3540
gcctgcacct tccgtgagtg cagagagcga cattaccatt ggttcagttg cctctgaaga    3600
tgttccacgc atcctcggga aaatagaaaa cgccggcgag atgcccaacc aggggctctt    3660
ggcgtccctt gaggaaaaac cggtgcacga ccaacctgcc gaagactccc ggatgccgtt    3720
```

```
gcggggttt dacgagagcg taacggctcc gtccgctggt acaggttgcg ctgactcacc    3780
cactgatttg tcgccttcag gtggtgtgga cgtggacggg ggggggcgt tacgggcggt    3840
aagaaagaaa gctgaaaggc tcttcgatca attgagccgc caggtttta acctcgtctc    3900
ccatctccct gtttcttct cacacctctt caaatctgac agtggttatt ctccgggtga    3960
ttggggtttt gcagctttta ctctattttg tctcttttta tgttacaact acccattttt    4020
tgggtttgct cccctcttgg gtgtgttttc tgggtcttct cggcgtgtgc gcatgggggt    4080
ttttggctgc tggttggctt ttgctgttgg cctgttcaaa cctgtgtccg acccagtcgg    4140
cactgcttgt gaatttgact cgccagagtg taggaacgtc cttcattctt ttgagcttct    4200
caaaccttgg gaccctgttc gcagccttgt tgtgggcccc gtcggtctcg gtcttgccat    4260
tcttggcagg ttactgggcg gggcacgcta catctggcat ttttgctta ggcttggcat    4320
tgttgcagat tgtgtcttgg ctggagctta tgtgctttct caaggtaggt gtaaaaagtg    4380
ctggggatct tgtgtaagaa ctgctcccaa tgaaattgcc ttcaacgtgt tcccttttac    4440
gcgtgcgacc aggtcgtcac tcatcgacct gtgcaaccgg tttcgtgcgc cgaaaggcat    4500
ggaccccatt tttctcgcta ctgggtggcg cgggtgctgg accggccaaa gtcccattga    4560
gcaaccctcc gaaaaaccca tcgcgttcgc ccagttggat gaaaagagga tcacggccag    4620
aactgtagtt gctcagcctt atgatcctaa ccaagccgta aagtgcctgc gggtgttaca    4680
ggcgggtggg gcgatggtgg ccgaggcagt cccgaaagtt gtcaaagttt ccgctatccc    4740
attccgagcc ccttttttc ccaccggagt gaaggttgat cctgagtgca ggatcgtagt    4800
cgacccgac actttcacta ctgctcttcg gtctggttac tccaccacaa acctcgtcct    4860
tggtgtgggg gactttgccc aactgaatgg attaaaaatc aggcaaattt ccaagccttc    4920
gggaggaggc ccacacctca ttgctgccct gcatgttgct tgctcgatgg cgttgcacat    4980
gcttgctggg gtttacgtaa ctgcagtggg gtcttgcggt accggcacca acgatccgtg    5040
gtgcaccaac ccattcgccg tccctggcta cggacctggc tctctctgca cgtccaggtt    5100
gtgcatctcc caacatggcc ttaccttgcc cttgacagca cttgtggcag gcttcggtct    5160
tcaggaaatt gccttggtcg ttctgatttt tgtttccatc ggaggcatgg ctcataggtt    5220
gagttgtaag gctgatatgc tgtgcgtctt gctcgcaatc gccagctatg tttgggtacc    5280
ccttacctgg ttgctctgcg tgtttccttg ctggttgcgc tggttctctt tgcaccccct    5340
caccatccta tggttggtgt ttttcttgat ttctgtaaat atgccttcag gaaccttagc    5400
cgtggtgtta ttggtcgctc tttggcttct aggccgttac actaatgttg ttggtcttgt    5460
caccccctac gatatccatc attacaccag cggcctcgc ggtgttgccg ccttggctac    5520
cgcaccagat ggaacttatt tggccgctgt ccgccgcgct gcgttgactg gccgtaccgt    5580
tctgtttacc ccgtctcagc ttgggtccct tcttgagggc gctttcagga ctcgaaagcc    5640
ctcattgaac accgttaatg tggtcgggtc tccatgggc tctggcggag tgttcactat    5700
cgatgggaaa attaagtgtg tgactgccgc acatgtcctt acgggcaact cagccagggt    5760
ttccggggtc ggcttcaatc agatgcttga ctttgatgta aaaggagatt tcgccatagc    5820
tgattgcccg aattggcaag ggactgctcc taagacccaa ttctgcaagg acgggtggac    5880
tggccgtgcc tattggctaa catcttctgg tgtcgaaccc ggtgtcattg gaaatgggtt    5940
cgccttctgc ttcaccgcgt gcggtgactc cgggtctcca gtgatcaccg aagccggtga    6000
gcttgtcggc gttcacacag gatcaaacaa acaaggagga ggcattgtta cgcgcccctc    6060
```

```
aggccagttt tgtaatgtgg cacccatcaa gctgagcgaa ttaagtgagt tctttgctgg    6120
acctaaggtc ccgctcggtg atgtgaaggt tggtagccac ataattaaag acatatgcga    6180
ggtaccttca gatctttgtg ccttgcttgc tgccaaaccc gaattggaag gaggcctctc    6240
caccgtccaa cttctatgtg tattttcct cctgtggaga atgatgggac atgcctggac     6300
acccttggtt gccgtgggtt ttttatttt gaatgagatt cttccagctg tactggtccg     6360
gagtgttttc tccttcggaa tgtttgtgtt atcttggctc acaccatggt ctgcacaagt    6420
tctgatgatc aggctcctca cagcagctct taataggaac agattgtcac tcgccttcta    6480
cagccttggt gcggcaaccg ttttgtcgc agacctagcg gcgacccaag ggcatccgtt     6540
gcacgcagta atgaatttga gtacctatgc cttcctgcct cgggtgatgg ttgtgacctc    6600
accagtccca gtaatcgcgt gtggtgttgt gcacctcctt gccataattt tgtacttgtt    6660
taggtaccgc tgcctgcatg gtgttcttgt tggcgatggg gcgttctctg cggcttttt    6720 tttgcgatac tttgctgagg ggaaattgag ggaaggggtg tcgcaatcct gcgggatgaa    6780
tcatgagtcg ctgactggtg ccctcgccat gagactcaat aacgaggatt tggatttcct    6840
cactaagtgg actgattta agtgctttgt ttctgcttcc aacatgagga atgcagcggg    6900
ccaattcatt gaggctgcct atgccaaagc acttagaata gaacttgccc agctggtgca    6960
ggtcgacaag gtccgaggca ctttggccaa acttgaagct tttgccgaca ccgtggcacc    7020
ccaactctcg cccggtgaca ttgttgtcgc tcttggccat acgcctgttg gcagtgtctt    7080
cgacctgaag gttggtaaca ccaagcacac tctccaagcc attgagacca gggtccttgc    7140
tgggtccaaa atgaccgtgg cgcgcgtcgt cgacccgacc cccacgcccc cacccgcacc    7200
cgtacccatc cccctcccac cgaaggtttt ggagaacggt ccaaacgctt gggggatga     7260 agatcgtttg aataaaaaga gaggcgcag atggaagct gtcggcatct ttgttatggg     7320
cggaaagaaa taccagaaat tttgggacaa gaattccggt gatgtgtttt atgaggaggt    7380
ccatgacaat acagacgcgt gggagtgcct cagggttgat aactctgccg actttgatcc    7440
cgagaaggga actctgtgtg gcatactac cattgagaat aaaacctaca atatctacgc    7500
ctccccatcc ggcaagaagt tcctggtccc tgccaactca gagggcggaa aagtccagtg    7560
ggaagctgca aagctctccg tggagcaggc ccttggcatg atgaatgtcg acggtgaact    7620
gacagccaga gaactggaga aactaaaaaa aataattgac aaactccagg acctgaccaa    7680
ggagcagtgt ttaaactgct agccgccagc ggcctgaccc gctgtggtcg cggcggctta    7740
gttgttactg agacagcggt aaaaatagtc aaatatcaca gccggacctt caccctagga    7800
cctgtaaatt taaagtggc tagtgaggtt gagctaaaag acgcggtcga gcataaccag    7860 caccgtcg caagaccggt tgatggtggt gttgtgcttc tgcgctccgc agttccttcg     7920
cttatagacg tcttgatctc cggcgctgat gcatctccta agttactcgc tcgccacggg    7980 ccggaaata ctgggatcga cggcacgctt tgggattttg aggccgaggc caccaaagag    8040
gagatcgcac tcagtgcgca gataatacag gcttgtgaca ttaggcgcgg cgacgcaccc    8100
gaaattggtc tcccttataa gctgtaccct gttaggggca atcccgagcg ggtaaaagga    8160
gttttacaga atacaaggtt cggggacatt ccttataaaa cccccagtga cactggaagc    8220
ccagtgcacg cggctgcctg cctcacgccc aatgccactc cggtgactga tgggcgctcc    8280
gtcttggcta caaccatgcc ctccggtttt gagttgtacg tgccgaccat tccagcatct    8340
gtccttgatt accttgactc caggcctgac tgccctaaac agttgacaga gcacggctgt    8400
gaggatgccg cattaagaga ccttccaag tatgacttgt ccactcaagg ctttgttttg    8460
```

-continued

```
ccaggagttc ttcgccttgt gcgtaagtac ctatttgctc atgtgggcaa gtgcccgcct    8520
attcatcggc cttccaccta ccctgccaag aattctatgg ctggaataaa tgggaacagg    8580
tttccaacca aggacatcca gggcgtccct gaaatcgacg tcctgtgcgc tcaggccgtg    8640
cgggaaaact ggcagactgt caccccttgt accctcaaga acagtattg tgggaagaag     8700 aagactagga caatactcgg caccaataat ttcattgcat tggcccaccg ggcagcgttg    8760
agtggcgtca cccagggctt tatgaaaaag gcgttcaatt cgcccatcgc cctcggaaaa    8820
aacaaattta aggagctaca aactccggtc ttaggcaggt gcctagaggc tgaccttgca    8880
tcctgcgatc gatccacacc tgcgattgtc cgctggtttg ccgccaatct tctttatgaa    8940
cttgcctgtg ctgaggaaca tctaccatcg tacgtgctga actgctgcca cgacttactg    9000
gtcacgcaat ccgcgcggt gactaagaga ggtggcctgt cgtctggcga cccgattact     9060
tctgtgtcaa acaccattta tagtttggtg atatatgcac agcacatggt gctcagttac    9120
tttaaaagtg gtcaccctca cggccttctg tttctgcaag accagctaaa gtttgaggac    9180
atgctcaagg ttcaacccct gatcgtctat tcggacgacc tcgtgttgta tgccgagtct    9240
cccactatgc caaactacca ctggtgggtt gaacatctga atcttatgtt gggttttcag    9300
acggacccaa gaaagacagc cataacagac tcaccatctt ttctaggctg tagaataata    9360
aatgggcgcc agctagtccc ccaccgtgac aggattctcg cggcccttgc ctaccatatg    9420
aaggcaagca atgtttctga atactacgct tcggcggccg cgatactcat ggacagctgt    9480
gcttgtctag agcatgatcc tgaatggttt gaagaacttg tggtcggaat ggcgcagtgt    9540
gcccgcaagg acggctacag cttcccggc cgccgttct tcttgtctat gtgggaaaaa      9600
ctcaggtcta attatgaggg gaagaagtcg agagcgtgcg gatactgcgg ggccccggct    9660
ccgtacgcta ccgcctgtgg cctcgacgtc tgcatttatc acacccattt ccaccagcat    9720
tgtccggtca taatctggtg tggtcatccg gcgggttctg gttcttgtag tgagtgcaaa    9780
cccccccttg ggaaaggtac aagccctcta gatgaggtgt tggaacaagt cccgtacaag    9840
cctccgcgga ccgtgatcat gcacgtagag caggtctta ctccactcga cccaggtaga     9900
taccaaaccc gccgcggatt agtctccgtt aggcgtggca ttaggggaaa cgaagttgaa    9960
ctaccagacg tgattatgc tagtaccgcc ttgctcccca cttgtaaaga gatcaacatg     10020
gttgctgttg cttctaacgt gttacgcagc aggttcatca tcggtccacc tggtgctggt    10080
aaaacatact ggctccttca acaggtccag gatggtgatg tcatttacac gccaactcat    10140
cagactatgc ttgacatgat taaggctttg gggacgtgcc ggttcaacgt tccagcaggc    10200
acaacgctgc aattccctgc cccctcccgc accggcccgt gggttcgcat cctggccggc    10260
ggttggtgtc ctggcaagaa ttccttcctg gatgaagcag cgtattgcaa tcatcttgac    10320
gtcttgaggc ttcttagcaa aactaccctc acctgctggg agatttcaa caactccac     10380 ccggtgggtt tgattccca ttgctatgtt tttgacatta tgcctcagac tcaactgaag     10440
accatctgga ggtttgggca gaacatctgt gacgccattc aaccagatta tagagacaaa    10500
cttgtgtcca tggtcaacac aacccgtgta acctacgtgg aaaaacctgt caagtatggg    10560
caagtcctca ccccctacca cagggaccga gaggacggcg ccgtcacaat tgactcaagt    10620
caaggcgcca catttgatgt ggttacactg catttgccca ctaaagattc actcaacagg    10680
caaagggccc ttgttgctat caccagggca agacatggca tctttgtgta tgacccacac    10740
aggcaattgc agagcttgtt tgatcttcct gcaaaaagca cacccgtcaa tctcgcagtg    10800
```

```
caccgtgacg agcagctgac cgtgttagat agaaataaca aagagtgcac ggttgctcag    10860
gctctaggca atggggataa atttagggcc acagacaagc gcgttgtaga ttctctccgc    10920
gccgtttgtg cagacctgga agggtctagc tccccgctcc ccaaggttgc acacaacttg    10980
ggattttatt tctcgcctga tttgacacag tttgctaagc ttccggtaga acttgcacct    11040
cactggcccg tggtgacaac ccagaacaat gaaaagtggc cagaccggtt ggttgctagc    11100
cttcgccctg tccatgagta tagccgtgcg tgtgtcggtg ccggctatat ggtgggcccc    11160
tcagtgttcc taggcactcc tggggttgtg tcatactatc tcacaaaatt tgttagaggc    11220
gaggctcaaa tgcttccgga gacagtcttc agcaccggcc gaattgaggt agattgccgg    11280
gagtaccttg atgatcggga gcgagaagtt gctgagtccc tcccacacgc cttcattggc    11340
gacgtcaaag gcactaccgt tgggggatgt caccatgtca cctctaaata cctcccgcgt    11400
ttcctcccca aggaatcggt tgcggtagtt ggggtttcga gccccgggaa agccgcaaaa    11460
gcagtttgca cattgacaga tgtgtacctc ccagaccttg aagcttatct ccacccagag    11520
acccagtcta agtgctggaa aatgatgttg gacttcaagg aggttcgact gatggtctgg    11580
aaagataaga cggcctattt tcaacttgaa ggccgccatt tcacctggta ccagcttgca    11640
agctatgcct cgtacatccg agttcctgtt aattctacgg tatatctgga cccttgcatg    11700
ggccctgccc tttgcaacag gagggttgtc gggtccaccc attgggaagc tgacctcgca    11760
gtcaccccct tatgattatg gtgccaaaat cattttgtct tgtgcatacca tggtgaaatg    11820
cctcccgggt acaagattct ggcgtgcgcg gagttctcgc ttgacgaccc agtcaggtac    11880
aaacacacct ggggatttgc atcggatata gcgtatttgt acgagttcac cggaaacggt    11940
gaggactggg aggattacaa tgatgcgttt cgtgcgcgcc agaaagggaa aatttacaaa    12000
gccactgccg ccagcatgag gtttttatttt ccccgggcc ctatcgttga ccaactttg    12060
ggcctagact gaaatgaaat ggggtctatg caaagcctct ttgacaaaat cggccaactt    12120
tttgtggatg ccttcacgga attttttggtg tccattgttg atatcatcat atttctggcc    12180
attttgtttg gctttaccat cgctggctgg ctggtggtct tctgcatccg actggttttgc    12240
tccgcggtac tccgtgcgcg ccctaccatt cactctgagc aattacagaa gatcctatga    12300
ggccttttctt tctcagtgcc aggtggacat tcccgcctgg gaactaaac accccttggg    12360
gatgttttgg caccataagg tgtcgaccct gattgatgaa atggtgtcgc gtcgaatgta    12420
ccgcaccatg gaaaaagcag gacaggctgc ctggagacag gtggtaagcg aggctacgtt    12480
gtctcgcatt agtggtttgg atgtggtggc tcattttcag catcttgccg ccattgaagc    12540
tgagacctgc aaatacttgg cctctcggct tcccatgctg cacaatctgc gcatgacagg    12600
gtcaaatgta accatagtgt ataatagcac tttgaatcag gtgtttgcta tttttccaac    12660
ccctgaatcc cggccgaagc ttcatgattt tcagcaatgg ctaatagctg tgcattcctc    12720
catatttttcc tccgttgcag cttcttgcac tctttttgtt gtgctgtggt tgcggattcc    12780
aacactacgt attgtttttg gtttccactg gtaaggggca attttttcctt cgagctcacg    12840
gtgaattaca cggtgtgccc gctttgcctc acccgacaag cagcctatga gatctatgaa    12900
tcacgcaggt cttttggtg caggatcggg catgaccgat gcagtgaggt cgaccacgac    12960
gagctagggt tcatggttcc gtctggcctc tccagcgaag gccacctgac cagtgtttac    13020
gcctggttgg cgttcctgtc cttcagctac acgcccagt tccatcccga gatatttggg    13080
atagggaatg tgagtcgagt ttatgttgac atcaagcacc aactcatctg cgccgttcac    13140
gacggggaga acaccacctt gcctcgtcat gacaacattt cagccgtatt tcagacctac    13200
```

```
taccagcatc aagtcgacgg cggcaattgg tttcacctag aatggctgcg tcccttcttt    13260
tcctcctggt tggttttaaa tgtctcgtgg tttctcaggc gttcgcctgc aagccatgtt    13320
tcagttcaag tctttcggac atcaaaacca acactaccgc agcatcaggc tttgttaccc    13380
tccaggacat cagctgtctt aggcatggcg actcgccctc tcagacgatt cgcaaaagcc    13440
ctccgtgccg cacggcgcta gggacacccg tgtacatcac tgttacagcc aatgtcacgg    13500
atgagaatta tttacactcc tctgatctcc tcatgctttc ttcttgcctt ttctatgctt    13560
ctgagatgag tgaaaaggga ttcaaggtga tatttggcaa tgtgtcaggc atcgtggccg    13620
tgtgtgttaa tttaccagc tacgtccaac atgtcaaaga gttcacccaa cgctctttgg    13680
tggtcgacca tgtgcggctg ctccatttca tgacacctga aaccatgagg tgggcaaccg    13740
ttttagcctg tcttgttgcc atcttgctgg caatttgaat gtttcagtat gttggggaga    13800
tgcttgaccg cgggctgctg cttgcgattg cttttctttgt ggtgtatcgt gccgttctgg    13860
tttgctgcac tcgtcagcgc caaccagaac cacagctctc atcttcaatt gatttacaac    13920
ttgacgctat gtgagctgaa tggcacagaa tggctgggag acaaatttaa ttgggcagtg    13980
gagacctttg tcatctttcc cgtgttaact cacattgtct catatggtgc actcaccact    14040
agccatttcc ttgacacagt cggtctggtt actgtgtcta ccgccgggta ttatcacggg    14100
cggtatgttt tgagtagtat ctacgcggtc tgcgctctgg ccgcgttaat ttgcttcgtc    14160
attcggcttg cgaagaactg catgtcctgg cgctactctt gtaccagata taccaatttc    14220
cttctggaca ctaagggcag actctatcgc tggcggtcgc ccgttatcat agagaaaagg    14280
ggtaaggttg aggtcggaag tcacctgatc gatctcaaga gagttgtgct tgatggttct    14340
gcggcaaccc ctttaaccag agtttcagcg gaacaatggg gtcgtctcta gacgactttt    14400
gctatgatag cacggctcca caaaaggtgt ttttggcgtt ttccattacc tacacgccag    14460
taatgattta tgccctgaag gtaagtcgcg gccgactgtt agggcttctg cacctttga    14520 tctttctgaa ttgtgcttttt accttcgggt acatgacatt tgtgcacttt gatagcacaa    14580
ataaggtcgc gctcactatg ggagcagtgg ttgcactcct ttgggggggtg tactcggcca    14640 tagaaacctg gaaattcatc acctccagat gccgtttgtg cttgctaggc cgcaagtaca    14700
ttctggcccc tgcccaccac gtcgaaagtg ccgcgggctt tcatccgatt gcggcaaatg    14760 ataaccacg atttgtcgtc cggcgtcccg gctccactac ggttaacggc acattggtgc    14820
ccgggttgaa aagcctcgtg ttgggtggca gaaaagctgt aaaacaggga gtggtaaacc    14880
ttgtcaaata tgccaaataa caacggcaag cagcaaaaga aaaaaaaggg gaatggccag    14940
ccagtcaacc agctgtgcca aatgttgggc aaaatcatcg cccagcagaa ccagtccaga    15000
ggtaagggac cgggaaagaa aattaaaaag aaaagcccgg agaagcccca ttttcctcta    15060
gcgactgagg atgacgtcag gcatcacttt acccctggtg agcggcaatt gtgtctgtcg    15120
tcaatccaga ctgcctttaa tcaaggcgct ggaacttgca ccctgtcaga ttcagggagg    15180
ataagttacg ctgtggagtt tagtttgccg acgcatcata ctgtgcgcct gattcgcgtc    15240
acagcaccac cttcagcgtg atgggctggc attcttgaga catcccggcg ttagaattgg    15300
aagaatgcgt ggtgaatggc actgattgac actgtgcctc taagtcacct attcagttag    15360
ggcgaccgtg tgggggtaga gtttaattgg cgagaaccac acggccgaaa ttaaaaaaaa    15420
aaaaaaaaaa aaaa                                                     15434
```

<210> SEQ ID NO 9

<211> LENGTH: 15047
<212> TYPE: DNA
<213> ORGANISM: Artificial Sequence
<220> FEATURE:
<223> OTHER INFORMATION: Synthetic Construct

<400> SEQUENCE: 9

| | | | | | |
|---|---|---|---|---|---|
| atgacgtata | ggtgtttgct | ttatgccgcg | gcatttgtat | tgtcaggagc | tgtgaccact | 60 |
| ggcacagccc | gaaacttgct | gcacagaaac | acccttctgt | gacagcctcc | ttcaggggag | 120 |
| tttaggggtt | tctccctaac | gccctgcttc | cggagttgca | ctgctttacg | gtctctccat | 180 |
| ccttttaacc | atgtctggga | ttcttgatcg | gtgcacgtgc | accccaatg | ccagggtgtt | 240 |
| tgtggcagag | ggccaagtct | actgcacacg | atgtctcagt | gcacggtccc | tccttcccct | 300 |
| aaatctccaa | gtttctgagc | ttggggtact | tggtttattc | tacaggcccg | aagagccatt | 360 |
| acggtggacg | ttgccacacg | cattccccac | tgtcgagtgt | gctcctgctg | gcgcttgttg | 420 |
| gctttctgca | atttttccaa | ttgcgcgaat | gaccagtgga | aacctgaatt | tccagcaaag | 480 |
| gctggtacgt | gtcgcagccg | agctttacag | agccggccag | ctcacccta | caagcctgaa | 540 |
| aaccttacag | gtctatgaaa | ggggttgccg | ttggtacccc | attgttggac | ctgttcctgg | 600 |
| agtggccgtt | tacgccaact | ccctacatgt | gagtgacaaa | cccttcccag | gagcgactca | 660 |
| cgtgctgacc | aacttaccac | tcccgcagag | accaaaatct | gaagatttct | gcccctttcga | 720 |
| gtgcgccacg | gccgccgtct | atgacatcgg | ccatgacgcc | gtcatgtatg | taaccgagga | 780 |
| aaaggtttcc | tgggctcctc | gtggcgggga | taaagggaaa | tttgagactg | ttcctgaggg | 840 |
| gttgaagttg | actgcggaac | gactctacac | ctccttcccg | cctcaccatg | cggtggacat | 900 |
| gtcccttttc | atcttcacag | accttgagtg | cggcgcttcc | atgcgggtcg | aacgccaata | 960 |
| tggttgcctc | tctgctggca | ctgtccctga | aggcaactgc | tggtggagtc | tgtttggctc | 1020 |
| gctttcgtta | aagctcagt | ataaagaaat | ccgctacgcc | gcccaatttg | gctatcagac | 1080 |
| caaacatggc | gttactggca | agtacctgca | gcggaggctg | caaattaatg | gtctccgagc | 1140 |
| agtggttgac | ccgaatgggc | ctcttgtcgt | acagtatttc | tccgttaagg | agagctggat | 1200 |
| gcgccacgtg | agactggcgg | aagagccagg | ctatcctggg | tttgaggatc | tcctcaggat | 1260 |
| aagagtcgag | cccaacacgt | tgcctttgtc | caacaaggac | gagaaaatct | tccgtttcgg | 1320 |
| cggttacaag | tggtacggtg | ctgggcggag | ggcaaggaga | acacgtgcaa | gagcagtcac | 1380 |
| cgcagttgct | agtcatgctc | cgcccgctcg | tggggcccag | caggccgaga | agcacgaagt | 1440 |
| tgctagtgcc | aacaagactg | agctccttac | gcactactcc | ccacctgctg | aagggaattg | 1500 |
| cggctggcac | tgcatctccg | ccatcatgaa | ccggatggtg | cattccaagt | ttgaaaccgc | 1560 |
| cctttccgaa | agagtgagat | ccccggaaga | ctgggcgact | gatgaggatc | ttgtgaatac | 1620 |
| tattcaaatc | ctcaggctcc | ctgcggcctt | agacaggaac | ggcgcctgta | aaaacgccaa | 1680 |
| gtacatcctt | aagctggaag | gtgagcactg | gactgtttca | gtgaccccg | gaatgccccc | 1740 |
| ctcttcactt | cctcttgaat | gcgttcaggg | ttgttgcgag | cataagggca | atttgactc | 1800 |
| tcaaaacgcg | gtcggtttct | ttgggttcga | ccctgccagc | cttaccgac | tcgctggggt | 1860 |
| aatgcatctg | cccagcagcg | ccatccctgc | cgccctggcc | gagttgtctg | gtgaacttga | 1920 |
| ttgttcaact | ccccggcca | ccactgtgtg | gactaccttg | cagttttatg | ctcgtcttgg | 1980 |
| tgggggggag | catcctgatc | aagagtgctt | gagaaaaatc | atcagcctct | gtgaggtgct | 2040 |
| cgggagttgc | tgctgttctc | agagtagggt | caaccgggtc | accccggaag | aggtcgcagc | 2100 |
| aaagattgac | ctgtatcttc | gtgacgcagc | gagtcttgaa | gagtgcttgg | ctaggcttga | 2160 |

```
gaaagctcgc cgccaagca tgctggacac ctcctttgac tgggatgttg tactccctgg    2220
tgttgggacg gctgctcggg cagcagaact accccccacc gatgagtgtc gcgctctagt    2280
cactgctgtg gcccaaaggc cttcgccgaa agttcagcct cgaaaggcgg ggtctgttaa    2340
gagtctacca gagatcaggc ctgtccctgc cccacgcagg aaggttaagt ctagttgtgg    2400
tgatctggcc ccgttgggcg gcaatttccc tgatagctgg gaagatttgg ctggtggctc    2460
ccttaatctc cagatcttac ctgagccggt ggcacaatcc tttgaacctg tgcctgtccc    2520
tgcaccgcgc aagactgcgc ctcgattagt gtcgtcatca ttggcgtcga ccccgtacc    2580
tacaccacga tgtgggtttc ggcagtttga gggaatgaat ttgacagctg tgaccctagc    2640
atgccaggat gagtccctca atttgtctgc atcctcgcag actgaatatg aggcttctcc    2700
tttggcattg cagcagggtg aggatgtcct tgcggtgggg ggacgagaag ccgaagaagt    2760
cctgagcgga atctcgggaa tgtcaggtgg cattagatta gcgcccgcat catcaagtag    2820
ctccttgtca agcgtggaga tcacacgccc gaagtactca gctcaagcca tcattgactc    2880
aggtggaccc tgttgcgggc accttcaaga ggtgaaagag aaataccttaa atgtcatgcg    2940
tgaggcatgt gatgcgacta agctcgatga ccctgccacg caagaatggc tctctcgcat    3000
gtgggagagg gtagacatgc taacctggcg caacacgtcc atctttcaag cgccttttac    3060
cttagctgac aagtttaagt ccctcccgaa gatgatactc gaaacgccgc caccctaccc    3120
ttgcgggttt gtgatgatgc cccgcacgcc cgcaccttct gtgggtgcgg aaagcgacat    3180
caccgttggt tcagttgcta ctgaagatgt cccgcgtata ctcggggagg tgggagatgt    3240
tggcaagatg accggccagg aaccttaga atccttcgca gatgaactgg cagatgacca    3300
acctgctagg gagtcccgaa cacaagctcc tcctgcaagc acaggtagcg ctggtttagt    3360
tttggattct ggagggtcgc tggggctcac tgacctgccg ctcccaaaca atatagacgc    3420
gggcgggaaa ggaccgtttc acgcggtcaa gaaaaaagct gtagggtgct ttgaccaact    3480
gagccgccgg gttttttgaca tcgtctccca tctccctgtt tttttttcac gccttttcgc    3540
gcccggtggt ttttactctt cgggtgactg gagttttgca gcttttactt tattgtgtct    3600
cttttatgt tacagttatc cggcctttgg ttttgctccc ctcgtgggtg tatttctctgg    3660
gtcttctcgg cgcgtgcgca tgggggtttt tggctgctgg ctggcttttg ctgttggttt    3720
gttcaagcct gcaccgacc cagtcggtgc tgcttgtgag tttgactcgc cagagtgtag    3780
agacatcctt cattctttg agctcctgca accttgggac cctgttcgca gccttgtggt    3840
gggccccgtc ggtctcggcc ttgccatttt tggcaggtta ctgggcgggg cacgctacgt    3900
ctggctgctt ttgcttaggc ttggcatcgt ttcagactgt atcctggctg agcctatgt    3960
gctttcgcaa gcaggtgta aaagtgttg gggatcttgt ataagaacag ccccagtga    4020
agttgccttc aatgtgtttc cctttacacg cgcaactaga tcgtcacttg tcaacctgtg    4080
cgaccggttc tgtgcaccca agggcatgga ccccatcttc cttgccacag gatgcgcgcg    4140
atgctggtcc ggccagagcc ccattgagca accctctgaa aaacccatag cgttcgccca    4200
gttggacgaa aagaaaatca cggctaggac tgtggttgcc cagccttatg accccaacca    4260
agctgtgaag tgcctgcgag tcctccaggc gggtggagcg atggtagccg aggcagttcc    4320
aaaagtagtc aaagtttctg ctgtcccgtt tcgagcccct tttttcctg ccggagtgaa    4380
agttgaccct gaatgcaggg tcgtggttga ccctgacacc tttacaaccg ctctccggac    4440
cggctactcc accacaaacc tcattcttgg tgttggggac tttgcccagc tgaatgggtt    4500
```

```
gaagatcaga caaatttcca agtccccagg agggggccct cacctcatgg cggctttaca    4560
tgttgcttgc tcgatgactt tgcacatgct tgttgggatt tatgtcacca tggtgggttc    4620
ttgtggctct ggcactaacg atccgtggtg cactaacccg tttgccgtcc ctgtctatgg    4680
gcctggctct ctctgcacgt ccaggttgtg catttcccag cgtggcctga ccctgccctt    4740
aacagcgctt gtggcagggt ttggcgttca ggaaatcgct ttggttgttt taatctttgt    4800
ctccatcggg ggtatggccc acaggttgag ttgcaaggct gacgtgctgt gtatcctgct    4860
tgctattgtc agctatgttt ggccacccct tacctggttg cttttgtgtgt tccttgctg    4920
gttgcgctgg ttttctttac atcccttac tattctatgg ttagtgtttt tcttgatttc    4980
tgtaaatacg ccctcgggaa tcttggcctt ggtcctgtta atctctcttt ggctccttgg    5040
tcgctatacc aatgttgccg gccttgtcac cccttatgac attcaccatt acaccaacgg    5100
ccctcgcggc gttgccgcct tggccactgc cccggatggg acctacctgg ctgctgtccg    5160
ccgtgctgcg ttgactggcc gtaccatgct gttcaccccg tcccaacttg gctcgctcct    5220
tgagggcgct tttagaaccc aaaagccttc actgaacact gtcaatgtag ttgggtcctc    5280
catgggctcc ggcggggtgt tcaccattga tgggaagatc aaatgtgtga ccgctgctca    5340
tgtcctcacg ggtaactctg ccaggggttc cgggggttggc ttcaatcaaa tgttggactt    5400
tgatgttaaa ggggattttg ccatagccga ttgtccgaat tggcaaggag tcgcccccaa    5460
gtcccggttc tgcaaggatg attggactgg ccgtgcttat tggctcacgt cctccggcgt    5520
cgaacccggc gtcattgggc aaggattcgc cttttgtttc accgcgtgcg gcgattccgg    5580
gtccccagtg atcaccgagg ccggggagct tgtcggtgtc cacacgggat caaacaaaca    5640
aggaggaggc attgttacgc gcccttcagg ccggttttgt aatgtgacac ccaccaaatt    5700
aagtgaattg agtgaattct tcgctggacc tagggtcccg cttggtgacg tgaaggttgg    5760
caatcacata atcaaagata taaatgaggt gccctcagat ctctgcgcct tactcgctgc    5820
caaacccgaa ttggaaggag gcctctccac cgttcaactt ctgtgcgtgt ttttctcct    5880
atggagaatg atgggacatg cctggacacc cttggttgcc gttggttttt tcatcttgaa    5940
tgaagttctc ccagcagtcc tggtccggag tgtcttctcc tttggaatgt tcgcactgtc    6000
ttggttcacg ccgtggtctg cacaaattct aatgatcagg ctcttgacag cagccctaaa    6060
cagaaacaga tcgtcacttg ccttttacag cctgggcgca ctaaccggtt ttgttgcaga    6120
tcttgcaacc aatcaggggt atttattgca cgcggtcatg aatgtgagca cctatgcatt    6180
cctgcctcgt gcaatggccg tgacctcacc agtcccaata gttgcgtgtg gcgttgtgca    6240
cttgcttgcc atcattctgt acttgttcaa gtaccgtagc ctgcatgccg tcctggtcgg    6300
cgatggtgcg ttttccgcgg cttttcttctt gcgatacttt gcggagggaa agttgaggga    6360
aggggtgtcg cagtcttgcg gcatgaatca tgagtcacta accggtgccc tcgccatgaa    6420
actcagcgac gaagacttgg acttcctcac aaaaattgact gatttttaagt gctttgtttc    6480
tgcatccaac atgaggaatg cggcgggtca atttatagag gccgcctacg ccaaagcact    6540
gagggtggaa cttgcccagt tggttcaagt cgataaagtt cgaggtgtcc tggccaaact    6600
tgaagctttc gctgacaccg tggcgcctca actttcaccc ggtgacattg ttgtcgccct    6660
tggacacaca cctgtcggca gcatttttga cctgaaggtc ggcaatgtta agcacactct    6720
ccagtccatt gagaccagaa cccttgccgg gtctaaaatg actgtggcgc gcgtcgtaga    6780
cccaaccccc acaccccgc ccgcacctgt gcccatttcc ctcccaccaa aggttttgga    6840
gaacggtccc aacgcctggg gggatgagaa cggtttgaac aaaaaaaagc ggcgcaagat    6900
```

```
ggaggccgtt ggcatttacg ttatgggcgg gaaaaagtat caaaaatttt gggataagaa     6960
ttctggtgat gtgttctatg aagaagtcca cgacaacaca gacgcgtggg aatgcctcag     7020
agttgacaac cctgccgact tggatcctga gaggggaacc ttgtgtggac acaccaccat     7080
agacaacagg ccttaccatg tttatgcttc tccgtctggt aggaagtttc tagtccctgt     7140
caacccggag agcggaaaag ctcagtggga agctgctaag ctttctttag atcaggccct     7200
cagtatgatg aatgtcgacg gcgaactgac cgccaaagaa gtggaaaaat tgaagagaat     7260
aattgacaaa ctccagggcc tgactaagga gcagtgttta aactgctagc cgccagcggc     7320
ttgacccgct gtggtcgcgg cggcttggtt gttactgaga cagcggtaaa gatagtcagg     7380
ttccacaacc ggacctttac cctagggcct gtgaatttga agtagctagc gaagttgag      7440 ttgaaggacg cggtcgagca cggccaacac ccggtcgcga taccagccga tggtggcgtc     7500
gtgctcctgc gttccgctgt tccttcgctt atagacgtcc tgatctccgg tgctgacgca     7560
tctcccaggt tgctcgcccg tcacggaccg ggaaatactg gggtcaatgg cgcgctttgg     7620
gattttgagt ctgaagctac caaagaggaa gtagcactta gtgcgcaaat aatacaggcc     7680
tgtgacatta gacgcggcga tgcacctgag attggccttc cttacaagtt gtaccctgtt     7740
aggggcaacc ctgaacgggc aagagggggtt ctaatgaaca caagatttgg agacatacct     7800
tacaagaccc ccagcgacac cgggagcccg gtgcacgcgg ccgcctgcct tacgcccaac     7860
gccactccag taactgatgg gcgctccatc ctggccacga ccatgccctc cgggtttgaa     7920
ctatatgtgc cgaccattcc agcgtctgtc cttgattacc ttgactccag accagactgt     7980
cctaaacagt tgactgagca cgggtgtgaa gatgccgcgt tgaaggacct ttctaaatat     8040
gacctgtcca cccaaggctt tgtgttacct ggagttctac gcctcgtgcg aaaatatctg     8100
tttgctcatg taggtaagtg cccgcctgtc caccggccct ctacctatcc tgccaagaac     8160
tccatggccg gaataaatgg gaacaggttc ccaaccaagg atattcaaag catccctgag     8220
atcgacgttt tgtgtgcaca agctgtgcga gaaaactggc aaactgttac ccctgcact      8280 cttaagaagc agtattgcgg taaaaagaag accaggacca tacttggcac caacaacttc     8340
gttgcgctgg cccaccgggc ggcgctgagt ggtgtcaccc agggtttcat gaagaaggcg     8400
tttaactcac ccatcgccct tgggaaaaat aaatttaagg agctacagac tccagtcttg     8460
ggtaggtgtc ttgaggctga tctcgcttcc tgcgatcgat ccacgcctgc aatcgttcgc     8520
tggtttgccg ccaaccttct ttatgaactt gcctgtgctg aggagcattt accgtcgtac     8580
gtgctgaact gttgtcacga cctattggtc acgcagtccg cgcagtgac taagagaggt      8640 ggcctgtcgt ccggtgaccc aatcacctct gtgtccaaca ccatttatag cttggtgatc     8700
tatgcacagc atatggtgct tagttacttc aaaagtggtc accccatgg ccttctgttt       8760 ttacaagacc agctaaagtt tgaagacatg ctcaaagttc aaccccttaat cgtctattcg     8820 gacgacctcg tgttgtatgc cgagtctccc accatgccaa actatcactg gtgggttgaa     8880
cacctgaatt tgatgttggg atttcagacg gacccaaaga agactgcaat aacagactca     8940
ccttcattcc taggttgtag aataataaat ggccgccagt tagtacccaa ccgtgacaga     9000
attctcgcgg cccttgccta tcacatgaag gcgagtaatg tttctgagta ctacgcctcc     9060
gcagccgcaa tactcatgga cagttgtgct tgtctagagt atgatcctga gtggtttgaa     9120
gaacttgtgg ttggaatggc gcagtgcgcc cgtaaggacg gctatagttt ccccggcccg     9180
ccgttcttct tgtccatgtg ggaaaagctc aggtcaaatt atgaggggaa gaagttgaga     9240
```

```
gtgtgtggtt attgcggagc ttcagccccg tatgctactg cctgtggcct tgacgtttgt    9300
gtttaccaca cccactttca ccagcattgt ccagtcataa tatggtgtgg ccacccggcg    9360
ggttctgggt cctgcgatga gtgcaaatcc cctacaggga agggtacaag ccctctggat    9420
gaggtcttaa gacaagtccc ttataagcct ccacggacta ttcttatgca tgtggagcag    9480
ggcctcaccc cccttgaccc aggcagatac cagacccgcc gtgggttggt tgctgtcagg    9540
cgcgggataa gggaaatgaa agttgacctg ccagatggtg attatgccag tactgcccta    9600
ctccccacct gcaaagacat agacatggtt gctgtggcct ccaatgtgtt gcgcagtagg    9660
ttcatcatcg gcccacctgg cgcagggaaa acacactggc ttcttcaaca ggttcaggat    9720
agtgatgtca tttacacgcc aacccatcag accatgcttg acatgatcaa ggctttgggg    9780
acgtgccggt tcaatgtccc ggcaggcaca acgctgcaat tccctgcccc ctcccgtacc    9840
ggcccgtggg ttcgcatcct tgccggcggt tggtgtccag gtaagaattc cttcctggat    9900
gaagcagcgt attgcaatca ccttgacgtc ttgaggcttc tcagcaaaac taccctcacc    9960
tgtctggggg atttcaaaca actccacccg gtgggttttg attctcattg ctatgttttt   10020
gatatcatgc ctcagactca actgaagacc atctggaggt ttggacagaa tatctgtgac   10080
gccattcagc cagattacag ggacaaactc gtgtccatgg tcaacacaac ccgtgtaacc   10140
tatgtggaaa gacctgtcaa gtatgggcaa gtcctcaccc cctaccacag agaccgagag   10200
gatggtgcta tcactattga ctccagtcaa ggcgccacat ttgatgtggt cacattgcat   10260
ttgcccacta agattcact caacaggcaa agagcccttg ttgctatcac cagggcaagg   10320
catgcaatct ttgtgtatga cccacacagg caactgcaga gcatgtttcg tcttcctgca   10380
aaaggcacac ctgtcaacct tgccgtgcac cgtgacgagc agctcatcgt attagataga   10440
aataacaaag agtgcacggt tgttcaggct ttaggcaatg gggacaaatt cagggccagt   10500
gacaagcgcg ttgtagattc tcttcgcgcc atttgtgcag atcttgaagg gtcgagctcc   10560
ccgctcccca aggtcgcaca caacttggga ttttatttct cacctgattt gacacagttt   10620
gctaaactcc cggcggaact tgcaccccac tggcccgtgg tgacaactca gaacaacgaa   10680
aattggccag accggctggt tgctagcctc cgccctatcc acaaatatag ccgcgcgtgc   10740
atcggagccg gctatatggt gggcccctca gtgtttctag gcactcctgg ggttgtgtca   10800
tactatctca cacaatttgt caaaggggag gctcaggtgc ttccggagac ggtcttcagc   10860
accggccgaa ttgaggtaga ttgtcgagag tatcttgatg atcgggaacg agaagttgct   10920
gagtccctcc cacatgcctt tattggcgac gtcaaaggca ctaccgttgg gggatgtcac   10980
catgtcactt ctaaatatct cccacgcttc cttcccaagg aatcagttgc ggtggttggg   11040
gtttcaagcc ccgggaaagc cgcaaaagca gtttgcacat taacagatgt gtacctccca   11100
gatcttgagg cttacctcca tccagagacc cagtctaagt gctggaaagt gatgttggac   11160
ttcaaggaag ttcgactgat ggtctggaga gataagacgg cctactttca acttgaaggc   11220
cgccatttca cctggtacca gcttgcaagt tatgcctcgt acatccgagt tcccgttaac   11280
tctacggtgt acctggaccc ctgtatgggc cctgcccttt gcaacagaag agtcgttggg   11340
tctgcacatt ggggagctga ccttgcagtt accccttatg attatggtgc caaaatcatt   11400
ctgtctagtg cgcaccatgg tgaaatgcct cctgggtaca gaattctagc gtgcgcggag   11460
ttctcgcttg atgacccagt gaggtacaaa cacacttggg ggtttgaatc ggatacagcg   11520
tatctgtacg agttcaccgg aaacggtgag gactgggagg attacaatga tgcgtttcgt   11580
gcacgccaga aagggaaaat ttataaggcc actgccacca gcatgagatt tcattttccc   11640
```

```
ccgggtcctg ccattgaacc aacattgggc ctgaactgaa atgaaatggg ggctgtgcag    11700
agccttttcg acaaaatttg ccaactttt gtggatgctt tcacggaatt tttggtgtcc    11760
attgttgata tcatcatatt tttggccatt ttgtttggct tcaccatcgc aggctggctg    11820
gttgtcttct gtatccgact ggtttgctcc acggtactcc gtgcgcgctc taccattcac    11880
cctgagcaat tacagaagat cctatgaggc cttcctttcc cagtgccaag tggacattcc    11940
cgcctgggga actaagcatc ccttgggggt gctttggcac cacaaggtgt caactctgat    12000
tgatgaaatg tgtcgcgtc gaatgtaccg catcatggaa aaagcaggac aggctgcctg    12060
gaaacaggtt gtgagcgaag ctacattgtc tcgcataagt ggcttggatg tggtggctca    12120
ttttcagcat cttgctgcca ttgaagccga gcttgcaaa tatttggcct ctcggctgcc    12180
catgctacac aacctagtca tgtcaggtc gaatgtaacc atagtgtata atagcacttt    12240
gggtcaagtg tttgccattt tcccaacccc tggttcccgg ccaaaacttt ctgattttca    12300
acaatggctc atagctgtgc attcttccat attttcttct gttgcggctt cttgtactct    12360
ttttgttgtg ctgtggctgc gaattccaat actacgtact gttttggtt tccgctggtt    12420 agggcaact tttctttcga actcacagtg aattacacgg tgtgcccacc ctgcctcacc    12480
cggcaagcag ccgctgagat ctacgaacac agcgggtctc tttggtgcag gatagggcat    12540
gaccgatgta gccagagtga tcatgacgaa ctagggttct tggttccacc tggccttttcc   12600 agcgagggcc acttgaccag tgtttacgcc tggctggcgt tcttgtcttt cagctacaca    12660
gcccagttcc accccgagat atttggaata gggaatgtga gtagagttta tgttgacgtc    12720
actcaccaac tcatctgcgc cgaacacgac gggcagaaca ccaccctgcg tcgccatgac    12780
aatatctcag ccgtgtttca gacctattac caacatcagg tcgatggcgg caattggttt    12840
cacctagaat ggctgcgtcc cttctttcc tcttggctgg ttttgaatgt ctcgtggttt    12900
ctcaggcgtt cgcctgcaaa ccgtgtttca gttcgagtct ttcagacatc aaaaccaaca    12960
ccaccgcagc tgcaggcttt gctgtcctcc aagacatcag ctgtcttagg catggctact    13020
cgtccattga ggcgattcgc aaaagccgtc aatgccgcac ggcgatagga acgcccgtgt    13080
acatcactgt cacggccaat gtaacagatg agaattactt gcattcctct gatctcctca    13140
tgctttcctc ttgcctcttc tatgcttctg agatgagtga aaagggattc aatgtggtct    13200
tcggcaacgt gtcaggcatt gtggctgtgt gtgtcaactt taccagctat gtccaacatg    13260
ttaaggagtt tactcagcgc tctttggtgg tcgaccacgt gcgactgctt catttcatga    13320
cacctgcgac catgaggtgg gcaacagttt tagcctgtct tttcgccatc ttgttggcga    13380
tttgaatgtt taagtatgtt ggggaaatgc ttgaccgcgg gctactgctc gcaattgctt    13440
tttttctggt gtatcgtgcc gttctgtttt gctgcgctcg tcaacgccgc cagcaacagc    13500
agctcccatt tacagttgat ttataacctg acgatatgcg agctgaatgg cacagattgg    13560
ttgaatcaaa agtttgattg gcagtggag acttttgtca ttttcctgt gttgacccac    13620 attgtctcct acggtgccct taccaccagc catttccttg acacggccgg cctaatcact    13680
gtgtctaccg ccggatatta ccatgggcgg tatgtgttga gtagcatcta cgccgtcttt    13740
gccctggctg cgttgatttg ttttgtcatt aggttgacaa aaaactgtat gtcctggcgc    13800
tactcatgta ccagatatac caactttctt ctggacacca aaggcaatct ctatcgttgg    13860
cggtcacccg tcgttataga gagaagggg aaagttgagg ttggagacca cctaatcgac    13920
ctcaaaagag ttgtgcttga tggttccgcg gcaaccccta taaccaagat ttcagcggaa    13980
```

```
caatgggtc gtccctagac gacttctgca atgacagcac agctgcacaa aaggtgcttt    14040
tggcgttttc catcacctat acgccaataa tgatatatgc cctgaaggta agtcgcggcc    14100
gactgttagg gcttttgcat cttttaattt tcttgaattg tgcttccacc ttcgggtaca    14160
tgacatttgt tcattttcag agtacaaaca aggtcgcgct cactatggga gcagttgttg    14220
cactcctttg ggggtgtac tcagccatag aaacctggaa attcatcact tccagatgcc      14280
gtttgtgctt gctaggccgc aggtacattc tggcccctgc ccaccacgtt gaaagtgccg    14340
cgggctttca tccgattgcg gcaagtgata accacgcatt tgtcgtccgg cgtcccggct    14400
ccactactgt taacggcaca ttggtgcccg ggttgaaaag cctcgtgttg ggtggcagaa    14460
aagctgttaa gcgggagtg gtaaacctcg ttaaatatgc caaataacaa cggcaggcag      14520
caaaaaata agaaggggag tggccagcca gtcaatcagc tgtgccaaat gctgggcaag      14580
atcatcgccc agcaaaatca gtccagaggc aagggaccgg gtaagaaaaa taagaagaga    14640
aacccggaga agccccattt tcctcttgcg accgaagatg acgtcaggca tcacttcacc    14700
cccagtgaac ggcaattgtg tctgtcgtcg atccagactg ccttcaacca gggcgctgga    14760
acttgcaccc tgtcagattc agggaggata agttacactg tggagtttag tttgccgacg    14820
caccacactg tgcgccttat tcgcgccaca gcatcacctc catcgtgatg ggcttacatt    14880
cttggagctc ctcagtttca caattggaag aatgtgtggt gaatggcact gattggcact    14940
gtgcctctaa gtcacctatt caattagggc gaccgtgtgg gggtagagtt taattggcga    15000
gaaccatacg gccgaaatta aaaaaaaaa aaaaaaaaa aaaaaa                     15047
```

<210> SEQ ID NO 10
<211> LENGTH: 15444
<212> TYPE: DNA
<213> ORGANISM: Artificial Sequence
<220> FEATURE:
<223> OTHER INFORMATION: Synthetic Construct

<400> SEQUENCE: 10

```
atgacgtata gttgttggct ctatgtcgtg acatttgtat agtcaggagc tgcgaccatt      60
ggtacagccc aaaacttgct gcgcgggaac gcccttccgt gacagccttc ttcaggggag    120
tttaggggtc tatccctagc accttgcttc cggagttgca ctgctttacg gtctctccac    180
cccttaaccc atgtctggga tacttgatcg gtgcacgtgt accccaatgc cagggtgtt     240
tgtggcggag ggccaagtct actgcacacg atgtctcagt gcacggtctc tccttccttt    300
gaatctccaa gttctgagc ttggggtgct gggcttattt tataggcccg aagagccgct      360
ccggtggacg ttgccacgtg cattccccac tgtcgagtgc tccccgccg gggcctgctg       420
gctttctgcg attttccaa ttgcacgaat gaccagtgga aacctgaact ttcaacaaag      480
aatagtgcgg gtcgcagctg agctctacag agccggtcag ctcacccccg tagtcttgaa    540
gaatctacag gttatgaac ggggttgccg ttggtacccc atcgttggac ctgttcctgg      600
agtggctgtt tatgccaatt ccttacacgt gagtgacaaa cctttcccgg agcaactca      660
tgtgttaacc aacctaccgc tcccgcagag gcccaagcct gaagactttt gccccttga      720
gtgtgctatg gctgacgtct atgacattgg tcatgacgct gtcatgtatg tggcggagg     780
gagagtctcc tgggcccctc gtggcgggga caaggaaaa tttgaaatag ttcccaagga      840
gttgaagttg attgcgaatc gactccacat ttccttcccg ccccaccacg cagtggacat    900
gtccaagttt gcctttataa gccctgggag tggtgttccc atgcgggtcg agtaccaaca    960
tggctgtctc cccgctgata ctgtccctga aggaaactgt tggtggcgct tgtttgactt    1020
```

```
gcttccaccg gaagttcaga acaaagagat tcgccatgct aaccaactcg gctatcagac    1080
caagcatggt gtcgctggca agtacctaca gcggaggctg caagttaatg gactccgagc    1140
agtaactgac gcgaatggac ctatcgtcat acagtatttt tgtgataggg aaagctggat    1200
ccgccactta agactggtag aagaacctag cctccctggg tttgaggacc tcctcagaat    1260
aagagttgag cccaatacgt tgccattggt tggcgaggat gagaaaatct tccgatttgg    1320
caatcacaaa tggtacggtg ctggaaagag ggcaaggaaa gcacgctttg gtgcggctgc    1380
cacggtcgct caccgcgctt tgcccgctca cgaaacccag caggccaaga agcacgaagt    1440
taccagcgcc aacagggctg agcatctcga gcactattcc ccgcctaccg acgggaactg    1500
tggttggcac tgcgtttccg ccattgtcaa ccggattgtg aattccaaat ttgaaaccac    1560
ccttcccgag agagtgagac ctttagatga ctgggctact gacgaggatc ttgtgaatac    1620
tatccaaatc ctcaggctcc ctgcggcctt ggacaggaac ggtgcttgtg tcggcgccaa    1680
gtacgtgctc aagctggaag gtgtgcactg gacagtctct gtggcccctg ggatgacccc    1740
ttctctgctc ccccttgaat gtgttcaggg ctgttgtgag cataagagcg gtcttggtcc    1800
cccagatgtg gctgaagttt ccggatttga ccctgcctgc cttaaccgac tggctgaggt    1860
aatgcacttg cctagttgtg tcatcccagc tgctctggct gaaatgtccg acgacccaa    1920
tcgcccggct tccccagtca ccactgtgtg gactatttcg caattctttg cccattatag    1980
aggaggagag caccctgatc aggtgtgctt agggaaaatc atcagccttt gtcaggtgat    2040
tgaggaatgc tgttgttccc agaacaaaac caaccgggcc accccggaag aggtcgcggc    2100
aaaaattgac cagtacctcc gtgatgcagc aagccttgga gaatgcttag ccaagcttga    2160
gagggctcgc ccgccgagcg cgatggacac ctcctttgat tggaatgttg tgcttcctgg    2220
ggttgaggcg gcgaaccaga cgaccaaaca gctccatgtc aaccagcacc gtgcttcggt    2280
tcctgccatg actcaggagc ctttggacaa agactcggtc cctttgaccg ccttctcgct    2340
gtctaattgc tactaccctg cacaaggtga cgaggttcgt caccgtgaga ggctgatctc    2400
cgtgctctct aagttggagg aggttgttcg tgaggaatat gggctcacgc caactggatc    2460
tggcccgcga cccgcactgc cgaacgggct cgacgagctc aaagaccaga tggaagagga    2520
tctgttgaaa ctggtcaacg cccaggcaac ttcagaaatg atggcccggg cagctgagca    2580
ggttgatcta aaagtttggg tcaaaaatta cccacgtggg acaccgccac ccctccacc    2640
aagagttcag cctcgaaaaa caaagtctgc taagagcctg ccagagaaca agcctgtccc    2700
tgctccgcgc aggaaagtca gatctgattg tggcagcccg actttgaggg gcaacaatgt    2760
tcctaacggt tgggaagact tggccgttgg tggtcctctt gatctttcga caccatccga    2820
gccgatgaca cctctgagtg agcctgcact tatgcccgtg ttgcaacata tttctggacc    2880
agtgacgcct ttgagcgtgc cggcccctat tcctgcaccg cgtaaagctg tgtcccgacc    2940
gatggcgccc tcgagtgagc caattttttgt gtctgcaccg cggcaaaaat ttcagcaggt    3000
ggaagaagca aatctggcgg caacaacgct gacataccag gacgaaccta tagatctgtc    3060
agcatcctca cagactgaat atgaggctcc ttccctagca ccactgcaga acataggtac    3120
tctggaggtg gggggcaag aagctgagga aattctgagt gaaacctcgg atataccgaa    3180
tgacatcaac cctgtgcctg tatcatcaag cagctccttg tcaagcgtta agatcacacg    3240
cccaagacac tcagctcaag ccatcatcga ctcgggcggg ccctgcagtg ggcatctcca    3300
aagggagaaa gaagcgtgcc tccgcatcat gcgtgaggct tgtgatgcga ctaagcttag    3360
```

-continued

```
tgaccctgcc acgcaggaat ggctttctcg catgtgggat agggtggaca tgctgacttg    3420
gcgcaacacg tctgctttcc aggcgtttcg catcttagac ggcaggcttg agtttcttcc    3480
aaagatgata ctcgagacgc cgccgcccta cccgtgtggg tttgtgatgc tgcctcacac    3540
ccctgcacct tccgtgagtg cagagagcga ccttaccatc ggttcagtcg ccactgaaga    3600
tattccacgc atcctcggga aaatagaaaa caccagtgag atgatcaacc agggacccct    3660 tggcatcctct gaggaaaaac cggcatacaa ccaacccgct aaggactccc tgatatcgtc    3720 gcggggttt gacgagagca cagcagctcc gtccgcaggt acgggtggcg ccggcttgtt    3780
tactgatttg ccaccttcag acggtgtaga tgcggacggg gggggccgc tgcagacggt    3840 gaaaaagaac gctgaaaggc tcctcgaccg attgagccgt caggttttta acctcgtctc    3900
ccatctccct gttttcctct cacacctctt caaatctgac agtggttatt ctccgggtga    3960 ttgggggtttt gcagctttta tctctatttttg cctctttttta tgttacagct acccattctt    4020
tggtttcgct cccctttttgg gtgtgttttc tgggtcttct cggcgcgtgc gcatggggt    4080 ttttggctgc tggttggctt ttgctgttgg tttgttcaag cctgtgtccg acccagtcgg    4140
cactgcttgt gagtttgatt cgccagagtg taggaatgtc cttcattctt ttgagcttct    4200
caaaccttgg gaccctgttc gcagccttgt tgtgggcccc gtcggtctcg gtcttgccat    4260
tcttggcagg ttactgggcg gggcacgcta catctggcat tttctgctta ggcttggcat    4320
tgttacagac tgtatcctgg ctggagctta tgtgctttct caaggtaggt gtaaaaagtg    4380
ctggggatct tgcataagaa cagctcctaa tgagattgcc tttaacgtgt tccctttttac    4440 acgtgcgact aggtcgtcac tcatcgacct gtgcaatcgg ttttgtgcgc caagggcat    4500 ggaccctatt ctcctcgcca ctgggtggcg tgggtgctgg accggccgaa gccccattga    4560
acaaccctct gaaaaaccca tcgcgtttgc ccagttggac gaaaagagga ttacggccag    4620
gaccgtggtc gcccagcctt atgaccccaa ccaagccgta aagtgcttgc gggtgttaca    4680
ggcgggcggg gcgatggtgg ctgaggcagt cccaaaagtg gtcaaagttt ccgctattcc    4740
attccgagcc cccttttttc ccaccggagt gaaagttgac cctgagtgta ggatcgtggt    4800
tgaccccgac acttttacta cagccctccg gtccggctat tccaccacaa acctcgttct    4860
tggtgtgggg gactttgccc agctgaatgg attaaaaatc aggcaaattt ccaagccttc    4920
gggaggaggc ccgcacctca ttgctgccct acatgttgcc tgctcgatgg cgttgcacat    4980
gcttgctggg gtttatgtaa ctgcagtggg gtcttgcggt accggcacca acgatccgtg    5040
gtgcaccaac ccgtttgccg tccctggcta cgggcctggg actctttgca cgtccagatt    5100
gtgcatctcc caacatggcc ttaccctgcc cttgacagca cttgtggcag gattcggtct    5160
tcaggaaatt gccttggttg ttttgattttt cgtttccatc ggaggcatgg ctcacaggtt    5220
gagttgcaag gctgacatgc tgtgcgtttt acttgcaatc gccagctatg tttgggtgcc    5280
ccttacctgg tttctttgtg tgtttccttg ctggttgcgc tggttctctt tgcatcccct    5340
caccatccta tggttggtgt ttttcttgat ttctgtaaat gtgccttcgg gaatcttggc    5400
tgtggtgttg ttagtttctc tttggctctt aggtcgttac actaatgttg ctggtcttgt    5460
caccccatat gacattcatc atcacaccag tggcccccga ggtgttgccg ccttggctac    5520
tgcaccggat gggacctact ggccgccgt tcgccgtgct gcgttgaccg tcgtaccat     5580 gctgtttacc ccgtctcagc ttgggtcccct tcttgagggt gctttcagaa ctcaaaagcc    5640
ctcactgaac accgtcaatg tggtcggatc ctctatgggc tccggcgggg tgttcaccat    5700
cgacgggaaa attaagtgcg taacagccgc acatgtcctt acgggtaatt cagctagggt    5760
```

-continued

```
ttccggggtc ggcttcaacc aaatgcttga ttttgatgtg aaaggggact tcgccatagc    5820
tgattgcccg aattggcaag gagctgcccc caagacccaa ttctgcgagg atggatggac    5880
tggccgtgcc tattggctga catcctctgg agtcgaaccc ggtgtcattg ggaatggatt    5940
cgccttctgc ttcaccgcgt gcggcgattc tggatcccg gtgattaccg aagccggtga    6000
gcttgtcggc gttcacacag gatcaaacaa acaaggagga ggcatagtca cacgcccctc    6060
aggccagttt tgtaatgtgg cgcccatcaa gctgagcgaa ttgagtgaat tcttcgctgg    6120
acctaaggtc ccgctcggtg atgtgaagat tggcagccac ataattaaag acgtatgcga    6180
ggtaccttca gatctttgcg ccttgctcgc tgccaaaccc gaactggaag gaggcctctc    6240
caccgtccaa cttctgtgtg tgtttttcct cctgtggaga atgatgggac atgcctggac    6300
gcccttggtt gctgtggggt tttttatctt gaatgaggtt ctcccagctg tcctggtccg    6360
gagtgtcttc tcctttggta tgtttgtgct atcttggctt acaccatggt ctgcgcaagt    6420
cctgatgatc aggcttctaa cagcagctct taacaggaac aggggtcac tcgccttcta    6480 cagcctcggt gcagtgaccg gatttatcgc agatcttgca gcaactcagg ggcatccgct    6540
gcaggcagtg atgaacttaa gcacctatgc cttcctgcct cggatgatgg ttgtgacctc    6600
accagtccca gtgcttgctt gtggtgttgt gcacctcctt gccataattt tgtacctgtt    6660
taagcaccgt tgcctgcatt atgtccttgt tggcgatgga gtgttctcta aagccttctt    6720
cttgcgatac tttgccgaag ggaagttgag ggaaggggtg tcgcagtcct gcgggatgaa    6780
tcacgagtca ctgactggtg ccctcgctat gagactcaat gacgaagact tggacttcct    6840
tacgaaatgg actgatttta agtgctttgt ttctgcgtcc aacatgagga atgcagcggg    6900
ccaattcatc gaggctgcct atgcaaaagc acttagaatt gagcttgccc agttagtaca    6960
ggttgataag gttcgaggta cttttggccaa acttgaagcc tttgctgata ccgtggcacc    7020
ccagctctcg cccggtgaca ttgttgttgc tcttggccac acgcctgttg gcagtatctt    7080
cgacctaaag gttggcagta ccaagcatac cctccaggcc attgagacca gagtccttgc    7140
cgggtccaaa atgaccgtgg cgcgtgtcgt tgatccaacc cccacgcccc cacccgcacc    7200
cgtgcccatc cccctcccac cgaaagtcct ggagaacggc cccaacgcct gggggatga    7260 ggaccggttg aataagagga agagacgcag gatggaagcc gtcggcatct ttgttatggg    7320
tgggaagaag taccaaaaat tttgggacaa gaattccggt gatgtgtttt acgaggaggt    7380
ccatgataac acagatgcgt gggagtgcct cagagttggt gaccctgccg actttgaccc    7440
tgagaaggga actctgtgtg ggcatactac cattgaagac aaggcttata atgtctacac    7500
ctccccatct ggcaggaagt tcctggtccc cgtcaaccca gagagcggaa gagcccaatg    7560
ggaagctgca aagctttccg tagagcaggc ccttagcatg atgaatgtcg acggtgagct    7620
gacagccaaa gaactggaga aactgaaaag aataattgac aaactccagg cctaactaa    7680 ggagcagtgt ttaaactgct agccgccagc ggcttgaccc gctgtggtcg cggcggcttg    7740
gttgttactg agacagcggt gaaaatagtt aaatttcaca accggacctt caccctagga    7800
cctgtgaatt taaagtggc cagtgaggtt gagctaaaag acgcagtcga gcataaccaa    7860
cacccggttg caagaccggt tgatggtggt gttgtgctcc tgcgctccgc agttccttcg    7920
cttatagacg tcttgatctc tggcgctgat gcatctccta agttactcgc ccaccacggg    7980
ccgggaaaca ctgggatcga tggttcgctt tgggattttg aggccgaggc caccaaagag    8040
gaaattgcac tcagtgcgca aataatacag gcttgtgaca ttaggcgcgg cgacgcaccc    8100
```

-continued

```
gaaattggtc ttccttataa gctgcaccct gttaggggca accctgagcg ggtaaaaggg    8160
gttttacaga atacaaggtt tggagacata ccttataaaa cccccagtga cactgggagc    8220
ccagtgcacg cggctgcctg cctcacgccc aatgccactc cggtgactga cggtcgttcc    8280
gtcttggcta cgaccatgcc ctccggtttt gagttgtatg taccgaccat tccagcgtct    8340
gtccttgatt atcttgattc caggcctgat tgccccaaac agttgacaga gcacggctgt    8400
gaggatgccg cattaagaga cctctccaag tatgacttgt ccacccaagg ctttgtcttg    8460
cctggagttc ttcgccttgt gcgtaagtac ctgtttgctc atgtgggtaa gtcccgcct     8520
attcatcggc cttccactta ccctgccaag aattccatgg ctggaataaa tgggaacagg    8580
tttccaacca aggacattca gagcgtccct gaaatcgacg ttttgtgcgc acaggccgtg    8640
cgagaaaact ggcaaactgt tactccttgt accctcaaga agcagtattg cgggaagaag    8700
aagactagga caatactcgg cactaataac ttcattgcgc tggcccaccg ggcagcattg    8760
agtggtgtca cccagggctt catgaaaaaa gcgtttaact cgcccatcgc actcgggaaa    8820
aacaaattca aggagctgca gactccggtc ttgggcagat gtcttgaagc tgaccttgca    8880
tcctgtgacc gatccacacc cgcaattgtc cgctggtttg ccgccaatct tctttatgaa    8940
cttgcctgtg ctgaggagca tataccatcg tacgtgttga actgctgcca cgacttactg    9000
gtcacgcagt ccggcgcggt gactaagaga ggtggcctat cgtctggcga cccgattact    9060
tctgtatcaa acaccattta cagcttggtg atatatgcac agcacatggt actcagttat    9120
tttaaaagtg gtcaccccca tggccttctg tttctacaag accagctaaa gtttgaggac    9180
atgctcaagg ttcagcccct gatcgtctat tcggacgacc tcgtgctgta cgccgagtct    9240
cccaccatgc caaactacca ctggtgggtt gaacatctga acctgatgct gggttttcag    9300
acggacccaa agaagacagc tataacagac tcgccatcat ttttgggttg taggataata    9360
aatggacgcc agttagtccc caaccgtgac aggatcctcg cggccctcgc ctaccatatg    9420
aaggcaaaca atgtttctga atactacgcc tcggcggctg caatactcat ggacagttgt    9480
gcttgtttgg agtacgatcc tgagtggttt gaagagctcg tggttgggat ggcgcagtgc    9540
gcccgcaagg acggctacag ttttcctggc ccgccgttct tcttgtccat gtgggaaaaa    9600
ctcaggtcca atcatgaggg gaagaagtct agaatgtgcg ggtactgtgg ggccccagct    9660
ccgtatgcca ctgcctgtgg ccttgatgtt tgtatttatc acacccactt ccaccagcat    9720
tgtccagtca taatctggtg tggccatccg gcgggttctg gctcttgtag tgagtgcaaa    9780
cccccccta ggaaaggcac aagccctcta gatgtggtgt tagaacaagt cccgtacaag    9840
cctccacgaa ctgtaatcat gcatgtggag cagggtctca cccctcttga cccaggcaga    9900
taccagactc gccgcggatt agtctccgtt aggcgtggca tcaggggaaa cgaaatcgac    9960
ctaccagacg gtgattatgc tagtaccgcc ttgctcccca cttgtaaaga tatcaacatg   10020
gtcgctgtcg cttccaatgt gttgcgcagc aggttcatca tcggtccacc cggtgctggt   10080
aaaacatact ggctccttca acaggtccag gatggtgatg tcatttacac gccaactcat   10140
cagaccatgc ttgacatgat caaggctttg gggacgtgcc ggttcaacgc cccagcaggc   10200
acaacgctgc aattccctgc tccctcccgt accggcccgt gggttcgcat cctgccggc    10260
ggttggtgtc ctggcaagaa ttccttcctg gatgaagcag cgtattgtaa tcaccttgat   10320
gtcttgaggc ttcttagcaa aactaccctc acctgtctgg agatttcaa acaactccac   10380
ccagtggggt ttgattctca ttgctatgtt tttgacatca tgcctcagac tcaactgaag   10440
accatctgga ggtttggaca gaatatctgt gatgccattc agccagatta cagggacaaa   10500
```

```
cttgtgtcca tggtcaacac aacccgtgta acctacgtgg aaagacctgt caagcatggg   10560
caggtcctca ccccttacca cagggaccga gaggacggcg ccatcacaat tgactccagt   10620
caaggcgcca catttgatgt ggttacattg catttgccca ctaaagattc actcaacagg   10680
caaagagccc ttgttgctat caccaggcg agacatgcta tctttgtgta tgacccacat   10740
aggcaactgc agagcatgtt tgatcttcct gcaaaaggca cacccgtcaa ccttgccgtg   10800
caccgtgacg agcagctgat cgtactagat agaaataaca aagagtgcac ggttgctcag   10860
gctctaggca atggggacaa attcagggcc acagacaagc gcgttgtaga ttctctccgc   10920
gccatttgtg cagatcttga agggtcgagc tccccgctcc ccaaggtcgc acataacttg   10980
ggattttatt tctcacctga tttgacacag tttgctaaac tcccggcaga acttgcaccc   11040
cactggcccg tggtgacaac ccagaacaat gaaaagtggc cagacaggct ggttgccagc   11100
ctccgcccta tccataaata tagccgcgca tgcattggag ccggctatat ggtgggccct   11160
tcggtgtttc taggcacccc tgggttgtg tcatactatc tcacaaaatt tgttaagggg   11220
gaggctcagg tgcttccgga gacagtcttc agcaccggcc gaattgaggt agattgccgg   11280
gagtatcttg atgatcggga acgagaagtt gctgagtccc tcccacatgc cttcattggc   11340
gacgtcaaag gcactaccgt tgggggatgt caccatgtca cctctaaata ccttccgcgc   11400
ttccttccta aggaatcagt tgcggtggtt ggggtttcga gccccgggaa agccgcaaaa   11460
gcagtctgca cattaacaga tgtgtatctc ccagaccttg aagtttacct ccacccagag   11520
acccaatcca gtgctggaa ataatgttg gacttcaagg aagtccgact gatggtctgg   11580
aaagacaaaa cggcctattt tcaacttgaa ggccgccatt tcacctggta tcagcttgca   11640
agctatgcct cgtacatccg agttcctgtt aactctacgg tgtatttgga ccctgcatg   11700 ggccctgccc tttgcaacag aagagttgtc gggtccactc attgggggc tgacctcgca   11760 gtcaccccctt atgattatgg tgccaaaatc attctgtcta gtgcatacca tggtgaaatg   11820
cctcctgggt acaaatcct ggcgtgcgcg gagttctcgc ttgacgaccc agtgaggtac   11880
aaacacacct gggggtttga atcggacaca gcgtatctgt acgagttcac cggaaacggt   11940
gaggactggg aggattacaa tgacgcattt cgtgcgcgcc agaaagggaa aatttataag   12000
gccactgcca ccagcatgag gtttcatttt ccccgggcc ccatcattga accaacttta   12060
ggcctgaact gaaatgagat gggggctatg caaagccttt tctacaaaat tggccaactt   12120
tttgtggatg cttcacgga attttttggtg tccattgttg atatcatcat attttttggcc   12180 attttgtttg gcttcaccat cgccggttgg ctggtggtct tctgcatccg attggtttgc   12240
tccgcggtac tccgtgcgcg ccctaccatt caccctgagc aattacagaa gatcctatga   12300
ggcctttctt tctcagtgcc gggtggacat tcccacctgg gaaccaaac atcccttggg   12360 gatactttgg caccataagg tgtcaaccct gattgatgaa atggtgtcgc gtcgaatgta   12420
ccgcatcatg gaaaaatcag gacaggctgc ctggaaacag gttgtgagcg aggctacgct   12480
gtctcgcatc agtggttgg atgtggtggc tcattttcag catcttgccg ccattgaagc   12540
cgagacctgt aaatatttgg cctctcggat gccatgcta cacaacctgc gcatgacagg   12600
gtcaaatgta accatagtgt ataatagtac tttgaatcag gtgttagcaa tcttcccgac   12660
ctctgaatcc cggccaaagc ttcatgattt tcaacaatgg ttaataactg tacattcctc   12720
catattttcc tccgttgtgg cttcctgtac tcttttttgtt gtgctgtggt tgcgaattcc   12780
aatgctacgt actgtttttg gtttccactg gttaggggca ttttttcttt cgaactcaca   12840
```

```
gtgaattaca cggtgtgccc accttgcctc acccggcaag cagccgctga gatctacgaa    12900
cccggcaggt ctctttggtg caggatagggg catgatcgat gtagcgagga cgatcatgac   12960
gaactagggt tcttggttcc gcctggcctc tccagcgaag gccacttgac cagtgtttac    13020
gcctggttgg cgttcctgtc cttcagctat acagcccagt tccatcccga gatatttggg    13080
atagggaatg tgagtaaaat ttatgttgac atcaagcacc aattcatctg cgccgaacac    13140
gacgggcaga acgccaccct gcctcgccat gacaacattt cagccgtgtt tcagacctac    13200
taccaacatc aggtcgatgg cggcaattgg tttcacctgg aatggctgcg ccccttcttt    13260
tcctcttggt tggttttaaa tgtttcgtgg tttctcaggc gttcgcctgc aagccatgtt    13320
tcagttcgag tctttcagac atcaaaacca acaccaccgc agcaccaaat tttgttgtcc    13380
tccaggacat cagctgcctt aggcatggcg acccgtcctc tccggcgatt cgcaaaagct    13440
ctcagtgccg cacggcgata ggaacacccg tgtatatcac catcacagcc aatgtgacag    13500
atgagaatta tttacattct tctgatctcc tcatgctttc ttcttgcctt ttctatgctt    13560
ctgagatgag tgaaaagggg ttcaaggtgg tattcggcaa tgtgtcaggc atcgtggctg    13620
tgtgtgtcaa ctttaccagt tacgtccaac atgtcaagga gtttacccaa cgctccttgg    13680
tggtcgagca tgtgcgactg cttcatttca tgacacctga aaccatgagg tgggcaaccg    13740
ttttagcctg tcttttttgcc attctgttgg caatttgaat gtttaagtat gttggggaaa    13800
tgcttgaccg cgggctgttg ctcgccgttg ctttttttgt ggtgtatcgt gccgtcttgc    13860
tttgttgcgc ccgtcaacgt cgacgggaac gacagctcaa agttacagct gatttacaac    13920
ttgacgctat gtgagctgaa tggcacagat tggctggctg gtagatttga ctgggcagtg    13980
gagtgttttg tcattttttcc cgtgttgact cacattgtct cctatggtgc cctcactact    14040
agccatttcc ttgacacagt cggtctggtc actgtgtctg ccgccgggtt ccttcatgaa    14100
cggtatgttt tgagtagcat ctacgcggtc tgtgccctgg ctgcgttgat ttgcttcgtc    14160
attaggcttg cgaagaactg catgtcctgg cgctactcgt gtaccagata taccaacttc    14220
cttttggaca ccaaggggag actctatcgt tggcgatcgc ccgtcatcat agagaaaaag    14280
ggtaaagttg aggttgaagg tcatttgatc gacctcaaaa gagttgtgct tgatggttcc    14340
gtggcaaccc ctataaccaa aattttcagcg gaacaatggg gtcgtccctta gatgacttct    14400 gccatgatag cacggctcca caaaaggtgc ttttggcgtt ttccattacc tatacaccag    14460
tgatgatata tgccctaaag gtaagtcgcg gccgactgct agggcttttg cacctttttga   14520 tctttctgaa ctgtgctttc accttcgggt atatgacatt cacgcacttt cagagtacaa    14580
acaaggtcgc gctcactatg ggagcagtag ttgcactcct ttgggggggtg tactcagcca    14640 tagaaacctg gaaattcatc acctccagat gccgtttgtg cttgctaggc cgcaagtaca    14700
ttctggcccc tgcccaccac gttgagagtg ccgcaggctt catccgatt gcggcaaatg    14760 ataaccacgc atttgtcgtc cggcgtcccg gttccactac ggtcaacggc acattggtcc    14820
ccgggttgaa aagcctcgtg ttgggtggca gaaaagctgt caaacaggga gtggtaaacc    14880
ttgttaaata tgccaagtaa caacggcagg cagcagaaaa aagaaaggg ggatggccag    14940 ccagtcaatc agctgtgtca gatgctgggt aaaattattg cccagcaaaa tcagtccagg    15000
ggcaagggac cgggaaagaa aaataacaag aaaaacccgg agaagcccca ttttcctcta    15060
gcgactgaag atgatgtcag acatcacttt accccgagtg agcgacaatt gtgtctgtcg    15120
tcaatccaga ctgccttcaa tcagggcgct ggaacttgta ccctgtcaga ttcaggcagg    15180
ataagttaca ctgtggagtt tagtttgccg acgcatcaca ctgtgcgcct gatccgcgct    15240
```

```
acagcatcac cctcagcatg atgagctggc attcctgggt atcccagtgt ttgaattgga    15300
agaatgtgtg gtgaatggca ctgattgaca ttgtgcttct aagtcaccta ttcaattagg    15360
gcgaccgtgt gggagtagaa tttaattggc gagaaccacg cggccgaaat taaaaaaaaa    15420
aaaaaaaaaa aaaaaaaaaa aaaa                                          15444

<210> SEQ ID NO 11
<211> LENGTH: 15444
<212> TYPE: DNA
<213> ORGANISM: Artificial Sequence
<220> FEATURE:
<223> OTHER INFORMATION: Synthetic Construct

<400> SEQUENCE: 11
atgacgtata gttgttggct ctatgtcgtg acatttgtat agtcaggagc tgcgaccatt      60
ggtacagccc aaaacttgct gcgcgggaac gcccttccgt gacagccttc ttcaggggag     120
tttaggggtc tatccctagc accttgcttc cggagttgca ctgctttacg gtctctccac     180 cccctttaacc atgtctggga tacttgatcg gtgcacgtgt accccaatg ccagggtgtt     240 tgtggcggag ggccaagtct actgcacacg atgtctcagt gcacggtctc tccttccttt     300
gaatctccaa gtttctgagc ttggggtgct gggcttattt tataggcccg aagagccgct     360
ccggtggacg ttgccacgtg cattccccac tgtcgagtgc tcccccgccg gggcctgctg     420
gctttctgcg attttccaa ttgcacgaat gaccagtgga aacctgaact ttcaacaaag     480
aatagtgcgg gtcgcagctg agctctacag agccggtcag ctcacccccg tagtcttgaa     540
gaatctacag gtttatgaac ggggttgccg ttggtacccc atcgttggac ctgttcctgg     600
agtggctgtt tatgccaatt ccttacacgt gagtgacaaa cctttcccgg gagcaactca     660
tgtgttaacc aacctaccgc tcccgcagag gcccaagcct gaagactttt gccccttttga    720 gtgtgctatg gctgacgtct atgacattgg tcatgacgct gtcatgtatg tggccggagg     780
gagagtctcc tgggcccctc gtggcgggga caaaggaaaa tttgaaatag ttcccaagga     840
gttgaagttg attgcgaatc gactccacat ttccttcccg ccccaccacg cagtggacat     900
gtccaagttt gcctttataa gccctgggag tggtgtttcc atgcgggtcg agtaccaaca     960
tggctgtctc cccgctgata ctgtccctga aggaaactgt tggtggcgct tgtttgactt    1020
gcttccaccg gaagttcaga acaaagagat tcgccatgct aaccaactcg ctatcagac      1080 caagcatggt gtcgctggca agtacctaca gcggaggctg caagttaatg gactccgagc    1140
agtaactgac gcgaatggac ctatcgtcat acagtatttt tgtgataggg aaagctggat    1200
ccgccactta agactggtag aagaacctag cctccctggg tttgaggacc tcctcagaat    1260
aagagttgag cccaatacgt tgccattggt tggcgaggat gagaaaatct tccgatttgg    1320
caatcacaaa tggtacggtg ctggaaagag ggcaaggaaa gcacgctttg gtgcggctgc    1380
cacggtcgct caccgcgctt tgcccgctca cgaaacccag caggccaaga agcacgaagt    1440
taccagcgcc aacagggctg agcatctcga gcactattcc ccgcctaccg acgggaactg    1500
tggttggcac tgcgtttccg ccattgtcaa ccggattgtg aattcaaat ttgaaaccac     1560 ccttcccgag agagtgagac ctttagatga ctgggcatact gacgaggatc ttgtgaatac    1620
tatccaaatc ctcaggctcc ctgcggcctt ggacaggaac ggtgcttgtg tcggcgccaa    1680
gtacgtgctc aagctggaag gtgtgcactg gacagtctct gtggcccctg ggatgacccc    1740
ttctctgctc ccccttgaat gtgttcaggg ctgttgtgag cataagagcg gtcttggtcc    1800
```

```
cccagatgtg gctgaagttt ccggatttga ccctgcctgc cttaaccgac tggctgaggt    1860
aatgcacttg cctagttgtg tcatcccagc tgctctggct gaaatgtccg acgaccccaa    1920
tcgcccggct tccccagtca ccactgtgtg gactatttcg caattctttg cccattatag    1980
aggaggagag caccctgatc aggtgtgctt agggaaaatc atcagccttt gtcaggtgat    2040
tgaggaatgc tgttgttccc agaacaaaac caaccgggcc accccggaag aggtcgcggc    2100
aaaaattgac cagtacctcc gtgatgcagc aagccttgga gaatgcttag ccaagcttga    2160
gagggctcgc ccgccgagcg cgatggacac ctcctttgat tggaatgttg tgcttcctgg    2220
ggttgaggcg gcgaaccaga cgaccaaaca gctccatgtc aaccagcacc gtgcttcggt    2280
tcctgccatg actcaggagc ctttggacaa agactcggtc cctttgaccg ccttctcgct    2340
gtctaattgc tactaccctg cacaaggtga cgaggttcgt caccgtgaga ggctgatctc    2400
cgtgctctct aagttggagg aggttgttcg tgaggaatat gggctcacgc caactggatc    2460
tggcccgcga cccgcactgc cgaacgggct cgacgagctc aaagaccaga tggaagagga    2520
tctgttgaaa ctggtcaacg cccaggcaac ttcagaaatg atggcccggg cagctgagca    2580
ggttgatcta aaagtttggg tcaaaaatta cccacggtgg acaccgccac cccctccacc    2640
aagagttcag cctcgaaaaa caaagtctgc taagagcctg ccagagaaca agcctgtccc    2700
tgctccgcgc aggaaagtca gatctgattg tggcagcccg actttgaggg gcaacaatgt    2760
tcctaacggt tgggaagact tggccgttgg tggtcctctt gatctttcga caccatccga    2820
gccgatgaca cctctgagtg agcctgcact tatgcccgtg ttgcaacata tttctggacc    2880
agtgacgcct ttgagcgtgc cggccccctat tcctgcaccg cgtaaagctg tgtcccgacc    2940
gatggcgccc tcgagtgagc caattttttgt gtctgcaccg cggcaaaaat ttcagcaggt    3000
ggaagaagca aatctggcgg caacaacgct gacataccag gacgaaccta tagatctgtc    3060
agcatcctca cagactgaat atgaggctcc ttccctagca ccactgcaga acataggtac    3120
tctggaggtg gggggggcaag aagctgagga aattctgagt gaaacctcgg atataccgaa    3180
tgacatcaac cctgtgcctg tatcatcaag cagctccttg tcaagcgtta agatcacacg    3240
cccaagacac tcagctcaag ccatcatcga ctcgggcggg ccctgcagtg ggcatctcca    3300
aagggagaaa gaagcgtgcc tccgcatcat gcgtgaggct tgtgatgcga ctaagcttag    3360
tgaccctgcc acgcaggaat ggctttctcg catgtgggat agggtggaca tgctgacttg    3420
gcgcaacacg tctgctttcc aggcgtttcg catcttagac ggcaggcttg agtttcttcc    3480
aaagatgata ctcgagacgc cgccgcccta cccgtgtggg tttgtgatgc tgcctcacac    3540
ccctgcacct tccgtgagtg cagagagcga ccttaccatc ggttcagtcg ccactgaaga    3600
tattccacgc atcctcggga aaatagaaaa caccagtgag atgatcaacc agggacccctt    3660 ggcatcctct gaggaaaaac cggcatacaa ccaacccgct aaggactccc tgatatcgtc    3720 gcggggttt gacgagagca cagcagctcc gtccgcaggt acgggtggcg ccggcttgtt    3780
tactgatttg ccaccttcag acggtgtaga tcgcgacggg ggggggccgc tgcagacggt    3840
gaaaaagaac gctgaaaggc tcctcgaccg attgagccgt caggttttta acctcgtctc    3900
ccatctccct gttttcctct cacacctctt caaatctgac agtggttatt ctccgggtga    3960 ttgggggtttt gcagctttta ctctatttttg cctctttttta tgttacagct acccattctt    4020
tggtttcgct cccctttttgg gtgtgttttc tgggtcttct cggcgcgtgc gcatgggggt    4080
ttttggctgc tggttggctt ttgctgttgg tttgttcaag cctgtgtccg acccagtcgg    4140
cactgcttgt gagtttgatt cgccagagtg taggaatgtc cttcattctt ttgagcttct    4200
```

```
caaaccttgg gaccctgttc gcagccttgt tgtgggcccc gtcggtctcg gtcttgccat    4260
tcttggcagg ttactgggcg gggcacgcta catctggcat tttctgctta ggcttggcat    4320
tgttacagac tgtatcctgg ctggagctta tgtgctttct caaggtaggt gtaaaaagtg    4380
ctggggatct tgcataagaa cagctcctaa tgagattgcc tttaacgtgt tcccttttac    4440
acgtgcgact aggtcgtcac tcatcgacct gtgcaatcgg ttttgtgcgc caaagggcat    4500
ggaccctatt ctcctcgcca ctgggtggcg tgggtgctgg accggccgaa gccccattga    4560
acaaccctct gaaaaaccca tcgcgtttgc ccagttggac gaaaagagga ttacggccag    4620
gaccgtggtc gcccagcctt atgaccccaa ccaagccgta aagtgcttgc gggtgttaca    4680
ggcgggcggg gcgatggtgg ctgaggcagt cccaaaagtg gtcaaagttt ccgctattcc    4740
attccgagcc cccttttttc ccaccggagt gaaagttgac cctgagtgta ggatcgtggt    4800 tgacccgac acttttacta cagccctccg gtccggctat tccaccacaa acctcgttct    4860
tggtgtgggg gactttgccc agctgaatgg attaaaaatc aggcaaattt ccaagccttc    4920
gggaggaggc ccgcacctca ttgctgccct acatgttgcc tgctcgatgg cgttgcacat    4980
gcttgctggg gtttatgtaa ctgcagtggg gtcttgcggt accggcacca acgatccgtg    5040
gtgcaccaac ccgtttgccg tccctggcta cgggcctggt actctttgca cgtccagatt    5100
gtgcatctcc caacatggcc ttaccctgcc cttgacagca cttgtggcag gattcggtct    5160
tcaggaaatt gccttggttg ttttgatttt cgtttccatc ggaggcatgg ctcacaggtt    5220
gagttgcaag gctgacatgc tgtgcgtttt acttgcaatc gccagctatg tttgggtgcc    5280
ccttacctgg tttctttgtg tgtttccttg ctggttgcgc tggttctctt tgcatcccct    5340
caccatccta tggttggtgt ttttcttgat ttctgtaaat gtgccttcgg gaatcttggc    5400
tgtggtgttg ttagtttctc tttggctctt aggtcgttac actaatgttg ctggtcttgt    5460 cacccccatat gacattcatc atcacaccag tggccccga ggtgttgccg ccttggctac    5520
tgcaccggat gggacctact ggccgccgt tcgccgtgct gcgttgaccg tcgtaccat    5580 gctgtttacc ccgtctcagc ttgggtccct tctttgagggt gctttcagaa ctcaaaagcc    5640
ctcactgaac accgtcaatg tggtcggatc ctctatgggc tccggcgggg tgttcaccat    5700
cgacgggaaa attaagtgcg taacagccgc acatgtcctt acgggtaatt cagctagggt    5760
ttccggggtc ggcttcaacc aaatgcttga ttttgatgtg aaaggggact cgccatagc    5820 tgattgcccg aattggcaag gagctgcccc caagacccaa ttctgcgagg atggatggac    5880
tggccgtgcc tattggctga catcctctgg agtcgaaccc ggtgtcattg gaatggatt    5940 cgccttctgc ttcaccgcgt gcggcgattc tggatccccg gtgattaccg aagccggtga    6000
gcttgtcggc gttcacacag gatcaaacaa acaaggagga ggcatagtca cacgcccctc    6060
aggccagttt tgtaatgtgg cgcccatcaa gctgagcgaa ttgagtgaat tcttcgctgg    6120
acctaaggtc ccgctcggtg atgtgaagat tggcagccac ataattaaag acgtatgcga    6180
ggtaccttca gatctttgcg ccttgctcgc tgccaaaccc gaactggaag gaggcctctc    6240
caccgtccaa cttctgtgtg tgttttttcct cctgtggaga atgatgggac atgcctggac    6300
gcccttggtt gctgtggggt ttttatctt gaatgaggtt ctcccagctg tcctggtccg    6360
gagtgtcttc tcctttggta tgtttgtgct atcttggctt acaccatggt ctgcgcaagt    6420
cctgatgatc aggcttctaa cagcagctct taacaggaac agggggtcac tcgccttcta    6480
cagcctcggt gcagtgaccg gatttatcgc agatcttgca gcaactcagg ggcatccgct    6540
```

```
gcaggcagtg atgaacttaa gcacctatgc cttcctgcct cggatgatgg ttgtgacctc    6600
accagtccca gtgcttgctt gtggtgttgt gcacctcctt gccataattt tgtacctgtt    6660
taagcaccgt tgcctgcatt atgtccttgt tggcgatgga gtgttctcta aagccttctt    6720
cttgcgatac tttgccgaag ggaagttgag ggaaggggtg tcgcagtcct gcgggatgaa    6780
tcacgagtca ctgactggtg ccctcgctat gagactcaat gacgaagact tggacttcct    6840
tacgaaatgg actgatttta agtgctttgt ttctgcgtcc aacatgagga atgcagcggg    6900
ccaattcatc gaggctgcct atgcaaaagc acttagaatt gagcttgccc agttagtaca    6960
ggttgataag gttcgaggta ctttggccaa acttgaagcc tttgctgata ccgtggcacc    7020
ccagctctcg cccggtgaca ttgttgttgc tcttggccac acgcctgttg gcagtatctt    7080
cgacctaaag gttggcagta ccaagcatac cctccaggcc attgagacca gagtccttgc    7140
cgggtccaaa atgaccgtgg cgcgtgtcgt tgatccaacc cccacgcccc cacccgcacc    7200
cgtgcccatc cccctcccac cgaaagtcct ggagaacggc cccaacgcct gggggatga    7260 ggaccggttg aataagagga agagacgcag gatgaagcc gtcggcatct tgttatggg    7320 tgggaagaag taccaaaaat tttgggacaa gaattccggt gatgtgtttt acgaggaggt    7380
ccatgataac acagatgcgt gggagtgcct cagagttggt gaccctgccg actttgaccc    7440
tgagaaggga actctgtgtg ggcatactac cattgaagac aaggcttata atgtctacac    7500
ctccccatct ggcaggaagt tcctggtccc cgtcaaccca gagagcggaa gagcccaatg    7560
ggaagctgca aagctttccg tagagcaggc ccttagcatg atgaatgtcg acggtgagct    7620
gacagccaaa gaactggaga aactgaaaag aataattgac aaactccagg cctaactaa    7680 ggagcagtgt ttaaactgct agccgccagc ggcttgaccc gctgtggtcg cggcggcttg    7740
gttgttactg agacagcggt gaaaatagtt aaatttcaca accggacctt caccctagga    7800
cctgtgaatt taaaagtggc cagtgaggtt gagctaaaag acgcagtcga gcataaccaa    7860
cacccggttg caagaccggt tgatggtggt gttgtgctcc tgcgctccgc agttccttcg    7920
cttatagacg tcttgatctc tggcgctgat gcatctccta agttactcgc ccaccacggg    7980
ccgggaaaca ctgggatcga tggttcgctt tgggattttg aggccgaggc caccaaagag    8040
gaaattgcac tcagtgcgca aataatacag gcttgtgaca ttaggcgcgg cgacgcaccc    8100
gaaattggtc ttccttataa gctgcaccct gttaggggca accctgagcg ggtaaaaggg    8160
gttttacaga atacaaggtt tggagacata ccttataaaa cccccagtga cactgggagc    8220
ccagtgcacg cggctgcctg cctcacgccc aatgccactc cggtgactga cggtcgttcc    8280
gtcttggcta cgaccatgcc ctccggtttt gagttgtatg taccgaccat tccagcgtct    8340
gtccttgatt atcttgattc caggcctgat tgccccaaac agttgacaga gcacggctgt    8400
gaggatgccg cattaagaga cctctccaag tatgacttgt ccacccaagg ctttgtcttg    8460 cctgagttc ttcgccttgt gcgtaagtac ctgtttgctc atgtgggtaa gtgcccgcct    8520
attcatcggc cttccactta ccctgccaag aattccatgg ctggaataaa tgggaacagg    8580
tttccaacca aggacattca gagcgtccct gaaatcgacg ttttgtgcgc acaggccgtg    8640
cgagaaaact ggcaaactgt tactccttgt accctcaaga agcagtattg cgggaagaag    8700
aagactagga caatactcgg cactaataac ttcattgcgc tggcccaccg gcagcattg    8760 agtggtgtca cccagggctt catgaaaaaa gcgtttaact cgcccatcgc actcgggaaa    8820
aacaaattca aggagctgca gactccggtc ttgggcagat gtcttgaagc tgaccttgca    8880
tcctgtgacc gatccacacc cgcaattgtc cgctggtttg ccgccaatct tctttatgaa    8940
```

```
cttgcctgtg ctgaggagca tataccatcg tacgtgttga actgctgcca cgacttactg    9000
gtcacgcagt ccggcgcggt gactaagaga ggtggcctat cgtctggcga cccgattact    9060
tctgtatcaa acaccattta cagcttggtg atatatgcac agcacatggt actcagttat    9120
tttaaaagtg gtcaccccca tggccttctg tttctacaag accagctaaa gtttgaggac    9180
atgctcaagg ttcagcccct gatcgtctat tcggacgacc tcgtgctgta cgccgagtct    9240
cccaccatgc caaactacca ctggtgggtt gaacatctga acctgatgct gggttttcag    9300
acggacccaa agaagacagc tataacagac tcgccatcat ttttgggttg taggataata    9360
aatgacgcc agttagtccc caaccgtgac aggatcctcg cggccctcgc ctaccatatg    9420
aaggcaaaca atgtttctga atactacgcc tcggcggctg caatactcat ggacagttgt    9480
gcttgtttgg agtacgatcc tgagtggttt gaagagctcg tggttgggat ggcgcagtgc    9540
gcccgcaagg acggctacag ttttcctggc ccgccgttct tcttgtccat gtgggaaaaa    9600
ctcaggtcca atcatgaggg gaagaagtct agaatgtgcg ggtactgtgg ggccccagct    9660
ccgtatgcca ctgcctgtgg ccttgatgtt tgtatttatc acacccactt ccaccagcat    9720
tgtccagtca taatctggtg tggccatccg gcgggttctg gctcttgtag tgagtgcaaa    9780
ccccccctag ggaaaggcac aagccctcta gatgtggtgt tagaacaagt cccgtacaag    9840
cctccacgaa ctgtaatcat gcatgtggag cagggtctca cccctcttga cccaggcaga    9900
taccagactc gccgcggatt agtctccgtt aggcgtggca tcaggggaaa cgaaatcgac    9960
ctaccgacg tgattatgc tagtaccgcc ttgctcccca cttgtaaaga tatcaacatg   10020
gtcgctgtcg cttccaatgt gttgcgcagc aggttcatca tcggtccacc cggtgctggt   10080
aaaacatact ggctccttca acaggtccag gatggtgatg tcatttacac gccaactcat   10140
cagaccatgc ttgacatgat caaggctttg gggacgtgcc ggttcaacgc cccagcaggc   10200
acaacgctgc aattccctgc tccctcccgt accggcccgt gggttcgcat cctggccggc   10260
ggttggtgtc ctggcaagaa ttccttcctg gatgaagcag cgtattgtaa tcaccttgat   10320
gtcttgaggc ttcttagcaa aactacccctc acctgtctgg agatttcaa acaactccac   10380
ccagtgggtt ttgattctca ttgctatgtt tttgacatca tgcctcagac tcaactgaag   10440
accatctgga ggtttggaca gaatatctgt gatgccattc agccagatta cagggacaaa   10500
cttgtgtcca tggtcaacac aacccgtgta acctacgtgg aaagacctgt caagcatggg   10560
caggtcctca cccccttacca cagggaccga gaggacggcg ccatcacaat tgactccagt   10620
caaggcgcca catttgatgt ggttacattg catttgccca ctaaagattc actcaacagg   10680
caaagagccc ttgttgctat caccagggcg agacatgcta tctttgtgta tgacccacat   10740
aggcaactgc agagcatgtt tgatcttcct gcaaaaggca cccccgtcaa ccttgccgtg   10800
caccgtgacg agcagctgat cgtactagat agaaataaca agagtgcac ggttgctcag   10860
gctctaggca atgggacaa attcagggcc acagacaagc gcgttgtaga ttctctccgc   10920
gccatttgtg cagatcttga agggtcgagc tccccgctcc ccaaggtcgc acataacttg   10980
ggatttttatt tctcacctga tttgacacag tttgctaaac tcccggcaga acttgcaccc   11040
cactggcccg tggtgacaac ccagaacaat gaaaagtggc cagacaggct ggttgccagc   11100
ctccgcccta tccataaata tagccgcgca tgcattggag ccggctatat ggtgggccct   11160
tcggtgtttc taggcacccc tggggttgtg tcatactatc tcacaaaatt tgttaagggg   11220
gaggctcagg tgcttccgga gacagtcttc agcaccggcc gaattgaggt agattgccgg   11280
```

```
gagtatcttg atgatcggga acgagaagtt gctgagtccc tcccacatgc cttcattggc   11340
gacgtcaaag gcactaccgt tgggggatgt caccatgtca cctctaaata ccttccgcgc   11400
ttccttccta aggaatcagt tgcggtggtt ggggtttcga gccccgggaa agccgcaaaa   11460
gcagtctgca cattaacaga tgtgtatctc ccagaccttg aagtttacct ccacccagag   11520
acccaatcca agtgctggaa ataatgttg  gacttcaagg aagtccgact gatggtctgg   11580
aaagacaaaa cggcctattt tcaacttgaa ggccgccatt tcacctggta tcagcttgca   11640
agctatgcct cgtacatccg agttcctgtt aactctacgg tgtatttgga cccctgcatg   11700
ggccctgccc tttgcaacag aagagttgtc gggtccactc attgggggc  tgacctcgca   11760 gtcaccccTt atgattatgg tgccaaaatc attctgtcta gtgcatacca tggtgaaatg   11820
cctcctgggt acaaaatcct ggcgtgcgcg gagttctcgc ttgacaccc  agtgaggtac   11880 aaacacacct gggggtttga atcggacaca gcgtatctgt acgagttcac cggaaacggt   11940
gaggactggg aggattacaa tgacgcattt cgtgcgcgcc agaaagggaa aatttataag   12000
gccactgcca ccagcatgag gtttcatttt ccccgggcc  ccatcattga accaacttta   12060
ggcctgaact gaaatgagat gggggctatg caaagccttt tctacaaaat tggccaactt   12120
tttgtggatg ctttcacgga attttTggtg tccattgttg atatcatcat attttTggcc   12180
attttgtttg gcttcaccat cgccggttgg ctggtggtct tctgcatccg attggtttgc   12240
tccgcggtac tccgtgcgcg ccctaccatt caccctgagc aattacagaa gatcctgatga  12300 ggcctttctt tctcagtgcc gggtggacat tcccacctgg ggaaccaaac atcccttggg   12360
gatactttgg caccataagg tgtcaaccct gattgatgaa atggtgtcgc gtcgaatgta   12420
ccgcatcatg gaaaaatcag gacaggctgc ctggaaacag gttgtgagcg aggctacgct   12480
gtctcgcatc agtggtttgg atgtggtggc tcattttcag catcttgccg ccattgaagc   12540
cgagacctgt aaatatttgg cctctcggat gcccatgcta cacaacctgc gcatgacagg   12600
gtcaaatgta accatagtgt ataatagtac tttgaatcag gtgttagcaa tcttcccgac   12660
ctctgaatcc cggccaaagc ttcatgattt tcaacaatgg ttaataactg tacattcctc   12720
catatttTcc tccgttgtgg cttcctgtac tctTtTTgtt gtgctgtggt tgcgaattcc   12780
aatgctacgt actgtttTtg gttTccactg gttaggggca attTttcttt cgaactcaca   12840
gtgaattaca cggtgtgccc accttgcctc acccggcaag cagccgctga gatctacgaa   12900
cccggcaggt ctctttggtg caggatagg  catgatcgat gtagcgagga cgatcatgac   12960
gaactagggt tcttggttcc gcctggcctc tccagcgaag gccacttgac cagtgtttac   13020
gcctggttgg cgttcctgtc cttcagctat acagcccagt tccatcccga gatatttggg   13080
atagggaatg tgagtaaaat ttatgttgac atcaagcacc aattcatctg cgccgaacac   13140
gacgggcaga acgccaccct gcctcgccat gacaacattt cagccgtgtt tcagacctac   13200
taccaacatc aggtcgatgg cggcaattgg tttcacctgg aatggctgcg ccccttcttt   13260
tcctcttggt tggtttttaa tgttTcgtgg tttctcaggc gttcgcctgc aagccatgtt   13320
tcagttcgag tctTtcagac atcaaaacca acaccaccgc agcaccaaat tTgttgtcc   13380 tccaggacat cagctgcctt aggcatggcg accgtcctc  tccggcgatt cgcaaaagct   13440
ctcagtgccg cacggcgata ggaacacccg tgtatatcac catcacagcc aatgtgacag   13500
atgagaatta tttacattct tctgatctcc tcatgctttc ttcttgcctt ttctatgctt   13560
ctgagatgag tgaaaagggg ttcaaggtgg tattcggcaa tgtgtcaggc atcgtggctg   13620
tgtgtgtcaa cttTaccagt tacgtccaac atgtcaagga gtttacccaa cgctccttgg   13680
```

```
tggtcgagca tgtgcgactg cttcatttca tgacacctga aaccatgagg tgggcaaccg   13740
ttttagcctg tcttttttgcc attctgttgg caatttgaat gtttaagtat gttggggaaa   13800
tgcttgaccg cgggctgttg ctcgccgttg cttttttttgt ggtgtatcgt gccgtcttgc   13860
tttgttgcgc ccgtcaacgt cgacgggaac gacagctcaa agttacagct gatttacaac   13920
ttgacgctat gtgagctgaa tggcacagat tggctggctg gtagatttga ctgggcagtg   13980
gagtgttttg tcattttttcc cgtgttgact cacattgtct cctatggtgc cctcactact   14040
agccatttcc ttgacacagt cggtctggtc actgtgtctg ccgccgggtt ccttcatgaa   14100
cggtatgttt tgagtagcat ctacgcggtc tgtgccctgg ctgcgttgat ttgcttcgtc   14160
attaggcttg cgaagaactg catgtcctgg cgctactcgt gtaccagata taccaacttc   14220
cttttggaca ccaagggggag actctatcgt tggcgatcgc ccgtcatcat agagaaaaag   14280
ggtaaagttg aggttgaagg tcatttgatc gacctcaaaa gagttgtgct tgatggttcc   14340
gtggcaaccc ctataaccaa aatttcagcg gaacaatggg gtcgtcctta gatgacttct   14400
gccatgatag cacggctcca caaaaggtgc ttttggcgtt ttccattacc tatacaccag   14460
tgatgatata tgccctaaag gtaagtcgcg gccgactgct agggcttttg cacctttga   14520 tctttctgaa ctgtgctttc accttcgggt atatgacatt cacgcacttt cagagtacaa   14580
acaaggtcgc gctcactatg ggagcagtag ttgcactcct ttgggggggtg tactcagcca   14640 tagaaacctg gaaattcatc acctccagat gccgtttgtg cttgctaggc cgcaagtaca   14700
ttctggcccc tgcccaccac gttgagagtg ccgcaggctt tcatccgatt gcggcaaatg   14760
ataaccacgc atttgtcgtc cggcgtcccg gttccactac ggtcaacggc acattggtcc   14820
ccgggttgaa aagcctcgtg ttgggtggca gaaaagctgt caaacaggga gtggtaaacc   14880
ttgttaaata tgccaagtaa caacggcagg cagcagaaaa aaagaaaggg ggatggccag   14940
ccagtcaatc agctgtgtca gatgctgggt aaaattattg cccagcaaaa tcagtccagg   15000
ggcaagggac cgggaaagaa aaataacaag aaaaacccgg agaagcccca ttttcctcta   15060
gcgactgaag atgatgtcag acatcacttt accccgagtg agcgacaatt gtgtctgtcg   15120
tcaatccaga ctgccttcaa tcagggcgct ggaacttgta ccctgtcaga ttcaggcagg   15180
ataagttaca ctgtggagtt tagttttgccg acgcatcaca ctgtgcgcct gatccgcgct   15240
acagcatcac cctcagcatg atgagctggc attcctgggt atcccagtgt ttgaattgga   15300
agaatgtgtg gtgaatggca ctgattgaca ttgtgcttct aagtcaccta ttcaattagg   15360
gcgaccgtgt gggagtagaa tttaattggc gagaaccacg cggccgaaat taaaaaaaaa   15420
aaaaaaaaaa aaaaaaaaaa aaaa                                           15444
```

<210> SEQ ID NO 12
<211> LENGTH: 15047
<212> TYPE: DNA
<213> ORGANISM: Artificial Sequence
<220> FEATURE:
<223> OTHER INFORMATION: Synthetic Construct

<400> SEQUENCE: 12

```
atgacgtata ggtgtttgct ttatgccgcg gcatttgtat tgtcaggagc tgtgaccact     60
ggcacagccc gaaacttgct gcacagaaac acccttctgt gacagcctcc ttcaggggag    120
tttaggggtt tctccctaac gccctgcttc cggagttgca ctgctttacg gtctctccat    180
ccttttaacc atgtctggga ttcttgatcg gtgcacgtgc accccaatg ccagggtgtt     240
```

```
tgtggcagag ggccaagtct actgcacacg atgtctcagt gcacggtccc tccttcccct    300
aaatctccaa gtttctgagc ttggggtact tggtttattc tacaggcccg aagagccatt    360
acggtggacg ttgccacacg cattccccac tgtcgagtgt gctcctgctg gcgcttgttg    420
gctttctgca atttttccaa ttgcgcgaat gaccagtgga aacctgaatt tccagcaaag    480
gctggtacgt gtcgcagccg agctttacag agccggccag ctcacccta caagcctgaa     540
aaccttacag gtctatgaaa ggggttgccg ttggtacccc attgttggac ctgttcctgg    600
agtggccgtt tacgccaact ccctacatgt gagtgacaaa cccttcccag gagcgactca    660
cgtgctgacc aacttaccac tcccgcagag accaaaatct gaagatttct gccccttcga    720
gtgcgccacg gccgccgtct atgacatcgg ccatgacgcc gtcatgtatg taaccgagga    780
aaaggtttcc tgggctcctc gtggcgggga taaagggaaa tttgagactg ttcctgaggg    840
gttgaagttg actgcggaac gactctacac ctccttcccg cctcaccatg cggtggacat    900
gtcccttttc atcttcacag accttgagtg cggcgcttcc atgcgggtcg aacgccaata    960
tggttgcctc tctgctggca ctgtccctga aggcaactgc tggtggagtc tgtttggctc   1020
gctttcgtta gaagctcagt ataaagaaat ccgctacgcc gcccaatttg ctatcagac    1080
caaacatggc gttactggca gtacctgca gcggaggctg caaattaatg gtctccgagc    1140
agtggttgac ccgaatgggc ctcttgtcgt acagtatttc tccgttaagg agagctggat   1200
gcgccacgtg agactggcgg aagagccagg ctatcctggg tttgaggatc tcctcaggat   1260
aagagtcgag cccaacacgt tgcctttgtc caacaaggac gagaaaatct tccgtttcgg   1320
cggttacaag tggtacggtg ctgggcgagg ggcaaggaga acacgtgcaa gagcagtcac   1380
cgcagttgct agtcatgctc cgcccgctcg tggggcccag caggccgaga agcacgaagt   1440
tgctagtgcc aacaagactg agctccttac gcactactcc ccacctgctg aagggaattg   1500
cggctggcac tgcatctccg ccatcatgaa ccggatggtg cattccaagt tgaaaccgc    1560
cctttccgaa agagtgagat ccccggaaga ctgggcgact gatgaggatc ttgtgaatac   1620
tattcaaatc ctcaggctcc ctgcggcctt agacaggaac ggcgcctgta aaaacgccaa   1680
gtacatcctt aagctggaag gtgagcactg gactgtttca gtgaccccg gaatgccccc    1740
ctcttcactt cctcttgaat gcgttcaggg ttgttgcgag cataagggca attttgactc   1800
tcaaaacgcg gtcggtttct ttgggttcga ccctgccagc cttgaccgac tcgctggggt   1860
aatgcatctg cccagcagcg ccatccctgc cgccctggcc gagttgtctg gtgaacttga   1920
ttgttcaact ccccggcca ccactgtgtg gactaccttg cagttttatg ctcgtcttgg    1980
tggggggag catcctgatc aagagtgctt gagaaaaatc atcagcctct gtgaggtgct    2040
cgggagttgc tgctgttctc agagtagggt caaccgggtc accccggaag aggtcgcagc   2100
aaagattgac ctgtatcttc gtgacgcagc gagtcttgaa gagtgcttgg ctaggcttga   2160
gaaagctcgc ccgccaagca tgctggacac ctccttttgac tgggatgttg tactccctgg   2220
tgttgggacg gctgctcggg cagcagaact acccccccacc gatgagtgtc gcgctctagt   2280
cactgctgtg gcccaaaggc cttcgccgaa agttcagcct cgaaaggcgg ggtctgttaa    2340
gagtctacca gagatcaggc ctgtccctgc cccacgcagg aaggttaagt ctagttgtgg   2400
tgatctggcc ccgttgggcg gcaatttccc tgatagctgg aagatttgg ctggtggctc    2460
ccttaatctc cagatcttac ctgagccggt ggcacaatcc tttgaacctg tgcctgtccc   2520
tgcaccgcgc aagactgcgc ctcgattagt gtcgtcatca ttggcgtcga cccccgtacc   2580
tacaccacga tgtgggtttc ggcagtttga gggaatgaat ttgacagctg tgaccctagc   2640
```

```
atgccaggat gagtccctca atttgtctgc atcctcgcag actgaatatg aggcttctcc    2700
tttggcattg cagcagggtg aggatgtcct tgcggtgggg ggacgagaag ccgaagaagt    2760
cctgagcgga atctcgggaa tgtcaggtgg cattagatta gcgcccgcat catcaagtag    2820
ctccttgtca agcgtggaga tcacacgccc gaagtactca gctcaagcca tcattgactc    2880
aggtggaccc tgttgcgggc accttcaaga ggtgaaagag aaatacctta atgtcatgcg    2940
tgaggcatgt gatgcgacta agctcgatga ccctgccacg caagaatggc tctctcgcat    3000
gtgggagagg gtagacatgc taacctggcg caacacgtcc atctttcaag cgccttttac    3060
cttagctgac aagtttaagt ccctcccgaa gatgatactc gaaacgccgc cacccctaccc   3120
ttgcgggttt gtgatgatgc cccgcacgcc cgcaccttct gtgggtgcgg aaagcgacat    3180
caccgttggt tcagttgcta ctgaagatgt cccgcgtata ctcggggagg tgggagatgt    3240
tggcaagatg accggccagg aacccttaga atccttcgca gatgaactgg cagatgacca    3300
acctgctagg gagtcccgaa cacaagctcc tcctgcaagc acaggtagcg ctggtttagt    3360
tttggattct ggagggtcgc tggggctcac tgacctgccg ctcccaaaca atatagacgc    3420
gggcgggaaa ggaccgtttc acgcggtcaa gaaaaaagct gtagggtgct ttgaccaact    3480
gagccgccgg gttttgaca tcgtctccca tctccctgtt ttttttcac gccttttcgc      3540
gcccggtggt ttttactctt cgggtgactg gagttttgca gcttttactt tattgtgtct    3600
cttttttatgt tacagttatc cggcctttgg ttttgctccc ctcgtgggtg tattttctgg   3660
gtcttctcgg cgcgtgcgca tgggggtttt tggctgctgg ctggcttttg ctgttggttt    3720
gttcaagcct gcacccgacc cagtcggtgc tgcttgtgag tttgactcgc cagagtgtag    3780
agacatcctt cattcttttg agctcctgca accttgggac cctgttcgca gccttgtggt    3840
gggccccgtc ggtctcggcc ttgccatttt tggcaggtta ctgggcgggg cacgctacgt    3900
ctggctgctt ttgcttaggc ttggcatcgt ttcagactgt atcctggctg agcctatgt     3960
gctttcgcaa ggcaggtgta aaaagtgttg gggatcttgt ataagaacag cccccagtga    4020
agttgccttc aatgtgtttc cctttacacg cgcaactaga tcgtcacttg tcaacctgtg    4080
cgaccggttc tgtgcaccca agggcatgga ccccatcttc cttgccacag gatggcgcgg    4140
atgctggtcc ggccagagcc ccattgagca accctctgaa aaacccatag cgttcgccca    4200
gttgacgaa aagaaaatca cggctaggac tgtggttgcc cagccttatg accccaacca     4260
agctgtgaag tgcctgcgag tcctccaggc gggtggagcg atggtagccg aggcagttcc    4320
aaaagtagtc aaagtttctg ctgtcccgtt tcgagcccct ttttttcctg ccggagtgaa    4380
agttgaccct gaatgcaggg tcgtggttga ccctgacacc tttacaaccg ctctccggac    4440
cggctactcc accacaaacc tcattcttgg tgttgggac tttgcccagc tgaatgggtt      4500
gaagatcaga caaatttcca gtccccagg aggggccct cacctcatgg cggctttaca       4560
tgttgcttgc tcgatgactt tgcacatgct tgttgggatt tatgtcacca tggtgggttc    4620
ttgtggctct ggcactaacg atccgtggtg cactaacccg tttgccgtcc ctgtctatgg    4680
gcctggctct ctctgcacgt ccaggttgtg catttcccag cgtggcctga ccctgccctt    4740
aacagcgctt gtgcagggt ttggcgttca ggaaatcgct ttggttgttt taatctttgt     4800
ctccatcggg ggtatggccc acaggttgag ttgcaaggct gacgtgctgt gtatcctgct    4860
tgctattgtc agctatgttt ggccacccct tacctggttg ctttgtgtgt tccttgctg     4920
gttgcgctgg ttttctttac atcccttac tattctatgg ttagtgtttt tcttgatttc     4980
```

```
tgtaaatacg ccctcgggaa tcttggcctt ggtcctgtta atctctcttt ggctccttgg    5040
tcgctatacc aatgttgccg gccttgtcac cccttatgac attcaccatt acaccaacgg    5100
ccctcgcggc gttgccgcct tggccactgc cccggatggg acctacctgg ctgctgtccg    5160
ccgtgctgcg ttgactggcc gtaccatgct gttcaccccg tcccaacttg gctcgctcct    5220
tgagggcgct tttagaaccc aaaagccttc actgaacact gtcaatgtag ttgggtcctc    5280
catgggctcc ggcggggtgt tcaccattga tgggaagatc aaatgtgtga ccgctgctca    5340
tgtcctcacg ggtaactctg ccagggtttc cggggttggc ttcaatcaaa tgttggactt    5400
tgatgttaaa ggggattttg ccatagccga ttgtccgaat tggcaaggag tcgcccccaa    5460
gtcccggttc tgcaaggatg attggactgg ccgtgcttat tggctcacgt cctccggcgt    5520
cgaacccggc gtcattgggc aaggattcgc cttttgtttc accgcgtgcg gcgattccgg    5580
gtccccagtg atcaccgagg ccggggagct tgtcggtgtc cacacgggat caaacaaaca    5640
aggaggaggc attgttacgc gcccttcagg ccggttttgt aatgtgacac ccaccaaatt    5700
aagtgaattg agtgaattct tcgctggacc tagggtcccg cttggtgacg tgaaggttgg    5760
caatcacata atcaaagata taaatgaggt gccctcagat ctctgcgcct tactcgctgc    5820
caaacccgaa ttggaaggag gcctctccac cgttcaactt ctgtgcgtgt ttttctcct    5880 atggagaatg atgggacatg cctggacacc cttggttgcc gttggttttt tcatcttgaa    5940
tgaagttctc ccagcagtcc tggtccggag tgtcttctcc tttggaatgt tcgcactgtc    6000
ttggttcacg ccgtggtctg cacaaattct aatgatcagg ctcttgacag cagccctaaa    6060
cagaaacaga tcgtcacttg cctttttacag cctgggcgca ctaaccggtt ttgttgcaga    6120
tcttgcaacc aatcaggggt atttattgca cgcggtcatg aatgtgagca cctatgcatt    6180
cctgcctcgt gcaatggccg tgacctcacc agtcccaata gttgcgtgtg gcgttgtgca    6240
cttgcttgcc atcattctgt acttgttcaa gtaccgtagc ctgcatgccg tcctggtcgg    6300
cgatggtgcg ttttccgcgg ctttcttctt gcgatacttt gcggagggaa agttgaggga    6360
aggggtgtcg cagtcttgcg gcatgaatca tgagtcacta accggtgccc tcgccatgaa    6420
actcagcgac gaagacttgg acttcctcac aaaattgact gatttaagt gctttgtttc    6480 tgcatccaac atgaggaatg cggcgggtca atttatagag gccgcctacg ccaaagcact    6540
gagggtggaa cttgcccagt tggttcaagt cgataaagtt cgaggtgtcc tggccaaact    6600
tgaagctttc gctgacaccg tggcgcctca actttcaccc ggtgacattg ttgtcgccct    6660
tggacacaca cctgtcggca gcattttttga cctgaaggtc ggcaatgtta agcacactct    6720
ccagtccatt gagaccagaa cccttgccgg gtctaaaatg actgtggcgc gcgtcgtaga    6780
cccaaccccc acaccccgc ccgcacctgt gcccatttcc ctcccaccaa aggttttgga    6840
gaacggtccc aacgcctggg gggatgagaa cggtttgaac aaaaaaaagc ggcgcaagat    6900
ggaggccgtt ggcatttacg ttatgggcgg aaaaagtat caaaaattttt gggataagaa    6960 ttctggtgat gtgttctatg aagaagtcca cgacaacaca gacgcgtggg aatgcctcag    7020
agttgacaac cctgccgact ggatcctga gggggaacc ttgtgtggac acaccaccat    7080
agacaacagg ccttaccatg tttatgcttc tccgtctggt aggaagtttc tagtccctgt    7140
caacccggag agcggaaaag ctcagtggga agctgctaag ctttctttag atcaggccct    7200
cagtatgatg aatgtcgacg cgaactgac cgccaaagaa gtggaaaaat tgaagagaat    7260
aattgacaaa ctccagggcc tgactaagga gcagtgttta aactgctagc cgccagcggc    7320
ttgacccgct gtggtcgcgg cggcttggtt gttactgaga cagcggtaaa gatagtcagg    7380
```

```
ttccacaacc ggacctttac cctagggcct gtgaatttga aagtagctag cgaagttgag    7440
ttgaaggacg cggtcgagca cggccaacac ccggtcgcga taccagccga tggtggcgtc    7500
gtgctcctgc gttccgctgt tccttcgctt atagacgtcc tgatctccgg tgctgacgca    7560
tcccccaggt tgctcgcccg tcacggaccg ggaaatactg gggtcaatgg cgcgctttgg    7620
gattttgagt ctgaagctac caaagaggaa gtagcactta gtgcgcaaat aatacaggcc    7680
tgtgacatta gacgcggcga tgcacctgag attggccttc cttacaagtt gtaccctgtt    7740
aggggcaacc ctgaacgggc aagaggggtt ctaatgaaca caagatttgg agacatacct    7800
tacaagaccc ccagcgacac cgggagcccg gtgcacgcgg ccgcctgcct tacgcccaac    7860
gccactccag taactgatgg gcgctccatc ctggccacga ccatgccctc cgggtttgaa    7920
ctatatgtgc cgaccattcc agcgtctgtc cttgattacc ttgactccag accagactgt    7980
cctaaacagt tgactgagca cgggtgtgaa gatgccgcgt tgaaggacct ttctaaatat    8040
gacctgtcca cccaaggctt tgtgttacct ggagttctac gcctcgtgcg aaaatatctg    8100
tttgctcatg taggtaagtg cccgcctgtc caccggccct ctacctatcc tgccaagaac    8160
tccatggccg gaataaatgg gaacaggttc ccaaccaagg atattcaaag catccctgag    8220
atcgacgttt tgtgtgcaca agctgtgcga gaaaactggc aaactgttac accctgcact    8280
cttaagaagc agtattgcgg taaaaagaag accaggacca tacttggcac caacaacttc    8340
gttgcgctgg cccaccgggc ggcgctgagt ggtgtcaccc agggtttcat gaagaaggcg    8400
tttaactcac ccatcgccct tgggaaaaat aaatttaagg agctacagac tccagtcttg    8460
ggtaggtgtc ttgaggctga tctcgcttcc tgcgatcgat ccacgcctgc aatcgttcgc    8520
tggtttgccg ccaaccttct ttatgaactt gcctgtgctg aggagcattt accgtcgtac    8580
gtgctgaact gttgtcacga cctattggtc acgcagtccg gcgcagtgac taagagaggt    8640
ggcctgtcgt ccggtgaccc aatcacctct gtgtccaaca ccatttatag cttggtgatc    8700
tatgcacagc atatggtgct tagttacttc aaaagtggtc accccatgg ccttctgttt    8760 ttacaagacc agctaaagtt tgaagacatg ctcaaagttc aaccctaat cgtctattcg    8820 gacgacctcg tgttgtatgc cgagtctccc accatgccaa actatcactg gtgggttgaa    8880
cacctgaatt tgatgttggg atttcagacg gacccaaaga agactgcaat aacagactca    8940
ccttcattcc taggttgtag aataataaat ggccgccagt tagtacccaa ccgtgacaga    9000
attctcgcgg cccttgccta tcacatgaag gcgagtaatg tttctgagta ctacgcctcc    9060
gcagccgcaa tactcatgga cagttgtgct tgtctagagt atgatcctga gtggtttgaa    9120
gaacttgtgg ttggaatggc gcagtgcgcc cgtaaggacg gctatagttt ccccggcccg    9180
ccgttcttct tgtccatgtg ggaaaagctc aggtcaaatt atgaggggaa gaagttgaga    9240
gtgtgtggtt attgcggagc ttcagccccg tatgctactg cctgtggcct tgacgtttgt    9300
gtttaccaca cccactttca ccagcattgt ccagtcataa tatggtgtgg ccacccggcg    9360
ggttctgggt cctgcgatga gtgcaaatcc cctacaggga agggtacaag ccctctggat    9420
gaggtcttaa gacaagtccc ttataagcct ccacggacta ttcttatgca tgtggagcag    9480
ggcctcaccc cccttgaccc aggcagatac cagacccgcc gtgggttggt tgctgtcagg    9540
cgcgggataa ggggaaatga agttgacctg ccagatggtg attatgccag tactgcccta    9600
ctccccacct gcaaagacat agacatggtt gctgtggcct ccaatgtgtt gcgcagtagg    9660
ttcatcatcg gcccacctgg cgcagggaaa acacactggc ttcttcaaca ggttcaggat    9720
```

```
agtgatgtca tttacacgcc aacccatcag accatgcttg acatgatcaa ggctttgggg    9780
acgtgccggt tcaatgtccc ggcaggcaca acgctgcaat tccctgcccc ctcccgtacc    9840
ggcccgtggg ttcgcatcct tgccggcggt tggtgtccag gtaagaattc cttcctggat    9900
gaagcagcgt attgcaatca ccttgacgtc ttgaggcttc tcagcaaaac taccctcacc    9960
tgtctggggg atttcaaaca actccacccg gtgggttttg attctcattg ctatgttttt   10020
gatatcatgc ctcagactca actgaagacc atctggaggt ttggacagaa tatctgtgac   10080
gccattcagc cagattacag ggacaaactc gtgtccatgg tcaacacaac ccgtgtaacc   10140
tatgtggaaa gacctgtcaa gtatgggcaa gtcctcaccc cctaccacag agaccgagag   10200
gatggtgcta tcactattga ctccagtcaa ggcgccacat ttgatgtggt cacattgcat   10260
ttgcccacta aagattcact caacaggcaa agagcccttg ttgctatcac cagggcaagg   10320
catgcaatct ttgtgtatga cccacacagg caactgcaga gcatgtttcg tcttcctgca   10380
aaaggcacac ctgtcaacct tgccgtgcac cgtgacgagc agctcatcgt attagataga   10440
aataacaaag agtgcacggt tgttcaggct ttaggcaatg gggacaaatt cagggccagt   10500
gacaagcgcg ttgtagattc tcttcgcgcc atttgtgcag atcttgaagg gtcgagctcc   10560
ccgctcccca aggtcgcaca caacttggga ttttatttct cacctgattt gacacagttt   10620
gctaaactcc cggcggaact tgcaccccac tggcccgtgg tgacaactca gaacaacgaa   10680
aattggccag accggctggt tgctagcctc cgccctatcc acaaatatag ccgcgcgtgc   10740
atcggagccg gctatatggt gggcccctca gtgtttctag gcactcctgg ggttgtgtca   10800
tactatctca cacaatttgt caaggggag gctcaggtgc ttccggagac ggtcttcagc   10860
accggccgaa ttgaggtaga ttgtcgagag tatcttgatg atcgggaacg agaagttgct   10920
gagtccctcc cacatgcctt tattggcgac gtcaaaggca ctaccgttgg gggatgtcac   10980
catgtcactt ctaaatatct cccacgcttc cttcccaagg aatcagttgc ggtggttggg   11040
gtttcaagcc ccgggaaagc cgcaaaagca gtttgcacat taacagatgt gtacctccca   11100
gatcttgagg cttacctcca tccagagacc cagtctaagt gctggaaagt gatgttggac   11160
ttcaaggaag ttcgactgat ggtctggaga gataagacgg cctactttca acttgaaggc   11220
cgccatttca cctggtacca gcttgcaagt tatgcctcgt acatccgagt tcccgttaac   11280
tctacggtgt acctgacccc ctgtatgggc cctgcccttt gcaacagaag agtcgttggg   11340
tctgcacatt ggggagctga ccttgcagtt accccttatg attatggtgc caaaatcatt   11400
ctgtctagtg cgcaccatgg tgaaatgcct cctgggtaca gaattctagc gtgcgcggag   11460
ttctcgcttg atgacccagt gaggtacaaa cacacttggg ggtttgaatc ggatacagcg   11520
tatctgtacg agttcaccgg aaacggtgag gactgggagg attacaatga tgcgtttcgt   11580
gcacgccaga aagggaaaat ttataaggcc actgccacca gcatgagatt tcatttttccc   11640
ccgggtcctg ccattgaacc aacattgggc ctgaactgaa atgaaatggg ggctgtgcag   11700
agccttttcg acaaaatttg ccaacttttt gtggatgctt tcacggaatt tttggtgtcc   11760
attgttgata tcatcatatt tttggccatt ttgtttggct tcaccatcgc aggctggctg   11820
gttgtcttct gtatccgact ggtttgctcc acggtactcc gtgcgcgctc taccattcac   11880
cctgagcaat tacagaagat cctatgaggc cttccttcc cagtgccaag tggacattcc   11940
cgcctgggga actaagcatc ccttgggggt gctttggcac cacaaggtgt caactctgat   12000
tgatgaaatg gtgtcgcgtc gaatgtaccg catcatggaa aaagcaggac aggctgcctg   12060
gaaacaggtt gtgagcgaag ctacattgtc tcgcataagt ggcttggatg tggtggctca   12120
```

```
ttttcagcat cttgctgcca ttgaagccga gacttgcaaa tatttggcct ctcggctgcc   12180
catgctacac aacctagtca tgtcagggtc gaatgtaacc atagtgtata atagcacttt   12240
gggtcaagtg tttgccattt tcccaacccc tggttcccgg ccaaaacttt ctgattttca   12300
acaatggctc atagctgtgc attcttccat attttcttct gttgcggctt cttgtactct   12360
ttttgttgtg ctgtggctgc gaattccaat actacgtact gttttttggtt ccgctggtt   12420 aggggcaact tttcttttcga actcacagtg aattacacgg tgtgcccacc ctgcctcacc   12480
cggcaagcag ccgctgagat ctacgaacac agcgggtctc tttggtgcag gatagggcat   12540
gaccgatgta gccagagtga tcatgacgaa ctagggttct tggttccacc tggccttttcc   12600 agcgagggcc acttgaccag tgtttacgcc tggctggcgt tcttgtcttt cagctacaca   12660
gcccagttcc accccgagat atttggaata gggaatgtga gtagagttta tgttgacgtc   12720
actcaccaac tcatctgcgc cgaacacgac gggcagaaca ccaccctgcg tcgccatgac   12780
aatatctcag ccgtgtttca gacctattac caacatcagg tcgatggcgg caattggttt   12840
cacctagaat ggctgcgtcc cttctttttcc tcttggctgg ttttgaatgt ctcgtggttt   12900
ctcaggcgtt cgcctgcaaa ccgtgtttca gttcgagtct ttcagacatc aaaaccaaca   12960
ccaccgcagc tgcaggcttt gctgtcctcc aagacatcag ctgtcttagg catggctact   13020
cgtccattga ggcgattcgc aaaagccgtc aatgccgcac ggcgatagga acgcccgtgt   13080
acatcactgt cacggccaat gtaacagatg agaattactt gcattcctct gatctcctca   13140
tgctttcctc ttgcctcttc tatgcttctg agatgagtga aaagggattc aatgtggtct   13200
tcggcaacgt gtcaggcatt gtggctgtgt gtgtcaactt taccagctat gtccaacatg   13260
ttaaggagtt tactcagcgc tctttggtgg tcgaccacgt gcgactgctt catttcatga   13320
cacctgcgac catgaggtgg gcaacagttt tagcctgtct tttcgccatc ttgttggcga   13380
tttgaatgtt taagtatgtt ggggaaatgc ttgaccgcgg gctactgctc gcaattgctt   13440
tttttctggt gtatcgtgcc gttctgtttt gctgcgctcg tcaacgccgc cagcaacagc   13500
agctcccatt tacagttgat ttataacctg acgatatgcg agctgaatgg cacagattgg   13560
ttgaatcaaa agtttgattg ggcagtggag acttttgtca ttttttcctgt gttgacccac   13620 attgtctcct acggtgccct taccaccagc catttccttg acacggccgg cctaatcact   13680
gtgtctaccg ccggatatta ccatgggcgg tatgtgttga gtagcatcta cgccgtcttt   13740
gccctggctg cgttgatttg ttttgtcatt aggttgacaa aaaactgtat gtcctggcgc   13800
tactcatgta ccagatatac caactttctt ctggacacca aaggcaatct ctatcgttgg   13860
cggtcacccg tcgttataga gagaaggggt aaagttgagg ttggagacca cctaatcgac   13920
ctcaaaagag ttgtgcttga tggttccgcg caaccccta taaccaagat tcagcggaa   13980 caatggggtc gtccctagac gacttctgca atgacagcac agctgcacaa aaggtgcttt   14040
tggcgttttc catcacctat acgccaataa tgatatatgc cctgaaggta agtcgcggcc   14100
gactgttagg gcttttgcat cttttaattt tcttgaattg tgctttcacc ttcgggtaca   14160
tgacatttgt tcattttcag agtacaaaca aggtcgcgct cactatggga gcagttgttg   14220
cactcctttg gggggtgtac tcagccatag aaacctggaa attcatcact tccagatgcc   14280
gtttgtgctt gctaggccgc aggtacattc tggcccctgc ccaccacgtt gaaagtgccg   14340
cgggctttca tccgattgcg gcaagtgata accacgcatt gtcgtccgg cgtcccggct   14400 ccactactgt taacggcaca ttggtgcccg ggttgaaaag cctcgtgttg ggtggcagaa   14460
```

```
aagctgttaa gcggggagtg gtaaacctcg ttaaatatgc caaataacaa cggcaggcag    14520
caaaaaaata agaaggggag tggccagcca gtcaatcagc tgtgccaaat gctgggcaag    14580
atcatcgccc agcaaaatca gtccagaggc aagggaccgg gtaagaaaaa taagaagaga    14640
aacccggaga agccccattt tcctcttgcg accgaagatg acgtcaggca tcacttcacc    14700
cccagtgaac ggcaattgtg tctgtcgtcg atccagactg ccttcaacca gggcgctgga    14760
acttgcaccc tgtcagattc agggaggata agttacactg tggagtttag tttgccgacg    14820
caccacactg tgcgccttat tcgcgccaca gcatcacctc catcgtgatg ggcttacatt    14880
cttggagctc ctcagtttca caattggaag aatgtgtggt gaatggcact gattggcact    14940
gtgcctctaa gtcacctatt caattagggc gaccgtgtgg gggtttagtt taattggcga    15000
gaaccacgcg gccgaaatta aaaaaaaaaa aaaaaaaaaa aaaaaaa                  15047

<210> SEQ ID NO 13
<211> LENGTH: 15047
<212> TYPE: DNA
<213> ORGANISM: Artificial Sequence
<220> FEATURE:
<223> OTHER INFORMATION: Synthetic Construct

<400> SEQUENCE: 13
atgacgtata ggtgtttgct ttatgccgcg gcatttgtat tgtcaggagc tgtgaccact      60
ggcacagccc gaaacttgct gcacagaaac acccttctgt gacagcctcc ttcaggggag     120
tttaggggtt tctccctaac gccctgcttc cggagttgca ctgctttacg gtctctccat     180
cctttaaacc atgtctggga ttcttgatcg gtgcacgtgc accccaatg ccagggtgtt      240 tgtggcagag ggccaagtct actgcacacg atgtctcagt gcacggtccc tccttcccct    300
aaatctccaa gttctgagc ttggggtact tggtttattc tacaggcccg aagagccatt     360
acggtggacg ttgccacacg cattccccac tgtcgagtgt gctcctgctg gcgcttgttg    420
gctttctgca atttttccaa ttgcgcgaat gaccagtgga aacctgaatt ccagcaaag    480 gctggtacgt gtcgcagccg agctttacag agccggccag ctcaccccta caagcctgaa    540
aaccttacag gtctatgaaa gggggttgcc gttggtaccc attgttggac ctgttcctgg    600
agtggccgtt tacgccaact ccctacatgt gagtgacaaa cccttcccag gagcgactca    660
cgtgctgacc aacttaccac tcccgcagag accaaaatct gaagatttct gccccttcga    720
gtgcgccacg gccgccgtct atgacatcgg ccatgacgcc gtcatgtatg taaccgagga    780 aaaggttttcc tgggctcctc gtggcgggga taaagggaaa tttgagactg ttcctgaggg    840
gttgaagttg actgcggaac gactctacac ctccttcccg cctcaccatg cggtggacat    900 gtccctttc atcttcacag accttgagtg cggcgcttcc atgcgggtcg aacgccaata    960 tgggttgcctc tctgctggca ctgtccctga aggcaactgc tggtggagtc tgtttggctc   1020
gctttcgtta gaagctcagt ataaagaaat ccgctacgcc gcccaatttg gctatcagac    1080
caaacatggc gttactggca gtacctgca gcggaggctg caaattaatg gtctccgagc    1140
agtggttgac ccgaatgggc ctcttgtcgt acagtatttc tccgttaagg agagctggat    1200
gcgccacgtg agactggcgg aagagccagg ctatcctggg tttgaggatc tcctcaggat    1260
aagagtcgag cccaacacgt tgcctttgtc caacaaggac gagaaaatct tccgtttcgg    1320
cggttacaag tggtacggtg ctgggcggag ggcaaggaga acacgtgcaa gagcagtcac    1380
cgcagttgct agtcatgctc cgcccgctcg tggggcccag caggccgaga agcacgaagt    1440
tgctagtgcc aacaagactg agctccttac gcactactcc ccacctgctg aagggaattg    1500
```

```
cggctggcac tgcatctccg ccatcatgaa ccggatggtg cattccaagt ttgaaaccgc    1560
cctttccgaa agagtgagat ccccggaaga ctgggcgact gatgaggatc ttgtgaatac    1620
tattcaaatc ctcaggctcc ctgcggcctt agacaggaac ggcgcctgta aaaacgccaa    1680
gtacatcctt aagctggaag gtgagcactg gactgtttca gtgaccccg gaatgccccc    1740 ctcttcactt cctcttgaat gcgttcaggg ttgttgcgag cataagggca attttgactc    1800
tcaaaacgcg gtcggtttct ttgggttcga ccctgccagc cttgaccgac tcgctggggt    1860
aatgcatctg cccagcagcg ccatccctgc cgccctggcc gagttgtctg gtgaacttga    1920
ttgttcaact cccccggcca ccactgtgtg gactaccttg cagttttatg ctcgtcttgg    1980
tgggggggag catcctgatc aagagtgctt gagaaaaatc atcagcctct gtgaggtgct    2040
cgggagttgc tgctgttctc agagtagggt caaccgggtc accccggaag aggtcgcagc    2100
aaagattgac ctgtatcttc gtgacgcagc gagtcttgaa gagtgcttgg ctaggcttga    2160
gaaagctcgc ccgccaagca tgctggacac ctcctttgac tgggatgttg tactccctgg    2220
tgttgggacg gctgctcggg cagcagaact accccccacc gatgagtgtc gcgctctagt    2280
cactgctgtg gcccaaaggc cttcgccgaa agttcagcct cgaaaggcgg ggtctgttaa    2340
gagtctacca gagatcaggc ctgtccctgc cccacgcagg aaggttaagt ctagttgtgg    2400
tgatctggcc ccgttgggcg gcaatttccc tgatagctgg gaagatttgg ctggtggctc    2460
ccttaatctc cagatcttac ctgagccggt ggcacaatcc tttgaacctg tgcctgtccc    2520
tgcaccgcgc aagactgcgc ctcgattagt gtcgtcatca ttggcgtcga cccccgtacc    2580
tacaccacga tgtgggtttc ggcagtttga gggaatgaat ttgacagctg tgaccctagc    2640
atgccaggat gagtccctca atttgtctgc atcctcgcag actgaatatg aggcttctcc    2700
tttggcattg cagcagggtg aggatgtcct tgcggtgggg ggacgagaag ccgaagaagt    2760
cctgagcgga atctcgggaa tgtcaggtgg cattagatta gcgcccgcat catcaagtag    2820
ctccttgtca agcgtggaga tcacacgccc gaagtactca gctcaagcca tcattgactc    2880
aggtggaccc tgttgcgggc accttcaaga ggtgaaagag aaataccttaa atgtcatgcg    2940 tgaggcatgt gatgcgacta agctcgatga ccctgccacg caagaatggc tctctcgcat    3000
gtgggagagg gtagacatgc taacctggcg caacacgtcc atctttcaag cgccttttac    3060
cttagctgac aagtttaagt ccctcccgaa gatgatactc gaaacgccgc caccctaccc    3120
ttgcgggttt gtgatgatgc cccgcacgcc cgcaccttct gtgggtgcgg aaagcgacat    3180
caccgttggt tcagttgcta ctgaagatgt cccgcgtata ctcggggagg tgggagatgt    3240
tggcaagatg accggccagg aacccttaga atccttcgca gatgaactgg cagatgacca    3300
acctgctagg gagtcccgaa cacaagctcc tcctgcaagc acaggtagcg ctggtttagt    3360
tttggattct ggagggtcgc tggggctcac tgacctgccg ctcccaaaca atatagacgc    3420
gggcgggaaa ggaccgtttc acgcggtcaa gaaaaaagct gtagggtgct ttgaccaact    3480
gagccgccgg gttttgaca tcgtctccca tctccctgtt ttttttcac gccttttcgc    3540 gcccggtggt tttactctt cgggtgactg gagttttgca gcttttactt tattgtgtct    3600 cttttatgt tacagttatc cggcctttgg ttttgctccc ctcgtgggtg tattttctgg    3660
gtcttctcgg cgcgtgcgca tggggtttt tggctgctgg ctggcttttg ctgttggttt    3720
gttcaagcct gcaccgacc cagtcggtgc tgcttgtgag tttgactcgc cagagtgtag    3780
agacatcctt cattctttg agctcctgca accttgggac cctgttcgca gccttgtggt    3840
```

```
gggcccgtc   ggtctcggcc   ttgccatttt   tggcaggtta   ctgggcgggg   cacgctacgt    3900
ctggctgctt   ttgcttaggc   ttggcatcgt   ttcagactgt   atcctggctg   gagcctatgt    3960
gctttcgcaa   ggcaggtgta   aaaagtgttg   gggatcttgt   ataagaacag   cccccagtga    4020
agttgccttc   aatgtgtttc   cctttacacg   cgcaactaga   tcgtcacttg   tcaacctgtg    4080
cgaccggttc   tgtgcaccca   agggcatgga   ccccatcttc   cttgccacag   gatggcgcgg    4140
atgctggtcc   ggccagagcc   ccattgagca   accctctgaa   aaacccatag   cgttcgccca    4200
gttggacgaa   aagaaaatca   cggctaggac   tgtggttgcc   cagccttatg   accccaacca    4260
agctgtgaag   tgcctgcgag   tcctccaggc   gggtggagcg   atggtagccg   aggcagttcc    4320
aaaagtagtc   aaagtttctg   ctgtcccgtt   tcgagcccct   ttttttcctg   ccggagtgaa    4380
agttgaccct   gaatgcaggg   tcgtggttga   ccctgacacc   tttacaaccg   ctctccggac    4440
cggctactcc   accacaaacc   tcattcttgg   tgttgggac    tttgcccagc   tgaatgggtt    4500
gaagatcaga   caaatttcca   agtccccagg   aggggccct    cacctcatgg   cggctttaca    4560
tgttgcttgc   tcgatgactt   tgcacatgct   tgttgggatt   tatgtcacca   tggtgggttc    4620
ttgtggctct   ggcactaacg   atccgtggtg   cactaacccg   tttgccgtcc   ctgtctatgg    4680
gcctggctct   ctctgcacgt   ccaggttgtg   catttcccag   cgtggcctga   ccctgccctt    4740
aacagcgctt   gtggcagggt   ttggcgttca   ggaaatcgct   ttggttgttt   taatctttgt    4800
ctccatcggg   ggtatggccc   acaggttgag   ttgcaaggct   gacgtgctgt   gtatcctgct    4860
tgctattgtc   agctatgttt   ggccacccct   tacctggttg   cttgtgtgt    ttccttgctg    4920 gttgcgctgg   ttttcttac    atcccctac    tattctatgg   ttagtgtttt   tcttgatttc    4980
tgtaaatacg   ccctcgggaa   tcttggcctt   ggtcctgtta   atctctcttt   ggctccttgg    5040
tcgctatacc   aatgttgccg   gccttgtcac   cccttatgac   attcaccatt   acaccaacgg    5100
ccctcgcggc   gttgccgcct   tggccactgc   cccggatggg   acctacctgg   ctgctgtccg    5160
ccgtgctgcg   ttgactggcc   gtaccatgct   gttcaccccg   tcccaacttg   gctcgctcct    5220
tgagggcgct   tttagaaccc   aaaagccttc   actgaacact   gtcaatgtag   ttgggtcctc    5280
catgggctcc   ggcggggtgt   tcaccattga   tgggaagatc   aaatgtgtga   ccgctgctca    5340
tgtcctcacg   ggtaactctg   ccagggtttc   cggggttggc   ttcaatcaaa   tgttggactt    5400
tgatgttaaa   ggggattttg   ccatagccga   ttgtccgaat   tggcaaggag   tcgcccccaa    5460
gtcccggttc   tgcaaggatg   attggactgg   ccgtgcttat   tggctcacgt   cctccggcgt    5520
cgaacccggc   gtcattgggc   aaggattcgc   cttttgtttc   accgcgtgcg   gcgattccgg    5580
gtccccagtg   atcaccgagg   ccggggagct   tgtcggtgtc   cacacgggat   caaacaaaca    5640
aggaggaggc   attgttacgc   gcccttcagg   ccggttttgt   aatgtgacac   caccaaatt    5700 aagtgaattg   agtgaattct   tcgctggacc   tagggtcccg   cttggtgacg   tgaaggttgg    5760
caatcacata   atcaaagata   taatgaggt    gccctcagat   ctctgcgcct   tactcgctgc    5820
caaacccgaa   ttggaaggag   gcctctccac   cgttcaactt   ctgtgcgtgt   tttttctcct    5880
atggagaatg   atgggacatg   cctggacacc   cttggttgcc   gttggttttt   tcatcttgaa    5940
tgaagttctc   ccagcagtcc   tggtccgag   tgtcttctcc   tttggaatgt   tcgcactgtc    6000
ttggttcacg   ccgtggtctg   cacaaattct   aatgatcagg   ctcttgacag   cagccctaaa    6060
cagaaacaga   tcgtcacttg   ccttttacag   cctgggcgca   ctaaccggtt   ttgttgcaga    6120
tcttgcaacc   aatcagggt    atttattgca   cgcggtcatg   aatgtgagca   cctatgcatt    6180
cctgcctcgt   gcaatggccg   tgacctcacc   agtcccaata   gttgcgtgtg   cgttgtgca    6240
```

```
cttgcttgcc atcattctgt acttgttcaa gtaccgtagc ctgcatgccg tcctggtcgg    6300
cgatggtgcg ttttccgcgg ctttcttctt gcgatacttt gcggagggaa agttgaggga    6360
aggggtgtcg cagtcttgcg gcatgaatca tgagtcacta accggtgccc tcgccatgaa    6420
actcagcgac gaagacttgg acttcctcac aaaattgact gattttaagt gctttgtttc    6480
tgcatccaac atgaggaatg cggcgggtca atttatagag gccgcctacg ccaaagcact    6540
gagggtggaa cttgcccagt tggttcaagt cgataaagtt cgaggtgtcc tggccaaact    6600
tgaagctttc gctgacaccg tggcgcctca actttcaccc ggtgacattg ttgtcgccct    6660
tggacacaca cctgtcggca gcattttttga cctgaaggtc ggcaatgtta agcacactct    6720
ccagtccatt gagaccagaa cccttgccgg gtctaaaatg actgtggcgc gcgtcgtaga    6780
cccaaccccc acaccccccgc ccgcacctgt gcccatttcc ctcccaccaa aggttttgga    6840
gaacggtccc aacgcctggg gggatgagaa cggtttgaac aaaaaaaagc ggcgcaagat    6900
ggaggccgtt ggcatttacg ttatgggcgg gaaaaagtat caaaaatttt gggataagaa    6960
ttctggtgat gtgttctatg aagaagtcca cgacaacaca gacgcgtggg aatgcctcag    7020
agttgacaac cctgccgact ggatcctga gggggaacc ttgtgtggac acaccaccat    7080
agacaacagg ccttaccatg tttatgcttc tccgtctggt aggaagtttc tagtccctgt    7140
caacccggag agcggaaaag ctcagtggga agctgctaag ctttctttag atcaggccct    7200
cagtatgatg aatgtcgacg gcgaactgac cgccaaagaa gtggaaaaat tgaagagaat    7260
aattgacaaa ctccagggcc tgactaagga gcagtgttta aactgctagc cgccagcggc    7320
ttgacccgct gtggtcgcgg cggcttggtt gttactgaga cagcggtaaa gatagtcagg    7380
ttccacaacc ggacctttac cctagggcct gtgaatttga aagtagctag cgaagttgag    7440
ttgaaggacg cggtcgagca cggccaacac ccggtcgcga taccagccga tggtggcgtc    7500
gtgctcctgc gttccgctgt tccttcgctt atagacgtcc tgatctccgg tgctgacgca    7560 tccccccaggt tgctcgcccg tcacggaccg ggaaatactg gggtcaatgg cgcgctttgg    7620
gattttgagt ctgaagctac caaagaggaa gtagcactta gtgcgcaaat aatacaggcc    7680
tgtgacatta gacgcggcga tgcacctgag attggccttc cttacaagtt gtaccctgtt    7740
aggggcaacc ctgaacgggc aagagggggtt ctaatgaaca caagatttgg agacatacct    7800
tacaagaccc ccagcgacac cgggagcccg gtgcacgcgg ccgcctgcct tacgcccaac    7860
gccactccag taactgatgg gcgctccatc ctggccacga ccatgccctc cgggtttgaa    7920
ctatatgtgc cgaccattcc agcgtctgtc cttgattacc ttgactccag accagactgt    7980
cctaaacagt tgactgagca cgggtgtgaa gatgccgcgt tgaaggacct ttctaaatat    8040
gacctgtcca cccaaggctt tgtgttacct ggagttctac gcctcgtgcg aaaatatctg    8100
tttgctcatg taggtaagtg cccgcctgtc caccggccct ctacctatcc tgccaagaac    8160
tccatggccg aataaatgg gaacaggttc ccaaccaagg atattcaaag catccctgag    8220
atcgacgttt tgtgtgcaca agctgtgcga gaaaactggc aaactgttac ccctgcact    8280 cttaagaagc agtattgcgg taaaaagaag accaggacca tacttggcac caacaacttc    8340
gttgcgctgg cccaccgggc ggcgctgagt ggtgtcaccc agggttcat gaagaaggcg    8400 tttaactcac ccatcgccct tgggaaaaat aaatttaagg agctacagac tccagtcttg    8460
ggtaggtgtc ttgaggctga tctcgcttcc tgcgatcgat ccacgcctgc aatcgttcgc    8520
tggtttgccg ccaaccttct ttatgaactt gcctgtgctg aggagcattt accgtcgtac    8580
```

```
gtgctgaact gttgtcacga cctattggtc acgcagtccg gcgcagtgac taagagaggt    8640
ggcctgtcgt ccggtgaccc aatcacctct gtgtccaaca ccatttatag cttggtgatc    8700
tatgcacagc atatggtgct tagttacttc aaaagtggtc accccatgg ccttctgttt     8760
ttacaagacc agctaaagtt tgaagacatg ctcaaagttc aacccctaat cgtctattcg    8820
gacgacctcg tgttgtatgc cgagtctccc accatgccaa actatcactg gtgggttgaa    8880
cacctgaatt tgatgttggg atttcagacg acccaaaga agactgcaat aacagactca     8940
ccttcattcc taggttgtag aataataaat ggccgccagt tagtacccaa ccgtgacaga    9000
attctcgcgg cccttgccta tcacatgaag gcgagtaatg tttctgagta ctacgcctcc    9060
gcagccgcaa tactcatgga cagttgtgct tgtctagagt atgatcctga gtggtttgaa    9120
gaacttgtgg ttggaatggc gcagtgcgcc cgtaaggacg gctatagttt ccccggcccg    9180
ccgttcttct tgtccatgtg ggaaaagctc aggtcaaatt atgagggaa gaagttgaga     9240
gtgtgtggtt attgcggagc ttcagccccg tatgctactg cctgtggcct tgacgtttgt    9300
gtttaccaca cccactttca ccagcattgt ccagtcataa tatggtgtgg ccaccggcg    9360
ggttctgggt cctgcgatga gtgcaaatcc cctacaggga agggtacaag ccctctggat    9420
gaggtcttaa gacaagtccc ttataagcct ccacggacta ttcttatgca tgtggagcag    9480
ggcctcaccc cccttgaccc aggcagatac cagacccgcc gtgggttggt tgctgtcagg    9540
cgcgggataa ggggaaatga agttgacctg ccagatggtg attatgccag tactgcccta    9600
ctccccacct gcaaagacat agacatggtt gctgtggcct ccaatgtgtt gcgcagtagg    9660
ttcatcatcg gccacctggc gcagggaaa acacactggc ttcttcaaca ggttcaggat    9720
agtgatgtca tttacacgcc aacccatcag accatgcttg acatgatcaa ggctttgggg    9780
acgtgccggt tcaatgtccc ggcaggcaca acgctgcaat tccctgcccc ctcccgtacc    9840
ggcccgtggg ttcgcatcct tgccggcggt tggtgtccag gtaagaattc cttcctggat    9900
gaagcagcgt attgcaatca ccttgacgtc ttgaggcttc tcagcaaaac taccctcacc    9960
tgtctggggg atttcaaaca actccacccg gtgggttttg attctcattg ctatgttttt    10020
gatatcatgc ctcagactca actgaagacc atctggaggt ttggacagaa tatctgtgac    10080
gccattcagc cagattacag ggacaaactc gtgtccatgg tcaacacaac ccgtgtaacc    10140
tatgtggaaa gacctgtcaa gtatgggcaa gtcctcaccc cctaccacag agaccgagag    10200
gatggtgcta tcactattga ctccagtcaa ggcgccacat ttgatgtggt cacattgcat    10260
ttgcccacta aagattcact caacaggcaa agagcccttg ttgctatcac cagggcaagg    10320
catgcaatct ttgtgtatga cccacacagg caactgcaga gcatgtttcg tcttcctgca    10380
aaaggcacac ctgtcaacct tgccgtgcac cgtgacgagc agctcatcgt attagataga    10440
aataacaaag agtgcacggt tgttcaggct ttaggcaatg gggacaaatt cagggccagt    10500
gacaagcgcg ttgtagattc tcttcgcgcc atttgtgcag atcttgaagg gtcgagctcc    10560
ccgctcccca aggtcgcaca caacttggga ttttatttct cacctgattt gacacagttt    10620
gctaaactcc cggcggaact tgcaccccac tggcccgtgg tgacaactca gaacaacgaa    10680
aattggccag accggctggt tgctagcctc cgccctatcc acaaatatag ccgcgcgtgc    10740
atcggagccg gctatatggt gggcccctca gtgtttctag gcactcctgg ggttgtgtca    10800
tactatctca cacaatttgt caaaggggag gctcaggtgc ttccggagac ggtcttcagc    10860
accggccgaa ttgaggtaga ttgtcgagag tatcttgatg atcgggaacg agaagttgct    10920
gagtccctcc cacatgcctt tattggcgac gtcaaaggca ctaccgttgg gggatgtcac    10980
```

```
catgtcactt ctaaatatct cccacgcttc cttcccaagg aatcagttgc ggtggttggg   11040
gtttcaagcc ccgggaaagc cgcaaaagca gtttgcacat taacagatgt gtacctccca   11100
gatcttgagg cttacctcca tccagagacc cagtctaagt gctggaaagt gatgttggac   11160
ttcaaggaag ttcgactgat ggtctggaga gataagacgg cctactttca acttgaaggc   11220
cgccatttca cctggtacca gcttgcaagt tatgcctcgt acatccgagt tcccgttaac   11280
tctacggtgt acctggaccc ctgtatgggc cctgcccttt gcaacagaag agtcgttggg   11340
tctgcacatt ggggagctga ccttgcagtt accccttatg attatggtgc caaaatcatt   11400
ctgtctagtg cgcaccatgg tgaaatgcct cctgggtaca gaattctagc gtgcgcggag   11460
ttctcgcttg atgacccagt gaggtacaaa cacacttggg ggtttgaatc ggatacagcg   11520
tatctgtacg agttcaccgg aaacggtgag gactgggagg attacaatga tgcgtttcgt   11580
gcacgccaga aagggaaaat ttataaggcc actgccacca gcatgagatt tcattttccc   11640
ccgggtcctg ccattgaacc aacattgggc ctgaactgaa atgaaatggg ggctgtgcag   11700
agccttttcg acaaaatttg ccaacttttt gtggatgctt tcacggaatt tttggtgtcc   11760
attgttgata tcatcatatt tttggccatt ttgtttggct tcaccatcgc aggctggctg   11820
gttgtcttct gtatccgact ggtttgctcc acggtactcc gtgcgcgctc taccattcac   11880
cctgagcaat tacagaagat cctatgaggc cttcctttcc cagtgccaag tggacattcc   11940
cgcctgggga actaagcatc ccttggggt gctttggcac cacaaggtgt caactctgat   12000
tgatgaaatg gtgtcgcgtc gaatgtaccg catcatggaa aaagcaggac aggctgcctg   12060
gaaacaggtt gtgagcgaag ctacattgtc tcgcataagt ggcttggatg tggtggctca   12120
ttttcagcat cttgctgcca ttgaagccga gacttgcaaa tatttggcct ctcggctgcc   12180
catgctacac aacctagtca tgtcagggtc gaatgtaacc atagtgtata atagcacttt   12240
gggtcaagtg tttgccattt tcccaacccc tggttcccgg ccaaaacttt ctgattttca   12300
acaatggctc atagctgtgc attcttccat attttcttct gttgcggctt cttgtactct   12360
ttttgttgtg ctgtggctgc gaattccaat actacgtact gttttttggtt tccgctggtt   12420 aggggcaact tttctttcga actcacagtg aattacacgg tgtgcccacc ctgcctcacc   12480
cggcaagcag ccgctgagat ctacgaacac agcgggtctc tttggtgcag gatagggcat   12540
gaccgatgta gccagagtga tcatgacgaa ctagggttct tggttccacc tggccttttcc   12600 agcgagggcc acttgaccag tgtttacgcc tggctggcgt tcttgtcttt cagctacaca   12660
gcccagttcc accccgagat atttggaata gggaatgtga gtagagttta tgttgacgtc   12720
actcaccaac tcatctgcgc cgaacacgac gggcagaaca ccaccctgcg tcgccatgac   12780
aatatctcag ccgtgtttca gacctattac caacatcagg tcgatggcgg caattggttt   12840
cacctagaat ggctgcgtcc cttcttttcc tcttggctgg ttttgaatgt ctcgtggttt   12900
ctcaggcgtt cgcctgcaaa ccgtgtttca gttcgagtct ttcagacatc aaaaccaaca   12960
ccaccgcagc tgcaggcttt gctgtcctcc aagacatcag ctgtcttagg catggctact   13020
cgtccattga ggcgattcgc aaaagccgtc aatgccgcac ggcgatagga acgcccgtgt   13080
acatcactgt cacggccaat gtaacagatg agaattactt gcattcctct gatctcctca   13140
tgctttcctc ttgccttctc tatgcttctg agatgagtga aaagggattc aatgtggtct   13200
tcggcaacgt gtcaggcatt gtggctgtgt gtgtcaactt taccagctat gtccaacatg   13260
ttaaggagtt tactcagcgc tctttggtgg tcgaccacgt gcgactgctt catttcatga   13320
```

```
cacctgcgac catgaggtgg gcaacagttt tagcctgtct tttcgccatc ttgttggcga    13380
tttgaatgtt taagtatgtt ggggaaatgc ttgaccgcgg gctactgctc gcaattgctt    13440
tttttctggt gtatcgtgcc gttctgtttt gctgcgctcg tcaacgccgc cagcaacagc    13500
agctcccatt tacagttgat ttataacctg acgatatgcg agctgaatgg cacagattgg    13560
ttgaatcaaa agtttgattg ggcagtggag acttttgtca tttttcctgt gttgacccac    13620
attgtctcct acggtgccct taccaccagc catttccttg acacggccgg cctaatcact    13680
gtgtctaccg ccggatatta ccatgggcgg tatgtgttga gtagcatcta cgccgtcttt    13740
gccctggctg cgttgatttg ttttgtcatt aggttgacaa aaaactgtat gtcctggcgc    13800
tactcatgta ccagatatac caactttctt ctggacacca aaggcaatct ctatcgttgg    13860
cggtcacccg tcgttataga gagaaggggt aaagttgagg ttggagacca cctaatcgac    13920
ctcaaaagag ttgtgcttga tggttccgcg gcaacccta taaccaagat ttcagcggaa    13980
caatggggtc gtccctagac gacttctgca atgacagcac agctgcacaa aaggtgcttt    14040
tggcgttttc catcacctat acgccaataa tgatatatgc cctgaaggta agtcgcggcc    14100
gactgttagg gcttttgcat ctttttaattt tcttgaattg tgctttcacc ttcgggtaca    14160
tgacatttgt tcattttcag agtacaaaca aggtcgcgct cactatggga gcagttgttg    14220
cactcctttg gggggtgtac tcagccatag aaacctggaa attcatcact tccagatgcc    14280
gtttgtgctt gctaggccgc aggtacattc tggccctgc ccaccacgtt gaaagtgccg    14340
cgggctttca tccgattgcg gcaagtgata accacgcatt tgtcgtccgg cgtcccggct    14400
ccactactgt taacggcaca ttggtgcccg ggttgaaaag cctcgtgttg ggtggcagaa    14460
aagctgttaa gcggggagtg gtaaacctcg ttaaatatgc caaataacaa cggcaggcag    14520
caaaaaaata agaaggggag tggccagcca gtcaatcagc tgtgccaaat gctgggcaag    14580
atcatcgccc agcaaaatca gtccagaggc aagggaccgg gtaagaaaaa taagaagaga    14640
aacccggaga agccccattt tcctcttgcg accgaagatg acgtcaggca tcacttcacc    14700
cccagtgaac ggcaattgtg tctgtcgtcg atccagactg ccttcaacca gggcgctgga    14760
acttgcaccc tgtcagattc agggaggata agttacactg tggagtttag tttgccgacg    14820
caccacactg tgcgccttat tcgcgccaca gcatcacctc catcgtgatg ggcttacatt    14880
cttggagctc ctcagtttca caattggaag aatgtgtggt gaatggcact gattggcact    14940
gtgcctctaa gtcacctatt caattagggc gaccgtgtgg gggtttagtt taattggcga    15000
gaaccacgcg gccgaaatta aaaaaaaaaa aaaaaaaaa aaaaaaa                    15047
```